United States Patent
Narayanan et al.

(10) Patent No.: US 11,230,523 B2
(45) Date of Patent: *Jan. 25, 2022

(54) SELECTIVE ANDROGEN RECEPTOR DEGRADER (SARD) LIGANDS AND METHODS OF USE THEREOF

(71) Applicant: University of Tennessee Research Foundation, Knoxville, TN (US)

(72) Inventors: Ramesh Narayanan, Cordova, TN (US); Duane D. Miller, Collierville, TN (US); Thamarai Ponnusamy, Memphis, TN (US); Dong-Jin Hwang, Arlington, TN (US); Yali He, Germantown, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/425,865

(22) Filed: May 29, 2019

(65) Prior Publication Data
US 2020/0039924 A1 Feb. 6, 2020

Related U.S. Application Data

(63) Continuation-in-part of application No. 15/981,849, filed on May 16, 2018, which is a continuation-in-part of application No. 15/923,668, filed on Mar. 16, 2018, which is a continuation-in-part of application No. 15/620,761, filed on Jun. 12, 2017, now Pat. No. 10,314,797.

(60) Provisional application No. 62/482,036, filed on Apr. 5, 2017, provisional application No. 62/455,397, filed on Feb. 6, 2017, provisional application No. 62/348,474, filed on Jun. 10, 2016.

(51) Int. Cl.
C07C 235/64 (2006.01)

(52) U.S. Cl.
CPC .................................. *C07C 235/64* (2013.01)

(58) Field of Classification Search
CPC ................ A61K 31/401; A61K 31/415; A61K 31/4164; A61K 31/5375; A61P 35/00; C07C 235/64; C07C 255/60; C07D 207/30; C07D 207/325; C07D 207/34; C07D 213/75; C07D 231/12; C07D 231/16; C07D 231/38; C07D 231/40; C07D 233/58; C07D 233/68; C07D 239/74; C07D 249/08; C07D 249/14; C07D 257/04; C07D 295/15; C07D 303/48; C07D 401/12
See application file for complete search history.

(56) References Cited

U.S. PATENT DOCUMENTS

| | | | |
|---|---|---|---|
| 5,480,656 A | 1/1996 | Okada et al. | |
| 5,575,987 A | 11/1996 | Kamei et al. | |
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 6,472,412 B1 | 10/2002 | Fenton et al. | |
| 6,472,415 B1 | 10/2002 | Milos et al. | |
| 7,118,552 B2 | 10/2006 | Shaw et al. | |
| 7,186,854 B2 | 3/2007 | Thijis et al. | |
| 7,220,247 B2 | 5/2007 | Shaw et al. | |
| 7,500,964 B2 | 3/2009 | Shaw et al. | |
| 7,741,371 B2 | 6/2010 | Dalton et al. | |
| 8,735,440 B2 | 5/2014 | McKnight et al. | |
| 9,550,742 B2 | 1/2017 | Marugan et al. | |
| 9,815,776 B2 * | 11/2017 | Narayanan | A61P 17/08 |

(Continued)

FOREIGN PATENT DOCUMENTS

| | | |
|---|---|---|
| CN | 1597662 A | 3/2005 |
| EP | 0 253 503 | 2/1988 |

(Continued)

OTHER PUBLICATIONS

West, Anthony R., Solid State Chemistry and Its Applications, Wiley, New York, 1988, 358. (Year: 1988).*

(Continued)

*Primary Examiner* — Erich A Leeser
(74) *Attorney, Agent, or Firm* — Knobbe, Martens, Olson & Bear LLP

(57) ABSTRACT

This invention is directed to pyrrole, pyrazole, imidazole, triazole, and morpholine based selective androgen receptor degrader (SARD) compounds including cyclic and heterocyclic anilide rings and their synthetic precursors, and mono-, di-, or multi-substituted N-heterocyclic rings, R-isomers, non-hydroxylated and/or non-chiral propanamides in treating androgen receptor dependent diseases and conditions such as hyperproliferations of the prostate including pre-malignancies and benign prostatic hyperplasia, prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

35 Claims, 89 Drawing Sheets

(56) References Cited

U.S. PATENT DOCUMENTS

| | | | |
|---|---|---|---|
| 9,834,507 B2* | 12/2017 | Narayanan | A61K 45/06 |
| 10,093,613 B2* | 10/2018 | Narayanan | A61P 5/28 |
| 10,314,797 B2 | 6/2019 | Narayanan et al. | |
| 10,654,809 B2* | 5/2020 | Narayanan | C07D 207/34 |
| 2005/0101657 A1 | 5/2005 | Furuya et al. | |
| 2006/0142387 A1 | 6/2006 | Cadilla et al. | |
| 2006/0173037 A1 | 8/2006 | Schlienger et al. | |
| 2006/0241180 A1 | 10/2006 | Dalton et al. | |
| 2007/0049629 A1 | 3/2007 | Scanlan et al. | |
| 2007/0123512 A1 | 5/2007 | Ratilainen | |
| 2007/0123563 A1 | 5/2007 | Dalton et al. | |
| 2007/0173546 A1 | 7/2007 | Dalton et al. | |
| 2007/0265290 A1 | 11/2007 | Dalton et al. | |
| 2008/0293766 A1 | 11/2008 | Diamond et al. | |
| 2009/0042844 A1 | 2/2009 | Labrie et al. | |
| 2009/0060873 A1 | 3/2009 | Sporn et al. | |
| 2009/0142323 A1 | 6/2009 | Quarles et al. | |
| 2010/0227846 A1 | 9/2010 | Ito et al. | |
| 2010/0331418 A1 | 12/2010 | Koh et al. | |
| 2011/0028719 A1 | 2/2011 | Slon-Usakiewicz | |
| 2014/0018433 A1 | 1/2014 | Dalton et al. | |
| 2014/0094474 A1 | 4/2014 | Törmakängas et al. | |
| 2015/0331777 A1 | 11/2015 | Lvin | |
| 2017/0029370 A1 | 2/2017 | Narayanan et al. | |
| 2017/0095446 A1 | 4/2017 | Narayanan et al. | |
| 2017/0166526 A1 | 6/2017 | Narayanan et al. | |
| 2017/0368003 A1 | 12/2017 | Narayanan et al. | |
| 2018/0118663 A1 | 5/2018 | Narayanan et al. | |
| 2018/0271849 A1 | 9/2018 | Ge et al. | |
| 2018/0273487 A1 | 9/2018 | Narayanan et al. | |
| 2018/0360805 A1 | 12/2018 | Narayanan et al. | |
| 2019/0015387 A1* | 1/2019 | Narayanan | A61K 31/655 |
| 2019/0060280 A1 | 2/2019 | Narayanan et al. | |

FOREIGN PATENT DOCUMENTS

| | | |
|---|---|---|
| EP | 0 524 781 A1 | 1/1993 |
| EP | 100172 A1 | 2/2004 |
| EP | 2159049 A1 | 3/2010 |
| WO | WO 2001/058855 A1 | 8/2001 |
| WO | WO 2002/016310 A1 | 2/2002 |
| WO | WO 2002/046164 A1 | 6/2002 |
| WO | WO 03/074473 A2 | 9/2003 |
| WO | WO 2003/106401 A1 | 12/2003 |
| WO | WO 2004/035737 A2 | 4/2004 |
| WO | WO 2004/035738 A3 | 4/2004 |
| WO | WO 2005/000794 A1 | 1/2005 |
| WO | WO 2005/120477 A2 | 12/2005 |
| WO | WO 2007/005887 A2 | 1/2007 |
| WO | WO 2007/126988 A2 | 11/2007 |
| WO | WO 2008/011072 A1 | 2/2008 |
| WO | WO 2008/044033 A1 | 4/2008 |
| WO | WO 2008/124000 A2 | 10/2008 |
| WO | WO 2008/137038 | 11/2008 |
| WO | WO 2009/010480 A1 | 1/2009 |
| WO | WO 2009/069736 A1 | 6/2009 |
| WO | WO 2009/082437 A2 | 7/2009 |
| WO | WO 2012/007644 A1 | 1/2012 |
| WO | WO 2013/064681 A1 | 5/2013 |
| WO | WO 2014/011220 A2 | 1/2014 |
| WO | WO 2014/113260 A1 | 7/2014 |
| WO | WO 2015/042297 A1 | 3/2015 |
| WO | WO 2016/172330 A1 | 10/2016 |
| WO | WO 2016/172358 A1 | 10/2016 |

OTHER PUBLICATIONS

Jin, et al, Synthesis and biological evaluation of 1-substituted-3(5)-(6-methylpyridin-2-yl)-4-(quinolin-6-yl)pyrazoles as transforming growth factor-type 1 receptor kinase inhibitors, Bioorganic & Medicinal Chemistry, 19(8), 2633-2640 (2011). (Year: 2011).*
Jin, et al, Synthesis and biological evaluation of 1-substituted-3(5)-(6-methylpyridin-2-yl)-4-(quinoxalin-6-yl)pyrazoles as transforming growth factor-type 1 receptor kinase inhibitors, European Journal of Medicinal Chemistry, 46(9), 3917-3925 (2011). (Year: 2011).*
Lallous et al. "Functional analysis of androgen receptor mutations that confer anti-androgen resistance identified in circulating cell-free DNA from prostate cancer patients" Genome biology. Dec. 2016;17(1):10.
La Spada et al. "Androgen receptor gene mutations in X-linked spinal and bulbar muscular atrophy" Nature. Jul. 1991;352(6330):77.
Li et al. "Androgen receptor splice variants mediate enzalutamide resistance in castration-resistant prostate cancer cell lines" Cancer research. Jan. 15, 2013;73(2):483-9.
Li et al. "On the physical origin of blue-shifted hydrogen bonds" Journal of the American Chemical Society. Aug. 14, 2002;124(32):9639-47.
Lieberman et al. "Peripheral androgen receptor gene suppression rescues disease in mouse models of spinal and bulbar muscular atrophy" Cell reports. May 8, 2014;7(3):774-84.
Locati et al. "Clinical activity of androgen deprivation therapy in patients with metastatic/relapsed androgen receptor-positive salivary gland cancers" Head & neck. May 1, 2016;38(5):724-31.
Maclean et al. "Spinal and bulbar muscular atrophy: androgen receptor dysfunction caused by a trinucleotide repeat expansion" Journal of the neurological sciences. Feb. 29, 1996;135(2):149-57.
Marhefka et al. "Homology modeling using multiple molecular dynamics simulations and docking studies of the human androgen receptor ligand binding domain bound to testosterone and nonsteroidal ligands" Journal of medicinal chemistry. May 24, 2001;44(11):1729-40.
Marhefka et al. "Design, synthesis, and biological characterization of metabolically stable selective androgen receptor modulators" Journal of medicinal chemistry. Feb. 12, 2004;47(4):993.
Mcbeth et al. "Involvement of the androgen and glucocorticoid receptors in bladder cancer" International journal of endocrinology. 2015;2015.
Mcginley et al. "Circumventing anti-androgen resistance by molecular design" Journal of the American Chemical Society. Apr. 4, 2007;129(13):3822-3.
Miller Irreversible Nonsteroida SARMs for Prostate Cancer at http://grantome.com/grant/NIH/R01-DK065227-20, 2003.
Miller et al. "Phase III, randomized, placebo-controlled study of once-daily oral zibotentan (ZD4054) in patients with non-metastatic castration-resistant prostate cancer" Prostate cancer and prostatic diseases. Jun. 2013;16(2):187.
Mitsiades N. "A road map to comprehensive androgen receptor axis targeting for castration-resistant prostate cancer" Cancer research. Aug. 1, 2013;73(15):4599-605.
Monge et al. "Unfaithfulness and promiscuity of a mutant androgen receptor in a hormone-refractory prostate cancer" Cellular and molecular life sciences. Feb. 1, 2006;63(4):487-97.
Nagata et al. "Preparation and reactions of cyclic α-monocarbonyl azo-compounds: 1-pyrazolin-3-one derivatives" Journal of the Chemical Society C: Organic. 1970(4):540-50.
Narayanan et al "Selective androgen receptor modulators (SARMs) negatively regulate triple-negative breast cancer growth and epithelial: mesenchymal stem cell signaling" PloS one. Jul. 29, 2014;9(7):e103202.
Narayanan et al. "Biological synthesis of metal nanoparticles by microbes" advances in colloid and interface science. Apr. 22, 2010;156(1-2):1-3.
Nazareth et al. "Activation of the human androgen receptor through a protein kinase A signaling pathway" Journal of Biological Chemistry. Aug. 16, 1996;271(33):19900-7.
Nyquist et al. "TALEN-engineered AR gene rearrangements reveal endocrine uncoupling of androgen receptor in prostate cancer" Proceedings of the National Academy of Sciences. Oct. 22, 2013;110(43):17492-7.
Office Action dated Jul. 5, 2019 issued in corresponding U.S. Appl. No. 15/981,892.
Pubmed, CID 20221988, Dec. 5, 2007, pp. 1-11; retrieved from the Internet <URL: https://pubchem.ncbi.nlm.nih.gov/compound/20221988>; p. 3, formula.

(56) References Cited

OTHER PUBLICATIONS

Rawel et al. "Determining the binding affinities of phenolic compounds to proteins by quenching of the intrinsic tryptophan fluorescence" Molecular nutrition & food research. Aug. 2006;50(8):705-13.
Remington et al. "Remington's pharmaceutical sciences", 1553-1593, current edition.
Remond et al. "Handbook Of Pharmaceutical Excipients" American Pharmaceutical Association.
Renier et al. "Antiandrogen flutamide protects male mice from androgen-dependent toxicity in three models of spinal bulbar muscular atrophy" Endocrinology. Jul. 1, 2014;155(7):2624-34.
Rosa et al. "Polymorphisms of CYP17A1, CYP19, and androgen in Brazilian women with uterine leiomyomas" Clinical chemistry and laboratory medicine. Jun. 1, 2008;46(6):814-23.
Rygula et al. "Raman spectroscopy of proteins: a review" Journal of Raman Spectroscopy. Aug. 2013;44(8):1061-76.
Sadar Md. "Androgen-independent induction of prostate-specific antigen gene expression via cross-talk between the androgen receptor and protein kinase A signal transduction pathways" Journal of Biological Chemistry. Mar. 19, 1999;274(12):7777-83.
Sadar et al. "Ligand-independent activation of the androgen receptor by the differentiation agent butyrate in human prostate cancer cells" Cancer research. Oct. 15, 2000;60(20):5825-31.
Sartor et al. "Androgen receptor variant-7: an important predictive biomarker in castrate resistant prostate cancer" Asian journal of andrology. May 2015;17(3):439.
Scher et al. "Increased survival with enzalutamide in prostate cancer after chemotherapy" New England Journal of Medicine. Sep. 27, 2012;367(13):1187-97.
Shortridge et al. "Estimating protein—ligand binding affinity using high-throughput screening by NMR" Journal of combinatorial chemistry. Oct. 3, 2008;10(6):948-58.
Sieber PR. "Treatment of bicalutamide-induced breast events" Expert review of anticancer therapy. Dec. 1, 2007;7(12):1773-9.
Siegel et al. "Cancer statistics" CA Cancer. J. Clin. 2014;64:9-29.
Sun et al. "Castration resistance in human prostate cancer is conferred by a frequently occurring androgen receptor splice variant" The Journal of clinical investigation. Aug. 2, 2010;120(8):2715-30.
Tan et al. "Dehydroepiandrosterone activates mutant androgen receptors expressed in the androgen-dependent human prostate cancer xenograft CWR22 and LNCaP cells" Molecular endocrinology. Apr. 1, 1997;11(4):450-9.
Tran et al. "Development of a second-generation antiandrogen for treatment of advanced prostate cancer" Science. May 8, 2009;324(5928):787-90.
Ueda et al. Ligand-independent activation of the androgen receptor by interleukin-6 and the role of steroid receptor coactivator-1 in prostate cancer cells: Journal of Biological Chemistry. Oct. 11, 2002;277(41):38087-94.
Wang et al. "Small molecule inhibition of the steroid receptor coactivators, SRC-3 and SRC-1" Molecular endocrinology. Dec. 1, 2011;25(12):2041-53.
Wang et al. "Effects of hydrogen bond and solvent polarity on the C=O stretching of bis (2-thienyl) ketone in solution" The Journal of chemical physics. Mar. 28, 2012;136(12):03B614.
Watson et al. "Constitutively active androgen receptor splice variants expressed in castration-resistant prostate cancer require full-length androgen receptor" Proceedings of the national academy of sciences. Sep. 28, 2010;107(39):16759-65.
Weiner LP. "Possible role of androgen receptors in amyotrophic lateral sclerosis: a hypothesis" Archives of neurology. Mar. 1, 1980;37(3):129-31.
Wen et al. "LHRH-conjugated micelles for targeted delivery of antiandrogen to treat advanced prostate cancer" Pharmaceutical research. Oct. 1, 2014;31(10):2784-95.
Wen et al. "Targeting fatty acid synthase with ASC-J9 suppresses proliferation and invasion of prostate cancer cells" Molecular carcinogenesis. Dec. 2016;55(12):2278-90.
West AR. "Solid state chemistry and its applications" John Wiley & Sons; 1988; pp. 358. 365.
Xu et al. "hSSB1 binds and protects p21 from ubiquitin-mediated degradation and positively correlates with p21 in human hepatocellular carcinomas" Oncogene. May 12, 2011;30(19):2219-29.
Yamashita et al. "ASC-J9 suppresses castration-resistant prostate cancer growth through degradation of full-length and splice variant androgen receptors" Neoplasia. Jan. 1, 2012;14(1):74IN9-83IN12.
Yepuru et al. "Steroidogenic enzyme AKR1C3 is a novel androgen receptor-selective coactivator that promotes prostate cancer growth" Clinical Cancer Research. Oct. 15, 2013;19(20):5613-25.
Yoshida et al. "Antiandrogen bicalutamide promotes tumor growth in a novel androgen-dependent prostate cancer xenograft model derived from a bicalutamide-treated patient" Cancer Research. Nov. 1, 2005;65(21):9611-6.
Zhou et al. "Study of the impact of the T877A mutation on ligand-induced helix-12 positioning of the androgen receptor resulted in design and synthesis of novel antiandrogens" Proteins: Structure, Function, and Bioinformatics. Feb. 15, 2010;78(3):623-37.
Aggarwal et al. "Androgens affect muscle, motor neuron, and survival in a mouse model of SOD1-related amyotrophic lateral sclerosis". Neurobiology of aging. Aug. 1, 2014;35(8):1929-38.
Andersen et al. "Regression of castrate-recurrent prostate cancer by a small-molecule inhibitor of the amino-terminus domain of the androgen receptor" Cancer cell. Jun. 15, 2010;17(6):535-46.
Antonarakis et al. "AR-V7 and resistance to enzalutamide and abiraterone in prostate cancer" New England Journal of Medicine. Sep. 11, 2014;371(11):1028-38.
Antonarakis et al. "Clinical significance of androgen receptor splice variant-7 mRNA detection in circulating tumor cells of men with metastatic castration-resistant prostate cancer treated with first-and second-line abiraterone and enzalutamide" Journal of Clinical Oncology. Apr. 6, 2017;35(19):2149-56.
Aradi et al. "DFTB+, a sparse matrix-based implementation of the DFTB method" The Journal of Physical Chemistry A. Jul. 5, 2007;111(26):5678-84.
Attard et al. "Selective inhibition of CYP17 with abiraterone acetate is highly active in the treatment of castration-resistant prostate cancer" Journal of clinical oncology. May 26, 2009;27(23):3742-8.
Baek et al. "Ligand-specific allosteric regulation of coactivator functions of androgen receptor in prostate cancer cells" Proceedings of the National Academy of Sciences of the United States of America. Feb. 28, 2006;103(9):3100-5.
Baniahmad A. "Inhibition of the androgen receptor by antiandrogens in spinobulbar muscle atrophy" Journal of Molecular Neuroscience. Mar. 1, 2016;58(3):343-7.
Berrevoets et al. "Effects of antiandrogens on transformation and transcription activation of wild-type and mutated (LNCaP) androgen receptors" The Journal of steroid biochemistry and molecular biology. Dec. 31, 1993;46(6):731-6.
Bohl et al. "Structural basis for antagonism and resistance of bicalutamide in prostate cancer" Proceedings of the National Academy of Sciences. Apr. 26, 2005;102(17):6201-6.
Bohl et al. "A ligand-based approach to identify quantitative structure-activity relationships for the androgen receptor" Journal of medicinal chemistry. Jul. 15, 2004;47(15):3765.
Bohl et al. "Structural basis for accommodation of nonsteroidal ligands in the androgen receptor" Journal of Biological Chemistry. Nov. 11, 2005;280(45):37747-54.
Bratenko et al. "Polyfunctional pyrazoles. 3.* Synthesis of 3-(3-aryl-4-formyl-1-pyrazolyl) propionic acids and their amides" Chemistry of Heterocyclic Compounds. Oct. 1, 2004;40(10):1279-82.
Bryce et al. "Androgen receptor splice variant 7 in castration-resistant prostate cancer: Clinical considerations" International Journal of Urology. Aug. 1, 2016;23(8):646-53.
Claessens et al. "Diverse roles of androgen receptor (AR) domains in AR-mediated signaling" Nuclear receptor signaling. Jun. 27, 2008;6:e008.
Clegg et al. "ARN-509: a novel antiandrogen for prostate cancer treatment" Cancer research. Mar. 15, 2012;72(6):1494-503.
Cochrane et al. "Role of the androgen receptor in breast cancer and preclinical analysis of enzalutamide" Breast Cancer Research. Feb. 2014;16(1):R7.

(56) References Cited

OTHER PUBLICATIONS

Dalvit et al. "Identification of compounds with binding affinity to proteins via magnetization transfer from bulk water" Journal of biomolecular NMR. Sep. 1, 2000;18(1):65-8.
Danquah et al. "Combination therapy of antiandrogen and XIAP inhibitor for treating advanced prostate cancer" Pharmaceutical research. Aug. 1, 2012;29(8):2079-91.
Database Caplus Chemical Abstracts Service; Database Accession No. 2005:14358, Abstract of WO 2005000794, published Jan. 6, 2005.
Davis et al. "Pharmacologic blockade and genetic deletion of androgen receptor attenuates aortic aneurysm formation" Journal of vascular surgery. Jun. 1, 2016;63(6):1602-12.
Dehm et al. "Alternatively spliced androgen receptor variants" Endocrine-related cancer. Oct. 1, 2011;18(5):R183-96.
Dehm et al. "Splicing of a novel androgen receptor exon generates a constitutively active androgen receptor that mediates prostate cancer therapy resistance" Cancer research. Jul. 1, 2008;68(13):5469-77.
De Bono et al. "Abiraterone and increased survival in metastatic prostate cancer" New England Journal of Medicine. May 26, 2011;364(21):1995-2005.
Dias et al. "NMR approaches in structure-based lead discovery: recent developments and new frontiers for targeting multi-protein complexes" Progress in biophysics and molecular biology. Nov. 1, 2014;116(2-3):101-12.
DUKE III, Charles B., et al. "Synthesis and biological studies of androgen receptor ligands: Towards mutation-resistant nonsteroidal antagonism." Abstracts of Papers of the American Chemical Society. vol. 240.
Elstner et al. "Self-consistent-charge density-functional tight-binding method for simulations of complex materials properties" Physical Review B. Sep. 15, 1998;58(11):7260.
Epps et al. "Determination of the affinity of drugs toward serum albumin by measurement of the quenching of the intrinsic tryptophan fluorescence of the protein" Journal of pharmacy and pharmacology. Jan. 1999;51(1):41-8.
Gal et al. "Efficient isothermal titration calorimetry technique identifies direct interaction of small molecule inhibitors with the target protein" Combinatorial chemistry & high throughput screening. Jan. 1, 2016;19(1):4-13.
Galbiati et al. "The anabolic/androgenic steroid nandrolone exacerbates gene expression modifications induced by mutant SOD1 in muscles of mice models of amyotrophic lateral sclerosis". Pharmacological research. Feb. 1, 2012;65(2):221-30.
Hara et al. "Novel mutations of androgen receptor: a possible mechanism of bicalutamide withdrawal syndrome" Cancer research. Jan. 1, 2003;63(1):149-53.
Hsieh et al. "Androgen receptor trinucleotide polymorphism in leiomyoma" Journal of assisted reproduction and genetics. Dec. 1, 2004;21(12):453-7.
Hu et al. "Distinct transcriptional programs mediated by the ligand-dependent full-length androgen receptor and its splice variants in castration-resistant prostate cancer" Cancer research. Jul. 15, 2012;72(14):3457-62.
Hwang et al. "Arylisothiocyanato selective androgen receptor modulators (SARMs) for prostate cancer" Bioorganic & medicinal chemistry. Oct. 1, 2006;14(19):6525-38.
International Search Report for PCT Application No. PCT/US2017/37063 dated Sep. 15, 2017.
Jin et al. "Synthesis and biological evaluation of 1-substituted-3(5)-(6-methylpyridin-2-yl)-4-(quinoline-6-yl)pyrazoles as transforming growth factor-β type 1 receptor kinase inhibitors". Bioorganic & Med. Chem. (2011) 19: 2633-2640.
Jin et al. "Synthesis and biological evaluation of 1-substituted-3(5)-(6-methylpyridin-2-yl)-4-(quinoxalin-6-yl)pyrazoles as transforming growth factor-β type 1 receptor kinase inhibitors". European J. of Med. Chem. (2011) 46: 3917-3925.
Joseph et al. "A clinically relevant androgen receptor mutation confers resistance to second-generation antiandrogens enzalutamide and ARN-509" Cancer discovery. Sep. 1, 2013;3(9):1020-9.
Kanda et al. "Androgen receptor signaling in hepatocellular carcinoma and pancreatic cancers" World Journal of Gastroenterology: WJG. Jul. 28, 2014;20(28):9229.
Kawahara et al. "ELK1 is up-regulated by androgen in bladder cancer cells and promotes tumor progression" Oncotarget. Oct. 6, 2015;6(30):29860.
Kim et al. "Ribosomal proteins as unrevealed caretakers for cellular stress and genomic instability" Oncotarget. Feb. 1, 2014;5(4):860-71.
Klotz L. "Maximal androgen blockade for advanced prostate cancer" Best Practice & Research Clinical Endocrinology & Metabolism. Apr. 30, 2008;22(2):331-40.
Lieberman et al., editors. Pharmaceutical Dosage Forms: Tablets: 1980. Marcel Dekker; 1980.
Sartor et al. "Androgen receptor variant-7: an important predictive biomarker in castrate resistant prostate cancer" Asian journal of andriology. May 2015;17(3):439.
European Search Report for EP 17811167 dated Feb. 28, 2020.
Japanese Office Action for 2018-564840 dated Jun. 23, 2020.
International Search Report for PCT/US20/35015 dated.
Michael L Mohler et al: "Androgen receptor antagonists: a patent review (2008-2011)", Expert Opinion on Therapeutic Patents, vol. 22, No. 5, May 1, 2012.
Pubchem. CID 3145286.09 Aug. 2005, pp. 1-12. Retrieved from the Internet <URL: 1-6 https:llpubchem.ncbl.nlm.nih.gov/compound/3145286>; p. 2.
Colin, et al. "New Access to Fluorinated Ketoglycolic Acid Derivatives from Trifluoropyruvamides." Tetrahedron Letters 45.29 (2004): 5611-5613.
Schragl et al. "Novel Pathway for the Synthesis of Arylpropionamide-Derived Selective Androgen Receptor Modulator (Sarm) Metabolites of Andarine And Ostarine." Tetrahedron Letters 54.18 (2013): 2239-2242.
Bassetto, et al., "Design and synthesis of novel bicalutamide and enzalutamide derivatives as antiproliferative agents for the treatment of prostate cancer", European Journal of Medicinal Chemistry, 2016, vol. 118, pp. 230-243.
CAS Registry No. 945553-38-8; STN Entry Date Aug. 24, 2007.
CAS Registry No. 1349723-51-8; STN Entry Date Dec. 6, 2011.
CAS Registry No. 1839720-91-0; STN Entry date Jan. 1, 2016.
CAS Registry No. 1919463-97-0; STN Entry date May 27, 2016.
CAS Registry No. 1928217-46-2; STN Entry date Jun. 9, 2016.
CAS Registry No. 55734-18-4; STN Entry date Nov. 16, 1984.
CAS Registry No. 1526624-00-9; STN Entry date Jan. 21, 2014.
CAS Registry No. 1480139-15-8; STN Entry date Nov. 24, 2013.
Hebenbrock, K.-F., "Preparation and reaction of 1-aryl-3-hydroxy-3-methyl-2,5-pyrrolidinediones", Justus Liebigs Annalen der Chemie, 1978, vol. 2, pp. 320-336 (Abstract).
Morris, et al., "Non-Steroidal Antiandrogens. Design of Novel Compounds Based on an Infrared Study of the Dominant Conformation and Hydrogen-Bonding Properties of a Series of Anilide Antiandrogens" Journal of Medicinal Chemistry, 1991, vol. 34, No. 1, pp. 447-455.
Tabolpgullari et al., Synthesis and Anticonvulsant Activity of Some Alkanamide Derivatives. Arzneimittelforschung, 2010, vol. 60, No. 10, pp. 593-598 (Abstract).
Tucker, et al., "Nonsteroidal antiandrogens. Synthesis and structure-activity relationships of 3-substituted derivatives of 2-hydroxypropionanilides", Journal of Medicinal Chemistry, 1988, vol. 31, No. 5, pp. 954-959.
Seligson, et al. "Development of fluridil, a topical suppressor of the androgen receptor in androgenetic alopecia." Drug development research 59.3 (2003): 292-306.

* cited by examiner

Figure 6A: Transactivation of 1006
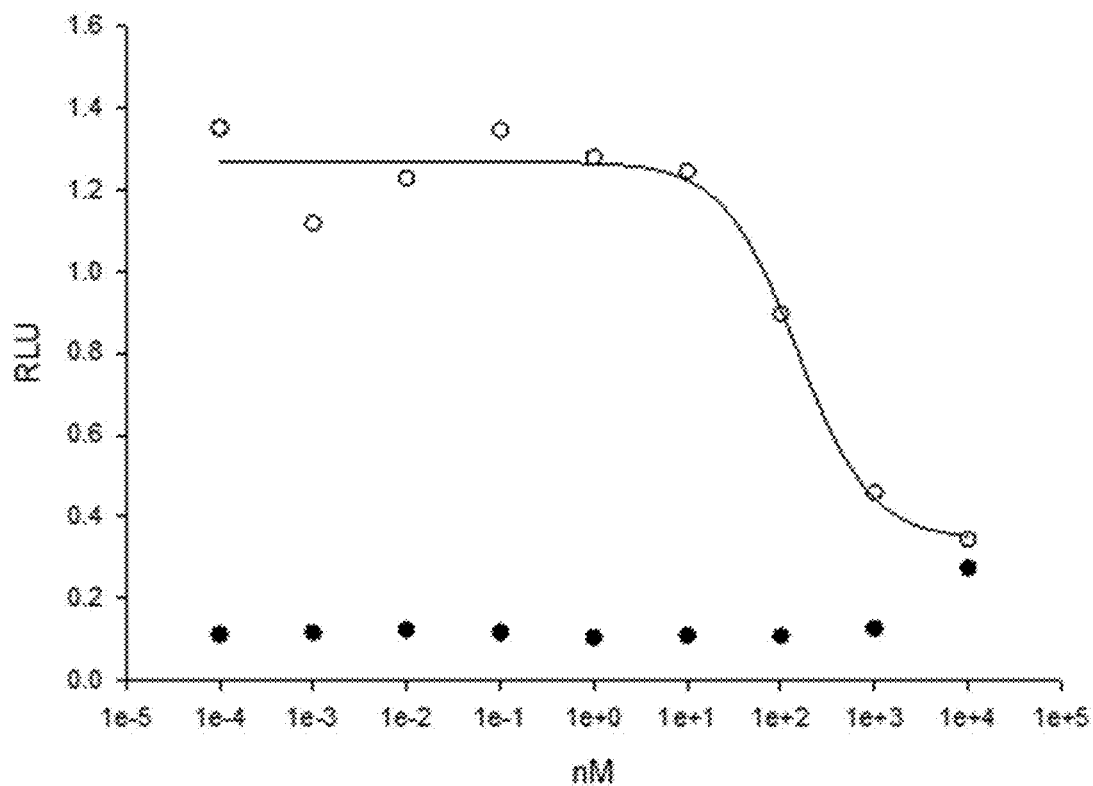
Figure 6B:
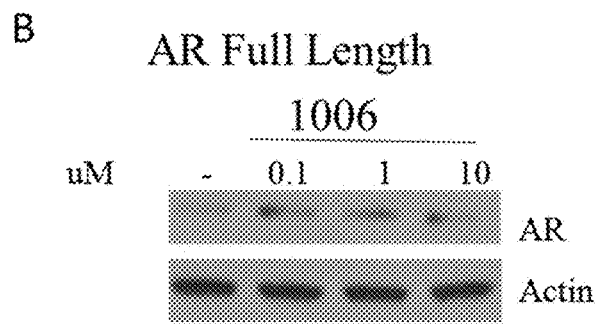

Figure 7:
AD1 Cells AR Full Length
Compound 17
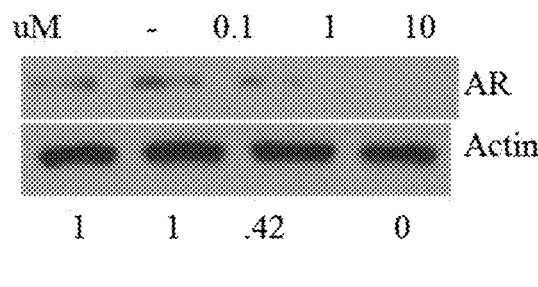
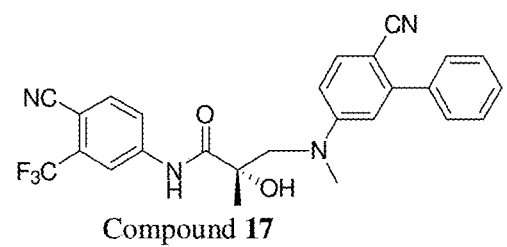
Compound 17

Figure 14: Phase I and Phase I&II Metabolism of 1002 in Mouse Liver Microsomes (MLM)

Phase I (MLM)

| Time | Anal/IS | % remaining |
|---|---|---|
| 0 | 0.242 | 100% |
| 5 | 0.245 | 101% |
| 10 | 0.216 | 90% |
| 30 | 0.139 | 58% |
| 60 | 0.079 | 33% |

Half-life (min) 36.53
Clearance     1.89

Phase II (MLM)

| Time | Anal/IS | % remaining |
|---|---|---|
| 0 | 0.221 | 100% |
| 5 | 0.195 | 88% |
| 10 | 0.240 | 109% |
| 30 | 0.176 | 80% |
| 60 | 0.125 | 57% |

Half-life (min) 77.96
Clearance     0.88

Figure 15A: Phase I Metabolism of 1002 in MLM (single experiment).
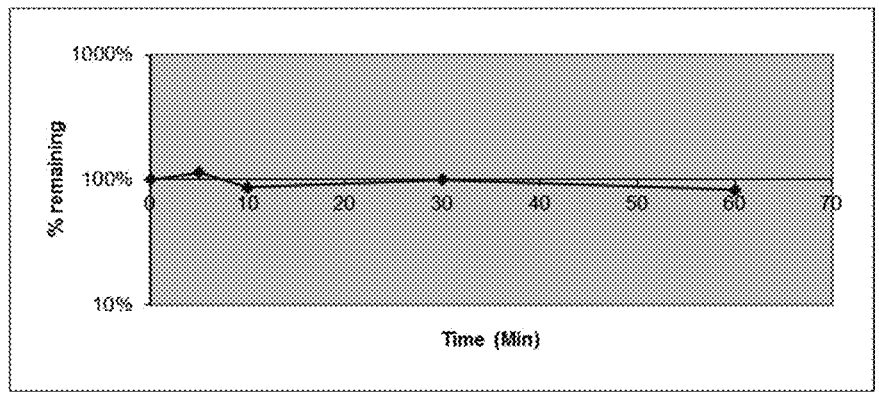
| Time | Anal/IS | % remaining |
|---|---|---|
| 0 | 1.291 | 100% |
| 5 | 1.484 | 115% |
| 10 | 1.126 | 87% |
| 30 | 1.294 | 100% |
| 60 | 1.079 | 84% |
Figure 15B: Phase I & II Metabolism of 1002 in MLM (Single Experiment).
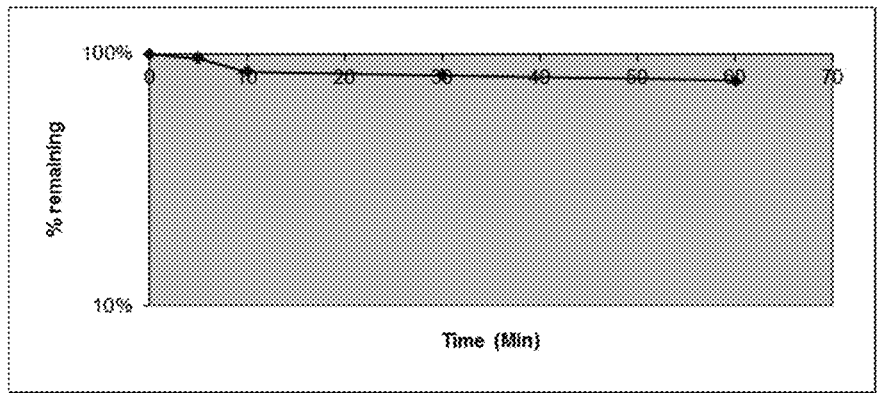
| Time | Anal/IS | % remaining |
|---|---|---|
| 0 | 1.332 | 100% |
| 5 | 1.277 | 96% |
| 10 | 1.132 | 85% |
| 30 | 1.094 | 82% |
| 60 | 1.045 | 78% |

Figure 16A: Phase I Metabolism of 1002 in Human Liver Microsomes (HLM) (single experiment)
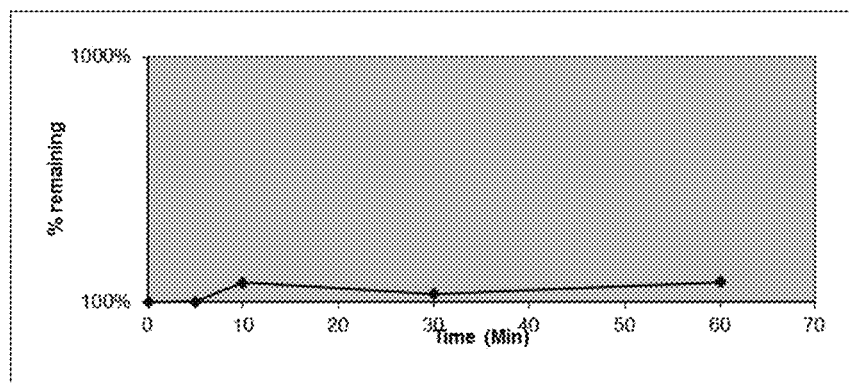
| Time | Anal/IS | % remaining |
|---|---|---|
| 0 | 2.074 | 100% |
| 5 | 2.089 | 101% |
| 10 | 2.488 | 120% |
| 30 | 2.238 | 108% |
| 60 | 2.510 | 121% |
Figure 16B: Phase I & II Metabolism of 1002 in Human Liver Microsomes (HLM) (single experiment)
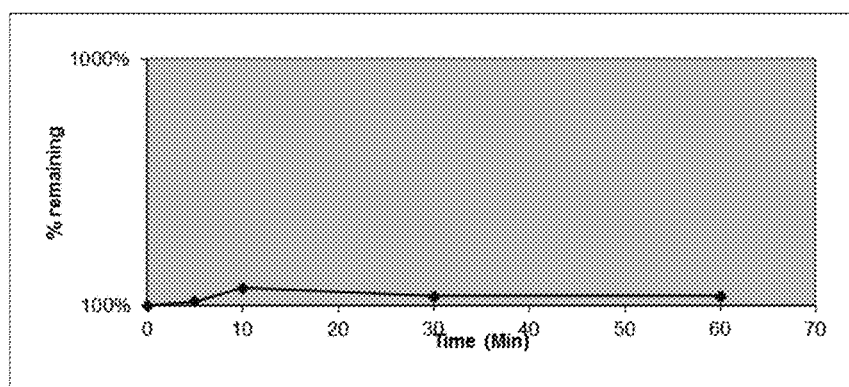
| Time | Anal/IS | % remaining |
|---|---|---|
| 0 | 2.256 | 100% |
| 5 | 2.349 | 104% |
| 10 | 2.664 | 118% |
| 30 | 2.473 | 110% |
| 60 | 2.467 | 109% |

Figure 17: Phase I Metabolism of 1001 in MLM.
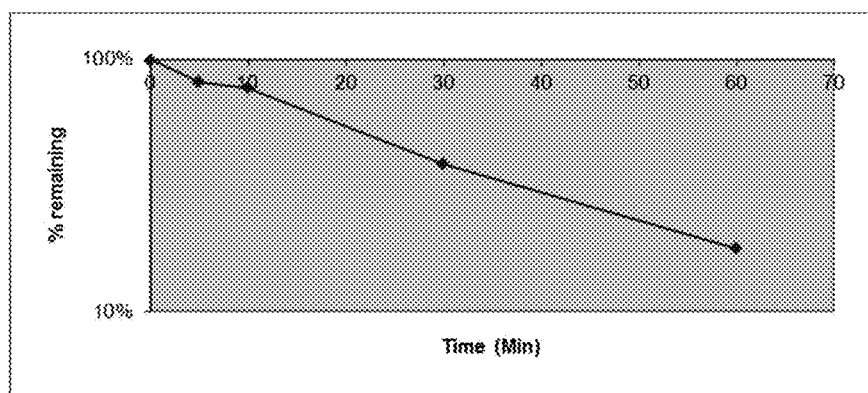
| Time | Anal/IS | % remaining |
|------|---------|-------------|
| 0    | 4.543   | 100%        |
| 5    | 3.694   | 81%         |
| 10   | 3.500   | 77%         |
| 30   | 1.751   | 39%         |
| 60   | 0.810   | 18%         |

Figure 20A: Full Length AR Degradation Assays
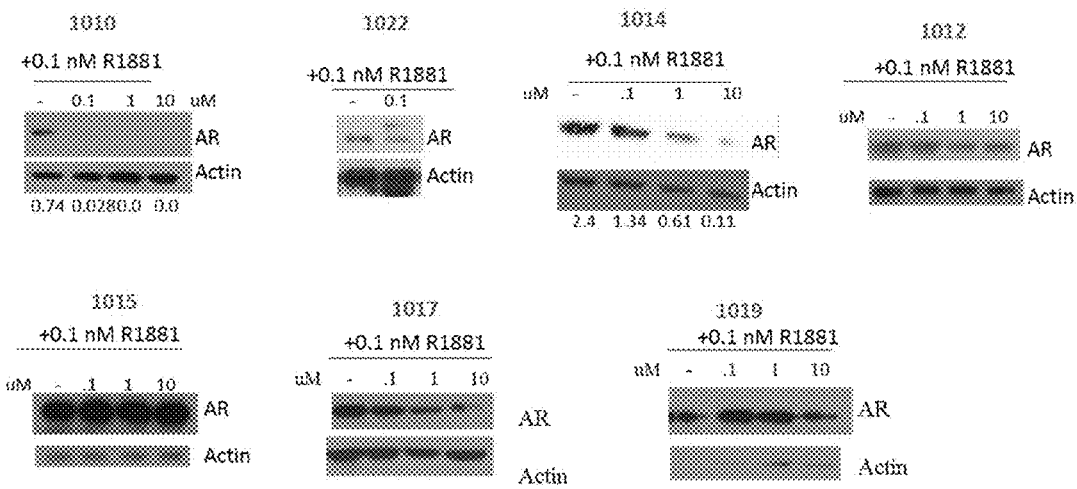
Figure 20B: Splice Variant AR Degradation Assays
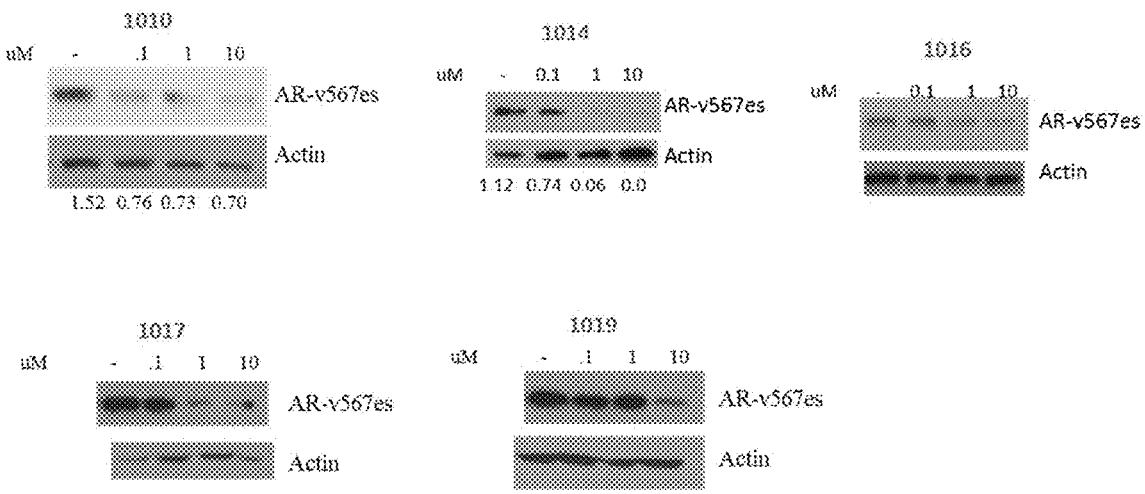

Figure 21B:
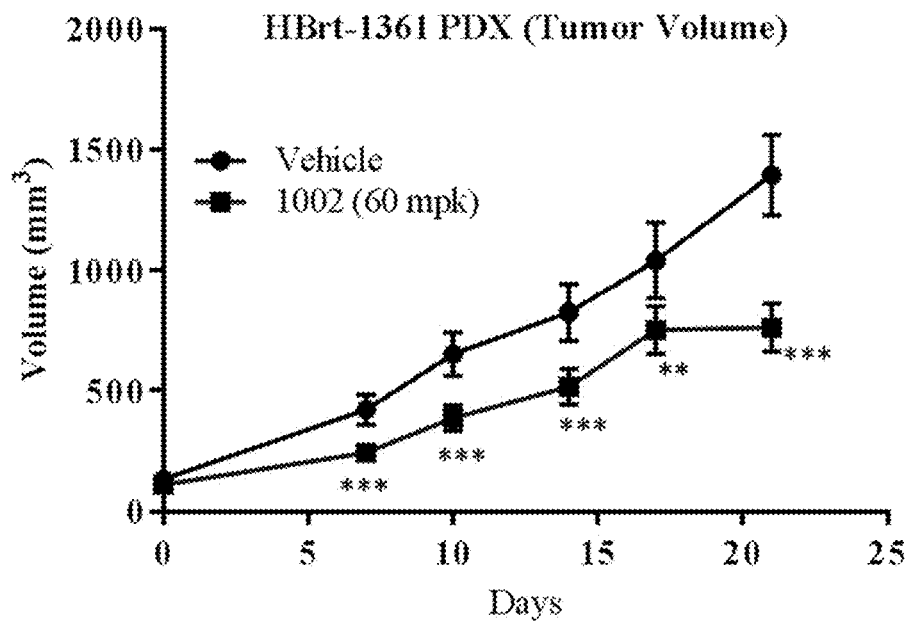
** p<0.01
*** p<0.001
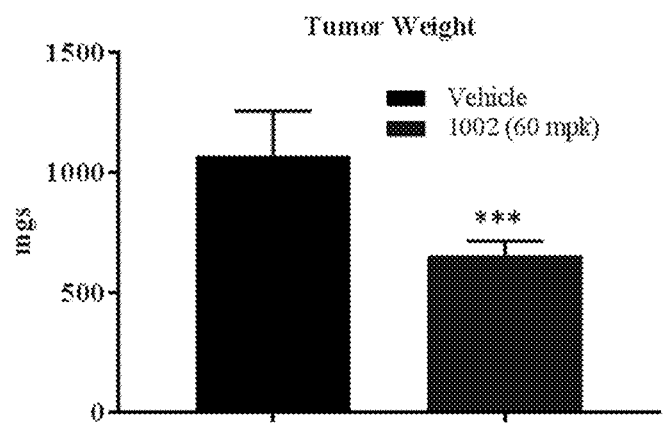

Figure 24:
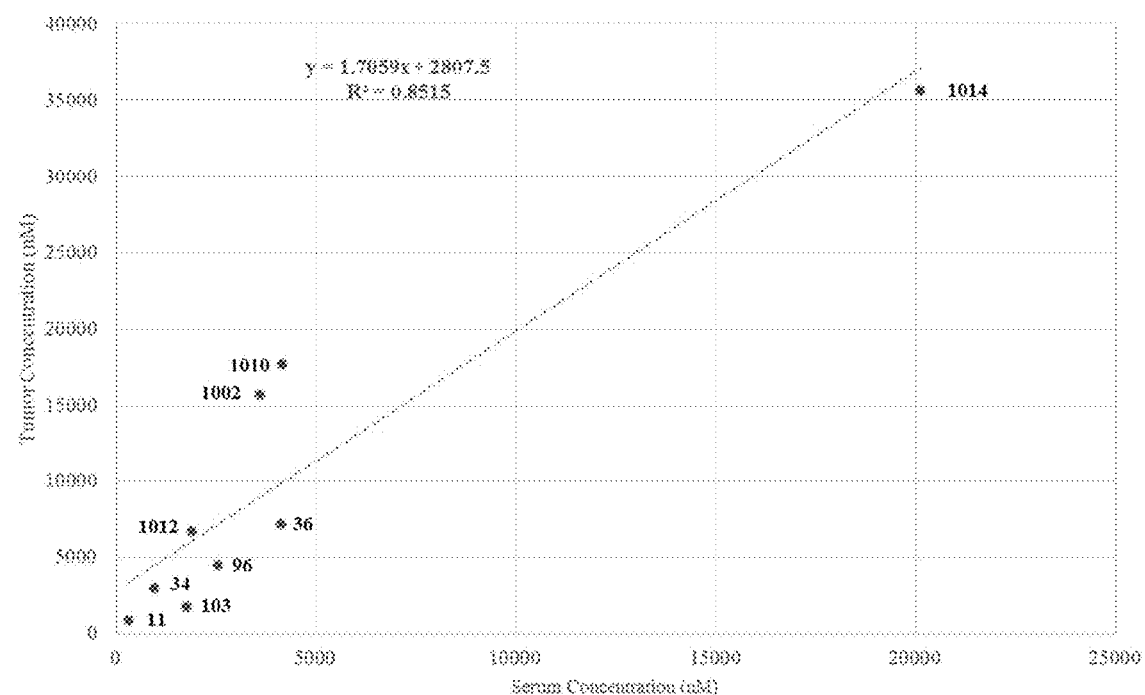
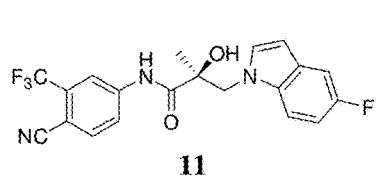
11
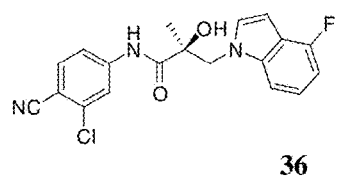
36
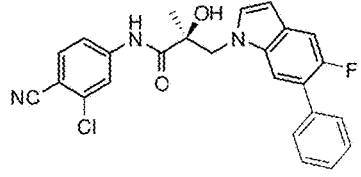
34
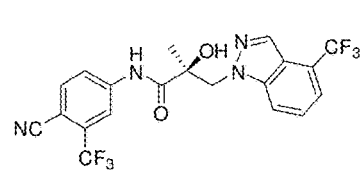
96
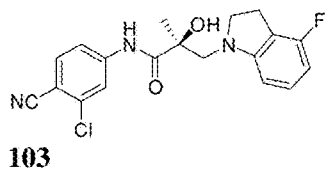
103

Figure 25: Hershberger Assay
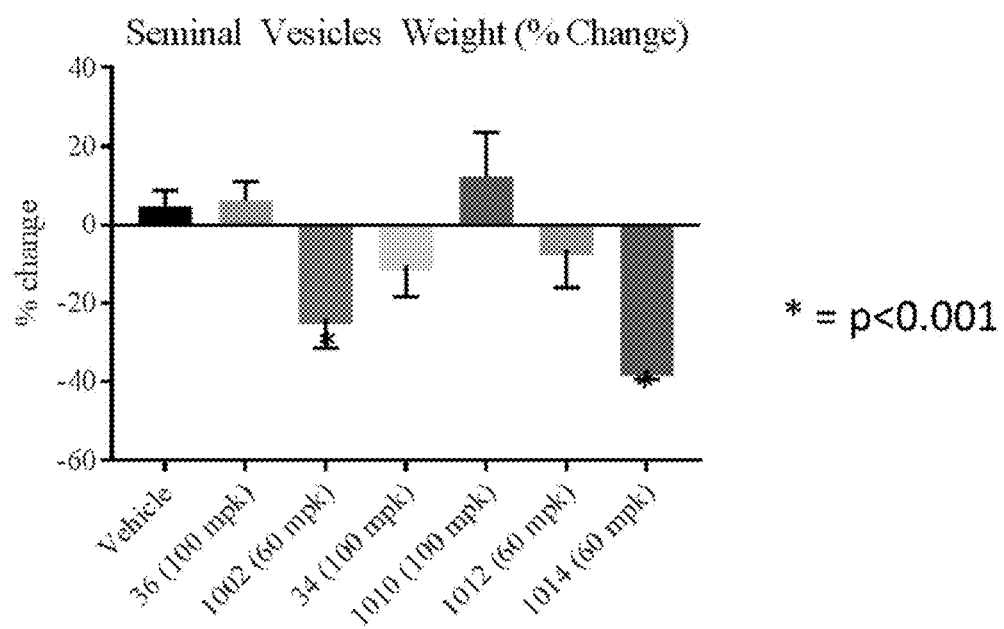
* = p<0.001
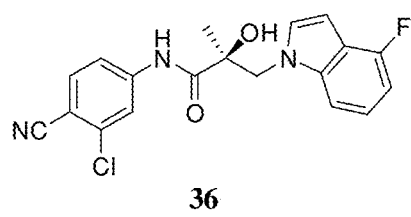
36
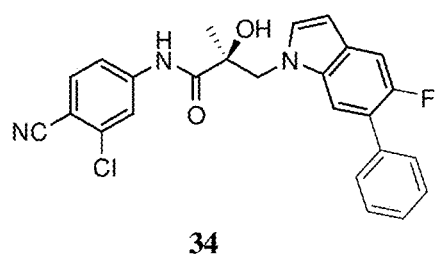
34

Experiment 1 (21 day duration) is the top row and Experiment 2 (14 day duration) is the bottom row:

36

Figure 28A: Full Length AR Degradation Assays
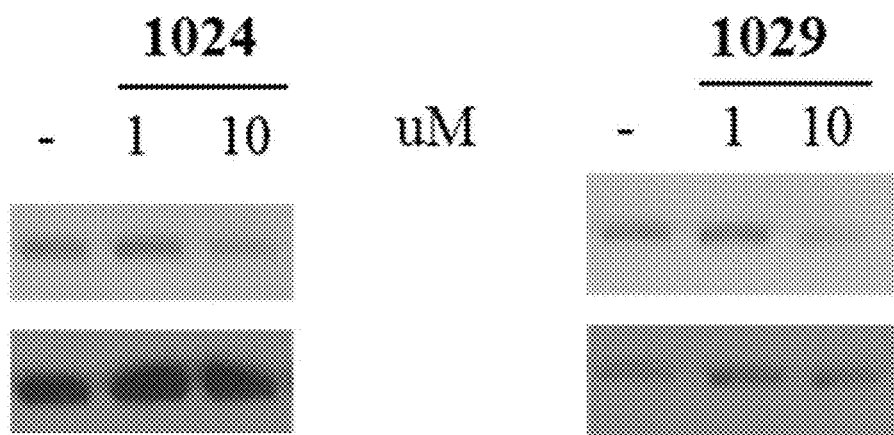
Figure 28B: Splice Variant (22RV1 cells) AR Degradation Assays
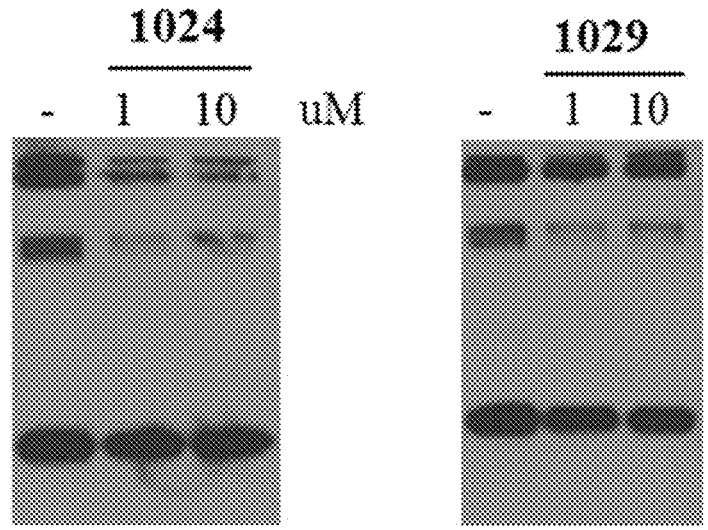

Figure 28C: Full Length AR Degradation Assays
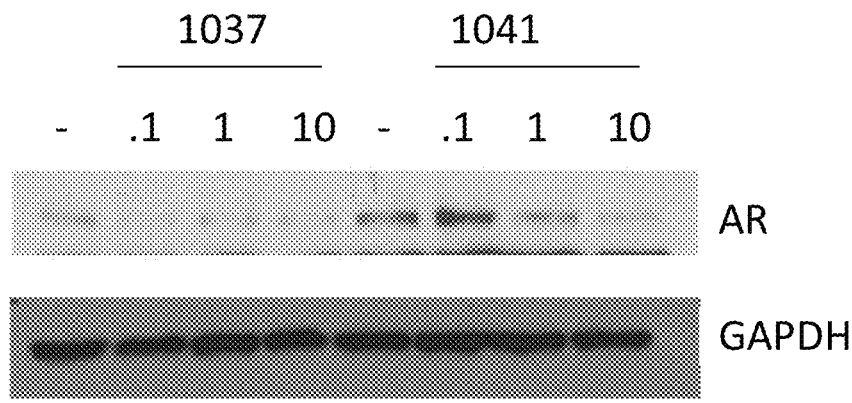
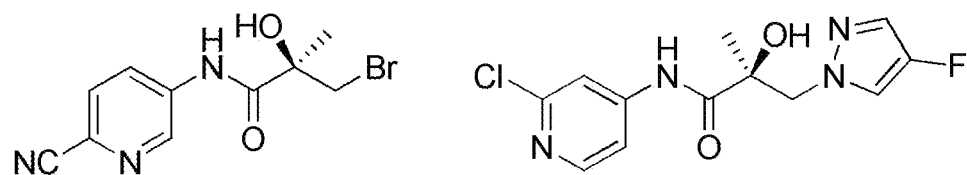
Figure 28D: Full Length AR Degradation Assays
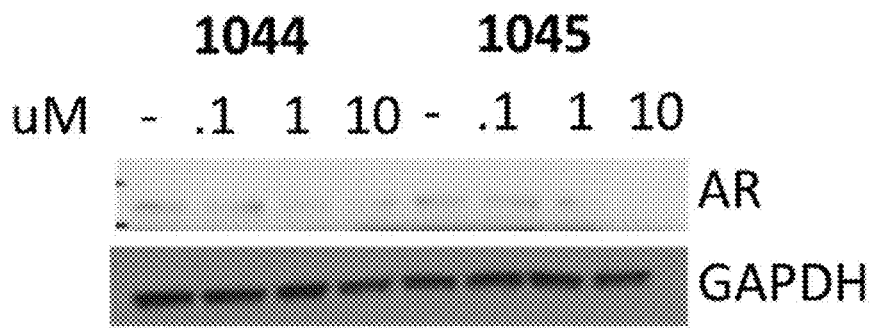
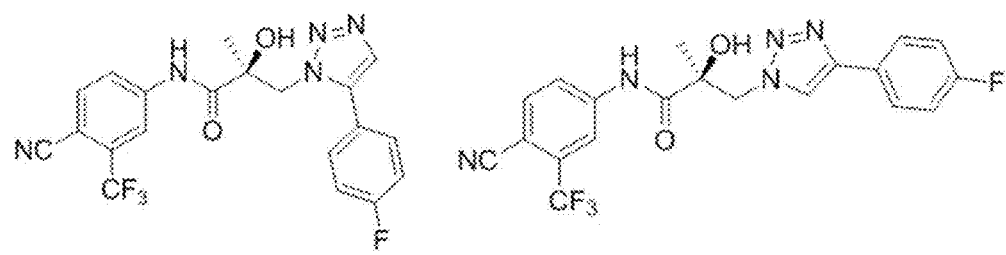

Compound 11

Compound 1002

Compound 1002

Figure 35B: VCaP CRPC Individual Animal Data:
Vehicle (solid lines)
Enzalutamide (larger dashes)
1002 (smaller dashed lines)
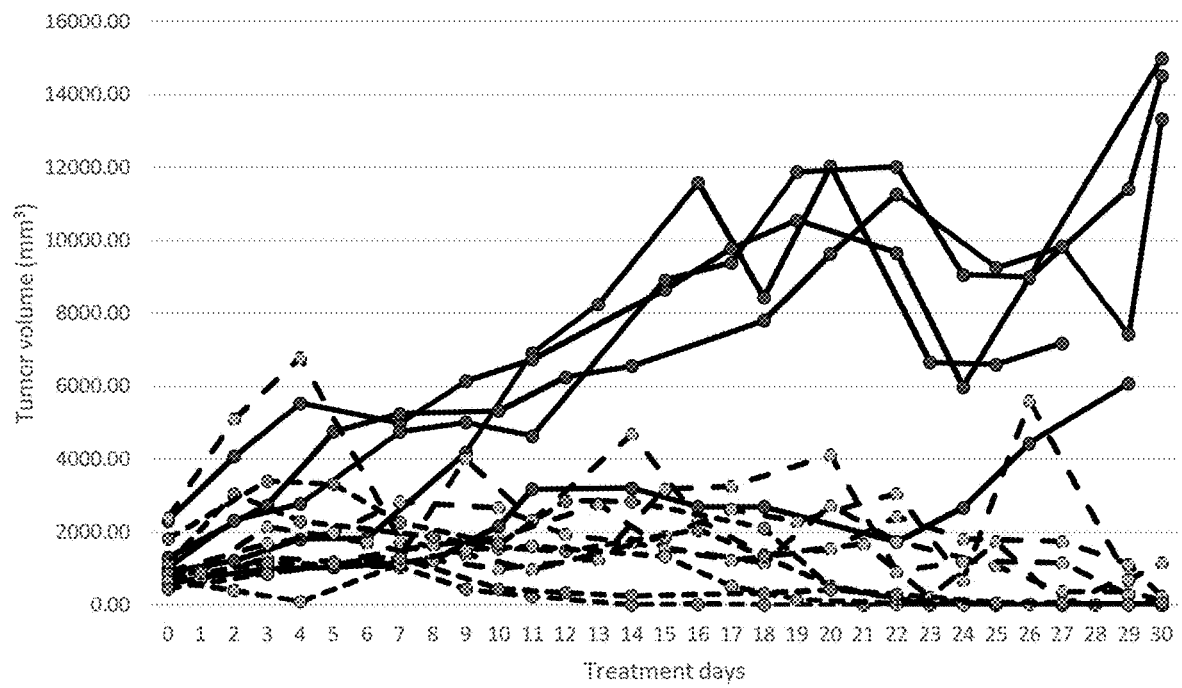

Figure 38
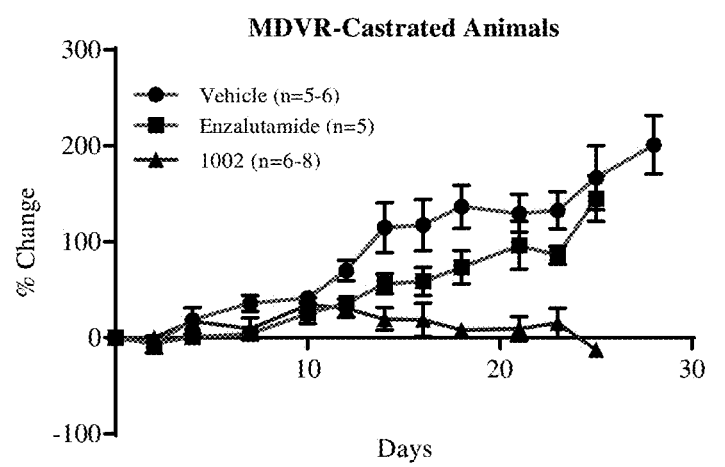
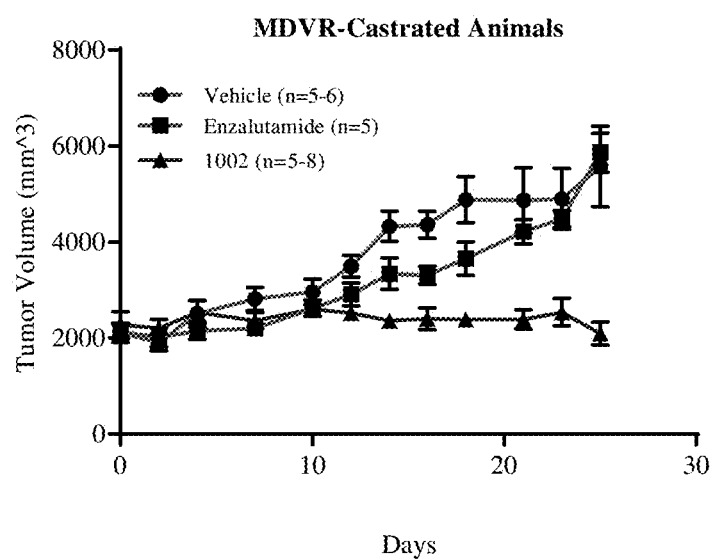

| MLM | | HLM | |
|---|---|---|---|
| $T_{1/2}$ | $Cl_{int}$ | $T_{1/2}$ | $Cl_{int}$ |
| 12.11 | 57.25 | 8.29 | 83.61 |

11

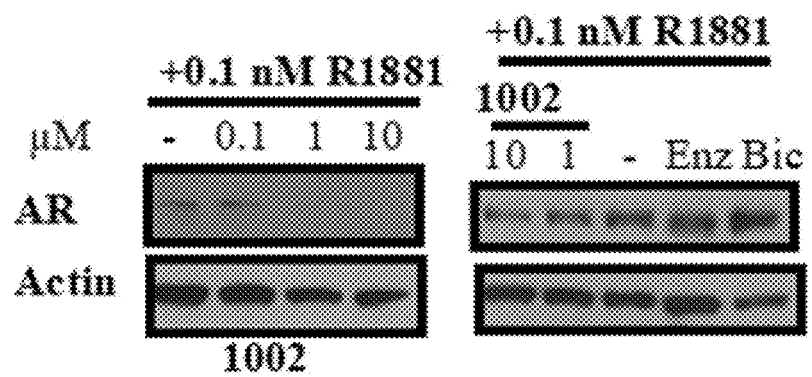
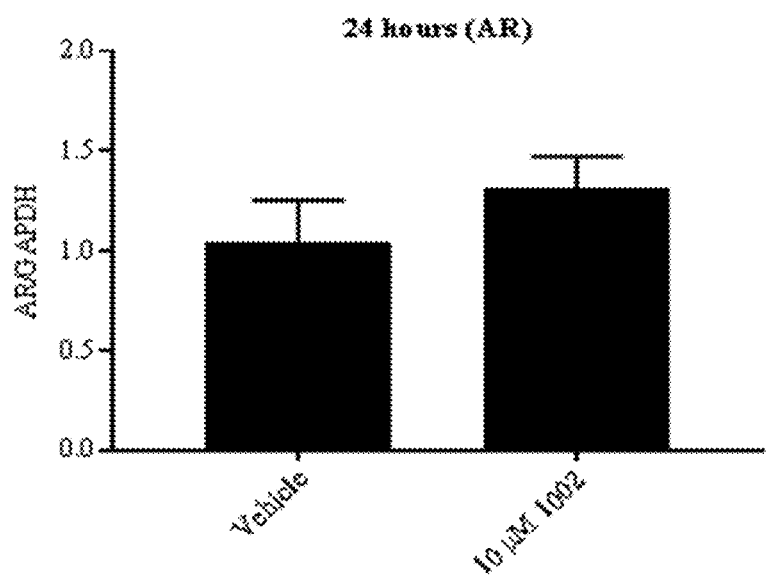
FIGURE 41A
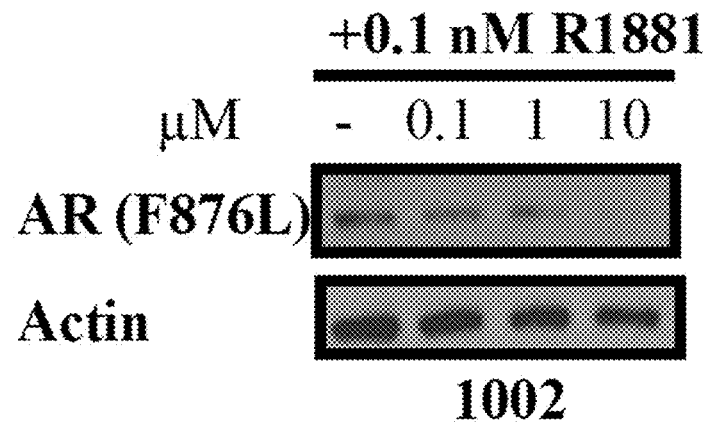
FIGURE 41B

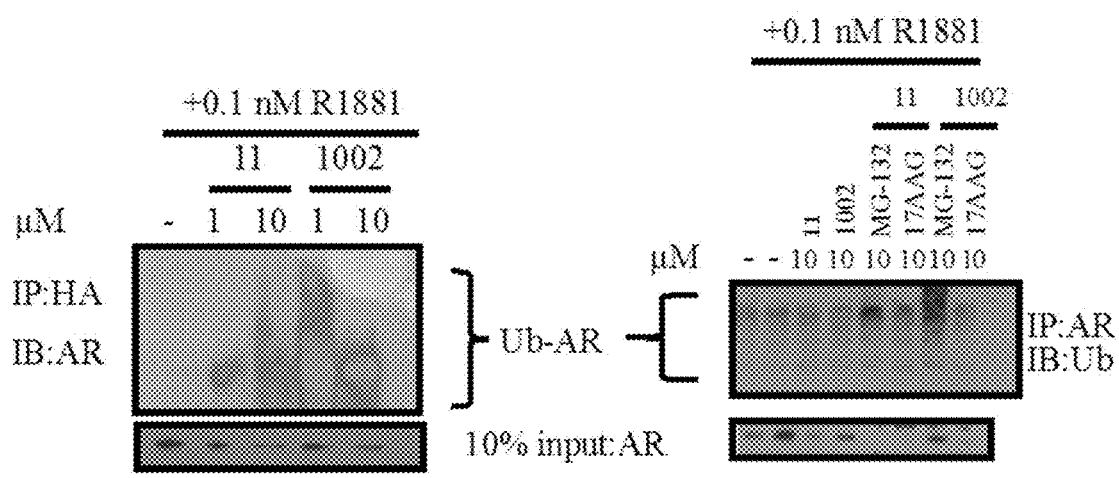
FIGURE 41F
FIGURE 41G
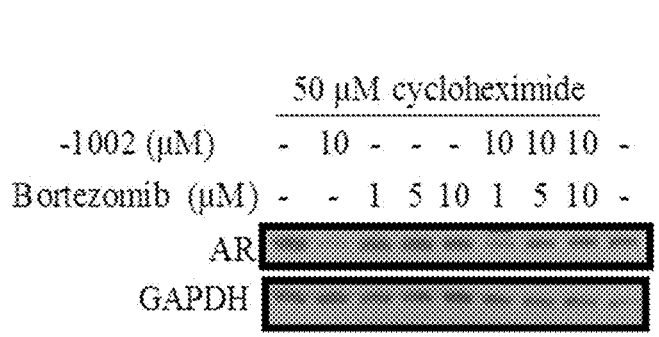
FIGURE 41H
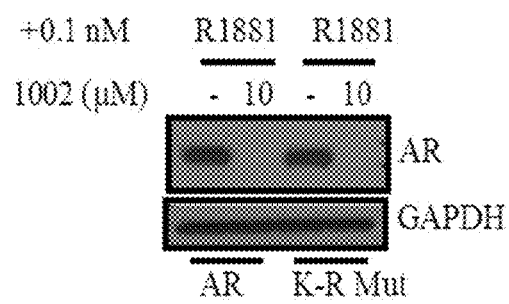
FIGURE 41I

| Amino Acid | Drug 1002 binding (eV) |
|---|---|
| Glycine | 0.235 |
| Alanine | 0.255 |
| Leucine | 0.363 |
| Valine | 0.238 |
| Histidine | 0.233 |
| Proline | 0.256 |
| Tyrosine | 0.418 |
| Phenylalanine | 0.408 |
| Serine | 0.435 |
| Cystine | 0.318 |

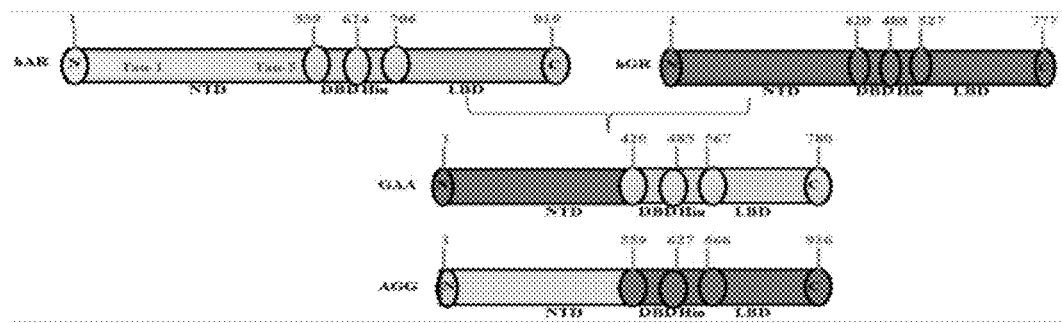
FIGURE 44A
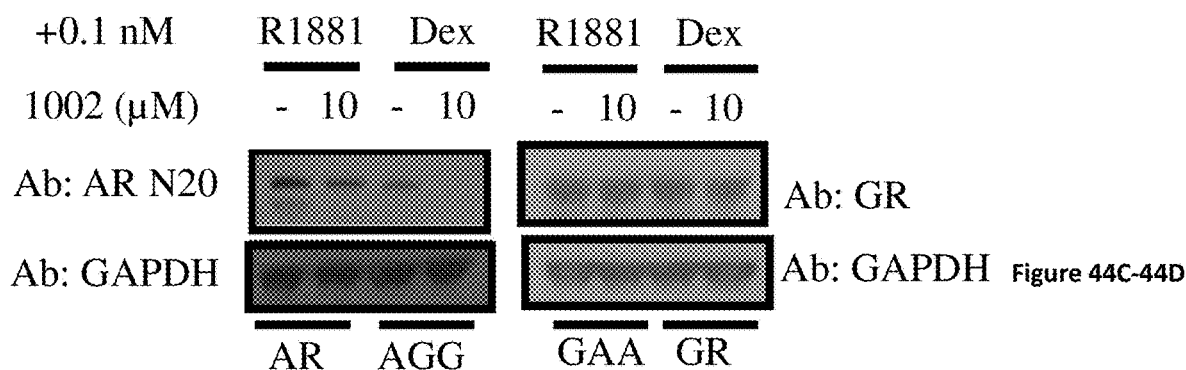
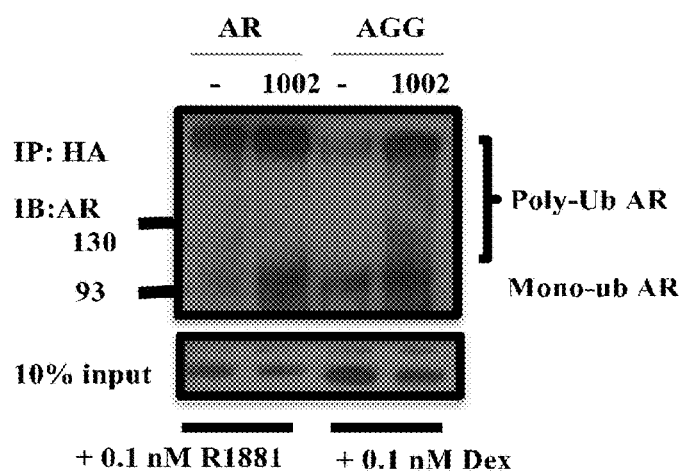
FIGURE 44B

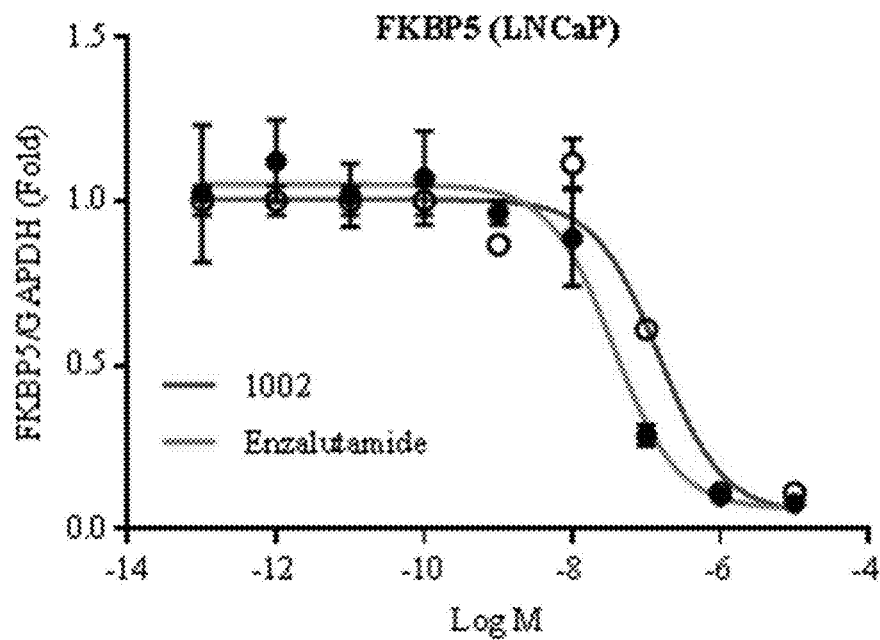
Figure 46A(ii)
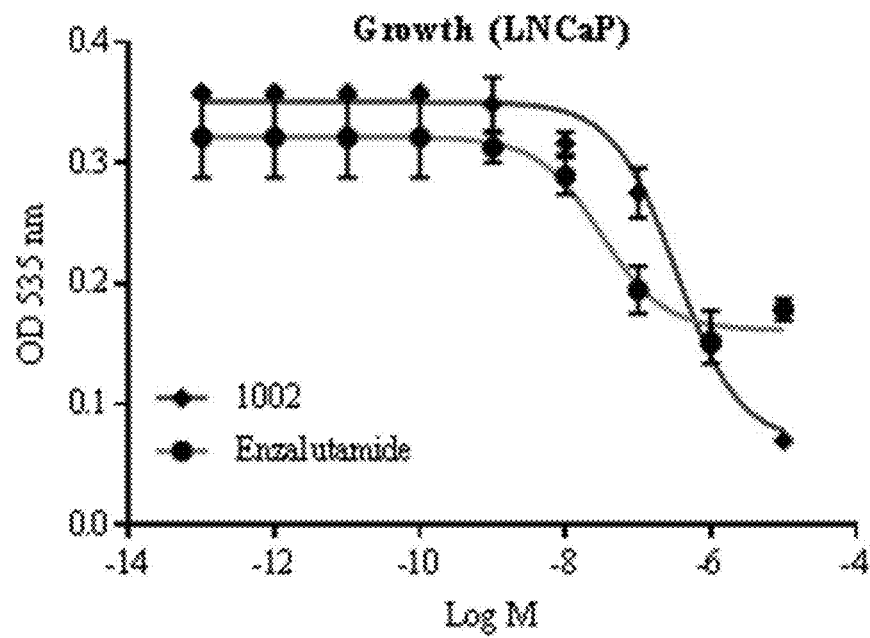
Figure 46A(iii)

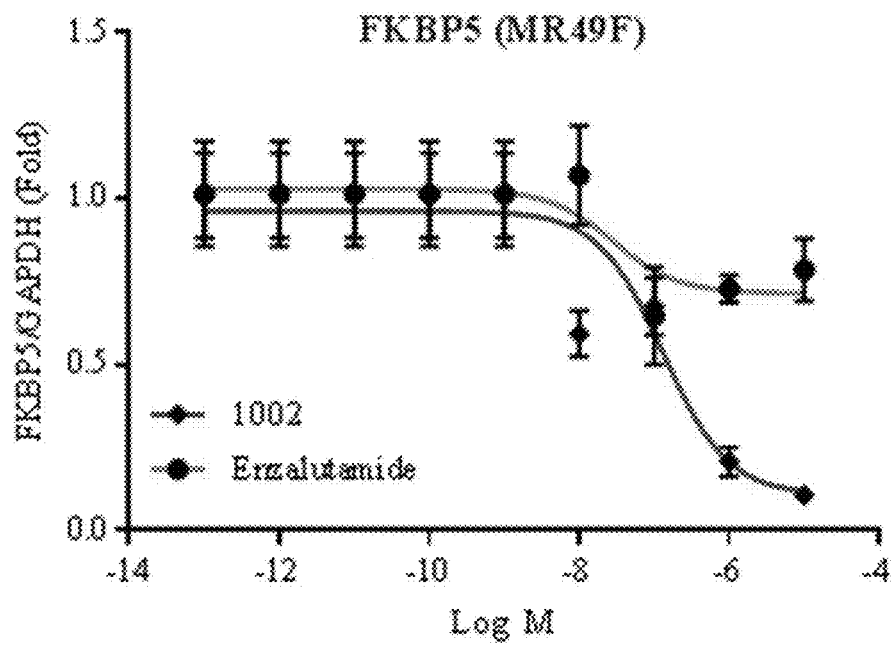
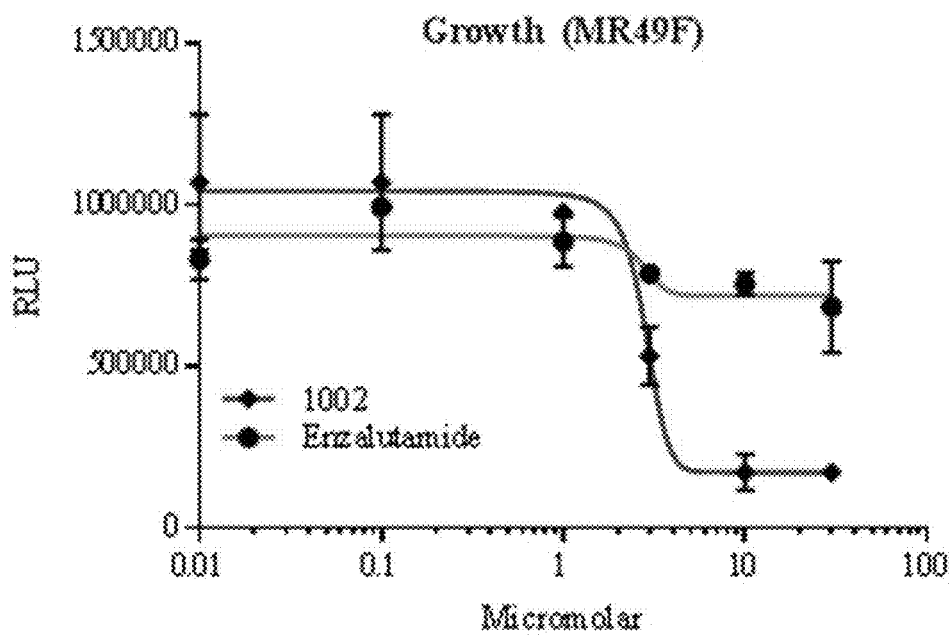
Figure 46B

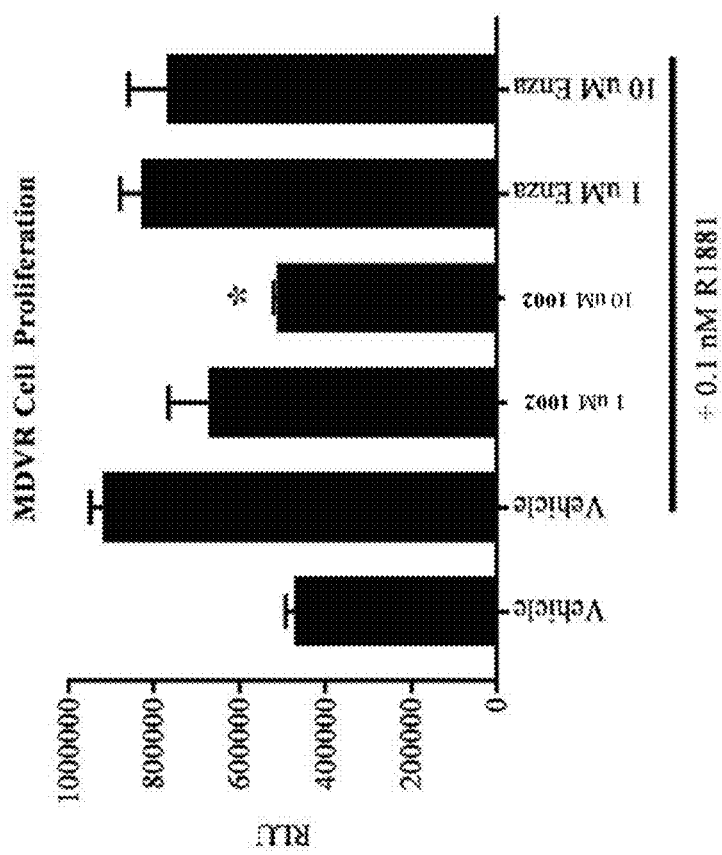
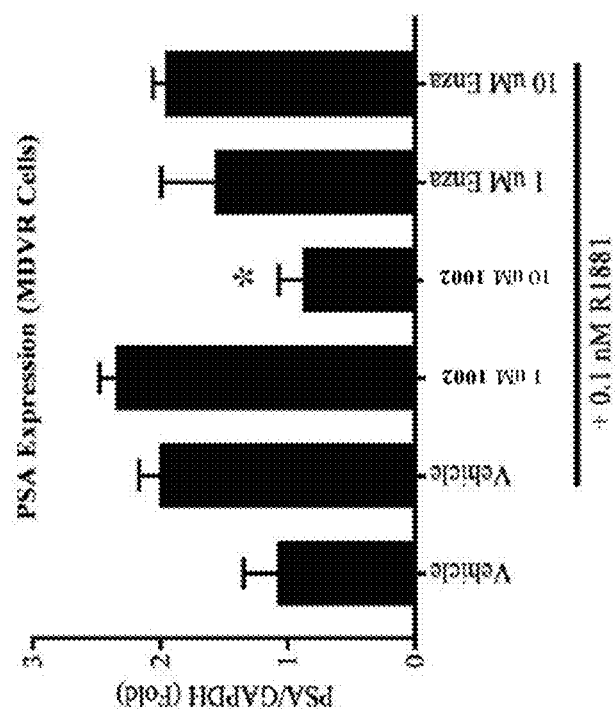
FIGURE 47B

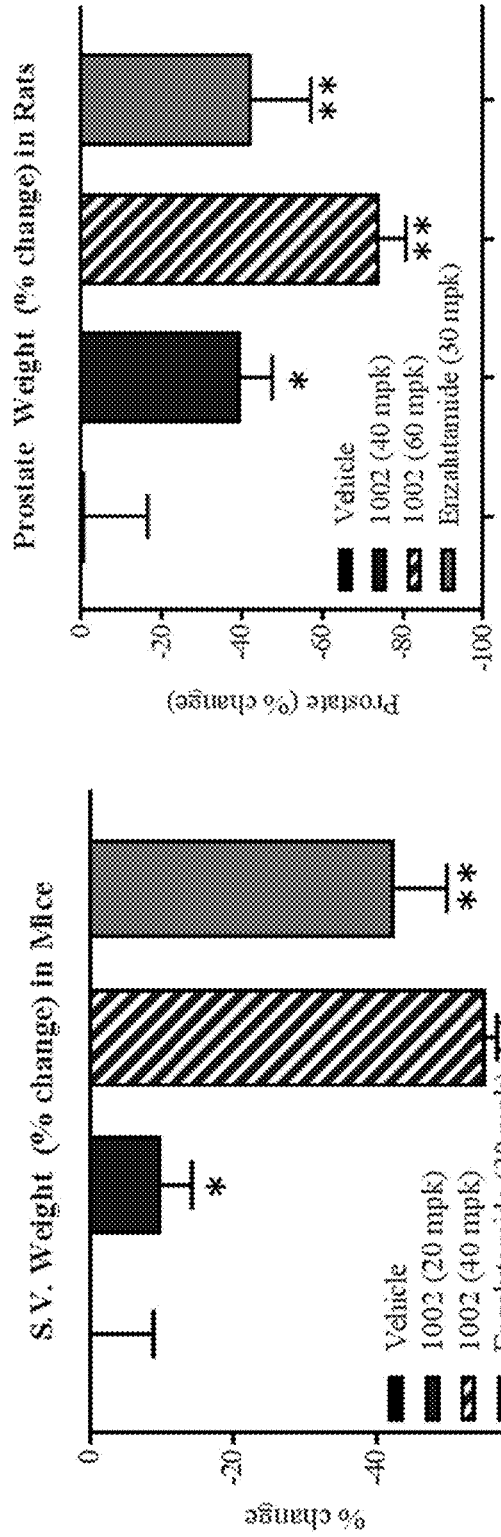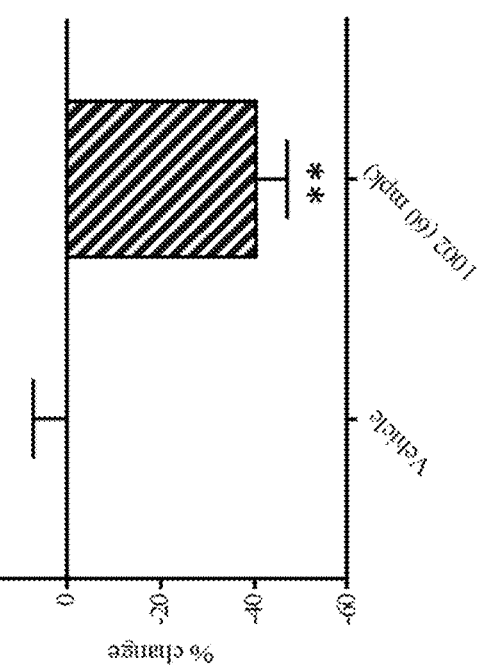
FIGURE 48C

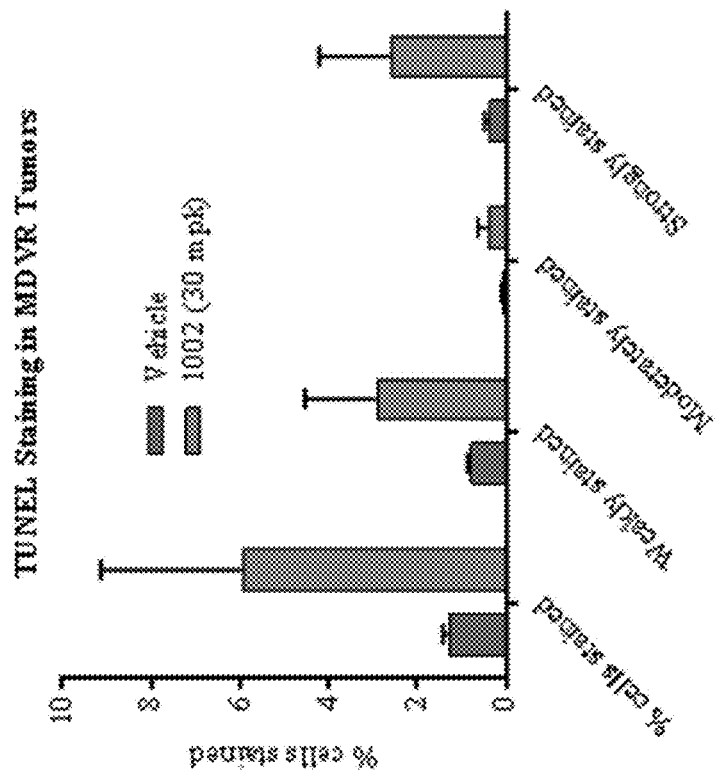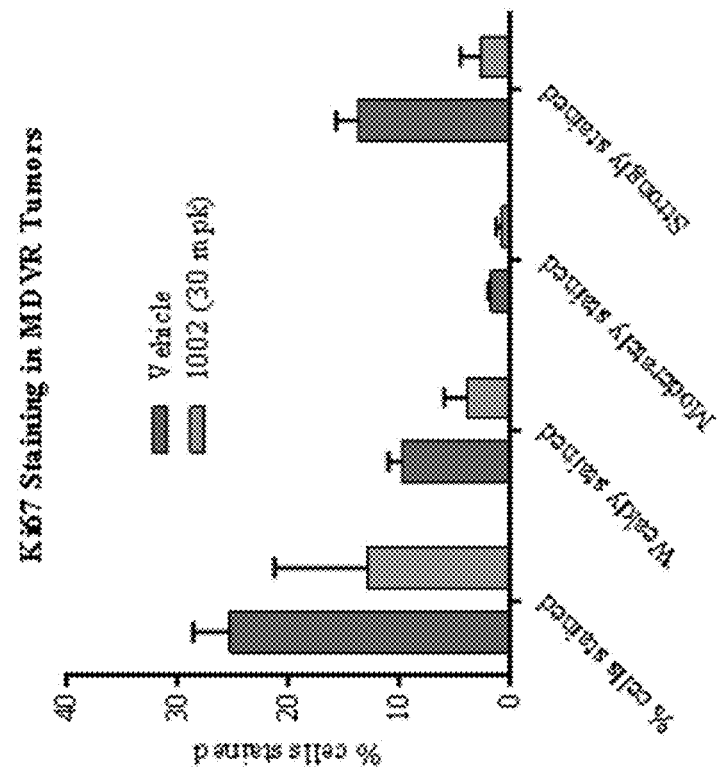
FIGURE 48E

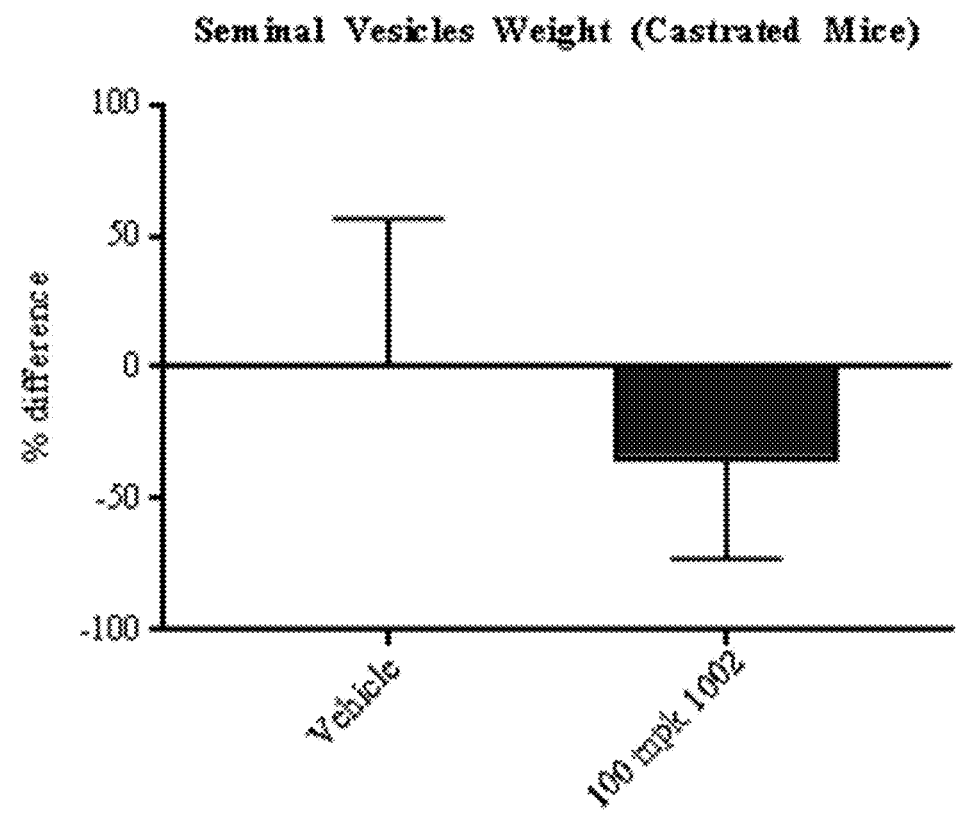
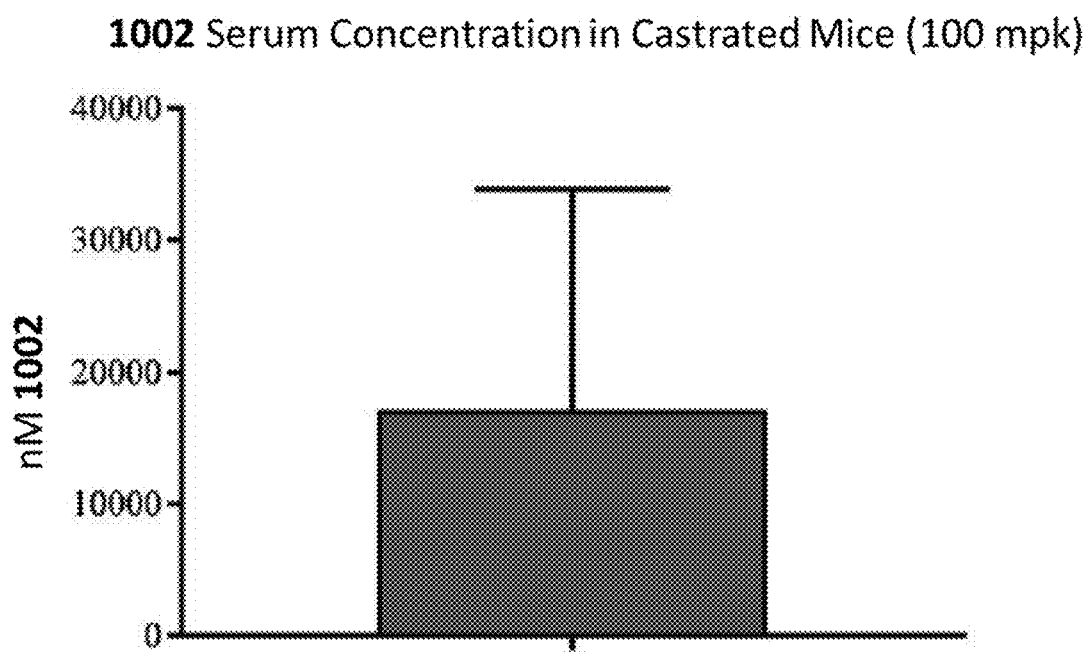
FIGURE 48F

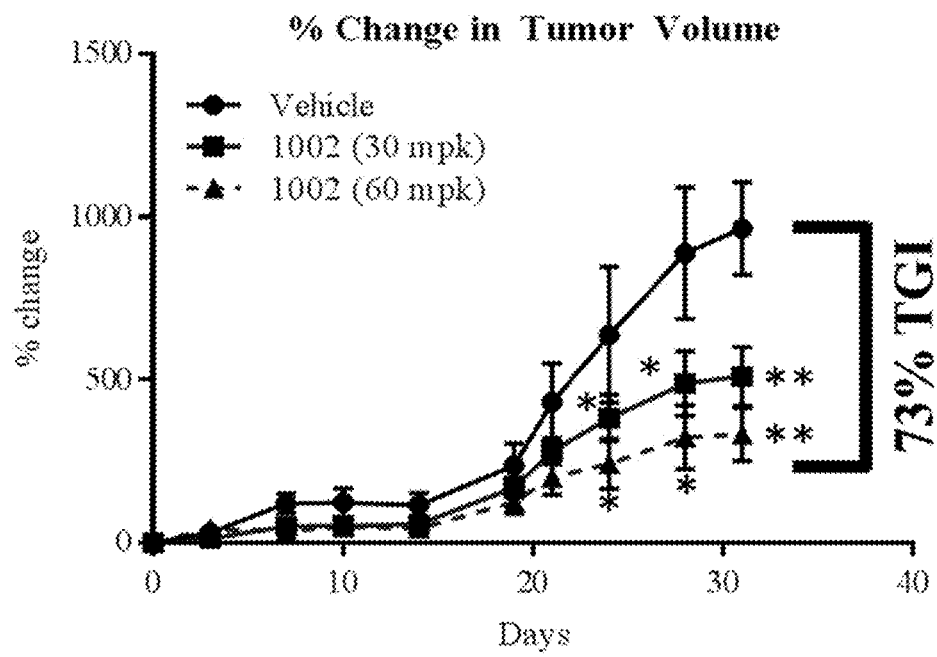
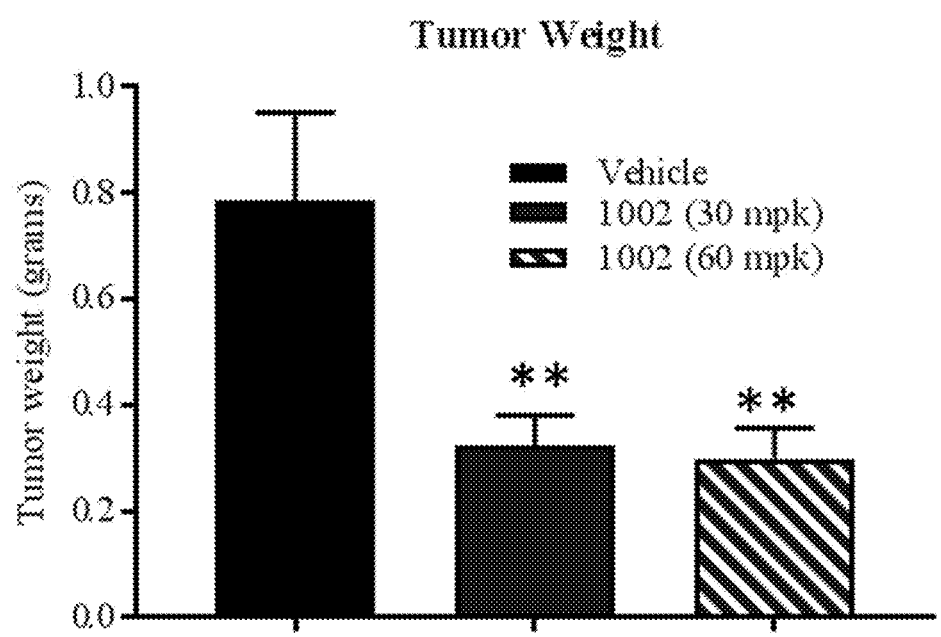
FIGURE 49A

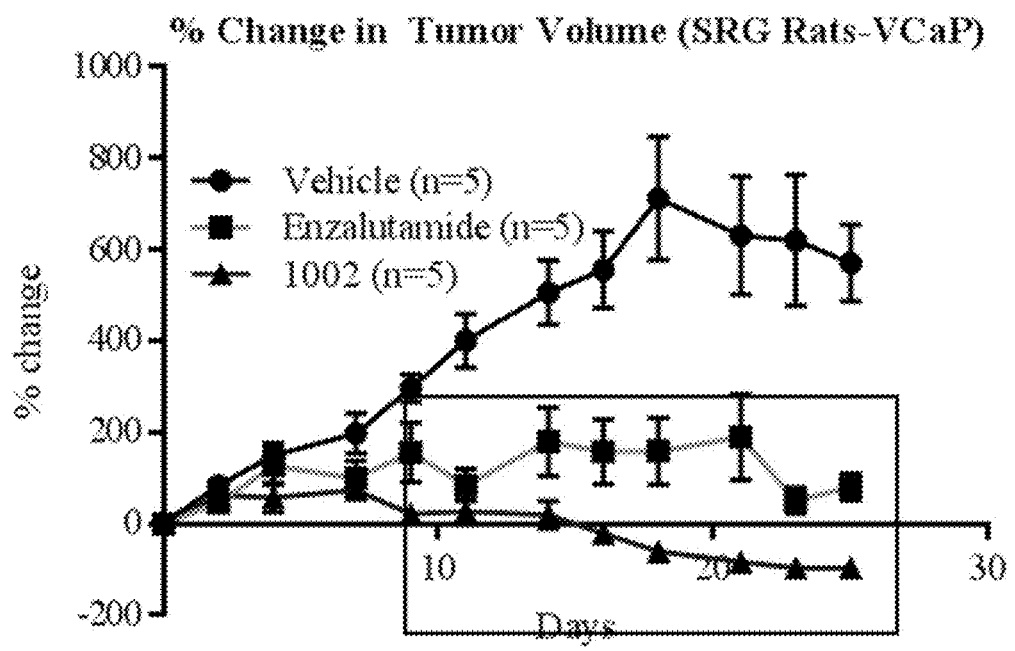
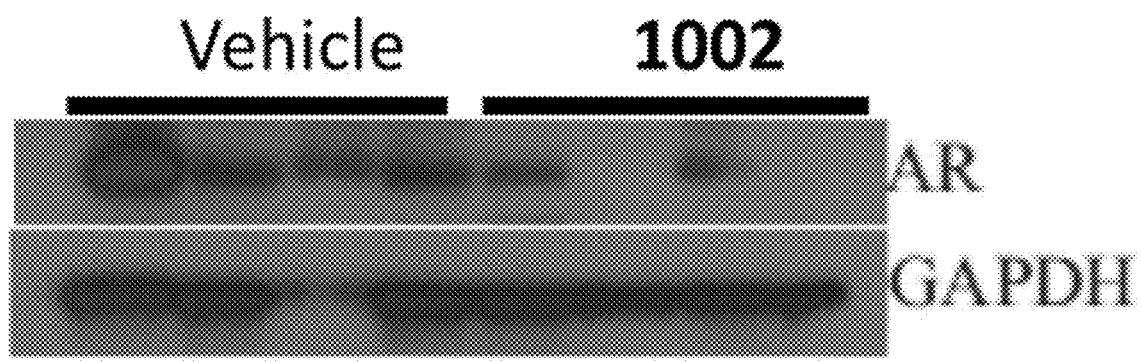
FIGURE 49B

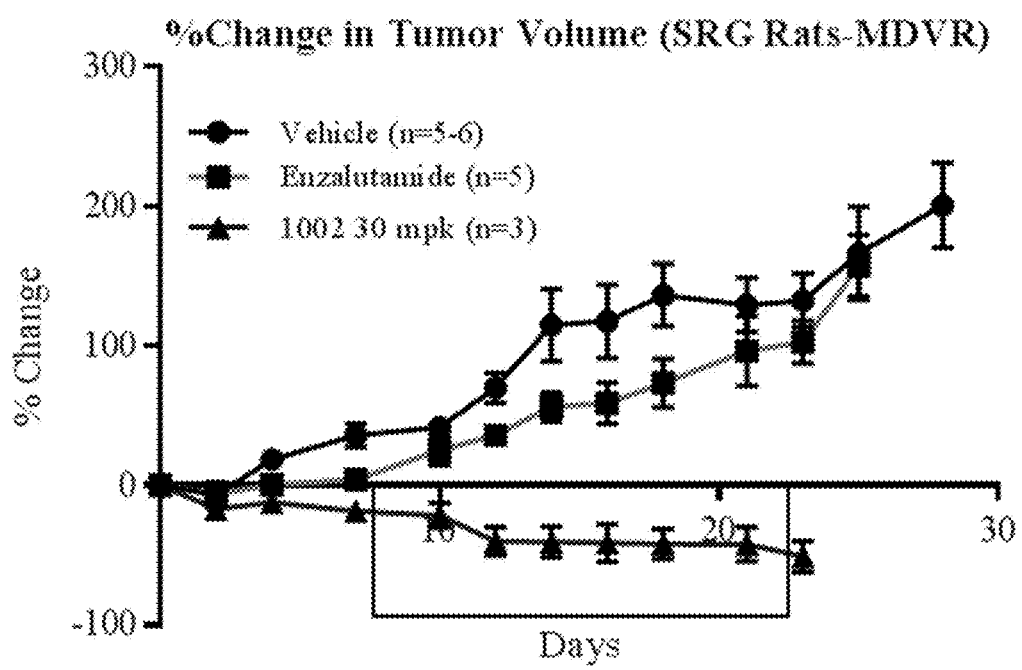
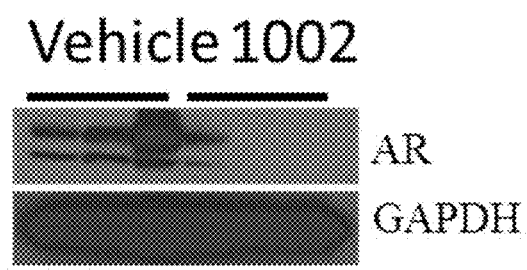
FIGURE 49C

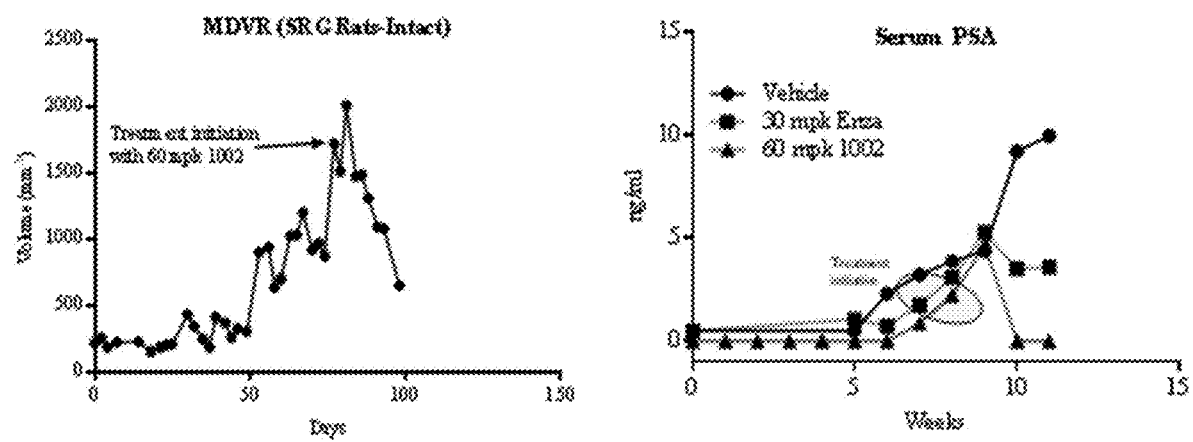
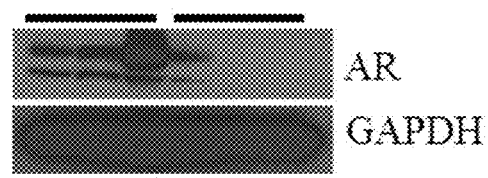
FIGURE 49D (Continued)

| M+H | Rel. Int. | No. of Labels | SA/label | Contribution |
|---|---|---|---|---|
| 357.00 | 77.35 | 0 | 28.8 | 0.00 |
| 359.00 | 100.00 | 1 | | 16.24 |
| 361.00 | 0.00 | 2 | | 0.00 |
| 363.00 | 0.00 | 3 | | 0.00 |
| 365.00 | 0.00 | 4 | | 0.00 |
| 367.00 | 0.00 | 5 | | 0.00 |
| 369.00 | 0.00 | 6 | | 0.00 |
| 371.00 | 0.00 | 7 | | 0.00 |
| 373.00 | 0.00 | 8 | | 0.00 |
| 375.00 | 0.00 | 9 | | 0.00 |
| 377.00 | 0.00 | 10 | | 0.00 |
| 379.00 | 0.00 | 11 | | 0.00 |
| 381.00 | 0.00 | 12 | | 0.00 |
| 198.00 | 0.00 | 13 | | 0.00 |
| 200.00 | 0.00 | 14 | | 0.00 |
| Total | 177.35 | | | 16.24 Ci/mmol |

FIGURE 50D

SELECTIVE ANDROGEN RECEPTOR DEGRADER (SARD) LIGANDS AND METHODS OF USE THEREOF

CROSS REFERENCE TO RELATED APPLICATIONS

This application is a Continuation-in-Part application of U.S. patent application Ser. No. 15/981,849, filed on May 16, 2018, which is a Continuation-in-Part application of U.S. patent application Ser. No. 15/923,668, filed on Mar. 16, 2018, which is a Continuation-in-Part application of U.S. patent application Ser. No. 15/620,761, filed on Jun. 12, 2017, which claims the benefit of U.S. Provisional Ser. No. 62/348,474, filed on Jun. 10, 2016, U.S. Provisional Ser. No. 62/455,397, filed on Feb. 6, 2017 and U.S. Provisional Ser. No. 62/482,036 filed on Apr. 5, 2017, which are all incorporated in their entirety herein by reference.

FIELD OF THE INVENTION

This invention is directed to pyrrole, pyrazole, imidazole, triazole, and morpholine based selective androgen receptor degrader (SARD) compounds including cyclic and heterocyclic anilide rings and their synthetic precursors and mono-, di-, or multi-substituted N-heterocyclic rings, R-isomers, non-hydroxylated and/or non-chiral propanamides in treating androgen receptor dependent diseases and conditions such as hyperproliferations of the prostate including pre-malignancies and benign prostatic hyperplasia, prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as: 1) intracrine androgen synthesis, 2) AR splice variants (AR-SV), e.g., that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations), 4) amplifications of the AR gene within the tumor (e.g., as driven by the fusion of other genes such as the ETS family of transcription factors (see for example PMID: 20478527, 30033370), and 5) rearrangements of the AR gene within the tumor, e.g., as described in PMID: 27897170. A critical barrier to progress in treating CRPC is that AR signaling inhibitors such as enzalutamide, bicalutamide, and abiraterone, acting through the LBD, fail to inhibit growth driven by the N-terminal domain (NTD)-dependent constitutively active AR-SV such as AR-V7, the most prominent AR-SV. Recent high-impact clinical trials with enzalutamide and abiraterone in CRPC patients demonstrated that just 13.9% of AR-V7-positive patients among 202 patients starting treatment with enzalutamide (Xtandi) or abiraterone acetate (Zytiga) had PSA responses to either of the treatments (Antonarakis E S, Lu C, Luber B, et al. *J. Clin. Oncol.* 2017 Apr. 6. doi: 10.1200/JCO.2016.70.1961), indicating the requirement for next generation AR antagonists that target AR-SVs. In addition, a significant number of CRPC patients are becoming refractory to abiraterone or enzalutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Herein the NTD is biophysically characterized to interact with the SARDs of this invention via fluorescence polarization (FP) and NMR (Example 9). Biochemical evidence also supports the SARDs of this invention binding to a domain other than the LBD. E.g., SARDs of this invention degrade AR-SV in D567es cells lacking the expression of any AR containing the LBD (Example 5). Further, the R- and S-isomers of the SARDs of this invention possess equipotent SARD activity despite demonstrated differences in the binding and inhibition of androgen-dependent transactivation via the LBD (Examples 3 and 4). The report of SARD activity mediated through the NTD of AR is an unprecedented observation that may help explanation the prodigious AR antagonism profiles seen with the SARDs of this invention.

Molecules that degrade the AR prevent any inadvertent AR activation through growth factors or signaling pathways, or promiscuous ligand-dependent activation. In addition, molecules that inhibit the constitutive activation of AR-SVs are extremely important to provide extended benefit to CRPC patients.

Currently only a few chemotypes are known to degrade AR which include the SARDs ARN-509, AZD-3514, and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists in some cases; bind to LBD and/or NTD), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation.

SARDs have the potential to evolve as new therapeutics to treat CRPCs that are untreatable with any other antagonists. This unique property of degrading AR-SV has extremely important health consequences for prostate cancer. Till date only one series of synthetic molecules (EPI-001, EPI-506, etc.) and some marine natural products such as the sinkotamides and glycerol ether Naphetenone B, are reported to bind to AR-NTD and inhibit AR function and PCa cell growth, albeit at lower affinity and inability to degrade the receptor. The SARDs reported herein also bind to AR-NTD and inhibit NTD-driven (e.g., ligand independent) AR activity.

The positive correlation between AR and PCa and the lack of a fail-safe AR antagonist, emphasizes the need for molecules that inhibit AR function through novel or alternate mechanisms and/or binding sites, and that can elicit antagonistic activities within an altered cellular environment.

Although traditional antiandrogens such as enzalutamide, bicalutamide and flutamide and androgen deprivation therapies (ADT) were approved for use in prostate cancer, there is significant evidence that antiandrogens could also be used in a variety of other hormone dependent and hormone independent cancers. For example, antiandrogens have been tested in breast cancer (enzalutamide; Breast Cancer Res. (2014) 16(1): R7), non-small cell lung cancer (shRNAi AR), renal cell carcinoma (ASC-J9), partial androgen insensitivity syndrome (PAIS) associated malignancies such as gonadal tumors and seminoma, advanced pancreatic cancer (*World J. Gastroenterology* 20(29), 9229), cancer of the ovary, fallopian tubes, or peritoneum, cancer of the salivary gland (*Head and Neck* (2016) 38, 724-731; ADT was tested in AR-expressing recurrent/metastatic salivary gland cancers and was confirmed to have benefit on progression free survival and overall survival endpoints), bladder cancer (*Oncotarget* 6(30), 29860-29876); *Int J. Endocrinol* (2015), Article ID 384860), pancreatic cancer, lymphoma (including mantle cell), and hepatocellular carcinoma. Use of a more potent antiandrogen such as a SARD in these cancers may more efficaciously treat the progression of these and other cancers. Other cancers may also benefit from SARD treatment such as breast cancer (e.g., triple negative breast cancer (TNBC)), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, enzalutamide and other LBD-directed traditional AR antagonists would not be able to antagonize AR-SVs in these TNBC's. However, SARDs of this invention which are capable of destroying AR-SVs (see Table 1 and Example 5) through a binding site in the NTD of AR (see Example 9) would be able to antagonize AR including AR-SV observed in TNBC patient derived xenograpfts and provide an anti-tumor effect, as shown in Example 8.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism (e.g., in female facial hair). Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CPRC discussed above, inhibition of ligand-dependent AR activity alone may not be sufficient as AR can be activated by various cellular factors other than the endogenous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR locally to the affected areas of the skin or other tissue without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions. Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that varies widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease characterized by selective loss of upper and lower motor neurons and skeletal muscle atrophy. Epidemiologic and experimental evidence suggest the involvement of androgens in ALS pathogenesis ("Anabolic/androgenic steroid nandrolone exacerbates gene expression modifications induced by mutant SOD1 in muscles of mice models of amyotrophic lateral sclerosis." Galbiati M, Onesto E, Zito A, Crippa V, Rusmini P, Mariotti R, Bentivoglio M, Bendotti C, Poletti A. *Pharmacol. Res.* 2012, 65(2), 221-230), but the mechanism through which androgens modify the ALS phenotype is unknown. A transgenic animal model of ALS demonstrated improved survival upon surgical castration (i.e., androgen ablation). Treatment of these castrated animals with the androgen agonist nandrolone decanoate worsened disease manifestations. Castration reduces the AR level, which may be the reason for extended survival. The survival benefit is reversed by androgen agonist ("Androgens affect muscle, motor neuron, and survival in a mouse model of SOD1-related amyotrophic lateral sclerosis." Aggarwal T, Polanco M J, Scaramuzzino C, Rocchi A, Milioto C, Emionite L, Ognio E, Sambataro F, Galbiati M, Poletti A, Pennuto M. *Neurobiol. Aging.* 2014 35(8), 1929-1938). Notably, stimulation with nandrolone decanoate promoted the recruitment of endogenous androgen receptor into biochemical complexes that were insoluble in sodium dodecyl sulfate, a finding consistent with protein aggregation. Overall, these results shed light on the role of androgens as modifiers of ALS pathogenesis via dysregulation of androgen receptor homeostasis. Antiandrogens should block the effects of nandrolone undecanoate or endogeneous androgens and reverse the toxicities due to AR aggregation. Further, an antiandrogen that can block action of LBD-dependent AR agonists and concomitantly lower AR protein levels, such as the SARDs of this invention, would be therapeutic in ALS. Riluzole is an available drug for ALS treatment, however, it only provides short-term effects. There is an urgent need for drugs that extend the survival of ALS patients.

Androgen receptor action promotes uterine proliferation. Hyperandrogenicity of the short polyQ AR has been associated with increased leiomyoma or uterine fibroids. (Hsieh Y Y, Chang C C, Tsai F J, Lin C C, Yeh L S, Peng C T. *J. Assist. Reprod. Genet.* 2004, 21(12), 453-457). A separate study of Brazilian women found that shorter and longer [CAG](n) repeat alleles of AR were exclusive to the leiomyoma group in their study (Rosa F E, Canevari Rde A, Ambrosio E P, Ramos Cirilo P D, Pontes A, Rainho C A, Rogatto S R. *Clin. Chem. Lab. Med.* 2008, 46(6), 814-823). Similarly, in Asian Indian women long polyQ AR was associated with endometriosis and leiomyoma and can be regarded as high-risk markers. SARDs could be used in women with uterine fibroids, especially those expressing shorter and longer [CAG](n) repeat alleles, to treat existing uterine fibroids, prevent worsening of fibroids and/or ameliorate carcinogenicity associated with fibroids.

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. *J Vasc Surg* (2016) 63(6): 1602-1612) showed that flutamide (50 mg/kg) or ketoconazole (150 mg/kg) attenuated porcine pancreatic elastase (0.35 U/mL) induced AAA by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

X-linked spinal-bulbar muscular atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogeneous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade all androgen receptors tested (full length, splice variant, antiandrogen resistance mutants, etc.) so degradation of polyQ AR polymorphism is also expected, indicating that they are promising leads for treatment of SBMA.

Here we describe, inter alia, pyrrole, pyrazole, triazole, imidazole, and morpholine based selective androgen receptor degrader (SARD) compounds that may bind to the LBD and/or an alternate binding and degradation domain (BDD) located in the NTD, antagonize AR, and degrade AR thereby blocking ligand-dependent and ligand-independent AR activities. This novel mechanism produces improved efficacy when dosed systemically (e.g., for prostate cancer) or topically (e.g., dermatological diseases).

SUMMARY OF THE INVENTION

In one aspect, this invention provides a method of treating an androgen receptor dependent disease or condition in a subject in need thereof, comprising administering to the subject a therapeutically effective amount of a selective androgen receptor degrader (SARD) compound represented by the structure of formula I

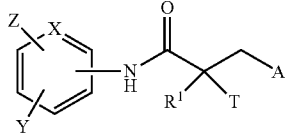

wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$ and $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, benzyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, $COOCOR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer or a racemic mixture thereof, isomer, pharmaceutically acceptable salt, pharmaceutical product, hydrate or any combination thereof.

In one embodiment, this invention provides a method of treating an androgen receptor dependent disease or condition in a subject in need thereof, comprising administering to the subject a therapeutically effective amount of a selective androgen receptor degrader (SARD) compound wherein the SARD compound is represented by the structure of formula IA:

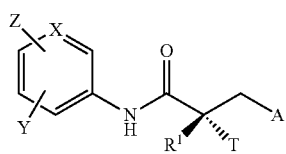

wherein T, $R^1$, Y, Z, X, and A are as described in the compound of formula I, or its isomer, pharmaceutically acceptable salt, pharmaceutical product, hydrate or any combination thereof.

In one aspect, this invention provides a method of treating an androgen receptor dependent disease or condition in a subject in need thereof, comprising administering to the subject a therapeutically effective amount of a selective androgen receptor degrader (SARD) compound wherein the SARD compound is represented by the structure of formula IB:

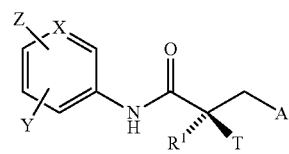

wherein T, $R^1$, Y, Z, X, and A are as described in the compound of formula I, or its isomer, pharmaceutically acceptable salt, pharmaceutical product, hydrate or any combination thereof.

In one embodiment, this invention provides a method of treating an androgen receptor dependent disease or condition in a subject in need thereof, comprising administering to the subject a therapeutically effective amount of a selective androgen receptor degrader (SARD) compound wherein the SARD compound is represented by the structure of formula II:

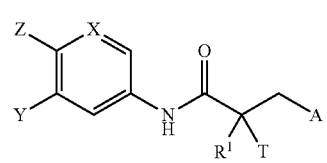

wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl,
F, Cl, Br, I, or OH;
A is $R^2$ or $R^3$
$R^2$ is a pyrrole, pyrrolidine, pyrazole, pyrazolidine, triazole, imidazole, imidazolidine, or morpholine ring, said ring optionally substituted with at least one of $Q^1$, $Q^2$, $Q^3$ and $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, benzyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, $COCl$, $COOCOR^4$, $COOR^4$, $OCOR^4$, $OCONHR^4$, $NHCOOR^4$, $NHCONHR^4$, $OCOOR^4$, $CN$, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, $CO(N\text{-heterocycle})$, $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its optical isomer or a racemic mixture thereof, isomer, pharmaceutically acceptable salt, pharmaceutical product, hydrate or any combination thereof.

In one embodiment of the method of this invention, the SARD compound is represented by the structure of formula IIA:

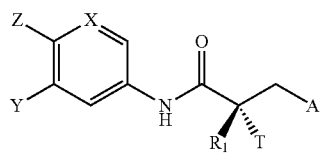

IIA wherein T, $R^1$, Y, Z, X, and A are as described in the compound of formula II, or its isomer, pharmaceutically acceptable salt, pharmaceutical product, hydrate or any combination thereof.

In one embodiment of the method of this invention, the SARD compound is represented by the structure of formula IIB:

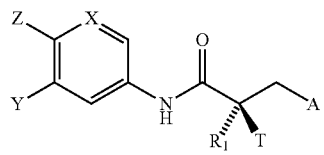

IIB wherein T, $R^1$, Y, Z, X, and A are as described in the compound of formula II, or its isomer, pharmaceutically acceptable salt, pharmaceutical product, hydrate or any combination thereof.

In one embodiment of the method of this invention, the SARD compound is represented by the structure of formula VII:

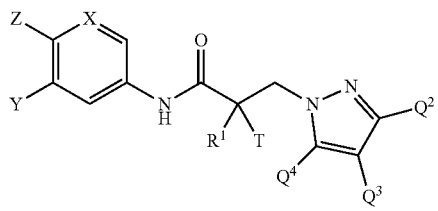

VII wherein
X is CH or N;
Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^2$, $Q^3$ and $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

or its optical isomer or a racemic mixture thereof, isomer, pharmaceutically acceptable salt, pharmaceutical product, hydrate or any combination thereof.

In one embodiment of the method of this invention, the SARD compound is represented by the structure of formula VIIA:

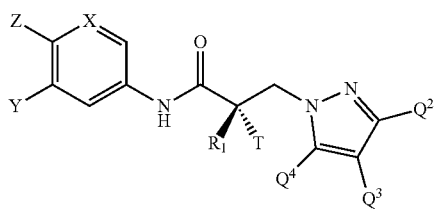

VIIA wherein T, $R^1$, Y, Z, X, $Q^2$, $Q^3$, and $Q^4$ are as described in the compound of formula VII, or its isomer, pharmaceutically acceptable salt, pharmaceutical product, hydrate or any combination thereof.

In one embodiment of the method of this invention, the SARD compound is represented by the structure of formula VIIB:

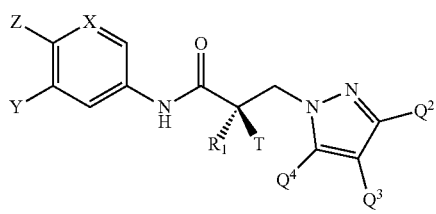

VIIB wherein T, $R^1$, Y, Z, X, $Q^2$, $Q^3$, and $Q^4$ are as described in the compound of formula VII, or its isomer, pharmaceutically acceptable salt, pharmaceutical product, hydrate or any combination thereof.

In one embodiment of the method of this invention, in the compounds of formulas I, IA, IB, IIA, and/or IIB, $Q^1$, $Q^2$, $Q^3$ and/or $Q^4$ is hydrogen, CN, $NO_2$, $CF_3$, F, Cl, Br, I, NHCOOR, $N(R)_2$, NHCOR, COR, alkyl, alkoxy, or substituted or unsubstituted phenyl.

In one embodiment of the method of this invention, the SARD compound is represented by the structure of any one of the following compounds:

-continued
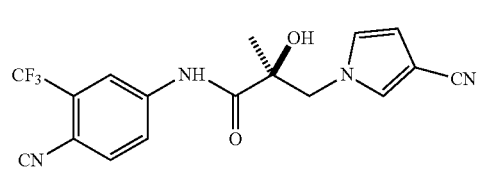
1001
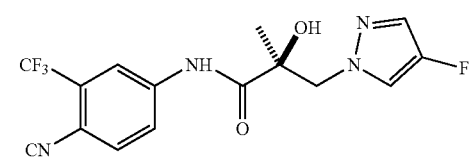
1002
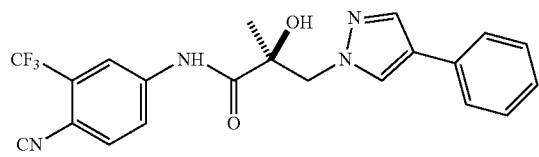
1003
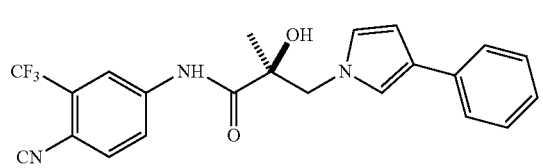
1004
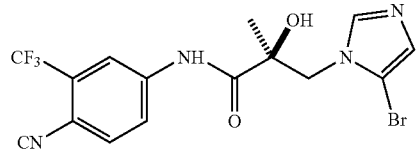
1005
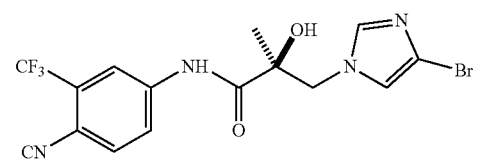
1006
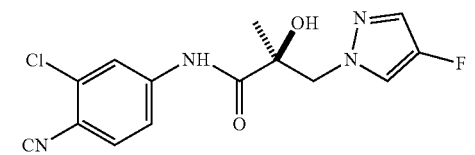
1007
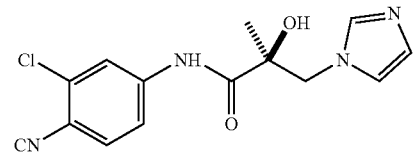
1008
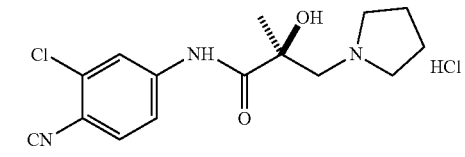
1009
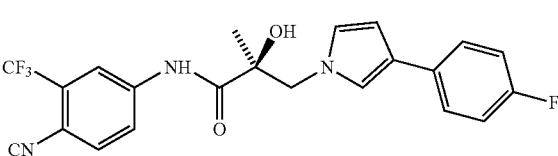
1010
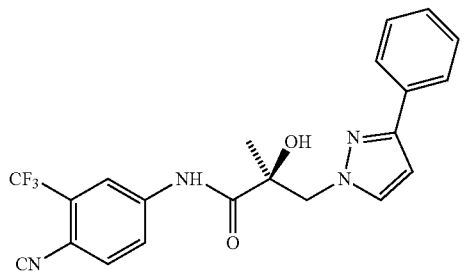
1011
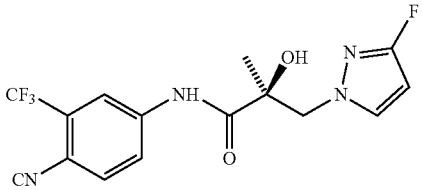
1012
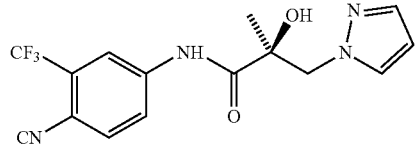
1013
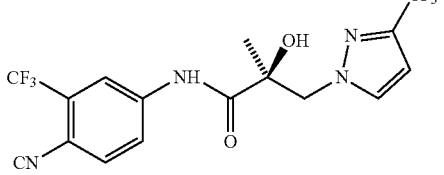
1014
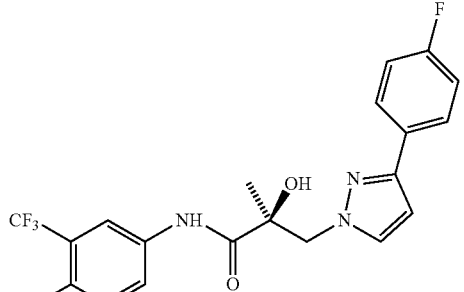
1015
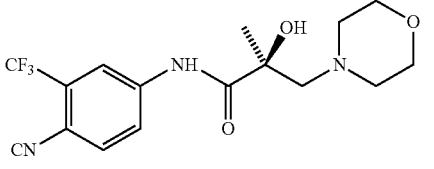
1016

-continued

1017

1018

1019

1020

1021

1022

1023

1024

1025

-continued

1026

1027

1028

1029

1030

1031

1032

1033

-continued
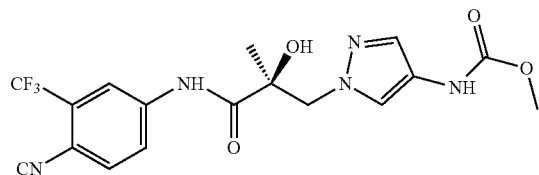
1034
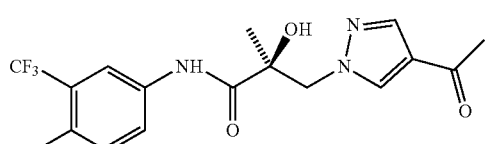
1035
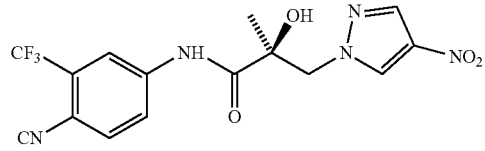
1036
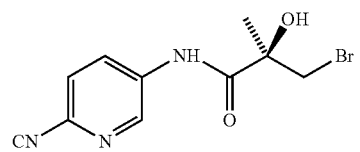
1037
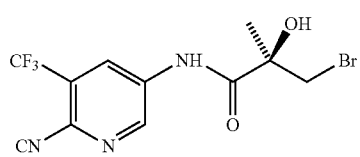
1038
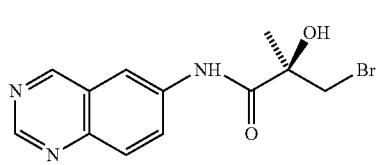
1039
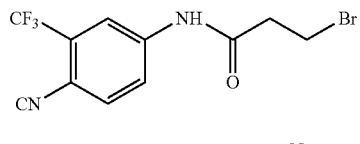
1040
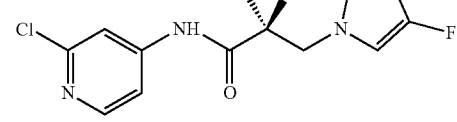
1041
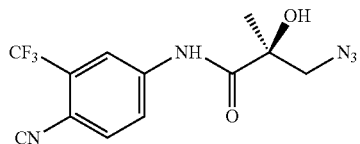
1042
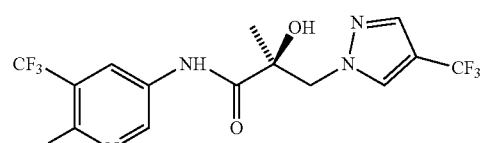
1043
-continued
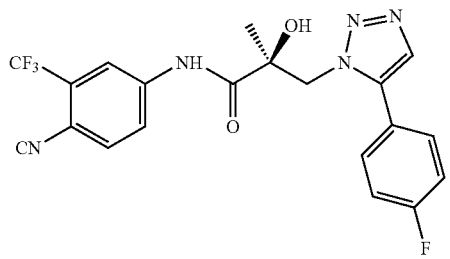
1044
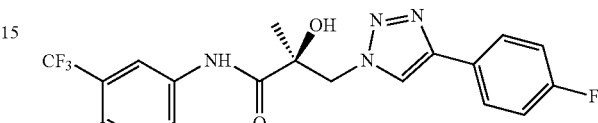
1045
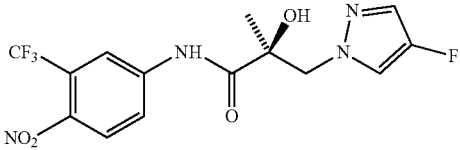
1046
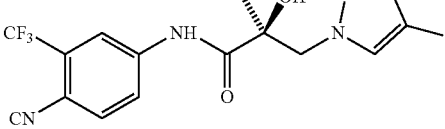
1047
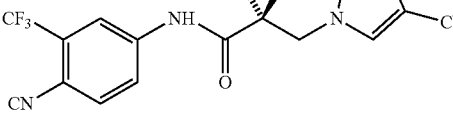
1048
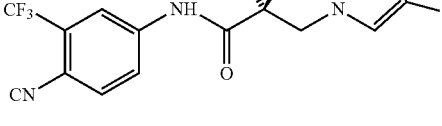
1049
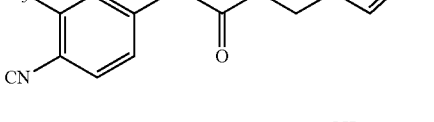
1050
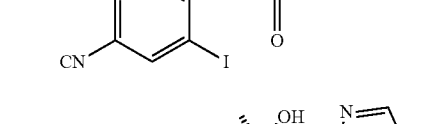
1051
1052

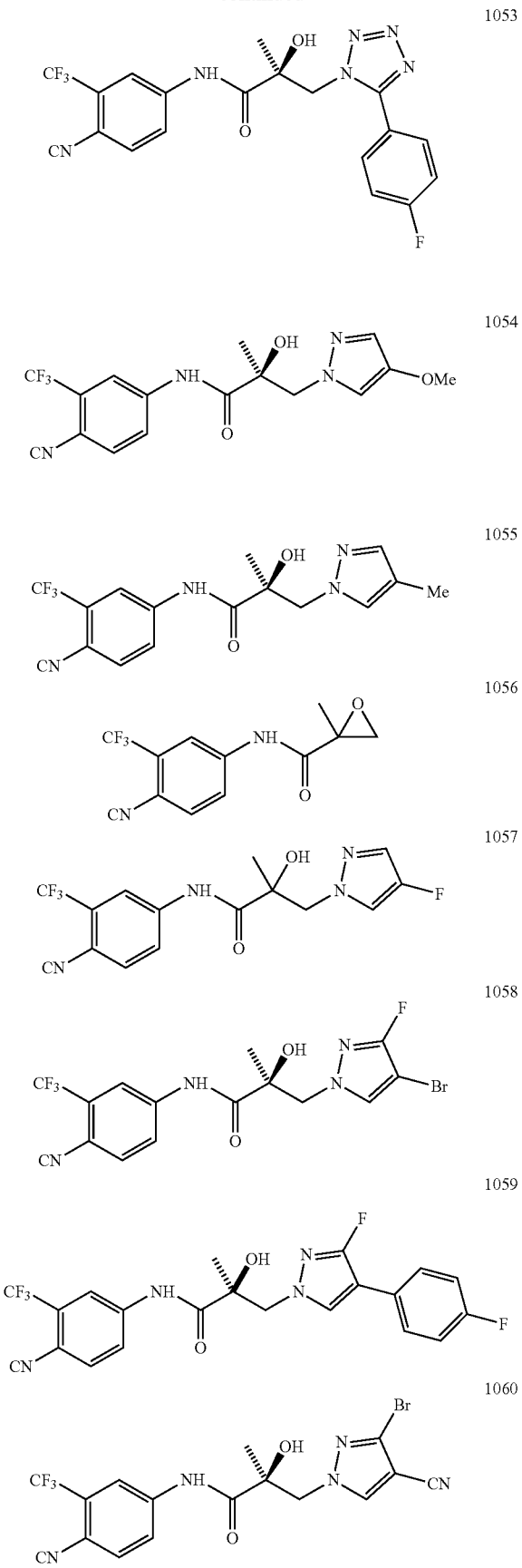
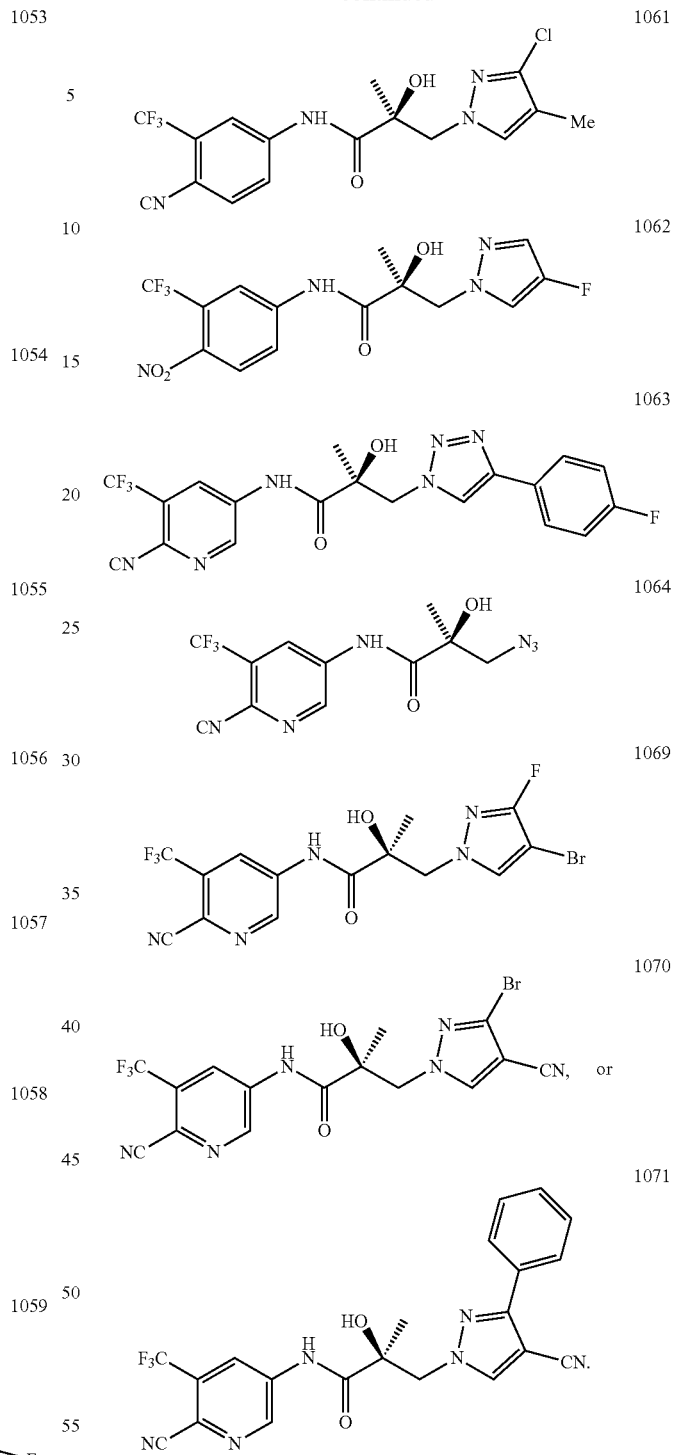

In one embodiment, the androgen receptor dependent disease or condition in the method of this invention responds to at least one of: 1) AR-splice variant (AR-SV) degradation activity, 2) full length (AR-FL) degradation activity, 3) AR-SV inhibitory, or 4) AR-FL inhibitory activity.

In one embodiment, the androgen receptor dependent disease or condition in the method of this invention is breast cancer.

In one embodiment, the androgen receptor dependent disease or condition in the method of this invention is breast cancer that is AR expressing breast cancer, AR-SV expressing breast cancer, and/or AR-V7 expressing breast cancer.

In one embodiment, the androgen receptor dependent disease or condition in the method of this invention is Kennedy's disease.

In one embodiment, the androgen receptor dependent disease or condition in the method of this invention is acne.

In one aspect of this embodiment, the androgen receptor dependent disease or condition in the method of this invention is acne vulgaris.

In one embodiment, the androgen receptor dependent disease or condition in the method of this invention is overproduction of sebum.

In one aspect of this embodiment, reducing the overproduction of sebum treats at least one of seborrhea, seborrheic dermatitis, or acne.

In one embodiment, the androgen receptor dependent disease or condition in the method of this invention is hirsutism or alopecia.

In one aspect of this embodiment, the alopecia of the method of this invention is at least one of androgenic alopecia, alopecia areata, alopecia secondary to chemotherapy, alopecia secondary to radiation therapy, alopecia induced by scarring, or alopecia induced by stress.

In one embodiment, the androgen receptor dependent disease or condition in the method of this invention is a hormonal disease or condition in a female.

In one embodiment, the hormonal disease or condition in a female of the method of this invention is at least one of precocious puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, or vaginal dryness.

In one embodiment, the androgen receptor dependent disease or condition in the method of this invention is a hormonal disease or condition in a male.

In one embodiment, the hormonal disease or condition in a male of the method of this invention is at least one of hypergonadism, hypersexuality, sexual dysfunction, gynecomastia, precocious puberty in a male, alterations in cognition and mood, depression, hair loss, hyperandrogenic dermatological disorders, pre-cancerous lesions of the prostate, benign prostate hyperplasia, prostate cancer and/or other androgen-dependent cancers.

In one embodiment, the androgen receptor dependent disease or condition in the method of this invention is sexual perversion, hypersexuality, or paraphilias.

In one embodiment, the androgen receptor dependent disease or condition in the method of this invention is androgen psychosis.

In one embodiment, the androgen receptor dependent disease or condition in the method of this invention is virilization.

In one embodiment, the androgen receptor dependent disease or condition in the method of this invention is androgen insensitivity syndrome.

In one embodiment, the androgen receptor dependent disease or condition in the method of this invention is cancer. In one embodiment, the cancer is an AR-expressing cancer.

In one embodiment, the AR-expressing cancer of the method of this invention is at least one of breast cancer, testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

In one embodiment, the androgen receptor dependent disease or condition in the method of this invention is amyotrophic lateral sclerosis (ALS).

In one embodiment, the androgen receptor dependent disease or condition in the method of this invention is uterine fibroids.

In one embodiment, the androgen receptor dependent disease or condition in the method of this invention is abdominal aortic aneurysm (AAA).

In one embodiment, the androgen receptor dependent disease or condition in the method of this invention is caused by polyglutamine (polyQ) AR polymorphs In one aspect of this embodiment, the polyQ-AR of the method of this invention is a short polyQ polymorph or a long polyQ polymorph. In one aspect of this embodiment, the polyQ-AR of the method is a short polyQ polymorph and the method further treats dermal disease.

In one aspect of this embodiment, the dermal disease of the method of this invention is at least one of alopecia, seborrhea, seborrheic dermatitis, or acne. In one aspect of this embodiment, the polyQ-AR of the invention is a long polyQ polymorph and the method further treats Kennedy's disease.

In one aspect, this invention provides a radioactively labeled SARD compound represented by the structure of formula I:

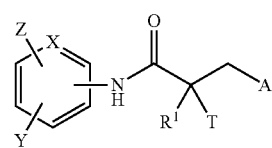

I wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$ and $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, benzyl, NCS, maleimide, NHCOOR, $N(R)_2$, NHCOR, CONHR, COOR or COR;

R³ is NHR², halide, N₃, OR⁴, CF₃, COR⁴, COCl, COO-COR⁴, COOR⁴, OCOR⁴, OCONHR⁴, NHCOOR⁴, NHCONHR⁴, OCOOR⁴, CN, CONH₂, CONH(R⁴), CON(R⁴)₂, SR⁴, SO₂R⁴, SOR⁴ SO₃H, SO₂NH₂, SO₂NH(R⁴), SO₂N(R⁴)₂, NH₂, NH(R⁴), N(R⁴)₂, CO(N-heterocycle), NO₂, cyanate, isocyanate, thiocyanate, isothiocyanate, mesylate, tosylate, triflate, PO(OH)₂ or OPO(OH)₂; and R⁴ is H, alkyl, haloalkyl, cycloalkyl, aryl or heteroaryl, wherein said alkyl, haloalkyl, cycloalkyl, aryl or heteroaryl groups are optionally substituted;

or its optical isomer or a racemic mixture thereof, isomer, pharmaceutically acceptable salt, pharmaceutical product, hydrate or any combination thereof;

wherein at least one of the protons of formula I is replaced by a tritium atom.

In one embodiment, the radioactively labeled compound is represented by the structure of ³H-1002:

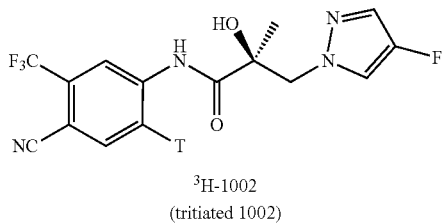

³H-1002
(tritiated 1002)

wherein T is tritium (³H).

In one embodiment this invention provides an assay for observing and quantitating competitive NTD binding of a candidate NTD binding compound, wherein said assay comprises a compound of formula I, wherein at least one of the protons of the compound of formula I is replaced by a tritium atom. In another embodiment, the compound is ³H-1002 (tritiated 1002).

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIG. 1A plotted the results with RLU reported on the y-axis and SARD concentration on the x-axis, where the antagonist mode was reported in closed dots. A curve was fitted to the closed dots. FIG. 1B illustrates the Western blot of the androgen receptor degradation assay with AD1 cells and the results were reported in Table 1, under SARD Activity: Full Length % Inhibition. FIG. 1C illustrates the Western blot of the androgen receptor degradation splice variant assay with D567es cells. (The results in 22RV1 cells were reported in Table 1, under 'SARD Activity: S.V. % Inhibition'.)

FIG. 2A plotted the results with RLU reported on the y-axis and SARD concentration on the x-axis, where the antagonist mode was reported for 11 and 1002. Compound 11 is represented in closed dots and solid line and 1002 is represented in open dots and dashed line. A curve was fitted to the open and closed dots for 1002 and 11, respectively. FIG. 2B illustrates the Western blots of an AR degradation assay with AD1 cells (Full Length AR) and a splice variant assay with 22RV1 cells for 11, 11R (R-isomer of 11), 1002, and 1020 (R-isomer of 1002). The results were reported in Table 1 in columns labeled 'SARD Activity: Full Length % Inhibition' and 'SARD Activity: S.V. % Inhibition', respectively. In short, the R-isomer of indole and pyrazole SARDs retained SARD activity, in contrast to LBD-dependent inhibitors.

FIG. 3A plotted the results with RLU reported on the y-axis and SARD concentration on the x-axis, where the agonist mode was reported in closed dots and the antagonist mode was reported in open dots. A curve was fitted to the open dots. FIG. 3B illustrates the Western blot of the full length androgen receptor degradation assay and the results were reported in Table 1, under SARD Activity: Full Length % Inhibition.

FIG. 4A plotted the results with RLU reported on the y-axis and SARD concentration on the x-axis, where the agonist mode was reported in closed dots and antagonist mode was reported in open dots. A curve was fitted to the open dots. FIG. 4B illustrates the Western blot of the full length androgen receptor degradation assay and the results were reported in Table 1, under SARD Activity: Full Length % Inhibition. The numbers under the Western blot indicate the ratio of AR to actin in each lane.

FIG. 5A plotted the results with RLU reported on the y-axis and SARD concentration on the x-axis, where the agonist mode was reported in closed dots and antagonist mode was reported in open. A curve was fitted to the open dots. FIG. 5B illustrates the Western blot of the full length androgen receptor degradation assay and the results were reported in Table 1, under SARD Activity: Full Length % Inhibition.

FIG. 6A and FIG. 6B: The transactivation result of 1006 was reported based on measured luciferase light emissions and reported as relative light unit intensity (RLU). FIG. 6A plotted the results with RLU reported on the y-axis and SARD concentration on the x-axis, where the agonist mode was reported in closed dots and antagonist mode was reported in open dots. A curve was fitted to the open dots. FIG. 6B illustrates the Western blot of the full length androgen receptor degradation assay and the results were reported in Table 1, under SARD Activity: Full Length % Inhibition.

FIG. 7: The Western blot of the full length androgen receptor degradation assay is shown for compound 17 and the results are reported in Table 1, under SARD Activity: Full Length % Inhibition.

FIG. 8 plotted the results with RLU reported on the y-axis and SARD concentration on the x-axis, where the antagonist mode was reported in closed dots. A curve was fitted to the closed dots.

FIG. 9 plotted the results with RLU reported on the y-axis and SARD concentration on the x-axis, where the antagonist mode was reported in closed dots. A curve was fitted to the closed dots.

FIG. 10 plotted the results with RLU reported on the y-axis and SARD concentration on the x-axis, where the antagonist mode was reported in closed dots. A curve was fitted to the closed dots.

FIG. 11 plotted the results with RLU reported on the y-axis and SARD concentration on the x-axis, where the antagonist mode was reported in closed dots. A curve was fitted to the closed dots.

FIG. 12 plotted the results with RLU reported on the y-axis and SARD concentration on the x-axis, where the antagonist mode was reported in closed dots. A curve was fitted to the closed dots.

FIG. 13A plotted the results with RLU reported on the y-axis and SARD concentration on the x-axis, where the antagonist mode was reported in closed dots. A curve was fitted to the closed dots. FIG. 13B illustrates the Western blot of the full length androgen receptor degradation assay and the results were reported in Table 1, under SARD Activity: Full Length % Inhibition. FIG. 13C illustrates the Western blot of the androgen receptor degradation splice variant assay with 22RV1 cells and the results were reported in Table 1, under SARD Activity: S.V. % Inhibition.

FIG. 14: FIG. 14 illustrates the phase I and phase I & II data as a raw data table for the determination of metabolic stability for 1002 in mouse liver microsomes (MLM) and the $T_{1/2}$ (half-life in minutes) and $CL_{int}$ (clearance in L/min/mg protein) values calculated therefrom.

FIG. 15A and FIG. 15B: FIG. 15A reports phase I data as a raw data table and graphed data for one experiment for 1002 in mouse liver microsomes (MLM). FIG. 15B reports phase I & II data as a raw data table and graphed data for one experiment for 1002 in mouse liver microsomes (MLM). Value for $T_{1/2}$ was 224 min. $CL_{int}$ was 3.12 µL/min/mg.

FIG. 16A and FIG. 16B: FIG. 16A reports phase I data for human liver microsomes (HLM). FIG. 16B reports phase I & II data as a raw data table and graphed data for one experiment for 1002 in human liver microsomes (HLM). For this experiment, the caluculated value for $T_{1/2}$ was infinity and $CL_{int}$ was 0. Suggesting greater stability for 1002 in HLM than MLM.

FIG. 17: FIG. 17 reports phase I data as a raw data table and graphed data for one experiment for 1001 in mouse liver microsomes (MLM). Value for $T_{1/2}$ was 23.5 min and $CL_{int}$ was 29.5 µL/min/mg. Results depict relatively poor stability for 1001, but still an improvement compared to 11.

FIG. 19A reports weights organs in intact Sprague Dawley rats with body weights of 165-180 grams treated daily with vehicle, 40 mg/kg 1002, 60 mg/kg 1002, or 20 mg/kg enzalutamide orally. After 13 days of treatment, the rats were sacrificed and the weights of prostate, seminal vesicles, and levator ani were measured. FIG. 19B reports the same data as a % decrease from vehicle. Bottom right pane illustrates intact vs. castrated % organ weights for vehicle treated rats.

FIG. 20A and FIG. 20B: Degradation of full length and splice variant (AR-v567ES) androgen receptors (in vitro) for 1010, 1012, 1014, 1015, 1016, 1017, 1019 and 1022: FIG. 20A illustrates for each compound the Western blot of the full length androgen receptor degradation assay. The results were reported in Table 1, under SARD Activity: Full Length % Inhibition. FIG. 20B illustrates the Western blot of the androgen receptor degradation splice variant assay with D567es.

FIG. 21A and FIG. 21B: Anti-tumor efficacy for 1002 in triple negative breast cancer (TNBC) patient-derived xenograft (PDX) is presented in HBrt 1071 triple negative breast cancer (FIG. 21A) and in HBrt 1361 triple negative breast cancer (FIG. 21B).

FIG. 24: depicts the serum and tumor levels of 11, 34, 36, 96, 103, 1002, 1010, 1012, and 1014 achieved in a 22RV1 xenograft experiment.

FIG. 25: depicts reductions in seminal vesicles weights (% change) for animals treated with 34, 36, 1002, 1010, 1012, and 1014 in a Hershberger assay.

FIG. 27A depicts the perturbation of the fluorescent signal of AR-NTD and AR-AF1 in the presence of urea (denaturant), TMAO (folding stabilizer), and buffer, but no SARD. FIGS. 27B-27D depict the perturbations of AR-NTD and AR-AF1 fluorescence associated with the titrations of 1002 (FIG. 27B), 1010 (FIG. 27C), and 36 (FIG. 27D), respectively.

FIGS. 28A-28D: depicts degradation of full length and/or splice variant (22RV1) androgen receptors (in vitro) for 1024 (FIG. 28A), 1029 (FIG. 28B), 1037 and 1041 (FIG. 28C), and 1044-1045 (FIG. 28D). FIGS. 28A, 28C, and 28D illustrate the Western blots of the full length androgen receptor degradation assay. The results were reported in Table 1, under SARD Activity: Full Length % Inhibition. FIG. 28B illustrates the Western blots of the androgen receptor degradation splice variant assay with 22RV1 cells which are represented in Table 1 in the column labeled 'SARD Activity: S.V. % Inhibition'.

(FIG. 29A) Enzalutamide inhibited F876L AR at doses more potent than wildtype AR but was a weaker antagonist of W741L AR (FIG. 29B). However, when the assay was run in agonist mode (FIG. 29C), enzalutamide, at higher doses acted as an agonist of F876L AR. This is characteristic of agonist switch mutations in which AR antagonists of wildtype AR become AR agonists in due to the AR mutation. By comparison, SARDs like 1002 possess no intrinsic transcriptional agonist activity on wildtype AR or F876L AR, suggesting that tumors possessing agonist switch mutations can be inhibited by SARDs of this invention. Similarly, W741L is an agonist switch mutation conferring resistance to bicalutamide, which is inhibited by SARDs.

FIGS. 30A-30E: SARDs degrade the AR, AR-SV, and AR-F876L (MR49F), but not PR and ER (see ZR-75-1 cells). FIG. 30A: LNCaP (compound 11); FIG. 30B: LNCaP (compound 1002); FIG. 30C: ZR-75-1 (compound 1002); FIG. 30D: LNCaP-AR-V7 (compounds 11 and 1002); and FIG. 30E: MR49F (compound 1002). LNCaP cells possess the T877A mutation which confers resistance to flutamide (or hydroxyflutamide, the active metabolite) which demonstrates that SARDs will degrade an agonist switch mutant AR. Likewise, the F876L AR mutation confers resistance to enzalutamide and abiraterone and FIG. 30E demonstrates the ability to degrade this mutant. Cumulatively, this is good evidence that agonist switch mutations to current anti-androgens can be overcome with the SARDs of this invention.

FIG. 31A: compounds 11 and 1002; and FIG. 31B: compound 1002 and bortezomib. The FIG. 31A shows an immunoblot in which a fusion portion with AR connected to hemagglutinin (HA) is expressed in cells. Then the cells are treated with the indicated SARDs or untreated, the AR complex is immunoprecipitated with anti-HA, and run on a Western blot and visualized with anti-ubiquitin antibody (anti-Ub). In the untreated lane, there is no observed ubiquitination of AR, whereas there is various degrees of ubiquitination of AR in the SARD (11 and 1002) treated lanes which are apparent as a smear of AR molecular weights extending up from the fusion protein molecular weight. This indicated that the SARDs induced the ubiquitination of AR. Relative AR levels are shown under each lane (10% input:AR). FIG. 31B indicates that 1002 degrades AR at 10 micromolar in the presence of 50 micromolar cycloheximide. Further, bortezomib, a protease inhibitor, does not induce AR expression at 1, 5 and 10 micromolar. However, co-treatment of cells with 1002 and 1, 5 and 10 micromolar resulted in a dose responsive reversal of the SARD activity of 1002. Reversal of SARD activity by a proteasome inhibitor indicates that the 1002 and other SARDs of this invention work by a proteasome-dependent protein degradation pathway.

FIG. 34A: FKBP5 expression in LNCaP cells; FIG. 34B: Growth inhibition of LNCaP cells; FIG. 34C: FKBP5 expression in enzalutamide resistant (EnzR)LNCaP cells; and FIG. 34D: Growth inhibition in LNCaP-EnzR cells. 1002 inhibited the AR-dependent gene FKBP5 in either LNCaP and LNCaP-EnzR cells demonstrating the ability to inhibit the AR-axis in either CRPC's such as LNCaP (T877A) or enzalutamide resistant prostate cancers, and, correspondingly, to also inhibit cell growth in these AR-dependent cell lines whereas enzalutamide was unable to significantly inhibit FKBP5 or growth in the LNCaP-EnzR cell line.

FIG. 35B shows tumor volume data for the individual animals in this experiment. Solid line is vehicle treated rats, larger dashes in the line are for enzalutamide treated rats, and smaller dashes are for 1002 treated rats.

FIG. 38 demonstrates that the SARD is able to fully inhibit MDVR VCaP tumors in castrated animals but did not regress the tumors as dramatically as in intact rats, whereas enzalutamide treated tumors growth comparably to vehicle. The preference for intact in this model was an unexpected results never before reported anywhere to our knowledge.

FIG. 39A. 11 has no effect on seminal vesicles when administered orally. C57BL6 mice weighing 20-25 grams (n=5/group) were treated orally with vehicle (15% DMSO+85% PEG-300) or the indicated doses of 11 or enzalutamide. Animals were sacrificed after 14 days of treatment and weights of seminal vesicles were recorded and normalized to body weight. The values are represented as percent change from vehicle-treated animals. *** p<0.001. FIG. 39B. 11 has no effect on the growth of enzalutamide-resistant xenograft when administered orally. Enzalutamide-resistant LNCaP cells (MR49F) were implanted subcutaneously in nude mice. Once the tumors reached 100-200 mm$^3$, the animals were castrated and the tumors were allowed to develop as castration-resistant tumors. Once the tumors reach 200-300 mm$^3$, the animals (n=8-10/group) were randomized and treated orally with vehicle (15% DMSO+85% PEG-300) or 100 mg/kg 11. Tumor volume was measured twice weekly. FIG. 39C. 11 has poor metabolism properties. Liver microsomes from mouse (MLM) and human (HLM) were incubated with 11 as indicated in the methods and the amount of compound present at different points was identified using LC-MS/MS method. Data from both phase I and II metabolism are presented here. The data are represented as half-life ($T_{1/2}$ (minutes)) and intrinsic clearance ($Cl_{int}$).

FIG. 40A. Structure of 1002. FIG. 40B left panel. 1002 does not bind to the AR-LBD. Purified GST-tagged AR-LBD protein was incubated for 16 hours at 4° C. with a dose response (1 pM to 100 μM) of the indicated compounds in the presence of 1 nM $^3$H mibolerone. Unbound $^3$H was washed and the bound $^3$H was counted using a scintillation counter. FIG. 40B right panel. COS7 cells were transfected with 50 ng of AR-LBD. Cells were treated 48 hours after transfection with a dose response (1 pM to 10 μM) of the indicated compounds in the presence of 1 nM $^3$H mibolerone for 4 hours. Unbound $^3$H mibolerone was washed with cold PBS and the bound $^3$H was eluted with ice cold ethanol. $^3$H was counted using a scintillation counter. FIG. 40C. 1002 comparably inhibits the transactivation of wildtype and mutant ARs. COS7 cells were transfected with 25 ng of cmv hAR, hAR F876L, or hAR W741L, 0.25 μg GRE-LUC, and 10 ng CMV-renilla LUC using lipofectamine. Cells were treated 24 hours after transfection with a dose response of 1002 or enzalutamide in combination with 0.1 nM R1881 (F876L agonist graph experiment was performed in the absence of 0.1 nM R1881) and luciferase assay was performed 48 hours after transfection. Firefly luciferase was divided by renilla luciferase. Values shown in the graphs are IC$_{50}$ values. Experiments were performed at least n=3 times and the representative graph is shown here. DHT-dihydrotestosterone; AR-androgen receptor; LBD-ligand binding domain; GST-glutathione S transferase.

FIG. 41A-41I: demonstrate that 1002 selectively degrades wildtype and enzalutamide-resistant ARs. FIG. 41A. 1002 destabilizes wildtype AR. LNCaP cells were maintained in charcoal-stripped serum-containing medium for 2 days. Cells were treated with the indicated doses of 1002 or enzalutamide (Enz) or bicalutamide (Bic) (right panel; enzalutamide and bicalutamide were used at 10 μM) in the presence of 0.1 nM R1881 for 24 hours, protein was extracted, and Western blot for AR and actin was performed. Lower bar graph shows no effect of 1002 on AR mRNA expression under the same experimental conditions. FIG. 41B. 1002 destabilizes enzalutamide-resistant AR. Enzalutamide-resistant LNCaP cells (MR49F) were cultured and treated as indicated above for LNCaP cells. Western blot for AR and actin was performed with the protein extracts. FIG. 41C. 1002 selectively degrades the AR. T47D cells maintained in full serum-containing medium were treated as indicated in the figure with 1002. Twenty four hours after treatment, cells were harvested, protein extracted, and Western blot for PR, ER, and actin was performed. FIG. 41D. ZR-75-1 breast cancer cells were maintained in 1% csFBS-containing medium for two days. Cells were treated as indicated in the figures for 48 hours with cells retreated after 24 hours. Cells were harvested and Western blot for AR, PR, ER, and GAPDH was performed.

FIG. 41E. 1002 destabilizes the AR. LNCaP cells cultured in full serum-containing medium were treated with 10 μM 1002, 50 μM cycloheximide, or combination of 1002 and cycloheximide. Cells were harvested at the indicated time-points and Western blot for AR and GAPDH was performed.

FIG. 41F. 1002 promotes ubiquitination of the AR. COS7 cells were transfected with 1 μg cmv hAR and HA-ubiquitin. Cells were treated 48 hours after transfection for 6 hours. Cells were harvested, protein extracted, and immunoprecipitation for HA and Western blot for AR were performed. 10% of the protein extract was loaded as input. FIG. 41G. LNCaP cells maintained in 1% charcoal-stripped serum-containing medium for 2 days were treated with 1002 or 11 in the presence and absence of proteasome inhibitor, MG-132 and HSP-90 inhibitor, 17AAG, for 6 hours. Immunoprecipitation for AR was performed with the protein extract and Western blot with mono- and poly-ubiquitin antibody was performed. FIG. 41H. 1002 degrades the AR by proteasome pathway. LNCaP cells plated in growth medium were treated as indicated in the figure for 8 hours. Western blot for AR and GAPDH was performed in the protein extracts. FIG. 41I. Known ubiquitin sites do not play a role in 1002-induced degradation of the AR. COS7 cells were transfected with 1 μg of wildtype AR or AR where three lysines (K311, K846, K848) were mutated to arginine (K to R). Cells were treated 24 hours after transfection for 24 hours and Western blot for AR and GAPDH was performed. Experiments were performed at least n=3 and representative blots are shown here. AR-androgen receptor; PR-progesterone receptor; ER-estrogen receptor; IP-immunoprecipitation; IB-immunoblot (Western blot); HA-hemagglutinin; Ub-ubiquitin; cyclohex-cycloheximide-protein-synthesis inhibitor; Enz-enzalutamide; Bic-bicalutamide.

FIG. 42A. Nuclear magnetic resonance (NMR). 1002 (250 μM) dissolved in deuterated DMSO (DMSO-d$_6$) was added to an NMR tube alone or in combination with 5 μM AF-1 purified protein. The intensity of nuclear spin was measured at different magnetic fields (6 ppm). The peaks between 7 and 8 correspond to the aromatic rings of 1002. FIG. 42B. Raman Spectroscopy. Raman spectra of 1002, AF-1 purified protein, and their mixtures is shown. Simulation of 1002 binding (trans conformation) to glycine. Binding energies of 1002 in trans conformation to different amino acids.

FIG. 43A. Steady state fluorescence emission spectra for purified AR-AF1 or AR-NTD proteins. AR-AF-1 or AR-N-terminus domain (NTD) (1 μM) and 1002 were pre-incubated for at least 30 minutes and steady state fluorescence was measured. The emission spectra were all corrected to buffer alone as necessary. FIG. 43B. $^3$H-1002 demonstrates binding to AR-NTD. HEK-293 cells were transfected with the indicated plasmids. Protein was extracted and incubated with the indicated compounds. Bound radioactive ligands were separated from unbound radioactive nucleotides using G-25 Sephadex columns. The incorporated radioactivity was counted in scintillation counter. FIG. 43C. Thermal shift assay. Thermal shift assay was performed in HEK-293 cells transfected with AR-NTD or AR-LBD as described in the methods. AR-androgen receptor; NTD-N-terminus domain; AF-1-activation function-1 domain.

FIG. 44A-44F demonstrate that AR N-terminus domain is sufficient for 1002 to degrade the AR. FIG. 44A. Map of the constructs used in studies to determine the domain important to degrade the AR. FIG. 44B. COS7 cells were transfected with 2.5 µg of the indicated constructs and HA-ubiquitin. Cells were treated 24 hours after transfection and harvested 24 hours after treatment. Western blot for AR and GAPDH (left panel) and GR and GAPDH (right panel) was performed. Bottom: COS7 cells were transfected with 2.5 µg of AR or AGG and HA-ubiquitin. Twenty-four hours after transfection, cells were treated with vehicle or 10 µM 1002 for 6 hours. Immunoprecipitation was performed with HA antibody and Western blot was performed with AR antibody. 10% loading control is shown below. FIG. 44C. COS7 cells were transfected with 0.25 µg GRE-LUC, 10 ng CMV-LUC, 25 ng of the respective receptor, and 0.25 µg HA-Ub. Cells were treated as indicated in the figure in combination with 0.1 nM R1881 or dexamethasone (Dex). Luciferase assay was performed 48 hours after treatment (n=3). * p<0.05. FIG. 44D. Tau-5 domain of the AR is important for 1002-dependent degradation of AR. COS7 cells were transfected with 2.5 µg of the indicated constructs and HA-ubiquitin and Western blot for AR using AR C19 antibody and GAPDH was performed (Right). HA-ubiquitin was immunoprecipitated and Western blot for AR was performed (Left). FIG. 44E. R-isomer (1020) and racemic mixture of 1002 antagonize the AR comparably to the S-isomer of 1002. COS7 cells were transfected with 0.25 µg GRE-LUC, 10 ng CMV-LUC, 25 ng cmv hAR. Cells were treated with a dose response of the indicated compounds in the presence of 0.1 nM R1881. Luciferase assay was performed 24 hours after treatment and firefly luciferase values were normalized to renilla luciferase. FIG. 44F. 1002 does not inhibit early induction of NDRG1 and MT2A pre-mRNAs. LNCaP cells maintained in charcoal-stripped serum-containing medium for 2 days were treated as indicated in the figures in triplicates. Cells were pre-treated with 10 µM 1002 for 30 minutes before treatment with 0.1 nM R1881. Cells were harvested, RNA isolated, and the expression of various pre-mRNAs was measured at the indicated time-points. All the experiments were repeated three times and a representative experiment is presented here. AR-androgen receptor; GR-glucocorticoid receptor; Ub-ubiquitin; dTau5-AR plasmid with transactivation function-5 (Tau5) domain deleted; NTD-N terminus domain; DBD-DNA binding domain; Hin-Hinge; LBD-ligand binding domain; Dex-dexamethasone; AGG-AR NTD, GR DBD and LBD; GAA-GR NTD, AR DBD and LBD.

FIG. 45A. 1002 degrades AR-SV. LNCaP-AR-V7 cells (LNCaP cells that stably express doxycycline-inducible AR-V7; left panel) or LNCaP-95 cells (middle panel) were maintained in charcoal-stripped serum-containing medium for 2 days. Doxycycline (10 ng/mL) was added to the LNCaP-AR-V7 cells during this period to induce the AR-V7 synthesis. After two days, medium was changed and the cells were treated with the indicated doses of 1002 (11 was used as a positive control in the left panel) for 24 hours. Protein was extracted and Western blot for the AR and GAPDH was performed. Bar graph shows the lack of effect on AR-V7 mRNA in the presence of 1002 under similar conditions. FIG. 45B. 1002 inhibits AR-V7-regulated gene. LNCaP-AR-V7 cells were maintained in charcoal-stripped serum-containing medium for 2 days. Cells were treated as indicated in the figure with 10 µM of the compounds in the presence of 0.1 nM R1881 or 10 ng/mL doxycycline (cells were pre-treated with 1002 for 30 minutes for combination with R1881 and for 24 hours for combination with doxycycline). Twenty four hours after treatment initiation the cells were harvested, RNA isolated, and the expression of FKBP5 or EDN2 was determined by realtime PCR. Gene expression values were normalized to the expression of GAPDH. * p<0.05. FIG. 45C. 1002 inhibits recruitment of AR and AR-V7 to promoters of responsive genes. LNCaP-ARV7 cells were maintained in charcoal stripped serum-containing medium for 2 days. Medium was changed and the cells were treated with 10 µM 1002 or enzalutamide in the presence of 0.1 nM R1881 (AR ChIP) or 10 ng/mL doxycycline (AR-V7 ChIP) for 6 hours (cells were pre-treated with 1002 for 30 minutes). ChIP assay was performed with AR antibody or AR-V7 antibody and real time PCR for the indicated DNA regions was performed. ChIP assays were performed at least three independent times and a representative experiment is shown here. FIG. 45D. 1002 inhibits recruitment of AR-V7 in 22RV1 cells. 22RV1 cells were maintained in charcoal stripped serum-containing medium for 2 days. Medium was changed and the cells were treated with 10 µM 1002, or enzalutamide in the presence of 0.1 nM R1881 for 6 hours (cells were pre-treated with 1002 for 30 minutes). ChIP assay was performed with AR-V7 antibody and real time PCR for the indicated DNA regions was performed. ChIP assays were performed at least three independent times and a representative experiment is shown here.

FIG. 46A(i), 46A(ii), 46A(iii). 1002 inhibits the expression of AR-target genes in LNCaP cells. LNCaP cells maintained in charcoal-stripped serum-containing medium for 2 days were treated with a dose response of 1002 or enzalutamide in the presence of 0.1 nM R1881. RNA was isolated 24 hours after treatment and the expression of PSA (FIG. 46A(i)) and FKBP5 (FIG. 46A(ii)) was quantified and normalized to GAPDH using real time PCR primers and probes. For the growth assay (FIG. 46A(iii)), cells were maintained and treated as indicated above for the gene expression studies, but were treated for 6 days with medium change and retreatment after 3 days. Sulforhodamine B (SRB) assay was performed to determine the number of viable cells. FIG. 46B. 1002 inhibits the expression of AR-target genes in enzalutamide-resistant cells. Enzalutamide-resistant AR-expressing LNCaP cells (MR49F) were cultured and treated as indicated in panel A. RNA was isolated and the expression of AR-target gene FKBP5 (top panel) was measured and normalized to GAPDH using realtime PCR primers and probe. Growth assay in MR49F cells was performed as indicated for LNCaP cells (bottom panel).

FIG. 47A-47B demonstrate that 1002 does not inhibit proliferation of AR-negative cells. FIG. 47A. PC-3 cells were plated in 1% charcoal-stripped serum-containing medium. Cells were treated with 1 or 10 μM of 1002 in the presence of 0.1 nM R1881. Cells were re-treated three days later and the number of viable cells was measured by cell titer glo assay. FIG. 47B. 1002 inhibits PSA expression and cell proliferation in enzalutamide-resistant VCaP (MDVR) cells. MDVR cells were plated in 1% charcoal stripped serum-containing medium. Cells were treated for 24 hours (left panel) or for 6 days (right panel). Expression of PSA was measured and normalized to GAPDH (left panel). Number of viable cells was measured by cell titer glo assay (right panel). * $p<0.05$. Enza-enzalutamide.

FIGS. 48A-48E demonstrate that 1002 has appropriate pharmacokinetic and pharmacodynamic properties. FIG. 48A-48B. 1002 is stable up to 24 hours in rats. Sprague Dawley rats (n=3-6/group) were dosed once with the indicated doses of 1002 once (A) or for 7 days (B). Blood was collected at the indicated time points on day 1 (A) or day 7 (B) and the amount of 1002 remaining in the plasma was measured using LC-MS/MS method. FIG. 48C. 1002 inhibits seminal vesicles weight in mice and prostate and seminal vesicles weight in rats. C57BL6 mice (top panel) weighing 20-25 grams (n=5/group) or Sprague Dawley rats (middle and bottom) weighing 200-250 grams (n=5/group) were treated orally with vehicle (15% DMSO+85% PEG-300) or the indicated doses of 1002 or enzalutamide. Animals were sacrificed after 14 days (top and middle) or after 4 days (bottom) of treatment and weights of prostate and seminal vesicles were recorded and normalized to body weight. The values are represented as percent change from vehicle-treated animals. FIG. 48D. 1002 penetrates and gets accumulated in the tumors. Drug was extracted from serum and tumors shown in FIG. 48E and 1002 was measured using LC-MS/MS (n=4/group). FIG. 48E. 1002 inhibits proliferation and increases apoptosis. Formalin-fixed tumor samples from FIG. 48E were stained for Ki67 (top panel) and TUNEL (bottom panel). Percent stained cells were quantified using an automated software. Seminal vesicles weight normalized to body weight is expressed as percent change from vehicle control (FIG. 48F) * $p<0.05$; ** $p<0.01$. mpk=mg/kg body weight. PK-pharmacokinetic; PD-pharmacodynamic.

FIG. 49A-49E demonstrate that 1002 inhibits the growth of androgen-dependent and enzalutamide-refractory castration-resistant prostate cancer xenografts. FIG. 49A. 1002 inhibits growth of enzalutamide-resistant xenograft. Enzalutamide-resistant LNCaP cells (MR49F) were implanted subcutaneously in NSG mice. Once the tumors reached 100-200 mm³, the animals were castrated and the tumors were allowed to develop as castration-resistant tumors. Once the tumors reach 200-300 mm³, the animals (n=8-10/group) were randomized and treated orally with vehicle (15% DMSO+85% PEG-300) or the indicated doses of 1002. Tumor volume was measured twice weekly. Animals were sacrificed on day 30 and tumor weights were recorded. Values are represented as average ±S.E. * $P<0.05$;  $P<0.01$. FIG. 49B. 1002 regresses tumors in immune-compromised rats. VCaP prostate cancer cells (10 million) were mixed with 50% matrigel implanted subcutaneously in SRG immune-compromised rats. Once the tumors reached 1000-2000 mm³, the animals were castrated and the tumors were allowed to regrow as CRPC. Once the tumors grew after castration to 2000 mm³, the animals were randomized and treated orally with vehicle (DMSO+PEG-300 (15:85)), 30 mg/kg enzalutamide, or 60 mg/kg 1002. Tumor volume was measured thrice weekly. Lines in the box indicate that the tumors in the treated groups are significantly different at $p<0.01$ to 0.001 from the vehicle group on the respective days. FIG. 49C. 1002 regresses the growth of enzalutamide-resistant VCaP tumors (MDVR). Tumor studies were conducted as indicated in panel B in SRG rats with MDVR enzalutamide-resistant VCaP cells. Western blot. Protein extracts from the tumors were fractionated on a SDS-PAGE and were Western blotted with AR and GAPDH antibodies. FIG. 49D. 1002 regresses tumors in intact SRG rats. MDVR cells (10 million) were implanted subcutaneously. Once the tumors reach above 2000 mm³, the animals were randomized and treated orally with vehicle, 30 mg/kg enzalutamide, or 60 mg/kg 1002. Individual animal data are presented. Serum PSA was measured using ELISA in three rats (one from each group) and represented in the bottom right panel. Western blots for AR and GAPDH are shown in the lower panel. FIG. 49**E. 1002 dose-dependently inhibits MDVR tumor growth in intact SRG rats. Xenograft studies were conducted in intact rats (n=5/group) as indicated above with a dose response of 1002. Tumor volume was measured thrice weekly. Lines in the box indicate that the tumors in the treated groups are significantly different at $p<0.01$ to 0.001 from the vehicle group on the respective days. Tumor weights and serum PSA were recorded at the end of the treatment period. Mpk-mg/kg body weight; Enza-enzalutamide.

FIGS. 50A-50D demonstrate that the synthesis of ³H-1002 produced a product that was pure by HPLC analysis (FIG. 50A) in which the radioactivity and UV absorption eluted at the same retention times as determined by HPLC using two different detectors (FIG. 50B); and mass spectroscopic analysis indicated that the tritium was added as seen in the 2 proton shift in m/z ratio (FIG. 50C) which possessed 16 Ci/mmol of radioactivity at m/z 359 but no radioactivity in the parent at m/z 357 (FIG. 50D). Taken together, this demonstrates successful synthesis of ³H-1002.

Figure 1A:
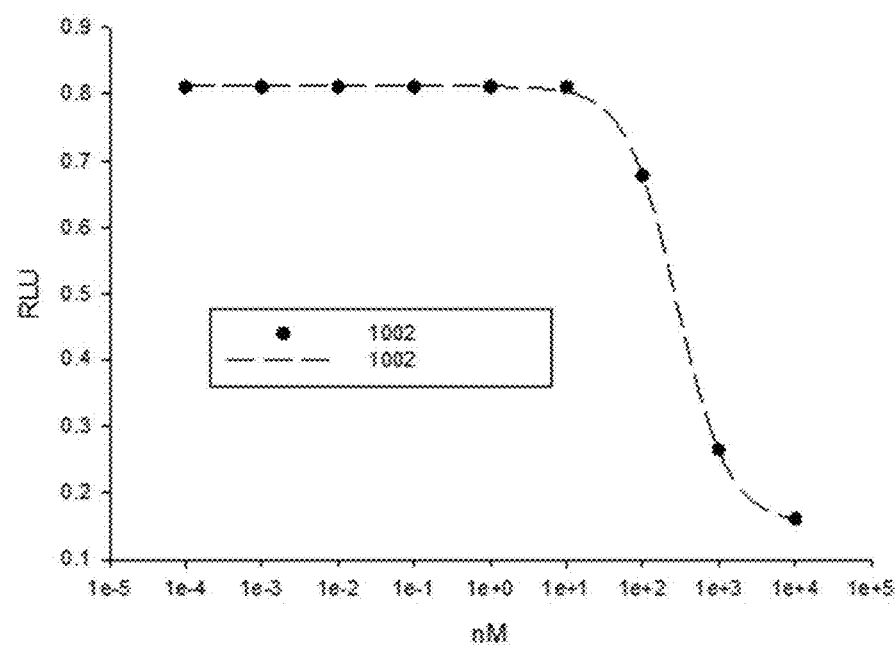
FIGS. 1A-1C: The transactivation result of 1002 was reported based on measured luciferase light emissions and reported as relative light unit intensity (RLU).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as enzalutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741 and T877 within AR converts bicalutamide and hydroxyflutamide, respectively, to agonists. Similarly, increased intracellular cytokines recruit coactivators instead of corepressors to AR-responsive promoters subsequently converting bicalutamide to an agonist. Similarly, mutations that have been linked to enzalutamide resistance include F876, H874, T877, and di-mutants T877/5888, T877/D890, F876/T877 (i.e., MR49 cells), and H874/T877 (Genome Biol. (2016) 17:10 (doi: 10.1186/s13059-015-0864-1)). Abiraterone resistance mutations include L702H mutations which results in activation of the AR by glucocorticoids such as prednisone, causing resistance to abiraterone because abiraterone is usually prescribed in combination with prednisone. If resistance develops to enzalutamide then often the patient is refractory to abiraterone also and vice versa; or the duration of response is very short. This situation highlights the need for a definitive androgen ablation therapy to prevent AR reactivation in advanced prostate cancers.

Despite initial response to androgen deprivation therapy (ADT), PCa disease progression is inevitable and the cancer emerges as castration-resistant prostate cancer (CRPC). The primary reason for castration resistant prostate cancer (CRPC) re-emergence is re-activation of androgen receptor (AR) by alternate mechanisms such as:
(a) intracrine androgen synthesis;
(b) expression of AR splice variants (AR-SV), e.g., that lack ligand binding domain (LBD);
(c) AR-LBD mutations with potential to resist antagonists;
(d) hyper-sensitization of AR to low androgen levels, e.g., due to AR gene amplification or AR mutation;
(e) amplification of the AR gene within the tumor; and
(f) over expression of coactivators and/or altered intracellular signal transduction.

The invention encompasses novel selective androgen receptor degrader (SARD) compounds encompassed by formula I, which inhibit the growth of prostate cancer (PCa) cells and tumors that are dependent on AR full length (AR-FL) including pathogenic and resistance mutations and wildtype, and/or AR splice variants (AR-SV) for proliferation.

As used herein, unless otherwise defined, a "selective androgen receptor degrader" (SARD) compound is an androgen receptor antagonist capable of inhibiting the growth of PCa cells and tumors that are dependent on AR-full length (AR-FL) and/or AR splice variants (AR-SV) for proliferation. The SARD compound may not bind to ligand binding domain (LBD). Alternatively, a "selective androgen receptor degrader" (SARD) compound is an androgen receptor antagonist capable of causing degradation of a variety of pathogenic mutant variant AR's and wildtype AR and hence are capable of exerting anti-androgenism is a wide variety of pathogenic altered cellular environments found in the disease states embodied in this invention. In one embodiment, the SARD is orally active. In another embodiment, the SARD is applied topically to the site of action.

The SARD compound may bind to the N-terminal domain (NTD) of the AR; to an alternate binding and degradation domain (BDD) of the AR; to both the AR ligand binding domain (LBD) and to an alternate binding and degradation domain (BDD); or to both the N-terminal domain (NTD) and to the ligand binding domain (LBD) of the AR. In one embodiment, the BDD may be located in the NTD. In one embodiment, the BDD is located in the AF-1 region of the NTD. Alternatively, the SARD compound may be capable of: inhibiting growth driven by the N-terminal domain (NTD)-dependent constitutively active AR-SV; or inhibiting the AR through binding to a domain that is distinct from the AR LBD. Also, the SARD compound may be a strong (i.e., highly potent and highly efficacious) selective androgen receptor antagonist, which antagonizes the AR stronger than other known AR antagonists (e.g., enzalutamide, bicalutamide and abiraterone).

The SARD compound may be a selective androgen receptor antagonist, which targets AR-SVs, which cannot be inhibited by conventional antagonists. The SARD compound may exhibit any one of several activities including, but not limited to: AR-SV degradation activity; AR-FL degradation activity; AR-SV inhibitory activity (i.e., is an AR-SV antagonist); AR-FL inhibitory activity (i.e., is an AR-FL antagonist); inhibition of the constitutive activation of AR-SVs; or inhibition of the constitutive activation of AR-FLs. Alternatively, the SARD compound may possess dual AR-SV degradation and AR-SV inhibitory functions, and/or dual AR-FL degradation and AR-FL inhibitory functions; or alternatively possess all four of these activities.

The SARD compound may also degrade AR-FL and AR-SV. The SARD compound may degrade the AR through binding to a domain that is distinct from the AR LBD. The SARD compound may possess dual degradation and AR-SV inhibitory functions that are distinct from any available CRPC therapeutics. The SARD compound may inhibit the re-activation of the AR by alternate mechanisms such as: intracrine androgen synthesis, expression of AR-SV that lack ligand binding domain (LBD) and AR-LBD mutations with potential to resist antagonists, or inhibit re-activated androgen receptors present in pathogenic altered cellular environments.

Examples of AR-splice variants include, but are not limited to, AR-V7 and ARv567es (a.k.a. AR-V12; S. Sun, et al. Castration resistance in human prostate cancer is conferred by a frequently occurring androgen receptor splice variant. *J Clin Invest*. (2010) 120(8), 2715-2730). Nonlimiting examples of AR mutations conferring antiandrogen resistance are: W741L, T877A, and F876L (J. D. Joseph et al. A clinically relevant androgen receptor mutation confers resistance to second-generation antiandrogens enzalutamide and ARN-509. *Cancer Discov*. (2013) 3(9), 1020-1029) mutations. Many other LBD resistance conferring mutations are known in the art and will continue to be discovered. AR-V7 is a splice variant of AR that lacks the LBD (A. H. Bryce & E. S. Antonarakis. Androgen receptor splice variant 7 in castration-resistant prostate cancer: Clinical considerations. *Int J Urol*. (2016 Jun. 3) 23(8), 646-53. doi: 10.1111/iju.13134). It is constitutively active and has been demonstrated to be responsible for aggressive PCa and resistance to endocrine therapy.

The invention encompasses novel selective androgen receptor degrader (SARD) compounds of formulas I-IX, IA-ID, IIA, IIB, VIIA, VIIB, VIIIA, VIIIB, IXA or IXB which bind to the AR through an alternate binding and degradation domain (BDD), e.g., the NTD or AF-1. The SARDs may further bind the AR ligand binding domain (LBD).

The SARD compounds may be used in treating CRPC that cannot be treated with any other antagonist. The SARD compounds may treat CRPC by degrading AR-SVs. The SARD compounds may maintain their antagonistic activity in AR mutants that normally convert AR antagonists to agonists. For instance, the SARD compounds maintain their antagonistic activity to AR mutants W741L, T877A, and F876L (J. D. Joseph et al. A clinically relevant androgen receptor mutation confers resistance to second-generation antiandrogens enzalutamide and ARN-509. *Cancer Discov.* (2013) 3(9), 1020-1029). Alternatively, the SARD compounds elicit antagonistic activity within an altered cellular environment in which LBD-targeted agents are not effective or in which NTD-dependent AR activity is constitutively active.

Selective Androgen Receptor Degrader (SARD) Compounds

The invention encompasses selective androgen receptor degrader (SARD) compounds represented by the structure of formula I:

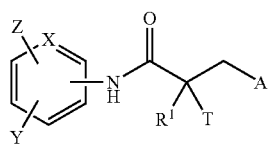

I wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, CON$(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, or a racemic mixture thereof, isomer, pharmaceutically acceptable salt, pharmaceutical product, polymorph, hydrate or any combination thereof.

In various embodiments, the SARD compound of formula I has a chiral carbon. In other embodiments, the SARD compound of formula I is a racemic mixture. In other embodiments, the SARD compound of formula I is an (S) isomer. In other embodiments, the SARD compound of formula I is an (R) isomer.

The invention encompasses selective androgen receptor degrader (SARD) compounds represented by the structure of formula IA:

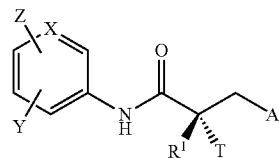

IA wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, CON$(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof.

The invention encompasses selective androgen receptor degrader (SARD) compounds represented by the structure of formula IB:

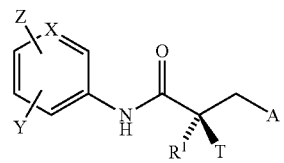

IB wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR, or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a five or six-membered saturated or unsaturated ring having at least one nitrogen atom and 0, 1, or 2 double bonds, optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
R$^3$ is NHR$^2$, halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof.

The invention encompasses selective androgen receptor degrader (SARD) compounds represented by the structure of formula IC:

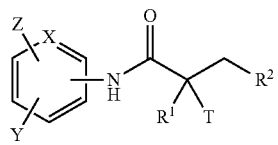

IC wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
R$^2$ is a five or six-membered saturated or unsaturated ring having at least one nitrogen atom and 0, 1, or 2 double bonds, optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
or its optical isomer or a racemic mixture thereof, isomer, pharmaceutically acceptable salt, pharmaceutical product, polymorph, hydrate or any combination thereof.

The invention encompasses selective androgen receptor degrader (SARD) compounds represented by the structure of formula ID:

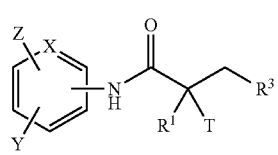

ID wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
R$^3$ is NHR$^2$, halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ H, is alkyl, haloalkyl, cycloalkyl, aryl or heteroaryl, wherein said alkyl, haloalkyl, cycloalkyl, aryl or heteroaryl groups are optionally substituted;
or its optical isomer or a racemic mixture thereof, isomer, pharmaceutically acceptable salt, pharmaceutical product, polymorph, hydrate or any combination thereof;
wherein if R$^3$ is Br or I, R$^1$ is CH$_3$, and T is OH, then X is N or the aniline ring forms a fused heterocyclic ring.

The invention encompasses a SARD compound represented by the structure of formula II:

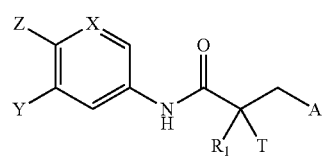

II wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$, $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its optical isomer or a racemic mixture thereof, isomer, pharmaceutically acceptable salt, pharmaceutical product, polymorph, hydrate or any combination thereof.

In various embodiments, the SARD compound of formula II has a chiral carbon. In other embodiments, the SARD compound of formula II is a racemic mixture. In other embodiments, the SARD compound of formula II is an (S) isomer. In other embodiments, the SARD compound of formula II is an (R) isomer.

The invention encompasses a SARD compound represented by the structure of formula IIA:

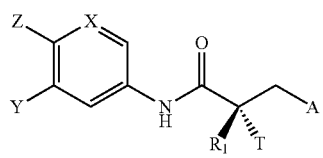

IIA wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$, $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof.

The invention encompasses a SARD compound represented by the structure of formula IIB:

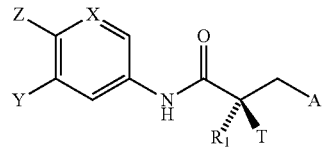

IIB wherein
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
T is H, OH, OR, OCOR, $CH_3$, —$NHCOCH_3$, or NHCOR;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ a pyrrole, pyrroline, pyrrolidine, pyrazole, pyrazoline, pyrazolidine, triazole, imidazole, imidazoline, imidazolidine, or morpholine ring, said ring optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$, $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its isomer or a racemic mixture thereof, pharmaceutically acceptable salt, pharmaceutical product, polymorph, hydrate or any combination thereof.

The invention encompasses a SARD compound represented by the structure of formula III:

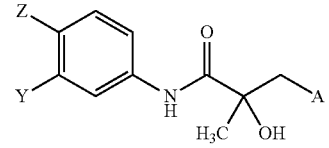

III wherein

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;

A is $R^2$ or $R^3$;

$R^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its optical isomer or a racemic mixture thereof, isomer, pharmaceutically acceptable salt, pharmaceutical product, polymorph, hydrate or any combination thereof.

In various embodiments, the SARD compound of formula III has a chiral carbon. In other embodiments, the SARD compound of formula III is a racemic mixture. In other embodiments, the SARD compound of formula III is an (S) isomer. In other embodiments, the SARD compound of formula III is an (R) isomer.

The invention encompasses a selective androgen receptor degrader compound represented by the structure of formula IV:

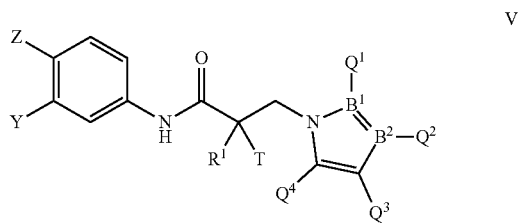

IV wherein $B^1$, $B^2$, $B^3$, and $B^4$ are each independently carbon or nitrogen;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^1$, $Q^2$, $Q^3$, or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; wherein if $B^1$, $B^2$, $B^3$, or $B^4$ is nitrogen then $Q^1$, $Q^2$, $Q^3$, or $Q^4$, respectively, is nothing; or its optical isomer or a racemic mixture thereof, isomer, pharmaceutically acceptable salt, pharmaceutical product, polymorph, hydrate or any combination thereof.

In various embodiments, the SARD compound of formula IV has a chiral carbon. In other embodiments, the SARD compound of formula IV is a racemic mixture. In other embodiments, the SARD compound of formula IV is an (S) isomer. In other embodiments, the SARD compound of formula IV is an (R) isomer.

The invention encompasses a selective androgen receptor degrader compound represented by the structure of formula V:

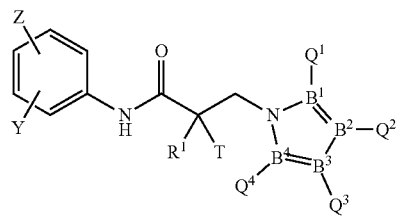

V wherein $B^1$ and $B^2$ are each independently carbon or nitrogen;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^1$, $Q^2$, $Q^3$, or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; wherein if $B^1$ or $B^2$ is nitrogen then $Q^1$ or $Q^2$, respectively, is nothing; or its optical isomer, or a racemic mixture thereof isomer, pharmaceutically acceptable salt, pharmaceutical product, polymorph, hydrate or any combination thereof.

In various embodiments, the SARD compound of formula V has a chiral carbon. In other embodiments, the SARD compound of formula V is a racemic mixture. In other embodiments, the SARD compound of formula V is an (S) isomer. In other embodiments, the SARD compound of formula V is an (R) isomer.

The invention encompasses a selective androgen receptor degrader compound represented by the structure of formula VI:

VI wherein
- - - - - - is a single or double bond;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^1$, Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its optical isomer, or a racemic mixture thereof, isomer, pharmaceutically acceptable salt, pharmaceutical product, polymorph, hydrate or any combination thereof.

In various embodiments, the SARD compound of formula VI has a chiral carbon. In other embodiments, the SARD compound of formula VI is a racemic mixture. In other embodiments, the SARD compound of formula VI is an (S) isomer. In other embodiments, the SARD compound of formula VI is an (R) isomer.

The invention encompasses a selective androgen receptor degrader compound represented by the structure of formula VII:

VII wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its optical isomer, or a racemic mixture thereof, isomer, pharmaceutically acceptable salt, pharmaceutical product, polymorph, hydrate or any combination thereof.

In various embodiments, the SARD compound of formula VII has a chiral carbon. In other embodiments, the SARD compound of formula VII is a racemic mixture. In other embodiments, the SARD compound of formula VII is an (S) isomer. In other embodiments, the SARD compound of formula VII is an (R) isomer.

The invention encompasses a selective androgen receptor degrader compound represented by the structure of formula VIIA:

VIIA wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

The invention encompasses a selective androgen receptor degrader compound represented by the structure of formula VIIB:

VIIB wherein

X is CH or N;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

In another embodiment, the invention encompasses a selective androgen receptor degrader compound represented by the structure of formula VIII:

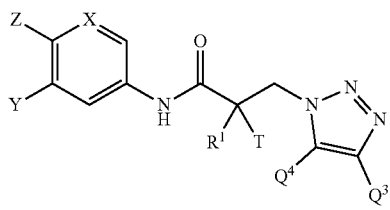

VIII wherein

X is CH or N;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and Q$^3$ and Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its optical isomer, or a racemic mixture thereof isomer, pharmaceutically acceptable salt, pharmaceutical product, polymorph, hydrate or any combination thereof.

In another embodiment, the invention encompasses a selective androgen receptor degrader compound represented by the structure of formula VIIIA:

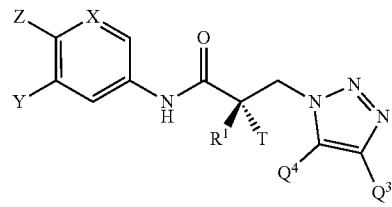

VIIIA wherein

X is CH or N;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and Q$^3$ and Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

In another embodiment, the invention encompasses a selective androgen receptor degrader compound represented by the structure of formula VIIIB:

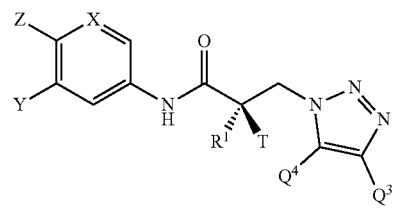

VIIIB wherein

X is CH or N;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;

and

Q$^3$ and Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

In another embodiment, the invention encompasses a selective androgen receptor degrader compound represented by the structure of formula IX:

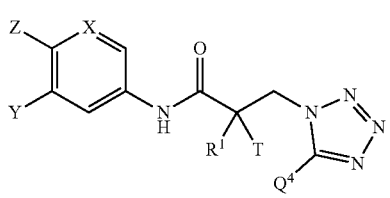

IX wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^4$ is selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its optical isomer, or a racemic mixture thereof, isomer, pharmaceutically acceptable salt, pharmaceutical product, polymorph, hydrate or any combination thereof.

In another embodiment, the invention encompasses a selective androgen receptor degrader compound represented by the structure of formula IXA:

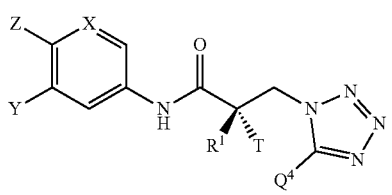

IXA wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
Q$^4$ is selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

In another embodiment, the invention encompasses a selective androgen receptor degrader compound represented by the structure of formula IXB:

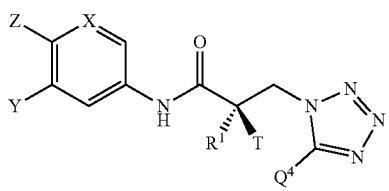

IXB wherein
X is CH or N;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
R$^1$ is H, CH$_3$, CH$_2$F, CHF$_2$, CF$_3$, CH$_2$CH$_3$, or CF$_2$CF$_3$;
T is H, OH, OR, OCOR, CH$_3$, —NHCOCH$_3$, or NHCOR;
or T and R$^1$ form a 3-8 carbocyclic or heterocyclic ring;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
and
Q$^4$ is selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

In one embodiment, A of formula I-III, IA, IB, IIA, and IIB and R$^2$ of formula IC is a five or six-membered saturated or unsaturated ring having at least one nitrogen atom. In another embodiment, A is a substituted or unsubstituted pyrrole, pyrroline, pyrrolidine, pyrazole, pyrazoline, pyrazolidine, imidazole, imidazoline, imidazolidine, triazole, tetrazole, pyridine, morpholine, or other heterocyclic ring. Each represents a separate embodiment of this invention. In another embodiment, A is a five or six-membered heterocyclic ring. In another embodiment, a nitrogen atom of the five or six membered saturated or unsaturated ring is attached to the backbone structure of the molecule. In another embodiment, a carbon atom of the five or six membered saturated or unsaturated ring is attached to the backbone structure of the molecule.

In one embodiment, A of formula I-III, IA, IB, IIA, and IIB and R$^3$ of formula ID is NHR$^2$, halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; wherein R$^4$ is H, alkyl, haloalkyl, cycloalkyl, aryl or heteroaryl, wherein said alkyl, haloalkyl, cycloalkyl, aryl or heteroaryl groups are optionally substituted.

In one embodiment, A of formula I-III, IA, IB, IIA, and IIB and $R^3$ of formula ID is $NHR^2$. In one embodiment, A of formula I-III, IA, IB, IIA, and IIB and $R^3$ of formula ID is halide. In one embodiment, A of formula I-III, IA, IB, IIA, and IIB and $R^3$ of formula ID is F. In one embodiment, A of formula I-III, IA, IB, IIA, and IIB and $R^3$ of formula ID is Br. In one embodiment, A of formula I-III, IA, IB, IIA, and IIB and $R^3$ of formula ID is Cl. In one embodiment, A of formula I-III, IA, IB, IIA, and IIB and $R^3$ of formula ID is I. In one embodiment, A of formula I-III, IA, IB, IIA, and IIB and $R^3$ of formula ID is $N_3$. In one embodiment, A of formula I-III, IA, IB, IIA, and IIB and $R^3$ of formula ID is $OR^4$. In one embodiment, A of formula I-III, IA, IB, IIA, and IIB and $R^3$ of formula ID is $CF_3$. In one embodiment, A of formula I-III, IA, IB, IIA, and IIB and $R^3$ of formula ID is $COR^4$. In one embodiment, A of formula I-III, IA, IB, IIA, and IIB and $R^3$ of formula ID is COCl. In one embodiment, A of formula I-III, IA, IB, IIA, and IIB and $R^3$ of formula ID is $COOCOR^4$. In one embodiment, A of formula I-III, IA, IB, IIA, and IIB and $R^3$ of formula ID is $COOR^4$. In one embodiment, A of formula I-III, IA, IB, IIA, and IIB and $R^3$ of formula ID is $OCOR^4$. In one embodiment, A of formula I-III, IA, IB, IIA, and IIB and $R^3$ of formula ID is $OCONHR^4$. In one embodiment, A of formula I-III, IA, IB, IIA, and IIB and $R^3$ of formula ID is $NHCOOR^4$. In one embodiment, A of formula I-III, IA, IB, IIA, and IIB and $R^3$ of formula ID is $NHCONHR^4$. In one embodiment, A of formula I-III, IA, IB, IIA, and IIB and $R^3$ of formula ID is $OCOOR^4$. In one embodiment, A of formula I-III, IA, IB, IIA, and IIB and $R^3$ of formula ID is CN. In one embodiment, A of formula I-III, IA, IB, IIA, and IIB and $R^3$ of formula ID is $CON(R^4)_2$. In one embodiment, A of formula I-III, IA, IB, IIA, and IIB and $R^3$ of formula ID is $SR^4$. In one embodiment, A of formula I-III, IA, IB, IIA, and IIB and $R^3$ of formula ID is $SO_2R^4$. In one embodiment, A of formula I-III, IA, IB, IIA, and IIB and $R^3$ of formula ID is $SOR^4$. In one embodiment, A of formula I-III, IA, IB, IIA, and IIB and $R^3$ of formula ID is $SO_3H$. In one embodiment, A of formula I-III, IA, IB, IIA, and IIB and $R^3$ of formula ID is $SO_2NH_2$. In one embodiment, A of formula I-III, IA, IB, IIA, and IIB and $R^3$ of formula ID is $SO_2NH(R^4)$. In one embodiment, A of formula I-III, IA, IB, IIA, and IIB and $R^3$ of formula ID is $SO_2N(R^4)_2$. In one embodiment, A of formula I-III, IA, IB, IIA, and IIB and $R^3$ of formula ID is $NH_2$. In one embodiment, A of formula I-III, IA, IB, IIA, and IIB and $R^3$ of formula ID is $NH(R^4)$. In one embodiment, A of formula I-III, IA, IB, IIA, and IIB and $R^3$ of formula ID is $N(R^4)_2$. In one embodiment, A of formula I-III, IA, IB, IIA, and IIB and $R^3$ of formula ID is $CONH_2$. In one embodiment, A of formula I-III, IA, IB, IIA, and IIB and $R^3$ of formula ID is $CONH(R^4)$. In one embodiment, A of formula I-III, IA, IB, IIA, and IIB and $R^3$ of formula ID is CO(N-heterocycle). In one embodiment, A of formula I-III, IA, IB, IIA, and IIB and $R^3$ of formula ID is $NO_2$. In one embodiment, A of formula I-III, IA, IB, IIA, and IIB and $R^3$ of formula ID is cyanate. In one embodiment, A of formula I-III, IA, IB, IIA, and IIB and $R^3$ of formula ID is isocyanate. In one embodiment, A of formula I-III, IA, IB, IIA, and IIB and $R^3$ of formula ID is thiocyanate. In one embodiment, A of formula I-III, IA, IB, IIA, and IIB and $R^3$ of formula ID is isothiocyanate. In one embodiment, A of formula I-III, IA, IB, IIA, and IIB and $R^3$ of formula ID is mesylate. In one embodiment, A of formula I-III, IA, IB, IIA, and IIB and $R^3$ of formula ID is tosylate. In one embodiment, A of formula I-III, IA, IB, IIA, and IIB and $R^3$ of formula ID is triflate. In one embodiment, A of formula I-III, IA, IB, IIA, and IIB and $R^3$ of formula ID is $PO(OH)_2$. In one embodiment, A of formula I-III, IA, IB, IIA, and IIB and $R^3$ of formula ID is $OPO(OH)_2$. In one embodiment, if A is Br or I, $R^1$ is $CH_3$, and T is OH, then X is N or the aniline ring forms a fused heterocyclic ring In one embodiment $R^4$ is H, alkyl, haloalkyl, cycloalkyl, aryl or heteroaryl, wherein said alkyl, haloalkyl, cycloalkyl, aryl or heteroaryl groups are optionally substituted. Each represents a separate embodiment of this invention. In other embodiment, $R^4$ is H. In other embodiments, $R^4$ is alkyl. In other embodiments, the alkyl is methyl, ethyl, propyl, iso-propyl, butyl, t-butyl, pentyl, neopentyl, iso-pentyl, hexyl, or heptyl, each represents a separate embodiment of this invention. In other embodiments, $R^4$ is haloalkyl In another embodiment, the haloalkyl is $CF_3$, $CF_2CF_3$, iodomethyl, bromomethyl, bromoethyl, bromopropyl, each represents a separate embodiment of the invention. In other embodiments, $R^4$ is cycloalkyl. In other embodiments the cycloalkyl is cyclobutyl, cyclopentyl, cyclohexyl. In various embodiments, the alkyl, haloalkyl, cycloalkyl, aryl or heteroaryl of $R^4$ are further substituted by one or more groups selected from: halide, CN, $CO_2H$, OH, SH, $NH_2$, $NO_2$, $CO_2$—($C_1$-$C_6$ alkyl) or O—($C_1$-$C_6$ alkyl); each represents a separate embodiment of this invention.

In a particular embodiment of formulas I-VI, IA-IC, IIA, or IIB, $Q^1$ is hydrogen. In a particular embodiment of formulas I-VI, IA-IC, IIA, or IIB, $Q^1$ is CN. In a particular embodiment of formulas I-VI, IA-IC, IIA, or IIB, $Q^1$ is F. In a particular embodiment of formulas I-VI, IA-IC, IIA, or IIB, $Q^1$ is NCS. In a particular embodiment of formulas I-VI, IA-IC, IIA, or IIB, $Q^1$ is maleimide. In a particular embodiment of formulas I-VI, IA-IC, IIA, or IIB, $Q^1$ is NHCOOR. In a particular embodiment of formulas I-VI, IA-IC, IIA, or IIB, $Q^1$ is $N(R)_2$. In a particular embodiment of formulas I-VI, IA-IC, IIA, or IIB, $Q^1$ is CONHR. In a particular embodiment of formulas I-VI, IA-IC, IIA, or IIB, $Q^1$ is NHCOR. In a particular embodiment of formulas I-VI, IA-IC, IIA, or IIB, $Q^1$ is Cl. In a particular embodiment of formulas I-VI, IA-IC, IIA, or IIB, $Q^1$ is Br. In a particular embodiment of formulas I-VI, IA-IC, IIA, or IIB, $Q^1$ is I. In a particular embodiment of formulas I-VI, IA-IC, IIA, or IIB, $Q^1$ is $NO_2$. In a particular embodiment of formulas I-VI, IA-IC, IIA, or IIB, $Q^1$ is phenyl. In a particular embodiment of formulas I-VI, IA-IC, IIA, or IIB, $Q^1$ is 4-fluorophenyl. In a particular embodiment of formulas I-VI, IA-IC, IIA, or IIB, $Q^1$ is $CF_3$. In a particular embodiment of formulas I-VI, IA-IC, IIA, or IIB, $Q^1$ is substituted or unsubstituted alkyl. In a particular embodiment of formulas I-VI, IA-IC, IIA, or IIB, $Q^1$ is substituted or unsubstituted cycloalkyl. In a particular embodiment of formulas I-VI, IA-IC, IIA, or IIB, $Q^1$ is substituted or unsubstituted heterocycloalkyl. In a particular embodiment of formulas I-VI, IA-IC, IIA, or IIB, $Q^1$ is haloalkyl. In a particular embodiment of formulas I-VI, IA-IC, IIA, or IIB, $Q^1$ is substituted or unsubstituted aryl. In a particular embodiment of formulas I-VI, IA-IC, IIA, or IIB, $Q^1$ is hydroxyl. In a particular embodiment of formulas I-VI, IA-IC, IIA, or IIB, $Q^1$ is alkoxy. In a particular embodiment of formulas I-VI, IA-IC, IIA, or IIB, $Q^1$ is OR. In a particular embodiment of formulas I-VI, IA-IC, IIA, or IIB, $Q^1$ is arylalkyl. In a particular embodiment of formulas I-VI, IA-IC, IIA, or IIB, $Q^1$ is amine. In a particular embodiment of formulas I-VI, IA-IC, IIA, or IIB, $Q^1$ is amide. In a particular embodiment of formulas I-VI, IA-IC, IIA, and IIB, $Q^1$ is COOR. In a particular embodiment of formulas I-VI, IA-IC, IIA, or IIB, $Q^1$ is COR. In a particular embodiment of formulas I-VI, IA-IC, IIA, or IIB, $Q^1$ is keto.

In a particular embodiment of formulas I-VII, IA-IC, IIA, IIB, VIIA, or VIIB, $Q^2$ is CN. In a particular embodiment of formulas I-VII, IA-IC, IIA, IIB, VIIA, or VIIB, $Q^2$ is hydrogen. In a particular embodiment of formulas I-VII, IA-IC, IIA, IIB, VIIA, or VIIB, $Q^2$ is keto. In a particular embodiment of formulas I-VII, IA-IC, IIA, IIB, VIIA, or VIIB, $Q^2$ is NCS. In a particular embodiment of formulas I-VII, IA-IC, IIA, IIB, VIIA, or VIIB, $Q^2$ is maleimide. In a particular embodiment of formulas I-VII, IA-IC, IIA, IIB, VIIA, or VIIB, $Q^2$ is NHCOOR. In a particular embodiment of formulas I-VII, IA-IC, IIA, IIB, VIIA, or VIIB, $Q^2$ is $N(R)_2$. In a particular embodiment of formulas I-VII, IA-IC, IIA, IIB, VIIA, or VIIB, $Q^2$ is CONHR. In a particular embodiment of formulas I-VII, IA-IC, IIA, IIB, VIIA, or VIIB, $Q^2$ is NHCOR. In a particular embodiment of formulas I-VII, IA-IC, IIA, IIB, VIIA, or VIIB, $Q^2$ is F. In a particular embodiment of formulas I-VII, IA-IC, IIA, IIB, VIIA, or VIIB, $Q^2$ is Cl. In a particular embodiment of formulas I-VII, IA-IC, IIA, IIB, VIIA, or VIIB, $Q^2$ is Br. In a particular embodiment of formulas I-VII, IA-IC, IIA, IIB, VIIA, or VIIB, $Q^2$ is I. In a particular embodiment of formulas I-VII, IA-IC, IIA, IIB, VIIA, or VIIB, $Q^2$ is $NO_2$. In a particular embodiment of formulas I-VII, IA-IC, IIA, IIB, VIIA, or VIIB, $Q^2$ is phenyl. In a particular embodiment of formulas I-VII, IA-IC, IIA, IIB, VIIA, or VIIB, $Q^2$ is 4-fluorophenyl. In a particular embodiment of formulas I-VII, IA-IC, IIA, IIB, VIIA, or VIIB, $Q^2$ is $CF_3$. In a particular embodiment of formulas I-VII, IA-IC, IIA, IIB, VIIA, or VIIB, $Q^2$ is substituted or unsubstituted alkyl. In a particular embodiment of formulas I-VII, IA-IC, IIA, IIB, VIIA, or VIIB, $Q^2$ is substituted or unsubstituted cycloalkyl. In a particular embodiment of formulas I-VII, IA-IC, IIA, IIB, VIIA, or VIIB, $Q^2$ is substituted or unsubstituted heterocycloalkyl. In a particular embodiment of formulas I-VII, IA-IC, IIA, IIB, VIIA, or VIIB, $Q^2$ is haloalkyl. In a particular embodiment of formulas I-VII, IA-IC, IIA, IIB, VIIA, or VIIB, $Q^2$ is substituted or unsubstituted aryl. In a particular embodiment of formulas I-VII, IA-IC, IIA, IIB, VIIA, or VIIB, $Q^2$ is hydroxyl. In a particular embodiment of formulas I-VII, IA-IC, IIA, IIB, VIIA, or VIIB, $Q^2$ is alkoxy. In a particular embodiment of formulas I-VII, IA-IC, IIA, IIB, VIIA, or VIIB, $Q^2$ is OR. In a particular embodiment of formulas I-VII, IA-IC, IIA, IIB, VIIA, or VIIB, $Q^2$ is arylalkyl. In a particular embodiment of formulas I-VII, IA-IC, IIA, IIB, VIIA, or VIIB, $Q^2$ is amine. In a particular embodiment of formulas I-VII, IA-IC, IIA, IIB, VIIA, or VIIB, $Q^2$ is amide. In a particular embodiment of formulas I-VII, IA-IC, IIA, IIB, VIIA, or VIIB, $Q^2$ is COOR. In a particular embodiment of formulas I-VII, IA-IC, IIA, IIB, VIIA, or VIIB, $Q^2$ is COR.

In a particular embodiment of formulas I-VIII, IA-IC, IIA, IIB, VIIA, VIIB, VIIIA or VIIIB, $Q^3$ is CN. In a particular embodiment of formulas I-VIII, IA-IC, IIA, IIB, VIIA, VIIB, VIIIA or VIIIB, $Q^3$ is F. In a particular embodiment of formulas I-VIII, IA-IC, IIA, IIB, VIIA, VIIB, VIIIA or VIIIB, $Q^3$ is NCS. In a particular embodiment of formulas I-VIII, IA-IC, IIA, IIB, VIIA, VIIB, VIIIA or VIIIB, $Q^3$ is maleimide. In a particular embodiment of formulas I-VIII, IA-IC, IIA, IIB, VIIA, VIIB, VIIIA or VIIIB, $Q^3$ is NHCOOR. In a particular embodiment of formulas I-VIII, IA-IC, IIA, IIB, VIIA, VIIB, VIIIA or VIIIB, $Q^3$ is $N(R)_2$. In a particular embodiment of formulas I-VIII, IA-IC, IIA, IIB, VIIA, VIIB, VIIIA or VIIIB, $Q^3$ is CONHR. In a particular embodiment of formulas I-VIII, IA-IC, IIA, IIB, VIIA, VIIB, VIIIA or VIIIB, $Q^3$, is NHCOR. In a particular embodiment of formulas I-VIII, IA-IC, IIA, IIB, VIIA, VIIB, VIIIA or VIIIB, $Q^3$ is hydrogen. In a particular embodiment of formulas I-VIII, IA-IC, IIA, IIB, VIIA, VIIB, VIIIA or VIIIB, $Q^3$ is keto. In a particular embodiment of formulas I-VIII, IA-IC, IIA, IIB, VIIA, VIIB, VIIIA or VIIIB, $Q^3$ is Cl. In a particular embodiment of formulas I-VIII, IA-IC, IIA, IIB, VIIA, VIIB, VIIIA or VIIIB, $Q^3$ is Br. In a particular embodiment of formulas I-VIII, IA-IC, IIA, IIB, VIIA, VIIB, VIIIA or VIIIB, $Q^3$ is I. In a particular embodiment of formulas I-VIII, IA-IC, IIA, IIB, VIIA, VIIB, VIIIA or VIIIB, $Q^3$ is $NO_2$. In a particular embodiment of formulas I-VIII, IA-IC, IIA, IIB, VIIA, VIIB, VIIIA or VIIIB, $Q^3$ is phenyl. In a particular embodiment of formulas I-VIII, IA-IC, IIA, IIB, VIIA, VIIB, VIIIA or VIIIB, $Q^3$ is 4-fluorophenyl. In a particular embodiment of formulas I-VIII, IA-IC, IIA, IIB, VIIA, VIIB, VIIIA or VIIIB, $Q^3$ is $CF_3$. In a particular embodiment of formulas I-VIII, IA-IC, IIA, IIB, VIIA, VIIB, VIIIA or VIIIB, $Q^3$ is substituted or unsubstituted alkyl. In a particular embodiment of formulas I-VIII, IA-IC, IIA, IIB, VIIA, VIIB, VIIIA or VIIIB, $Q^3$ is substituted or unsubstituted cycloalkyl. In a particular embodiment of formulas I-VIII, IA-IC, IIA, IIB, VIIA, VIIB, VIIIA or VIIIB, $Q^3$ is substituted or unsubstituted heterocycloalkyl. In a particular embodiment of formulas I-VIII, IA-IC, IIA, IIB, VIIA, VIIB, VIIIA or VIIIB, $Q^3$ is haloalkyl. In a particular embodiment of formulas I-VIII, IA-IC, IIA, IIB, VIIA, VIIB, VIIIA or VIIIB, $Q^3$ is substituted or unsubstituted aryl. In a particular embodiment of formulas I-VIII, IA-IC, IIA, IIB, VIIA, VIIB, VIIIA or VIIIB, $Q^3$ is hydroxyl. In a particular embodiment of formulas I-VIII, IA-IC, IIA, IIB, VIIA, VIIB, VIIIA or VIIIB, $Q^3$ is alkoxy. In a particular embodiment of formulas I-VIII, IA-IC, IIA, IIB, VIIA, VIIB, VIIIA or VIIIB, $Q^3$ is OR. In a particular embodiment of formulas I-VIII, IA-IC, IIA, IIB, VIIA, VIIB, VIIIA or VIIIB, $Q^3$ is arylalkyl. In a particular embodiment of formulas I-VIII, IA-IC, IIA, IIB, VIIA, VIIB, VIIIA or VIIIB, $Q^3$ is amine. In a particular embodiment of formulas I-VIII, IA-IC, IIA, IIB, VIIA, VIIB, VIIIA or VIIIB, $Q^3$ is amide. In a particular embodiment of formulas I-VIII, IA-IC, IIA, IIB, VIIA, VIIB, VIIIA or VIIIB, $Q^3$ is COOR. In a particular embodiment of formulas I-VIII, IA-IC, IIA, IIB, VIIA, VIIB, VIIIA or VIIIB, $Q^3$ is COR.

In a particular embodiment of formulas I-IX, IA-IC, IIA, IIB, VIIA, VIIB, VIIIA, VIIIB, IXA or IXB, $Q^4$ is CN. In a particular embodiment of formulas I-IX, IA-IC, IIA, IIB, VIIA, VIIB, VIIIA, VIIIB, IXA or IXB, $Q^4$ is F. In a particular embodiment of formulas I-IX, IA-IC, IIA, IIB, VIIA, VIIB, VIIIA, VIIIB, IXA or IXB, $Q^4$ is NCS. In a particular embodiment of formulas I-IX, IA-IC, IIA, IIB, VIIA, VIIB, VIIIA, VIIIB, IXA or IXB, $Q^4$ is maleimide. In a particular embodiment of formulas I-IX, IA-IC, IIA, IIB, VIIA, VIIB, VIIIA, VIIIB, IXA or IXB, $Q^4$ is NHCOOR. In a particular embodiment of formulas I-IX, IA-IC, IIA, IIB, VIIA, VIIB, VIIIA, VIIIB, IXA or IXB, $Q^4$ is $N(R)_2$. In a particular embodiment of formulas I-IX, IA-IC, IIA, IIB, VIIA, VIIB, VIIIA, VIIIB, IXA or IXB, $Q^4$ is CONHR. In a particular embodiment of formulas I-IX, IA-IC, IIA, IIB, VIIA, VIIB, VIIIA, VIIIB, IXA or IXB, $Q^4$, is NHCOR. In a particular embodiment of formulas I-IX, IA-IC, IIA, IIB, VIIA, VIIB, VIIIA, VIIIB, IXA or IXB, $Q^4$ is hydrogen. In a particular embodiment of formulas I-IX, IA-IC, IIA, IIB, VIIA, VIIB, VIIIA, VIIIB, IXA or IXB, $Q^4$ is keto. In a particular embodiment of formulas I-IX, IA-IC, IIA, IIB, VIIA, VIIB, VIIIA, VIIIB, IXA or IXB B, $Q^4$ is Cl. In a particular embodiment of formulas I-IX, IA-IC, IIA, IIB, VIIA, VIIB, VIIIA, VIIIB, IXA or IXB, $Q^4$ is Br. In a particular embodiment of formulas I-IX, IA-IC, IIA, IIB, VIIA, VIIB, VIIIA, VIIIB, IXA or IXB, $Q^4$ is I. In a particular embodiment of formulas I-IX, IA-IC, IIA, IIB, VIIA, VIIB, VIIIA, VIIIB, IXA or IXB, $Q^4$ is $NO_2$. In a particular embodiment of formulas I-IX, IA-IC, IIA, IIB, VIIA, VIIB, VIIIA, VIIIB, IXA or IXB, $Q^4$ is phenyl. In a particular embodiment of formulas I-IX, IA-IC, IIA, IIB, VIIA, VIIB, VIIIA, VIIIB, IXA or IXB, $Q^4$ is 4-fluorophenyl. In a particular embodiment of formulas I-IX, IA-IC, IIA, IIB, VIIA, VIIB, VIIIA, VIIIB, IXA or IXB, $Q^4$ is $CF_3$. In a particular embodiment of formulas I-IX, IA-IC, IIA, IIB, VIIA, VIIB, VIIIA, VIIIB, IXA or IXB, $Q^4$ is substituted or unsubstituted alkyl. In a particular embodiment of formulas I-IX, IA-IC, IIA, IIB, VIIA, VIIB, VIIIA, VIIIB, IXA or IXB, $Q^4$ is substituted or unsubstituted cycloalkyl. In a particular embodiment of formulas I-IX, IA-IC, IIA, IIB, VIIA, VIIB, VIIIA, VIIIB, IXA or IXB, $Q^4$ is substituted or unsubstituted heterocycloalkyl. In a particular embodiment of formulas I-IX, IA-IC, IIA, IIB, VIIA, VIIB, VIIIA, VIIIB, IXA or IXB, $Q^4$ is haloalkyl. In a particular embodiment of formulas I-IX, IA-IC, IIA, IIB, VIIA, VIIB, VIIIA, VIIIB, IXA or IXB, $Q^4$ is substituted or unsubstituted aryl. In a particular embodiment of formulas I-IX, IA-IC, IIA, IIB, VIIA, VIIB, VIIIA, VIIIB, IXA or IXB, $Q^4$ is hydroxyl. In a particular embodiment of formulas I-IX, IA-IC, IIA, IIB, VIIA, VIIB, VIIIA, VIIIB, IXA or IXB, $Q^4$ is alkoxy. In a particular embodiment of formulas I-IX, IA-IC, IIA, IIB, VIIA, VIIB, VIIIA, VIIIB, IXA or IXB, $Q^4$ is OR. In a particular embodiment of formulas I-IX, IA-IC, IIA, IIB, VIIA, VIIB, VIIIA, VIIIB, IXA or IXB, $Q^4$ is arylalkyl. In a particular embodiment of formulas I-IX, IA-IC, IIA, IIB, VIIA, VIIB, VIIIA, VIIIB, IXA or IXB, $Q^4$ is amine. In a particular embodiment of formulas I-IX, IA-IC, IIA, IIB, VIIA, VIIB, VIIIA, VIIIB, IXA or IXB, $Q^3$ is amide. In a particular embodiment of formulas I-IX, IA-IC, IIA, IIB, VIIA, VIIB, VIIIA, VIIIB, IXA or IXB, $Q^4$ is COOR. In a particular embodiment of formulas I-IX, IA-IC, IIA, IIB, VIIA, VIIB, VIIIA, VIIIB, IXA or IXB, $Q^4$ is COR.

In a particular embodiment of formulas I, IA, IB, IC, ID, II, IIA, IIB, VII, VIIA, VIIB, VIII, VIIIA, VIIIB, IX, IXA or IXB, X is CH. In a particular embodiment of formulas I, IA, IB, IC, ID, II, IIA, IIB, VII, VIIA, VIIB, VIII, VIIIA, VIIIB, IX, IXA or IXB, X is N.

In some embodiments, wherein if A or $R^3$ is Br or I, $R^1$ is $CH_3$, and T is OH, then X is N or the aniline ring forms a fused heterocyclic ring.

In a particular embodiment of formulas I-IX, IA, IB, IC, ID, IIA, IIB, VIIA, VIIB, VIIIA, VIIIB, IXA, or IXB, Y is H. In a particular embodiment of formulas I-IX, IA, IB, IC, ID, IIA, IIB, VIIA, VIIB, VIIIA, VIIIB, IXA, or IXB, Y is $CF_3$. In a particular embodiment of formulas I-IX, IA, IB, IC, ID, IIA, IIB, VIIA, VIIB, VIIIA, VIIIB, IXA, or IXB, Y is F. In a particular embodiment of formulas I-IX, IA, IB, IC, ID, IIA, IIB, VIIA, VIIB, VIIIA, VIIIB, IXA, or IXB, Y is I. In a particular embodiment of formulas I-IX, IA, IB, IC, ID, IIA, IIB, VIIA, VIIB, VIIIA, VIIIB, IXA, or IXB, Y is Br. In a particular embodiment of formulas I-IX, IA, IB, IC, ID, IIA, IIB, VIIA, VIIB, VIIIA, VIIIB, IXA, or IXB, Y is Cl. In a particular embodiment of formulas I-IX, IA, IB, IC, ID, IIA, IIB, VIIA, VIIB, VIIIA, VIIIB, IXA, or IXB, Y is CN. In a particular embodiment of formulas I-IX, IA, IB, IC, ID, IIA, IIB, VIIA, VIIB, VIIIA, VIIIB, IXA, or IXB, Y is $C(R)_3$.

In a particular embodiment of formulas I-IX, IA, IB, IC, ID, IIA, IIB, VIIA, VIIB, VIIIA, VIIIB, IXA, or IXB, Z is H. In a particular embodiment of formulas I-IX, IA, IB, IC, ID, IIA, IIB, VIIA, VIIB, VIIIA, VIIIB, IXA, or IXB, Z is $NO_2$. In a particular embodiment of formulas I-IX, IA, IB, IC, ID, IIA, IIB, VIIA, VIIB, VIIIA, VIIIB, IXA, or IXB, Z is CN. In a particular embodiment of formulas I-IX, IA, IB, IC, ID, IIA, IIB, VIIA, VIIB, VIIIA, VIIIB, IXA, or IXB, Z is a halide. In a particular embodiment of formulas I-VII, IA, IB, IC, ID, IIA, IIB, VIIA, or VIIB, Z is F. In a particular embodiment of formulas I-IX, IA, IB, IC, ID, IIA, IIB, VIIA, VIIB, VIIIA, VIIIB, IXA, or IXB, Z is Cl. In a particular embodiment of formulas I-IX, IA, IB, IC, ID, IIA, IIB, VIIA, VIIB, VIIIA, VIIIB, IXA, or IXB, Z is Br. In a particular embodiment of formulas I-IX, IA, IB, IC, ID, IIA, IIB, VIIA, VIIB, VIIIA, VIIIB, IXA, or IXB, Z is I. In a particular embodiment of formulas I-IX, IA, IB, IC, ID, IIA, IIB, VIIA, VIIB, VIIIA, VIIIB, IXA, or IXB, Z is COOH. In a particular embodiment of formulas I-IX, IA, IB, IC, ID, IIA, IIB, VIIA, VIIB, VIIIA, VIIIB, IXA, or IXB, Z is COR. In a particular embodiment of formulas I-IX, IA, IB, IC, ID, IIA, IIB, VIIA, VIIB, VIIIA, VIIIB, IXA, or IXB, Z is NHCOR. In a particular embodiment of formulas I-IX, IA, IB, IC, ID, IIA, IIB, VIIA, VIIB, VIIIA, VIIIB, IXA, or IXB, Z is CONHR.

In a particular embodiment of formulas I I-IX, IA, IB, IC, ID, IIA, IIB, VIIA, VIIB, VIIIA, VIIIB, IXA, or IXB, Y and Z forms a fused ring with the phenyl. In other embodiments, the fused ring with the phenyl is a 5 to 8 membered ring. In other embodiments, the fused ring with the phenyl is a 5 or 6 membered ring. In other embodiments, the ring is a carbocyclic or heterocyclic. In other embodiments, Y and Z form together with the phenyl to form a naphthyl, quinolinyl, benzimidazolyl, indazolyl, indolyl, isoindolyl, indenyl, or quinazolinyl. In a particular embodiment, Y and Z form together with the phenyl to form a quinazolin-6-yl ring system.

In a particular embodiment of formulas I, II, IV, V, VI, VII, VIII, IX IA, IB, IC, ID, IIA, IIB, VIIA, VIIB, VIIIA, VIIIB, IXA or IXB $R^1$ is H. In a particular embodiment of formulas I, II, IV, V, VI, VII, VIII, IX IA, IB, IC, ID, IIA, IIB, VIIA, VIIB, VIIIA, VIIIB, IXA or IXB, $R^1$ is $CH_3$. In a particular embodiment of formulas I, II, IV, V, VI, VII, VIII, IX IA, IB, IC, ID, IIA, IIB, VIIA, VIIB, VIIIA, VIIIB, IXA or IXB, $R^1$ is $CH_2F$. In a particular embodiment of formulas I, II, IV, V, VI, VII, VIII, IX IA, IB, IC, ID, IIA, IIB, VIIA, VIIB, VIIIA, VIIIB, IXA or IXB, $R^1$ is $CHF_2$. In a particular embodiment of formulas I, II, IV, V, VI, VII, VIII, IX IA, IB, IC, ID, IIA, IIB, VIIA, VIIB, VIIIA, VIIIB, IXA or IXB, $R_1$ is $CF_3$. In a particular embodiment of formulas I, II, IV, V, VI, VII, VIII, IX IA, IB, IC, ID, IIA, IIB, VIIA, VIIB, VIIIA, VIIIB, IXA or IXB, $R^1$ is $CH_2CH_3$. In a particular embodiment of formulas I, II, IV, V, VI, VII, VIII, IX IA, IB, IC, ID, IIA, IIB, VIIA, VIIB, VIIIA, VIIIB, IXA or IXB, $R^1$ is $CF_2CF_3$.

In a particular embodiment of formulas I, II, IV, V, VI, VII, VIII, IX, IA, IB, IC, ID, IIA, IIB, VIIA, VIIB, VIIIA, VIIIB, IXA or IXB, T is H. In a particular embodiment of formulas I, II, IV, V, VI, VII, VIII, IX, IA, IB, IC, ID, IIA, IIB, VIIA, VIIB, VIIIA, VIIIB, IXA or IXB, T is OH. In a particular embodiment of formulas I, II, IV, V, VI, VII, VIII, IX, IA, IB, IC, ID, IIA, IIB, VIIA, VIIB, VIIIA, VIIIB, IXA or IXB, T is OR. In a particular embodiment of formulas I, II, IV, V, VI, VII, VIII, IX, IA, IB, IC, ID, IIA, IIB, VIIA, VIIB, VIIIA, VIIIB, IXA or IXB, T is OCOR In a particular embodiment of formulas I, II, IV, V, VI, VII, VIII, IX, IA, IB, IC, ID, IIA, IIB, VIIA, VIIB, VIIIA, VIIIB, IXA or IXB, T is $CH_3$. In a particular embodiment of formulas I, II, IV, V, VI, VII, VIII, IX, IA, IB, IC, ID, IIA, IIB, VIIA, VIIB, VIIIA, VIIIB, IXA or IXB, T is —$NHCOCH_3$. In a particular embodiment of formulas I, II, IV, V, VI, VII, VIII, IX, IA, IB, IC, ID, IIA, IIB, VIIA, VIIB, VIIIA, VIIIB, IXA or IXB, T is NHCOR.

In a particular embodiment of formulas I, II, IV, V, VI, VII, VIII, IX, IA, IB, IC, ID, IIA, IIB, VIIA, VIIB, VIIIA, VIIIB, IXA or IXB, T and $R^1$ form a 3-8 carbocyclic or heterocyclic ring. In other embodiments, T and $R^1$ form a 3, 4, 5, 6, 7, or 8 membered carbocyclic or heterocyclic ring. Each represents a separate embodiment of this invention. In some embodiments T and $R^1$ form a carbocyclic ring such as cyclopropyl, cyclobutyl, cyclopentyl, cyclohexyl, etc. In some embodiments T and $R^1$ form a heterocyclic ring such as piperidine, pyridine, furan, thiphene, pyrrole, pyrazole, pyrimidine, etc.

In a particular embodiment of formulas I-IX, IA, IB, IC, ID, IIA, IIB, VIIA, VIIB, VIIIA, VIIIB, IXA or IXB, R is H. In a particular embodiment of formulas I-IX, IA, IB, IC, ID, IIA, IIB, VIIA, VIIB, VIIIA, VIIIB, IXA, R is alkyl. In a particular embodiment of formulas I-IX, IA, IB, IC, ID, IIA, IIB, VIIA, VIIB, VIIIA, VIIIB, IXA, R is alkenyl. In a particular embodiment of formulas I-IX, IA, IB, IC, ID, IIA, IIB, VIIA, VIIB, VIIIA, VIIIB, IXA, R is haloalkyl. In a particular embodiment of formulas I-IX, IA, IB, IC, ID, IIA, IIB, VIIA, VIIB, VIIIA, VIIIB, IXA, R is alcohol. In a particular embodiment of formulas I-VII, IA, IB, IC, ID, IIA, IIB, VIIA, or VIIB, R is $CH_2CH_2OH$. In a particular embodiment of formulas I-IX, IA, IB, IC, ID, IIA, IIB, VIIA, VIIB, VIIIA, VIIIB, IXA, R is $CF_3$. In a particular embodiment of formulas I-VII, IA, IB, IC, ID, IIA, IIB, VIIA, or VIIB, R is $CH_2Cl$. In a particular embodiment of formulas I-IX, IA, IB, IC, ID, IIA, IIB, VIIA, VIIB, VIIIA, VIIIB, IXA, R is $CH_2CH_2Cl$. In a particular embodiment of formulas I-IX, IA, IB, IC, ID, IIA, IIB, VIIA, VIIB, VIIIA, VIIIB, IXA, R is aryl. In a particular embodiment of formulas I-IX, IA, IB, IC, ID, IIA, IIB, VIIA, VIIB, VIIIA, VIIIB, IXA, R is F. In a particular embodiment of formulas I-IX, IA, IB, IC, ID, IIA, IIB, VIIA, VIIB, VIIIA, VIIIB, IXA, R is Cl. In a particular embodiment of formulas I-IX, IA, IB, IC, ID, IIA, IIB, VIIA, VIIB, VIIIA, VIIIB, IXA, R is Br. In a particular embodiment of formulas I-IX, IA, IB, IC, ID, IIA, IIB, VIIA, VIIB, VIIIA, VIIIB, IXA, R is I. In a particular embodiment of formulas I-IX, IA, IB, IC, ID, IIA, IIB, VIIA, VIIB, VIIIA, VIIIB, IXA, R is OH.

In a particular embodiment of formula IV, $Q^1$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^1$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^1$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IV, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VII, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIA, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIB, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IV, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VII, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIII, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IV, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VII, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIA, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIB, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIII, VIIIA, or VIIIB, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IX, IXA, or IXB, $Q^4$ is H, CN, $CF_3$, phenyl, 4-fluorophenyl, F, Br, Cl, I, COMe, NHCOOMe, NHCOMe or $NHCOOC(CH_3)_3$.

The invention encompasses a selective androgen receptor degrader (SARD) compound selected from any one of the following structures:

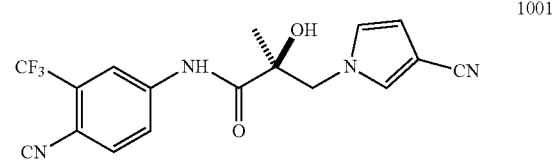

1001

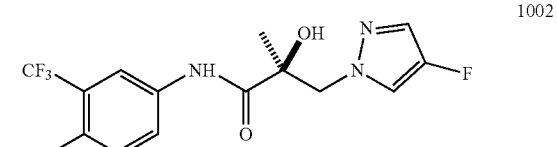

1002

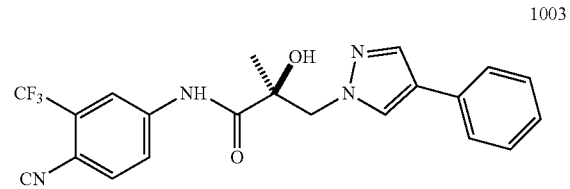

1003

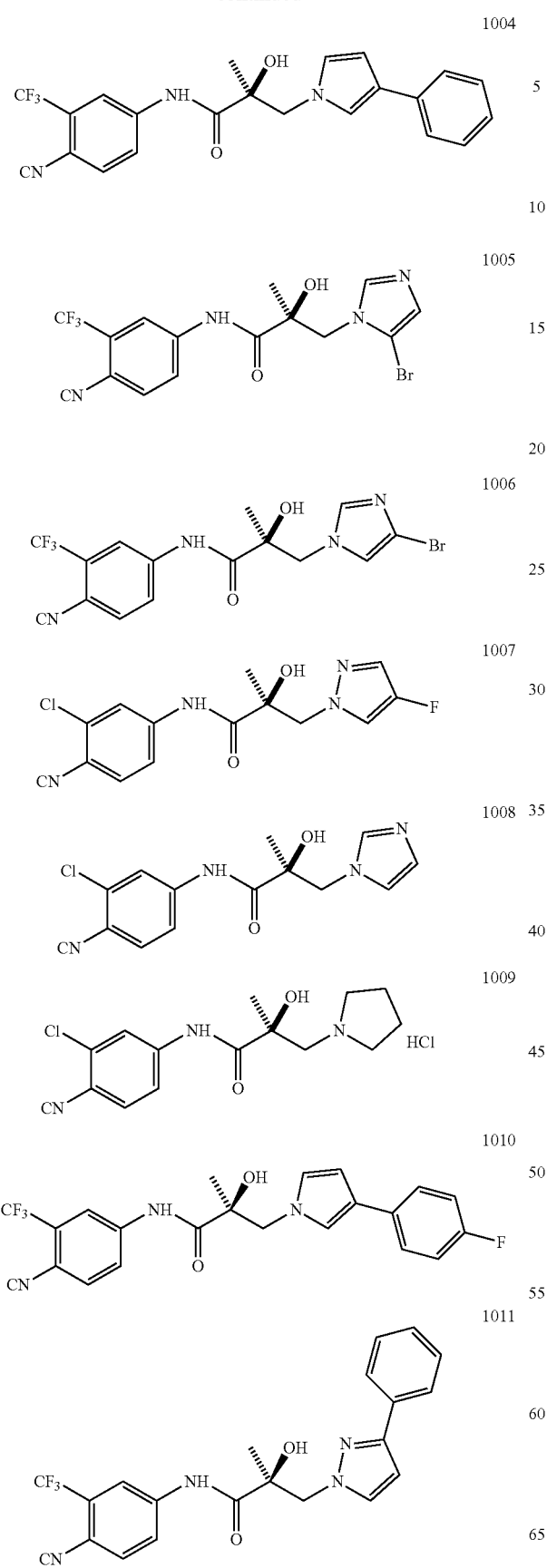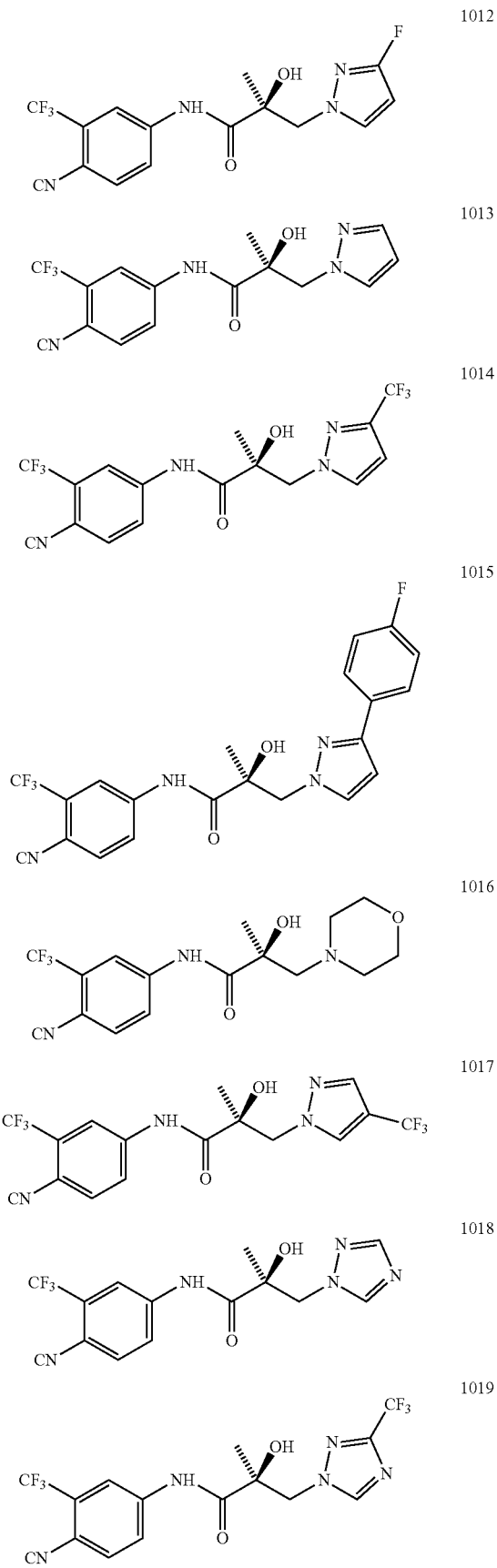

-continued
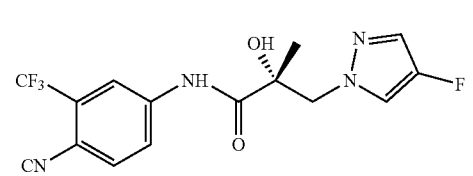 1020
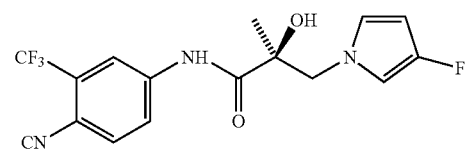 1021
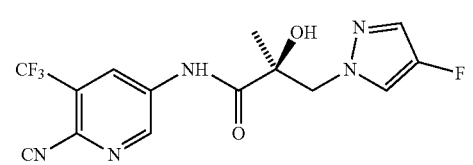 1022
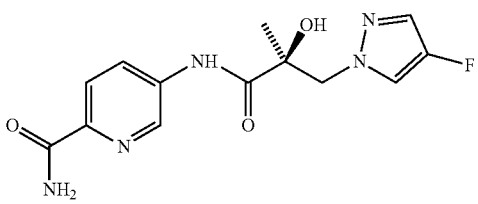 1023
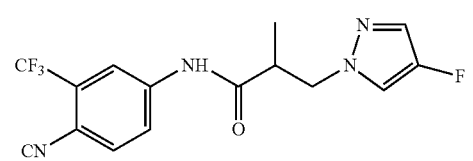 1024
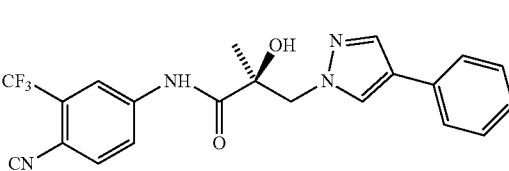 1025
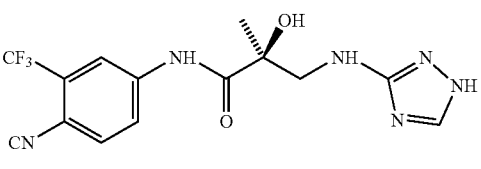 1026
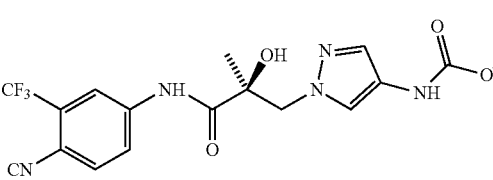 1027
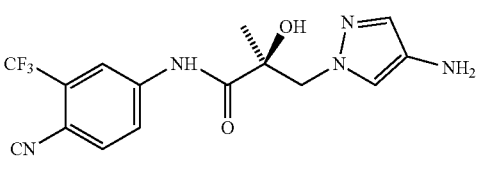 1028
-continued
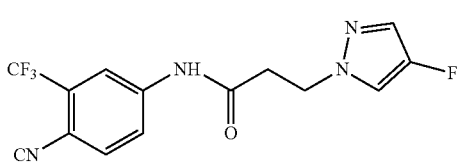 1029
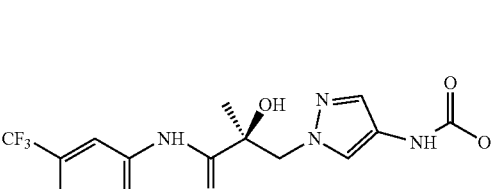 1030
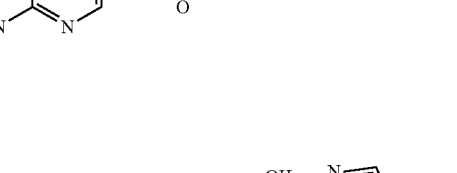 1031
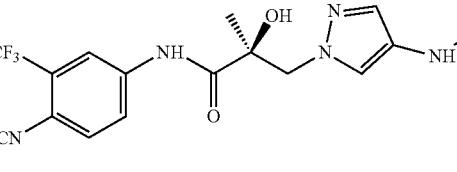 1032
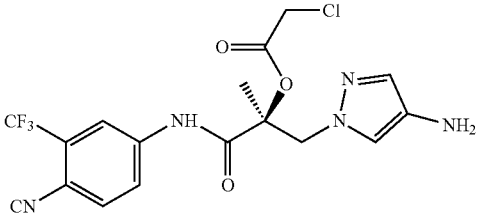 1033
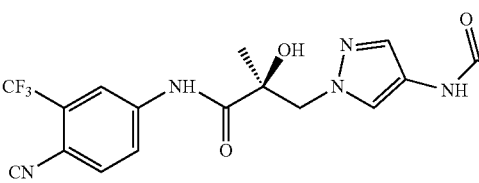 1034
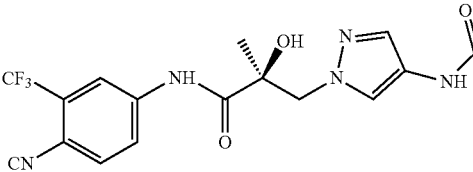 1035
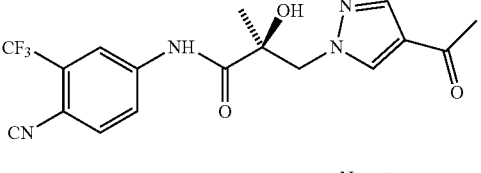 1036
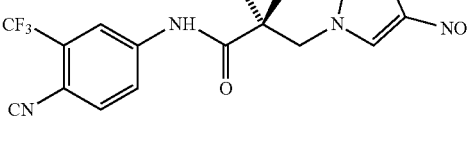

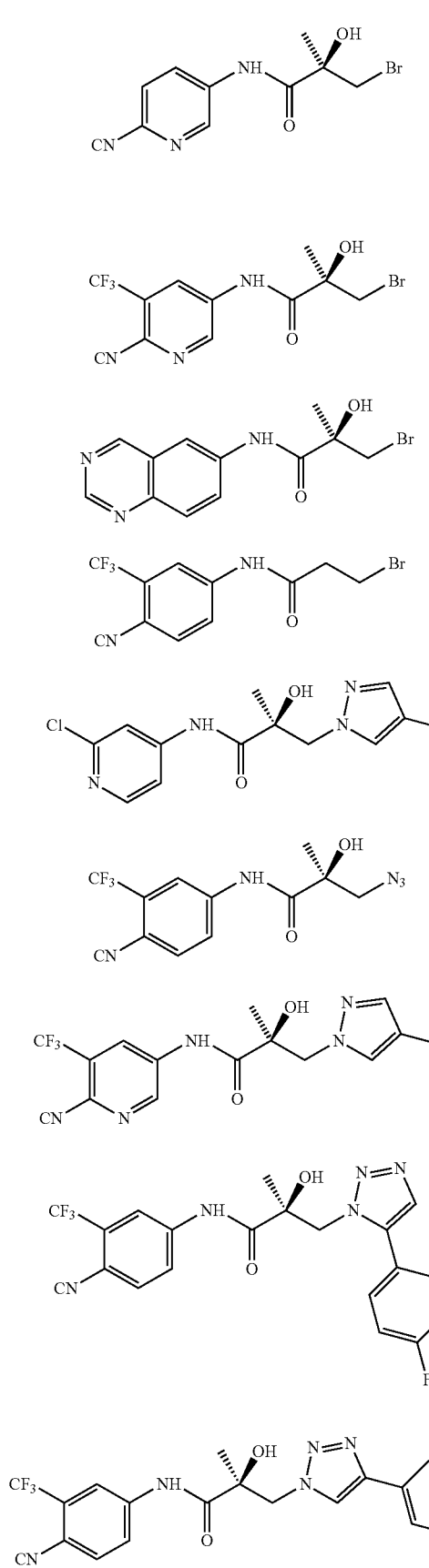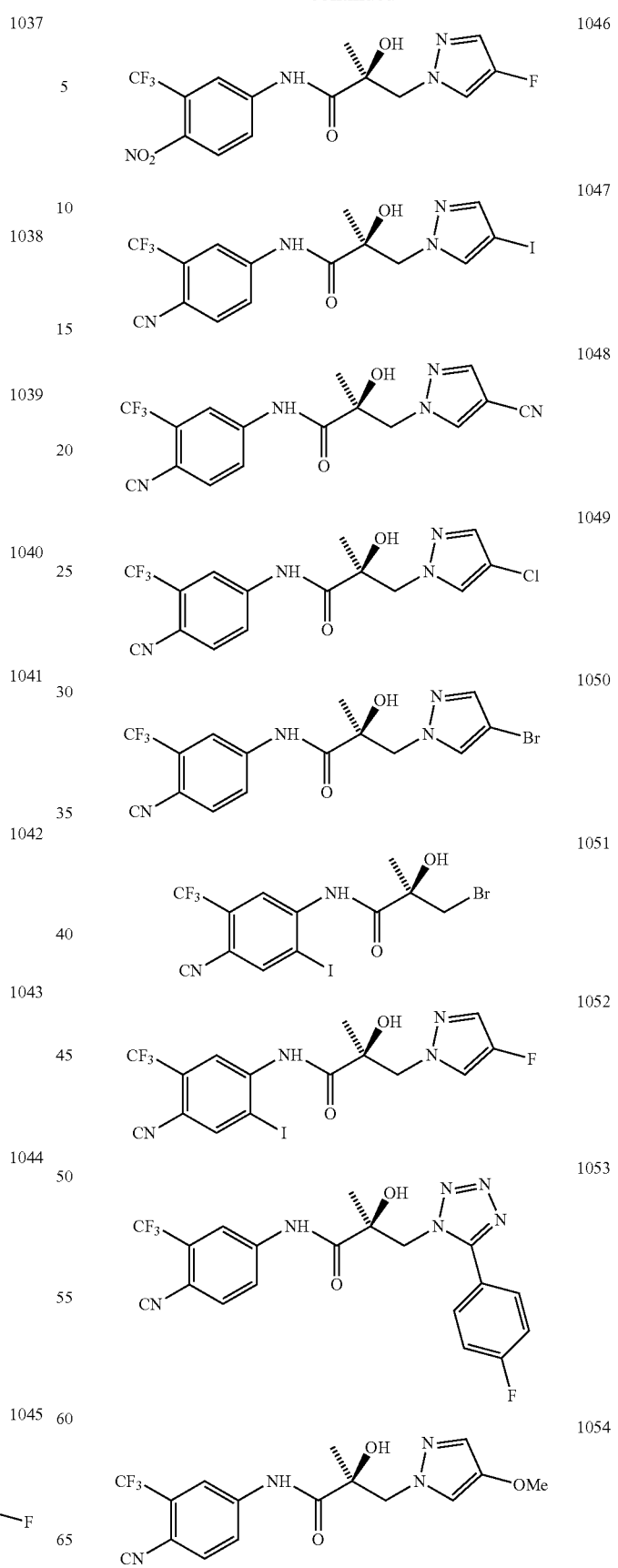

1055 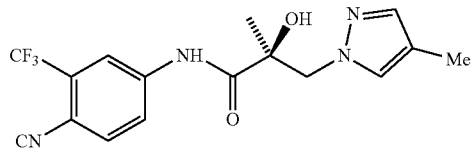

1056 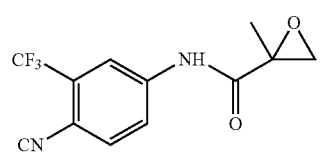

1057 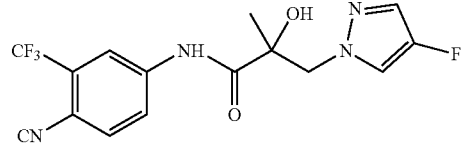

1058 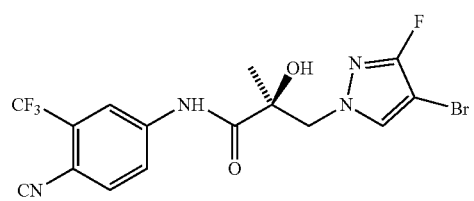

1059 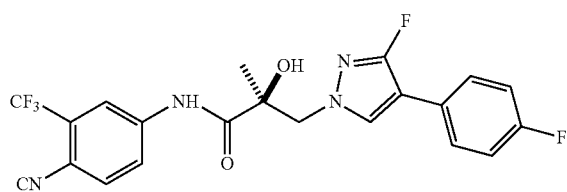

1060 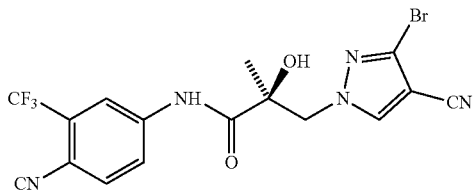

1061 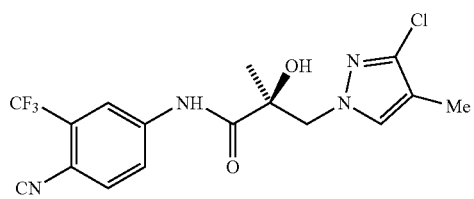

1062 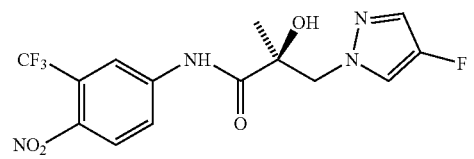

1063 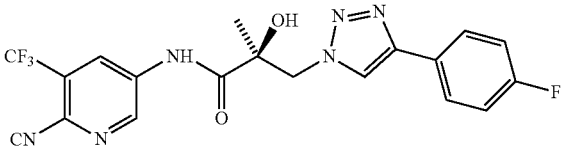

1064 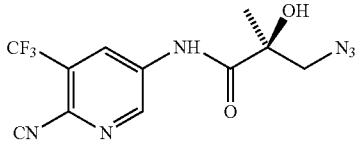

1069 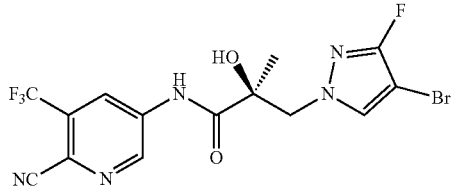

1070 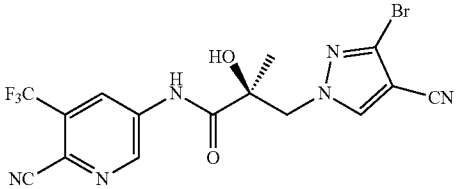

1071 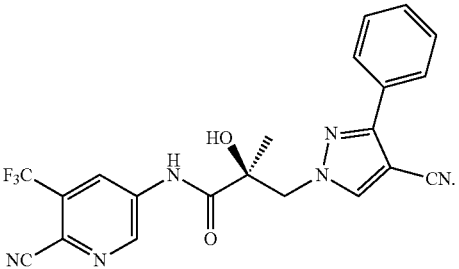

As used herein, the term "heterocycle" or "heterocyclic ring" group refers to a ring structure comprising in addition to carbon atoms, at least one atom of sulfur, oxygen, nitrogen or any combination thereof, as part of the ring. The heterocycle may be a 3-12 membered ring; 4-8 membered ring; a 5-7 membered ring; or a 6 membered ring. Preferably, the heterocycle is a 5 to 6 membered ring. Typical examples of heterocycles include, but are not limited to, piperidine, pyridine, furan, thiophene, pyrrole, pyrrolidine, pyrazole, pyrazine, piperazine or pyrimidine. Examples of $C_5$-$C_8$ heterocyclic rings include pyran, dihydropyran, tetrahydropyran, dihydropyrrole, tetrahydropyrrole, pyrazine, dihydropyrazine, tetrahydropyrazine, pyrimidine, dihydropyrimidine, tetrahydropyrimidone, pyrazole, dihydropyrazole, tetrahydropyrazole, triazole, tetrazole, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like. The heterocycle ring may be fused to another saturated or unsaturated cycloalkyl or a saturated or unsaturated heterocyclic ring. When the heterocycle ring is substituted, the substituents include at least one of halogen, haloalkyl, hydroxyl, alkoxy, carbonyl, amido, alkylamido, dialkylamido, cyano, nitro, $CO_2H$, amino, alkylamino, dialkylamino, carboxyl, thiol, or thioalkyl.

The term "aniline ring system" refers to the conserved ring represented to the left of the structures in this document which is substituted by X, Y, and/or Z.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes and ($C_3$-$C_7$) cycloalkenyl groups, such as cyclopropenyl, cyclobutenyl, cyclopentenyl, cyclohexenyl, and cycloheptenyl, and unsaturated cyclic and bicyclic terpenes. Examples of $C_5$-$C_8$ carbocyclic include cyclopentane, cyclopentene, cyclohexane, and cyclohexene rings. A cycloalkyl group can be unsubstituted or substituted by at least one substituent. Preferably, the cycloalkyl group is a monocyclic ring or bicyclic ring.

The term "alkyl" refers to a saturated aliphatic hydrocarbon, including straight-chained and branched-chained. Typically, the alkyl group has 1-12 carbons, 1-7 carbons, 1-6 carbons, or 1-4 carbon atoms. A branched alkyl is an alkyl substituted by alkyl side chains of 1 to 5 carbons. The branched alkyl may have an alkyl substituted by a $C_1$-$C_5$ haloalkyl. Additionally, the alkyl group may be substituted by at least one of halogen, haloalkyl, hydroxyl, alkoxy carbonyl, amido, alkylamido, dialkylamido, nitro, CN, amino, alkylamino, dialkylamino, carboxyl, thio or thioalkyl.

An "arylalkyl" group refers to an alkyl bound to an aryl, wherein alkyl and aryl are as defined herein. An example of an arylalkyl group is a benzyl group.

An "alkenyl" group refers to an unsaturated hydrocarbon, including straight chain and branched chain having one or more double bonds. The alkenyl group may have 2-12 carbons, preferably the alkenyl group has 2-6 carbons or 2-4 carbons. Examples of alkenyl groups include, but are not limited to, ethenyl, propenyl, butenyl, cyclohexenyl, etc. The alkenyl group may be substituted by at least one halogen, hydroxy, alkoxy carbonyl, amido, alkylamido, dialkylamido, nitro, amino, alkylamino, dialkylamino, carboxyl, thio, or thioalkyl.

As used herein the term "aryl" group refers to an aromatic group having at least one carbocyclic aromatic group or heterocyclic aromatic group, which may be unsubstituted or substituted. When present, substituents include, but are not limited to, at least one halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. The aryl group may be a 4-12 membered ring, preferably the aryl group is a 4-8 membered ring. Also the aryl group may be a 6 or 5 membered ring.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, indolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

As used herein, the term "haloalkyl" group refers to an alkyl group that is substituted by one or more halogen atoms, e.g. by F, Cl, Br or I.

A "hydroxyl" group refers to an OH group. It is understood by a person skilled in the art that when T, $Q^1$, $Q^2$, $Q^3$, or $Q^4$, in the compounds of the present invention is OR, then R is not OH.

The term "halogen" or "halo" or "halide" refers to a halogen; F, Cl, Br or I.

In one embodiment, this invention provides the compounds and/or its use and/or, its derivative, optical isomer, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

The compounds of the invention may be converted into pharmaceutically acceptable salts. A pharmaceutically acceptable salt may be produced by reaction of a compound with an acid or base.

Suitable pharmaceutically acceptable salts of amines may be prepared from an inorganic acid or from an organic acid. Examples of inorganic salts of amines include, but are not limited to, bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphates, sulfates, sulfamates, sulfanilates, sulfonic acids (alkylsulfonates, arylsulfonates, halogen substituted alkylsulfonates, halogen substituted arylsulfonates), sulfonates, or thiocyanates.

Examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates. Examples of inorganic salts of carboxylic acids or phenols may be selected from ammonium, alkali metals, and alkaline earth metals. Alkali metals include, but are not limited to, lithium, sodium, potassium, or cesium. Alkaline earth metals include, but are not limited to, calcium, magnesium, aluminium; zinc, barium, cholines, or quaternary ammoniums. Examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolines, piperazines, procaine, tris(hydroxymethyl)methylamines, triethylamines, triethanolamines, trimethylamines, tromethamines and ureas.

In various embodiments, the pharmaceutically acceptable salts of the compounds of this invention include: HCl salt, oxalic acid salt, L-(+)-tartaric acid salt, HBr salt and succinic acid salt. Each represents a separate embodiment of this invention.

Salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

The methods of the invention may use an uncharged compound or a pharmaceutically acceptable salt of the compound. In particular, the methods use pharmaceutically acceptable salts of compounds of formulas I-IX, IA, IB, IC, ID, IIA, IIB, VIIA, VIIB, VIIIA, VIIIB, IXA or IXB. The pharmaceutically acceptable salt may be an amine salt or a salt of a phenol of the compounds of formulas I-IX, IA, IB, IC, ID, IIA, IIB, VIIA, VIIB, VIIIA, VIIIB, IXA or IXB.

In one embodiment, the methods of this invention make use of a free base, free acid, non charged or non-complexed compounds of formulas I-IX, IA, IB, IC, ID, IIA, IIB, VIIA, VIIB, VIIIA, VIIIB, IXA or IXB, and/or its isomer, pharmaceutical product, hydrate, polymorph, or combinations thereof.

In one embodiment, the methods of this invention make use of an optical isomer of a compound of formulas I-IX, IA, IB, IC, ID, IIA, IIB, VIIA, VIIB, VIIIA, VIIIB, IXA or IXB. In one embodiment, the methods of this invention make use of an isomer of a compound of formulas I-IX, IA, IB, IC, ID, IIA, IIB, VIIA, VIIB, VIIIA, VIIIB, IXA or IXB. In one embodiment, the methods of this invention make use of a pharmaceutical product of a compound of formulas I-IX, IA, IB, IC, ID, IIA, IIB, VIIA, VIIB, VIIIA, VIIIB, IXA or IXB. In one embodiment, the methods of this invention make use of a hydrate of a compound of I-IX, IA, IB, IC, ID, IIA, IIB, VIIA, VIIB, VIIIA, VIIIB, IXA or IXB. In one embodiment, the methods of this invention make use of a polymorph of a compound of formulas I-IX, IA, IB, IC, ID, IIA, IIB, VIIA, VIIB, VIIIA, VIIIB, IXA or IXB. In one embodiment, the methods of this invention make use of a metabolite of a compound of formulas I-IX, IA, IB, IC, ID, IIA, IIB, VIIA, VIIB, VIIIA, VIIIB, IXA or IXB. In another embodiment, the methods of this invention make use of a composition comprising a compound of formulas I-IX, IA, IB, IC, ID, IIA, IIB, VIIA, VIIB, VIIIA, VIIIB, IXA or IXB, as described herein, or, in another embodiment, a combination of isomer, metabolite, pharmaceutical product, hydrate, polymorph of a compound of formulas I-IX, IA, IB, IC, ID, IIA, IIB, VIIA, VIIB, VIIIA, VIIIB, IXA or IXB.

As used herein, the term "isomer" includes, but is not limited to, optical isomers, structural isomers, or conformational isomers.

The term "isomer" is meant to encompass optical isomers of the SARD compound. It will be appreciated by those skilled in the art that the SARDs of the present invention contain at least one chiral center. Accordingly, the compounds may exist as optically-active (such as an (R) isomer or (S) isomer) or racemic forms. Optically active compounds may exist as enantiomerically enriched mixtures. Some compounds may also exhibit polymorphism. It is to be understood that the present invention encompasses any racemic, optically active, polymorphic, or stereoisomeric form, or mixtures thereof. Thus, the invention may encompass SARD compounds as pure (R)-isomers or as pure (S)-isomers. It is known in the art how to prepare optically active forms. For example, by resolution of the racemic form by recrystallization techniques, by synthesis from optically active starting materials, by chiral synthesis, or by chromatographic separation using a chiral stationary phase.

Compounds of the invention may be hydrates of the compounds. As used herein, the term "hydrate" includes, but is not limited to, hemihydrate, monohydrate, dihydrate, or trihydrate. The invention also includes use of N-oxides of the amino substituents of the compounds described herein.

This invention provides, in other embodiments, use of metabolites of the compounds as herein described. In one embodiment, "metabolite" means any substance produced from another substance by metabolism or a metabolic process.

In one embodiment, the compounds of this invention are prepared according to Example 1.

Biological Activity of Selective Androgen Receptor Degraders

A method of treating prostate cancer (PCa) or increasing the survival of a male subject suffering from prostate cancer comprising administering to the subject a therapeutically effective amount of a compound or its pharmaceutically acceptable salt, represented by a compound of formula I:

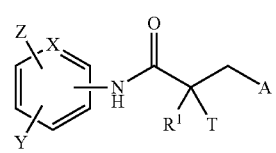

wherein
T is H, OH, OR, OCOR, $CH_3$, —$NHCOCH_3$, or $NHCOR$;
$R^1$ is H, $CH_3$, $CH_2F$, $CHF_2$, $CF_3$, $CH_2CH_3$, or $CF_2CF_3$;

or T and R¹ form a 3-8 carbocyclic or heterocyclic ring;
Y is H, $CF_3$, F, I, Br, Cl, CN, or $C(R)_3$;
Z H, is $NO_2$, CN, halide, COOH, COR, NHCOR, CONHR, or Y and Z form a 5 to 8 membered ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, benzyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, CONH2, CONH(R4), CON(R4)2, $SR^4$, $SO_2R^4$, $SOR^4$ $SO_3H$, $SO_2NH_2$, $SO_2NH(R^4)$, $SO_2N(R^4)_2$, $NH_2$, $NH(R^4)$, $N(R^4)_2$, CO(N-heterocycle), $C(O)(C_1\text{-}C_{10})$alkyl, $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, or a racemic mixture thereof, isomer, pharmaceutically acceptable salt, pharmaceutical product, polymorph, hydrate or any combination thereof.

A method of treating prostate cancer (PCa) or increasing the survival of a male subject suffering from prostate cancer comprising administering to the subject a therapeutically effective amount of a compound or its pharmaceutically acceptable salt, or isomer, represented by a compound of formulas I-IX, IA-ID, IIA, IIB, VIIA, VIIB, VIIIA, VIIIB, IXA or IXB.

The prostate cancer may be advanced prostate cancer, refractory prostate cancer, castration resistant prostate cancer (CRPC), metastatic CRPC (mCRPC), non-metastatic CRPC (nmCRPC), high-risk nmCRPC or any combination thereof.

The prostate cancer may depend on AR-FL and/or AR-SV for proliferation. The prostate or other cancer may be resistant to treatment with an androgen receptor antagonist. The prostate or other cancer may be resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, spironolactone, or any combination thereof. The method may also reduce the levels of AR, AR-FL, AR-FL with antiandrogen resistance-conferring AR-LBD mutations, AR-SV, gene-amplified AR, or any combination thereof.

In one embodiment, this invention provides a method of treating enzalutamide resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating abiraterone resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating triple negative breast cancer (TNBC) comprising administering to the subject a therapeutically effective amount of a compound of this invention, or its optical isomer, isomer, pharmaceutically acceptable salt, pharmaceutical product, polymorph, hydrate or any combination thereof.

The method may further comprise a second therapy such as androgen deprivation therapy (ADT) or LHRH agonist or antagonist. LHRH agonists include, but are not limited to, leuprolide acetate.

The invention encompasses a method of treating or inhibiting the progression of prostate cancer (PCa) or increasing the survival of a male subject suffering from prostate cancer comprising administering to the subject a therapeutically effective amount of a SARD compound or pharmaceutically acceptable salt, wherein the compound is at least one of compounds 1001 to 1064 and 1069 to 1071.

The invention encompasses a method of treating or inhibiting the progression of refractory prostate cancer (PCa) or increasing the survival of a male subject suffering from refractory prostate cancer comprising administering to the subject a therapeutically effective amount of a SARD compound or pharmaceutically acceptable salt, wherein the compound is represented by a compound of formulas I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating or increasing the survival of a male subject suffering from castration resistant prostate cancer (CRPC) comprising administering to the subject a therapeutically effective amount of a SARD wherein the compound is represented by a compound of formulas I-IX, IA, IB, IC, ID, IIA, IIB, VIIA, VIIB, VIIIA, VIIIB, IXA or IXB, or at least one of compounds 1001 to 1064 and 1069 to 1071.

The method may further comprise administering androgen deprivation therapy to the subject.

The invention encompasses a method of treating or inhibiting the progression of enzalutamide resistant prostate cancer (PCa) or increasing the survival of a male subject suffering from enzalutamide resistant prostate cancer comprising administering to the subject a therapeutically effective amount of a SARD compound or pharmaceutically acceptable salt, wherein the compound is represented by a compound of formulas I-IX, IA, IB, IC, ID, IIA, IIB, VIIA, VIIB, VIIIA, VIIIB, IXA or IXB, or the compound is at least one of compounds 1001 to 1064 and 1069 to 1071.

The method may further comprise administering androgen deprivation therapy to the subject.

The invention encompasses a method of treating or inhibiting the progression of triple negative breast cancer (TNBC) or increasing the survival of a female subject suffering from triple negative breast cancer comprising administering to the subject a therapeutically effective amount of a SARD compound or pharmaceutically acceptable salt, wherein the compound is represented by a compound of formulas I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating breast cancer in a subject in need thereof, wherein said subject has AR expressing breast cancer, AR-SV expressing breast cancer, and/or AR-V7 expressing breast cancer, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating AR expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating AR-SV expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating AR-V7 expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

As used herein, the term "increase the survival" refers to a lengthening of time when describing the survival of a subject. Thus in this context, the compounds of the invention may be used to increase the survival of men with advanced prostate cancer, refractory prostate cancer, castration resistant prostate cancer (CRPC); metastatic CRPC (mCRPC); non-metastatic CRPC (nmCRPC); or high-risk nmCRPC; or women with TNBC.

Alternatively, as used herein, the terms "increase", "increasing", or "increased" may be used interchangeably and refer to an entity becoming progressively greater (as in size, amount, number, or intensity), wherein for example the entity is sex hormone-binding globulin (SHBG) or prostate-specific antigen (PSA).

The compounds and compositions of the invention may be used for increasing metastasis-free survival (MFS) in a subject suffering from non-metastatic prostate cancer. The non-metastatic prostate cancer may be non-metastatic advanced prostate cancer, non-metastatic CRPC (nmCRPC), or high-risk nmCRPC.

The SARD compounds described herein may be used to provide a dual action. For example, the SARD compounds may treat prostate cancer and prevent metastasis. The prostate cancer may be refractory prostate cancer; advanced prostate cancer; castration resistant prostate cancer (CRPC); metastatic CRPC (mCRPC); non-metastatic CRPC (nmCRPC); or high-risk nmCRPC.

The SARD compounds described herein may be used to provide a dual action. For example, the SARD compounds may treat TNBC and prevent metastasis.

Men with advanced prostate cancer who are at high risk for progression to castration resistant prostate cancer (CRPC) are men on ADT with serum total testosterone concentrations greater than 20 ng/dL or men with advanced prostate cancer who at the time of starting ADT had either (1) confirmed Gleason pattern 4 or 5 prostate cancer, (2) metastatic prostate cancer, (3) a PSA doubling time <3 months, (4) a PSA ≥20 ng/mL, or (5) a PSA relapse in <3 years after definitive local therapy (radical prostatectomy or radiation therapy).

Normal levels of prostate specific antigen (PSA) are dependent on several factors, such as age and the size of a male subject's prostate, among others. PSA levels in the range between 2.5-10 ng/mL are considered "borderline high" while levels above 10 ng/mL are considered "high." A rate change or "PSA velocity" greater than 0.75/year is considered high. PSA levels may increase despite ongoing ADT or a history of ADT, surgical castration or despite treatment with antiandrogens and/or LHRH agonist.

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. "Phase III, randomized, placebo-controlled study of once-daily oral zibotentan (ZD4054) in patients with non-metastatic castration-resistant prostate cancer," *Prostate Canc Prost Dis*. February; 16:187-192). This relatively rapid progression of their disease underscores the importance of novel therapies for these individuals.

The methods of the invention may treat subjects with PSA levels greater than 8 ng/mL where the subject suffers from high-risk nmCRPC. The patient population includes subjects suffering from nmCRPC where PSA doubles in less than 8 months or less than 10 months. The method may also treat patient populations where the total serum testosterone levels are greater than 20 ng/mL in a subject suffering from high-risk nmCRPC. In one case, the serum free testosterone levels are greater than those observed in an orchiectomized male in a subject suffering from high-risk nmCRPC.

The pharmaceutical compositions of the invention may further comprise at least one LHRH agonist or antagonist, antiandrogen, anti-programmed death receptor 1 (anti-PD-1) drug or anti-PD-L1 drug. LHRH agonists include, but are not limited to, leuprolide acetate (Lupron®) (U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). LHRH antagonists include, but are not limited to, degarelix or abarelix. Antiandrogens include, but are not limited to, bicalutamide, flutamide, apalutamide, finasteride, dutasteride, enzalutamide, nilutamide, chlormadinone, abiraterone, or any combination thereof. Anti-PD-1 drugs include, but are not limited to, AMP-224, nivolumab, pembrolizumab, pidilizumab, and AMP-554. Anti-PD-L1 drugs include, but are not limited to, BMS-936559, atezolizumab, durvalumab, avelumab, and MPDL3280A. Anti-CTLA-4 drugs include, but are not limited to, ipilimumab and tremelimumab.

Treatment of prostate cancer, advanced prostate cancer, CRPC, mCRPC and/or nmCRPC may result in clinically meaningful improvement in prostate cancer related symptoms, function and/or survival. Clinically meaningful improvement can be determined by an increase in radiographic progression free survival (rPFS) if cancer is metastatic, or an increase metastasis-free survival (MFS) if cancer is non-metastatic, among others.

The invention encompasses methods of lowering serum prostate specific antigen (PSA) levels in a male subject suffering from prostate cancer, advanced prostate cancer, metastatic prostate cancer or castration resistant prostate cancer (CRPC) comprising administering a therapeutically effective amount of a SARD compound, wherein the compound is represented by the structure of formulas I-IX, IA, IB, IC, ID, IIA, IIB, VIIA, VIIB, VIIIA, VIIIB, IXA or IXB or the compound is at least one of compounds 1001 to 1064 and 1069 to 1071.

The invention encompasses a method of secondary hormonal therapy that reduces serum PSA in a male subject suffering from castration resistant prostate cancer (CRPC) comprising administering a therapeutically effective amount of a compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071 that reduces serum PSA in a male subject suffering from castration resistant prostate cancer.

The invention encompasses a method of reducing levels of AR, AR-full length (AR-FL), AR-FL with antiandrogen resistance-conferring AR-LBD mutations, AR-splice variant (AR-SV), and/or amplifications of the AR gene within the tumor in the subject in need thereof comprising administering a therapeutically effective amount of a compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071 to reduce the level of AR, AR-full length (AR-FL), AR-FL with antiandrogen resistance-conferring AR-LBD or other AR mutations, AR-splice variant (AR-SV), and/or amplifications of the AR gene within the tumor.

The method may increase radiographic progression free survival (rPFS) or metastasis-free survival (MFS).

Subjects may have non-metastatic cancer; failed androgen deprivation therapy (ADT), undergone orchidectomy, or have high or increasing prostate specific antigen (PSA) levels; subjects may be a patient with prostate cancer, advanced prostate cancer, refractory prostate cancer, CRPC patient, metastatic castration resistant prostate cancer (mCRPC) patient, or non-metastatic castration resistant prostate cancer (nmCRPC) patient. In these subjects, the refractory may be enzalutamide resistant prostate cancer. In these subjects, the nmCRPC may be high-risk nmCRPC. Further the subject may be on androgen deprivation therapy (ADT) with or without castrate levels of total T.

As used herein, the phrase "a subject suffering from castration resistant prostate cancer" refers to a subject with at least one of the following characteristics: has been previously treated with androgen deprivation therapy (ADT); has responded to the ADT and currently has a serum PSA >2 ng/mL or >2 ng/mL and representing a 25% increase above the nadir achieved on the ADT; a subject which despite being maintained on androgen deprivation therapy is diagnosed to have serum PSA progression; a castrate level of serum total testosterone (<50 ng/dL) or a castrate level of serum total testosterone (<20 ng/dL). The subject may have rising serum PSA on two successive assessments at least 2 weeks apart; been effectively treated with ADT; or has a history of serum PSA response after initiation of ADT.

As used herein, the term "serum PSA progression" refers to a 25% or greater increase in serum PSA and an absolute increase of 2 ng/ml or more from the nadir; or to serum PSA >2 ng/mL, or >2 ng/mL and a 25% increase above the nadir after the initiation of androgen deprivation therapy (ADT). The term "nadir" refers to the lowest PSA level while a patient is undergoing ADT.

The term "serum PSA response" refers to at least one of the following: at least 90% reduction in serum PSA value prior to the initiation of ADT; to <10 ng/mL undetectable level of serum PSA (<0.2 ng/mL) at any time; at least 50% decline from baseline in serum PSA; at least 90% decline from baseline in serum PSA; at least 30% decline from baseline in serum PSA; or at least 10% decline from baseline in serum PSA.

The methods of this invention comprise administering a combination of forms of ADT and a compound of this invention. Forms of ADT include a LHRH agonist. LHRH agonist includes, but is not limited to, leuprolide acetate (Lupron®)(U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). Forms of ADT include, but are not limited to LHRH antagonists, reversible antiandrogens, or bilateral orchidectomy. LHRH antagonists include, but are not limited to, degarelix and abarelix. Antiandrogens include, but are not limited to, bicalutamide, flutamide, apalutamide, finasteride, dutasteride, enzalutamide, EPI-001, EPI-506, ARN-509, ODM-201, nilutamide, chlormadinone, abiraterone, or any combination thereof.

The methods of the invention encompass administering at least one compound of the invention and a lyase inhibitor (e.g., abiraterone).

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. Patients with significant risk of progressive disease and/or death from prostate cancer should be included in the definition and any patient with cancer outside the prostate capsule with disease stages as low as IIB clearly has "advanced" disease. "Advanced prostate cancer" can refer to locally advanced prostate cancer. Similarly, "advanced breast cancer" refers to metastatic cancer having originated in the breast, and having widely metastasized to beyond the breast to surrounding tissues or other parts of the body such as the liver, brain, lungs, or bone.

The term "refractory" may refer to cancers that do not respond to treatment. E.g., prostate or breast cancer may be resistant at the beginning of treatment or it may become resistant during treatment. "Refractory cancer" may also be referred to herein as "resistant cancer".

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. CRPC may be the result of AR activation by intracrine androgen synthesis; expression of AR splice variants (AR-SV) that lack ligand binding domain (LBD); or expression of AR-LBD or other AR mutations with potential to resist antagonists. Castration resistant prostate cancer (CRPC) is an advanced prostate cancer which developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, apalutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Castration resistant prostate cancer may be defined as hormone naïve prostate cancer. In men with castration resistant prostate cancer, the tumor cells may have the ability to grow in the absence of androgens (hormones that promote the development and maintenance of male sex characteristics).

Many early prostate cancers require androgens for growth, but advanced prostate cancers are androgen-independent, or hormone naïve.

The term "androgen deprivation therapy" (ADT) may include orchiectomy; administering luteinizing hormone-releasing hormone (LHRH) analogs; administering luteinizing hormone-releasing hormone (LHRH) antagonists; administering 5α-reductase inhibitors; administering antiandrogens; administering inhibitors of testosterone biosynthesis; administering estrogens; or administering 17α-hydroxylase/C17,20 lyase (CYP17A1) inhibitors. LHRH drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). Antiandrogens block the body's ability to use any androgens. Examples of antiandrogens drugs include enzalutamide (Xtandi®), flutamide (Eulexin®), apalutamide (Erleada®), bicalutamide (Casodex®), and nilutamide (Nilandron®). Luteinizing hormone-releasing hormone (LHRH) antagonists include abarelix (Plenaxis®) or degarelix (Firmagon®) (approved for use by the FDA in 2008 to treat advanced prostate cancer). 5α-Reductase inhibitors block the body's ability to convert testosterone to the more active androgen, 5α-dihydrotestosterone (DHT) and include drugs such as finasteride (Proscar®) and dutasteride (Avodart®). Inhibitors of testosterone biosynthesis include drugs such as ketoconazole (Nizoral®). Estrogens include diethylstilbestrol or 17β-estradiol. 17α-Hydroxylase/C17,20 lyase (CYP17A1) inhibitors include abiraterone (Zytiga®).

The invention encompasses a method of treating antiandrogen-resistant prostate cancer. The antiandrogen may include, but is not limited to, bicalutamide, hydroxyflutamide, flutamide, apalutamide, enzalutamide, darolutamide, or abiraterone.

The invention encompasses a method of treating prostate cancer in a subject in need thereof, wherein said subject has a rearranged AR, AR overexpressing prostate cancer, castration-resistant prostate cancer, castration-sensitive prostate cancer, AR-V7 expressing prostate cancer, or d567ES expressing prostate cancer, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

In one embodiment, the castration-resistant prostate cancer is a rearranged AR, AR overexpressing castration-resistant prostate cancer, F876L mutation expressing castration-resistant prostate cancer, F876L_T877A double mutation expressing castration-resistant prostate cancer, AR-V7 expressing castration-resistant prostate cancer, d567ES expressing castration-resistant prostate cancer, and/or castration-resistant prostate cancer characterized by intratumoral androgen synthesis.

In one embodiment, the castration-sensitive prostate cancer is F876L mutation expressing castration-sensitive prostate cancer, F876L_T877A double mutation castration-sensitive prostate cancer, and/or castration-sensitive prostate cancer characterized by intratumoral androgen synthesis.

In one embodiment, the treating of castration-sensitive prostate cancer is conducted in a non-castrate setting, or as monotherapy, or when castration-sensitive prostate cancer tumor is resistant to enzalutamide, apalutamide, and/or abiraterone.

The invention encompasses a method of treating AR overexpressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating castration-resistant prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071. In one embodiment, the castration-resistant prostate cancer is a rearranged AR, AR overexpressing castration-resistant prostate cancer, F876L mutation expressing castration-resistant prostate cancer, F876L_T877A double mutation expressing castration-resistant prostate cancer, AR-V7 expressing castration-resistant prostate cancer, d567ES expressing castration-resistant prostate cancer, and/or castration-resistant prostate cancer characterized by intratumoral androgen synthesis.

The invention encompasses a method of treating castration-sensitive prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071. In one embodiment, the castration-sensitive prostate cancer is F876L mutation expressing castration-sensitive prostate cancer, F876L_T877A double mutation castration-sensitive prostate cancer, and/or castration-sensitive prostate cancer characterized by intratumoral androgen synthesis. In one embodiment, the treating of castration-sensitive prostate cancer is conducted in a non-castrate setting, or as monotherapy, or when castration-sensitive prostate cancer tumor is resistant to enzalutamide, apalutamide, and/or abiraterone.

The invention encompasses a method of treating AR-V7 expressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

The invention encompasses a method of treating d567ES expressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

Treatment of Triple Negative Breast Cancer (TNBC)

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, enzalutamide and other LBD-directed traditional AR antagonists would not be able to antagonize AR-SVs in these TNBC's. However, SARDs of this invention which are capable of destroying AR-SVs (see Table 1 and Example 5) through a binding site in the NTD of AR (see Example 9) would be able to antagonize AR in these TNBC's and provide an anti-tumor effect, as shown in Example 8.

Treatment of Kennedy's Disease

Muscle atrophy (MA) is characterized by wasting away or diminution of muscle and a decrease in muscle mass. For example, post-polio MA is muscle wasting that occurs as part of the post-polio syndrome (PPS). The atrophy includes weakness, muscle fatigue, and pain. Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR).

Binding and activation of the polyQ AR by endogeneous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Peripheral polyQ AR antisense therapy rescues disease in mouse models of SBMA (*Cell Reports* 7, 774-784, May 8, 2014). Further support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). These steps are required for pathogenesis and result in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic intervention.

Selective androgen receptor degraders such as those reported herein bind to, inhibit transactivation, and degrade all androgen receptors tested to date (full length, splice variant, antiandrogen resistance mutants, etc.), indicating that they are promising leads for treatment diseases whose pathogenesis is androgen-dependent such as SBMA.

The invention encompasses methods of treating Kennedy's disease comprising administering a therapeutically effective amount of a compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071.

The term "androgen receptor dependent disease or condition" refers to diseases or conditions that have pathological origins or propagated by the altered, increased, dysregulated, or aberrant activity of an androgen receptor. In some embodiments, the androgen receptor is a full-length androgen receptor. In another embodiment, the androgen receptor is a wildtype full-length androgen receptor (AR-FL). In another embodiment, the androgen receptor is a point mutation of the full-length androgen receptor. In another embodiment, the androgen receptor is a polyQ polymorph. In another embodiment, the androgen receptor is a splice-variant of the androgen receptor (AR-SV). In another embodiment, the androgen receptor is any of the above or a combination thereof. In another embodiment, the androgen receptor is any of the above and is additionally overexpressed. In another embodiment, the androgen receptor is any of the above and further recombined with another gene to form a fusion protein. Examples of common AR fusion proteins include but are not limited to TMPRSS2 or ETS-family of transcription factors. In some embodiments, the androgen receptor is any of the above and presence in a pathologically changed cellular milieau. In another embodiment, the altered, increased, dysregulated or abberant activity of an androgen receptor is caused by endogeneous androgens acting at the androgen receptor. In another embodiment, the altered, increased, dysregulated, or abberant activity of an androgen receptor is caused by exogenously administered compounds acting at the androgen receptor. In another embodiment, the altered, increased, dysregulated, or abberant activity of an androgen receptor is ligand-independent. In another embodiment, the ligand-independent activity is caused by the constitutive activity of the androgen receptor. In another embodiment, the ligand-independent activity is caused by constitutively active mutants of the androgen receptor. In another embodiment, the ligand-independent activity is caused by pathologic cellular milieau. In another embodiment, these androgen receptor dependent diseases and conditions are improved by the administration of androgen receptor antagonists. In another embodiment, these androgen receptor dependent diseases and conditions are improved by the administration of androgen deprivation therapies (ADT) as described herein. In another embodiment, these androgen receptor dependent diseases and conditions are made worse by the administration of androgen receptor agonists. In another embodiment, these androgen receptor dependent diseases and conditions are improved by decreasing androgen receptor expression by biochemical treatments. In another embodiment, these androgen receptor dependent diseases and conditions are the result of hormonal imbalances. In another embodiment, the hormonal imbalance in a subject is a result of ageing, or in the other embodiments, the result of disease. In another embodiment, these androgen receptor dependent diseases and conditions are responsive to the administration of androgen receptor antagonists such as anti-androgens. In another embodiment, these androgen receptor dependent diseases and conditions are conditions, diseases, or disorders that are modulated by or whose pathogenesis is dependent upon the activity of the androgen receptor.

In some embodiments, the androgen receptor dependent diseases and conditions are improved by administration of the selective androgen receptor degraders of the invention. In some embodiments, the benefit of selective androgen receptor degraders of the invention is their degradation of at least one form of the androgen receptor. In some embodiments, the benefit of selective androgen receptor degraders of the invention is their inhibition of at least one form of the androgen receptor. In some embodiments, the benefit of selective androgen receptor degraders of the invention is their degradation and inhibition of at least one form of the androgen receptor.

Many examples of androgen receptor dependent diseases and conditions are described herein, and these include but are not limited to prostate cancers, breast cancers, hormone-dependent cancers, hormone-independent cancers, AR-expressing cancers, and precursors to hormone-dependent cancers as are each described in detail herein below; dermatological disorders, hormonal conditions of a male or hormonal conditions of a female as are each described in detail herein below; androgen insufficiency syndromes as are described in detail below; uterine fibroids, Kennedy's disease (SBMA), amyotrophic lateral sclerosis (ALS), abdominal aortic aneurysm (AAA), improving wound healing, sexual perversion, hypersexuality, paraphilias, androgen psychosis, and virilization and the like.

As used herein, the term "androgen receptor associated conditions" or "androgen sensitive diseases or disorders" or "androgen-dependent diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and SARDs may also be useful in treating various prostate cancers, benign prostatic hypertrophy, prostamegaly, and other maladies of the prostate.

The invention encompasses methods of treating benign prostatic hypertrophy comprising administering a therapeutically effective amount of at least one compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071.

The invention encompasses methods of treating prostamegaly comprising administering a therapeutically effective amount of at least one compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071.

The invention encompasses methods of treating hyperproliferative prostatic disorders and diseases comprising administering a therapeutically effective amount of a compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although anti-androgens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and (in some cases) have short biological half-lives in the serum, suggesting that topically formulated SARDs of this invention could be applied to the areas affected by acne, seborrheic dermatitis, and/or hirsutism without risk of systemic side effects.

The invention encompasses methods of treating acne, acne vulgaris, seborrhea, seborrheic dermatitis, hidradenitis supporativa, hirsutism, hypertrichosis, hyperpilosity, or alopecia comprising administering a therapeutically effective amount of a compound of formulas I-IX, IA, IB, IC, ID, IIA, IIB, VIIA, VIIB, VIIIA, VIIIB, IXA or IXB, or any of compounds 1001 to 1064 and 1069 to 1071.

The compounds and/or compositions described herein may be used for treating hair loss, alopecia, androgenic alopecia, alopecia areata, alopecia secondary to chemotherapy, alopecia secondary to radiation therapy, alopecia induced by scarring or alopecia induced by stress. Generally "hair loss" or "alopecia" refers to baldness as in the very common type of male-pattern baldness. Baldness typically begins with patch hair loss on the scalp and sometimes progresses to complete baldness and even loss of body hair. Hair loss affects both males and females.

The invention encompasses methods of treating androgenic alopecia comprising administering a therapeutically effective amount of a compound of formula I-IX, IA, IB, IC, ID, IIA, IIB, VIIA, VIIB, VIIIA, VIIIB, IXA or IXB, or any of compounds 1001 to 1064 and 1069 to 1071.

The invention encompasses methods of treating, suppressing, reducing the incidence, reducing the severity, or inhibiting the progression of a hormonal condition in a male in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of formula I-IX, IA, IB, IC, ID, IIA, IIB, VIIA, VIIB, VIIIA, VIIIB, IXA or IXB, or the compound is at least one of compounds 1001 to 1064 and 1069 to 1071.

In one embodiment, the condition is hypergonadism, hypersexuality, sexual dysfunction, gynecomastia, precocious puberty in a male, alterations in cognition and mood, depression, hair loss, hyperandrogenic dermatological disorders, pre-cancerous lesions of the prostate, benign prostate hyperplasia, prostate cancer and/or other androgen-dependent cancers.

SARDs of this invention may also be useful in the treatment of hormonal conditions in females which can have hyperandrogenic pathogenesis such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and/or vaginal dryness.

The invention encompasses methods of treating precocious puberty or early puberty, dysmenorrhea or amenorrhea, multilocular uterus syndrome, endometriosis, hysteromyoma, abnormal uterine bleeding, hyper-androgenic diseases (such as polycystic ovary syndrome (PCOS)), fibrocystic breast disease, fibroids of the uterus, ovarian cysts, polycystic ovary syndrome, pre-eclampsia, eclampsia of pregnancy, preterm labor, premenstrual syndrome, or vaginal dryness comprising administering a therapeutically effective amount of a compound of formulas I-IX, IA, IB, IC, ID, IIA, IIB, VIIA, VIIB, VIIIA, VIIIB, IXA or IXB, or any of compounds 1001 to 1064 and 1069 to 1071.

SARDs of this invention may also find utility in treatment of sexual perversion, hypersexuality, paraphilias, androgen psychosis, virilization, androgen insensitivity syndromes (AIS) (such as complete AIS (CAIS) and partial AIS (PAIS)), and improving ovulation in an animal.

The invention encompasses methods of treating sexual perversion, hypersexuality, paraphilias, androgen psychosis, virilization androgen, insensitivity syndromes, increasing or modulating or improving ovulation comprising administering a therapeutically effective amount of a compound of formulas I-IX, IA, IB, IC, ID, IIA, IIB, VIIA, VIIB, VIIIA, VIIIB, IXA or IXB, or any of compounds 1001 to 1064 and 1069 to 1071.

SARDs of this invention may also be useful for treating hormone-dependent cancers such as prostate cancer, breast cancer, testicular cancer, ovarian cancer, hepatocellular carcinoma, urogenital cancer, etc. In another embodiment, the breast cancer is triple negative breast cancer. Further, local or systemic SARD administration may be useful for treatment of precursors of hormone-dependent cancers such as prostatic intraepithelial neoplasia (PIN) and atypical small acinar proliferation (ASAP).

The invention encompasses methods of treating breast cancer, testicular cancer, uterine cancer, ovarian cancer, urogenital cancer, precursors of prostate cancer, or AR related or AR expressing solid tumors, comprising administering a therapeutically effective amount of a compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071. A precursor of prostate cancers may be prostatic intraepithelial neoplasia (PIN) or atypical small acinar proliferation (ASAP). The tumor may be hepatocellular carcinoma (HCC) or bladder cancer. Serum testosterone may be positively linked to the development of HCC. Based on epidemiologic, experimental observations, and notably the fact that men have a substantially higher risk of bladder cancer than women, androgens and/or the AR may also play a role in bladder cancer initiation.

Although traditional antiandrogens such as enzalutamide, bicalutamide and flutamide and androgen deprivation therapies (ADT) such as leuprolide were approved for use in prostate cancer, there is significant evidence that antiandrogens could also be used in a variety of other hormone-dependent and hormone-independent cancers. For example, antiandrogens may be used in a wide variety of AR-expressing cancers as described below. For example, antiandrogens have been successfully tested in breast cancer (enzalutamide; Breast Cancer Res (2014) 16(1): R7), non-small cell lung cancer (shRNAi AR), renal cell carcinoma (ASC-J9), partial androgen insensitivity associated malignancies such as gonadal tumors and seminoma, advanced pancreatic cancer (World J Gastroenterology 20(29):9229), cancer of the ovary, fallopian tubes, or peritoneum, cancer of the salivary gland (Head and Neck (2016) 38: 724-731; ADT was tested in AR-expressing recurrent/metastatic salivary gland cancers and was confirmed to have benefit on progression free survival and overall survival endpoints), bladder cancer (Oncotarget 6 (30): 29860-29876); Int J Endocrinol (2015), Article ID 384860), pancreatic cancer, lymphoma (including mantle cell), and hepatocellular carcinoma. Use of a more potent antiandrogen such as a SARD in these cancers may treat the progression of these and other cancers. Other cancers may also benefit from SARD treatment such as testicular cancer, uterine cancer, ovarian cancer, urogenital cancer, breast cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, or central nervous system cancer.

SARDs of this invention may also be useful for treating other cancers containing AR such as breast, brain, skin, ovarian, bladder, lymphoma, liver, kidney, pancreas, endometrium, lung (e.g., NSCLC), colon, perianal adenoma, osteosarcoma, CNS, melanoma, hypercalcemia of malignancy and metastatic bone disease, etc.

Thus, the invention encompasses methods of treating hypercalcemia of malignancy, metastatic bone disease, brain cancer, skin cancer, bladder cancer, lymphoma, liver cancer, renal cancer, osteosarcoma, pancreatic cancer, endometrial cancer, lung cancer, central nervous system cancer, gastric cancer, colon cancer, melanoma, amyotrophic lateral sclerosis (ALS), and/or uterine fibroids comprising administering a therapeutically effective amount of a compound of formulas I-IX, IA, IB, IC, ID, IIA, IIB, VIIA, VIIB, VIIIA, VIIIB, IXA or IXB, or any of compounds 1001 to 1064 and 1069 to 1071. The lung cancer may be non-small cell lung cancer (NSCLC).

SARDs of this invention may also be useful for the treating of non-hormone-dependent cancers. Non-hormone-dependent cancers include liver, salivary duct, etc.

In another embodiment, the SARDs of this invention are used for treating gastric cancer. In another embodiment, the SARDs of this invention are used for treating salivary duct carcinoma. In another embodiment, the SARDs of this invention are used for treating bladder cancer. In another embodiment, the SARDs of this invention are used for treating esophageal cancer. In another embodiment, the SARDs of this invention are used for treating pancreatic cancer. In another embodiment, the SARDs of this invention are used for treating colon cancer. In another embodiment, the SARDs of this invention are used for treating non-small cell lung cancer. In another embodiment, the SARDs of this invention are used for treating renal cell carcinoma.

AR plays a role in cancer initiation in hepatocellular carcinoma (HCC). Therefore, targeting AR may be an appropriate treatment for patients with early stage HCC. In late-stage HCC disease, there is evidence that metastasis is suppressed by androgens. In another embodiment, the SARDs of this invention are used for treating hepatocellular carcinoma (HCC).

Locati et al. in Head & Neck, 2016, 724-731 demonstrated the use of androgen deprivation therapy (ADT) in AR-expressing recurrent/metastatic salivary gland cancers and confirmed improved progression free survival and overall survival endpoints with ADT. In another embodiment, the SARDs of this invention are used for treating salivary gland cancer.

Kawahara et al. in Oncotarget, 2015, Vol 6 (30), 29860-29876 demonstrated that ELK1 inhibition, together with AR inactivation, has the potential of being a therapeutic approach for bladder cancer. McBeth et al. Int J Endocrinology, 2015, Vol 2015, Article ID 384860 suggested that the combination of antiandrogen therapy plus glucocorticoids as treatment of bladder cancer as this cancer is believed to have an inflammatory etiology. In another embodiment, the SARDs of this invention are used for treating bladder cancer, optionally in combination with glucocorticoids.

Abdominal Aortic Aneurysm (AAA)

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated AAA induced by porcine pancreatic elastase (0.35 U/mL) by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

Treatment of Wounds

Wounds and/or ulcers are normally found protruding from the skin or on a mucosal surface or as a result of an infarction in an organ. A wound may be a result of a soft tissue defect or a lesion or of an underlying condition. The term "wound" denotes a bodily injury with disruption of the normal integrity of tissue structures, sore, lesion, necrosis, and/or ulcer. The term "sore" refers to any lesion of the skin or mucous membranes and the term "ulcer" refers to a local defect, or excavation, of the surface of an organ or tissue, which is produced by the sloughing of necrotic tissue. "Lesion" generally includes any tissue defect. "Necrosis" refers to dead tissue resulting from infection, injury, inflammation, or infarctions. All of these are encompassed by the term "wound," which denotes any wound at any particular stage in the healing process including the stage before any healing has initiated or even before a specific wound like a surgical incision is made (prophylactic treatment).

Examples of wounds which can be treated in accordance with the present invention are aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores include, but are not limited to, bed sores, canker sores, chrome sores, cold sores, pressure sores, etc. Examples of ulcers include, but are not limited to, peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g., caused by gonorrhoea (including urethritis, endocervicitis and proctitis). Conditions related to wounds or sores which may be successfully treated according to the invention include, but are not limited to, burns, anthrax, tetanus, gas gangrene, scalatina, erysipelas, sycosis barbae, folliculitis, impetigo contagiosa, impetigo bullosa, etc. It is understood, that there may be an overlap between the use of the terms "wound" and "ulcer," or "wound" and "sore" and, furthermore, the terms are often used at random.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is by tissue loss, where: i) small tissue loss (due to surgical incisions, minor abrasions, and minor bites) or ii) significant tissue loss. The latter group includes ischemic ulcers, pressure sores, fistulae, lacerations, severe bites, thermal burns and donor site wounds (in soft and hard tissues) and infarctions. Other wounds include ischemic ulcers, pressure sores, fistulae, severe bites, thermal burns, or donor site wounds.

Ischemic ulcers and pressure sores are wounds, which normally only heal very slowly and especially in such cases an improved and more rapid healing is of great importance to the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

In one case, the wound to be treated is selected from the group consisting of aseptic wounds, infarctions, contused wounds, incised wounds, lacerated wounds, non-penetrating wounds, open wounds, penetrating wounds, perforating wounds, puncture wounds, septic wounds, and subcutaneous wounds.

The invention encompasses methods of treating a subject suffering from a wound comprising administering to the subject a therapeutically effective amount of a compound of formulas I-IX, IA, IB, IC, ID, IIA, IIB, VIIA, VIIB, VIIIA, VIIIB, IXA or IXB, or the compound is at least one of compounds 1001 to 1064 and 1069 to 1071; or pharmaceutically acceptable salt thereof, or a pharmaceutical composition thereof.

The invention encompasses methods of treating a subject suffering from a burn comprising administering to the subject a therapeutically effective amount of a compound of formulas I-IX, IA, IB, IC, ID, IIA, IIB, VIIA, VIIB, VIIIA, VIIIB, IXA or IXB, or the compound is at least one of compounds 1001 to 1064 and 1069 to 1071; or pharmaceutically acceptable salt thereof, or a pharmaceutical composition thereof.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing. The invention encompasses methods for treating a subject suffering from a wound or a burn by administering at least one SARD compound according to this invention. The SARD may promote resolving of the burn or wound, participates in the healing process of a burn or a wound, or, treats a secondary complication of a burn or wound.

The treatment of burns or wounds may further use at least one growth factor such as epidermal growth factor (EGF), transforming growth factor-$\alpha$ (TGF-$\alpha$), platelet derived growth factor (PDGF), fibroblast growth factors (FGFs) including acidic fibroblast growth factor ($\alpha$-FGF) and basic fibroblast growth factor ($\beta$-FGF), transforming growth factor-$\beta$ (TGF-$\beta$) and insulin like growth factors (IGF-1 and IGF-2), or any combination thereof, which promote wound healing.

Wound healing may be measured by many procedures known in the art, including, but not limited to, wound tensile strength, hydroxyproline or collagen content, procollagen expression, or re-epithelialization. As an example, a SARD as described herein may be administered orally or topically at a dosage of about 0.1-100 mg per day. Therapeutic effectiveness is measured as effectiveness in enhancing wound healing as compared to the absence of the SARD compound. Enhanced wound healing may be measured by known techniques such as decrease in healing time, increase in collagen density, increase in hydroxyproline, reduction in complications, increase in tensile strength, and increased cellularity of scar tissue.

The term "reducing the pathogenesis" is to be understood to encompass reducing tissue damage, or organ damage associated with a particular disease, disorder or condition. The term may include reducing the incidence or severity of an associated disease, disorder or condition, with that in question or reducing the number of associated diseases, disorders or conditions with the indicated, or symptoms associated thereto.

Pharmaceutical Compositions

The compounds of the invention may be used in pharmaceutical compositions. As used herein, "pharmaceutical composition" means either the compound or pharmaceutically acceptable salt of the active ingredient with a pharmaceutically acceptable carrier or diluent. A "therapeutically effective amount" as used herein refers to that amount which provides a therapeutic effect for a given indication and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. The subjects may be a male or female subject or both.

Numerous standard references are available that describe procedures for preparing various compositions or formulations suitable for administration of the compounds of the invention. Examples of methods of making formulations and preparations can be found in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions of the invention can be administered to a subject by any method known to a person skilled in the art. These methods include, but are not limited to, orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, or intratumorally. These methods include any means in which the composition can be delivered to tissue (e.g., needle or catheter). Alternatively, a topical administration may be desired for application to dermal, ocular, or mucosal surfaces. Another method of administration is via aspiration or aerosol formulation. The pharmaceutical compositions may be administered topically to body surfaces, and are thus formulated in a form suitable for topical administration. Suitable topical formulations include gels, ointments, creams, lotions, drops and the like. For topical administrations, the compositions are prepared and applied as solutions, suspensions, or emulsions in a physiologically acceptable diluent with or without a pharmaceutical carrier.

Suitable dosage forms include, but are not limited to, oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. Depending on the indication, formulations suitable for oral or topical administration are preferred.

Topical Administration: The compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 may be administered topically. As used herein, "topical administration" refers to application of the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 (and optional carrier) directly to the skin and/or hair. The topical composition can be in the form of solutions, lotions, salves, creams, ointments, liposomes, sprays, gels, foams, roller sticks, and any other formulation routinely used in dermatology.

Topical administration is used for indications found on the skin, such as hirsutism, alopecia, acne, and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allow the drug to diffuse to the site of action. More specifically "site of action", it refers to a site where inhibition of androgen receptor or degradation of the androgen receptor is desired.

The compounds of formulas I-IX, IA, IB, IC, ID, IIA, IIB, VIIA, VIIB, VIIIA, VIIIB, IXA or IXB, or the compound is at least one of compounds 1001 to 1064 and 1069 to 1071 may be used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 will most typically be used to alleviate androgenic alopecia, the compounds may be used to alleviate any type of alopecia. Examples of non-androgenic alopecia include, but are not limited to, alopecia areata, alopecia due to radiotherapy or chemotherapy, scarring alopecia, or stress related alopecia.

The compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 can be applied topically to the scalp and hair to prevent, or treat balding. Further, the compound of formulas I-IX, IA, IB, IC, ID, IIA, IIB, VIIA, VIIB, VIIIA, VIIIB, IXA or IXB or the compound is at least one of compounds 1001 to 1064 and 1069 to 1071 can be applied topically in order to induce or promote the growth or regrowth of hair on the scalp.

The invention also encompasses topically administering a compound of formula I-IX, IA, IB, IC, ID, IIA, IIB, VIIA, VIIB, VIIIA, VIIIB, IXA or IXB or the compound is at least one of compounds 1001 to 1064 and 1069 to 1071 to treat or prevent the growth of hair in areas where such hair growth in not desired. One such use will be to alleviate hirsutism. Hirsutism is excessive hair growth in areas that typically do not have hair (e.g., a female face). Such inappropriate hair growth occurs most commonly in women and is frequently seen at menopause. The topical administration of the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 will alleviate this condition leading to a reduction, or elimination of this inappropriate, or undesired, hair growth.

The compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. The compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 inhibit the secretion of sebum and thus reduce the amount of sebum on the surface of the skin. The compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 can be used to treat a variety of dermal diseases such as acne or seborrheic dermatitis.

In addition to treating diseases associated with excess sebum production, the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 can also be used to achieve a cosmetic effect. Some consumers believe that they are afflicted with overactive sebaceous glands. They feel that their skin is oily and thus unattractive. These individuals may use the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 to decrease the amount of sebum on their skin. Decreasing the secretion of sebum will alleviate oily skin in individuals afflicted with such conditions.

To treat these topical indications, the invention encompasses cosmetic or pharmaceutical compositions (such as dermatological compositions), comprising at least one of the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071. Such dermatological compositions will contain from 0.001% to 10% w/w % of the compound(s) in admixture with a dermatologically acceptable carrier, and more typically, from 0.1 to 5 w/w % of the compounds. Such compositions will typically be applied from 1 to 4 times daily. The reader's attention is directed to Remington's Pharmaceutical Science, Edition 17, Mark Publishing Co., Easton, Pa. for a discussion of how to prepare such formulations.

The compositions of the invention may also include solid preparations such as cleansing soaps or bars. These compositions are prepared according to methods known in the art.

Formulations such as aqueous, alcoholic, or aqueous-alcoholic solutions, or creams, gels, emulsions or mousses, or aerosol compositions with a propellant may be used to treat indications that arise where hair is present. Thus, the composition can also be a hair care composition. Such hair care compositions include, but are not limited to, shampoo, a hair-setting lotion, a treating lotion, a styling cream or gel, a dye composition, or a lotion or gel for preventing hair loss. The amounts of the various constituents in the dermatological compositions are those conventionally used in the fields considered.

Medicinal and cosmetic agents containing the compounds of formulas I-IX, IA, IB, IC, ID, IIA, IIB, VIIA, VIIB, VIIIA, VIIIB, IXA or IXB or the compound is at least one of compounds 1001 to 1064 and 1069 to 1071 will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen levels or block androgen action in the skin to some extent but suffer from undesirable systemic effects. An alternative approach is to topically apply a selective androgen receptor degrader (SARD) compound to the affected areas. Such SARD compound would exhibit potent but local inhibition of AR activity, and local degradation of the AR, would not penetrate to the systemic circulation of the subject, or would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral and Parenteral Administration:

In preparing the compositions in oral dosage form, any of the usual pharmaceutical media may be employed. Thus, for liquid oral preparations, such as, suspensions, elixirs, and solutions, suitable carriers and additives include water, glycols, oils, alcohols, flavoring agents, preservatives, coloring agents, and the like. For solid oral preparations such as, powders, capsules, and tablets, suitable carriers and additives include starches, sugars, diluents, granulating agents, lubricants, binders, disintegrating agents, and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients may be included, such as ingredients that aid solubility or for preservation. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Methods of treatment using formulations suitable for oral administration may be presented as discrete units such as capsules, cachets, tablets, or lozenges, each containing a predetermined amount of the active ingredient. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more ingredient selected from diluents, buffers, flavoring agents, binders, disintegrants, surface active agents, thickeners, lubricants, preservatives (including antioxidants), and the like.

The formulations may be of immediate release, sustained release, delayed-onset release or any other release profile known to one skilled in the art.

For administration to mammals, and particularly humans, it is expected that the physician will determine the actual dosage and duration of treatment, which will be most suitable for an individual and can vary with the age, weight, genetics and/or response of the particular individual.

The methods of the invention comprise administration of a compound at a therapeutically effective amount. The therapeutically effective amount may include various dosages.

In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day.

The methods may comprise administering a compound at various dosages. For example, the compound may be administered at a dosage of 3 mg, 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg.

Alternatively, the compound may be administered at a dosage of 0.1 mg/kg/day. The compound may administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

The pharmaceutical composition may be a solid dosage form, a solution, or a transdermal patch. Solid dosage forms include, but are not limited to, tablets and capsules.

The following examples are presented in order to more fully illustrate the preferred embodiments of the invention. They should in no way, however, be construed as limiting the broad scope of the invention.

EXAMPLES

Example 1

Synthesis of SARDs

Synthesis of Intermediates 9-10

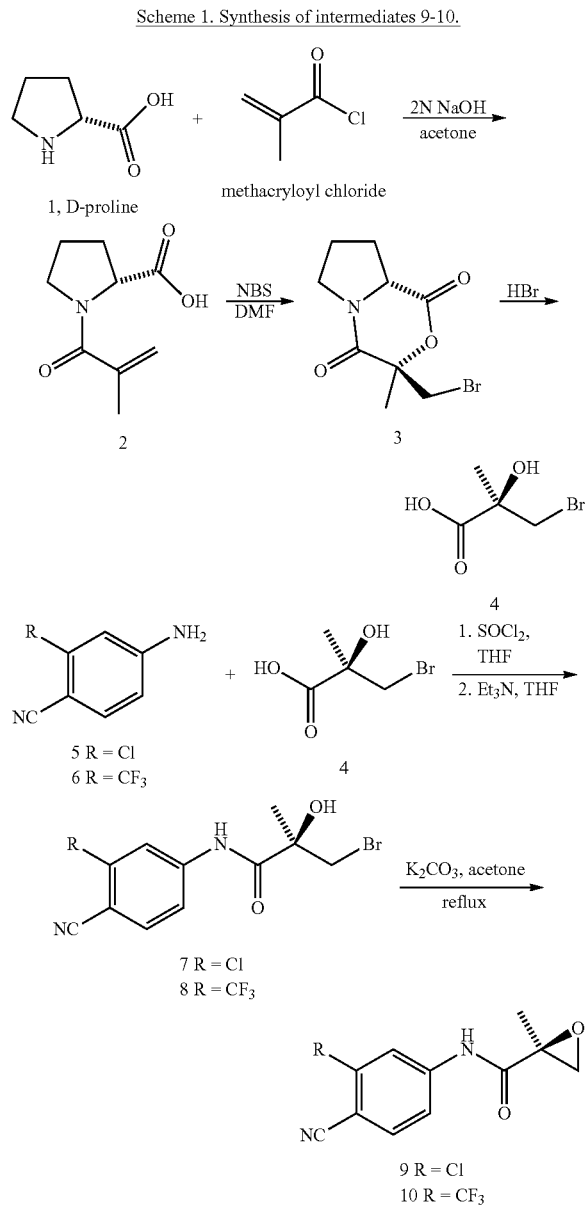

Scheme 1. Synthesis of intermediates 9-10.

(2R)-1-Methacryloylpyrrolidin-2-carboxylic acid (2)

D-Proline (1, 14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 hours (h), room temperature (RT)), the mixture was evaporated in vacuo at a temperature of 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (lit. mp 102.5-103.5° C.); the NMR spectrum of this compound demonstrated the existence of two rotamers of the title compound.

$^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral center), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 $cm^{-1}$; $[\alpha]_D^{26}$+ 80.8° (c=1, MeOH); Anal. Calcd. for $C_9H_{13}NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo [2,1-c][1,4]oxazine-1,4-dione (3)

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the titled compound as a yellow solid: mp 158.1-160.3° C.;

$^1$H NMR (300 MHz, DMSO-$d_6$) δ 4.69 (dd, J=9.6 Hz, J=6.7 Hz, 1H, CH at the chiral center), 4.02 (d, J=11.4 Hz, 1H, $CHH_a$), 3.86 (d, J=11.4 Hz, 1H, $CHH_b$), 3.53-3.24 (m, 4H, $CH_2$), 2.30-2.20 (m, 1H, CH), 2.04-1.72 (m, 3H, $CH_2$ and CH), 1.56 (s, 2H, Me); $^{13}$C NMR (75 MHz, DMSO-$d_6$) 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 $cm^{-1}$; $[\alpha]_D^{26}$+124.5° (c=1.3, chloroform); Anal. Calcd. for $C_9H_{12}BrNO_3$: C, 41.24, H, 4.61, N, 5.34. Found: C, 41.46, H, 4.64, N, 5.32.

(2R)-3-Bromo-2-hydroxy-2-methylpropanoic acid (4)

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated $NaHCO_3$ (100 mL×4). The aqueous solution was acidified with concentrated HCl to pH=1, which, in turn, was extracted with ethyl acetate (100 mL×4). The combined organic solution was dried over $Na_2SO_4$, filtered through Celite®, and evaporated in vacuo to dryness. Recrystallization from toluene afforded 10.2 g (86%) of the desired compound as colorless crystals: mp 110.3-113.8° C.;

$^1$H NMR (300 MHz, DMSO-$d_6$) δ 3.63 (d, J=10.1 Hz, 1H, $CHH_a$), 3.52 (d, J=10.1 Hz, 1H, $CHH_b$), 1.35 (s, 3H, Me);

IR (KBr) 3434 (OH), 3300-2500 (COOH), 1730 (C=O), 1449, 1421, 1380, 1292, 1193, 1085 cm$^{-1}$; $[\alpha]_D^{26}$+10.5° (c=2.6, MeOH); Anal. Calcd. for $C_4H_7BrO_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (4, 51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (6, 40.0 g, 0.21 mol), 400 mL of THF were added and then the mixture was allowed to stir overnight at RT. The solvent was removed under reduced pressure to give a solid which was treated with 300 mL of H$_2$O, and extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). MS (ESI) 349.0 [M–H]$^-$; mp 124-126° C.

(2R)-3-Bromo-N-(4-cyano-3-chlorophenyl)-2-hydroxy-2-methylpropanamide (7)

Under an argon atmosphere, thionyl chloride (15 mL, 0.20 mol) was added dropwise to a cooled solution (less than 4° C.) of (R)-3-bromo-2-hydroxy-2-methylpropanoic acid (4, 24.3 g, 0.133 mol) in 300 mL of THF at ice-water bath. The resulting mixture stirred for 3 h under the same condition. To this was added Et$_3$N (35 mL, 0.245 mol) and stirred for 20 min under the same condition. After 20 min, a solution of 4-amino-2-chlorobenzonitrile (5. 15.6 g, 0.10 mol) in 100 mL of THF were added and then the mixture was allowed to stir overnight at RT. The solvent removed under reduced pressure to give a solid, which treated with 300 mL of H$_2$O, and extracted with EtOAc (2×150 mL). The combined organic extracts washed with saturated NaHCO$_3$ solution (2×150 mL) and brine (300 mL). The organic layer was dried over MgSO$_4$ and concentrated under reduced pressure to give a solid, which purified by flash column chromatography using CH$_2$Cl$_2$/EtOAc (80:20) to give a solid. This solid was recrystallized from CH$_2$Cl$_2$/hexane to give 31.8 g (73%) of (2R)-3-bromo-N-(4-cyano-3-chlorophenyl)-2-hydroxy-2-methylpropanamide (7) as a light-yellow solid.

$^1$H NMR (CDCl$_3$, 400 MHz) δ 1.7 (s, 3H, CH$_3$), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS: 342 (M+23); mp 129° C.

(S)—N-(3-Chloro-4-cyanophenyl)-2-methyloxirane-2-carboxamide (9)

A mixture of 3-bromo-N-(4-cyano-3-chlorophenyl)-2-hydroxy-2-methylpropanamide (7, 0.84 mmol) and potassium carbonate (1.68 mmol) in 10 mL acetone was heated to reflux for 30 min. After complete conversion of starting bromide 7 to desired epoxide 9 as monitored by TLC, the solvent was evaporated under reduced pressure to give yellowish residue, which was poured into 10 mL of anhydrous EtOAc. The solution was filtered through Celite® pad to remove K$_2$CO$_3$ residue and condensed under reduced pressure to give epoxide 9 as a light yellowish solid.

$^1$H NMR (CDCl$_3$, 400 MHz) δ 8.41 (bs, NH), 8.02 (d, J=2.0 Hz, 1H, ArH), 7.91 (dd, J=2.0, 8.4 Hz, 1H, ArH), 7.79 (d, J=2.0 Hz, 1H, ArH), 3.01 (s, 2H), 1.69 (s, 3H). MS (ESI) m/z 235.0 [M–H]$^-$.

5-Membered Ring Compounds

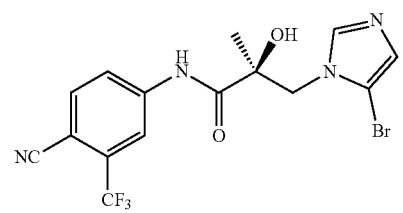

1005

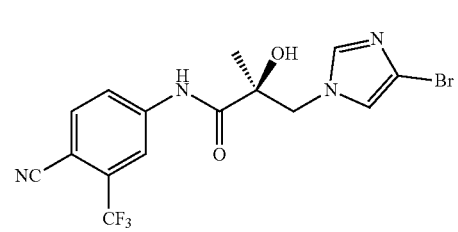

1006

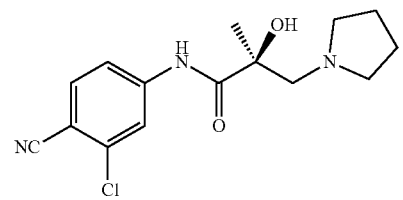

1009

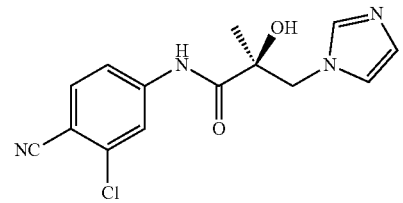

1008

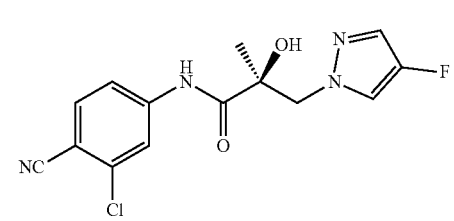

1007

Five membered ring compounds of the invention were made using the following general synthetic routes (Method A and Method B) where m=0. Variables X and Y are defined as necessary to obtain the desired compound.

Method A:

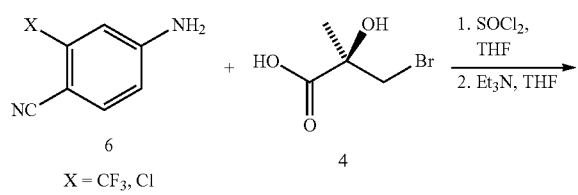

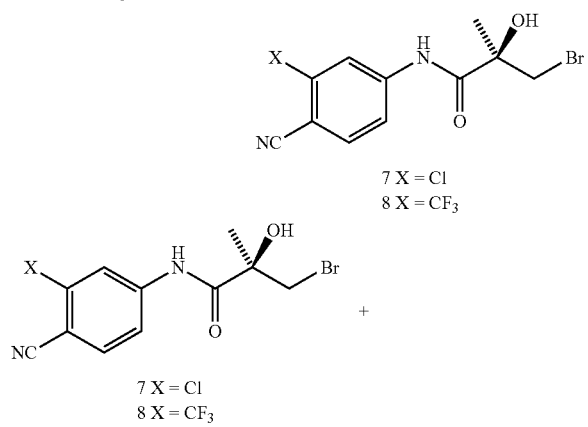

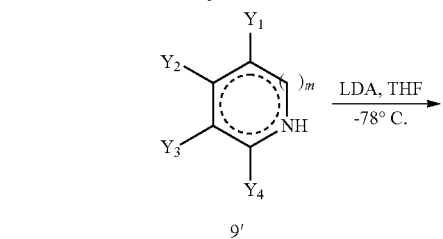

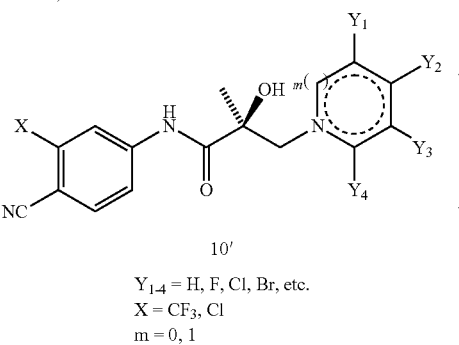

Preparation of lithium diisopropylamide (LDA) solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or commercial 2.0 M LDA was slowly warmed to 0° C. and stirred for 10 min and cooled again to −78° C. To the LDA solution was added dropwise a solution of 9' (1.0 mmol) in 5 mL of THF for 20 min. Compound 7 or 8 in THF was added dropwise through dropping funnel under argon atmosphere at −78° C. The reaction mixture was stirred at the same temperature for 30 min and quenched by addition of sat. NH₄Cl. The solution was concentrated under reduced pressure and dispersed into excess EtOAc and dried over Na₂SO₄. The solution was concentrated and the resulting solid was recrystallized from EtOAc/hexane or DCM/hexane to give designed compound 10'. The mother liquor was concentrated and purified by flash column chromatography (EtOAc/hexane) to give a second crop of 10'.

Method B:

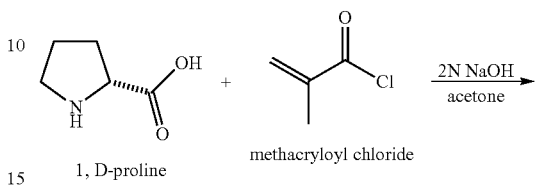

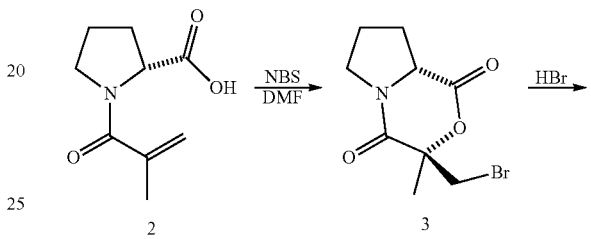

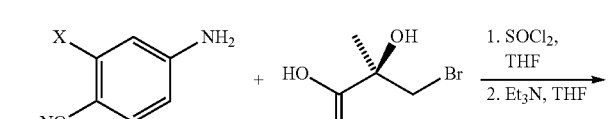

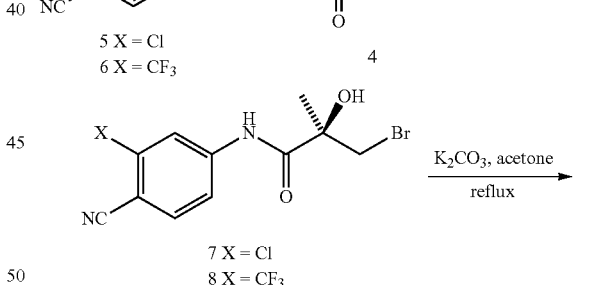

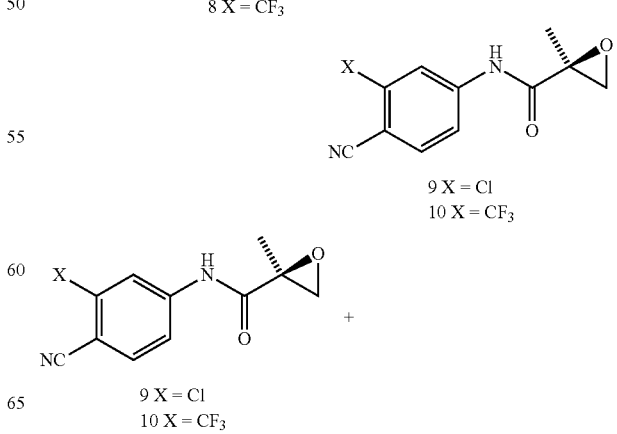

-continued

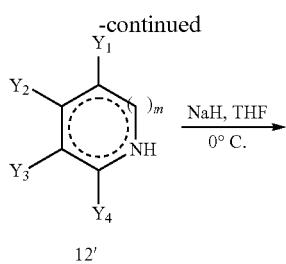

12'

Y$_{1-4}$ = H, F, Cl, Br, CO$_2$H, etc.

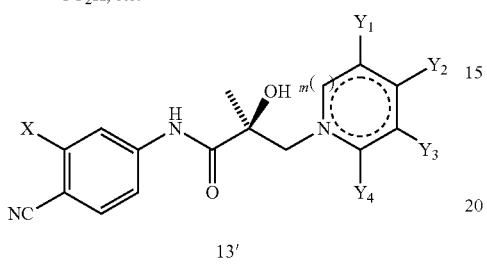

13'

Y$_{1-4}$ = H, F, Cl, Br, CH$_3$, CO$_2$H, Ph, etc.
X = CF$_3$, Cl

The steps through the synthesis of the oxiranes 9 and 10 are the same as above for Scheme 1. NaH of 60% dispersion in mineral oil (228 mg, 5.7 mmol) was added in 20 mL of anhydrous THF solvent into a 100 mL dried two necked round bottom flask equipped with a dropping funnel. A compound of general structure 12' (2.84 mmol) was added to the solution under argon atmosphere in ice-water bath, and the resulting solution was stirred for 30 min at the ice-water bath. Into the flask, epoxide 9 or 10 (2.84 mmol in THF) was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography with an eluent of EtOAc/hexane, and the condensed compounds were then recrystallized in EtOAc/hexane to give a product of general structure 13'.

The synthetic procedure for 1001 as an example:

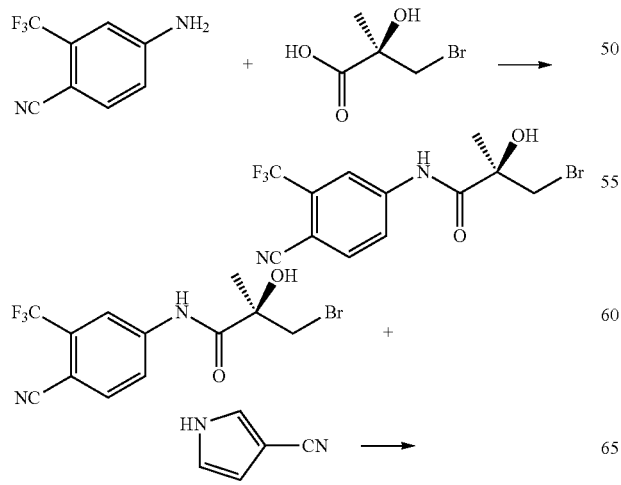

-continued

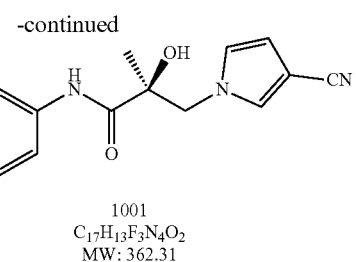

1001
C$_{17}$H$_{13}$F$_3$N$_4$O$_2$
MW: 362.31

(S)-3-(3-Cyano-H-pyrrol-1-yl)-N-(4-cyano-3-(trifluoromethyl)phenyl)-2-hydroxy-2-methylpropanamide (C$_{17}$H$_{13}$F$_3$N$_4$O$_2$) (1001)

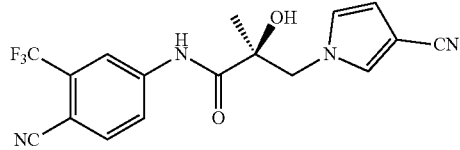 [SMILES: C[C@](O)(Cn1ccc(C#N)c1)C(=O)Nc1ccc(C#N)c(C(F)(F)F)c1]

To a solution of 1H-pyrrole-3-carbonitrile (0.10 g, 0.00108 mol) in anhydrous THF (10 mL), which was cooled in an ice water bath under an argon atmosphere, was added sodium hydride (60% dispersion in oil, 0.090 g, 0.00217 mol). After addition, the resulting mixture was stirred for 3 h. (R)-3-Bromo-N-(4-cyano-3-(trifluoromethyl)phenyl)-2-hydroxy-2-methylpropanamide (8, 0.38 g, 0.00108 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:1) as eluent to afford 0.26 g of the titled compound as pinkish solid.

Compound 1001 was characterized as follows: $^1$H NMR (400 MHz, DMSO-d$_6$) δ 10.44 (s, 1H, NH), 8.44 (s, 1H, ArH), 8.24 (d, J=8.8 Hz, 1H, ArH), 8.10 (d, J=8.8 Hz, 1H, ArH), 7.49 (s, 1H, Pyrrole-H), 6.38 (t, J=2.0 Hz, 1H, Pyrrole-H), 6.41-6.40 (m, 2H, OH and Pyrrole-H), 4.30 (d, J=14.0 Hz, 1H, CH), 4.14 (d, J=14.0 Hz, 1H, CH), 1.34 (s, 3H, CH$_3$); (ESI, Positive): 363.1079 [M+H]$^+$.

(S)—N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$) (1002)

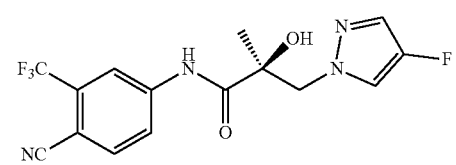 [SMILES: C[C@](O)(Cn1cc(F)cn1)C(=O)Nc1ccc(C#N)c(C(F)(F)F)c1]

To a solution of 4-fluoro-pyrazole (0.10 g, 0.00116 mol) in anhydrous THF (10 mL), which was cooled in an ice water bath under an argon atmosphere, was added sodium hydride (60% dispersion in oil, 0.12 g, 0.00291 mol). After addition, the resulting mixture was stirred for 3 h. (R)-3-

Bromo-N-(4-cyano-3-(trifluoromethyl)phenyl)-2-hydroxy-2-methylpropanamide (8) (0.41 g, 0.00116 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:1) as eluent to afford 0.13 g of the titled compound as white solid.

Compound 1002 was characterized as follows: $^1$H NMR (400 MHz, DMSO-d$_6$) δ 10.39 (s, 1H, NH), 8.47 (d, J=1.6 Hz, 1H, ArH), 8.24 (dd, J=8.4 Hz, J=2.0 Hz, 1H, ArH), 8.10 (d, J=8.4 Hz, 1H, ArH), 7.73 (d, J=4.4 Hz, 1H, Pyrazole-H), 7.41 (d, J=4.4 Hz, 1H, Pyrazole-H), 6.31 (s, 1H, OH), 4.38 (d, J=14.0 Hz, 1H, CH), 4.21 (d, J=14.0 Hz, 1H, CH), 1.34 (s, 3H, CH₃); Mass (ESI, Positive): 357.0966[M+H]⁺; mp 109-111° C.

(S)—N-(4-Cyano-3-(trifluoromethyl)phenyl)-3-(4-fluoro-1H-pyrazol-1-yl)-2-hydroxy-2-methylpropanamide hydrochloride (C₁₅H₁₃ClF₄N₄O₂) (1002-HCl)

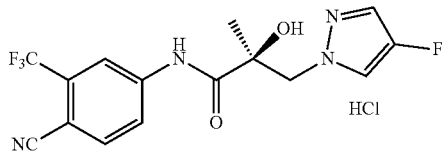 [SMILES: C[C@](O)(Cn1cc(F)cn1)C(=O)Nc1ccc(C#N)c(C(F)(F)F)c1 ; Cl]

To a solution of (S)—N-(4-cyano-3-(trifluoromethyl)phenyl)-3-(4-fluoro-1H-pyrazol-1-yl)-2-hydroxy-2-methylpropanamide (0.100 g, 0.2807 mmol) in 3 mL of methanol was added hydrochloride (2 M HCl in ether, 0.15 mL, 0.2947 mol). After addition, the resulting mixture was stirred for 1-2 h at RT. Solvent was removed under vacuum, and dried to afford 0.11 g (99%) of the titled compound as white foam.

(S)—N-(4-Cyano-3-(trifluoromethyl)phenyl)-3-(4-fluoro-1H-pyrazol-1-yl)-2-hydroxy-2-methylpropanamide oxalate (C₁₇H₁₄F₄N₄O₆) (1002-Oxalic Acid Salt)

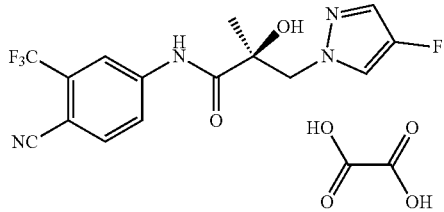 [SMILES: C[C@](O)(Cn1cc(F)cn1)C(=O)Nc1ccc(C#N)c(C(F)(F)F)c1 ; O=C(O)C(=O)O]

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added oxalic acid (0.0177 g, 0.14034 mol). After addition, the resulting mixture was stirred for 1-2 h at RT. Diethyl ether was added to above solution, and the solid was filtered, and dried under vacuum to afford 0.058 g (92%) of the titled compound as white solid.

Compound 1002-oxalate was characterized as follows: $^1$H NMR (400 MHz, DMSO-d$_6$) δ 14.02 (bs, 2H), 10.38 (s, 1H, NH), 8.46 (s, 1H, ArH), 8.24 (d, J=8.4 Hz, 1H, ArH), 8.10 (d, J=8.4 Hz, 1H, ArH), 7.73 (d, J=4.8 Hz, 1H, Pyrazole-H), 7.41 (d, J=4.0 Hz, 1H, Pyrazole-H), 6.30 (s, 1H, OH), 4.38 (d, J=14.0 Hz, 1H, CH), 4.31 (s, 2H), 4.21 (d, J=14.0 Hz, 1H, CH), 2.42 (s, 4H), 1.34 (s, 3H, CH₃).

(S)—N-(4-Cyano-3-(trifluoromethyl)phenyl)-3-(4-fluoro-1H-pyrazol-1-yl)-2-hydroxy-2-methylpropanamide 2,3-dihydroxysuccinate (C₁₉H₁₈F₄N₄O₈) (1002-Tartaric Acid Salt)

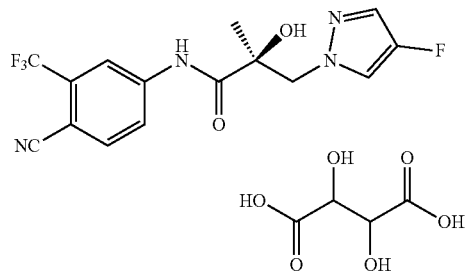 [SMILES: C[C@](O)(Cn1cc(F)cn1)C(=O)Nc1ccc(C#N)c(C(F)(F)F)c1 ; O=C(O)C(O)C(O)C(=O)O]

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added L-(+)-tartaric acid (0.021 g, 0.14034 mol). After addition, the resulting mixture was stirred for 1-2 h at RT. Diethyl ether was added to above solution, and the solid was filtered and dried under vacuum to afford 0.067 g (94%) of the titled compound as white solid.

Compound 1002-tartaric acid salt was characterized as follows: $^1$H NMR (400 MHz, DMSO-d$_6$) δ 12.69 (s, 2H), 10.38 (s, 1H, NH), 8.46 (s, 1H, ArH), 8.24 (d, J=8.4 Hz, 1H, ArH), 8.10 (d, J=8.4 Hz, 1H, ArH), 7.73 (d, J=4.4 Hz, 1H, Pyrazole-H), 7.41 (d, J=4.0 Hz, 1H, Pyrazole-H), 6.30 (s, 1H, OH), 5.08 (s, 2H, OH), 4.38 (d, J=14.0 Hz, 1H, CH), 4.31 (s, 2H), 4.21 (d, J=14.0 Hz, 1H, CH), 2.42 (s, 4H), 1.34 (s, 3H, CH₃).

(S)—N-(4-Cyano-3-(trifluoromethyl)phenyl)-3-(4-fluoro-1H-pyrazol-1-yl)-2-hydroxy-2-methylpropanamide hydrobromide (C₁₅H₁₃BrF₄N₄O₂) (1002-HBr)

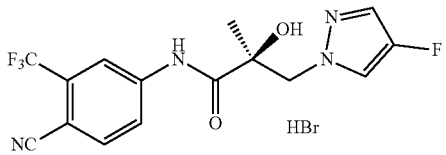 [SMILES: C[C@](O)(Cn1cc(F)cn1)C(=O)Nc1ccc(C#N)c(C(F)(F)F)c1 ; Br]

To a solution of (S)—N-(4-cyano-3-(trifluoromethyl)phenyl)-3-(4-fluoro-1H-pyrazol-1-yl)-2-hydroxy-2-methylpropanamide (0.050 g, 0.1403 mmol) in 2 mL of methanol was added hydrobromide (48% w/w aqueous solution, 0.0159 mL, 0.1403 mol). After addition, the resulting mixture was stirred for 1-2 h at RT. Solvent was removed under vacuum, and dried to afford 0.061 g (99%) of the titled compound as yellowish foam.

(S)—N-(4-Cyano-3-(trifluoromethyl)phenyl)-3-(4-fluoro-1H-pyrazol-1-yl)-2-hydroxy-2-methylpropanamide succinate (1002-succinic acid salt) ($C_{19}H_{18}F_4N_4O_6$)

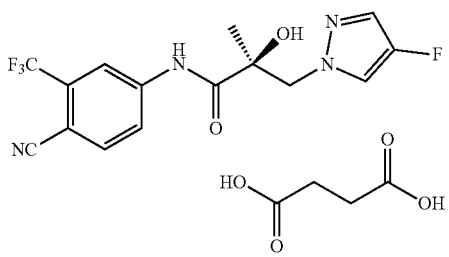

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added succinic acid (0.0166 g, 0.14034 mol). After addition, the resulting mixture was stirred for 1-2 h at RT. Diethyl ether was added to above solution, and the solid was filtered and dried under vacuum to afford 0.063 g (95%) of the titled compound as white solid.

Compound 1002-tartaric acid salt was characterized as follows: $^1$H NMR (400 MHz, DMSO-$d_6$) δ 12.14 (s, 2H), 10.39 (s, 1H, NH), 8.46 (s, 1H, ArH), 8.24 (d, J=8.8 Hz, 1H, ArH), 8.10 (d, J=8.8 Hz, 1H, ArH), 7.73 (d, J=4.4 Hz, 1H, Pyrazole-H), 7.41 (d, J=4.4 Hz, 1H, Pyrazole-H), 6.30 (s, 1H, OH), 4.39 (d, J=14.0 Hz, 1H, CH), 4.21 (d, J=14.0 Hz, 1H, CH), 2.42 (s, 4H), 1.34 (s, 3H, $CH_3$).

(S)—N-(4-Cyano-3-(trifluoromethyl)phenyl)-2-hydroxy-2-methyl-3-(4-phenyl-1H-pyrazol-1-yl)propanamide ($C_{21}H_{17}F_3N_4O_2$) (1003)

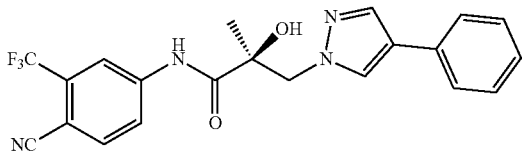

To a solution of 4-phenyl-pyrazole (0.50 g, 0.003468 mol) in anhydrous THF (10 mL), which was cooled in an ice water bath under an argon atmosphere, was added sodium hydride (60% dispersion in oil, 0.35 g, 0.00867 mol). After addition, the resulting mixture was stirred for 3 h. (R)-3-Bromo-N-(4-cyano-3-(trifluoromethyl)phenyl)-2-hydroxy-2-methylpropanamide (8, 1.22 g, 0.003468 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using ethyl acetate and hexanes (1:2) as eluent to afford 0.90 g of the titled compound as white needles.

Compound 1003 was characterized as follows: $^1$H NMR (400 MHz, DMSO-$d_6$) δ 10.40 (s, 1H, NH), 8.46 (d, J=2.0 Hz, 1H, ArH), 8.24 (dd, J=8.4 Hz, J=2.0 Hz, 1H, ArH), 8.09 (d, J=8.4 Hz, 1H, ArH), 8.05 (s, 1H, Pyrazole-H), 7.82 (s, 1H, Pyrazole-H), 7.52-7.45 (m, 2H, ArH), 7.35-7.31 (m, 2H, ArH), 7.20-7.16 (m, 1H, ArH), 6.33 (s, 1H, OH), 4.50 (d, J=14.0 Hz, 1H, CH), 4.30 (d, J=14.0 Hz, 1H, CH), 1.40 (s, 3H, $CH_3$); Mass (ESI, Positive): 415.1455[M+H]$^+$.

(S)—N-(4-Cyano-3-(trifluoromethyl)phenyl)-2-hydroxy-2-methyl-3-(3-phenyl-1H-pyrrol-1-yl)propanamide ($C_{22}H_{18}F_3N_3O_2$) (1004)

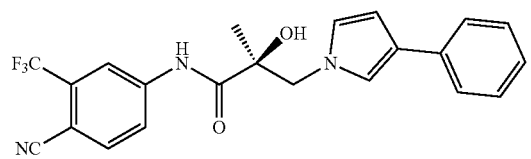 [SMILES: C[C@](O)(Cn1ccc(-c2ccccc2)c1)C(=O)Nc1ccc(C#N)c(C(F)(F)F)c1]

To a solution of 3-phenyl-pyrrole (0.50 g, 0.00349 mol) in anhydrous THF (10 mL), which was cooled in an ice water bath under an argon atmosphere, was added sodium hydride (60% dispersion in oil, 0.35 g, 0.00873 mol). After addition, the resulting mixture was stirred for 3 h. (R)-3-Bromo-N-(4-cyano-3-(trifluoromethyl)phenyl)-2-hydroxy-2-methylpropanamide (8, 1.23 g, 0.00349 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using ethyl acetate and hexanes (1:2) as eluent to afford 0.90 g of the titled compound as pink solid.

Compound 1004 was characterized as follows: $^1$H NMR (400 MHz, DMSO-$d_6$) δ 10.41 (s, 1H, NH), 8.24 (d, J=1.6 Hz, 1H, ArH), 8.17 (dd, J=8.4 Hz, J=2.0 Hz, 1H, ArH), 8.07 (d, J=8.4 Hz, 1H, ArH), 7.38-7.33 (m, 4H, ArH), 7.28-7.24 (m, 1H, ArH), 6.96 (t, J=3.0 Hz, 1H, Pyrrole-H), 6.28 (s, 1H, OH), 6.07 (t, J=3.5 Hz, 1H, Pyrrole-H), 6.03 (m, 1H, Pyrrole-H), 4.30-4.22 (m, 2H, $CH_2$), 1.01 (s, 3H, $CH_3$); Mass (ESI, Positive): 414.1432[M+H]$^+$.

Bromo-1H-imidazol-1-yl)-N-(4-cyano-3-(trifluoromethyl)phenyl)-2-hydroxy-2-methylpropanamides (1005 and 1006)

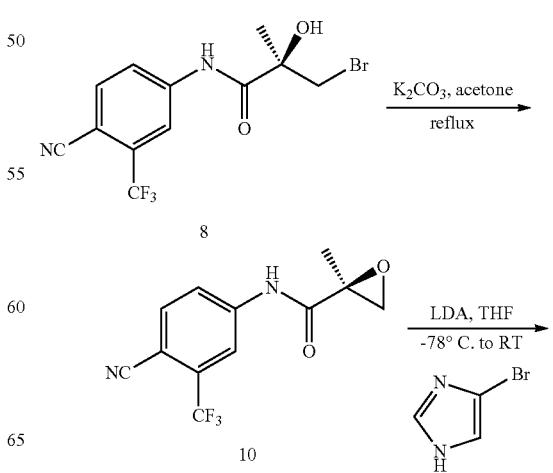

-continued

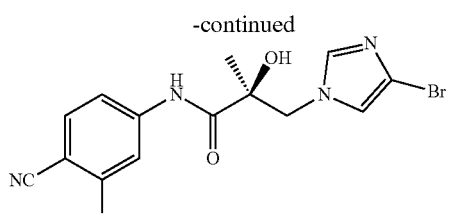

1006

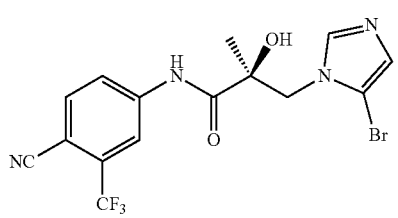

1005

Lithium diisopropylamide solution (2.0 M) in THF/heptane/ethylbenzene (1 mL) was slowly added to a solution of 4-bromo-1H-imidazole (1.0 mmol, 2 mmol) in 5 mL of anhydrous THF at −78° C. and warmed to 0° C. and stirred for 10 min and cooled again to −78° C. To the solution was added dropwise a solution of (S)—N-(4-cyano-3-(trifluoromethyl)phenyl)-2-methyloxirane-2-carboxamide (10, 1 mmol) prepared from 8 (1 mmol) and the reaction mixture was stirred for overnight. After quenching by addition of sat. NH₄Cl, the solution was concentrated under reduced pressure and dispersed into excess EtOAc and dried over Na₂SO₄. The solution was concentrated and purified by flash column chromatography (EtOAc/hexane) to give the desired products as total yield of 69% (37% for 1005 and 32% for 1006) as white solids.

The compounds were characterized as follows:

(S)-3-(5-Bromo-1H-imidazol-1-yl)-N-(4-cyano-3-(trifluoromethyl)phenyl)-2-hydroxy-2-methylpropanamide ($C_{15}H_{12}BrF_3N_4O_2$) (1005)

Method A (using bromoamide 8 and 4-bromo-1H-imidazole instead of general structure 9') gave a white solid; $^1$H NMR (acetone-d6, 400 MHz) δ 9.93 (bs, 1H, NH), 8.44 (d, J=2.0 Hz, 1H), 8.26 (dd, J=8.6, 2.0 Hz, 1H), 8.03 (d, J=8.6 Hz, 1H), 7.47 (s, 1H), 7.11 (s, 1H), 5.83 (s, 1H, OH), 4.50 (d, J=14.0 Hz, 1H), 4.23 (d, J=14.0 Hz, 1H), 1.55 (s, 3H); $^{19}$F NMR (acetone-d6, 400 MHz) δ 114.69; MS (ESI): 415.0 [M−H]⁻; LCMS (ESI) m/z calcd for $C_{15}H_{11}N_4O_2F_3Br$: 415.0088. Found: 415.0017 [M−H]⁻.

(S)-3-(4-Bromo-1H-imidazol-1-yl)-N-(4-cyano-3-(trifluoromethyl)phenyl)-2-hydroxy-2-methylpropanamide ($C_{15}H_{12}BrF_3N_4O_2$) (1006)

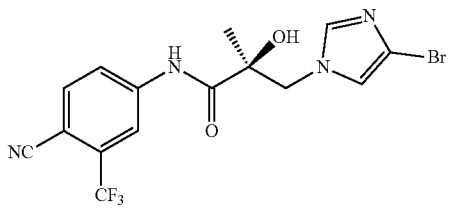 [SMILES: C[C@](O)(Cn1cnc(Br)c1)C(=O)Nc1ccc(C#N)c(C(F)(F)F)c1]

Method A (using bromoamide 8 and 4-bromo-1H-imidazole instead of general structure 9') gave a white solid; $^1$H NMR (CDCl₃, 400 MHz) δ 9.48 (bs, 1H, NH), 8.15 (s, 1H), 7.97 (d, J=8.6 Hz, 1H), 7.83 (d, J=8.6 Hz, 1H), 7.71 (s, 1H), 6.75 (s, 1H), 4.53 (d, J=14.4 Hz, 1H), 4.09 (d, J=14.4 Hz, 1H), 2.84 (s, 1H, OH), 1.45 (s, 3H); $^{19}$F NMR (CDCl₃, 400 MHz) δ −62.19; MS (ESI): 415.0 [M−H]⁻.

(S)—N-(3-Chloro-4-cyanophenyl)-2-hydroxy-3-(1H-imidazol-1-yl)-2-methylpropanamide ($C_{14}H_{13}ClN_4O_2$) (1008)

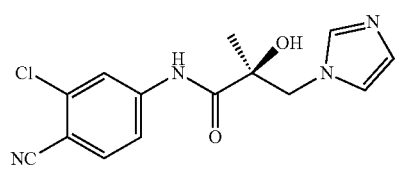 [SMILES: C[C@](O)(Cn1ccnc1)C(=O)Nc1ccc(C#N)c(Cl)c1]

Method A (using bromoamide 7 and 1H-imidazole instead of general structure 9') gave a yellowish solid. Yield 53%; $^1$H NMR (DMSO-d6, 400 MHz) δ 10.24 (bs, 1H, NH), 8.19 (s, 1H), 7.90 (m, 2H), 7.53 (s, 1H), 7.05 (s, 1H), 6.83 (s, 1H), 6.40 (bs, 1H, OH), 4.31 (d, J=14.4 Hz, 1H), 4.11 (d, J=14.4 Hz, 1H), 1.34 (s, 3H); LCMS (ESI) m/z calcd for $C_{14}H_{14}ClN_4O_2$: 305.0805. Found: 305.0809 [M+H]⁺.

(S)—N-(3-Chloro-4-cyanophenyl)-2-hydroxy-2-methyl-3-(pyrrolidin-1-yl)propanamide ($C_{15}H_{18}ClN_3O_2$) (1009)

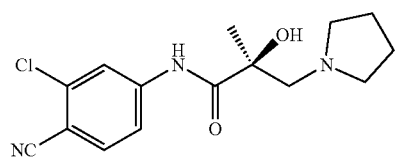 [SMILES: C[C@](O)(CN1CCCC1)C(=O)Nc1ccc(C#N)c(Cl)c1]

Method A (using bromoamide 7 and pyrrolidine instead of general structure 9') gave a yield of 89%; $^1$H NMR (CDCl₃, 400 MHz) δ 9.41 (bs, 1H, NH), 7.98 (d, J=2.0 Hz, 1H), 7.62 (d, J=8.8 Hz, 1H), 7.51 (dd, J=8.8, 2.0 Hz, 1H), 5.20 (s, 1H), 3.15 (d, J=12.4 Hz, 1H), 2.72 (d, J=12.4 Hz, 1H), 2.64-2.58 (m, 4H), 1.76 (m, 4H), 1.41 (s, 3H); $^{13}$C NMR (CDCl₃, 100 MHz) δ 175.6 (—NHCO—), 142.5, 137.9, 134.6, 119.9, 117.3, 116.1, 108.0, 72.9, 62.3, 54.6 (2C), 25.5, 24.0; LCMS (ESI) m/z calcd for $C_{15}H_{19}ClN_3O_2$: 308.1166. Found: 308.1173 [M+H]⁺.

Preparation of HCl Salt Type of (S)—N-(3-chloro-4-cyanophenyl)-2-hydroxy-2-methyl-3-(pyrrolidin-1-yl)propanamide To a solution of 1009 in EtOH (20 mL) was added dropwise acetyl chloride (1 mL) at 0° C. and further stirred at RT overnight and removed the solvent to gain target salt of 1009.

(S)—N-(3-Chloro-4-cyanophenyl)-3-(4-fluoro-1H-pyrazol-1-yl)-2-hydroxy-2-methylpropanamide C$_{14}$H$_{12}$ClFN$_4$O$_2$) (1007)

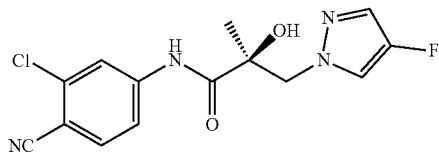 [SMILES: C[C@](O)(Cn1cc(F)cn1)C(=O)Nc1ccc(C#N)c(Cl)c1]

Method B (using oxirane 9 and 4-fluoro-1H-pyrazole instead of general structure 12') gave a yellowish solid; yield 72%; $^1$H NMR (CDCl$_3$, 400 MHz) δ 8.97 (bs, 1H, NH), 7.88 (d, J=2.0 Hz, 1H), 7.60 (d, J=8.4 Hz, 1H), 7.45 (dd, J=8.4, 2.0 Hz, 1H), 7.36 (d, J=4.0 Hz, 1H), 7.35 (d, J=4.4 Hz, 1H), 5.86 (bs, 1H, OH), 4.54 (d, J=14.0 Hz, 1H), 4.15 (d, J=14.0 Hz, 1H), 1.46 (s, 3H); $^{19}$F NMR (CDCl$_3$, 400 MHz) δ −176.47; LCMS (ESI) m/z calcd for C$_{14}$H$_{13}$ClFN$_4$O$_2$: 323.0711. Found: 323.0710 [M+H]$^+$.

(S)—N-(4-Cyano-3-(trifluoromethyl)phenyl)-3-(3-(4-fluorophenyl)-1H-pyrrol-1-yl)-2-hydroxy-2-methylpropanamide (C$_{22}$H$_{17}$F$_4$N$_3$O$_2$) (1010)

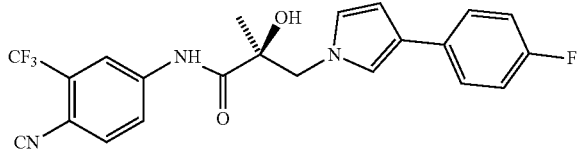

To a solution of 3-(4-fluorophenyl)-pyrrole (0.50 g, 0.003102 mol) in anhydrous THF (10 mL), which was cooled in an ice water bath under an argon atmosphere, was added sodium hydride (60% dispersion in oil, 0.37 g, 0.009306 mol). After addition, the resulting mixture was stirred for 3 h. (R)-3-Bromo-N-(4-cyano-3-(trifluoromethyl)phenyl)-2-hydroxy-2-methylpropanamide (8) (1.09 g, 0.003102 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:2 to 1:1) as eluent to afford 0.60 g (45%) of the compound as yellowish solid.

Compound 1010 was characterized as follows: $^1$H NMR (400 MHz, DMSO-d$_6$) δ 10.40 (s, 1H, NH), 8.42 (d, J=2.0 Hz, 1H, ArH), 8.24 (dd, J=8.8 Hz, J=2.0 Hz, 1H, ArH), 8.07 (d, J=8.8 Hz, 1H, ArH), 7.43-7.38 (m, 2H, ArH), 7.11-7.05 (m, 3H, ArH), 6.73 (t, J=2.0 Hz, 1H, Pyrrole-H), 6.33 (s, 1H, OH), 4.24 (d, J=14.0 Hz, 1H, CH), 4.05 (d, J=14.0 Hz, 1H, CH), 1.37 (s, 3H, CH$_3$); Mass (ESI, Positive): 432.1352[M+H]$^+$; mp 187-189° C.

(S)—N-(4-Cyano-3-(trifluoromethyl)phenyl)-2-hydroxy-2-methyl-3-(3-phenyl-1H-pyrazol-1-yl)propanamide (C$_{21}$H$_{17}$F$_3$N$_4$O$_2$) (1011)

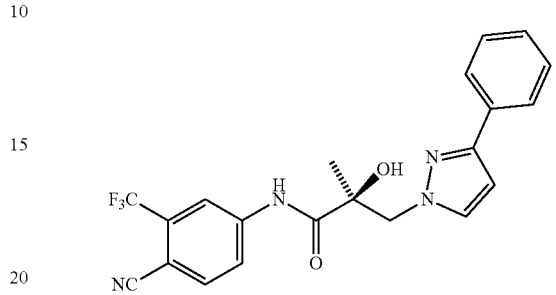

To a solution of 3-phenyl-pyrazole (0.50 g, 0.003468 mol) in anhydrous THF (10 mL), which was cooled in an ice water bath under an argon atmosphere, was added sodium hydride (60% dispersion in oil, 0.35 g, 0.00867 mol). After addition, the resulting mixture was stirred for 3 h. (R)-3-Bromo-N-(4-cyano-3-(trifluoromethyl)phenyl)-2-hydroxy-2-methylpropanamide (8, 1.22 g, 0.003468 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:3 to 1:2) as eluent to afford 0.60 g of the titled compound as white needles.

Compound 1011 was characterized as follows: $^1$H NMR (400 MHz, DMSO-d$_6$) δ 10.33 (s, 1H, NH), 8.48 (d, J=2.0 Hz, 1H, ArH), 8.22 (dd, J=8.2 Hz, J=2.0 Hz, 1H, ArH), 8.05 (d, J=8.2 Hz, 1H, ArH), 7.69 (d, J=2.0 Hz, 1H, ArH), 7.60-7.57 (m, 2H, ArH), 7.28-7.21 (m, 3H, ArH), 6.66 (d, J=3.0 Hz, 1H, ArH), 6.31 (s, 1H, OH), 4.52 (d, J=14.6 Hz, 1H, CH), 4.32 (d, J=14.6 Hz, 1H, CH), 1.43 (s, 3H, CH$_3$).

(S)—N-(4-Cyano-3-(trifluoromethyl)phenyl)-3-(3-fluoro-1H-pyrazol-1-yl)-2-hydroxy-2-methylpropanamide (C$_{15}$H$_{12}$F$_4$N$_4$O$_2$) (1012)

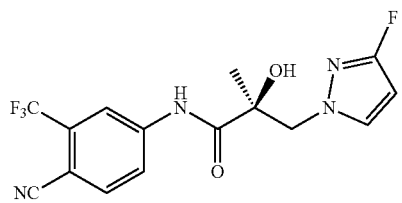 [SMILES: C[C@](O)(Cn1ccc(F)n1)C(=O)Nc1ccc(C#N)c(C(F)(F)F)c1]

To a solution of 3-fluoro-pyrazole (0.20 g, 0.00232 mol) in anhydrous THF (10 mL), which was cooled in an ice water bath under an argon atmosphere, was added sodium hydride (60% dispersion in oil, 0.24 g, 0.00582 mol). After addition, the resulting mixture was stirred for 3 h. (R)-3-Bromo-N-(4-cyano-3-(trifluoromethyl)phenyl)-2-hydroxy-2-methylpropanamide (8, 0.82 g, 0.00232 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.36 g of the compound as white needles.

Compound 1012 was characterized as follows: $^1$H NMR (400 MHz, DMSO-d$_6$) δ 10.39 (s, 1H, NH), 8.47 (d, J=2.0 Hz, 1H, ArH), 8.24 (dd, J=8.8 Hz, J=2.0 Hz, 1H, ArH), 8.11 (d, J=8.8 Hz, 1H, ArH), 7.55 (t, J=3.0 Hz, 1H, Pyrazole-H), 6.29 (s, 1H, OH), 5.93-5.91 (m, 1H, Pyrazole-H), 4.34 (d, J=13.6 Hz, 1H, CH), 4.15 (d, J=13.6 Hz, 1H, CH), 1.36 (s, 3H, CH$_3$); Mass (ESI, Positive): 357.0966 [M+H]$^+$.

(S)—N-(4-Cyano-3-(trifluoromethyl)phenyl)-2-hydroxy-2-methyl-3-(1H-pyrazol-1-yl)propanamide (C$_{15}$H$_{13}$F$_3$N$_4$O$_2$) (1013)

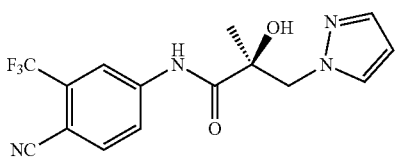 [SMILES: C[C@](O)(Cn1cccn1)C(=O)Nc1ccc(C#N)c(C(F)(F)F)c1]

To a solution of 1H-pyrazole (0.20 g, 0.002938 mol) in anhydrous THF (10 mL), which was cooled in an ice water bath under an argon atmosphere, was added sodium hydride (60% dispersion in oil, 0.29 g, 0.007344 mol). After addition, the resulting mixture was stirred for 3 h. (R)-3-Bromo-N-(4-cyano-3-(trifluoromethyl)phenyl)-2-hydroxy-2-methylpropanamide (8, 1.03 g, 0.002938 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.52 g of the compound as white solid.

Compound 1013 was characterized as follows: $^1$H NMR (400 MHz, DMSO-d$_6$) δ 10.39 (s, 1H, NH), 8.48 (d, J=2.0 Hz, 1H, ArH), 8.22 (dd, J=8.2 Hz, J=2.0 Hz, 1H, ArH), 8.08 (d, J=8.2 Hz, 1H, ArH), 7.66-7.65 (m, 1H, Pyrazole-H), 7.39-7.38 (m, 1H, Pyrazole-H), 6.28 (s, 1H, OH), 6.25-6.23 (m, 1H, Pyrazole-H), 4.50 (d, J=13.6 Hz, 1H, CH), 4.29 (d, J=13.6 Hz, 1H, CH), 1.35 (s, 3H, CH$_3$); Mass (ESI, Positive): 339.1105 [M+H]$^+$.

(S)—N-(4-Cyano-3-(trifluoromethyl)phenyl)-2-hydroxy-2-methyl-3-(3-(trifluoromethyl)-1H-pyrazol-1-yl)propanamide (C$_{16}$H$_{12}$F$_6$N$_4$O$_2$) (1014)

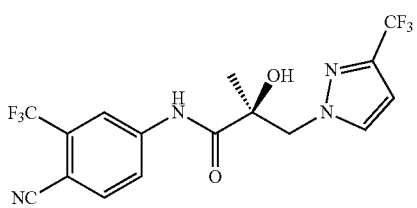 [SMILES: C[C@](O)(Cn1ccc(C(F)(F)F)n1)C(=O)Nc1ccc(C#N)c(C(F)(F)F)c1]

To a solution of 3-trifluoromethyl-pyrazole (0.20 g, 0.00147 mol) in anhydrous THF (10 mL), which was cooled in an ice water bath under an argon atmosphere, was added sodium hydride (60% dispersion in oil, 0.15 g, 0.003674 mol). After addition, the resulting mixture was stirred for 3 h. (R)-3-Bromo-N-(4-cyano-3-(trifluoromethyl)phenyl)-2-hydroxy-2-methylpropanamide (8) (0.516 g, 0.00147 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford the titled compound (103 mg, 70%) as a white solid.

Compound 1014 was characterized as follows: $^1$H NMR (400 MHz, DMSO-d$_6$) δ 10.31 (bs, 1H, NH), 8.42 (d, J=2.0 Hz, 1H, ArH), 8.19 (dd, J=8.8, 2.0 Hz, 1H, ArH), 8.09 (d, J=8.8 Hz, 1H, ArH), 7.83 (d, J=1.2 Hz, 1H, ArH), 6.67 (d, J=2.0 Hz, 1H, ArH), 6.41 (bs, OH), 4.56 (d, J=14.0 Hz, 1H, CHH), 4.37 (d, J=14.0 Hz, 1H, CHH), 1.41 (s, 3H, CH$_3$); $^{19}$F NMR (CDCl$_3$, decoupling) 8-60.44, −61.25; HRMS (ESI) m/z calcd for C$_{16}$H$_{12}$F$_6$N$_4$O$_2$: 407.0943 [M+H]$^+$; Found: 407.0943 [M+H]$^+$; mp 153-155° C.

(S)—N-(4-Cyano-3-(trifluoromethyl)phenyl)-3-(3-(4-fluorophenyl)-1H-pyrazol-1-yl)-2-hydroxy-2-methylpropanamide (C$_{21}$H$_{16}$F$_4$N$_4$O$_2$) (1015)

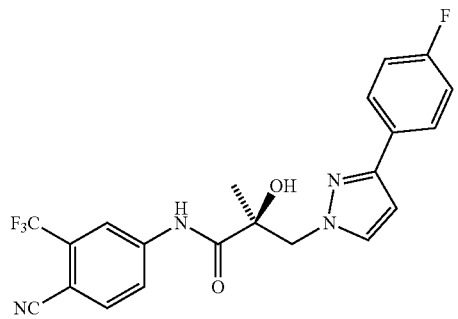 [SMILES: C[C@](O)(Cn1ccc(-c2ccc(F)cc2)n1)C(=O)Nc1ccc(C#N)c(C(F)(F)F)c1]

To a solution of 3-(4-fluorophenyl)-pyrazole (0.30 g, 0.00185 mol) in anhydrous THF (10 mL), which was cooled in an ice water bath under an argon atmosphere, was added sodium hydride (60% dispersion in oil, 0.22 g, 0.00555 mol). After addition, the resulting mixture was stirred for 3 h. (R)-3-Bromo-N-(4-cyano-3-(trifluoromethyl)phenyl)-2-hydroxy-2-methylpropanamide (8) (0.65 g, 0.00185 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.32 g (40%) of the titled compound as pinkish solid.

Compound 1015 was characterized as follows: $^1$H NMR (400 MHz, DMSO-d$_6$) δ 10.30 (s, 1H, NH), 8.41 (d, J=2.0 Hz, 1H, ArH), 8.21 (dd, J=8.2 Hz, J=2.0 Hz, 1H, ArH), 8.05 (d, J=8.2 Hz, 1H, ArH), 7.68 (d, J=2.0 Hz, 1H, ArH), 7.64-7.59 (m, 2H, ArH), 7.11-7.05 (m, 2H, ArH), 6.65 (d, J=3.0 Hz, 1H, ArH), 6.31 (s, 1H, OH), 4.50 (d, J=13.6 Hz, 1H, CH), 4.30 (d, J=13.6 Hz, 1H, CH), 1.42 (s, 3H, CH$_3$); Mass (ESI, Positive): 433.1312 [M+H]$^+$.

(S)—N-(4-Cyano-3-(trifluoromethyl)phenyl)-2-hydroxy-2-methyl-3-morpholinopropanamide (C₁₆H₁₈F₃N₃O₃) (1016)

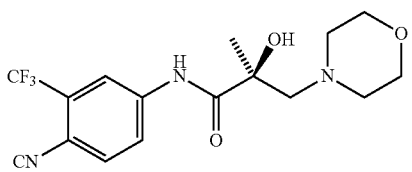

Under an argon atmosphere, 1.0 mL of lithium bis(trimethylsilyl)amide in THF (1 mmol, Aldrich, 1 M solution in THF) was slowly added to a solution of 0.09 mL of morpholine (0.67 mmol) in THF (10 mL) at −78° C. and stirred for 30 min at that temperature. A solution of 8 (234 mg, 0.67 mmol) in 5 mL of THF was added dropwise to the solution. The reaction mixture was stirred at the same temperature for 30 min, then stirred overnight at RT, and quenched by an addition of sat. NH₄Cl solution. The mixture was concentrated under reduced pressure, dispersed into excess EtOAc, dried over Na₂SO₄, concentrated and purified by flash column chromatography (EtOAc/hexane) to give the target compound (209 mg, yield 88%) as white solid.

Compound 1016 was characterized as follows: $^1$H NMR (CDCl₃, 400 MHz) δ 9.36 (bs, 1H, NH), 8.08 (d, J=1.6 Hz, 1H), 7.94 (dd, J=8.4, 1.6 Hz, 1H), 7.80 (d, J=8.4 Hz, 1H), 3.68 (m, 4H), 3.28 (d, J=13.2 Hz, 1H), 2.55 (m, 4H), 2.42 (d, J=13.2 Hz, 1H), 1.50 (bs, 1H, OH), 1.42 (s, 3H); $^{19}$F NMR (acetone-d6, 400 MHz) δ −62.20; LCMS (ESI) m/z calcd for C₁₆H₁₉F₃N₃O₃: 358.1379. Found: 358.1383 [M+H]⁺.

(S)—N-(4-Cyano-3-(trifluoromethyl)phenyl)-2-hydroxy-2-methyl-3-(4-(trifluoromethyl)-1H-pyrazol-1-yl)propanamide (C₁₆H₁₂F₆N₄O₂) (1017)

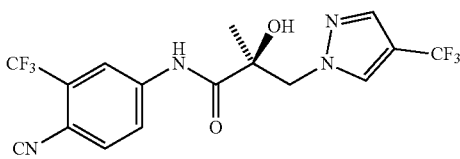

To a solution of 4-trifluoromethyl-pyrazole (0.20 g, 0.00147 mol) in anhydrous THF (10 mL), which was cooled in an ice water bath under an argon atmosphere, was added sodium hydride (60% dispersion in oil, 0.18 g, 0.004409 mol). After addition, the resulting mixture was stirred for 3 h. (R)-3-Bromo-N-(4-cyano-3-(trifluoromethyl)phenyl)-2-hydroxy-2-methylpropanamide (8) (0.516 g, 0.00147 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.30 g (50%) of the titled compound as white foam.

Compound 1017 was characterized as follows: $^1$H NMR (400 MHz, DMSO-d₆) δ 10.38 (s, 1H, NH), 8.45 (d, J=2.0 Hz, 1H, ArH), 8.25-8.22 (m, 2H, ArH & Pyrazole-H), 8.11 (d, J=8.2 Hz, 1H, ArH), 7.82 (s, 1H, Pyrazole-H), 6.39 (s, 1H, OH), 4.55 (d, J=14.0 Hz, 1H, CH), 4.37 (d, J=14.0 Hz, 1H, CH), 1.40 (s, 3H, CH₃); Mass (ESI, Positive): 407.0945 [M+H]⁺. Triazoles 1018 and 1019:

(S)—N-(4-Cyano-3-(trifluoromethyl)phenyl)-2-hydroxy-2-methyl-3-(1H-1,2,4-triazol-1-yl)propanamide (C₁₄H₁₂F₃N₅O₂) (1018)

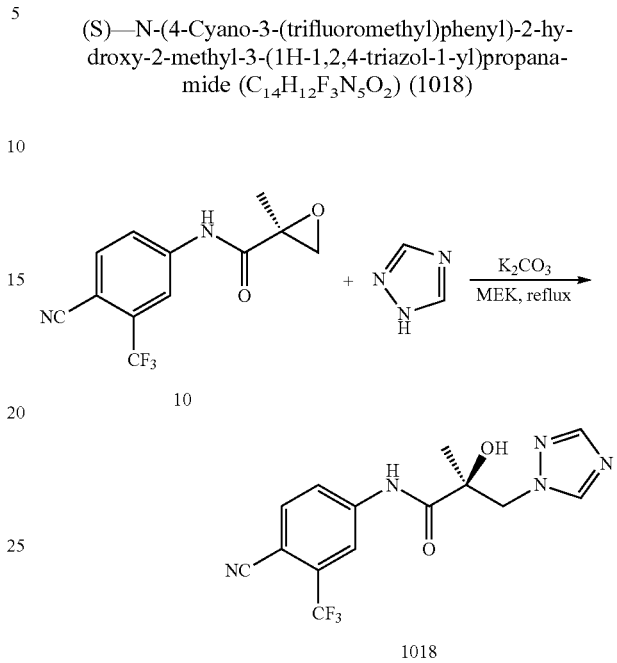

To a dry, nitrogen-purged 50 mL round-bottom flask, epoxide (10, 270 mg, 1 mmol), 1,2,4-triazole (69 mg, 1 mmol) and K₂CO₃ (268 mg, 2 mmol) were dispersed into 10 mL of 2-butanone (methylethylketone (MEK)). The mixture was heated to reflux for 12 h. The resulting mixture was cooled down to RT. The volume of mixture was reduced under reduced pressure, poured into water, and extracted with ethyl acetate (3 times). The organic layer was dried over MgSO₄, concentrated and purified by flash column chromatography (ethyl acetate/hexane 2:3 v/v) on silica gel to produce target product (143 mg, 43% yield). Compound 1018 was characterized as follows: $^1$H NMR (CDCl₃, 400 MHz) δ 9.10 (bs, 1H, NH), 8.15 (s, 1H), 8.02 (d, J=2.0 Hz, 1H), 7.88 (dd, J=8.4, 2.0 Hz, 1H), 7.78 (d, J=8.4 Hz, 1H), 5.70 (bs, 1H, OH), 4.79 (d, J=14.0 Hz, 1H), 4.35 (d, J=14.0 Hz, 1H), 1.53 (s, 3H); $^{19}$F NMR (CDCl₃, 400 MHz) δ −62.22; HRMS (ESI) m/z calcd for C₁₄H₁₂F₃N₅O₂ Exact Mass: 340.1021 [M+H]⁺. Found: 340.1067 [M+H]⁺.

(S)—N-(4-Cano-3-(trifluoromethyl)phenyl)-2-hydroxy-2-methyl-3-(3-(trifluoromethyl)-1H-1,2,4-triazol-1-yl)propanamide (C₁₅H₁₁F₆N₅O₂) (1019)

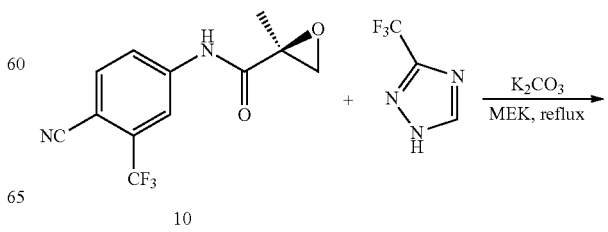

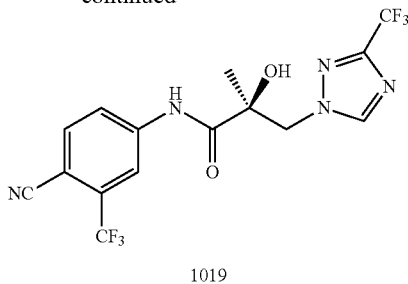

1019

To a dry, nitrogen-purged 50 mL round-bottom flask, epoxide (10, 270 mg, 1 mmol), 3-(trifluoromethyl)-1H-1,2,4-triazole (137 mg, 1 mmol) and K$_2$CO$_3$ (268 mg, 2 mmol) were dispersed into 10 mL of 2-butanone (methylethylketone or MEK). The mixture was heated to reflux for 12 h. The resulting mixture was cooled down to RT. The volume of mixture was reduced under reduced pressure, poured into water, and extracted with ethyl acetate (3 times). The organic layer was dried over MgSO$_4$, concentrated and purified by flash column chromatography (ethyl acetate/hexane 2:3 v/v) on silica gel to produce target product (213 mg, 53% yield).

Compound 1019 was characterized as follows: $^1$H NMR (acetone-d6, 400 MHz) δ 9.88 (bs, 1H, NH), 9.44 (s, 1H), 8.44 (s, 1H), 8.25 (d, J=8.4 Hz, 1H), 8.04 (d, J=8.4 Hz, 1H), 4.82 (d, J=14.4 Hz, 1H), 4.61 (d, J=14.4 Hz, 1H), 2.88 (bs, 1H, OH), 1.61 (s, 3H); $^{19}$F NMR (CDCl$_3$, 400 MHz) δ −62.26, −65.25; HRMS (ESI) m/z calcd for C$_{15}$H$_{11}$F$_6$N$_5$O$_2$ Exact Mass: 408.0895 [M+H]$^+$. Found: 408.0898 [M+H]$^+$.

(R)—N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$) (1020)

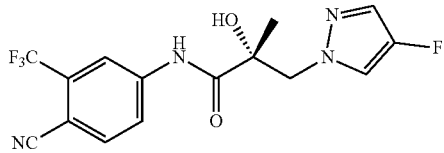 [SMILES: C[C@@](O)(Cn1cc(F)cn1)C(=O)Nc1ccc(C#N)c(C(F)(F)F)c1]

To a solution of 4-fluoro-1H-pyrazole (0.1 g, 1.16 mmol) in anhydrous THF (10 mL), which was cooled in an ice bath under an argon atmosphere, was added sodium hydride (60% dispersion in mineral oil, 0.12 g, 2.91 mmol). After addition, the resulting mixture was stirred for 3 h. (S)-3-Bromo-N-(4-cyano-3-(trifluoromethyl)phenyl)-2-hydroxy-2-methylpropanamide (S-isomer of 8 (8S)*; 0.41 g, 1.16 mmol) was added to the above solution, and the resulting reaction mixture was allowed to stir overnight at RT under argon atmosphere. The reaction was quenched by water and extracted with ethyl acetate. The organic layer was washed with brine, dried with anhydrous MgSO$_4$, filtered, and concentrated under reduced pressure. The mixture was purified by flash column chromatography using ethyl acetate and hexanes (2/3, v/v) as eluent to afford the titled compound (127 mg, 71%) as white solid.

Compound 1020 was characterized as follows: $^1$H NMR (400 MHz, CDCl$_3$) δ 9.07 (bs, 1H, NH), 8.01 (d, J=2.0 Hz, 1H), 7.95 (dd, J=8.4, 2.0 Hz, 1H), 7.78 (d, J=8.4 Hz, 1H), 7.38 (d, J=4.0 Hz, 1H), 7.34 (d, J=4.4 Hz, 1H), 5.92 (s, OH), 4.54 (d, J=14.0 Hz, 1H), 4.16 (d, J=14.4 Hz, 1H), 1.47 (s, 3H); $^{19}$F NMR (CDCl$_3$, decoupling) δ −62.23, −176.47; HRMS (ESI) m/z calcd for C$_{15}$H$_{12}$F$_4$N$_4$O$_2$: 357.0975 [M+H]$^+$; Found: 357.0984 [M+H]$^+$; [α]$_D^{24}$+126.7° (c=1.0, MeOH) (compared with S-isomer: [α]$_D^{24}$−136.0° (c=0.5, MeOH)).

*: 8S was synthesized from L-proline using the same procedure as for 8 (i.e., the R-isomer), as outlined in Scheme 1.

(S)—N-(4-Cyano-3-(trifluoromethyl)phenyl)-3-(3-fluoro-1H-pyrrol-1-yl)-2-hydroxy-2-methylpropanamide (C$_{16}$H$_{13}$F$_4$N$_3$O$_2$) (1021)

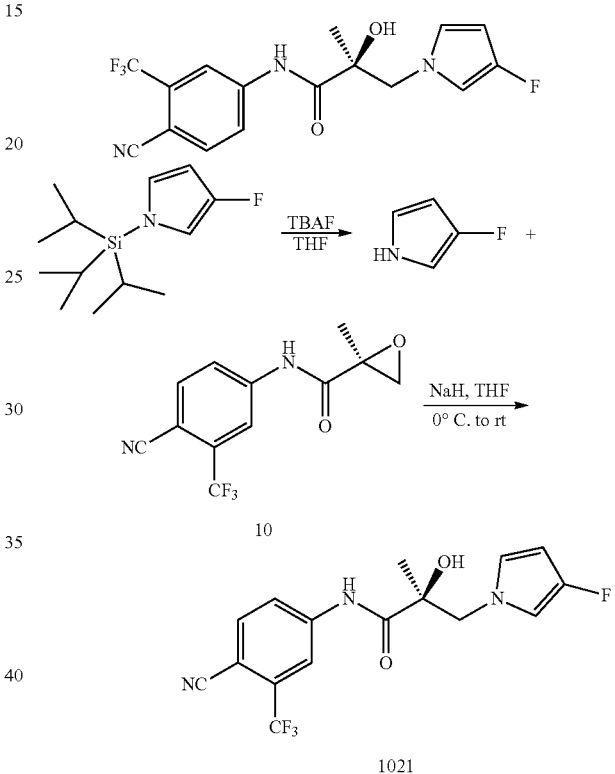

1021

To a solution of 3-fluoro-1-(triisopropylsilyl)-1H-pyrrole (1.21 g, 5 mmol) in 20 mL of anhydrous THF, n-tetrabutylammonium fluoride trihydrate in tetrahydrofuran (7.5 mL, 7.5 mmol; 1M) was added at RT under argon atmosphere. The solution was stirred for 1 h. Without work-up procedure, the flask was cooled down to 0° C. at ice-water bath. To the solution, NaH of 60% in mineral oil (133 mg, 3.33 mmol) was added. The reaction mixture was stirred for 30 min and epoxide 10 (450 mg, 1.67 mmol) in anhydrous THF was added through dropping funnel under argon atmosphere at the ice-water bath and stirred overnight at RT. After quenching with 1 mL of H$_2$O, the reaction was condensed under reduced pressure, and then dispersed into 50 mL of EtOAc, washed with water, evaporated, dried over anhydrous MgSO$_4$, and evaporated to dryness. The mixture was purified with flash column chromatography by EtOAc/hexane=1/1 as eluent, and then the condensed compounds were recrystallized with EtOAc/hexane to give a target product 1021 (181 mg, 31%) as white solid.

Compound 1021 was characterized as follows: $^1$H NMR (400 MHz, CDCl$_3$) δ 8.91 (bs, 1H, NH), 8.03 (d, J=2.0 Hz, 1H), 7.90 (dd, J=8.4, 2.0 Hz, 1H), 7.81 (d, J=8.4 Hz, 1H), 6.47 (m, 1H), 6.41 (m, 1H), 5.91 (dd, J=2.8, 2.0 Hz, 1H), 4.36 (d, J=14.4 Hz, 1H), 3.98 (d, J=14.4 Hz, 1H), 1.54 (s, 3H); $^{19}$F NMR (CDCl$_3$, decoupling) δ −62.18, −164.26; HRMS (ESI) m/z calcd for $C_{16}H_{14}F_4N_3O_2$: 356.1022 [M+H]$^+$, Found: 356.1021 [M+H]$^+$; 378.0839 [H+Na]$^+$.

(S)—N-(6-Cyano-5-(trifluoromethyl)pyridin-3-yl)-3-(4-fluoro-1H-pyrazol-1-yl)-2-hydroxy-2-methylpropanamide ($C_{14}H_{11}F_4N_5O_2$) (1022)

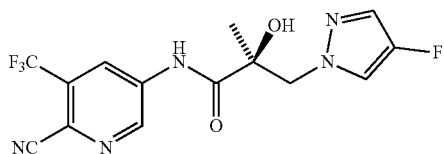 [SMILES: C[C@](O)(Cn1cc(F)cn1)C(=O)Nc1cnc(C#N)c(C(F)(F)F)c1]

(R)-3-Bromo-N-(6-cyano-5-(trifluoromethyl)pyridin-3-yl)-2-hydroxy-2-methylpropanamide

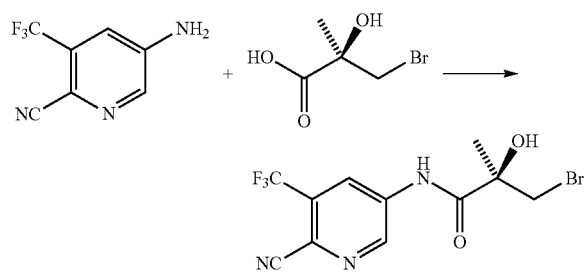

(R)-3-Bromo-2-hydroxy-2-methylpropanoic acid (4, 1.03 g, 0.005625 mol) reacted with thionyl chloride (0.80 g, 0.006751 mol), trimethylamine (0.74 g, 0.007313 mol), and 5-amino-3-(trifluoromethyl)picolinonitrile (1.00 g, 0.005344 mol) to afford the titled compound. The product was purified by a silica gel column using hexanes and ethyl acetate (2:1) as eluent to afford 1.70 g (90%) of the titled compound as a yellowish solid.

$^1$H NMR (400 MHz, DMSO-d$_6$) δ 10.82 (s, 1H, NH), 9.41 (d, J=2.0 Hz, 1H, ArH), 8.90 (d, J=2.0 Hz, 1H, ArH), 6.51 (s, 1H, OH), 3.84 (d, J=10.4 Hz, 1H, CH), 3.61 (d, J=10.4 Hz, 1H, CH), 1.50 (s, 3H, CH$_3$); Mass (ESI, Positive): 351.9915 [M+H]$^+$.

(S)—N-(6-Cyano-5-(trifluoromethyl)pyridin-3-yl)-3-(4-fluoro-1H-pyrazol-1-yl)-2-hydroxy-2-methylpropanamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. (R)-3-Bromo-N-(6-cyano-5-(trifluoromethyl)pyridin-3-yl)-2-hydroxy-2-methylpropanamide (0.82 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using hexanes and ethyl acetate (1:1) as eluent to afford 0.50 g (60.2%) of the titled compound as white solid.

Compound 1022 was characterized as follows: $^1$H NMR (400 MHz, DMSO-d$_6$) δ 10.64 (s, 1H, NH), 9.32 (d, J=2.0 Hz, 1H, ArH), 8.82 (d, J=2.0 Hz, 1H, ArH), 7.75 (d, J=4.8 Hz, 1H, Pyrazole-H), 7.40 (d, J=4.0 Hz, 1H, Pyrazole-H), 6.41 (s, 1H, OH), 4.39 (d, J=14.0 Hz, 1H, CH), 4.22 (d, J=14.0 Hz, 1H, CH), 1.36 (s, 3H, CH$_3$); (ESI, Positive): 358.0939 [M+H]$^+$, 380.0749 [M+Na]$^+$.

(S)-5-(3-(4-Fluoro-1H-pyrazol-1-yl)-2-hydroxy-2-methylpropanamido)picolinamide ($C_{13}H_{14}FN_5O_3$) (1023)

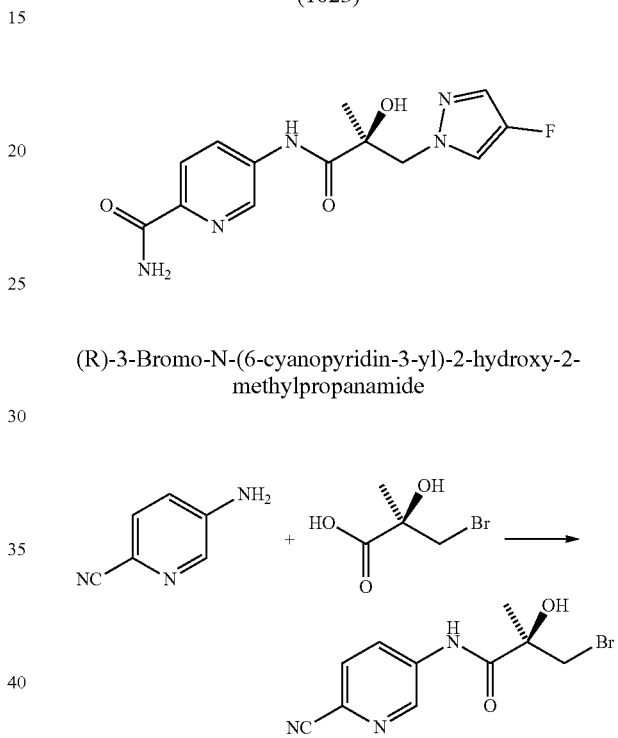

(R)-3-Bromo-N-(6-cyanopyridin-3-yl)-2-hydroxy-2-methylpropanamide (R)-3-Bromo-2-hydroxy-2-methylpropanoic acid (4, 3.24 g, 0.017674 mol) reacted with thionyl chloride (2.53 g, 0.021208 mol), trimethylamine (2.33 g, 0.022976 mol), and 5-aminopicolinonitrile (2.00 g, 0.01679 mol) to afford the titled compound. The product was purified by a silica gel column using dichloromethane (DCM) and methanol (19:1) as eluent to afford 4.40 g (92%) of the titled compound as yellowish solid.

$^1$H NMR (400 MHz, DMSO-d$_6$) δ 10.42 (s, 1H, NH), 9.12 (d, J=2.4 Hz, 1H, ArH), 8.44 (dd, J=8.8 Hz, J=2.4 Hz, 1H, ArH), 8.00 (d, J=8.8 Hz, 1H, ArH), 6.40 (s, 1H, OH), 3.83 (d, J=10.4 Hz, 1H, CH), 3.59 (d, J=10.4 Hz, 1H, CH), 1.49 (s, 3H, CH$_3$); Mass (ESI, Positive): 284.0042 [M+H]$^+$.

(S)-5-(3-(4-Fluoro-1H-pyrazol-1-yl)-2-hydroxy-2-methylpropanamido)picolinamide

To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. (R)-3-Bromo-N-(6-cyanopyridin-3-yl)-2-hydroxy-2-methylpropanamide (0.66 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and methanol (9:1) as eluent to afford 0.10 g (15%) of the titled compound as white solid.

Compound 1023 was characterized as follows: ¹H NMR (400 MHz, DMSO-d₆) δ 10.08 (s, 1H, NH), 8.89 (d, J=2.4 Hz, 1H, ArH), 8.30 (dd, J=8.2 Hz, J=2.4 Hz, 1H, ArH), 8.01 (s, 1H, NH), 7.98 (d, J=8.2 Hz, 1H, ArH), 7.73 (d, J=4.4 Hz, 1H, Pyrazole-H), 7.51 (s, 1H, NH), 7.42 (d, J=4.0 Hz, 1H, Pyrazole-H), 6.24 (s, 1H, OH), 4.38 (d, J=14.0 Hz, 1H, CH), 4.42 (d, J=14.0 Hz, 1H, CH), 1.34 (s, 3H, CH₃); Mass (ESI, Positive): 308.1177 [M+H]⁺, 330.0987 [M+Na]⁺.

N-(4-Cyano-3-(trifluoromethyl)phenyl)-3-(4-fluoro-1H-pyrazol-1-yl)-2-methylpropanamide (C₁₅H₁₂F₄N₄O) (1024)

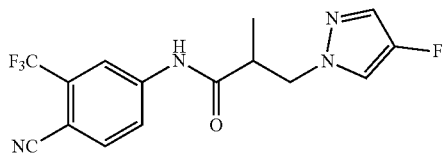 [SMILES: CC(Cn1cc(F)cn1)C(=O)Nc1ccc(C#N)c(C(F)(F)F)c1]

3-Bromo-N-(4-cyano-3-(trifluoromethyl)phenyl)-2-methylpropanamide

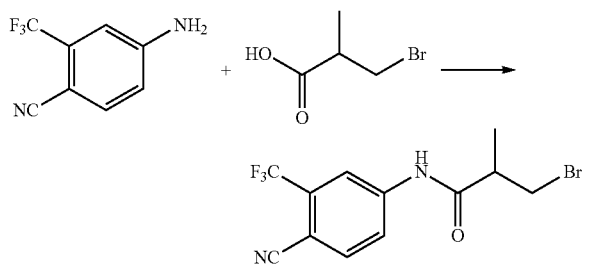

3-Bromo-2-methylpropanoic acid (2.00 g, 0.011976 mol) reacted with thionyl chloride (1.71 g, 0.014371 mol), trimethylamine (1.58 g, 0.015569 mol), and 4-amino-2-(trifluoromethyl)benzonitrile (2.12 g, 0.011377 mol) to afford the titled compound. The product was purified by a silica gel column using hexanes and ethyl acetate (2:1) as eluent to afford 3.50 g (91%) of the titled compound as a yellow to light brown solid.

¹H NMR (400 MHz, DMSO-d₆) δ 10.85 (s, 1H, NH), 8.30 (s, 1H, ArH), 8.12 (d, J=8.2 Hz, 1H, ArH), 8.03 (d, J=8.2 Hz, 1H, ArH), 3.72-3.67 (m, 1H, CH), 3.63-3.59 (m, 1H, CH), 3.03-2.97 (m, 1H, CH), 1.24 (d, J=6.8 Hz, 3H, CH₃); Mass (ESI, Negative): 334.85[M−H]⁻.

N-(4-Cyano-3-(trifluoromethyl)phenyl)-3-(4-fluoro-1H-pyrazol-1-yl)-2-methylpropanamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. 3-Bromo-N-(4-cyano-3-(trifluoromethyl)phenyl)-2-methyl-propanamide (0.78 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (1:1) as eluent to afford 0.050 g of the titled compound as yellowish solid.

Compound 1024 was characterized as follows: ¹H NMR (400 MHz, DMSO-d₆) δ 10.77 (s, 1H, NH), 8.25 (s, 1H, ArH), 8.10 (d, J=8.2 Hz, 1H, ArH), 7.96 (d, J=8.2 Hz, 1H, ArH), 7.85 (d, J=4.4 Hz, 1H, Pyrazole-H), 7.47 (d, J=4.4 Hz, 1H, Pyrazole-H), 4.35-4.30 (m, 1H, CH), 4.12-4.07 (m, 1H, CH), 3.12-3.10 (m, 1H, CH), 1.22 (d, J=6.8 Hz, 3H, CH₃).

(S)—N-(4-Cyano-3-(trifluoromethyl)phenyl)-3-(4-(4-fluorophenyl)-1H-pyrazol-1-yl)-2-hydroxy-2-methylpropanamide (C₂₁H₁₆F₄N₄O₂) (1025)

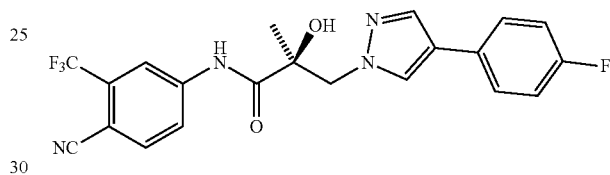

To a solution of 4-(4-fluorophenyl)-1H-pyrazole (0.20 g, 0.0012334 mol) in anhydrous THF (10 mL), which was cooled in an ice water bath under an argon atmosphere, was added sodium hydride (60% dispersion in oil, 0.15 g, 0.0037001 mol). After addition, the resulting mixture was stirred for 3 h. (R)-3-Bromo-N-(4-cyano-3-(trifluoromethyl)phenyl)-2-hydroxy-2-methylpropanamide (0.43 g, 0.0012334 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.33 g (62%) of the titled compound as white solid.

Compound 1025 was characterized as follows: ¹H NMR (400 MHz, DMSO-d₆) δ 10.29 (s, 1H, NH), 8.41 (s, 1H, ArH), 8.21 (d, J=8.8 Hz, 1H, ArH), 8.05 (d, J=8.8 Hz, 1H, ArH), 7.68 (s, 1H, Pyrazole-H), 7.61 (t, J=6.4 Hz, 2H, ArH), 7.08 (t, J=8.4 Hz, 2H, ArH), 6.65 (s, 1H, Pyrazole-H), 6.30 (s, 1H, OH), 4.51 (d, J=14.0 Hz, 1H, CH), 4.31 (d, J=14.0 Hz, 1H, CH), 1.42 (s, 3H, CH₃); Mass (ESI, Negative): 431.12 [M−H]⁻.

(S)-3-((1H-1,2,4-Triazol-3-yl)amino)-N-(4-cyano-3-(trifluoromethyl)phenyl)-2-hydroxy-2-methylpropanamide (C₁₄H₁₃F₃N₆O₂) (1026)

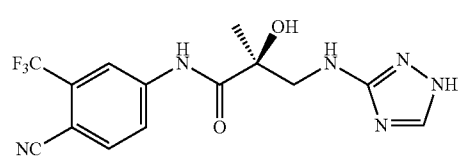

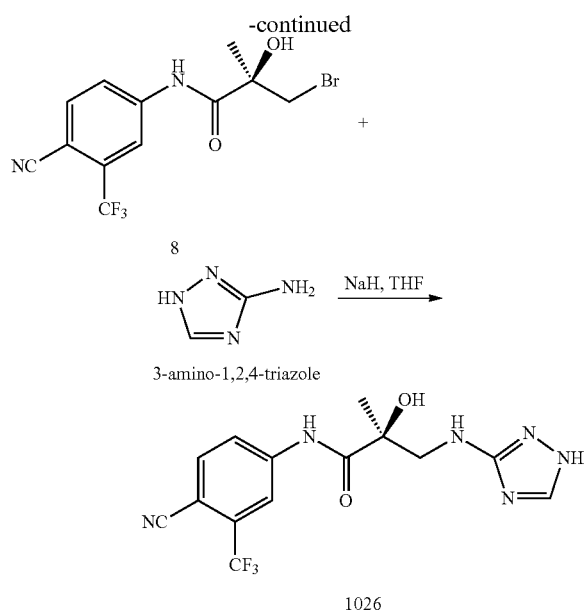

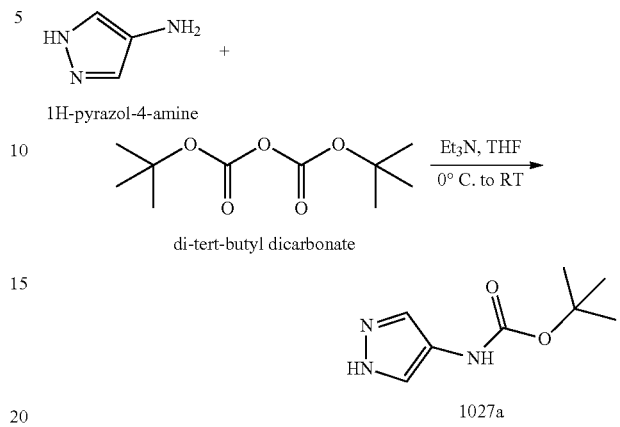

tert-Butyl-1H-pyrazol-4-ylcarbamate (1027a)

Under argon atmosphere, 100 mL round bottom flask was cooled down to 0° C. at ice-water bath. NaH of 60% in mineral oil (265 mg, 6.6 mmol) was added to the flask at the ice-water bath and anhydrous THF (20 mL) was poured into the flask at that temperature. Into the flask, 3-amino-1,2,4-triazole (164 mg, 2 mmol) was added into the flask at that temperature and the reaction mixture was stirred for 30 min. Then, a prepared solution of (R)-3-bromo-N-(4-cyano-3-(trifluoromethyl)phenyl)-2-hydroxy-2-methylpropanamide (8, 702 mg, 2 mmol) in anhydrous THF (10 mL) was added through dropping funnel under argon atmosphere at the ice-water bath and stirred overnight at RT. After quenching with 1 mL of H$_2$O, the reaction mixture was condensed under reduced pressure, and then dispersed into 50 mL of EtOAc, washed with water, evaporated, dried over anhydrous MgSO$_4$, and evaporated to dryness. The mixture was purified with flash column chromatography with an eluent of EtOAc/hexane (2:1 v/v) to give a target product as brown solid.

Compound 1026 was characterized as follows: $^1$H NMR (CDCl$_3$, 400 MHz) δ 9.10 (bs, 1H, C(O)NH), 8.01 (m, 1H, ArH), 7.87 and 7.81 (dd, J=8.4, 2.0 Hz, 1H, ArH), 7.78 (d, J=8.4 Hz, 1H, ArH), 7.72 and 7.51 (s, 1H, ArH), 5.90 and 5.65 (bs, 1H, NH), 4.74 (bs, 1H, NH), 4.56 and 4.55 (d, J=14.4 and 13.6 Hz, 1H, CH$_2$), 4.24 (bs, 1H, OH), 4.07 and 3.97 (d, J=13.6 and 14.4 Hz, 1H, CH$_2$), 1.56 and 1.48 (s, 3H, CH$_3$); $^{19}$F NMR (acetone-d6, 400 MHz) δ −62.24; MS (ESI) m/z 353.03 [M−H]$^-$ ; 355.10 [M+H]$^+$; HRMS (ESI) m/z calcd for C$_{14}$H$_{13}$F3N$_6$O$_2$: 355.1130 [M+H]$^+$, Found: 355.1128 [M+H]$^+$.

tert-Butyl (S)-(1-(3-((4-cyano-3-(trifluoromethyl)phenyl)amino)-2-methyl-3-oxopropyl)-1H-pyrazol-4-yl)carbamate (C$_{20}$H$_{22}$F$_3$N$_5$O$_4$) (1027)

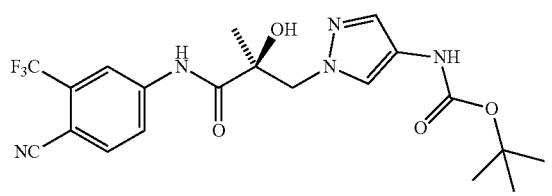 [SMILES: CC(C)(C)OC(=O)Nc1cnn(C[C@](C)(O)C(=O)Nc2ccc(C#N)c(C(F)(F)F)c2)c1]

Under argon atmosphere, to a solution of 1H-pyrazol-4-amine (2 g, 28.9 mmol) and di-tert-butyl dicarbonate (6.3 g, 28.9 mmol) in 100 mL of anhydrous THF was added triethylamine (1.68 mL, 12 mmol) at 0° C. After stirring for 30 min, the temperature was raised to RT and the mixture was stirred for 2 h. The reaction mixture was condensed under reduced pressure, and then dispersed into 50 mL of EtOAc, washed with water, evaporated, dried over anhydrous MgSO$_4$, and evaporated to dryness. The mixture was purified with flash column chromatography with an eluent of EtOAc/hexane in a 1:1 v/v ratio, and then the condensed compounds were then recrystallized using EtOAc/hexane (1:1 v/v) to give a target product. $^1$H NMR (CDCl$_3$, 400 MHz) δ 7.63 (s, 2H, ArH), 6.29 (bs, 1H, NH), 1.51 (s, 9H, C(CH$_3$)$_3$); MS (ESI) m/z 182.1 [M−H]$^-$.

(S)-tert-Butyl (1-(3-((4-cyano-3-(trifluoromethyl)phenyl)amino)-2-hydroxy-2-methyl-3-oxopropyl)-1H-pyrazol-4-yl)carbamate

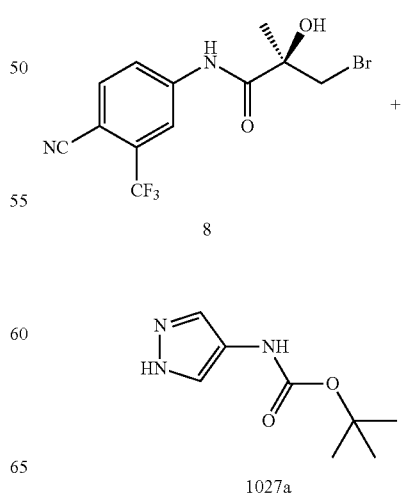

-continued

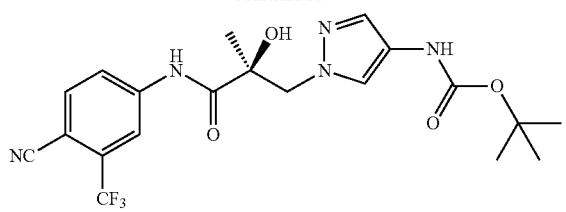

1027

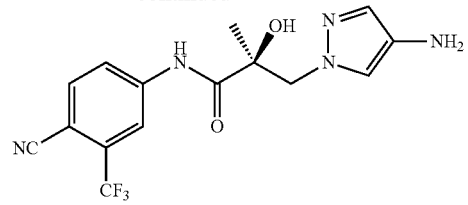

1028

Under argon atmosphere, a 100 mL round bottom flask was cooled down to 0° C. at ice-water bath. NaH of 60% in mineral oil (160 mg, 4 mmol) was added to the flask at the ice-water bath and anhydrous THF (20 mL) was poured into the flask at that temperature. Into the flask, tert-butyl-1H-pyrazol-4-ylcarbamate (1027a, 366 mg, 2 mmol) was added at that temperature and the reaction mixture was stirred for 30 min, then a prepared solution of (R)-3-bromo-N-(4-cyano-3-(trifluoromethyl)phenyl)-2-hydroxy-2-methylpropanamide (8, 702 mg, 2 mmol) in anhydrous THF was added through a dropping funnel under argon atmosphere at the ice-water bath and stirred overnight at RT. After quenching with 1 mL of H₂O, the reaction was condensed under reduced pressure, and then dispersed into 50 mL of EtOAc, washed with water, evaporated, dried over anhydrous MgSO₄, and evaporated to dryness. The mixture was purified with flash column chromatography using EtOAc/hexane (2:1 v/v) as an eluent to give a target product (563 mg, 62%) as yellowish solid.

Compound 1027 was characterized as follows: ¹H NMR (CDCl₃, 400 MHz) δ 9.13 (bs, 1H, C(O)NH), 8.01 (d, 1H, J=8.4 Hz, ArH), 7.85 (dd, J=8.4, 1.6 Hz, 1H, ArH), 7.76 (d, J=8.4 Hz, 1H, ArH), 7.63 (s, 1H, ArH), 7.43 (s, 1H, ArH), 6.21 (bs, 1H, C(O)NH), 6.17 (bs, 1H, OH), 4.54 (d, J=14.0 Hz, 1H, CH₂), 4.17 (d, J=14.0 Hz, 1H, CH₂), 1.47 (s, 9H, C(CH₃)₃), 1.45 (s, 3H, CH₃); ¹⁹F NMR (acetone-d6, 400 MHz) δ −62.10; MS (ESI) m/z 452.11 [M−H]⁻ ; 454.06 [M+H]⁺.

(S)-3-(4-Amino-1H-pyrazol-1-yl)-N-(4-cyano-3-(trifluoromethyl)phenyl)-2-hydroxy-2-methylpropanamide (C₁₅H₁₄F₃N₅O₂) (1028)

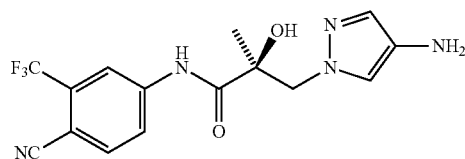

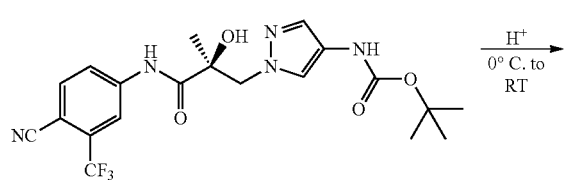

Under argon atmosphere, a 100 mL round bottom flask was cooled down to 0° C. at ice-water bath. 5 mL of acetyl chloride was added dropwise to the solution of 1027 (815 mg, 1.80 mmol) of anhydrous EtOH (20 mL) at the ice-water bath. The reaction mixture was stirred for 30 min at that temperature. The solvent was concentrated under reduced pressure, and then dispersed into 50 mL of EtOAc, washed with water, evaporated, dried over anhydrous MgSO₄, and evaporated to dryness. The mixture was purified with flash column chromatography EtOAc/hexane (using 3:1 to 6:1 v/v ratios) as an eluent to give the target product (583 mg, 92%) as brown solid.

Compound 1028 was characterized as follows: ¹H NMR (acetone-d6, 400 MHz) δ 10.07 (bs, 1H, C(O)NH), 8.50 (s, 1H, ArH), 8.46 (s, 1H, ArH), 8.26 (d, J=8.0 Hz, 1H, ArH), 8.01 (d, J=8.0 Hz, 1H, ArH), 7.83 (s, 1H, ArH), 4.73 (d, J=14.0 Hz, 1H, CH₂), 4.53 (d, J=14.0 Hz, 1H, CH₂), 2.95 (bs, 1H, OH), 1.51 (s, 3H, CH₃); ¹⁹F NMR (acetone-d6, 400 MHz) δ 114.77; MS (ESI) m/z 351.98 [M−H]⁻ ; 354.08 [M+H]⁺.

N-(4-Cyano-3-(trifluoromethyl)phenyl)-3-(4-fluoro-1H-pyrazol-1-yl)propanamide (C₁₄H₁₀F₄N₄O) (1029)

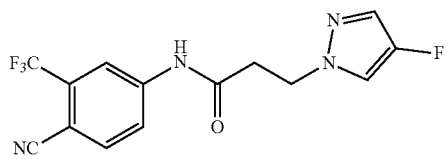 [SMILES: N#Cc1ccc(NC(=O)CCn2cc(F)cn2)cc1C(F)(F)F]

3-Bromo-N-(4-cyano-3-(trifluoromethyl)phenyl) propanamide (C₁₁H₈BrF₃N₂O)

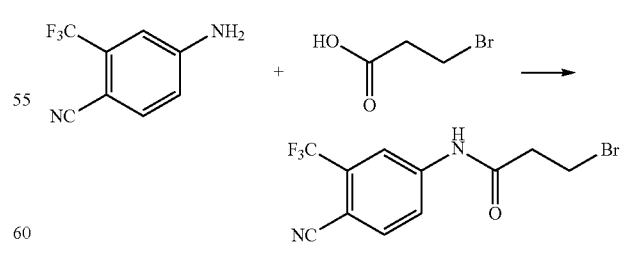

1029a

3-Bromopropanoic acid (2.00 g, 0.0130745 mol) reacted with thionyl chloride (1.87 g, 0.0156894 mol), trimethylamine (1.72 g, 0.0169968 mol), and 4-amino-2-(trifluoromethyl)benzonitrile (2.31 g, 0.0124207 mol) to afford the titled compound. The product was purified by a silica gel column using DCM and methanol (19:1) as eluent to afford 2.31 g (55%) of the titled compound as yellowish solid. $^1$H NMR (400 MHz, DMSO-d$_6$) δ 10.85 (s, 1H, NH), 8.28 (d, J=2.4 Hz, 1H, ArH), 8.12 (dd, J=8.8 Hz, J=2.4 Hz, 1H, ArH), 7.99 (d, J=8.8 Hz, 1H, ArH), 3.76 (t, J=6.0 Hz, 2H, CH$_2$), 3.06 (t, J=6.0 Hz, 2H, CH$_2$).

N-(4-Cyano-3-(trifluoromethyl)phenyl)-3-(4-fluoro-1H-pyrazol-1-yl)propanamide (C$_{14}$H$_{10}$F$_4$N$_4$O)

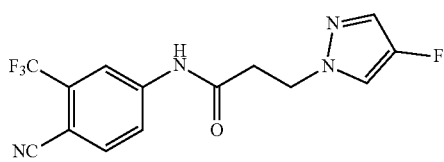

1029

To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. 3-Bromo-N-(4-cyano-3-(trifluoromethyl)phenyl)propanamide (1029a, 0.75 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using DCM and methanol (19:1) as eluent to afford 0.75 mg (10%) of the titled compound as white solid.

Compound 1029 was characterized as follows: $^1$H NMR (400 MHz, DMSO-d$_6$) δ 10.81 (s, 1H, NH), 8.25 (d, J=2.4 Hz, 1H, ArH), 8.10 (dd, J=8.8 Hz, J=2.4 Hz, 1H, ArH), 7.95 (d, J=8.8 Hz, 1H, ArH), 7.88 (s, 1H, Pyrazole-H), 7.46 (s, 1H, Pyrazole-H), 4.35 (t, J=6.0 Hz, 2H, CH$_2$), 2.79 (t, J=6.0 Hz, 2H, CH$_2$); Mass (ESI, Negative): 325.03 [M–H]$^-$.

(S)-tert-Butyl (1-(3-(((6-cyano-5-(trifluoromethyl)pyridin-3-yl)amino)-2-hydroxy-2-methyl-3-oxopropyl)-1H-pyrazol-4-yl)carbamate (C$_{19}$H$_{21}$F$_3$N$_6$O$_4$) (1030)

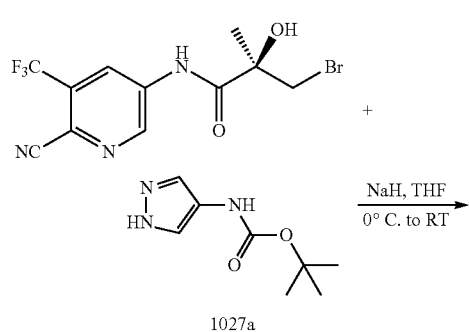

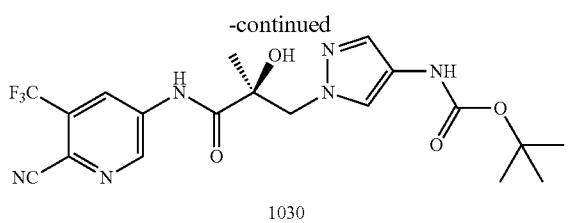

1030

Under argon atmosphere, a 50 mL round bottom flask was cooled down to 0° C. at an ice-water bath. NaH of 60% in mineral oil (160 mg, 4 mmol) was added to the flask at the ice-water bath and anhydrous THF (10 mL) was poured into the flask at that temperature. Tert-butyl-1H-pyrazol-4-ylcarbamate (1027a, 183 mg, 1 mmol) was added into the flask at that temperature and the reaction mixture was stirred for 30 min. Then a prepared solution of (R)-3-bromo-N-(6-cyano-5-(trifluoromethyl)pyridin-3-yl)-2-hydroxy-2-methylpropanamide (352 mg, 1 mmol) in anhydrous THF was added through dropping funnel under argon atmosphere at the ice-water bath and stirred overnight at RT. After quenching with 1 mL of H$_2$O, the reaction was condensed under reduced pressure, and then dispersed into 30 mL of EtOAc, washed with water, evaporated, dried over anhydrous MgSO$_4$, and evaporated to dryness. The mixture was purified with flash column chromatography as an eluent EtOAc/hexane to give the target product (273 mg, 60%) as yellowish solid.

Compound 1030 was characterized as follows: $^1$H NMR (CDCl$_3$, 400 MHz) δ 9.28 (bs, 1H, C(O)NH), 8.80 (s, 1H, ArH), 8.67 (s, 1H, ArH), 7.63 (bs, 1H, C(O)NH), 7.43 (s, 1H, ArH), 6.29 (bs, 1H, OH), 6.21 (s, 1H, ArH), 4.55 (d, J=14.0 Hz, 1H, CH$_2$), 4.18 (d, J=14.0 Hz, 1H, CH$_2$), 1.51 (s, 3H, CH$_3$) 1.47 (s, 9H, C(CH$_3$)$_3$); $^{19}$F NMR (CDCl$_3$, 400 MHz) δ −62.11; MS (ESI) m/z 453.16 [M–H]$^-$ ; 477.16 [M+Na]$^+$.

(S)-3-(4-Acetamido-1H-pyrazol-1-yl)-N-(4-cyano-3-(trifluoromethyl)phenyl)-2-hydroxy-2-methylpropanamide (C$_{17}$H$_{16}$F$_3$N$_5$O$_3$) (1031)

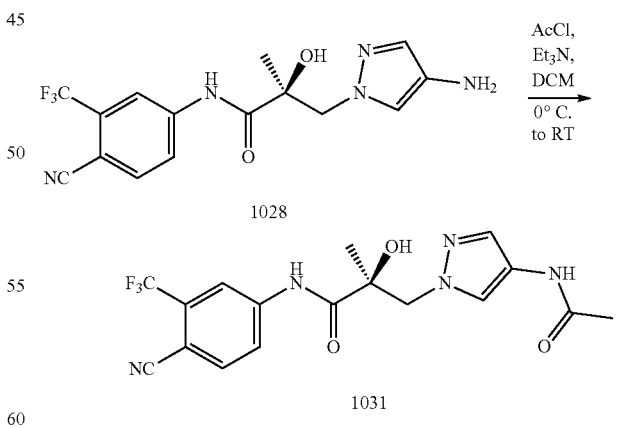

Under argon atmosphere, to a solution of 1028 (150 mg, 0.43 mmol) and triethyl amine (0.09 mL, 0.64 mmol) in 10 mL of anhydrous DCM was added acetyl chloride (AcCl, 0.038 mL, 0.53 mmol) at an ice-water bath. After stirring for 30 min, the temperature was raised to RT and the mixture was stirred for 2 h. The reaction mixture was condensed under reduced pressure, and then dispersed into 10 mL of EtOAc, washed with water, evaporated, dried over anhydrous MgSO$_4$, and evaporated to dryness. The mixture was purified with flash column chromatography as an eluent acetone/hexane (1/2, v/v) to produce 1031 (150 mg, 89%) as white solids.

Compound 1031 was characterized as follows: $^1$H NMR (CDCl$_3$, 400 MHz) δ 9.08 (bs, 1H, C(O)NH), 7.92 (bs, 1H, C(O)NH), 7.82-7.80 (m, 2H, ArH), 7.69 (d, J=8.4 Hz, 1H, ArH), 7.44 (s, 1H, ArH), 7.15 (s, 1H, ArH), 6.10 (bs, 1H, OH), 4.49 (d, J=13.6 Hz, 1H, CH$_2$), 4.13 (d, J=13.6 Hz, 1H, CH$_2$), 2.04 (s, 3H, NH(CO)CH$_3$), 1.39 (s, 3H, CH$_3$); $^{19}$F NMR (CDCl$_3$, 400 MHz) δ −62.20; MS (ESI) m/z 394.06 [M−H]$^-$ ; 396.11 [M+H]$^+$.

(S)-3-(4-Amino-1H-pyrazol-1-yl)-1-((4-cyano-3-(trifluoromethyl)phenyl)amino)-2-methyl-1-oxopropan-2-yl 2-chloroacetate (C$_{17}$H$_{15}$ClF$_3$N$_5$O$_3$) (1032); and (S)-3-(4-(2-Chloroacetamido)-1H-pyrazol-1-yl)-N-(4-cyano-3-(trifluoromethyl)phenyl)-2-hydroxy-2-methylpropanamide (C$_{17}$H$_{15}$ClF$_3$N$_5$O$_3$) (1033)

EtOAc/hexane (3/1, v/v) to produce 1032 (105 mg, 33%) and 1033 (117 mg, 36%) as yellowish solids. Total yield 70%.

Compound 1032 was characterized as follows: $^1$H NMR (CDCl$_3$, 400 MHz) δ 9.22 (bs, NH$_2$), 8.10 (bs, 1H, C(O)NH), 7.93 (d, J=1.8 Hz, 1H, ArH), 7.86 (d, J=1.8 Hz, 1H, ArH), 7.79 (d, J=8.4 Hz, 1H, ArH), 5.16 (d, J=14.8 Hz, 1H, CH$_2$), 4.62 (d, J=14.8 Hz, 1H, CH$_2$), 4.11 (s, 2H, CH$_2$Cl), 1.77 (s, 3H, CH$_3$); $^{19}$F NMR (CDCl$_3$, 400 MHz) δ 114.77; MS (ESI) m/z 428.03 [M−H]$^-$; 452.02 [M+Na]$^+$.

Compound 1033 was characterized as follows: $^1$H NMR (CDCl$_3$, 400 MHz) δ 9.12 (bs, 1H, C(O)NH), 8.12 (bs, 1H, C(O)NH), 7.99 (d, J=1.6 Hz, 1H, ArH), 7.92 (s, 1H, ArH), 7.87 (dd, J=8.8, 1.6 Hz, 1H, ArH), 7.76 (d, J=8.8 Hz, 1H, ArH), 7.61 (s, 1H, ArH), 6.11 (bs, 1H, OH), 4.60 (d, J=13.6 Hz, 1H, CH$_2$), 4.22 (d, J=13.6 Hz, 1H, CH$_2$), 4.17 (s, 2H, CH$_2$Cl), 1.47 (s, 3H, CH$_3$); $^{19}$F NMR (CDCl$_3$, 400 MHz) δ −62.19; MS (ESI) m/z 428.00 [M−H]$^-$ ; 452.01 [M+Na]$^+$.

(S)-Methyl (1-(3-((4-cyano-3-(trifluoromethyl)phenyl)amino)-2-hydroxy-2-methyl-3-oxopropyl)-1H-pyrazol-4-yl)carbamate (C$_{17}$H$_{16}$F$_3$N$_5$O$_4$) (1034)

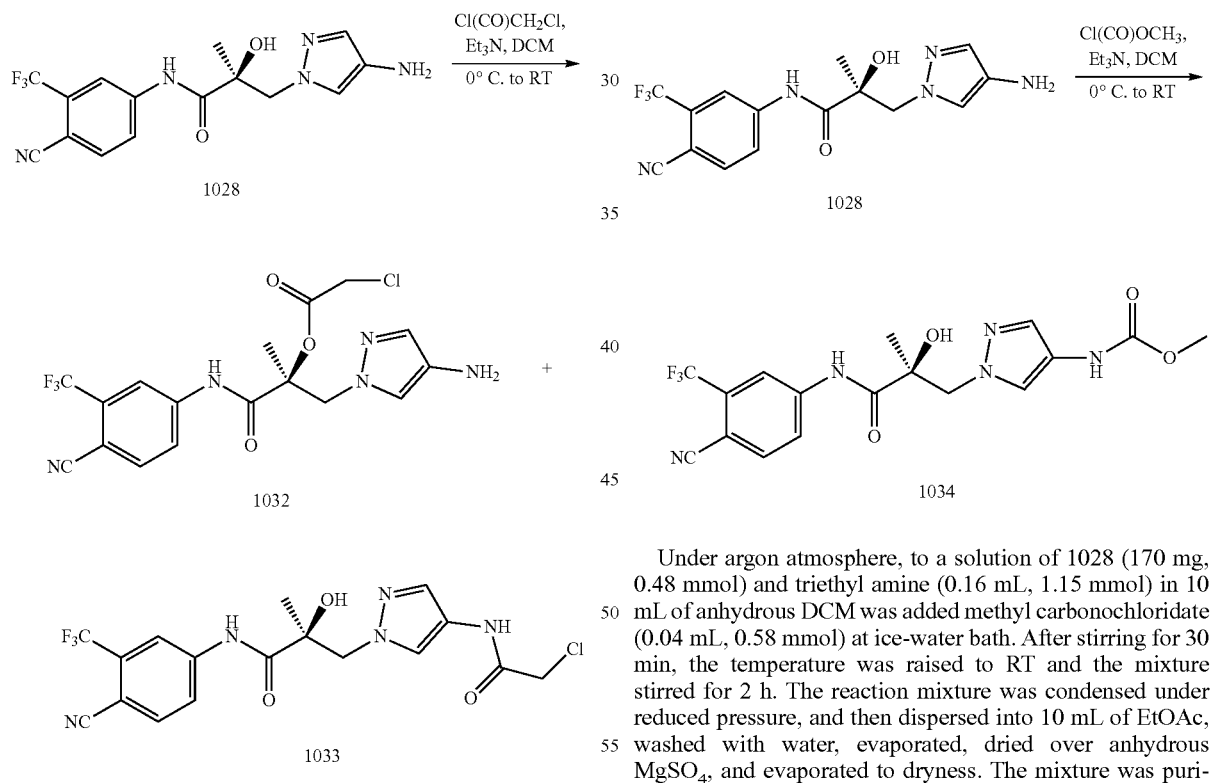

Under argon atmosphere, to a solution of 1028 (263 mg, 0.75 mmol) and triethyl amine (0.16 mL, 1.12 mmol) in 50 mL of anhydrous DCM was added chloroacetyl chloride (0.074 mL, 0.94 mmol) at an ice-water bath. After stirring for 30 min, the temperature was raised to RT and the mixture was stirred for 2 h. The reaction mixture was condensed under reduced pressure, and then dispersed into 30 mL of EtOAc, washed with water, evaporated, dried over anhydrous MgSO$_4$, and evaporated to dryness. The mixture was purified with flash column chromatography as an eluent Under argon atmosphere, to a solution of 1028 (170 mg, 0.48 mmol) and triethyl amine (0.16 mL, 1.15 mmol) in 10 mL of anhydrous DCM was added methyl carbonochloridate (0.04 mL, 0.58 mmol) at ice-water bath. After stirring for 30 min, the temperature was raised to RT and the mixture stirred for 2 h. The reaction mixture was condensed under reduced pressure, and then dispersed into 10 mL of EtOAc, washed with water, evaporated, dried over anhydrous MgSO$_4$, and evaporated to dryness. The mixture was purified with flash column chromatography as an eluent EtOAc/hexane (2/1, v/v) to produce 1034 (141 mg, 71%) as white solids.

Compound 1034 was characterized as follows: $^1$H NMR (CDCl$_3$, 400 MHz) δ 9.07 (bs, 1H, C(O)NH), 7.91 (s, 1H, ArH), 7.79 (d, J=7.2 Hz, 1H, ArH), 7.69 (d, J=7.2 Hz, 1H, ArH), 7.57 (s, 1H, ArH), 7.40 (s, 1H, ArH), 6.33 (bs, 1H, NH), 6.08 (bs, 1H, OH), 4.50 (d, J=13.6 Hz, 1H, CH$_2$), 4.12 (d, J=13.6 Hz, 1H, CH$_2$), 3.67 (s, 3H, NH(CO)OCH$_3$), 1.39 (s, 3H, CH$_3$); $^{19}$F NMR (CDCl$_3$, 400 MHz) δ −62.21; MS (ESI) m/z 410.30 [M−H]$^-$ ; 413.21 [M+H]$^+$.

(S)-3-(4-Acetyl-1H-pyrazol-1-yl)-N-(4-cyano-3-(trifluoromethyl)phenyl)-2-hydroxy-2-methylpropanamide (C₁₇H₁₅F₃N₄O₃) (1035)

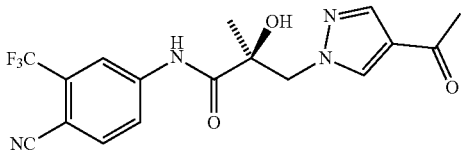 [SMILES: CC(=O)c1cnn(C[C@](C)(O)C(=O)Nc2ccc(C#N)c(C(F)(F)F)c2)c1]

To a solution of 1-(1H-pyrazol-4-yl)ethanone (0.10 g, 0.000908 mol) in anhydrous THF (5 mL), which was cooled in an ice water bath under an argon atmosphere, was added sodium hydride (60% dispersion in oil, 0.11 g, 0.002725 mol). After addition, the resulting mixture was stirred for 3 h. (R)-3-Bromo-N-(4-cyano-3-(trifluoromethyl)phenyl)-2-hydroxy-2-methylpropanamide (8, 0.32 g, 0.000908 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 70 mg (20%) of the titled compound as yellowish solid.

Compound 1035 was characterized as follows: ¹H NMR (400 MHz, DMSO-d₆) δ 10.37 (s, 1H, NH), 8.45 (d, J=1.2 Hz, 1H, ArH), 8.25 (s, 1H, Pyrazole-H), 8.23 (d, J=8.2 Hz, J=1.2 Hz, 1H, ArH), 8.10 (d, J=8.2 Hz, 1H, ArH), 7.86 (s, 1H, Pyrazole-H), 6.37 (s, 1H, OH), 4.50 (d, J=14.0 Hz, 1H, CH), 4.33 (d, J=14.0 Hz, 1H, CH), 2.34 (s, 3H, CH₃), 1.39 (s, 3H, CH₃); mass (ESI, Negative): 379.14 [M−H]⁻; (ESI, Positive): 413.18 [M+Na]⁺.

(S)—N-(4-Cyano-3-(trifluoromethyl)phenyl)-2-hydroxy-2-methyl-3-(4-nitro-1H-pyrazol-1-yl)propanamide (C₁₅H₁₂F₃N₅O₄) (1036)

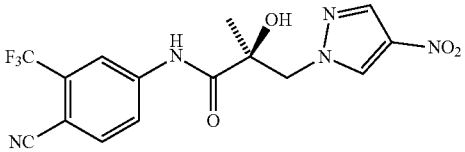 [SMILES: C[C@](O)(Cn1cc([N+](=O)[O-])cn1)C(=O)Nc1ccc(C#N)c(C(F)(F)F)c1]

To a solution of 4-nitro-1H-pyrazole (0.10 g, 0.0008844 mol) in anhydrous THF (5 mL), which was cooled in an ice water bath under an argon atmosphere, was added sodium hydride (60% dispersion in oil, 0.106 g, 0.002653 mol). After addition, the resulting mixture was stirred for 3 h. (R)-3-Bromo-N-(4-cyano-3-(trifluoromethyl)phenyl)-2-hydroxy-2-methylpropanamide (8, 0.31 g, 0.0008844 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (1:1) as eluent to afford 0.15 g (44%) of the titled compound as off-white solid.

Compound 1036 was characterized as follows: ¹H NMR (400 MHz, DMSO-d₆) δ 10.36 (s, 1H, NH), 8.69 (s, 1H, Pyrazole-H), 8.45 (d, J=1.2 Hz, 1H, ArH), 8.23 (d, J=8.8 Hz, J=1.2 Hz, 1H, ArH), 8.19 (s, 1H, Pyrazole-H), 8.11 (d, J=8.8 Hz, 1H, ArH), 6.47 (s, 1H, OH), 4.56 (d, J=14.0 Hz, 1H, CH), 4.38 (d, J=14.0 Hz, 1H, CH), 1.41 (s, 3H, CH₃); mass (ESI, Negative): 382.13 [M−H]⁻.

(R)-3-Bromo-N-(6-cyanopyridin-3-yl)-2-hydroxy-2-methylpropanamide (C₁₀H₁₀BrN₃O₂) (1037)

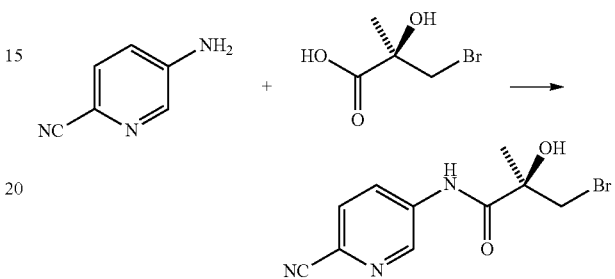

(R)-3-Bromo-2-hydroxy-2-methylpropanoic acid (4, 3.24 g, 0.017674 mol) reacted with thionyl chloride (2.53 g, 0.021208 mol), trimethylamine (2.33 g, 0.022976 mol), and 5-aminopicolinonitrile (2.00 g, 0.01679 mol) to afford the titled compound. The product was purified by a silica gel column using DCM and methanol (19:1) as eluent to afford 4.40 g (92%) of the titled compound as yellowish solid.

Compound 1037 was characterized as follows: ¹H NMR (400 MHz, DMSO-d₆) δ 10.42 (s, 1H, NH), 9.12 (d, J=2.4 Hz, 1H, ArH), 8.44 (dd, J=8.8 Hz, J=2.4 Hz, 1H, ArH), 8.00 (d, J=8.8 Hz, 1H, ArH), 6.40 (s, 1H, OH), 3.83 (d, J=10.4 Hz, 1H, CH), 3.59 (d, J=10.4 Hz, 1H, CH), 1.49 (s, 3H, CH₃); mass (ESI, Positive): 284.0042 [M+H]⁺.

(R)-3-Bromo-N-(6-cyano-5-(trifluoromethyl)pyridin-3-yl)-2-hydroxy-2-methylpropanamide (C₁₁H₉BrF₃N₃O₂) (1038)

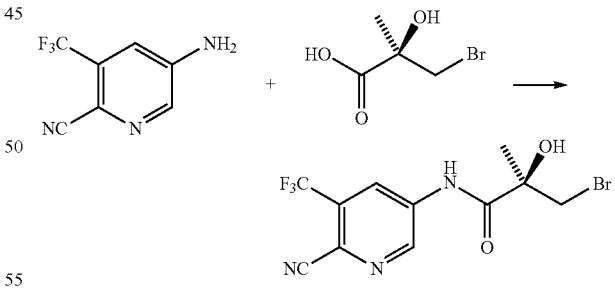

(R)-3-Bromo-2-hydroxy-2-methylpropanoic acid (4, 1.03 g, 0.005625 mol) reacted with thionyl chloride (0.80 g, 0.006751 mol), trimethylamine (0.74 g, 0.007313 mol), and 5-amino-3-(trifluoromethyl)picolinonitrile (1.00 g, 0.005344 mol) to afford the titled compound. The product was purified by a silica gel column using hexanes and ethyl acetate (2:1) as eluent to afford 1.70 g (90%) of the titled compound as yellowish solid.

Compound 1038 was characterized as follows: ¹H NMR (400 MHz, DMSO-d₆) δ 10.82 (s, 1H, NH), 9.41 (d, J=2.0 Hz, 1H, ArH), 8.90 (d, J=2.0 Hz, 1H, ArH), 6.51 (s, 1H, OH), 3.84 (d, J=10.4 Hz, 1H, CH), 3.61 (d, J=10.4 Hz, 1H, CH), 1.50 (s, 3H, CH$_3$); mass (ESI, Positive): 351.9915 [M+H]$^+$.

(R)-3-Bromo-2-hydroxy-2-methyl-N-(quinazolin-6-yl)propanamide (C$_{12}$H$_{12}$BrN$_3$O$_2$) (1039)

(R)-3-Bromo-2-hydroxy-2-methylpropanoic acid (2.65 g, 0.014503 mol) was reacted with thionyl chloride (2.07 g, 0.017404 mol), trimethylamine (1.91 g, 0.018854 mol), and quinazolin-6-amine (2.00 g, 0.013778 mol) to afford the titled compound. The product was purified by a silica gel column using hexanes and ethyl acetate (3:1 to 2:1) as eluent to afford 0.71 g of the titled compound as yellowish solid.

Compound 1039 was characterized as follows: Mass (ESI, Positive) 309.98 [M+H]$^+$.

3-Bromo-N-(4-cyano-3-(trifluoromethyl)phenyl)propanamide (C$_{11}$H$_8$BrF$_3$N$_2$O) (1040)

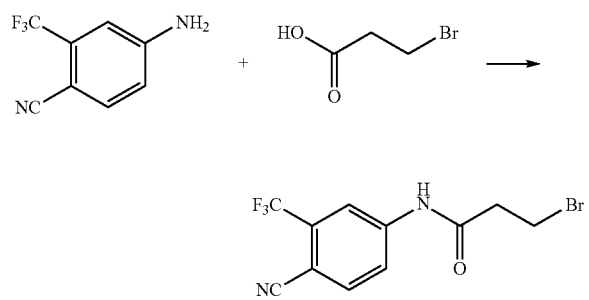

3-Bromopropanoic acid (2.00 g, 0.0130745 mol) reacted with thionyl chloride (1.87 g, 0.0156894 mol), trimethylamine (1.72 g, 0.0169968 mol), and 4-amino-2-(trifluoromethyl)benzonitrile (2.31 g, 0.0124207 mol) to afford the titled compound. The product was purified by a silica gel column using DCM and methanol (19:1) as eluent to afford 2.31 g (55%) of the titled compound as yellowish solid.

Compound 1040 was characterized as follows: $^1$H NMR (400 MHz, DMSO-d$_6$) δ 10.85 (s, 1H, NH), 8.28 (d, J=2.4 Hz, 1H, ArH), 8.12 (dd, J=8.8 Hz, J=2.4 Hz, 1H, ArH), 7.99 (d, J=8.8 Hz, 1H, ArH), 3.76 (t, J=6.0 Hz, 2H, CH$_2$), 3.06 (t, J=6.0 Hz, 2H, CH$_2$).

(S)—N-(2-Chloropyridin-4-yl)-3-(4-fluoro-1H-pyrazol-1-yl)-2-hydroxy-2-methylpropanamide (C$_{12}$H$_{12}$ClFN$_4$O$_2$) (1041)

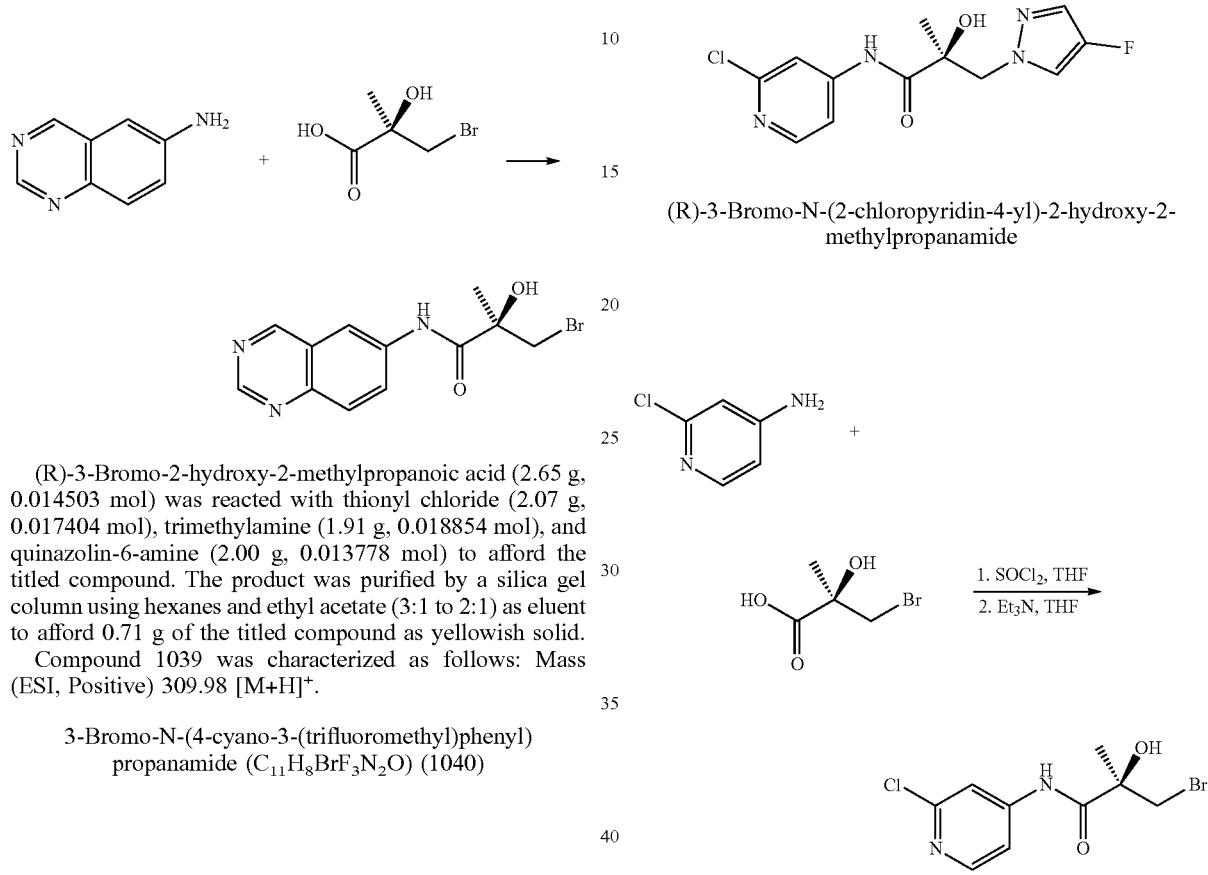

1041

Thionyl chloride (11.2 mL, 0.154 mol) was added dropwise to a cooled solution (less than 4° C.) of (R)-3-bromo-2-hydroxy-2-methylpropanoic acid (4, 18.3 g, 0.100 mol) in 100 mL of THF under an argon atmosphere. The resulting mixture stirred for 3 h under the same condition. To this was added Et$_3$N (25.7 mL, 0.185 mol) and then stirred for 20 min under the same condition. After 20 min, 2-chloropyridin-4-amine (9.89 g, 0.077 mol), 100 mL of THF were added and then the mixture was allowed to stir overnight at RT. The solvent was removed under reduced pressure to give a solid, which was treated with 100 mL of H$_2$O, and extracted with EtOAc (2×50 mL). The combined organic extracts were washed with saturated NaHCO$_3$ solution (2×100 mL) and brine (100 mL). The organic layer was dried over MgSO$_4$ and concentrated under reduced pressure to give a solid, which was dissolved and purified by column chromatography using CH$_2$Cl$_2$/EtOAc (80:20) to give a solid. This solid recrystallized from CHzCl$_2$/hexane to give 12.6 g (43%) of (R)-3-bromo-N-(2-chloropyridin-4-yl)-2-hydroxy-2-methylpropanamide as a light-yellow solid. $^1$H NMR (400 MHz, CDCl$_3$) δ 9.06 (bs, 1H, NH), 8.31 (d, J=5.6 Hz, 1H), 7.77 (d, J=0.8 Hz, 1H), 7.45 (dd, J=5.6, 0.8 Hz, 1H), 4.81 (bs, 1H, OH), 3.97 (d, J=10.6 Hz, 1H), 3.60 (d, J=10.6 Hz, 1H), 1.64 (s, 3H); MS (ESI) m/z 295.28 [M+H]$^+$.

(S)—N-(2-Chloropyridin-4-yl)-3-(4-fluoro-1H-pyrazol-1-yl)-2-hydroxy-2-methylpropanamide (C₁₂H₁₂ClFN₄O₂)

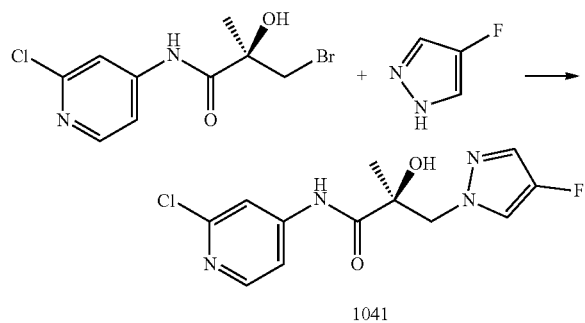

1041

To a dry, nitrogen-purged 100 mL round-bottom flask equipped with a dropping funnel under argon atmosphere, NaH of 60% dispersion in mineral oil (96 mg, 2.4 mmol) was added in 10 mL of anhydrous THF solvent at ice-water bath. 4-Fluoro-1H-pyrazole (103 mg, 1.2 mmol) was added and the solution stirred 30 min at the ice-water bath. Into the flask, the solution of (R)-3-bromo-N-(2-chloropyridin-4-yl)-2-hydroxy-2-methylpropanamide (293 mg, 1.0 mmol) in 5 mL of anhydrous THF was added through dropping funnel under argon atmosphere at the ice-water bath and stirred overnight at RT. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography using as an eluent EtOAc/hexane as a 1:2 ratio to produce compounds to produce the titled compound (55%) as a white solid.

Compound 1041 was characterized as follows: $^1$H NMR (400 MHz, CDCl₃) δ 8.90 (bs, 1H, NH), 8.26 (d, J=5.6 Hz, 1H), 7.63 (s, 1H), 7.75 (d, J=4.2 Hz, 1H), 7.33 (d, J=4.2 Hz, 1H), 7.31 (dd, J=5.6, 1.2 Hz, 1H), 5.88 (s, 1H, OH), 4.53 (d, J=13.6 Hz, 1H), 4.14 (d, J=13.6 Hz, 1H), 1.45 (s, 3H); $^{19}$F NMR (CDCl₃, decoupled) δ −176.47; MS (ESI) m/z 298.98 [M+H]⁺; 296.96 [M−H]⁻.

(S)-3-Azido-N-(4-cyano-3-(trifluoromethyl)phenyl)-2-hydroxy-2-methylpropanamide (C₁₂H₁₀F₃N₅O₂) (1042)

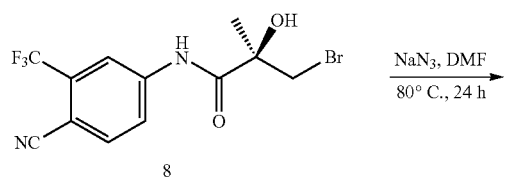

A solution of 8 (351 mg, 1 mmol) in DMF (10 mL) was treated with NaN₃ (325 mg, 5 mmol) under argon at 80° C. for 24 h. The reaction mixture was then, cooled and extracted with CH₂Cl₂ (3×20 mL). The combined organic layers were washed with H₂O (3×20 mL) and brine, dried and evaporated to give a crude oil, which was purified by silica gel chromatography (EtOAc/n-hexane=1:2, v/v) to afford the titled compound as a yellow solid (224 mg, 72%).

Compound 1042 was characterized as follows: $^1$H NMR (400 MHz, CDCl₃) δ 9.00 (bs, 1H, NH), 8.08 (s, 1H), 7.95 (d, J=8.4 Hz, 1H), 7.81 (d, J=8.4 Hz, 1H), 3.92 (d, J=12.4 Hz, 1H), 3.50 (d, J=12.4 Hz, 1H), 2.96 (s, 1H, OH), 1.54 (s, 3H); $^{19}$F NMR (CDCl₃, decoupled) δ −62.21; MS (ESI) m/z 314.03 [M+H]⁺; 312.18 [M−H]⁻.

(S)—N-(6-Cyano-5-(trifluoromethyl)pyridin-3-yl)-2-hydroxy-2-methyl-3-(4-(trifluoromethyl)-1H-pyrazol-1-yl)propanamide (C₁₅H₁₁F₆N₅O₂) (1043)

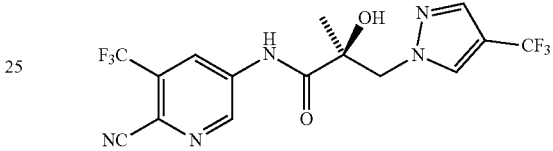

To a solution of 4-trifluoromethyl-pyrazole (0.10 g, 0.0007349 mol) in anhydrous THF (5 mL), which was cooled in an ice water bath under an argon atmosphere, was added sodium hydride (60% dispersion in oil, 0.09 g, 0.002025 mol). After addition, the resulting mixture was stirred for 3 h. (R)-3-Bromo-N-(6-cyano-5-(trifluoromethyl) pyridin-3-yl)-2-hydroxy-2-methylpropanamide (0.26 g, 0.0007349 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.18 g (60%) of the titled compound as white solid.

Compound 1043 was characterized as follows: $^1$H NMR (400 MHz, DMSO-d₆) δ 10.63 (s, 1H, NH), 9.31 (s, 1H, ArH), 8.80 (s, 1H, ArH), 8.32 (s, 1H, Pyrazole-H), 7.81 (s, 1H, Pyrazole-H), 6.48 (s, 1H, OH), 4.55 (d, J=14.0 Hz, 1H, CH), 4.37 (d, J=14.0 Hz, 1H, CH), 1.42 (s, 3H, CH₃); mass (ESI, Negative): 406.08 [M−H]⁻; (ESI, Positive): [M+H]⁺, 430.13 [M+Na]⁺.

(S)—N-(4-Cyano-3-(trifluoromethyl)phenyl)-3-(5-(4-fluorophenyl)-1H-1,2,3-triazol-1-yl)-2-hydroxy-2-methylpropanamide (C₂₀H₁₅F₄N₅O₂) (1044)

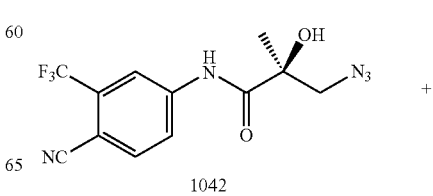

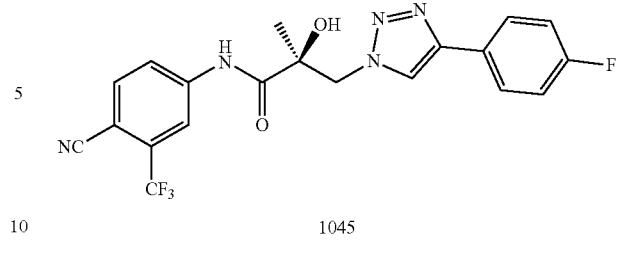

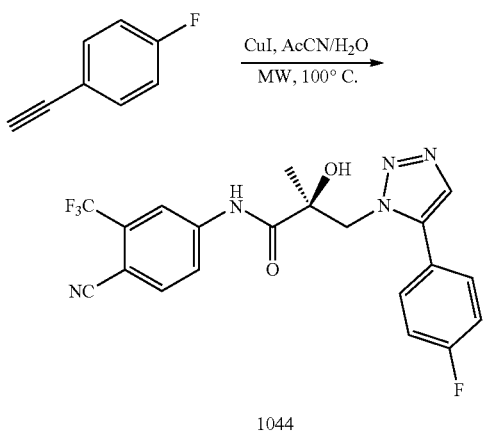

1044

A mixture of 1042 (57 mg, 0.18 mmol), 1-ethylnyl-4-fluorobenzene (0.015 mL, 0.18 mmol), and copper iodide (11 mg, 0.055 mmol) in AcCN/H₂O (1/0.5 mL) were loaded into a vessel with a cap. The reaction vessels were placed in a reactor block in the microwave reactor. A programmable microwave (MW) irradiation cycle of 30 min on (300 W) at 100° C. and 25 min off (fan-cooled) was executed twice because starting materials were shown on TLC after the first cycle (total irradiation time, 60 min). The mixture was transferred to a round bottom flask to be concentrated under reduced pressure and poured into EtOAc, which was washed with water and dried over MgSO₄, concentrated, and purified by silica gel chromatography (EtOAc/hexane=2:1) to afford the titled compound as yellow solid (69.8 mg, 90%).

Compound 1044 was characterized as follows: ¹H NMR (400 MHz, acetone-d₆) δ 9.00 (bs, 1H, NH), 8.44 (s, 1H), 8.30 (s, 1H), 8.25 (d, J=8.4 Hz, 1H), 8.02 (d, J=8.4 Hz, 1H), 7.89 (dd, J=8.0, 2.4 Hz, 2H), 7.20 (d, J=8.8 Hz, 2H), 5.67 (s, 1H, OH), 4.92 (d, J=14.0 Hz, 1H), 4.72 (d, J=14.0 Hz, 1H), 1.60 (s, 3H); ¹⁹F NMR (acetone-d6, decoupled) δ 114.68, 61.64; MS (ESI) m/z 432.11 [M−H]⁻ 434.08 [M+H]⁺. The structure of 1044 was distinguished from its isomer 1045 (see below) by the 2D NMR techniques of NOESY and COSY.

(S)—N-(4-Cyano-3-(trifluoromethyl)phenyl)-3-(4-(4-fluorophenyl)-1H-1,2,3-triazol-1-yl)-2-hydroxy-2-methylpropanamide (C₂₀H₁₅F₄N₅O₂) (1045)

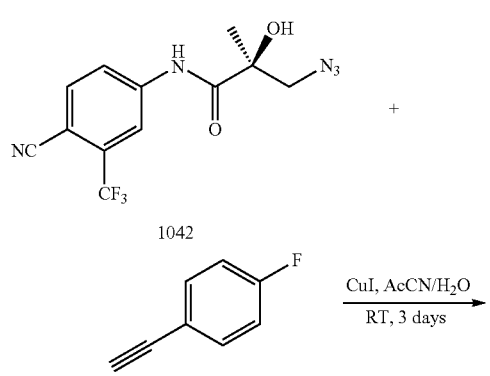

1042

To a suspension of copper(I)iodide (11 mg, 0.055 mmoL) in acetonitrile (7 mL)/water (3 mL) was added 1042 (57 mg, 0.182 mmol) at RT and then 1-ethynyl-4-fluorobenzene (0.015 mL, 0.182 mmol) was added. The resulting reaction mixture was stirred at RT for 3 days. The mixture was evaporated under reduced pressure, poured into water:brine (1:1, v/v) and then extracted with ethyl acetate. The combined organic extracts were then washed with brine, dried over sodium sulfate, filtered and evaporated. Purification was by chromatography (silica, 60% ethyl acetate in hexane) to afford a yellow solid (51.3 mg, 65%).

Compound 1045 was characterized as follows: ¹H NMR (400 MHz, CDCl₃) δ 9.07 (bs, 1H, NH), 7.82-7.80 (m, 1H), 7.79 (s, 1H), 7.76-7.74 (m, 2H), 7.72 (dd, J=8.2, 2.8 Hz, 2H), 7.10 (t, J=8.8 Hz, 2H), 5.15 (bs, 1H, OH), 4.96 (d, J=14.0 Hz, 1H), 4.61 (d, J=14.0 Hz, 1H), 1.62 (s, 3H); ¹⁹F NMR (CDCl₃, decoupled) δ−62.24, −112.36; MS (ESI) m/z 432.17 [M−H]⁻ 434.09 [M+H]⁺. The structure of 1045 was distinguished from its isomer 1044 (see above) by the 2D NMR techniques of NOESY and COSY. E.g, 1045 showed an NOE cross-peak between the methylene proton and the triazole proton indicating that these protons are within ~4.5 Å of each other as would be the case for 1045 but not 1044. This cross-peak was not seen for 1044.

(S)-3-(4-Fluoro-1H-pyrazol-1-yl)-2-hydroxy-2-methyl-N-(4-nitro-3-(trifluoromethyl)phenyl)-propanamide (C₁₄H₁₂F₄N₄O₄) (1046)

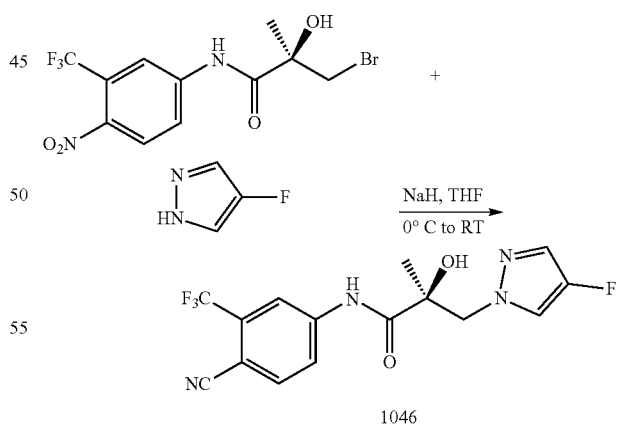

1046

To a dry, nitrogen-purged 100 mL round-bottom flask equipped with a dropping funnel under argon atmosphere containing 4-fluoro-1H-pyrazole (691 mg, 8.03 mmol), NaH of 60% dispersion in mineral oil (674 mg, 16.9 mmol) was added in 60 mL of anhydrous THF solvent at ice-water bath. The mixture was stirred 30 min at the ice-water bath. Into the flask through dropping funnel, a solution of (R)-3-bromo- 2-hydroxy-2-methyl-N-(4-nitro-3-(trifluoromethyl)phenyl) propanamide (2.98 g, 8.03 mmol) in 10 mL of anhydrous THF was added under argon atmosphere at the ice-water bath, and stirred overnight at RT. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography using as an eluent EtOAc/hexane in a 1:2 ratio to produce the titled compound (2.01 g, 67%) as yellow solid.

Compound 1046 was characterized as follows: $^1$H NMR (400 MHz, CDCl₃) δ 9.14 (bs, 1H, NH), 8.01 (s, 1H), 7.97-7.91 (m, 2H), 7.38 (d, J=3.6 Hz, 1H), 7.35 (d, J=4.4 Hz, 1H), 5.95 (s, 1H, OH), 4.56 (d, J=14.0 Hz, 1H), 4.17 (d, J=14.0 Hz, 1H), 1.48 (s, 3H); $^{19}$F NMR (CDCl₃, decoupled) δ −60.13, −176.47; MS (ESI) m/z 375.08 [M−H]$^−$; 377.22 [M+H]$^+$; 399.04 [M+Na]$^+$.

(S)—N-(4-Cyano-3-(trifluoromethyl)phenyl)-2-hydroxy-3-(4-iodo-1H-pyrazol-1-yl)-2-methylpropanamide ($C_{15}H_{12}F_3IN_4O_2$) (1047)

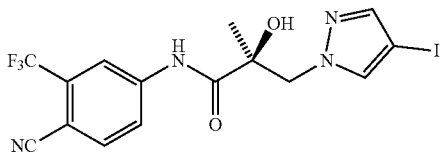 [SMILES: C[C@](O)(Cn1cc(I)cn1)C(=O)Nc1ccc(C#N)c(C(F)(F)F)c1]

To a solution of 4-iodo-1H-pyrazole (0.20 g, 0.001031 mol) in anhydrous THF (5 mL), which was cooled in an ice water bath under an argon atmosphere, was added sodium hydride (60% dispersion in oil, 0.124 g, 0.003093 mol). After addition, the resulting mixture was stirred for 3 h. (R)-3-Bromo-N-(4-cyano-3-(trifluoromethyl)phenyl)-2-hydroxy-2-methylpropanamide (8, 0.36 g, 0.001031 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.25 g (52%) of the titled compound as off-white solid.

Compound 1047 was characterized as follows: $^1$H NMR (400 MHz, DMSO-d₆) δ 10.36 (s, 1H, NH), 8.45 (s, 1H, ArH), 8.23 (d, J=8.8 Hz, J=1.2 Hz, 1H, ArH), 8.10 (d, J=8.8 Hz, 1H, ArH), 7.78 (s, 1H, Pyrazole-H), 7.46 (s, 1H, Pyrazole-H), 6.31 (s, 1H, OH), 4.48 (d, J=14.0 Hz, 1H, CH), 4.31 (d, J=14.0 Hz, 1H, CH), 1.35 (s, 3H, CH₃); mass (ESI, Negative): 463.18 [M−H]$^+$; (ESI, Positive): 486.96 [M+Na]$^+$.

(S)-3-(4-Cyano-1H-pyrazol-1-yl)-N-(4-cyano-3-(trifluoromethyl)phenyl)-2-hydroxy-2-methylpropanamide ($C_{16}H_{12}F_3N_5O_2$) (1048)

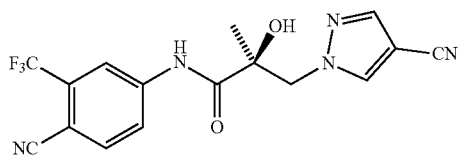 [SMILES: C[C@](O)(Cn1cc(C#N)cn1)C(=O)Nc1ccc(C#N)c(C(F)(F)F)c1]

To a solution of 1H-pyrazole-4-carbonitrile (0.10 g, 0.001074 mol) in anhydrous THF (5 mL), which was cooled in an ice water bath under an argon atmosphere, was added sodium hydride (60% dispersion in oil, 0.11 g, 0.003223 mol). After addition, the resulting mixture was stirred for 3 h. (R)-3-Bromo-N-(4-cyano-3-(trifluoromethyl)phenyl)-2-hydroxy-2-methylpropanamide (8, 0.377 g, 0.001074 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using hexane and ethyl acetate (1:1 to 1:2) as eluent to afford 0.18 g (46%) of the titled compound as white solid.

Compound 1048 was characterized as follows: $^1$H NMR (400 MHz, DMSO-d₆) δ 10.35 (s, 1H, NH), 8.45 (d, J=1.2 Hz, 1H, ArH), 8.43 (s, 1H, Pyrazole-H), 8.22 (d, J=8.8 Hz, J=1.2 Hz, 1H, ArH), 8.10 (d, J=8.8 Hz, 1H, ArH), 7.98 (s, 1H, Pyrazole-H), 6.41 (s, 1H, OH), 4.45 (d, J=14.0 Hz, 1H, CH), 4.36 (d, J=14.0 Hz, 1H, CH), 1.38 (s, 3H, CH₃); mass (ESI, Negative): 362.11 [M−H]$^−$; (ESI, Positive): 386.07 [M+Na]$^+$.

(S)-3-(4-Chloro-1H-pyrazol-1-yi)-N-(4-cyano-3-(trifluoromethyl)phenyl)-2-hydroxy-2-methylpropanamide ($C_{15}H_{12}ClF_3N_4O_2$) (1049)

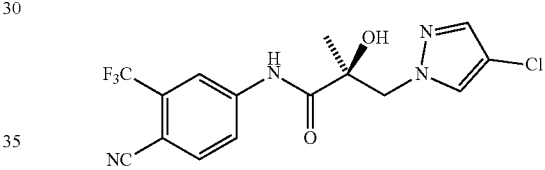

To a solution of 4-chloro-1H-pyrazole (0.15 g, 0.001463 mol) in anhydrous THF (5 mL), which was cooled in an ice water bath under an argon atmosphere, was added sodium hydride (60% dispersion in oil, 0.18 g, 0.004389 mol). After addition, the resulting mixture was stirred for 3 h. (R)-3-Bromo-N-(4-cyano-3-(trifluoromethyl)phenyl)-2-hydroxy-2-methylpropanamide (8, 0.51 g, 0.001463 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using dichloromethane and ethyl acetate (19:1) as eluent to afford 0.30 g (55%) of the titled compound as white solid.

Compound 1049 was characterized as follows: $^1$H NMR (400 MHz, DMSO-d₆) δ 10.38 (s, 1H, NH), 8.46 (s, 1H, ArH), 8.23 (d, J=8.6 Hz, J=1.2 Hz, 1H, ArH), 8.10 (d, J=8.6 Hz, 1H, ArH), 7.83 (s, 1H, Pyrazole-H), 7.47 (s, 1H, Pyrazole-H), 6.34 (s, 1H, OH), 4.45 (d, J=14.0 Hz, 1H, CH), 4.27 (d, J=14.0 Hz, 1H, CH), 1.36 (s, 3H, CH₃); mass (ESI, Negative): 371.68 [M−H]$^−$.

Example 2

Octanol-Water Partition Coefficient (Log P)

Log P is the log of the octanol-water partition coefficient, commonly used early in drug discovery efforts as a rough estimate of whether a particular molecule is likely to cross biological membranes. Log P was calculated using ChemDraw Ultra version is 12.0.2.1016 (Perkin-Elmer, Waltham, Mass. 02451). Calculated Log P values are reported in Table 1 in the column labeled 'Log P (−0.4 to +5.6)'. Lipinski's rule of five is a set of criteria intended to predict oral bioavailability. One of these criteria for oral bioavailability is that the Log P is between the values shown in the column heading (−0.4 (relatively hydrophilic) to +5.6 (relatively lipophilic) range), or more generally stated <5. One of the goals of SARD design was to improve water solubility. The monocyclic templates of this invention such as the pyrazoles, pyrroles, etc. were more water soluble than earlier analogs. For instance, one may compare the Log P values of SARDs from other templates, e.g., alkyl-amine 17, indoline 100 and indole 11, to the monocyclics of the invention (1001-1064, and 1069-1071).

TABLE 1

In vitro screening of LBD binding ($K_i$), AR antagonism ($IC_{50}$), SARD activity, and metabolic stability

| Compound # | Structure | Log P (−0.4 to +5.6) | M.W. | wtAR Binding ($K_i$ (left)) & Transactivation ($IC_{50}$ (right)) (nM) $K_i$ (nM) (DHT = 1 nM) |
|---|---|---|---|---|
| Enobosarm (agonist) | 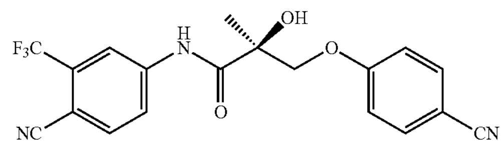 [SMILES: C[C@](O)(COc1ccc(C#N)cc1)C(=O)Nc1ccc(C#N)c(C(F)(F)F)c1] | 3.44 | 389.89 | 20.21 |
| R-Bicalutamide | 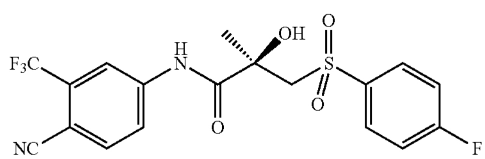 [SMILES: C[C@](O)(CS(=O)(=O)c1ccc(F)cc1)C(=O)Nc1ccc(C#N)c(C(F)(F)F)c1] | 2.57 | 430.37 | 508.84 |
| Enzalutamide | 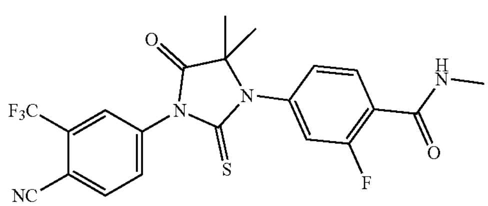 [SMILES: CNC(=O)c1ccc(N2C(=S)N(c3ccc(C#N)c(C(F)(F)F)c3)C(=O)C2(C)C)cc1F] | 4.56 | 464.44 | 3641.29 |
| ARN-509 | 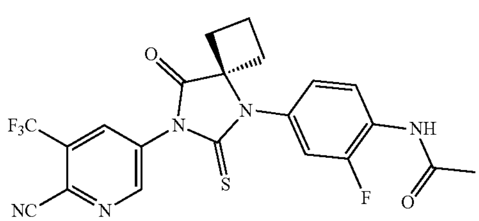 | 3.47 | 477.43 | 1452.29 |
| 17 | 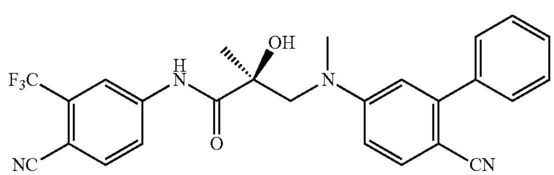 [SMILES: CN(C[C@](C)(O)C(=O)Nc1ccc(C#N)c(C(F)(F)F)c1)c1ccc(C#N)c(-c2ccccc2)c1] | 5.69 | 478.48 | 28.4 |
| 100 | 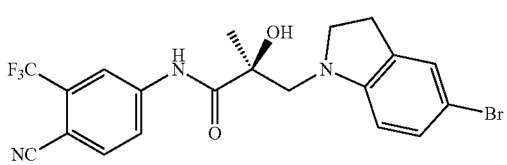 [SMILES: C[C@](O)(CN1CCc2cc(Br)ccc21)C(=O)Nc1ccc(C#N)c(C(F)(F)F)c1] | 4.62 | 468.27 | 197.67 |

TABLE 1-continued

In vitro screening of LBD binding (K$_i$), AR antagonism (IC$_{50}$), SARD activity, and metabolic stability

| # | Structure | | | |
|---|---|---|---|---|
| 11 | | 3.47 | 405.35 | 267.39 |
| 1001 | | 2.29 | 362.31 | 327.97 |
| 1002 | | 2.03 | 356.27 | No binding |
| 1003 | | 3.54 | 414.38 | No binding |
| 1004 | | 3.93 | 413.39 | 322.11 |
| 1005 | | 1.78 | 417.18 | No binding |
| 1006 | | 2.3 | 417.18 | 905.71 |
| 1007 | | 1.66 | 322.72 | No binding |
| 1008 | | 0.71 | 304.73 | No binding |

TABLE 1-continued

In vitro screening of LBD binding (K_i), AR antagonism (IC_50), SARD activity, and metabolic stability

| # | Structure | K_i | IC_50 | SARD |
|---|---|---|---|---|
| 1009 | | 1.69 (for free amine) | 307.78 (for free amine) | No binding |
| 1010 | | 4.09 | 431.38 | 259.29 |
| 1011 | | 3.97 | 414.38 | 3660 |
| 1012 | | 2.49 | 356.27 | 820.97 |
| 1013 | | 1.87 | 338.28 | 7398 |
| 1014 | | 3.21 | 406.28 | 512.3 |
| 1015 | | 4.13 | 432.37 | >10000 |
| 1016 | | 1.34 | 357.33 | 1874.68 |

TABLE 1-continued

In vitro screening of LBD binding (K$_i$), AR antagonism (IC$_{50}$), SARD activity, and metabolic stability

| # | Structure | | | |
|---|---|---|---|---|
| 1017 | [structure] | 2.79 | 406.28 | 898.23 |
| 1018 | [structure] | 1.42 | 339.27 | No binding |
| 1019 | [structure] | 3.23 | 407.23 | No binding |
| 1020 | [structure] | 2.03 | 356.27 | No binding |
| 1021 | [structure] | 2.41 | 355.39 | 633.23 |
| 1022 | [structure] | 1.11 | 357.26 | No binding |
| 1023 | [structure] | −0.93 | 307.28 | No binding |
| 1024 | [structure] | 2.86 | 340.28 | No binding |
| 1025 | [structure] | 3.7 | 432.37 | 612.4 |

TABLE 1-continued

In vitro screening of LBD binding (K$_i$), AR antagonism (IC$_{50}$), SARD activity, and metabolic stability

| # | Structure | | | |
|---|---|---|---|---|
| 1026 | (structure) | 1.19 | 354.29 | — |
| 1027 | (structure) | 2.24 | 453.41 | 1382.06 |
| 1028 | (structure) | 1.07 | 353.30 | 227.48 |
| 1029 | (structure) | 2.29 | 326.25 | No Binding |
| 1030 | (structure) | 1.32 | 454.40 | No binding |
| 1031 | (structure) | 0.78 | 395.34 | No binding |
| 1032 | (structure) | 1.82 | 429.78 | No binding |
| 1033 | (structure) | 1.3 | 411.34 | No binding |

TABLE 1-continued

In vitro screening of LBD binding (K_i), AR antagonism (IC_50), SARD activity, and metabolic stability

| # | Structure | Col3 | Col4 | Col5 |
|---|---|---|---|---|
| 1034 | | 1.3 | 411.34 | |
| 1035 | | 1.2 | 380.32 | |
| 1036 | | 1.9 | 383.28 | 2225 |
| 1037 | | 0.7 | 284.11 | 4547 |
| 1038 | | 1.6 | 352.11 | |
| 1039 | | 1.1 | 310.15 | |
| 1040 | | 2.8 | 321.09 | |
| 1041 | | 0.6 | 298.70 | |
| 1042 | | 0.8 | 313.24 | |
| 1043 | | 1.8 | 407.27 | |

TABLE 1-continued

In vitro screening of LBD binding (K$_i$), AR antagonism (IC$_{50}$), SARD activity, and metabolic stability

| | | | |
|---|---|---|---|
| 1044 | [structure] | 3.4 | 433.36 |
| 1045 | [structure] | 3.7 | 433.36 |
| 1046 | [structure] | 2.0 | 376.24 |
| 1047 | [structure] | 3.2 | 464.19 |
| 1048 | [structure] | 1.9 | 363.30 |
| 1049 | [structure] | 2.4 | 372.73 |
| 1002-oxalic acid salt | | | |
| 1002-succinic acid salt | | | |
| 1002-HBr | | | |
| 1002-tartaric acid salt | | | |
| 1002-HCl | | | |
| 1050 | [structure] | 2.70 | 417.18 | >10000 |

TABLE 1-continued

In vitro screening of LBD binding (K$_i$), AR antagonism (IC$_{50}$), SARD activity, and metabolic stability

| # | Structure | | | |
|---|---|---|---|---|
| 1051 | 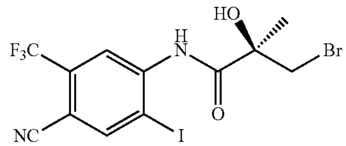 [SMILES: C[C@](O)(CBr)C(=O)Nc1cc(C(F)(F)F)c(C#N)cc1I] | 3.93 | 477.02 | |
| 1052 | 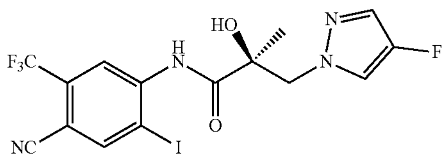 [SMILES: C[C@](O)(Cn1cc(F)cn1)C(=O)Nc1cc(C(F)(F)F)c(C#N)cc1I] | 3.38 | 482.17 | |
| 1053 | 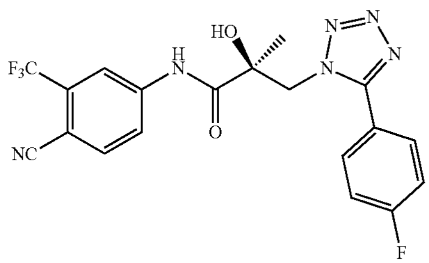 [SMILES: C[C@](O)(Cn1nnnc1-c1ccc(F)cc1)C(=O)Nc1ccc(C#N)c(C(F)(F)F)c1] | 3.44 | 434.35 | |
| 1054 | 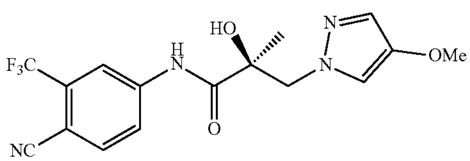 [SMILES: COc1cnn(C[C@](C)(O)C(=O)Nc2ccc(C#N)c(C(F)(F)F)c2)c1] | 1.74 | 368.31 | |
| 1055 | 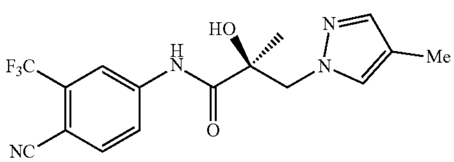 [SMILES: Cc1cnn(C[C@](C)(O)C(=O)Nc2ccc(C#N)c(C(F)(F)F)c2)c1] | 2.3 | 352.31 | 1552 |
| 1057 (Racemate) | 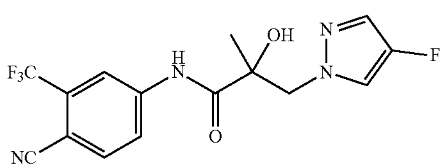 [SMILES: CC(O)(Cn1cc(F)cn1)C(=O)Nc1ccc(C#N)c(C(F)(F)F)c1] | 2.0 | 356.27 | |
| 1058 | 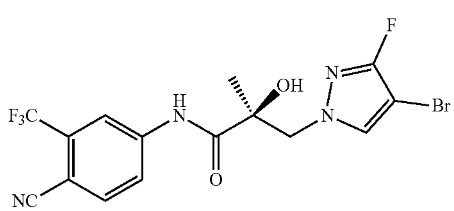 | 3.3 | 435.17 | 606.5 |
| 1059 | 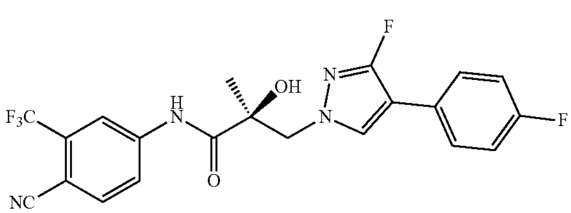 [SMILES: C[C@](O)(Cn1cc(-c2ccc(F)cc2)c(F)n1)C(=O)Nc1ccc(C#N)c(C(F)(F)F)c1] | 4.3 | 450.36 | 600.58 |

TABLE 1-continued

In vitro screening of LBD binding (K$_i$), AR antagonism (IC$_{50}$), SARD activity, and metabolic stability

| | | | | |
|---|---|---|---|---|
| 1060 | [structure] | 3.1 | 422.19 | 202.3 |
| 1061 | [structure] | 3.2 | 386.76 | 1345.6 |
| 1062 | [structure] | 2.0 | 376.24 | |
| 1062a | [structure] | — | 188.16 | |
| 1063 | [structure] | 2.8 | 434.35 | 1486 |
| 1069 | [structure] | 2.41 | 436.16 | 566.5 |
| 1070 | [structure] | 2.22 | 443.18 | |

TABLE 1-continued

In vitro screening of LBD binding (K$_i$), AR antagonism (IC$_{50}$), SARD activity, and metabolic stability 1071     3.09     440.38

[Structure: F$_3$C- and NC- substituted pyridine connected via NH to a chiral carbon bearing HO and methyl, CH$_2$ linker to pyrazole ring with phenyl and CN substituents]

| Compound # | wtAR Binding (K$_i$ (left)) & Transactivation (IC$_{50}$ (right)) (nM) IC$_{50}$ (nM) | SARD Activity (% inh): Full Length (left) and S.V. (right) | | DMPK (MLM) T$_{1/2}$ (min) & CL$_{int}$ (μL/min/mg) |
|---|---|---|---|---|
| | | Full Length % inhibition at 1, 10 μM | S.V. % inhibition at 10 μM | |
| Enobosarm (agonist) | ~20 (EC$_{50}$) | Not applicable | Not applicable | |
| R-Bicalutamide | 248.2 | 0 | 0 | |
| Enzalutamide | 216.3 | 0 | 0 | |
| ARN-509 | | 0 | 0 | |
| 17 | 95 | | | |
| 100 | 530.95 | 60 | 41 | 66.87 |
| | | | | 10.38 |
| 11 | 85.10 | 65-83 | 60-100 | 12.35 |
| | | | | 56.14 |
| 1001 | partial agonist | 0 | 0 | 23.5 |
| | | | | 29.5 |
| 1002 | 199.36 | 100 | 100 | 77.96 |
| | | | | 0.89 |
| 1003 | 1152.78 | 0 | 0 | 48.45 |
| | | | | 14.31 |
| 1004 | 178.77 (partial agonist) | 0%, 40% @ 10 μM | 0 | 3.96 |
| | | | | 175.2 |
| 1005 | 1019.38 | 50 | 70 | 16.51 |
| | | | | 41.58 |
| 1006 | 148.94 (partial agonist) | 0 | 0 | |
| 1007 | 958.77 | 0 | 0 | |
| 1008 | 1856.8 | 0 | 30 | 24.61 |
| | | | | 28.16 |
| 1009 | No inhibition | 0 | 0 | |
| 1010 | 225.91 | 100 | 60 | 17.93 |
| | | | | 38.66 |
| 1011 | 4770 | 0 | 0 | |
| 1012 | 219.48 | 82 | 73 | 64.07 |
| | | | | 1.02 |
| 1013 | 1441.58 | 0 | | |
| 1014 | 204.59 | 67 (comparable to 11 in the same exp) | 54 (comparable to 11 in the same exp) | 330 0 |
| 1015 | 1742 | 72 | 0 | |
| 1016 | 1018.68 | 52 | 80 | |
| 1017 | 404.39 | 80 | 100 | Infinity 0 |
| 1018 | 1091.56 | 0 | 0 | |
| 1019 | 1012.75 | 68 | 100 | |
| 1020 | 192 | 84 | | |
| 1021 | partial | 0 | 0 | |
| 1022 | 92.17 | 54 | 81 | |
| 1023 | No effect | 0 | | Infinity 0 |
| 1024 | 463.9 | 60 | 70 | Infinity 0 |
| 1025 | 969 | 60 | 0 | |
| 1026 | — | 0 | | |
| 1027 | 1153 | 20 | | |
| 1028 | Agonist | | | |
| 1029 | 2124 | 35 | 40 | |

TABLE 1-continued

In vitro screening of LBD binding ($K_i$), AR antagonism ($IC_{50}$), SARD activity, and metabolic stability

| | | | |
|---|---|---|---|
| 1030 | 6108 | — | |
| 1031 | No effect | — | |
| 1032 | 900.86 | | |
| 1033 | No effect | | |
| 1034 | 827 | | |
| 1035 | 757.7 | | |
| 1036 | 36.22 | 20 | |
| 1037 | 350.5 | >50 | |
| 1038 | 2490 | | |
| 1039 | 1750 | | |
| 1040 | — | | |
| 1041 | 2470 | >75 | |
| 1042 | — | | |
| 1043 | 57.91 | 10 | |
| 1044 | 316.7 | 73 | |
| 1045 | 250.9 | 84 | |
| 1046 | Partial | | |
| 1047 | | | |
| 1048 | | | |
| 1049 | | | |
| 1002-oxalic acid salt | 57.99 | | |
| 1002-succinic acid salt | 83.06 | | |
| 1002-HBr | 77.2 | | |
| 1002-tartaric acid salt | 259.1 (similar to 1002 in this experiment) | | |
| 1002-HCl | 123.5 | | |
| 1050 | 427 | 42 | 0 |
| 1051 | No effect | | |
| 1052 | 5450 | | |
| 1053 | No effect | | |
| 1054 | — | 0 | 0 |
| 1055 | 8087 | | |
| 1057 (Racemate) | | | |
| 1058 | 132.5 | 70 | 80 |
| 1059 | 285.1 | 70 | toxic |
| 1060 | 180.5 | 41, 23 | 32 |
| 1061 | 331.6 | 41, 83 | |
| 1062 | Partial | | |
| 1062a | No effect | | |
| 1063 | 216.9 | | |
| 1069 | 34.9 | 0, 0 | 0 |
| 1070 | 5481 | 90, 90 | 84 |
| 1071 | 578.5 | 0, 54 | 0 |

TABLE 2

| Compd ID | Structure | MLM | | HLM | |
|---|---|---|---|---|---|
| | | $T_{1/2}$ (min) | $CL_{Int}$ (μL/min/mg) | $T_{1/2}$ (min) | $CL_{Int}$ (μL/min/mg) |
| 11 | [structure] | 14.35 | 48.30 | 14.62 | 47.40 |
| 1001 | [structure] | 23.5 | 29.5 | | |

TABLE 2-continued

| Compd ID | Structure | MLM | | HLM | |
|---|---|---|---|---|---|
| | | $T_{1/2}$ (min) | $CL_{Int}$ (μL/min/mg) | $T_{1/2}$ (min) | $CL_{Int}$ (μL/min/mg) |
| 1002 | 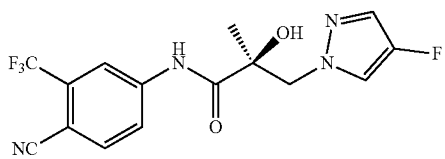 [SMILES: C[C@](O)(Cn1cc(F)cn1)C(=O)Nc1ccc(C#N)c(C(F)(F)F)c1] | 77.96 | 0.89 | 73.36 | 0.949 |
| 1004 | 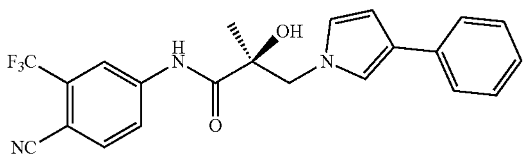 [SMILES: C[C@](O)(Cn1ccc(-c2ccccc2)c1)C(=O)Nc1ccc(C#N)c(C(F)(F)F)c1] | 3.96 | 175.2 | 2.261 | 306.5 |
| 1012 | 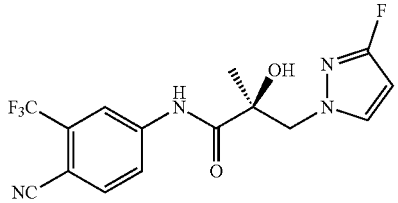 [SMILES: C[C@](O)(Cn1ccc(F)n1)C(=O)Nc1ccc(C#N)c(C(F)(F)F)c1] | 64.07 | 1.02 | | |

Example 3

Transactivation Assay

Methods:

HEK-293 cells were transfected with the indicated receptors and GRE-LUC and CMV-renilla luc. Cells were treated 24 h after transfection and luciferase assay performed 48 h after transfection. The SARD compounds did not inhibit transactivation of receptors other than AR until 10 μM. The experimental method is described below.

Human AR was cloned into a CMV vector backbone and was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 μg GRE-LUC, 0.01 μg CMV-LUC (renilla luciferase) and 25 ng of the AR. The cells were treated 24 h after transfection and the luciferase assay performed 48 h after transfection. Transactivation results were based on measured luciferase light emissions and reported as relative light unit intensity (RLU). The assay was run in antagonist mode ($IC_{50}$) using known agonist R1881 at its $EC_{50}$ concentration of 0.1 nM and increasing concentrations of SARDs of this invention. Agonist mode data was reported qualitatively, e.g., partial agonist or an approximate $EC_{50}$ for enobosarm, for some compounds in Table 1. Antagonist data are represented as $IC_{50}$ (nM) obtained from four parameter logistics curve and are reported in Table 1 in the column labeled '$IC_{50}$'.

Figure 2A:
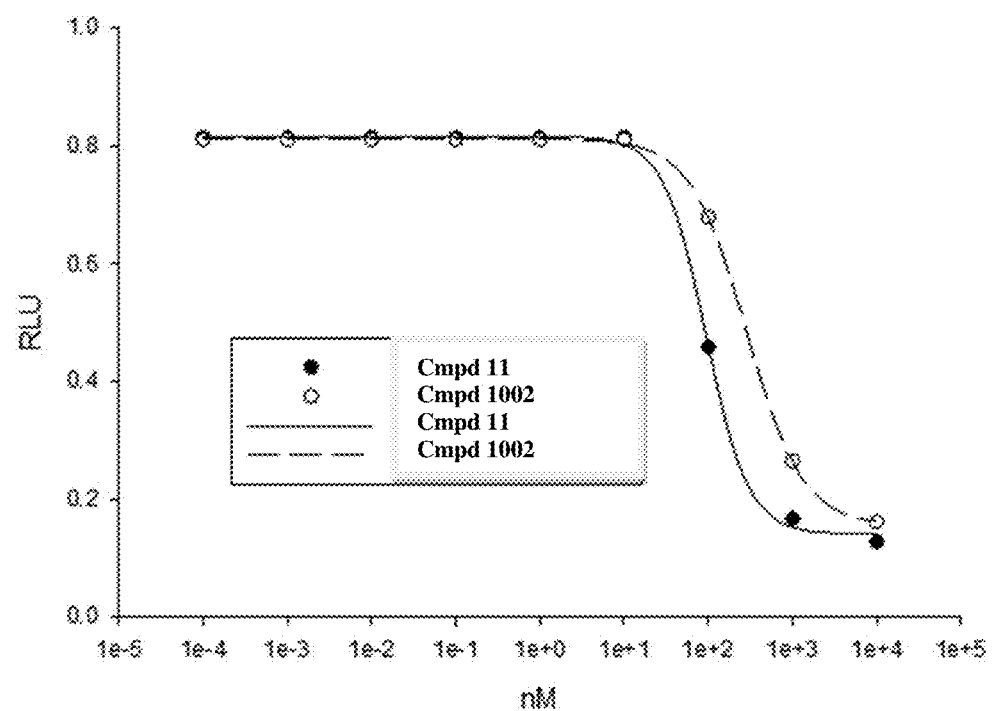
FIG. 2A and FIG. 2B: The transactivation results for 11 (an indole) and 1002 (a pyrazole of this invention) were reported based on measured luciferase light emissions and reported as relative light unit intensity (RLU).

Results:

Representative example graphs are shown in FIGS. 1A (1002), 2A (11 vs. 1002), 3A (1003), 4A (1004), 5A (1005), 6A (1006), 8-12 (1007-1011), and 13A (1001) with results plotted as RLU reported on the y-axis and SARD concentration on the x-axis (nM). In these Figures, antagonist mode data was shown as curve fitted data, whereas agonist mode data (if present) is reported without curve fitting. Only weak and partial agonism was seen. In vivo pharmacodynamics demonstrate potent and highly efficacious antagonism of androgen dependent tissues (see Examples 7 and 10 herein). FIG. 2 is a direct comparison of antagonism between 11 (closed dots) and 1002 (open dots). Other $IC_{50}$ values reported in Table 1 were calculated by the same method.

1002 was a potent antagonist (199.36 nM; Table 1 and FIG. 1A) with comparable inhibition as 11 (85.1 nM; FIG. 2) which is an extremely potent indole SARD lacking oral bioavailability. Despite the 2-fold increased $IC_{50}$ (Table 1) and lack of AR-LBD binding (see Example 4 and Table 1), 1002 was a more potent AR degrader in vitro (see Example 5 and Table 1). Further and unlike 11, 1002 was very stable in vitro in mouse (Table 1) and human liver microsomes (Table 2) which translated into improved in vivo pharmacodynamics (see Example 7 herein) in mice and rats. Based on the structural differences alone, the increased SARD activity in vitro and metabolic stability were each unexpected results. Likewise, the greatly improved in vivo efficacy could not have been predicted (i.e., was unexpected) based on structural differences alone. 1012, 1014, and 1017 also demonstrated improved metabolic stability in vitro suggesting that the pyrazole moiety may be responsible for the unexpected stability of 1002.

As discussed below, 1002 and 1014 also demonstrated significant anti-tumor activity in in vivo xenograft studies (see Examples 8 and 10), suggesting that the bioavailability of these compounds is sufficient for their intended uses.

Figure 4A:
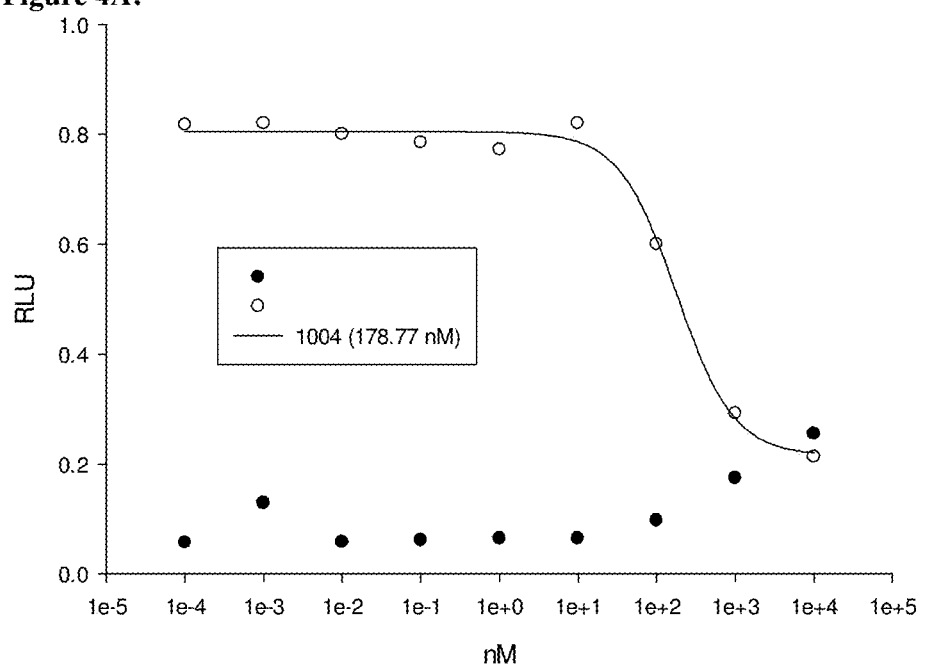
FIG. 4A and FIG. 4B: The transactivation result of 1004 was reported based on measured luciferase light emissions and reported as relative light unit intensity (RLU).
Figure 4B:
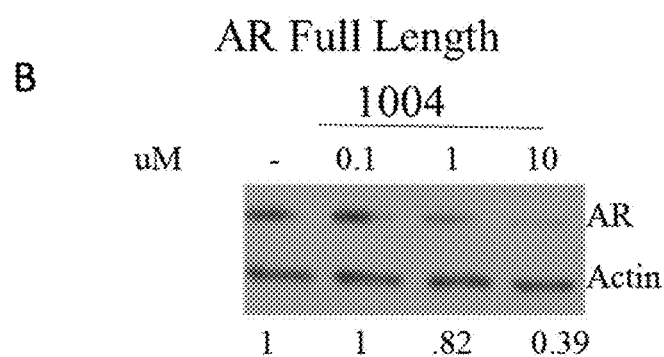
Figure 5A:
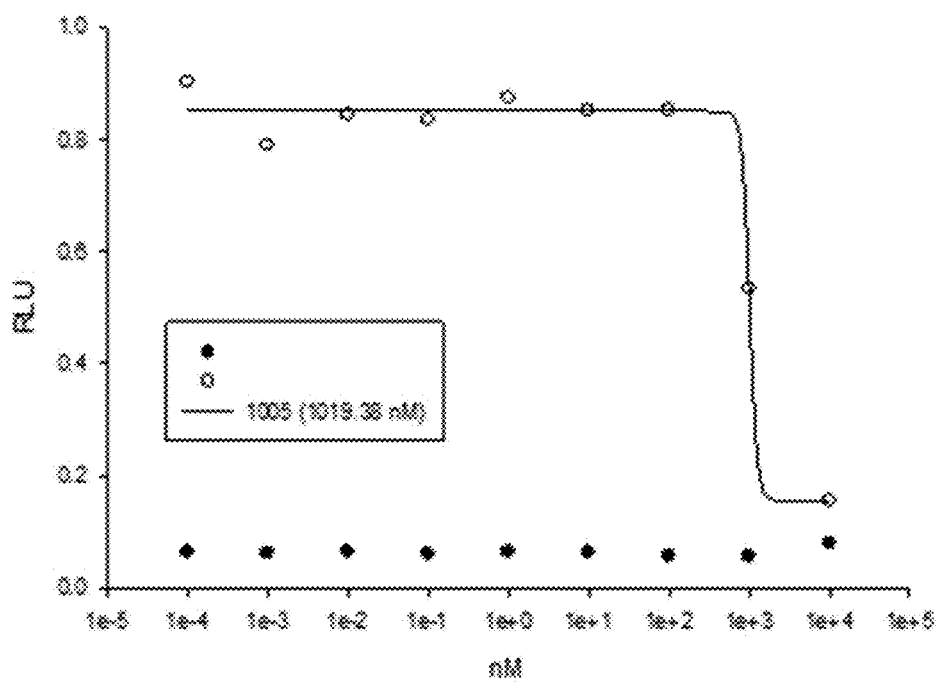
FIG. 5A and FIG. 5B: The transactivation results of 1005 were reported based on measured luciferase light emissions and reported as relative light unit intensity (RLU).
Figure 5B:
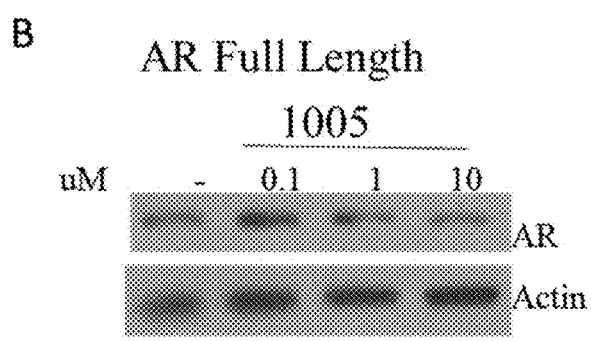

1004 (pyrrole) and 1006 (imidazole) demonstrated potent inhibition (178.77 nM and 148.94 nM; Table 1; FIGS. 4A and 6A) but weak SARD activity, whereas 1005 and 1016 demonstrated weak inhibition but strong SARD activity, suggesting that in vitro inhibition is not well correlated with SARD activity. However, 1010 (pyrrole), 1012 (pyrazole), and 1014 (pyrazole) were potent inhibitors and degraders. In general, LBD binding or LBD-dependent inhibition and in vitro SARD activity seem to be separate but highly tolerant structure activity relationships. Values for other compounds of the invention are reported in Tables 1 and 2.

Potent inhibition of transactivation was also seen for 1020 (192 nM), 1022 (92 nM), and 1024 (464 nM). 1020 is an R-isomer of pyrazole 1002, and like 1002, does not bind to the LBD yet has strong SARD activity. Similarly, the indole SARD 11 and the R-isomer of 11 have comparable SARD activities (Table 1 and FIG. 2B) for AR-FL (LNCaP) and AR-SV (22RV1). This is in sharp contrast to propanamide SARMs such as enobosarm which typically have 100-fold lower LBD binding and agonist activity for R-isomers (data not shown). This is further evidence that SARD activity is not mediated through the LBD, as will be discussed in more detail in Example 9 below. Example 9 demonstrates a novel binding site in the N-terminal domain (NTD), providing a basis for the distinct structure activity relationships from traditional AR antagonists that bind to the LBD and SARD of this invention which act through the NTD. The retention of SARD activity in opposite isomers (unlike SARMs) suggests that the NTD binding site does not require stereo-specificity in its ligands. Further, the NTD binding site does not seem to require the chiral hydroxyl group which is conserved for LBD-binding (agonists and) antagonists. E.g., 1024 is a non-chiral propanamide racemate which lacks the hydroxyl but retains SARD activity (Table 1: 60% degradation of AR-FL) and the ability to inhibit the AR (Table 1: $IC_{50}$=464 nM) despite not binding the LBD (Table 1: $K_i$: no binding). Also, 1029 replaces the chiral center with a methylene group and yets retains some SARD activity (Table 1: 35% degradation of AR-FL) and AR antagonism (Table 1: $IC_{50}$=2124 nM). 1032 has its hydroxyl group protected by acylation and does not bind the LBD yet is an antagonist of AR. Another possible divergence in SAR's is the A-ring which is conserved for LBD binders as 4-cyano or nitro and 3-trifluoromethyl or 3-chloro. However, changing the $CF_3$ of 1002 to the Cl of 1007 ablated SARD activity. Further, 1022 has a novel pyridine A-ring and does not bind to the LBD yet retains potent inhibition of transactivation (92 nM) and SARD activity (Table 1). Similarly, SARD activity is shown for 1037 and 1041 that contain pyridine A-rings (Table 1 and FIG. 28C), and 1043 is a highly potent pyridine antagonist but weak SARD activity (Table 1). Further, 1037 is a 3-bromopropanamide (i.e., lacks a heterocyclic B-ring) which binds weakly to the LBD (4547 nM) but is a potent antagonist (350.5 nM) and retains SARD activity, demonstrating that the B-ring may not be necessary (Table 1) for SARDs of this invention. Such observations confirm that SARD activity can be optimized in the absence of LBD binding data and provide a rationale for the degradation of AR splice variants lacking the LBD.

Example 4

Human Androgen Receptor (hAR) Ligand Binding Domain (LBD) Affinity Assay

Methods:

hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for the ligand binding curve with one site saturation was used to determine the $K_d$ of mibolerone.

Increasing concentrations of SARDs or DHT (range: $10^{-12}$ to $10^{-4}$ M) were incubated with [$^3$H]mibolerone and AR-LBD using the conditions described above. Following incubation, the ligand bound AR-LBD complex was isolated using BiogelHT hydroxyapatite, washed and counted in a scintillation counter after adding scintillation cocktail.

Results:

The results of this assay are reported as $K_i$ values (nM) in Table 1 in the column labeled 'wt AR Binding ($K_i$(left))'. As discussed above and is apparent from Table 1, there is a poor correlation between AR-LBD affinity and SARD activity. E.g., see in vitro SARD activity for 1002, 1005, 1015, 1019, 1020, and 1022 despite no binding affinity for the LBD (Table 1).

Example 5

In Vitro Assays to Determine SARD Activity

LNCaP or AD1 Androgen Receptor Degradation (Full Length AR):

The compounds of the invention were tested for their effect on full length AR protein expression. Methods: LNCaP or AD1 cells expressing full length AR were plated at 750,000-1,000,000 cells/well of a 6 well plate in growth medium (RPMI+10% FBS). Twenty four hours after plating, the medium was changed to RPMI+1% csFBS without phenol red and maintained in this medium for 2 days. The medium again was changed to RPMI+1% csFBS without phenol red and cells were treated with SARDs (1 nM to 10 mM) in combination with 0.1 nM R1881. After 24 h of treatment, cells were washed with cold PBS and harvested. Protein was extracted using salt-containing lysis buffer with three freeze-thaw cycles. The protein concentration was estimated and five microgram of total protein was loaded on a SDS-PAGE, fractionated, and transferred to a PVDF membrane. The membrane was probed with AR N-20 antibody (SantaCruz Biotechnology, Inc., Dallas, Tex. 75220) and actin antibody (Sigma-Aldrich, St. Louis, Mo.).

Figure 1B:
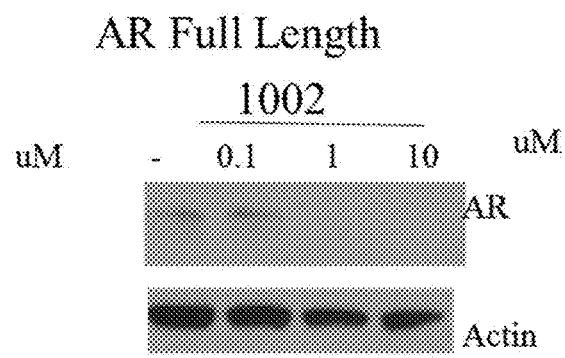

Results:

Degradation in LNCaP or AD1 cells are reported in Table 1 in the column labeled 'Full Length % Inhibition at 1, 10 µM'. The results of this assay were reported in FIGS. 1B (1002), 2B (11, 11R, 1002, 1020), 3B-6B (1003-1006), 7 (17), 13B (1001), 20A (1010, 1012, 1014, 1015, 1017, 1019 and 1022), 28A (1024 and 1029), 28C (1037 and 1041), 28D (1044 and 1045) as images of Western blot films (chemiluminescence exposed films).

22RV1 or D567es Androgen Receptor Degradation (Splice Variant (S.V.) AR):

The effect of SARD treatment on the AR levels was measured in androgen-refractory 22RV-1 or D567es prostate cancer cells. Methods: 22RV1 or D567es cells expressing AR splice variants (AR-SV) were plated at 750,000-1,000, 000 cells/well of a 6 well plate in growth medium (RPMI+ 10% FBS). Twenty four hours after plating, medium was changed and treated. After 24-30 h of treatment, cells were washed with cold PBS and harvested. Protein was extracted using salt-containing lysis buffer with three freeze-thaw cycles. Protein concentration was estimated and five microgram of total protein was loaded on a SDS-PAGE, fractionated, and transferred to a PVDF membrane. The membrane was probed with AR N-20 antibody (Santa Cruz Biotechnology, Inc., Dallas, Tex. 75220) and actin antibody (Sigma-Aldrich, St. Louis, Mo.).

Figure 1C:
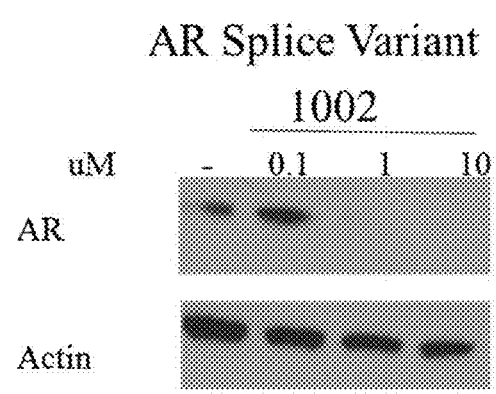
Figure 2B:
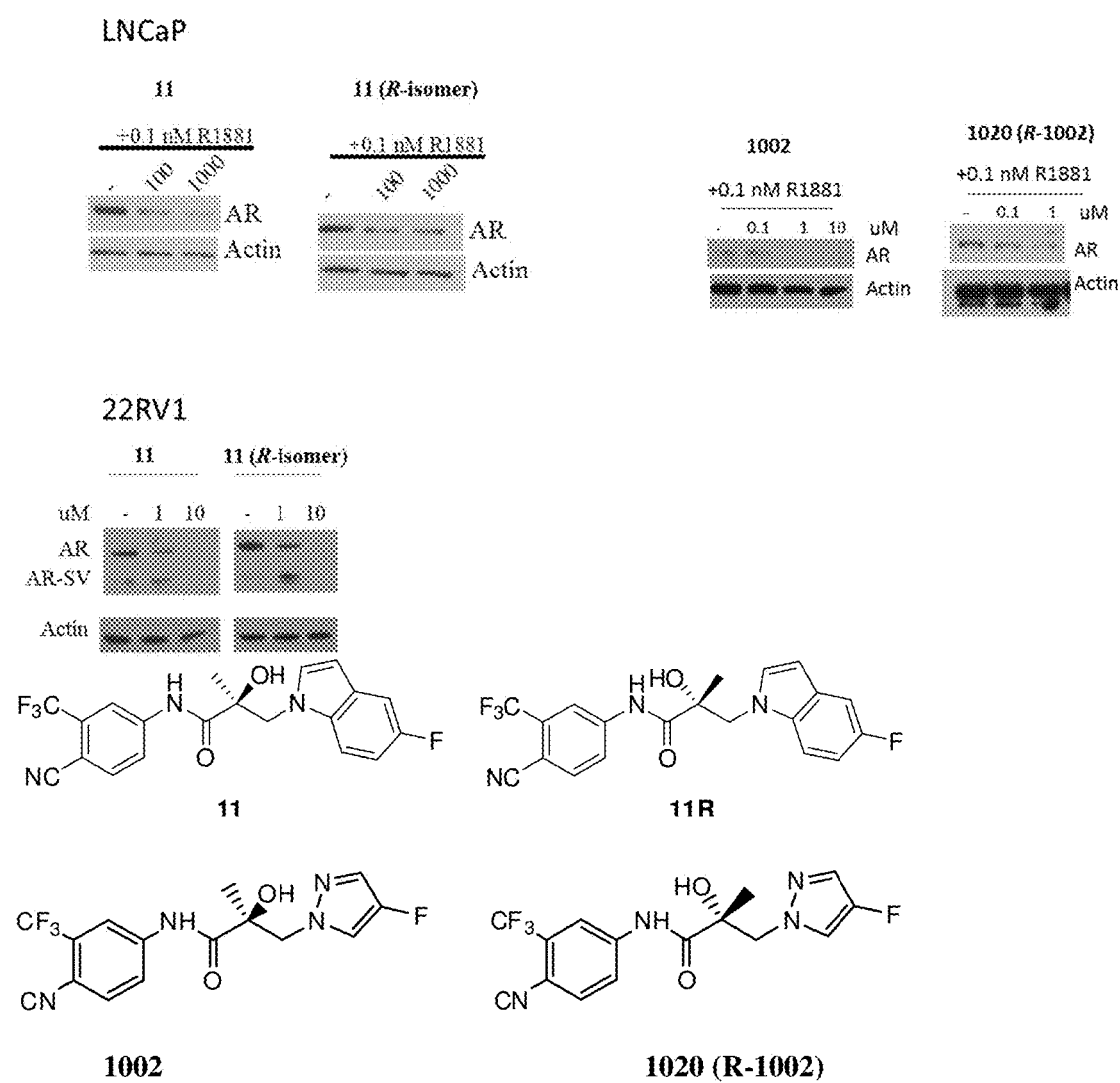
Figure 3A:
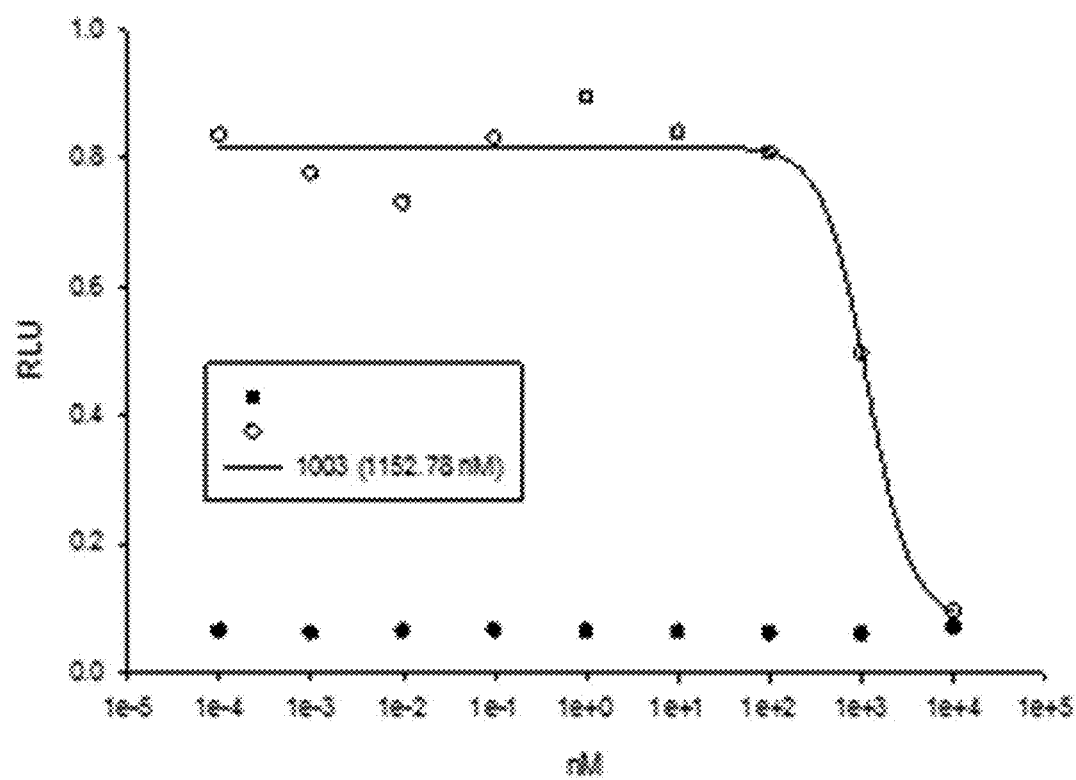
FIG. 3A and FIG. 3B: The transactivation result of 1003 was reported based on measured luciferase light emissions and reported as relative light unit intensity (RLU).
Figure 3B:
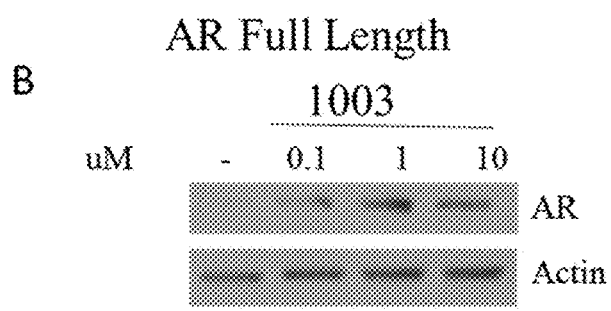

Results:

Degradation in 22RV1 or D567es cells are reported in Table 1 in the column labeled "S.V. % inhibition at 10 µM." The results of this assay in D567es cells were reported in FIGS. 1C (1002) and 20B (1010, 1012, 1014-1017, 1019 and 1022), and in 22RV1 cells in FIGS. 2B (11, 11R), 13C (1001), and 28B (1024 and 1029) as images of Western blot films (chemiluminescence exposed films).

Example 6

Metabolism Studies with Mouse Liver Microsomes (DMPK (MLM))

Determination of Metabolic Stability (In Vitro $CL_{int}$) of Test Compounds: Phase I Metabolism:

The assay was done in a final volume of 0.5 mL in duplicates (n=2). The test compound (1 mM) was pre-incubated for 10 minutes at 37° C. in 100 mM Tris-HCl, pH 7.5 containing 0.5 mg/mL liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes). 100 mL aliquots were removed and quenched with 100 mL of acetonitrile containing internal standard. Samples were vortex mixed and centrifuged at 4000 rpm for 10 min. The supernatants were transferred to 96 well plates and submitted for LC-MS/MS analysis. As a control, sample incubations done in the absence of NADPH were included. From % PCR (% Parent Compound Remaining), rate of compound disappearance was determined (slope) and in vitro $CL_{int}$ (µl/min/mg protein) was calculated.

Results:

FIG. 14 reported phase I data as a raw data table for one experiment in MLM for compound 1002 and the $T_{1/2}$ (half-life) and $CL_{int}$ (clearance) values calculated therefrom. FIGS. 15A and 16A report phase I data as a raw data table and graphed data for one experiment for 1002 in mouse liver microsomes (MLM) and human liver microsomes (HLM), respectively. Similarly, FIG. 17 reported MLM data for 1001 and the $T_{1/2}$ (half-life) and $CL_{int}$ (clearance) values in Tables 1 and 2 were calculated therefrom.

Metabolic Stability in Phase I & Phase II Pathways

In this assay, the test compound was incubated with liver microsomes and disappearance of drug was determined using discovery grade LC-MS/MS. To simulate Phase II metabolic pathway (glucuronidation), UDPGA and alamethicin were included in the assay. From % PCR (% Parent Compound Remaining), rate of compound disappearance is determined (slope of concentration vs. time plot) and in vitro $CL_{int}$ (µl/min/mg protein) was calculated. The results of this assay utilizing mouse liver microsomes (MLM) are reported in Table 1 in the column labeled "DMPK (MLM) $T_{1/2}$ (min) & $CL_{int}$ (µL/min/mg)". The first value is the calculated half-life ($T_{1/2}$) of the test article in MLM expressed in minutes and the $2^{nd}$ value is the intrinsic CL ($CL_{int}$) of the test article in MLM expressed as mL/min/mg protein.

Results:

FIG. 14 reported phase I & II data as a raw data table for one experiment and the $T_{1/2}$ (half-life) and $CL_{int}$ (clearance) values calculated therefrom. FIGS. 15B (using mouse liver microsomes (MLM)) and 16B (using human liver microsomes (HLM)) reported phase I & II data for 1002 as a raw data table for separate single experiments and graphed data. This data demonstrated that 1002 is stable in MLM and very stable in HLM. The LC-MS/MS analysis was performed as described below.

The metabolic stability of 1002 and other pyrazoles of this invention was unexpected in view of previous SARDs (100, 17, & 11; see Table 1). See also Examples 8 and 10 for comparisons of pyrazoles to previous SARD templates and their unexpected results in terms of metabolic stabilities, in vivo pharmacodynamics, in vivo serum and tumor concentrations, and in vivo anti-tumor efficacies in advanced prostate cancer (Example 10) and triple negative breast cancer (Example 8). Further, MLM data for 1024 (Table 1), a non-hydroxy variant, and 1023, a pyridine A-ring compound (non-carbonitrile), both revealed a lack of metabolism after incubation with MLM for 60 minutes. This demonstrates metabolic stability of SARDs of this invention including those with pyrazole B-rings, that lack the hydroxyl group, and/or include alternative A-rings.

Lc-Ms/Ms Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 µm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

Example 7

In Vivo Antagonism Demonstrated by SARD Compound 1002

Hershberger Method:

Male mice (20-25 grams body weight; n=5-7/group) were either left intact or castrated and treated as indicated in the figures for 13 days. Treatment of castrated mice was initiated 3 days after castration. Mice were sacrificed on day 14 of treatment and seminal vesicles were removed and weighed. Seminal vesicles weights were either represented as is or were normalized to body weight and represented.

Figure 18A:
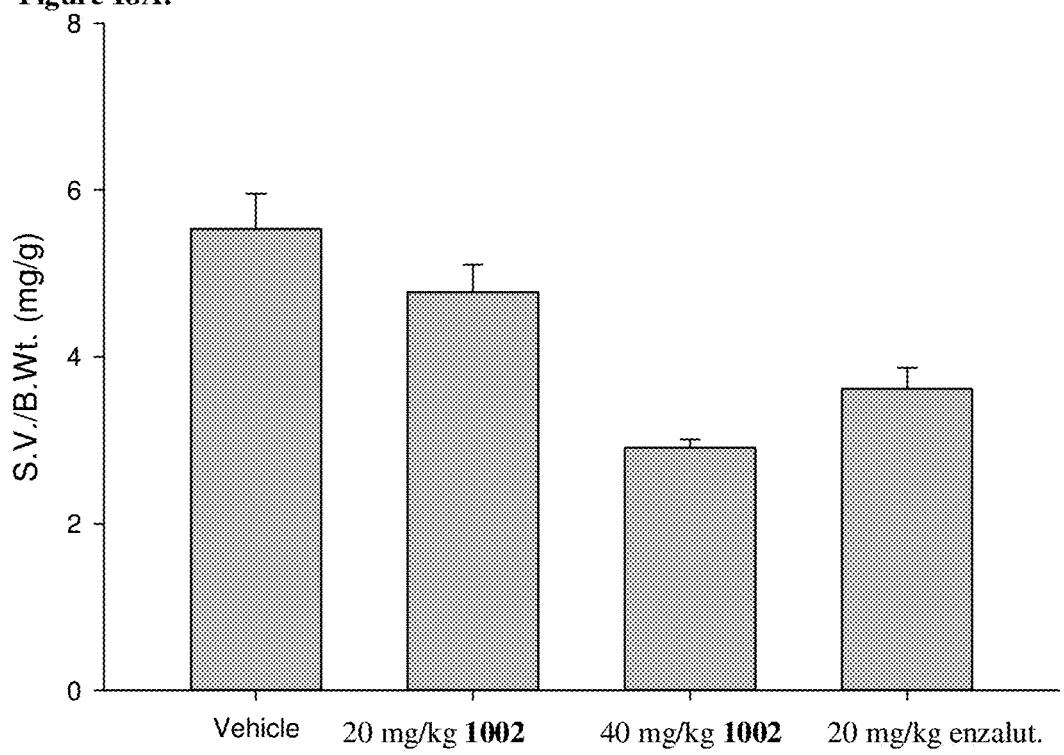
FIG. 18A and FIG. 18B: Hershberger method (mice): Male mice (20-25 grams body weight; n=5-7/group) were either left intact (FIG. 18A) or castrated (FIG. 18B) and treated as indicated in the figures for 13 days. Treatment of castrated mice was initiated 3 days after castration. Mice were sacrificed on day 14 after treatment initiation and seminal vesicles were removed and weighed. Seminal vesicles weights were either represented as is or were normalized to body weight and represented.
Figure 18B:
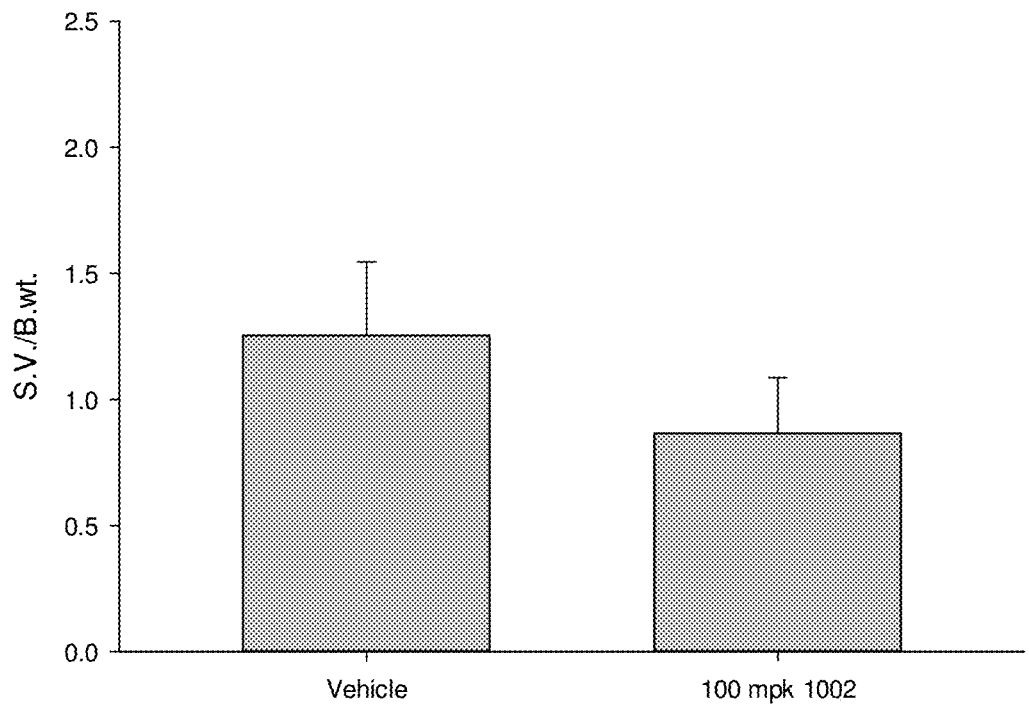

Results:

1002 significantly reduced the weight of seminal vesicles at 40 mg/kg oral daily dose in intact (FIG. 18A) and 100 mg/kg in castrated (FIG. 18B). The reduction in seminal vesicles weight, which is representative of androgen receptor (AR) antagonism, was more pronounced than that of the 20 mg/kg/day enzalutamide dose. 1002 was effective even in castrated mice, indicating that even any residual AR activity in castrated AR-target tissues was further inhibited by the potent activity of 1002 which bodes well for the abilities of SARDs of this invention to treat ADT-treated prostate cancer patients. This suggests that even though some weak partial AR agonism is observed in in vitro transactivation experiments, the predominant tone in vivo is AR antagonism. Further, in vivo activity at 40 mg/kg (40 mpk) for 1002 was a dramatic improvement over previously tested SARDs from our laboratory which typically only produced in vivo effects at 100 mg/kg or more despite comparable in vitro transcriptional inhibition potencies. This suggests the unexpected metabolic stability of 1002 translated into clinically significant oral bioavailability.

Figure 19A:
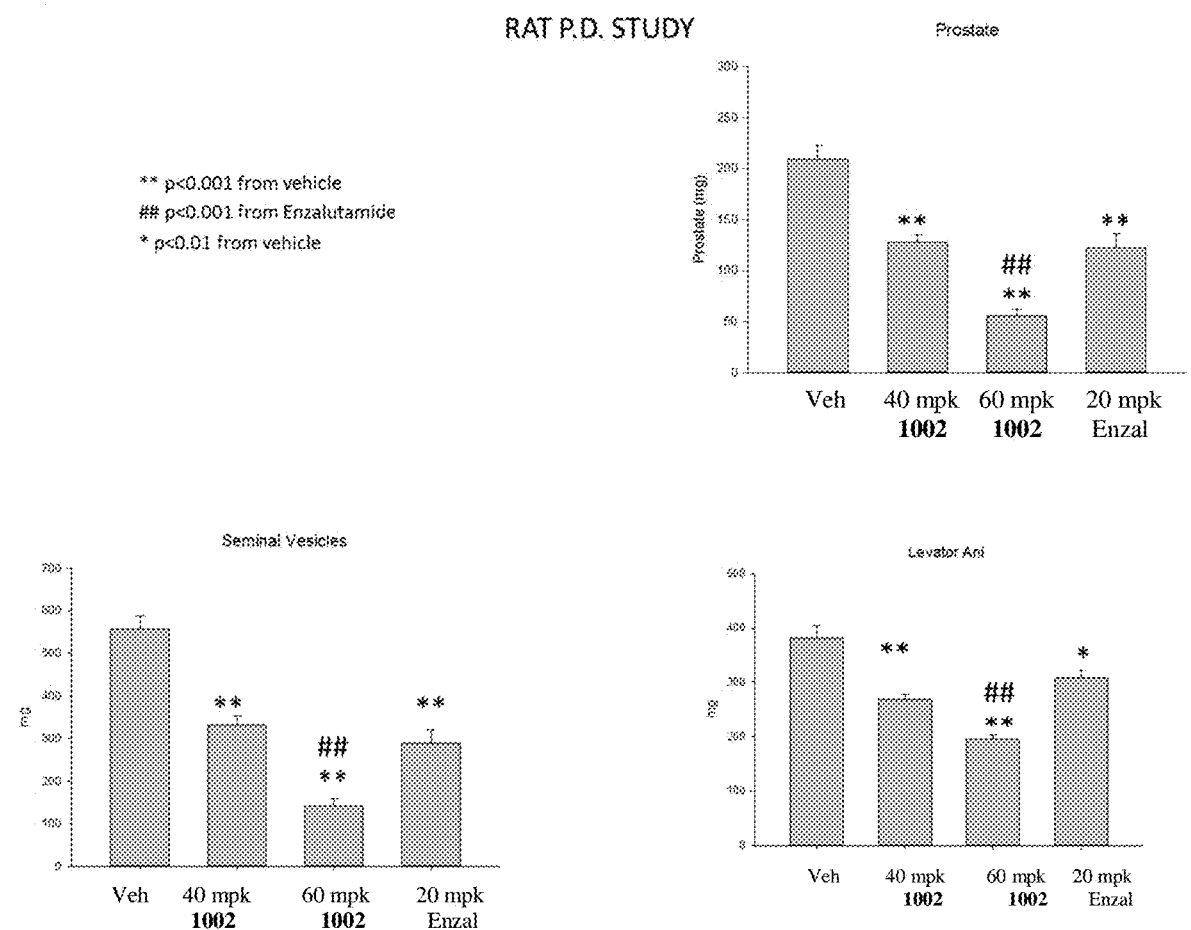
FIG. 19A and FIG. 19B: Hershberger method (rat)
Figure 19B:
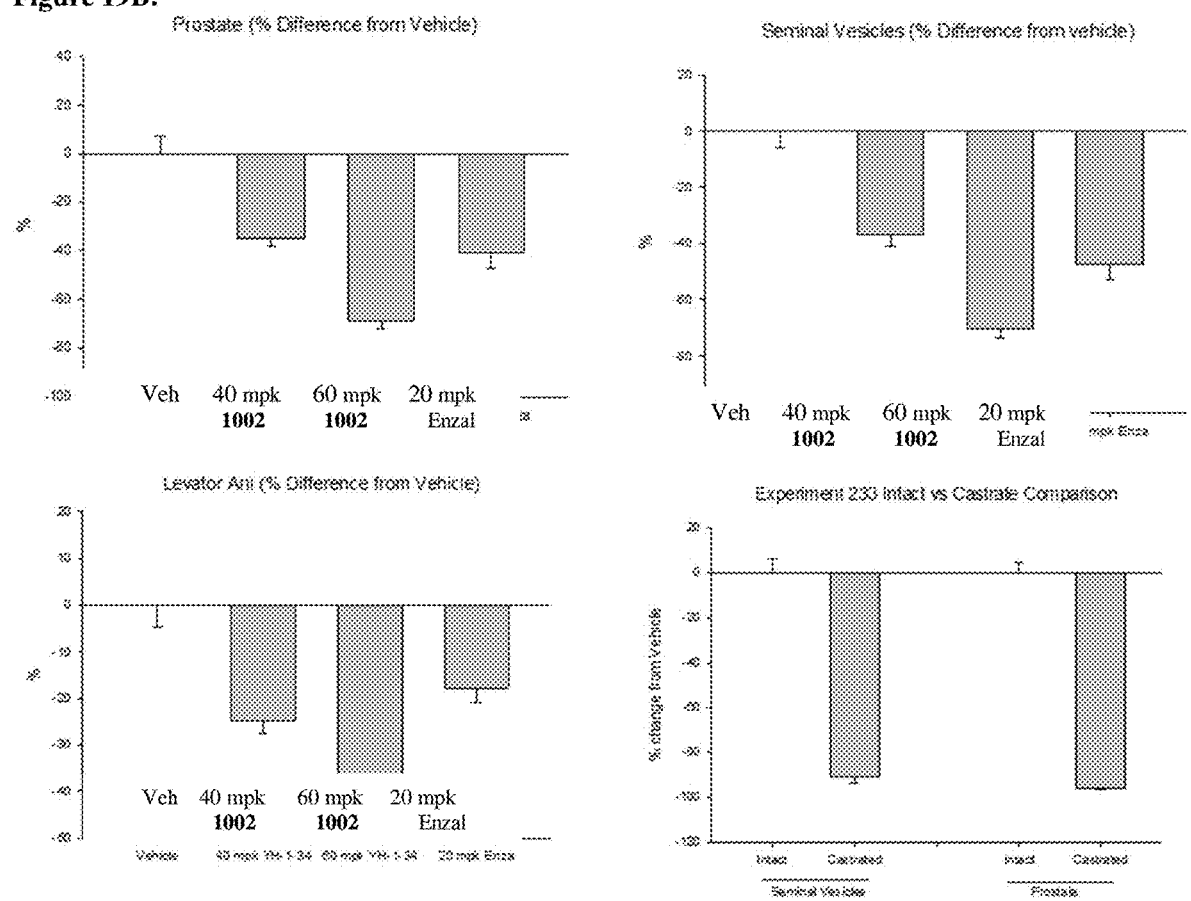

The Hershberger experiments were repeated in rats since rats are known to be more sensitive models of androgenic and anabolic activities of AR agonists and antagonists. Sprague Dawley rats (165-180 gms) body weight were treated with vehicle, 40 mpk 1002, 60 mpk 1002, or 20 mpk enzalutamide orally. After 13 days of treatment, the rats were sacrificed and the weights of prostate, seminal vesicles, and levator ani were measured. 1002 at 40 mg/kg antagonized the weights of seminal vesicles, prostate and levator ani muscle to approximately the same extent as 20 mg/kg enzalutamide and 60 mg/kg 1002 further suppressed the weights of each of these tissues to near castration levels (FIG. 19A). FIG. 19A shows the reductions in absolute organ weights in intact rats and FIG. 19B represents the same data of % inhibition relative to vehicle treated control. The bottom right panel of FIG. 19B presents the effect of castration on the weights of seminal vesicles and prostate. 1002 at 60 mg/kg reduced prostate and seminal vesicles weights by ~70% each compared to 90% and 85% reductions, respectively, produced by castration (not shown). 1002 is the first SARD with sufficient bioavailability to produce in vivo AR antagonism in excess of enzalutamide despite inferior in vitro potencies in transactivation ($IC_{50}$) and a lack of binding to LBD ($K_i$). 1002 possesses potent SARD degradation activities in vitro. Correspondingly, the unexpectedly superior in vivo antagonism of 1002 compared to enzalutamide (the IND of enzalutamide indicated that 100 mpk and 30 mpk had comparable in vivo efficacy, so the 20 mpk dose presumably was near $E_{max}$ and was barely soluble) is not explainable in terms of conventional inhibition of the AR through the LBD but rather suggests that the AR antagonism is attributable to the potent degradation of the AR which is a unique property to compounds of this invention.

See also Example 9 for multiple biophysical lines of evidence supporting NTD binding of 1002 and other SARDs of this invention. See also Example 10 for unexpected results for 1014 in a Hershberger assay, and other in vivo assays.

Example 8

In Vivo Anti-Tumor Activity Demonstrated by SARD Compound 1002 in Triple Negative Breast Cancer (TNBC) Patient Derived Xenografts (PDX)

Patient Specimen Collection and PDX Creation:

Specimens from breast cancer patients were collected with patient consent under a protocol approved by the University of Tennessee Health Science Center (UTHSC) Institutional Review Board (IRB). Briefly, specimens were collected immediately after surgery in RPMI medium containing penicillin:streptomycin and Fungizone (Thermo Fischer Scientific) and transported to the laboratory on ice. The tissues were minced finely and treated with collagenase for 2 h. The digested tissues were washed with serum-free medium and implanted as 1 $mm^3$ fragments subcutaneously in female Nod Scid Gamma (NSG) mice. Two such PDX from triple-negative patients (TNBC), HBrT-1071 and HBrT-1361, characterized as TNBC at the time of collection, were implanted in ovariectomized mice. All animal studies were conducted under the UTHSC Animal Care and Use Committee (ACUC) approved protocols. Female NSG mice (6-8 weeks old) purchased from JAX labs (Bar Harbor, Me.) were housed as five animals per cage and were allowed free access to water and commercial rodent chow (Harlan Teklad 22/5 rodent diet-8640). HBrT-1071 and HBrT-1361 were implanted (1 $mm^3$) under the mammary fat pad surgically under isofluorane anesthesia. Once tumor sizes reached 100-200 $mm^3$, the animals were randomized and treated with vehicle (polyethylene glycol-300: DMSO 85:15 ratio) or 1002 (60 mg/kg/day p.o.). Tumors were measured thrice weekly using caliper and the tumor volume was calculated using the formula length*width*width*0.5236. At the end of the experiments, animals were sacrificed, tumors were weighed and collected for further processing. Blood was collected, serum was separated, and stored in −80° C.

Figure 21A:
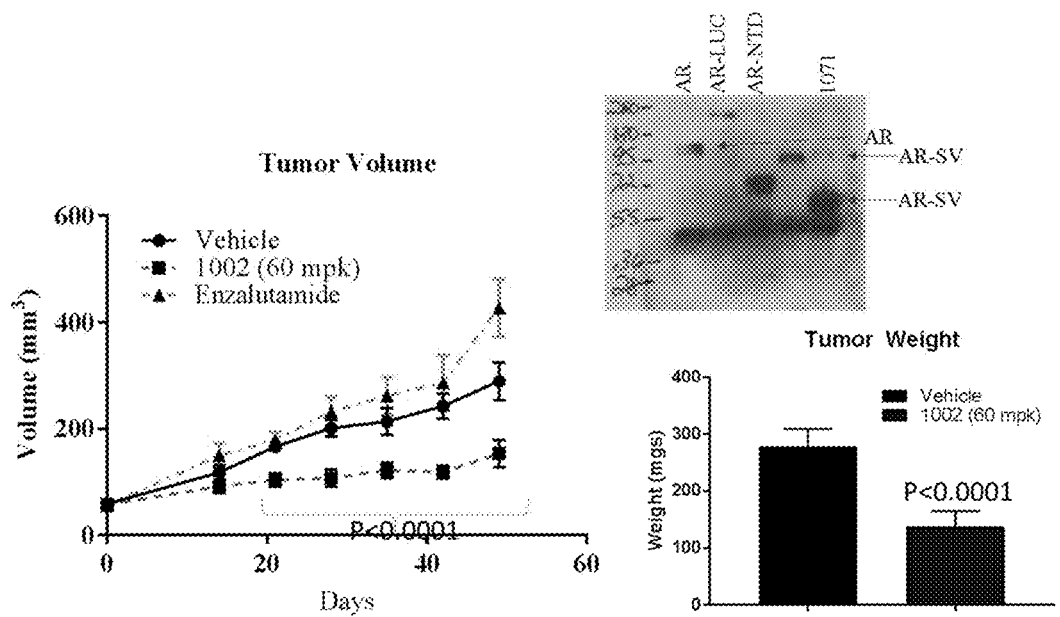

Results:

The SARD compound 1002 was able to inhibit tumor growth in two different TNBC PDX models (FIGS. 21A and 21B) whereas enzalutamide failed to inhibit tumor growth (FIG. 21A). 1002 significantly inhibited the growth of HBrt 1071 TNBC PDX with a percent tumor growth inhibition of 65%. Similarly, 1002 inhibited the tumor weight by over 50% (FIG. 21A). In contrast, tumors from enzalutamide treated animals were indistinguishable in size from vehicle treated animals, or possibled trended toward promoting tumor growth. 1002 significantly inhibited the growth of HBrt-1361 TNBC PDX with a percent tumor growth inhibition of ~50% and inhibited the tumor weight by over 40% (FIG. 21B). Further, analyses of the AR which was present in these tumors revealed high levels of AR splice variants (FIG. 21A, lane labeled 1071). This observation helps to rationalize why 1002, an NTD-binding SARD (see Example 9 below for biophysical evidence of NTD binding), was able to inhibit tumor growth whereas the LBD-dependent AR antagonist enzalutamide failed. This suggests that SARDs are able to inhibit AR splice variant dependent cancers such as TNBC and advanced prostate cancers (see Example 10), e.g. those expressing AR-V7 or other AR's lacking the LBD. Further, this is confirmation that the unexpected oral bioavailability of 1002 and other SARDs of this invention, e.g. 1014 and 1010, allowed serum and tumor (see also Example 10) levels following oral administration to be sufficient for treatment of advanced and refractory AR-dependent cancers.

Example 9

SARDs Bind to AF-1 Region of the N-Terminal Domain (NTD) of the Androgen Receptor Nuclear Magnetic Resonance (NMR):

AF-1 and various fragments of AF-1 were cloned in pGex4t. 1 and pGex6p. 1 vectors. To purify proteins, large scale Luria broth cultures were induced with 1 mM isopropyl 3-D-1-thiogalactopyranoside (IPTG) when the O.D. reached 0.6 and incubated at 25° C. for 6 h. Cells were harvested and lysed in a lysis buffer (50 mM Tris pH 7.5, 25-250 mM NaCl, DNase, protease inhibitors, glycerol, EGTA, DTT, and sucrose). Protein lysates were purified using glutathione sepharose beads by incubating overnight at 4° C. with gentle rocking and the purified protein was eluted with elution buffer (lysis buffer without DNase) containing 50 mM reduced glutathione. Purified proteins were concentrated using Amicon or GE protein concentrators. In cases where GST needed to be cleaved, PreScission Protease (GE Life Sciences) was used to cleave the GST. The proteins were further purified using FPLC (GE AKTA FPLC) with gel filtration (Superdex75 10/300 GL) and ion exchange (HiPrep Q FF 16/10) columns. Compounds alone or in combination with purified protein were run in $^1$H NMR (Bruker 400) in a total volume of 500 μL with 5 mM protein and 200-500 mM small molecule (made in deuterated DMSO (DMSO-d$_6$)) in 20 mM phosphate buffer made in 100% deuterated water.

NMR data were collected using a Bruker AVANCE III 400 MHz NMR spectrometer (Bruker BioSpin Co. Billerica, Mass. USA) equipped with a BBO 5 mm NMR probe, and TopSpin 3.0 software. $^1$H proton NMR and Saturation-Transfer Difference (STD) experiments were acquired using standard pulse sequences in the TopSpin library. Spectral width was set to 16 ppm with H$_2$O peak at center. 32K time domain (TD) complex data points and 256 scans were used for $^1$H proton NMR and 1024 scans for STD acquisition. For STD, on- and off-resonance [signals] were collected using interleaved method. Irradiation frequencies for on- and off-resonance were set at 0.8 ppm and −20 ppm, respectively. STD was acquired on a sample with ligand compound alone using identical settings to make sure the STD signals originated from protein in the protein-compound complex sample. Data were collected at room temperature. Chemical shift was referenced according to H$_2$O peak at 4.70 ppm.

Results:

$^1$H NMR has been used in high-throughput screens to detect the binding of small molecules less than 500 Da to large proteins greater than 5 Kda. As opposed to other biophysical methods, it is easier to use one dimension NMR to observe changes in line-width or line broadening as a high-throughput method to identify the binding of the molecules to proteins and then use Water ligand-observed spectroscopy (WaterLOGSY) or Saturation-Transfer Difference (STD) NMR as confirmatory methodologies. These experiments are based on the fact that NMR observables such as linewidths and NOEs vary dramatically between small molecules and large molecules. The decreased rotational correlation times upon binding of a small molecule ligand to a heavy target molecule produces an atypical heavy molecule NMR result characterized by broadening and weakening of ligand peaks in $^1$H NMR and negative NOE peaks in the waterLOGSY as compared to the free state. In the absence of any affinity, the small molecule NMR result is obtained (sharp peaks in $^1$H NMR and positive NOEs) even in the presence of target protein. This distinction provides the basis for NMR screening experiments.

Figure 22:
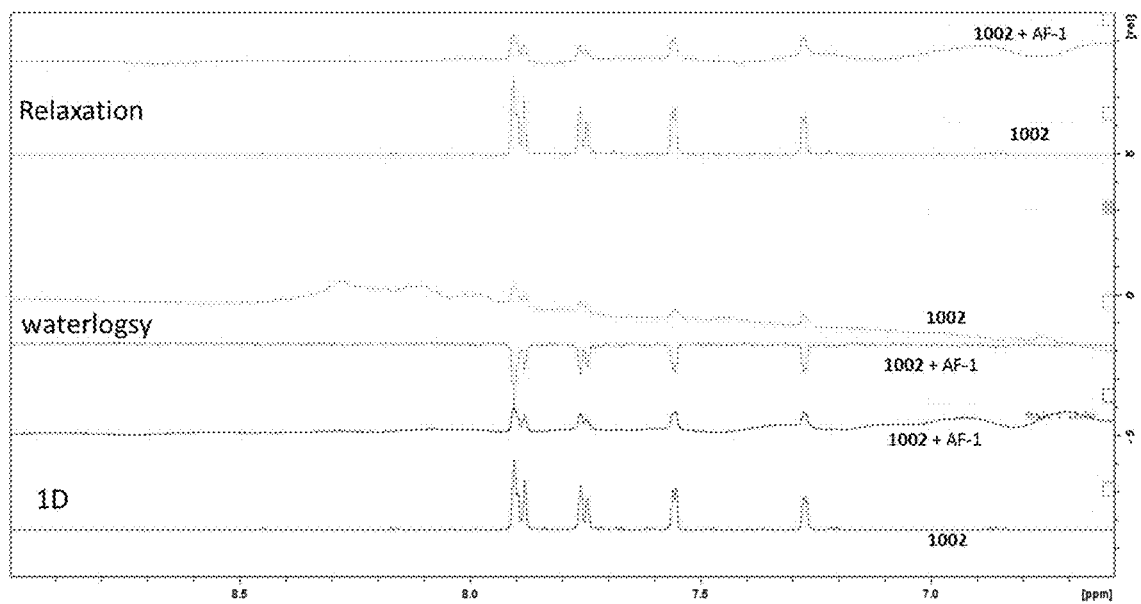
FIG. 22: depicts binding of 1002 to AF-1 region of the N-terminal domain (NTD) of the androgen receptor. 1D and waterLogsy NMR experiments demonstrate that 1002 bandwidth are broadened in the presence of a peptide derived from the AF-1 region of the NTD. Moreover, relaxation and waterLogsy demonstrate that the tumbling rate in solution for 1002 is slowed upon addition of AF-1, strongly suggestive of 1002 binding to AF-1 region as its targeted protein interaction.

Using these principles, $^1$H NMR was utilized to confirm the binding of 1002 to the AF-1 region. 1002 (500 mM) was dissolved in deuterated DMSO (DMSO-d$_6$) and was incubated alone or mixed with 5 mM AF-1 and the binding of the molecules to the protein was determined by NMR. While 1002 alone exhibited sharp peaks revealing the ligand present in the free state, 1002 in combination with AF-1 provided broad, diffused, and shorter ligand peaks revealing that 1002 has affinity for AF-1 (FIG. 22). To further confirm the 1D NMR results, we performed WaterLOGSY with 1002 alone or in combination with AF-1. While the 1002 alone gave a flattened positive signal, 1002 in combination with AF-1 provided a negative signal, characteristic of binding to the protein (FIG. 22). These results provide evidence that 1002 binds to AF-1 in the NTD of AR, explaining how a molecule that does not bind the LBD of AR (Table 1) can inhibit the AR in vitro and in vivo.

Steady State Fluorescence:

Recombinant histidine tagged AR-NTD (amino acids 1-559) and AR-AF1 (amino acids 141-486) were purified as previously described. The steady-fluorescence spectrum for the proteins (1 μM) alone or after titration with increasing concentrations of 1002 (1 μM, 2 μM, 5 μM, 10 μM, 25 μM, & 50 μM) was measured after excitation at 278 nm on a Shimadzu Fluorescence spectrophotometer. Proteins were preincubated on ice for 30 minutes with 1002. The results represent three independent experiments (n-3) measured in duplicate.

Figures 27A, 27B:
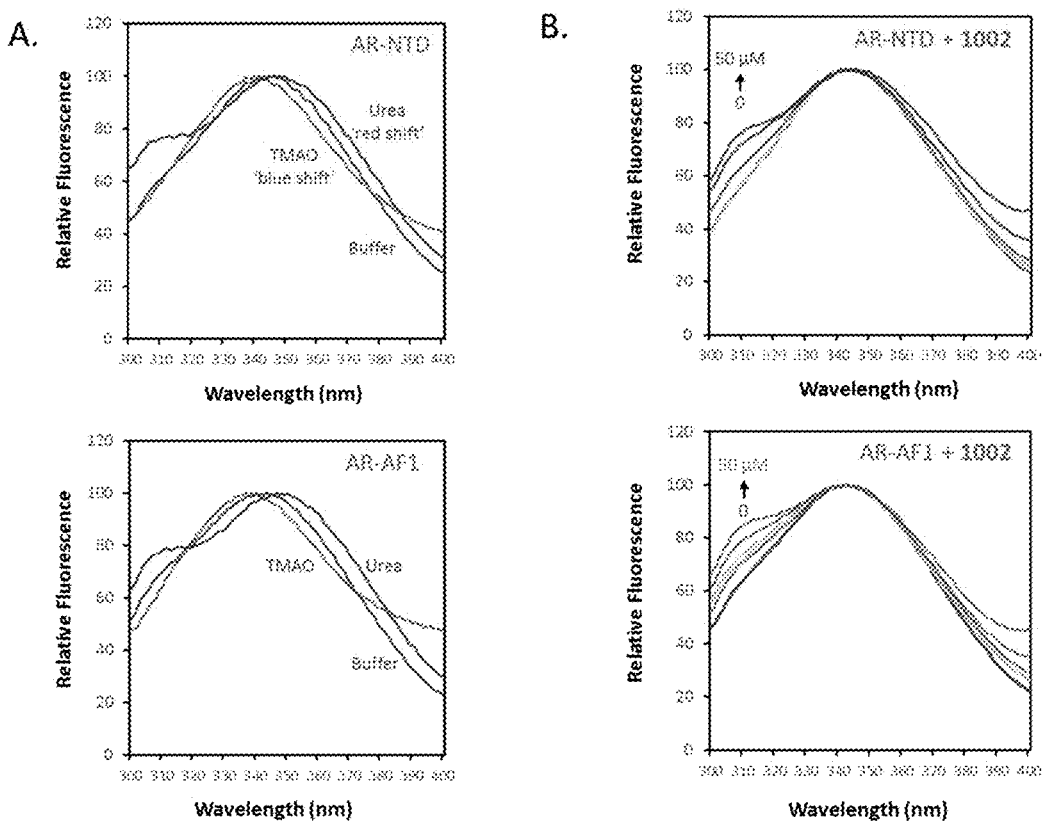
FIGS. 27A-27D: depict steady state fluorescence studies demonstrating interactions between SARDs 1002, 1010, and 36 (indole), and N-terminal fragments of the AR such AR-NTD (amino acids 1-559) and AR-AF1 (amino acids 141-486).

Results:

The pyrazole SARD 1002 showed a dramatic increase in the fluorescence signal in the region seen for tyrosine emission (FIG. 27B, 307 nm). Normally, the tyrosine signal is not seen due to energy transfer to tryptophan residues in folded/partially folded polypeptides. The increase in the tyrosine signal is similar to what is seen in unfolded/ denatured AR-NTD or AR-AF1, e.g., upon addition of urea (FIG. 27A). However, there is no corresponding 'red shift' (increase in wavelength) in the tryptophan signal (compare FIGS. 27A and 27B, in urea km 344 nm to 347 nm). 1002 may unfold the receptor polypeptides (resulting in tyrosine emission), but shield the tryptophan residues.

Figure 27C:
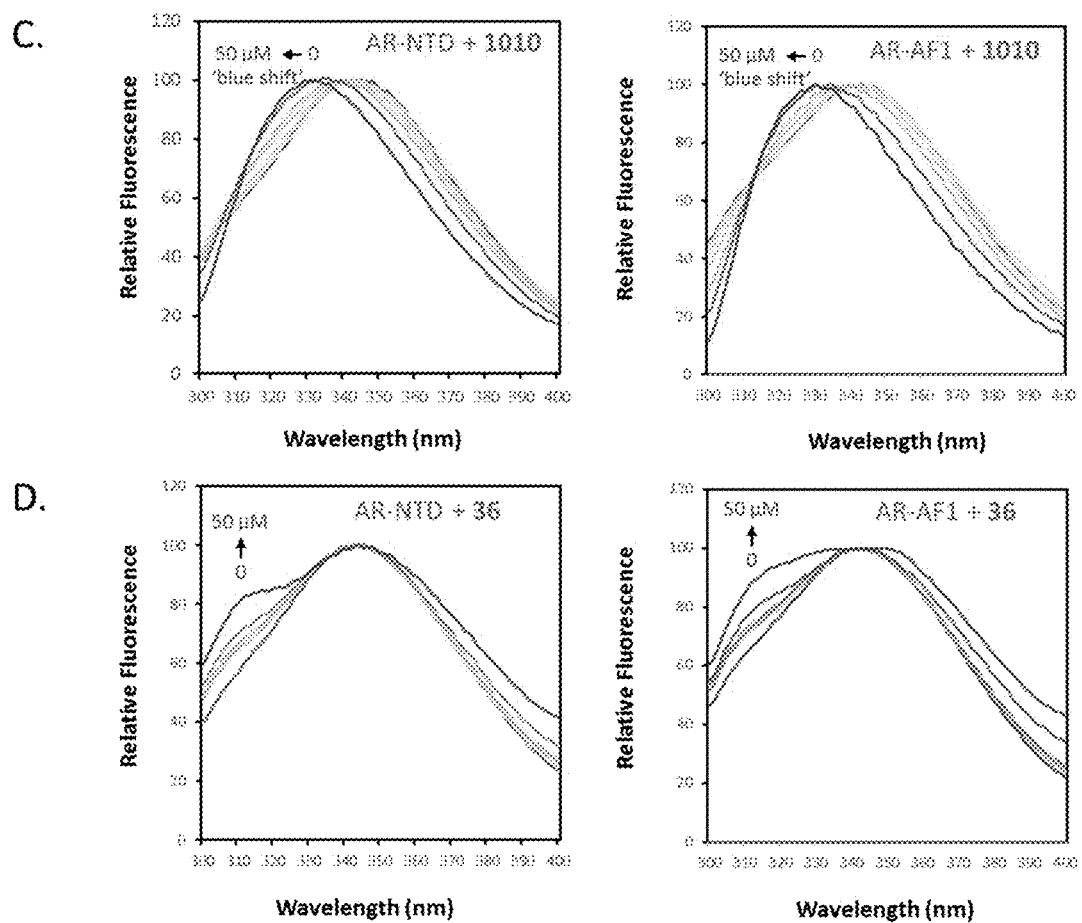
Figure 27D:
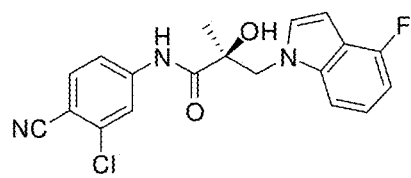

For the pyrrole SARD 1010, some evidence for quenching was observed, but the concentration dependence was poor. However, more strikingly there was a consistent and dramatic 'blue shift' (toward smaller wavelengths), which was consistent with the folded form of AR-NTD/AF (i.e. TMAO spectrum in FIG. 27C, $\lambda_{max}$ 344 nm to 340 nm). On the basis of data so far it seems 1010 may stabilize the structure of the AR polypeptides. The data with the indole SARD 36 (FIG. 27D) was similar to what was seen with 1002, but the changes in fluorescence were weaker. In each case, an interaction was observed between the SARD and the AR-1 or NTD. Though the perturbation of fluorescence polarization (FP) was not identical, these similar results across multiple templates of SARDs suggest that the interaction with the N-terminus of the androgen receptor is a conserved feature for the SARDs of this invention. Further, 1002 lacks an interaction with the LBD yet retains potent AR antagonism and SARD activity.

Example 10

Metabolic Stability of Pyrazoles Such as 1014 and 1002 Reveals the Therapeutic Potential of SARDs In Vivo In Vitro Characteristics:

Transactivation (IC$_{50}$):

As reported in Table 1 using the method of Example 3, 1014 is a potent inhibitor of the AR with an IC$_{50}$ value of 205 nM which is similar to 1002 (199 nM).

LBD Binding (K$_i$):

As reported in Table 1 using the method of Example 4, 1014 binds to the LBD of the AR with a K$_i$ value of 512 nM, whereas 1002 does not bind to the LBD.

SARD Activity:

As reported in Table 1 using the methods of Example 5, 1014 and 1002 are capable of potently degrading full length and splice variant androgen receptors.

LNCaP-Enzalutamide Resistant (LNCaP-EnzR) Cells MR49F Growth Assay:

Cells were plated at 10,000 cells/well in RPMI+1% csFBS without phenol red medium in 96 well plates. Cells were treated in the indicated medium with a dose response of the SARDs. At the end of three days, medium was changed and the cells were re-treated. At the end of 6 days, the live cells were measured by Cell-Titer-Glo (Promega) assay.

Figure 23:
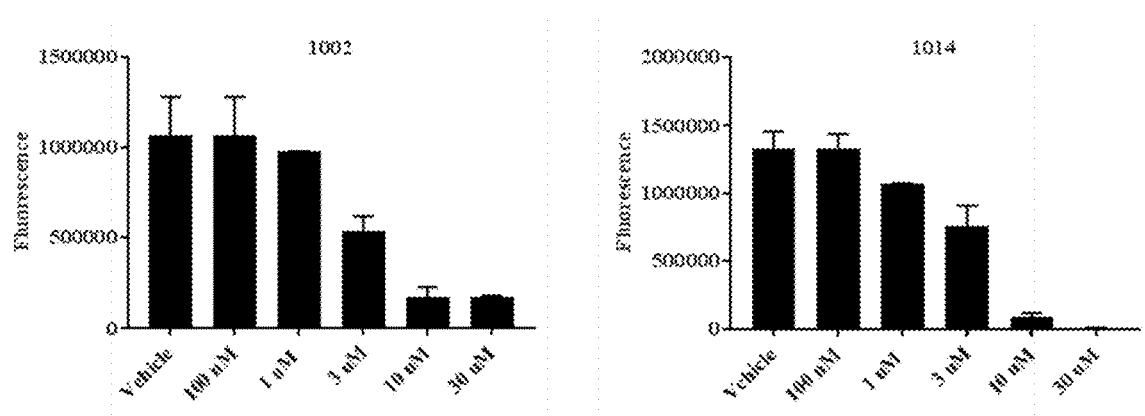
FIG. 23: depicts a LNCaP-enzalutamide resistant (LNCaP-EnzR) cells MR49F growth assay using 1002 and 1014. 1002 and 1014 inhibit the growth of LNCaP-EnzR cells in the low micromolar range.

Results:

1002 and 1014 demonstrated comparable growth inhibition of an enzalutamide resistant variation of the LNCaP (LNCaP-EnzR) cell line which bears the double mutant F876L/T877A, conferring resistance to enzalutamide. 1002 and 1014 both had $IC_{50}$ values of ~3 µM and almost complete inhibition at 10 µM (FIG. 23), suggesting that either SARD could be beneficial for enzalutamide resistant prostate cancer patients if these levels could be achieved in the tumor. (see Table 4 below)

Liver Microsome Metabolism Study:

Materials:

Microsomes were purchased from Xenotech, LLC. Solution 'A' and 'B' (Cat #451220, and 451200, respectively) for NADPH regenerating system (NRS) solution were obtained from Corning Life Sciences. Verapamil, genistein, UDPGA, alamethicin and magnesium chloride were purchased from Sigma-Aldrich. Saccharolactone was obtained from Santa Cruz Biotechnology.

Method: Phase I

Test compound stock solutions were prepared at 10 mM in DMSO. They were diluted to a concentration of 50 µM in 50% acetonitrile (ACN)/$H_2O$ resulting in a working stock solution of 100×. Liver microsomes were utilized at a final concentration of 1.0 mg/mL of protein. Duplicate wells were used for each time point (0, 5, 10, 30, and 60 minutes). Reactions were carried out at 37° C. in a shaking water bath, and the final concentration of solvent was kept constant at 0.5%. At each time point, 100 µL of reaction was removed and added to a sample well containing 100 µL of ice-cold, 100% ACN (plus internal standard), to stop the reaction. The final volume for each reaction was 200 µL, composed of: 66 µL of 0.2 M $KPO_4$ buffer, (pH 7.4); 50 µL of NRS solution; and 10 µL of microsomes (20 mg/mL stock).

The NRS is a solution of glucose-6-phosphate dehydrogenase, $NADP^+$, $MgCl_2$, and glucose-6-phosphate, prepared per manufacturer's instructions. Each 5.0 mL stock of NRS solution contains 3.8 mL $H_2O$, 1.0 mL solution "A", and 0.2 mL solution "B". The reaction from the positive control wells (verapamil, 0.5 µM) were stopped with ice cold acetonitrile containing internal standard.

Phase I and II

Reaction conditions were followed similarly as described above. Additional cofactors were also included in each reaction. UDPGA was added at a final concentration of 5.0 mM. Saccharolactone (β-glucuronidase inhibitor) and alamethicin (pore forming peptide) were added to each reaction at a final concentration of 5.0 mM and 50 µg/mL, respectively. Each 200 µL of microsomal reaction was comprised of 65 µL of 0.2 M $KPO_4$ (pH 7.4), 50 µL of NRS mixture, 66 µL of UDPGA (15 Mm stock); 5.0 µL of saccharolactone (200 mM stock); 0.5 µL of alamethicin (20 mg/mL); 0.6 µL of $MgCl_2$ (1 M stock), and 10 µL of microsomes (20 mg/mL stock). The reaction from the positive control wells (genistein, 2.0 µM) was stopped with ice cold acetonitrile containing internal standard.

Samples were centrifuged at 3,000 rpm for 10 minutes to remove debris and precipitated protein. Approximately 150 µL of supernatant was subsequently transferred to a new sample block for analysis.

Data Analysis

For half-life determination and clearance, data was fitted using GraphPad Prism with a non-linear regression equation, and one phase exponential decay.

Results:

1014 was compared to other compounds, including 1002 in liver microsome metabolism studies. Interestingly, while 1002 showed a half-life around 1 h in vitro, 1014 had a half-life of infinity in the same test, i.e., after 120 min of incubation over 50% of the compound still remained in the reaction (Table 3). As seen in Table 3, the pyrazoles 1002, 1014, and 1022 (see also Table 1 for 1023 and 1024) demonstrated much improved in vitro metabolic stabilities compared to indole (11, 34, 36) and indoline (103) based compounds (and the pyrrole 1010) (Table 3) while retaining SARD activity (Table 1). This suggested that significant in vivo bioavailabilities may be possible for 1002 and 1014.

TABLE 3

| | Liver microsomes MLM/RLM | |
|---|---|---|
| | $t_{1/2}$ (min) | $CL_{int}$ (µl/min/mg) |
| 1002 | 77.96 | 0.89 |
| 1014 | infinity | ~0 |
| 96 | 54.44 | 12.73 |
| (S)-N-(4-Cyano-3-(trifluoromethyl)phenyl)-2-hydroxy-2-methyl-3-(4-(trifluoromethyl)-1H-indazol-1-yl)propanamide | | |
| 1010 | 17.93 | 38.66 |
| 36 | 11.77 | 58.8 |
| (S)-N-(3-Chloro-4-cyanophenyl)-3-(4-fluoro-1H-indol-1-yl)-2-hydroxy-2-methylpropanamide | | |
| 34 | 15.50 | 58.87 |
| (S)-N-(3-Chloro-4-cyanophenyl)-3-(5-fluoro-6-phenyl-1H-indol-1-yl)-2-hydroxy-2-methylpropanamide | | |
| 11 | 14.35 | 48.30 |
| (S)-N-(4-Cyano-3-(trifluoromethyl)phenyl)-3-(5-fluoro-1H-indol-1-yl)-2-hydroxy-2-methylpropanamide | | |
| 103 | 15 | 46.22 |
| (S)-N-(3-Chloro-4-cyanophenyl)-3-(4-fluoroindolin-1-yl)-2-hydroxy-2-methylpropanamide | | |
| 1022 | 58.06 | 11.94 |

In Vivo Characteristics:

1014 Drug Concentrations in Serum and Tumor in a Xenograft Experiment:

Nude mice implanted with 22RV1 cells subcutaneously were randomized when the tumors reached between 100 and 200 $mm^3$. The mice were treated with vehicle (20:80 water: PEG-400) or 60 mg/kg/day 1014 (or indicated doses of other SARDs) in vehicle for 21 days. At the end of 21 days, the mice were sacrificed and blood and tumors were collected for further analysis. Measurement of drug concentration in animals treated with 1014 demonstrated a significant accumulation of the drug in serum (20.1 µM) and tumor (35.6 µM) (Table 4 and FIG. 24) compared to other molecules tested in parallel in the same experiment. These in vivo levels for 1014, even in view of structurally similar pyrazoles 1002 and 1012, was unexpected. Further, these levels help to explain the efficacy in LNCaP-EnzR xenografts (see FIG. 26 and its description below). Although 22RV1 tumors were not susceptible to SARDs in this particular experiment, likely due to androgen independent growth, this result suggests that androgen-dependent tumors, e.g., LNCaP-EnzR, would be susceptible. Another observation from these data is that tumor concentrations were in excess of serum concentrations, suggesting accumulation of drug in the tumor. The results are shown in Table 4 and FIG. 24.

TABLE 4

| Xenograft dose (mg/kg) | Tumor concentration (nM) At sacrifice (8 hrs) | Xenograft PK Serum concentration (nM) | |
|---|---|---|---|
| | | 2 hrs | 8 hrs |
| 1002  60 | 15,725 | 3,560 | 3,620 |
| 11    100 | 854 | 365 | 338 |
| 1012  60 | 6,655 | 2,114 | 1,914 |
| 1014  60 | 35,638 | 4,469 | 20,119 |
| 96    100 | 4,458 | 1,207 | 2,563 |
| 1010  100 | 17,683 | 862 | 4,173 |
| 103   100 | 1,748 | 380 | 1,776 |
| 36    100 | 7,128 | 570 | 4,142 |
| 34    100 | 2,948 | 261 | 965 |

Hershberger Assay:

Intact C57BL/6 male mice (6-8 weeks old) were randomized based on body weight and treated with various compounds indicated in FIG. 25 for 14 days. At the end of 14 days, the mice were sacrificed and seminal vesicles were weighed. 1014 demonstrated the best inhibition of seminal vesicles weight compared to other compounds, following by 1002, suggesting that these orally administered SARDs were present in levels sufficient to antagonize the AR in androgen-dependent tissues of intact animals. The indoles 34 and 36, pyrrole 1010, and the pyrazole 1012 did not exhibit strong AR antagonism in vivo in this assay.

Figure 26:
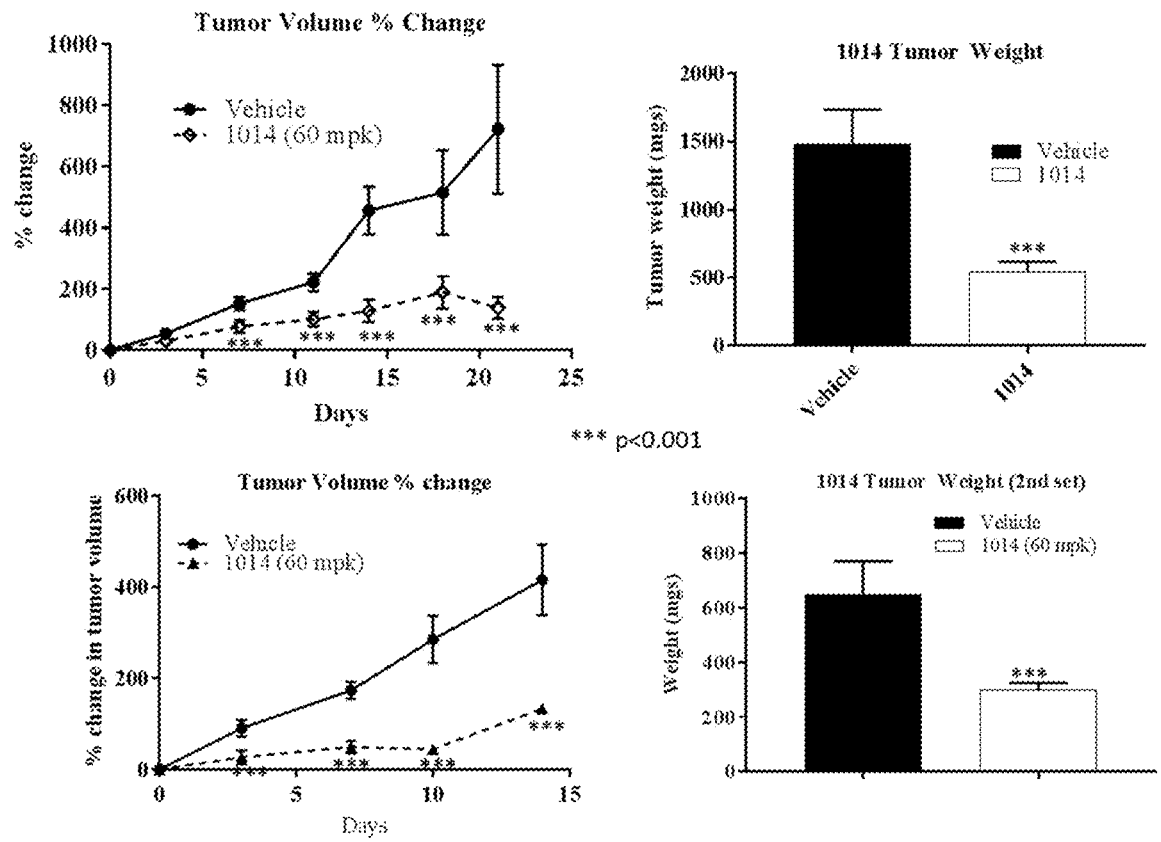
FIG. 26: depicts tumor growth inhibition of LNCaP-enzalutamide-resistant (LNCaP-EnzR) xenografts treated with 1014 at 60 mg/kg administered orally. Two different experiments (Experiment 1 and Experiment 2) are shown.

LNCaP-Enzalutamide-Resistant (LNCaP-EnzR) Xenograft:

LNCaP-EnzR cells MR49F in RPMI+10% FBS were mixed with Matrigel (BD Biosciences) (1:1) and injected subcutaneously in NOD SCID Gamma (NSG) mice (100 µL). Once the tumors reached 100-200 mm$^3$, the animals were randomized and were treated with vehicle (20:80 water:PEG-300) or 1014 (60 mg/kg/day) in vehicle. Tumor volume was measured twice weekly. At the end of the study, animals were sacrificed, tumors isolated, weighed, and stored for further analysis. The experiment was performed twice with two different batches of cells and the results are shown in FIG. 26. Results: In two separate experiments, 1014 was able attain high efficacy tumor growth inhibition, reducing tumor volumes by approximately 60-70% compared to vehicle treated animals. These results suggest that 1014 and other SARDs of this invention administered orally were capable of therapeutic efficacy in enzalutamide resistant (i.e., advanced and refractory) prostate cancers.

Conclusion:

All these results indicate that 1014 has unexpected properties due to its slow metabolism and tumor accumulation. Although, 1014 structurally is comparable to 1002, only differing slightly in the substitution with a CF$_3$ in the third position of the pyrazole ring (vs. 4-fluoro for 1002), it is extremely resistant to metabolism by liver microsomes and thereby has significant accumulation in serum, androgen dependent organs, and in tumors which is unexpected in view of other SARDs tested and in the prior art. This allowed for unexpected in vivo efficacies following oral administration, such as pharmacodynamics (Hershberger assay demonstrated most efficacious seminal vesicles weight effect seen with a SARD) and xenograft tumor growth inhibition (LNCaP-EnzR xenograft), that would not have been possible with our earlier reported SARD templates such as 11, 100, and 17, or other SARDs known in the prior art.

Example 11

SARDs Antagonize F876L

Figure 29A:
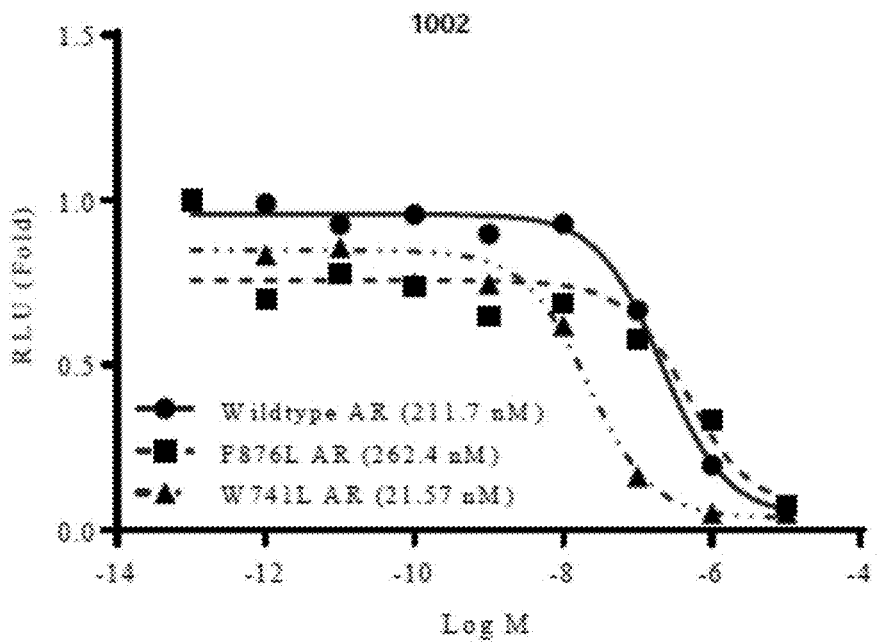
FIGS. 29A-29C: depict that SARDs such as 1002 can antagonize F876L AR at doses comparable to the wildtype AR and W741L AR at more potent doses than wildtype AR.
Figure 29B:
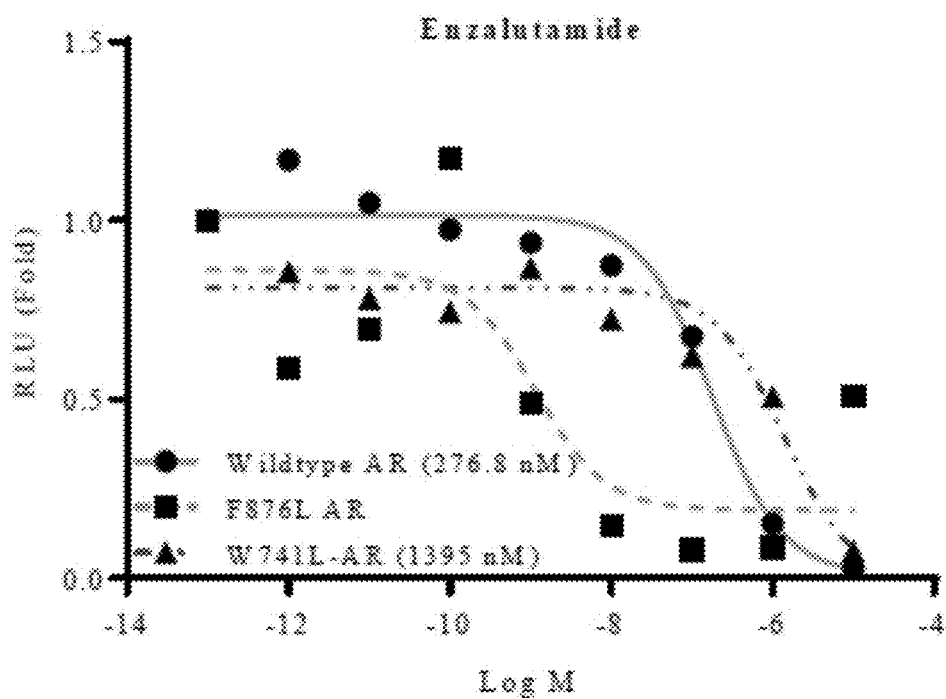
Figure 29C:
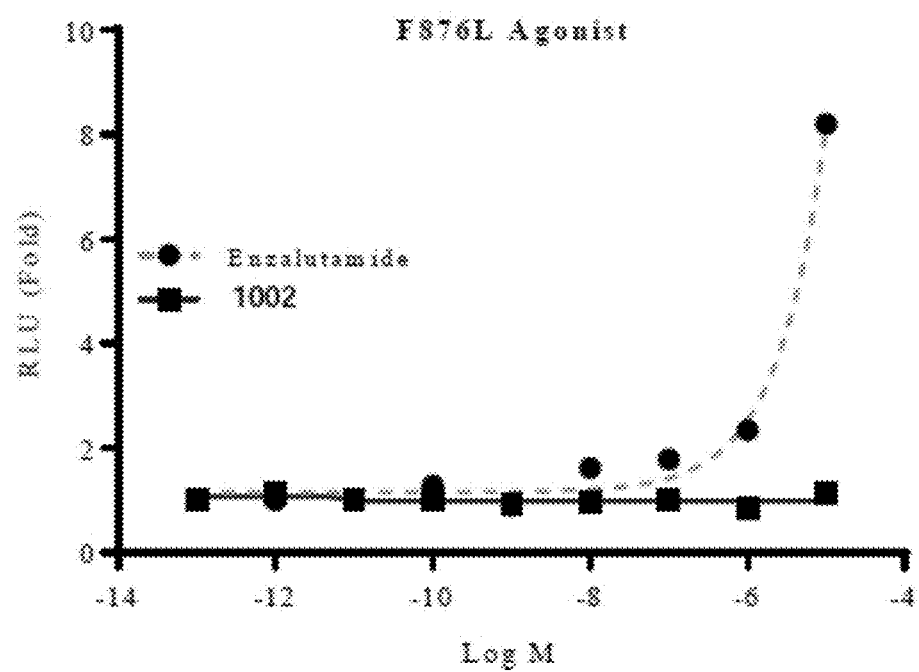
Figure 30A:
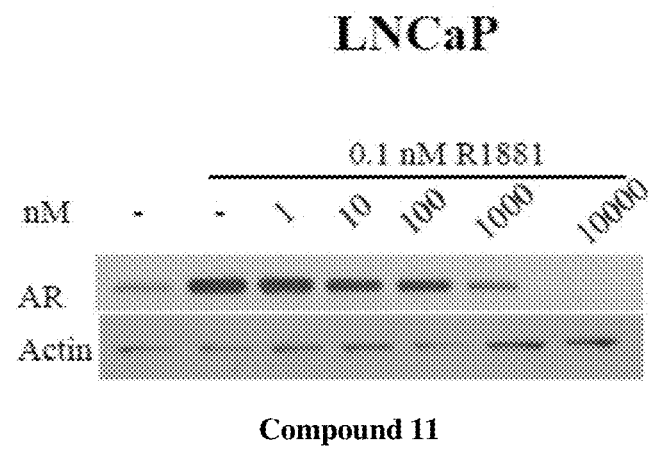
Figure 30B:
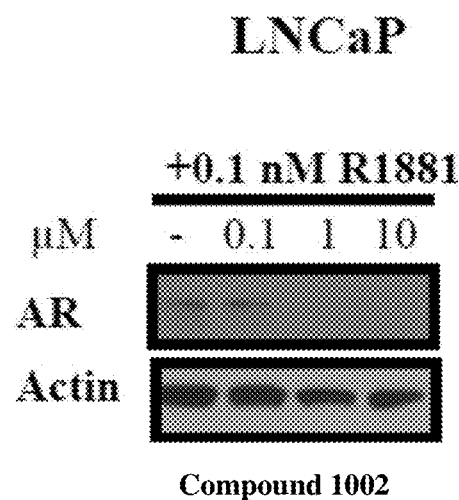
Figure 30C:
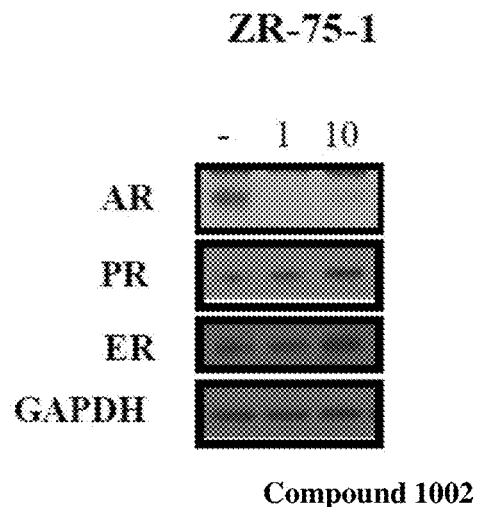
Figure 30D:
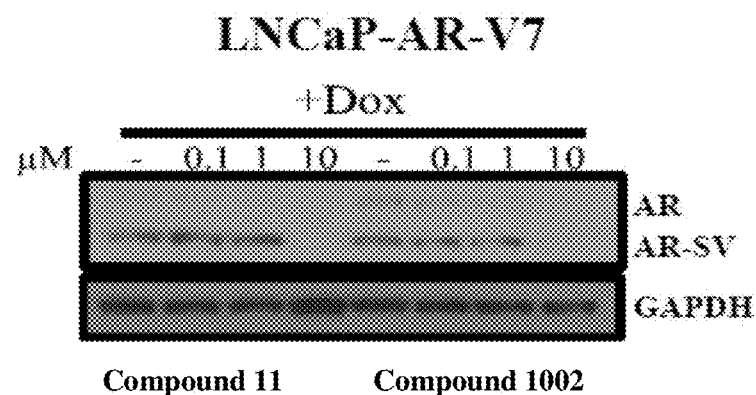
Figure 30E:
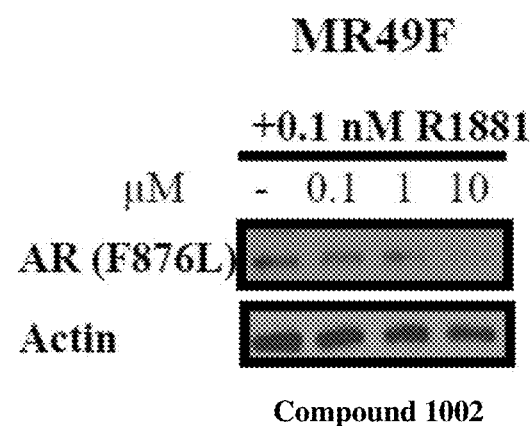
FIG. 30E demonstrates that SARDs of this invention can degrade F876L AR.
Figure 31A:
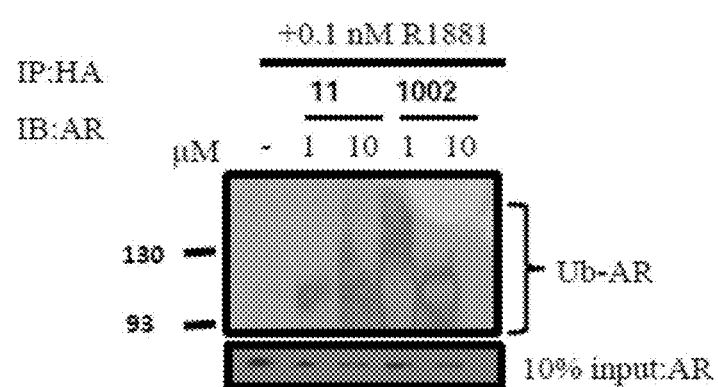
FIGS. 31A and 31B: SARDs promote ubiquitination and require the proteasome to degrade the AR.
Figure 31B:
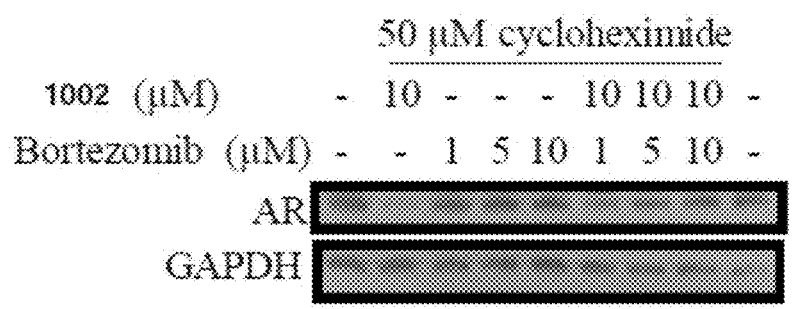

FIGS. 29A-29C illustrate that SARDs antagonized F876L AR at doses comparable to the wildtype AR and do not have any intrinsic agonist activity in F876L, showing their ability to overcome enzalutamide resistance. In FIGS. 29A-29C, compound 1002 was able to inhibit the transcriptional activation of wtAR and F876L (enzalutamide resistance) and W741L (bicalutamide resistance). Enzalutamide behaved similarly, however enzalutamide acted as an agonist at higher levels of treatment of F876L. This demonstrated the ability of SARDs to overcome antagonist switch mechanisms of resistance which are prevalent in CPRC. Further, Example 10 shows the ability of SARDs to overcome enzalutamide resistance with regard to cellular growth and with regard to xenograft growth.

Example 12

Binding to AR-NTD to Degrade

Figure 32:
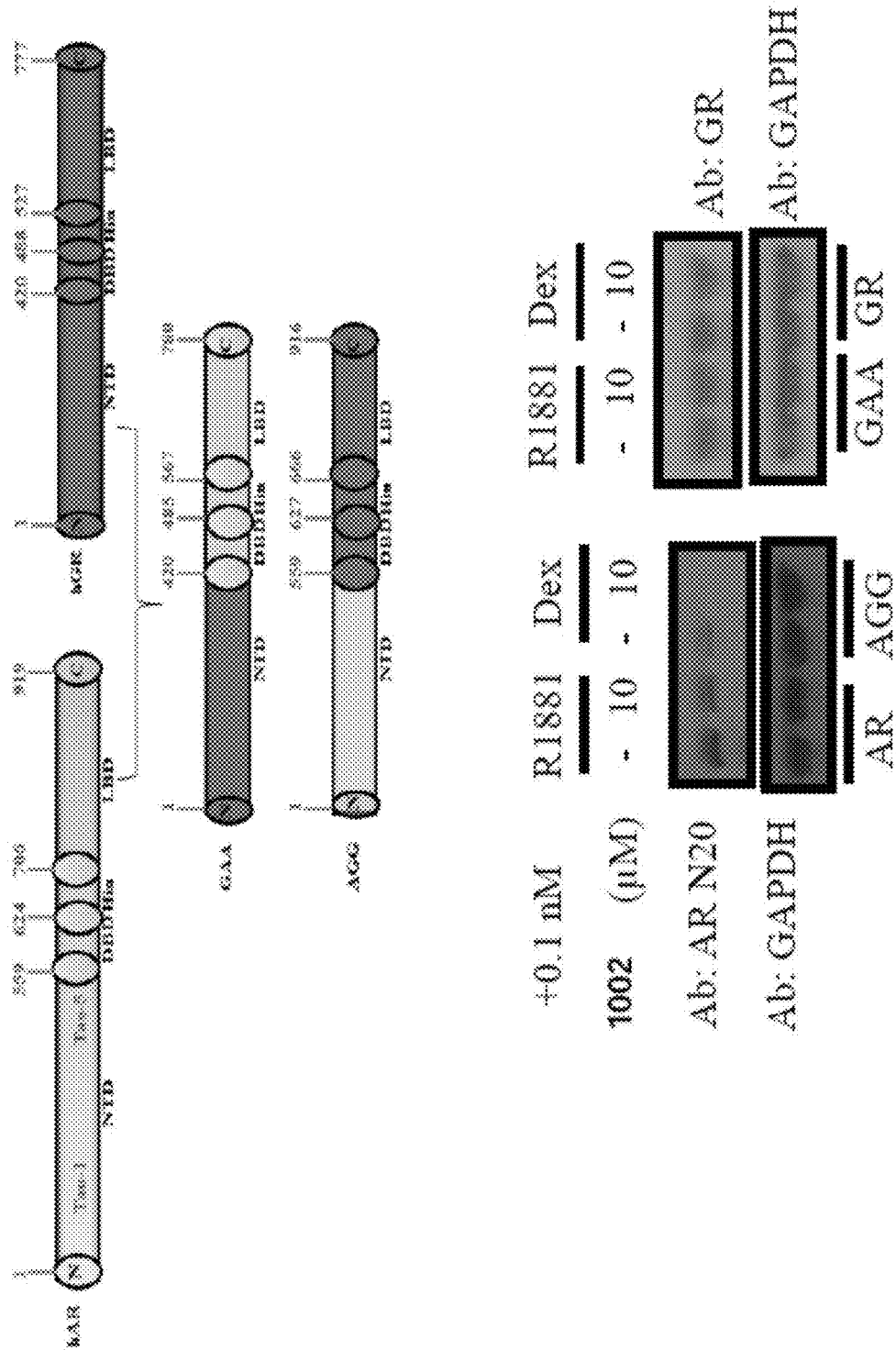
FIG. 32: SARDs require AR-NTD containing constructs (e.g. AR or AGG chimera) to degrade the AR whereas SARDs were unable to degrade GR-NTD containing constructs (GR and GAA chimera).
Figure 33:
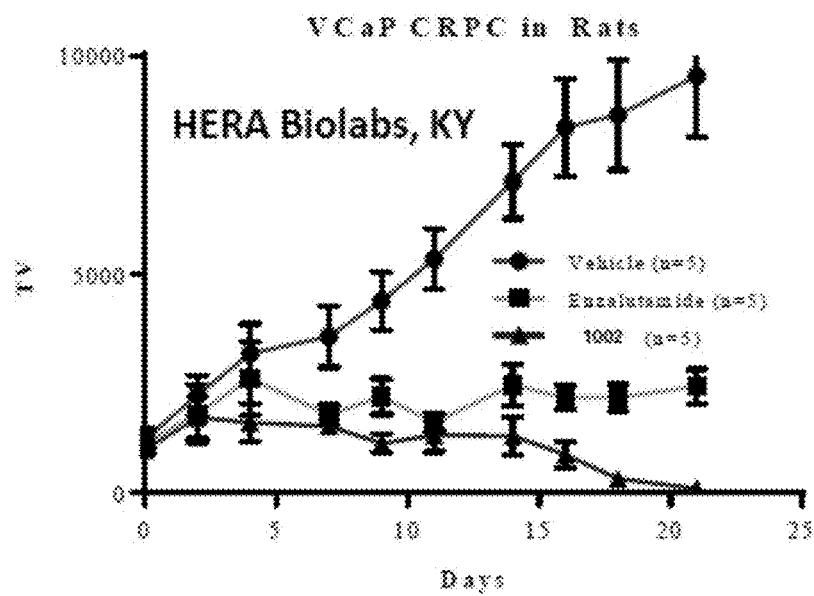
FIG. 33: SARDs inhibit the growth of enzalutamide-resistant VCaP CPRC xenografts in rats. The graph of tumor volume (TV) over time of VCaP CRPC in rats showed the ability of compound 1002 in rats (there is less metabolism of compound 1002 in rats than mice) to completely resolve VCaP xenografts (tumor volumes plotted as triangles) within 21 days, whereas enzalutamide only caused partial regression (tumor volumes plotted as squares). VCaP is an androgen-dependent CRPC cell line that is partially sensitive to enzalutamide, but fully sensitive to SARDs of this invention. Cai et al. (PM ID: 21868758) have characterized VCaP cells as expressing high levels of androgen biosynthesis enzymes CYP17A1 and AKR1C3 resulting in high intratumoral androgen levels and reactivation of the AR-axis. This model demonstrated that in the absence of pharmacokinetic barriers (i.e., high levels of metabolism and/or poor absorption and distribution in mice tumor xenograft models), that SARDs can lead to the complete resolution of castration resistant prostate cancers.
Figure 34A:
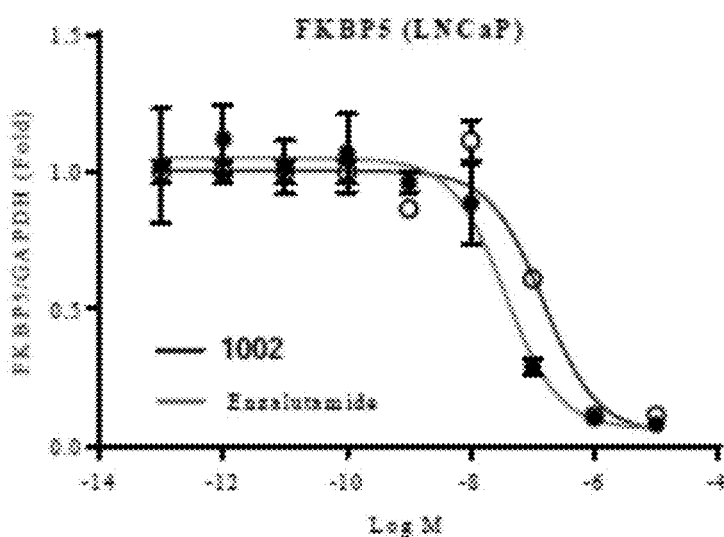
FIGS. 34A-34D: SARDs inhibit AR and Enz-R-AR function and cell growth.
Figure 34B:
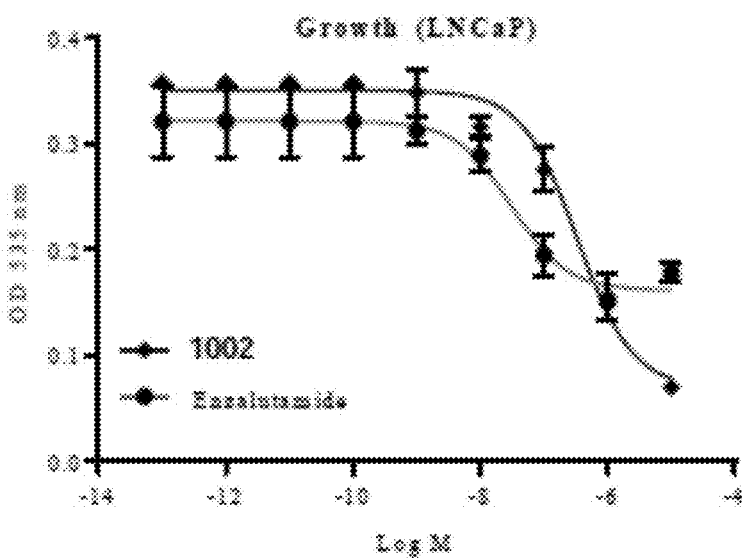
Figure 34C:
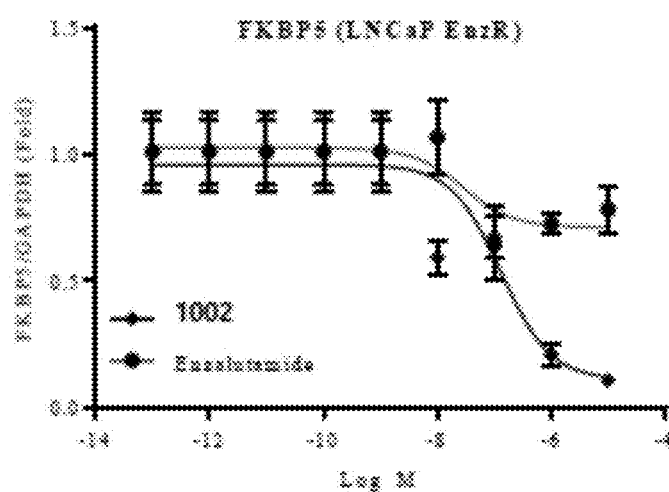
Figure 34D:
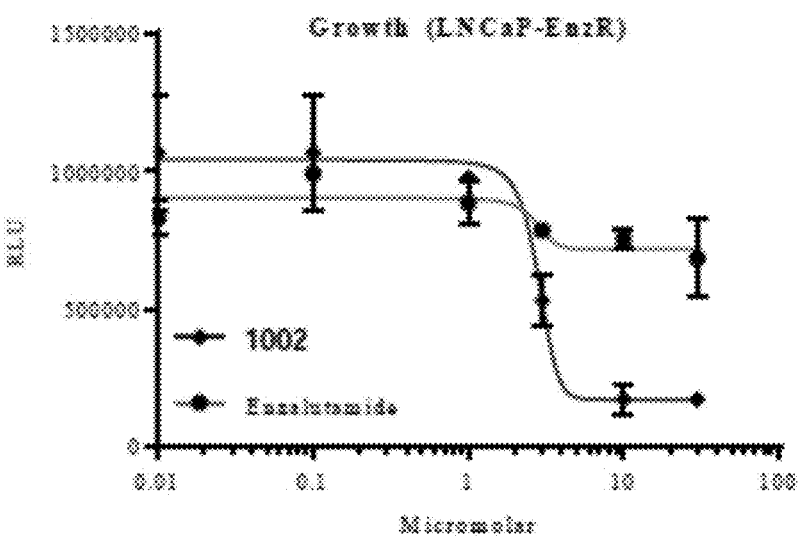

FIG. 32 shows that AR NTD binding of 1002 for required for degradation. Chimeric constructs were created in which the AR and GR were cloned such that the entire sequence was AR or GR, or the N-terminal domain was derived from AR but the DNA binding and ligand binding domains were derived from GR (AGG) or vice versa (GAA). Several lines of evidence summarized below suggested either NTD binding and/or dependence upon NTD for SARD activity. Further to that line of reasoning, the SARD 1002 was tested for its ability to degrade the AR, GR, AGG or GAA constructs as a way to demonstrate that AR NTD was required in order for the SARD to degrade the protein (i.e., demonstrate NTD-dependence). Other lines of evidence suggesting NTD-dependent SARD activity included: FIGS. 22 (NMR) and 27 (fluorescent polarization) demonstrated 1002 binding to NTD and their ability to degrade SV's which lack any LBD further suggested NTD binding. Example 3 discusses potent transcriptional activity in the absence of demonstrable LBD binding and structure-activity relationships of NTD binding that differ from known LBD SAR patterns. Example 8 discusses the ability of 1002 to inhibit SV-driven growth (i.e., FL AR is not expressed) of TNBC xenografts with SARD 1002, suggesting NTD binding. Consistent with this interpretation, the LBD-dependent AR antagonist enzalutamide failed to inhibit TNBC xenograft growth in these same TNBC xenografts.

The chimeric receptor data as provided in FIG. 32 is a strong evidence for NTD-dependence of SARD activity. From the Western blots of FIG. 32, it is apparent that SARDs degraded AR and/or AGG (NTD is AR and rest is GR) but not GR or GAA (NTD is GR and rest is AR). This suggests that AR NTD is required for SARD activity.

Example 13

(S)-3-(4-Bromo-1H-pyrazol-1-yl)-N-(4-cyano-3-(trifluoromethyl)phenyl)-2-hydroxy-2-methylpropanamide ($C_{15}H_{12}BrF_3N_4O_2$) (1050)

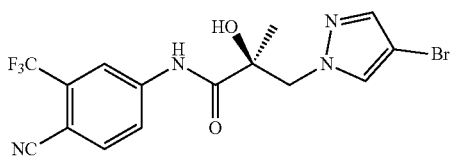 [SMILES: C[C@](O)(Cn1cc(Br)cn1)C(=O)Nc1ccc(C#N)c(C(F)(F)F)c1]

To a solution of 4-bromo-1H-pyrazole (0.20 g, 0.0013608 mol) in anhydrous THF (5 mL), which was cooled in an ice water bath under an argon atmosphere, was added sodium hydride (60% dispersion in oil, 0.16 g, 0.0040827 mol). After addition, the resulting mixture was stirred for three hours. (R)-3-Bromo-N-(4-cyano-3-(trifluoromethyl)phenyl)-2-hydroxy-2-methylpropanamide (0.478 g, 0.001608 mol) was added to the above solution, and the resulting reaction mixture was allowed to stir overnight at room temperature under argon. The reaction was quenched by water and extracted with ethyl acetate. The organic layer was washed with brine, dried with MgSO₄, filtered, and concentrated under vacuum. The product was purified by a silica gel column using DCM and ethyl acetate (19:1) as eluent to afford 0.47 g (79.6%) of the titled compound as white foam.

$^1$H NMR (400 MHz, CDCl₃) δ 9.08 (s, 1H, NH), 8.00 (d, J=2.0 Hz, 1H, ArH), 7.87 (dd, J=8.4 Hz, J=2.0 Hz, 1H, ArH), 7.79 (d, J=8.4 Hz, 1H, ArH), 7.49 (s, 1H, Pyrazole-H), 7.47 (s, 1H, Pyrazole-H), 5.92 (s, 1H, OH), 4.64 (d, J=14.0 Hz, 1H, CH), 4.24 (d, J=14.0 Hz, 1H, CH), 1.47 (s, 3H, CH₃).

Mass (ESI, Negative): 371.68 [M–H]⁻; (ESI, Positive): 440.94 [M+Na]⁺.

(R)-3-Bromo-N-(4-cyano-2-iodo-5-(trifluoromethyl)phenyl)-2-hydroxy-2-methylpropanamide ($C_{12}H_9BrF_3IN_2O_2$) (1051)

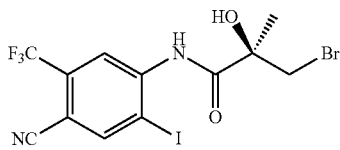 [SMILES: C[C@](O)(CBr)C(=O)Nc1cc(C(F)(F)F)c(C#N)cc1I]

3-Bromo-2-methyl-2-hydroxypropanoic acid (0.50 g, 0.00273224 mol) was reacted with thionyl chloride (0.39 g, 0.0032787 mol), trimethylamine (0.36 g, 0.0035519 mol), and 4-amino-5-iodo-2-(trifluoromethyl)benzonitrile (0.81 g, 0.0025956 mol) to afford the titled compound. The product was purified by a silica gel column using DCM and ethyl acetate (9:1) as eluent to afford 0.80 g (64.6%) of the titled compound as a light brown solid.

$^1$H NMR (400 MHz, CDCl₃) δ 9.53 (s, 1H, NH), 8.92 (s, 1H, ArH), 8.24 (s, 1H, ArH), 7.26 (s, 1H, OH), 4.04 (d, J=10.4 Hz, 1H, CH), 3.62 (d, J=10.4 Hz, 1H, CH), 1.67 (s, 3H, CH₃).

Mass (ESI, Positive): 479.25[M+H]⁺.

(S)—N-(4-Cyano-2-iodo-5-(trifluoromethyl)phenyl)-3-(4-fluoro-1H-pyrazol-1-yl)-2-hydroxy-2-methylpropanamide ($C_{15}H_{11}F_4IN_4O_2$) (1052)

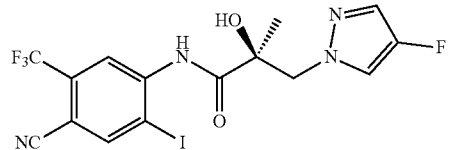 [SMILES: C[C@](O)(Cn1cc(F)cn1)C(=O)Nc1cc(C(F)(F)F)c(C#N)cc1I]

To a solution of 4-fluoro-1H-pyrazole (0.09 g, 0.001048 mol) in anhydrous THF (5 mL), which was cooled in an ice water bath under an argon atmosphere, was added sodium hydride (60% dispersion in oil, 0.15 g, 0.003669 mol). After addition, the resulting mixture was stirred for three hours. (R)-3-Bromo-N-(4-cyano-2-iodo-5-(trifluoromethyl)phenyl)-2-hydroxy-2-methylpropanamide (0.50 g, 0.001048 mol) was added to above solution, and the resulting reaction mixture was allowed to stir overnight at room temperature under argon. The reaction was quenched by water and extracted with ethyl acetate. The organic layer was washed with brine, dried with MgSO₄, filtered, and concentrated under vacuum. The product was purified by a silica gel column using hexanes and ethyl acetate (2:1 to 1:1) as eluent to afford 0.32 g (64%) of the titled compound as a white solid.

$^1$H NMR (400 MHz, CDCl₃) δ 9.60 (s, 1H, NH), 8.76 (s, 1H, ArH), 8.69 (s, 1H, ArH), 7.76 (d, J=4.8 Hz, 1H, Pyrazole-H), 7.36 (d, J=4.4 Hz, 1H, Pyrazole-H), 6.85 (s, 1H, OH), 4.39 (d, J=14.0 Hz, 1H, CH), 4.20 (d, J=14.0 Hz, 1H, CH), 1.41 (s, 3H, CH₃).

Mass (ESI, Negative): 481.00 [M–H]⁻;

(S)—N-(4-Cano-3-(trifluoromethyl)phenyl)-3-(5-(4-fluorophenyl)-1H-tetrazol-1-yl)-2-hydroxy-2-methylpropanamide ($C_{19}H_{14}F_4N_6O_2$) (1053)

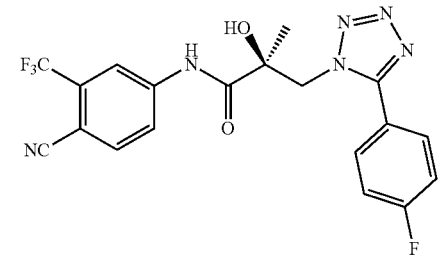 [SMILES: C[C@](O)(Cn1nnnc1-c1ccc(F)cc1)C(=O)Nc1ccc(C#N)c(C(F)(F)F)c1]

To a solution of 5-(4-fluorophenyl)-1H-tetrazole (0.20 g, 0.001219 mol) in anhydrous THF (5 mL), which was cooled in an ice water bath under an argon atmosphere, was added sodium hydride (60% dispersion in oil, 0.17 g, 0.004265 mol). After addition, the resulting mixture was stirred for three hours. (R)-3-Bromo-N-(4-cyano-3-(trifluoromethyl)phenyl)-2-hydroxy-2-methylpropanamide (0.43 g, 0.001219 mol) was added to above solution, and the resulting reaction mixture was allowed to stir 2 days at room temperature under argon. The reaction was quenched by water and extracted with ethyl acetate. The organic layer was washed with brine, dried with MgSO₄, filtered, and concentrated under vacuum. The product was purified by a silica gel column using DCM and ethyl acetate (9:1) as eluent to afford 0.053 g (10%) of the titled compound as a yellowish solid.

$^1$H NMR (400 MHz, CDCl$_3$) δ 10.39 (s, 1H, NH), 8.44 (s, 1H, ArH), 8.26 (d, J=8.2 Hz, 1H, ArH), 8.10 (d, J=8.2 Hz, 1H, ArH), 7.93-7.89 (m, 2H, ArH), 7.30 (t, J=8.2 Hz, 2H, ArH), 6.64 (s, 1H, OH), 5.09 (d, J=14.0 Hz, 1H, CH), 4.92 (d, J=14.0 Hz, 1H, CH), 1.55 (s, 3H, CH$_3$).

Mass (ESI, Negative): 433.17 [M−H]$^-$.

(S)—N-(4-Cyano-3-(trifluoromethyl)phenyl)-2-hydroxy-3-(4-methoxy-1H-pyrazol-1-yl)-2-methylpropanamide (C$_{16}$H$_{15}$F$_3$N$_4$O$_3$) (1054)

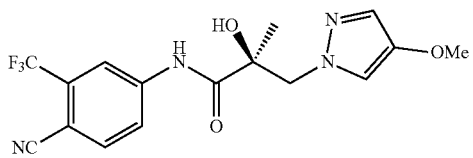 [SMILES: COc1cnn(C[C@](C)(O)C(=O)Nc2ccc(C#N)c(C(F)(F)F)c2)c1]

To a solution of 4-methoxy-1H-pyrazole (0.12 g, 0.001233 mol) in anhydrous THF (5 mL), which was cooled in an ice water bath under an argon atmosphere, was added sodium hydride (60% dispersion in oil, 0.17 g, 0.004281 mol). After addition, the resulting mixture was stirred for three hours. (R)-3-Bromo-N-(4-cyano-3-(trifluoromethyl) phenyl)-2-hydroxy-2-methylpropanamide (0.43 g, 0.001233 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using DCM and ethyl acetate (9:1) as eluent to afford 0.30 g (60%) of the titled compound as a white solid.

$^1$H NMR (400 MHz, DMSO-d$_6$) δ 10.38 (s, 1H, NH), 8.46 (d, J=2.0 Hz, 1H, ArH), 8.24 (dd, J=8.2 Hz, J=2.0 Hz, 1H, ArH), 8.10 (d, J=8.2 Hz, 1H, ArH), 7.35 (d, J=0.8 Hz, 1H, Pyrazole-H), 7.15 (d, J=0.8 Hz, 1H, Pyrazole-H), 6.25 (s, 1H, OH), 4.35 (d, J=14.0 Hz, 1H, CH), 4.18 (d, J=14.0 Hz, 1H, CH), 3.61 (s, 3H, CH$_3$), 1.36 (s, 3H, CH$_3$).

HRMS [C$_{16}$H$_{16}$F$_3$N$_4$O$_3$$^+$]: calcd 369.1175, found 369.1182[M+H]$^+$. Purity: 99.28% (HPLC).

(S)—N-(4-Cyano-3-(trifluoromethyl)phenyl)-2-hydroxy-2-methyl-3-(4-methyl-1H-pyrazol-1-yl)propanamide (C$_{16}$H$_{15}$F$_3$N$_4$O$_2$) (1055)

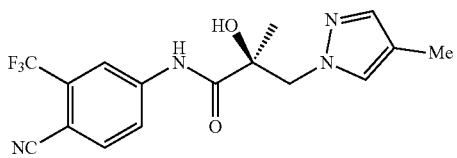 [SMILES: Cc1cnn(C[C@](C)(O)C(=O)Nc2ccc(C#N)c(C(F)(F)F)c2)c1]

To a solution of 4-methyl-1H-pyrazole (0.10 g, 0.001218 mol) in anhydrous THF (5 mL), which was cooled in an ice water bath under an argon atmosphere, was added sodium hydride (60% dispersion in oil, 0.17 g, 0.004263 mol). After addition, the resulting mixture was stirred for three hours. (R)-3-Bromo-N-(4-cyano-3-(trifluoromethyl)phenyl)-2-hydroxy-2-methylpropanamide (0.428 g, 0.001218 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using DCM and ethyl acetate (19:1) as eluent to afford 0.28 g (66%) of the titled compound as a white solid.

$^1$H NMR (400 MHz, DMSO-d$_6$) δ 10.38 (s, 1H, NH), 8.46 (d, J=2.0 Hz, 1H, ArH), 8.23 (dd, J=8.8 Hz, J=2.0 Hz, 1H, ArH), 8.10 (d, J=8.8 Hz, 1H, ArH), 7.41 (s, 1H, Pyrazole-H), 7.17 (s, 1H, Pyrazole-H), 6.24 (s, 1H, OH), 4.40 (d, J=14.0 Hz, 1H, CH), 4.22 (d, J=14.0 Hz, 1H, CH), 1.97 (s, 3H, CH$_3$), 1.36 (s, 3H, CH$_3$).

HRMS [C$_{16}$H$_{16}$F$_3$N$_4$O$_2$+]: calcd 353.1225, found 353.1232[M+H]$^+$. Purity: 99.75% (HPLC).

N-(4-Cyano-3-(trifluoromethyl)phenyl)-2-methyloxirane-2-carboxamide (C$_{12}$H$_9$F$_3$N$_2$O$_2$) (1056)

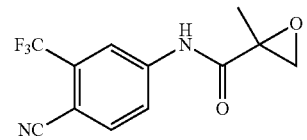 [SMILES: CC1(C(=O)Nc2ccc(C#N)c(C(F)(F)F)c2)CO1]

2-Methyloxirane-2-carboxylic acid (1.00 g, 0.009892 mol) was reacted with thionyl chloride (1.41 g, 0.011871 mol), trimethylamine (1.30 g, 0.01286 mol), and 4-amino-2-(trifluoromethyl)benzonitrile (1.84 g, 0.009892 mol) to afford the titled compound. The product was purified by a silica gel column using DCM and ethyl acetate (19:1) as eluent to afford 1.52 g (57%) of the titled compound as a yellowish solid.

$^1$H NMR (400 MHz, DMSO-d$_6$) δ 10.54 (s, 1H, NH), 8.55 (d, J=1.6-2.0 Hz, 1H, ArH), 8.32 (dd, J=8.8 Hz, J=2.0 Hz, 1H, ArH), 8.12 (d, J=8.8 Hz, 1H, ArH), 6.39 (s, 1H, OH), 3.94 (d, J=11.2 Hz, 1H, CH), 3.70 (d, J=11.2 Hz, 1H, CH), 1.44 (s, 3H, CH$_3$).

Mass (ESI, Negative): [M−H]$^-$; (ESI, Positive): [M+Na]$^+$.

N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$) (1057)

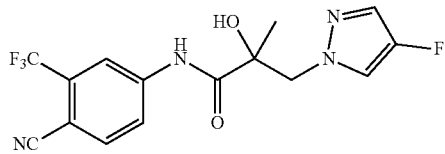 [SMILES: CC(O)(Cn1cc(F)cn1)C(=O)Nc1ccc(C#N)c(C(F)(F)F)c1]

To a solution of 4-fluoro-pyrazole (0.10 g, 0.001162 mol) in anhydrous THF (10 mL), which was cooled in an ice water bath under an argon atmosphere, was added sodium hydride (60% dispersion in oil, 0.14 g, 0.003486 mol). After addition, the resulting mixture was stirred for three hours. N-(4-Cyano-3-(trifluoromethyl)phenyl)-2-methyloxirane-2-carboxamide (0.31 g, 0.001162 mol) was added to above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using hexanes and ethyl acetate (2:1 to 1:1) as eluent to afford 0.37 g (90%) of the titled compound as a yellowish solid.

$^1$H NMR (400 MHz, DMSO-d$_6$) δ 10.38 (s, 1H, NH), 8.47 (d, J=2.0 Hz, 1H, ArH), 8.24 (dd, J=8.8 Hz, J=2.0 Hz, 1H, ArH), 8.10 (d, J=8.8 Hz, 1H, ArH), 7.74 (d, J=4.4 Hz, 1H, Pyrazole-H), 7.41 (d, J=4.0 Hz, 1H, Pyrazole-H), 6.31 (s, 1H, OH), 4.39 (d, J=14.0 Hz, 1H, CH), 4.21 (d, J=14.4 Hz, 1H, CH), 1.34 (s, 3H, CH$_3$).

Mass (ESI, Negative): [M−H]$^−$; (ESI, Positive): [M+Na]$^+$.

(S)-3-Bromo-N-(4-cyano-3-(trifluoromethyl)phenyl)-2-hydroxy-2-methylpropanamide (C$_{12}$H$_9$F$_3$N$_2$O$_2$)

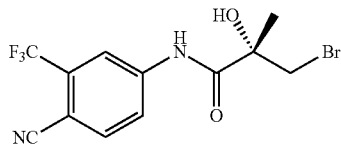 [SMILES: C[C@@](O)(CBr)C(=O)Nc1ccc(C#N)c(C(F)(F)F)c1]

(S)-3-Bromo-2-hydroxy-2-methylpropanoic acid (1.00 g, 0.0054645 mol) reacted with thionyl chloride (0.78 g, 0.0065574 mol), trimethylamine (0.72 g, 0.0071038 mol), and 4-amino-2-(trifluoromethyl)benzonitrile (1.02 g, 0.0054645 mol) to afford the titled compound. The product was purified by a silica gel column using DCM and ethyl acetate (19:1) as eluent to afford 1.75 g (90%) of the titled compound as a yellowish solid.

Mass (ESI, Positive): 351.08 [M+Na]$^+$.

(R)—N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$)

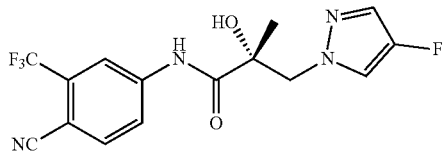 [SMILES: C[C@@](O)(Cn1cc(F)cn1)C(=O)Nc1ccc(C#N)c(C(F)(F)F)c1]

To a solution of 4-fluoro-pyrazole (0.10 g, 0.001162 mol) in anhydrous THF (10 mL), which was cooled in an ice water bath under an argon atmosphere, was added sodium hydride (60% dispersion in oil, 0.16 g, 0.0040665 mol). After addition, the resulting mixture was stirred for three hours. (S)-3-Bromo-N-(4-cyano-3-(trifluoromethyl)phenyl)-2-hydroxy-2-methylpropanamide (0.41 g, 0.001162 mol) was added to above solution, and the resulting reaction mixture was allowed to stir overnight at room temperature under argon. The reaction was quenched by water, extracted with ethyl acetate. The organic layer was washed with brine, dried with MgSO$_4$, filtered, and concentrated under vacuum. The product was purified by a silica gel column using hexanes and ethyl acetate (2:1 to 1:1) as eluent to afford 0.27 g (64%) of the titled compound as yellowish solid.

$^1$H NMR (400 MHz, DMSO-d$_6$) δ 10.38 (s, 1H, NH), 8.47 (d, J=1.6-2.0 Hz, 1H, ArH), 8.24 (dd, J=8.4 Hz, J=2.0 Hz, 1H, ArH), 8.10 (d, J=8.4 Hz, 1H, ArH), 7.74 (d, J=4.4 Hz, 1H, Pyrazole-H), 7.41 (d, J=4.4 Hz, 1H, Pyrazole-H), 6.31 (s, 1H, OH), 4.39 (d, J=14.0 Hz, 1H, CH), 4.21 (d, J=14.4 Hz, 1H, CH), 1.34 (s, 3H, CH$_3$).

Mass (ESI, Positive): 357.11 [M+Na]$^+$.

(S)-3-(4-Bromo-3-fluoro-1H-pyrazol-1-yl)-N-(4-cyano-3-(trifluoromethyl)phenyl)-2-hydroxy-2-methylpropanamide (C$_{15}$H$_{11}$BrF$_4$N$_4$O$_2$) (1058)

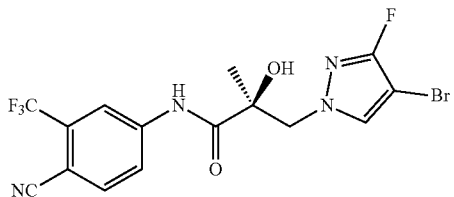

To a solution of 4-bromo-3-fluoro-1H-pyrazole (0.30 g, 0.001819 mol) in anhydrous THF (10 mL), which was cooled in an ice water bath under an argon atmosphere, was added sodium hydride (60% dispersion in oil, 0.26 g, 0.006365 mol). After addition, the resulting mixture was stirred for three hours. (R)-3-Bromo-N-(4-cyano-3-(trifluoromethyl)phenyl)-2-hydroxy-2-methylpropanamide (0.64 g, 0.001819 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.34 g (34%) of the titled compound as a pinkish solid.

$^1$H NMR (400 MHz, DMSO-d$_6$) δ 10.38 (s, 1H, NH), 8.45 (d, J=2.0-1.6 Hz, 1H, ArH), 8.23 (dd, J=8.2 Hz, J=2.0 Hz, 1H, ArH), 8.11 (d, J=8.2 Hz, 1H, ArH), 7.82 (d, J=2.0 Hz, 1H, Pyrazole-H), 6.35 (s, 1H, OH), 4.35 (d, J=14.0 Hz, 1H, CH), 4.04 (d, J=14.0 Hz, 1H, CH), 1.37 (s, 3H, CH$_3$).

HRMS [C$_{15}$H$_{12}$BrF$_4$N$_4$O$_2$+]: calcd 435.0080, found 435.0080[M+H]$^+$. Purity: 96.98% (HPLC).

(S)—N-(4-Cyano-3-(trifluoromethyl)phenyl)-3-(3-fluoro-4-(4-fluorophenyl)-1H-pyrazol-1-yl)-2-hydroxy-2-methylpropanamide (C$_{21}$H$_{15}$F$_5$N$_4$O$_2$) (1059)

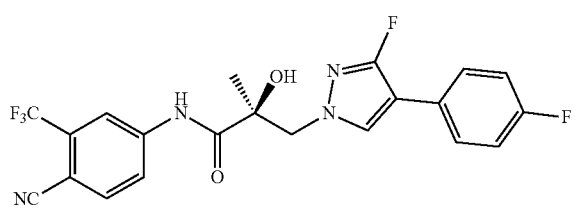 [SMILES: C[C@](O)(Cn1cc(-c2ccc(F)cc2)c(F)n1)C(=O)Nc1ccc(C#N)c(C(F)(F)F)c1]

The mixture of (S)-3-(4-bromo-3-fluoro-1H-pyrazol-1-yl)-N-(4-cyano-3-(trifluoromethyl)phenyl)-2-hydroxy-2-methylpropanamide (0.20 g, 0.4596 mmol), 4-fluoro boronic acid (77 mg, 0.5515 mmol), Pd(II)(OAc)$_2$ (2-3 mg, 0.009192 mmol), PPh$_3$ (7-8 mg, 0.02758 mmol), and K$_2$CO$_3$ (0.13 g, 0.965 mmol) in the mixture of ACN (4-5 mL) and $H_2O$ (2-3 mL) was degassed and refilled with argon three times. The resulting reacting mixture was heated at reflux for 3 hours under argon. The product was purified by a silica gel column using hexanes and ethyl acetate (2:1 to 1:1) as eluent to afford 51 mg (25%) of the titled compound as a off-white solid.

$^1$H NMR (400 MHz, CDCl$_3$) δ 9.12 (s, 1H, NH), 8.06 (d, J=1.6 Hz, 1H, ArH), 7.85 (dd, J=8.2 Hz, J=1.6 Hz, 1H, ArH), 7.77 (d, J=8.2 Hz, 1H, ArH), 7.51 (d, J=3.0 Hz, 1H, Pyrazole-H), 7.43-7.40 (m, 2H, ArH), 7.08-7.04 (m, 2H, ArH), 4.57 (d, J=10.5 Hz, 1H, CH), 4.7 (d, J=10.5 Hz, 1H, CH), 1.26 (s, 3H, CH$_3$).

HRMS [C21H$_{16}$F$_5$N$_4$O$_2$$^+$]: calcd 451.1193, found 451.1196[M+H]$^+$. Purity: % (HPLC).

(S)-3-(3-Bromo-4-cyano-1H-pyrazol-1-yl)-N-(4-cyano-3 trifluoromethyl)phenyl)-2-hydroxy-2-methylpropanamide (C$_{16}$H$_{11}$BrF$_3$N$_5$O$_2$) (1060)

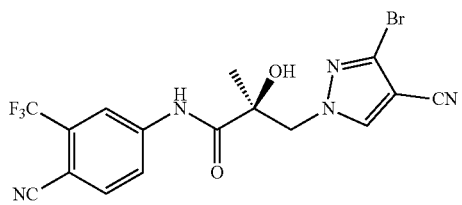 [SMILES: C[C@](O)(Cn1cc(C#N)c(Br)n1)C(=O)Nc1ccc(C#N)c(C(F)(F)F)c1]

To a solution of 3-bromo-4-cyano-1H-pyrazole (0.20 g, 0.0011629 mol) in anhydrous THF (10 mL), which was cooled in an ice water bath under an argon atmosphere, was added sodium hydride (60% dispersion in oil, 0.163 g, 0.00407 mol). After addition, the resulting mixture was stirred for three hours. (R)-3-Bromo-N-(4-cyano-3-(trifluoromethyl)phenyl)-2-hydroxy-2-methylpropanamide (0.41 g, 0.0011629 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.10 g (20%) of the titled compound as an off-white solid.

$^1$H NMR (400 MHz, DMSO-d$_6$) δ 10.32 (s, 1H, NH), 8.40 (s 1H, Pyrazole-H), 8.41 (s, 1H, ArH), 8.20 (d, J=8.4 Hz, 1H, ArH), 8.11 (d, J=8.4 Hz, 1H, ArH), 6.47 (s, 1H, OH), 4.52 (d, J=13.6 Hz, 1H, CH), 4.33 (d, J=13.6 Hz, 1H, CH), 1.41 (s, 3H, CH$_3$).

HRMS [C$_{16}$H12BrF$_3$N$_5$O$_2$+]: calcd 442.0126, found 442.0109[M+H]$^+$. Purity: 98.84% (HPLC).

(S)-3-(3-Chloro-4-methyl-1H-pyrazol-1-yl)-N-(4-cyano-3-(trifluoromethyl)phenyl)-2-hydroxy-2-methylpropanamide (C$_{16}$H$_{14}$ClF$_3$N$_4$O$_2$) (1061)

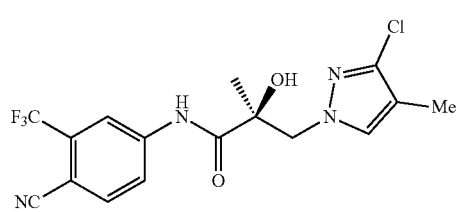 [SMILES: Cc1cn(C[C@](C)(O)C(=O)Nc2ccc(C#N)c(C(F)(F)F)c2)nc1Cl]

To a solution of 3-chloro-4-methyl-1H-pyrazole (0.15 g, 0.001287 mol) in anhydrous THF (10 mL), which was cooled in an ice water bath under an argon atmosphere, was added sodium hydride (60% dispersion in oil, 0.18 g, 0.0045045 mol). After addition, the resulting mixture was stirred for three hours. (R)-3-Bromo-N-(4-cyano-3-(trifluoromethyl)phenyl)-2-hydroxy-2-methylpropanamide (0.45 g, 0.001287 mol) was added to above solution, and the resulting reaction mixture was allowed to stir overnight at room temperature under argon. The reaction was quenched by water and extracted with ethyl acetate. The organic layer was washed with brine, dried with MgSO$_4$, filtered, and concentrated under vacuum. The product was purified by a silica gel column using DCM and ethyl acetate (98:2 to 95:5) as eluent to afford 0.27 g (54%) of the titled compound as a white solid.

$^1$H NMR (400 MHz, DMSO-d$_6$) δ 10.33 (s, 1H, NH), 8.42 (d, J=0.8 Hz, 1H, ArH), 8.21 (dd, J=8.4 Hz, J=0.8 Hz, 1H, ArH), 8.10 (d, J=8.2 Hz, 1H, ArH), 7.50 (s 1H, Pyrazole-H), 6.29 (s, 1H, OH), 4.36 (d, J=14.4 Hz, 1H, CH), 4.18 (d, J=14.4 Hz, 1H, CH), 1.91 (s, 3H, CH$_3$), 1.35 (s, 3H, CH$_3$).

HRMS [C$_{16}$H$_{15}$ClF$_3$N$_4$O$_2$+]: calcd 387.0836, found 387.0839[M+H]$^+$. Purity: 97.07% (HPLC).

(S)-3-(4-Fluoro-1H-pyrazol-1-yl)-2-hydroxy-2-methyl-N-(4-nitro-3-(trifluoromethyl)phenyl)propanamide (1062)

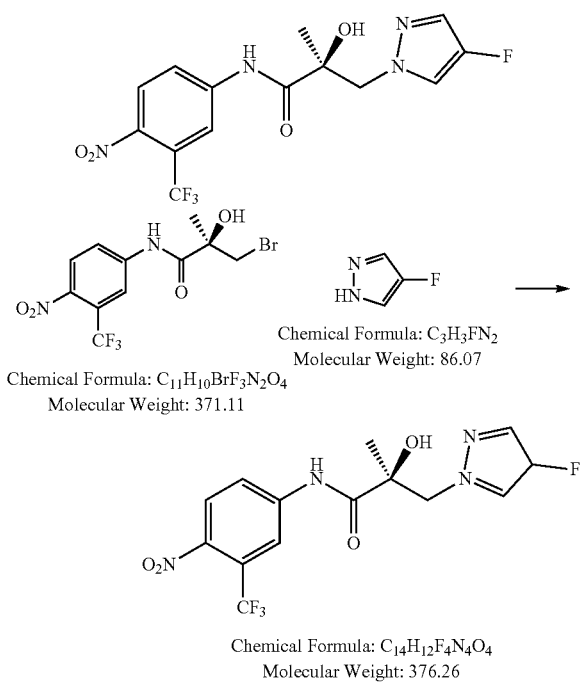

To a dry, nitrogen-purged 100 mL round-bottom flask equipped with a dropping funnel under argon atmosphere, NaH of 60% dispersion in mineral oil (674 mg, 16.9 mmol) was added in 60 mL of anhydrous THF solvent in the flask at ice-water bath, and 4-fluoro-1H-pyrazole (691 mg, 8.03 mmol) was stirred in over 30 min at the ice-water bath. Into the flask, the solution of (R)-3-bromo-2-hydroxy-2-methyl-N-(4-nitro-3-(trifluoromethyl)phenyl)propanamide (2.98 g, 8.03 mmol) in 10 mL of anhydrous THF was added through dropping funnel under argon atmosphere at the ice-water bath and stirred overnight at room temperature. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography as an eluent EtOAc/hexane=1/2 to produce designed compound (2.01 g, 67%) as yellowish solid.

MS (ESI) m/z 375.08 [M−H]⁻ ; 377.22 [M+H]⁺; 399.04 [M+Na]⁺;

¹⁹F NMR (CDCl₃, decoupled) δ −60.13, −176.47; assigned by NOE and COSY; ¹H NMR (400 MHz, CDCl₃) δ 9.14 (bs, 1H, NH), 8.01 (s, 1H), 7.97-7.91 (m, 2H), 7.38 (d, J=3.6 Hz, 1H), 7.35 (d, J=4.4 Hz, 1H), 5.95 (s, 1H, OH), 4.56 (d, J=14.0 Hz, 1H), 4.17 (d, J=14.0 Hz, 1H), 1.48 (s, 3H).

(S)-3-(4-Fluoro-1H-pyrazol-1-yl)-2-hydroxy-2-methylpropanoic acid (1062a)

Preparation of (S)—N-(6-Cyano-5-(trifluoromethyl)pyridin-3-yl)-3-(4-(4-fluorophenyl)-1H-1,2,3-triazol-1-yl)-2-hydroxy-2-methylpropanamide (1063)

(S)-3-Azido-N-(6-cyano-5-(trifluoromethyl)pyridin-3-yl)-2-hydroxy-2-methylpropanamide (1064)

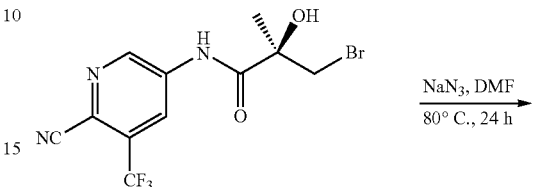

Chemical Formula: C₁₁H₉BrF₃N₃O₂
Molecular Weight: 352.11

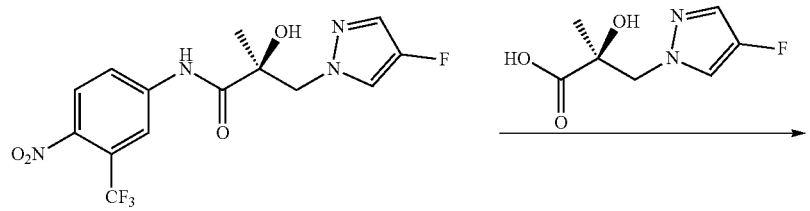

Chemical Formula: C₁₄H₁₂F₄N₄O₄
Molecular Weight: 376.2631

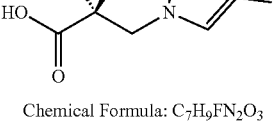

Chemical Formula: C₇H₉FN₂O₃
Molecular Weight: 188.16

To a solution of 1062 (1.886 g, 5.29 mmol) in EtOH (40 ml) and water (20 ml) was added NaOH (424 mg, 10.59 mmol) and the reaction mixture was heated to reflux for 2 h, evaporated (to remove the EtOH) and then extracted with EtOAc. The aqueous phase was acidified to pH 1 and extracted with EtOAc. The extract was dried over Na₂SO₄, filtered and evaporated to afford the title compound (845 mg, 85%) as a brown oil. MS (ESI) m/z 187.06 [M−H]⁻ ; 188.91 [M+H]⁺;

¹⁹F NMR (acetone-d6, decoupled) δ −0.24; assigned by NOE and COSY.

¹H NMR (400 MHz, acetone-d₆) δ 7.66 (d, J=4.4 Hz, 1H), 7.36 (d, J=4.0 Hz, 1H), 4.45 (d, J=14.0 Hz, 1H), 4.27 (d, J=14.0 Hz, 1H), 1.38 (s, 3H). ¹³C NMR (100 MHz, acetone-d₆) δ 175.70, 150.36 (d, J=24.12 Hz), 126.53 (d, J=13.6 Hz), 118.21 (d, J=28.0 Hz), 74.86, 60.59, 23.77.

-continued

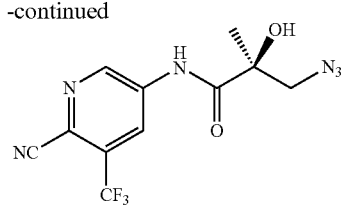

Chemical Formula: C₁₁H₉F₃N₆O₂
Molecular Weight: 314.22

A solution of (R)-3-bromo-N-(6-cyano-5-(trifluoromethyl)pyridin-3-yl)-2-hydroxy-2-methylpropanamide (352 mg, 1 mmol) in 10 mL of DMF was treated with NaN₃ (325 mg, 5 mmol) under Ar at 80° C. for 24 h. The reaction mixture was then cooled and extracted with CH₂Cl₂ (3×20 mL). The combined organic layers were washed with H₂O (3×20 mL) and brine, dried and evaporated to give a crude oil, which purified by silica gel chromatography (EtOAc/n-hexane=1:2, v/v) to afford product. Yield=87%;

MS (ESI) m/z 313.03 [M–H]⁺; ¹⁹F NMR (CDCl₃, decoupled) δ –62.11;
¹H NMR (400 MHz, CDCl₃) δ 9.16 (bs, 1H, NH), 8.89 (s, 1H), 8.77 (s, 1H), 3.90 (d, J=12.0 Hz, 1H), 3.52 (d, J=12.0 Hz, 1H), 3.20 (bs, 1H, OH), 1.55 (s, 3H).

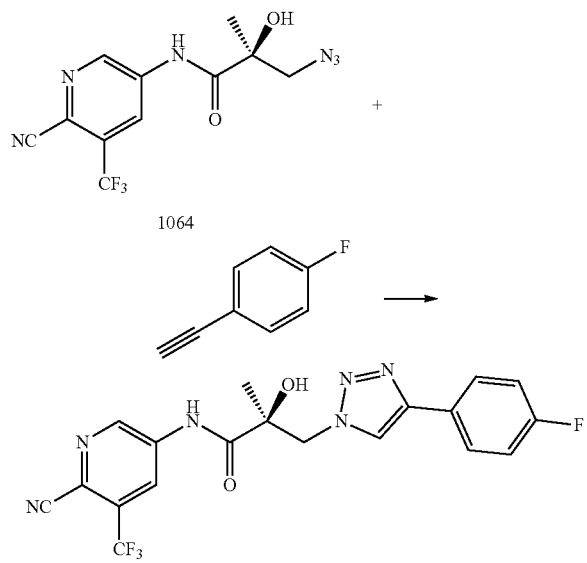

1064

(S)—N-(6-Cyano-5-(trifluoromethyl)pyridin-3-yl)-3-(4-(4-fluorophenyl)-1H-1,2,3-triazol-1-yl)-2-hydroxy-2-methylpropanamide (1063)

To a suspension of copper(I)iodide (11 mg, 0.055 mmoL) in acetonitrile (7 mL)/water (3 mL) mixture was added 1064 (57 mg, 0.182 mmol) at room temperature and then 1-ethynyl-4-fluorobenzene (0.015 mL, 0.182 mmol) was added. The resulting reaction mixture was stirred at room temperature for 3 days. The mixture was evaporated under reduced pressure, poured into water:brine (1:1) and then extracted with ethyl acetate. The combined organic extracts were then washed with brine, dried over sodium sulphate, filtered and evaporated. Purification by chromatography (silica, 60% ethyl acetate in hexane) to afford the product as a yellow solid (51.3 mg, 65%).
MS (ESI) m/z 433.09 [M–H]⁻ 435.06 [M+H]⁺;
¹⁹F NMR (acetone-d6, decoupled) δ 114.58, 61.66; assigned by NOE and COSY; ¹H NMR (400 MHz, acetone-d₆) δ 10.16 (bs, 1H, NH), 9.28 (s, 1H), 8.88 (s, 1H), 8.31 (s, 1H), 7.90 (t, J=7.8 Hz, 2H), 7.20 (t, J=8.8 Hz, 2H), 5.73 (bs, 1H, OH), 4.94 (d, J=14.2 Hz, 1H), 4.73 (d, J=14.2 Hz, 1H), 1.62 (s, 3H).

(S)-3-(4-Bromo-3-fluoro-1H-pyrazol-1-yl)-N-(6-cyano-5-(trifluoromethyl)pyridin-3-yl)-2-hydroxy-2-methylpropanamide (1069)

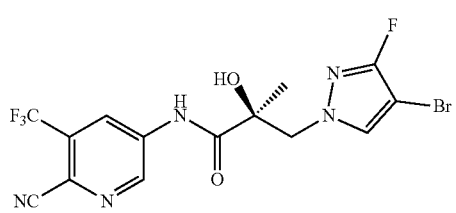 [SMILES: C[C@](O)(Cn1cc(Br)c(F)n1)C(=O)Nc1cnc(C#N)c(C(F)(F)F)c1]

To a solution of 4-bromo-3-fluoro-pyrazole (0.20 g, 0.0012124 mol) in anhydrous THF (10 mL), which was cooled in an ice water bath under an argon atmosphere, was added sodium hydride (60% dispersion in oil, 0.17 g, 0.0042434 mol). After addition, the resulting mixture was stirred for three hours. (R)-3-Bromo-N-(6-cyano-5-(trifluoromethyl)pyridin-3-yl)-2-hydroxy-2-methylpropanamide (0.327 g, 0.0012124 mol) was added to above solution, and the resulting reaction mixture was allowed to stir overnight at room temperature under argon. The reaction was quenched by water and extracted with ethyl acetate. The organic layer was washed with brine, dried with MgSO₄, filtered, and concentrated under vacuum. The product was purified by a silica gel column using hexanes and ethyl acetate (2:1 to 1:1) as eluent to afford 0.28 g (54%) of the titled compound as white solid.
HRMS [C₁₅H₁₂BrClF₃N₄O₂+]: calcd 434.9954, found 435.9997 [M+H]⁺. Purity: 93.41% (HPLC).
¹H NMR (400 MHz, DMSO-d₆) δ 10.67 (s, 1H, NH), 9.32 (d, J=2.0 Hz, 1H, ArH), 8.82 (d, J=2.0 Hz, 1H, ArH), 7.85 (d, J=2.0 Hz 1H, Pyrazole-H), 6.47 (s, 1H, OH), 4.35 (d, J=14.0 Hz, 1H, CH), 4.17 (d, J=14.0 Hz, 1H, CH), 1.39 (s, 3H, CH₃).

(S)-3-(3-Bromo-4-cyano-1H-pyrazol-1-yl)-N-(6-cyano-5-(trifluoromethyl)pyridin-3-yl)-2-hydroxy-2-methylpropanamide (1070) and (S)—N-(6-cyano-5-(trifluoromethyl)pyridin-3-yl)-3-(4-cyano-3-phenyl-1H-pyrazol-1-yl)-2-hydroxy-2-methylpropanamide (1071)

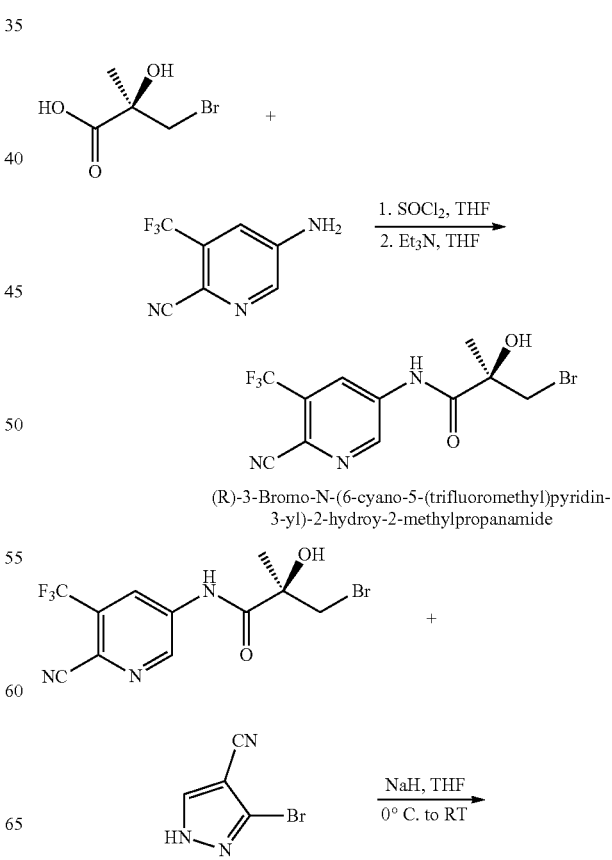

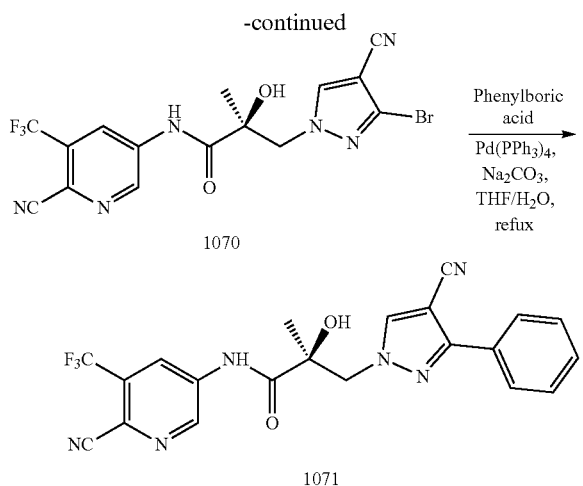

(R)-3-Bromo-N-(6-cyano-5-(trifluoromethyl)pyridin-3-yl)-2-hydroxy-2-methylpropanamide Thionyl chloride (0.8 mL, 1.07 mol) was added dropwise to a cooled solution (less than 4° C.) of (R)-3-bromo-2-hydroxy-2-methylpropanoic acid (1.27 g, 6.94 mmol) in 50 mL of THF under an argon atmosphere. The resulting mixture was stirred for 3 h under the same condition. To this was added Et₃N (1.8 mL, 1.28 mmol) and stirred for 20 min under the same condition. After 20 min, 5-amino-3-(trifluoromethyl)picolinonitrile (1 g, 5.34 mmol) and 50 mL of THF were added, and then the mixture was allowed to stir overnight at room temperature. The solvent was removed under reduced pressure to give a solid which was treated with 50 mL of H₂O and extracted with EtOAc (2×400 mL). The combined organic extracts were washed with saturated NaHCO₃ solution (2×50 mL) and brine (50 mL). The organic layer was dried over MgSO₄ and concentrated under reduced pressure to give a solid which was purified from column chromatography using CH₂Cl₂/EtOAc (80:20) to give a solid. This solid was recrystallized from CH₂Cl₂/hexane to give 1.32 g (70.2%) of (R)-3-bromo-N-(6-cyano-5-(trifluoromethyl)pyridin-3-yl)-2-hydroxy-2-methylpropanamide as a light-yellow solid.

MS (ESI) m/z 351.08 [M−H]⁻

¹⁹F NMR (CDCl₃, 400 MHz) δ −62.09.

¹H NMR (CDCl₃, 400 MHz) δ 9.15 (bs, 1H, NH), 8.90 (s, 1H), 8.78 (s, 1H), 4.02 (d, J=10.8 Hz, 1H), 3.60 (d, J=10.8 Hz, 1H), 3.17 (bs, 1H, OH), 1.66 (s, 3H).

(S)-3-(3-Bromo-4-cyano-1H-pyrazol-1-yl)-N-(6-cyano-5-(trifluoromethyl)pyridin-3-yl)-2-hydroxy-2-methylpropanamide (1070)

To a dry, nitrogen-purged 50 mL round-bottom flask equipped with a dropping funnel under argon atmosphere, NaH of 60% dispersion in mineral oil (232 mg, 5.81 mmol) was added in 10 mL of anhydrous THF solvent in the flask at ice-water bath, and 3-bromo-1H-pyrazole-4-carbonitrile (500 mg, 2.91 mmol) was added and stirred 30 min at the ice-water bath. Into the flask, (R)-3-bromo-N-(6-cyano-5-(trifluoromethyl)pyridin-3-yl)-2-hydroxy-2-methylpropanamide (1.023 g, 2.91 mmol) in 10 mL of anhydrous THF was added through dropping funnel under argon atmosphere at the ice-water bath and stirred overnight at room temperature. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography as an eluent EtOAc/hexane=1/1, v/v to produce the designed compound (1070, 1.043 g, yield 81%) as white solid.

MP 172.5-173.6° C.;

MS (ESI) m/z 442.1 [M−H]⁻; HRMS (ESI) m/z calcd for C₁₅H₁₀BrF₃N₆O₂ 443.0079 [M+H]⁺ found 443.0083 [M+H]⁺; 464.9903 [M+Na]⁺;

¹⁹F NMR (CDCl₃, 400 MHz) δ −61.25; The structure of product was confirmed with 2D NMR (COSY and NOESY);

¹H NMR (DMSO-d6, 400 MHz) δ 10.60 (bs, 1H, NH), 9.29 (s, 1H), 8.79 (s, 1H), 8.53 (s, 1H), 6.59 (s, OH), 4.50 (d, J=14.0 Hz, 1H), 4.32 (d, J=14.0 Hz, 1H), 1.43 (s, 3H).

(S)—N-(6-Cyano-5-(trifluoromethyl)pyridin-3-yl)-3-(4-cyano-3-phenyl-1H-pyrazol-1-yl)-2-hydroxy-2-methylpropanamide (1071)

A flask equipped with a reflux condenser, a septum inlet and a magnetic stirring bar was charged with (S)-3-(3-bromo-4-cyano-1H-pyrazol-1-yl)-N-(6-cyano-5-(trifluoromethyl)pyridin-3-yl)-2-hydroxy-2-methylpropanamide (1070, 53 mg, 0.23 mmol), tetrakis(triphenylphosphine) palladium (0) (9 mg, 0.07 mmol), and phenyl boronic acid (35 mg, 0.28 mmol) in THF/MeOH (5 mL/1 mL) with sodium carbonate (50 mg, 0.48 mmol) in deoxygenated water (1 mL), and was stirred and heated to reflux for 2 h until bromopyrazole was not detectable on TLC. The mixture was cooled to room temperature and the solvent was removed in vacuo and then poured into EtOAc (10 mL), and extracted with EtOAc. The combined organic layers were washed with sat. NH₄Cl, water and dried over MgSO₄. The solvent was removed in vacuo and then purified by flash column chromatography on silica gel using EtOAc/hexane (1/1, v/v) as an eluent to give the targeted compound (1071, 36 mg, 69%) as yellowish solid.

MP 112.3-124.4° C.;

MS (ESI) m/z 439.2 [M−H]⁻; HRMS (ESI) m/z calcd for C₂₁H₁₅F₃N₆O₂ 441.1287 [M+H]⁺ found 441.1291 [M+H]⁺; 463.1111 [M+Na]⁺;

¹⁹F NMR (CDCl₃, 400 MHz) δ −62.09; The structure of product was confirmed with 2D NMR (COSY and NOESY);

¹H NMR (CDCl₃, 400 MHz) δ 9.17 (bs, 1H, NH), 8.76 (s, 1H), 8.60 (s, 1H), 7.77 (s, 1H), 7.57-7.52 (m, 3H), 7.18 (d, J=8.8 Hz, 2H), 5.32 (s, OH), 4.60 (d, J=14.0 Hz, 1H), 4.23 (d, J=14.0 Hz, 1H), 1.47 (s, 3H).

Example 14

SARDs Regressed CPRC VCaP Tumors

VCaP prostate cancer cells were implanted (in combination with matrigel (1:1 mix)) on the flanks subcutaneously in SRG rats (10 million cells/rat). When the tumors reach 300-500 mm³, the animals were castrated and the tumors were allowed to regrow as castration-resistant prostate cancer. When the tumors regrew, the animals were randomized into three groups, vehicle (15% DMSO+85% PEG-300), enzalutamide (30 mg/kg/day), or compound 1002 (60 mg/kg/day). The animals were orally treated and tumor volume and body weight were recorded thrice weekly. Tumor volume or percent change in tumor volume was calculated.

Figure 35A:
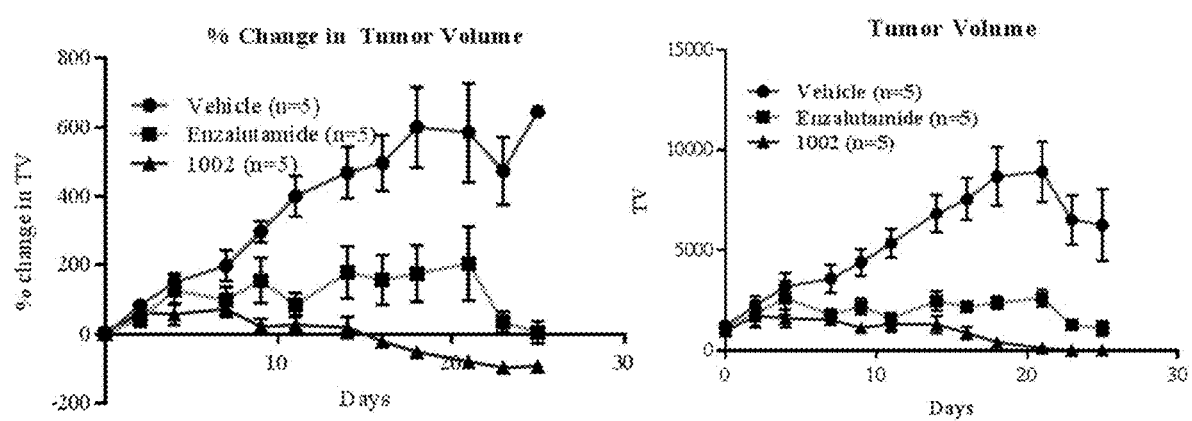
FIG. 35A: SARDs of this invention regressed the VCaP (enzalutamide sensitive) tumors grown in castrated rats to undetectable levels.

Vehicle-treated tumors grew robustly in castrated environment indicating that the tumors were castration-resistant, i.e., tumor were CRPC. Enzalutamide inhibited the growth of the tumors, while compound 1002 regressed the tumors to undetectable levels (FIG. 35A). All individual animals treated with 1002 had tumor volume reduced to unmeasurable by 22 days (FIG. 35B), whereas enzalutamide response was more variable and incomplete even at 30 days.

Example 15

SARDs Inhibited Growth of Tumor and Caused Rapid Tumor Regression in Anti-Androgen Resistant (MDVR) VCaP Cells in Intact and Castrated Animals VCaP cells that have been rendered enzalutamide resistant were implanted (in combination with matrigel (1:1 mix)) on the flanks subcutaneously in SRG rats (10 million cells/rat). When the tumor reached 10,800 mm$^3$, the animal was treated orally with compound 1002 (60 mg/kg/day) to determine if the tumor growth is slowed. Tumor volume and body weight was recorded thrice weekly.

Figure 36A:
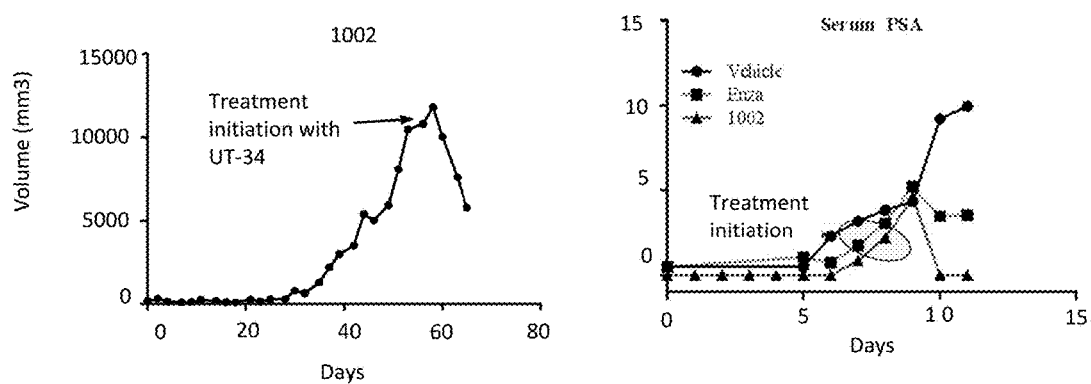
FIG. 36A: SARDs inhibited growth of tumor, caused rapid tumor regression, and rapidly reduced PSA serum to zero in a single cryptorchid animal (i.e., androgen replete milieu) implanted with VCaP cells which were rendered enzalutamide resistant (MDVR). The left pane shows the tumor volume for this animal. The right pane show that 1002 immediately and completely reduced PSA to zero, whereas enzalutamide treated xenograft has only a modest PSA response.
Figure 36B:
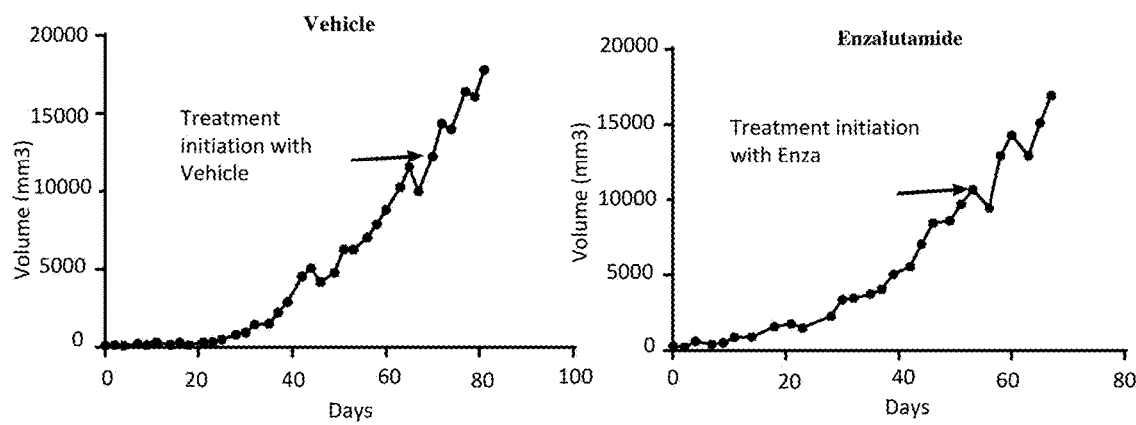
FIG. 36B: demonstrates that vehicle treated and enzalutamide treated MDVR VCaP xenograft continued to grow rapidly. This established that the MDVR VCaP model was a good model of enzalutamide resistance.

Animal No. 803 was cryptorchid and there were complications upon trying to remove testes, so the animal was left intact. Before initiation of 1002 treatments, the MDV3100 (enzalutamide) resistant (MDVR) VCaP cells grew robustly, presumably supported by the endogenous androgens. 1002 quickly inhibited growth and caused rapid tumor regression, however, the animal was sacrificed due to loose stools (FIG. 36). Interestingly, the response to treatment in this animal was rapid despite the androgen replete milieu of an intact rat. E.g., FIG. 36A demonstrates that as the tumor began to grow, the serum PSA levels began to rise as shown by the numbers above each time point in the tumor volume graph (left panel in FIG. 36A), however, immediately after initiation of 1002 treatments the PSA levels fell to zero.

Figure 37:
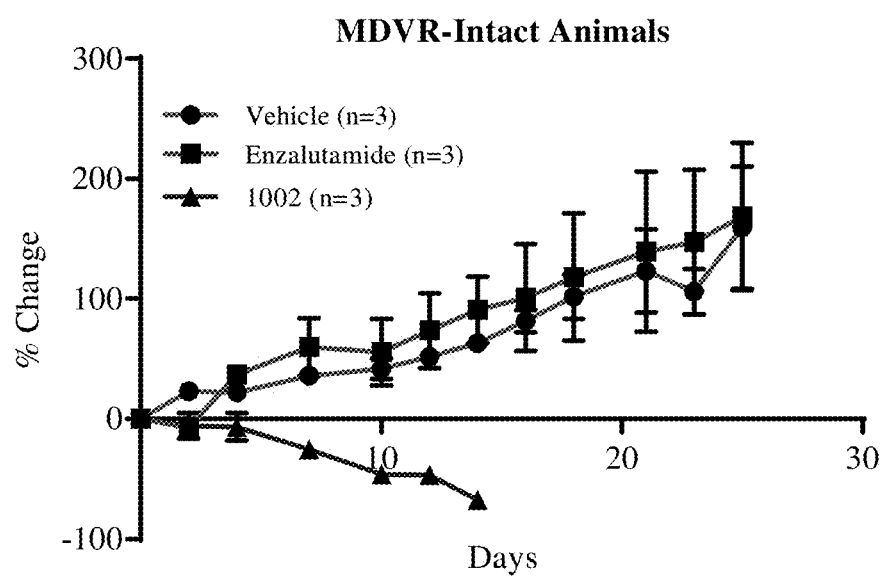
FIG. 37 demonstrates that the experiment, when repeated in multiple (N=3) intact (not cryptorchid) rats, again produces rapid and complete tumor regression with SARD treatment but rapid growth with enzalutamide treatment which was similar to vehicle.

In the right panel of FIG. 36A, serum PSA levels are graphed (number provided on the graph are serum PSA values (ng/mL); blood was obtained weekly and serum separated and stored for PSA analysis; tumor volume was measured thrice weekly) for this animal allowing visualization of the dramatic rise in PSA with tumor growth and rapid PSA response upon initiation around day 58. By comparison in FIG. 36B, vehicle treated and enzalutamide treated animal experienced rapid tumor volume increases. This is preliminary evidence that SARDs of this invention can overcome enzalutamide resistance in the presence of androgens and that the rapid tumor response is based on blocking the AR-axis. This provided the inspiration to test MDVR xenografts in intact animals. The experiment was repeated with three rats per group and the same result was observed. Rapid and robust tumor response in MDVR VCaP tumors in intact rats treated with 1002 and rapid progression in enzalutamide and vehicle treated intact rats (FIG. 37). This is the first evidence that an AR antagonist can inhibit CRPC tumor growth in an intact animal species (rat). This result provides evidence that SARDs of this invention can be used to treat prostate cancer even in the presence of endogenous agonist (i.e., intact animals) which is an unexpected result and differs from the standard of care in which the first pharmacotherapy is typically androgen-deprivation therapy. Although this result is in an enzalutamide resistant CPRC, it provides a basis for testing in early prostate cancers and suggests the possibility of adjuvant or neoadjuvant use of SARDs of this invention in intact men.

MDVR VCaP Xenograft Growth in Castrated Rats:

MDVR VCaP prostate cancer cells were implanted (in combination with matrigel (1:1 mix)) on the flanks subcutaneously in SRG rats (10 million cells/rat). When the tumors reach 300-500 mm$^3$, the animals were castrated and the tumors were allowed to regrow as castration-resistant prostate cancer. When the tumors regrew, the animals were randomized into three groups, vehicle (15% DMSO+85% PEG-300), enzalutamide (30 mg/kg/day), or compound 1002 (60 mg/kg/day). The animals were orally treated and tumor volume and body weight were recorded thrice weekly. Tumor volume or percent change in tumor volume was calculated.

Vehicle-treated tumors grew robustly in castrated environment indicating that the tumors were castration-resistant, i.e., tumor were CRPC. Enzalutamide treated tumors also continued to grow almost comparably to vehicle, while compound 1002 regressed the tumors to inhibited tumor growth significantly (FIG. 38) with tumor at sacrifice (approximately day 26) slightly smaller than at initiation of treatment or ~2000 mm$^3$. By comparison, vehicle and enzalutamide tumor grew by from ~2000 mm$^3$ to ~6000 mm$^3$ or ~200% increased tumor volume. This demonstrated that SARDs of this invention are able to treat antiandrogen resistant castration resistant prostate cancer (MDVR VCaP) which over expresses CYP17A1 such that there is intratumoral androgen synthesis as well. Correspondingly, SARDs of this invention are expected to be able to treat CRPC (and possibly CSPC) including patients that have failed enzalutamide or apalutamide and possibly abiraterone treatments, or patients overexpressing CYP17A1 or AKR1C3.

Example 16

X-Linked Spinal-Bulbar Muscular Atrophy (SBMA) Method

Transgenic mice that express AR121Q (121 polyglutamine repeats instead of the usual 15-24 repeats) will be treated with vehicle or SARD orally. One group of mice will be castrated to serve as positive control as circulating androgens will worsen the SBMA condition. Body weight, composition, and grip strength will be measured before the initiation of the experiment. Animals will be treated and weekly measurements will be performed. Animals will be treated and monitored until they die. AR121Q mice lives only up to 60-80 days and hence evaluating the survival in the presence of SARD treatment is possible.

Example 17

ALS Method

All experiments will be performed in male hSOD1-G93A mice (Jax labs; PMID: 26786249) as a model of anterior lateral sclerosis (ALS). Mice will be randomized and treated with either vehicle or SARD of this invention dissolved in DMSO+PEG-300 (15%+85%). Simultaneously, a group of mice will be castrated and used as positive control as castration has been shown to extend survival and disease duration in this model (PMID: 24630363). Mice will be treated orally every day until they reach morbidity. Weekly body weight and composition by magnetic resonance imaging (MRI) will be recorded. The mice performance will be measured each week by using a grip strength meter (Columbus instruments) or rotarod. Inability for the mice to move will be considered as a terminal disease state and the mice will be sacrificed.

Example 18

1002 as an Orally-Bioavailable Selective Androgen Receptor Degrader: Potential Next-Generation Therapeutic for Enzalutamide-Resistant Prostate Cancer

(Some of the experiments of Example 18 can also be found, in part, in other examples herein such as Examples 1, 3-7, 9-12, 14 and 15, but are presented in a more complete and cohesive fashion in Example 18. Literature references in this section are called out by sequential numbers and listed at the end of Example 18.)

Abstract:

Androgen receptor (AR)-targeting prostate cancer drugs, which are competitive ligand binding domain (LBD)-binding antagonists, are inactivated by common resistance-mechanisms. It is important to develop next-generation mechanistically-distinct drugs to treat castration- and drug-resistant prostate cancers. Here, we have discovered a second-generation AR pan-antagonist (1002) that binds to the activation function-1 domain (AF-1) of the AR and degrades the AR and AR splice variants. 1002 inhibits the wildtype and LBD mutant ARs comparably and inhibits the proliferation and growth of enzalutamide-sensitive and -resistant prostate cancer xenografts. In preclinical models, 1002 regresses enzalutamide-resistant tumors to unmeasurable levels at doses when the AR is degraded but completely inhibits, but not regresses, the tumors at lower doses when the AR is antagonized, and not degraded. This is the first indication that degradation might provide a complete tumor regression. Mechanistically, 1002 promotes a conformation of AR that is distinct from the LBD-binding competitive antagonist, enzalutamide, and degrades the AR through the ubiquitin proteasome mechanism. Early toxicology studies suggest that 1002 is safe and has a broad safety margin. Collectively, 1002 exhibits the properties necessary for a next-generation drug for the treatment of advanced prostate cancer.

Introduction:

About 3.3 million men are surviving with prostate cancer (PCa) in the United States and this number is expected to increase to 4.5 million by 2026 [1]. In addition to radical prostatectomy combined with gonadotrophins, androgen-synthesizing enzyme inhibitor and androgen receptor (AR) antagonists have been the mainstay of PCa treatment paradigm [2, 3]. PCa that progresses after initial treatment choices, called castration-resistant prostate cancer (CRPC), grows rapidly and metastasizes to distant organs [4, 5]. Three targeted treatments, enzalutamide and apalutamide, AR antagonists, and abiraterone, an androgen-synthesizing enzyme inhibitor, which have been approved in the last 5-10 years to combat CRPC, provided clear evidence that the CRPC, despite being castration-resistant, is still dependent on the AR axis for continued growth [2, 3].

About 30-40% of CRPCs fail to respond to enzalutamide or abiraterone [2, 3, 6, 7], while the remaining develop resistance after a brief period of response [8]. Although several potential mechanisms for the resistance development have been identified, mutations in the AR ligand binding domain (LBD) and expression of AR splice variants (AR-SVs) have been broadly shown in the clinic [9, 10]. AR antagonists in the market (enzalutamide and apalutamide) and in clinical trials (darolutamide) are all competitive antagonists and do not mechanistically differ from each other. Abiraterone manipulates the levels of endogenous LBD targeted androgens and is cross-resistant with the enzalutamide conferring point mutations discussed below. Hence, all AR targeted therapy relies on LBD for suppression of the AR-axis.

AR is a member of the steroid receptor family of ligand-activated transcription factors. Structurally, AR, like other steroid receptors, contains an N-terminus domain (NTD) that expresses an activation function-1 (AF-1) domain, a DNA-binding domain (DBD) that recognizes hormone response elements (HREs), a hinge region, and a ligand-binding domain (LBD) that contains an AF-2 [11]. The AF-1 contains two transcription activation regions, tau-1 and tau-5, which retain the majority of the AR function. Drugs that target the steroid receptors act by predominantly binding to the LBD. Prolonged treatment with AR antagonists results in mutations in the LBD, leading to resistance. W741 mutation to leucine or cysteine in the AR leads to resistance to bicalutamide [12], while F876 mutation to leucine confers resistance to enzalutamide and apalutamide [9, 13, 14].

While mutations in the AR LBD can be ideally overcome with antagonists that bind to the LBD in a distinct conformation, resistance due to AR-SVs confers a serious challenge due to the absence of the LBD. Current AR-targeting drugs that bind to the LBD will be unable to inhibit AR-SV function. AR-SVs have been shown to be responsible for aggressive CRPC phenotype, shorter overall survival, and failure of the cancer to respond to AR-targeted treatments or to chemotherapeutic agents [10, 15-18]. Although most of the recent studies on PCa resistance have focused on AR-SVs, activation of other pathways are also considered to play roles in resistance development [19, 20].

Although degraders of estrogen receptor have been successfully discovered [21, 22], for unknown reasons, AR degraders have not been developed yet. Degraders confer added advantage of preventing AR activation by alternate signaling pathways and by intra-tumoral androgens and hence might provide a sustained treatment option for CRPC. As AR and AR-SVs are detected as heterodimer in the clinic, it is believed that degrading the AR could potentially result in AR-SV degradation [23]. Discovery of PROTACs and small molecules from our group has provided some confidence that AR degraders could be developed using alternate strategies [24-27]. Unfortunately, the PROTACs are large molecules with molecular weights greater than 1000 Da and hence might not possess ideal drug-like properties and our first generation molecules have poor oral bioavailability and hence lack drug-like properties. It is also important to develop molecules that bind to domains other than the LBD [26, 28] to inhibit AR-SVs and to overcome resistance due to mutations in the LBD.

Here we report the discovery of a novel small molecule pan-antagonist and degrader, 1002, a second-generation molecule, that binds to the AR, and degrades wildtype, enzalutamide-resistant, and splice-variant ARs. 1002, which possesses appropriate pharmacokinetic (PK) properties, was effective in various in vivo models. 1002 inhibited androgen-dependent tissues such as prostate and seminal vesicles in rats and growth of enzalutamide-resistant CRPC xenografts. 1002 also potently regressed tumors in intact immunocompromised rats, data that has not been observed before with competitive antagonists due to their inability to compete with the abundant circulating testosterone. These data provide the first evidence of the potential of an orally-bioavailable AR degrader in advanced prostate cancer.

Materials and Methods.

Reagents.

The source of the several reagents used in this example has been described previously [26, 27]. $^3$H mibolerone and R1881 were purchased from Perkin Elmer (Waltham, Pa.). Enzalutamide was obtained from MedKoo (Morrisville, N.C.). Dual-luciferase and CellTiter-Glo assay reagents were procured from Promega (Madison, Wis.). AR (N20 and C19), mono- and poly-ubiquitin (SC-8017), and glucocorticoid receptor (GR) antibodies were obtained from Santa-Cruz Biotechnology (SantaCruz, Cali.). AR PG-21 antibody was obtained from Millipore (Burlington, Mass.). Dihydrotestosterone (DHT), dexamethasone, GAPDH antibody, and cycloheximide were procured from Sigma (St. Louis, Mo.). Progesterone receptor (PR) and estrogen receptor (ER) antibodies were obtained from Cell Signaling (Danvers, Mass.). Bortezomib was procured from Selleckchem (Houston, Tex.). AR-V7 antibody and serum PSA kit were procured from Abcam (Cambridge, UK). Lipofectamine and TaqMan primers and probes and real time PCR reagents were purchased from Life Technologies (Carlsbad, Calif.). HA (hemagglutinin) antibody was purchased from Novus Biologicals (Littleton, Colo.). 17-AAG (MedChem Express) and doxycycline were procured from Fisher Scientific (Hampton, N.H.). Liver microsomes were obtained from Xenotech LLC (Kansas city, KS). DAPI was obtained from Vector Laboratories (Burlingame, Calif.). MG-132 was purchased from R&D Systems (Minneapolis, Minn.).

Cell Culture.

LNCaP, PC-3, HEK-293, 22RV1, and COS7 cell lines were procured from the American Type Culture Collection (ATCC, Manassas, Va.). All cells were cultured in accordance to ATCC recommendations. LNCaP cell line stably transfected with doxycycline-inducible AR-V7 was a kind gift from Dr. Nancy L. Weigel (Baylor College of Medicine, Houston, Tex.) [29, 30]. Enzalutamide-resistant MR49F cells were a kind gift from Dr. Martin Gleave (University of British Columbia, Vancouver). Enzalutamide-resistant VCaP cells (MDVR) were licensed from Dr. Donald McDonnell (Duke University, NC). All cell lines were authenticated by short terminal DNA repeat assay (Genetica Cell Line Authentication testing, Burlington, N.C.).

Chromatin Immunoprecipitation Assay (ChIP).

ChIP assays were performed as described previously [26, 31-33] and under the conditions described in the figures. Briefly, proteins were cross-linked to DNA using 1% formaldehyde and incubated at room temperature for 10 min. Medium was aspirated from cell culture dishes and washed twice with ice cold PBS. Cells were lysed in a lysis buffer containing protease and phosphatase inhibitors. DNA was fragmented by sonication using a probe sonicator and the respective proteins were immunoprecipitated with selective antibodies. The protein-antibody complex was pulled down using magnetic beads (Dynabeads, Life Technologies), the complex was reverse cross-linked at 65° C. for 6 hours, and the DNA was purified. Primers and fluorescent probes for realtime PCR were described previously [26, 29, 30].

Gene Expression.

RNA extraction and cDNA preparations were performed using cells-to-ct kit. Gene expression studies were performed using TaqMan probes on ABI 7900 realtime PCR machine.

Growth Assay.

Growth assay was performed using CellTiter-Glo or sulforhodamine blue (SRB) reagents.

Plasmid Constructs and Transient Transfection.

Many plasmids (CMV hAR, AR-LBD, PR, GR, MR, ER, GRE-LUC, CMV-LUC, AR AF-1, and AR NTD plasmids) used in the study were described earlier [26, 32, 33]. Mouse AR, rat GR, GAA (GR-NTD, AR-DBD and AR-LBD), and AGG (AR-NTD, GR-DBD and GR-LBD) were kind gifts from Dr. Diane Robins [34]. Constructs dtau1 (tau-1 deleted AR), dtau5 (tau-5 deleted AR), and AR-NTD-DBD were kind gifts from Dr. Frank Claessens [35, 36]. Transfections were performed using Lipofectamine reagent (Life Technologies, Carlsbad, Calif.).

Competitive Ligand Binding Assay:

Ligand binding assay with purified GST-tagged AR-LBD and $^3$H mibolerone was performed as described previously [26]. Whole cell ligand binding assay was performed using the method described previously [37]. Briefly, COS cells were plated in 24 well plates at 100,000 cells/well in DME+5% csFBS without phenol red medium. Cells were transfected with the indicated amounts of hAR-LBD using lipofectamine reagent. Cells were treated with a dose response of the compounds in the presence of $^3$H mibolerone. Cells were washed four hours after treatment with ice cold PBS and the intracellular proteins and radioactive mibolerone were extracted using ice cold 100% ethanol. Radioactivity was counted using a scintillation counter.

Western Blotting and Immunoprecipitation.

Cells were plated in 60 mm dishes in growth medium. Medium was changed to the respective medium described in the figures and treated with compounds under various conditions. Protein extracts were prepared and Western blot was performed as described earlier [32, 33]. Immunoprecipitation was performed using protein A/G agarose.

Fluorescence Polarization (FP).

FP studies were performed with GST-AF-1 and GST-NTD purified protein as described earlier [28].

1002 NTD Binding Assay.

$^3$H-1002 was synthesized at Perkin Elmer from iodinated 1002 precursor. HEK-293 cells were transfected with 1 µg of the indicated plasmids using lipofectamine. Twenty-four hours after transfection, the cells were fed with growth medium. The cells were harvested 48 hours after transfection and protein was extracted. The protein extract was incubated with 5 µM $^3$H-1002 in an AR-binding assay buffer at 4° C. for 16 hours. The reaction mixture was added to G25 Sephadex column (GE Life Sciences, PD-10 columns Cat. No. 17085101) to separate the unbound radioactive nucleotides from labeled compound bound to the protein. The amount of radioactive material incorporated in the protein was counted using a scintillation counter.

Demonstration of NTD binding proved difficult as chronicled below due to the lack of any precedent regarding how the assay should be formulated and the absence of any high affinity NTD binding ligands to use as standard agents. Finally, the addition of G25 Sephadex column reduced the background (unbound) radiation to allow observation of NTD bound radiation ($^3$H-1002 NTD binding) and its displacements by cold NTD ligand (1002).

Standard NTD ligands need to bind to NTD only (i.e., not LBD also) and bind to NTD reversibly such that it could be displaced. In the absence of any prior art NTD ligand of the above description, $^3$H-1002 was synthesized and used for this purpose even though its properties were not optimal (e.g., NTD binding affinity was not known but not believe to be low nM affinity like LBD standard agents) to serve as a standard agent. Correspondingly, formulating the competitive NTD binding assay still proved difficult. Multiple iterations were required in order to figure out how to produce an assay that reduces the background radiation enough to see NTD binding which multiple biochemical and biophysical methods reported herein all suggest.

Failed Attempts to Demonstrate NTD Binding Using Displacement of $^3$H-1002 Experiment 609. Aug. 24, 2017

COS cells were plated in 24 well plates at 90,000 cells per well in DMEM+5% charcoal stripped-fetal bovine serum (csFBS) without phenol red. After overnight, changed medium to OptiMEM (0.25 ml). The cells were transfected with vector, AR-LBD, AR-NTD, or full length AR. The cells were treated with $^3$H-1002 for 48 h after transfection and were harvested 4 h after treatment. After incubation, the cells were washed 3 times with ice cold PBS to remove unbound hormone. Bound hormone was extracted using 100% ice-cold ethanol, and counted on Beckman scintillation counter (Alaina James, Weigel, *Mol Endo* paper on A748T mutation). $10^{\wedge}-5$ M=3.1 µL/0.5 mL medium.

Reason for Failure.

High background precluded the detection of any binding.

Experiment 625. Sep. 21, 2017

HEK-293 cells were plated in 60 mm dishes at 2 million cells per dish in DMEM+5% csFBS without phenol red. After overnight, medium was changed to OptiMEM (1 mL). The dishes were transfected vector or AR full length. The cells were treated with 10 µM $^3$H-1002 for 24 hrs after transfection and were harvested 4 h after treatment, and immunoprecipitated with the AR antibody (AR PG 21) was performed. Gel was run and the gel piece between 70 and 120 kDa was cut and counted in a scintillation counter.

Reason for Failure.

High background precluded the detection of any binding.

Experiment 640. Oct. 2, 2017

HEK-293 cells were plated in 60 mm dishes at 2 million cells per dish in DMEM+5% csFBS without phenol red. After overnight, medium was changed to OptiMEM (1 mL). The dishes were transfected with either vector or full length AR. The cells were treated with $^3$H-1002 24 h after transfection and were fixed with 4% formaldehyde for 2 h after treatment, harvested, and immunoprecipitated with AR antibody (AR PG 21) was performed. The immunoprecipitated beads were counted in a scintillation counter.

Reason for Failure.

High background precluded the detection of any binding.

Experiment 647. Oct. 7, 2017

HEK-293 cells were plated in 60 mm dishes at 2 million cells per dish in DMEM+5% csFBS without phenol red. After overnight, medium was changed to OptiMEM (1 mL). The dishes were transfected with either vector or full length AR. The cells were treated with $^3$H-1002 alone or in combination with 100 fold excess of cold 1002 or R1881 (in order to reduce the counts to prove that there is binding) 24 h after transfection and were fixed with 4% formaldehyde for 2 h after treatment, harvested, and immunoprecipitated with AR antibody (AR PG 21) was performed. The immunoprecipitated beads were counted in a scintillation counter.

Reason for Failure.

No binding detected

Experiment 652. Oct. 12, 2017

HEK-293 cells were plated in 150 mm dishes at 5 million cells per dish in DMEM+5% csFBS without phenol red. After overnight, medium was changed to OptiMEM (10 mL). All the dishes were transfected with AR full length. Twenty four hours after transfection, medium was changed to DME+5% csFBS without phenol red and were allowed to incubate for 24 hours. Cells were harvested 48 h after transfection, protein extracted, and the protein extracts were used for in vitro binding assay with $^3$H-1002.

Binding Assay.

(a) Incubated the protein extract with $^3$H-1002 alone or in combination with cold compounds at 4° C. on ice for 16 h.

(b) 200 µL hydroxyapatite was added, vortexed, and incubated on ice for 30 min. Centrifuged at 2000 g for 5 min.

(c) Washed 3× with Tris buffer (50 mM pH 7.4). Vortexed after each wash and centrifuged at 2000 g for 5 min.

(d) Eluted with 1 mL of 100% cold ethanol. Incubated at room temperature for 30 min.

(e) Centrifuged and added the supernatant to scintillation vials with 10 mL scintillation cocktail and counted.

Results. No binding was detected

Experiment 684. Nov. 26, 2017

COS cells were plated in 24 well plates at 90,000 cells per well in DMEM+5% csFBS without phenol red. After overnight, change medium to OptiMEM (0.25 mL). The cells were transfected with vector, AR full length, or AR-LBD. The cells were treated with $^3$H-1002 or $^3$H-mibolerone for 24 h after transfection and were harvested 4 h after treatment. The cells were washed 3 times with ice cold PBS to remove unbound hormone. Bound hormone was extracted using 100% ice-cold ethanol, and counted on Beckman scintillation counter (Alaina James, Weigel, *Mol Endo paper on A*748T mutation). $10^{\wedge}-5$ M=3.1 ul/0.5 ml medium.

Results.

While $^3$H-mibolerone showed binding to both AR-LBD and AR full length, $^3$H-1002 failed to bind to either construct. In view of the absence of standard ligand and the absence of known methodology, the composition of matter of $^3$H-1002 and its use for detecting NTD binding are regarding as non-obvious and outside the skill of the ordinarily skilled artisan.

Thermal-Shift Assay.

Thermal-shift assay was performed using InCell pulse kit from DiscoverX (Fremont, Calif.; Cat. No. 94-4007). AR-NTD and AR-LBD were cloned in-frame into pICP-ePL-N and pICP-ePL-C vectors. The plasmid constructs were evaluated for their activity. The N vector plasmids provided the optimum activity and hence were selected for the assays. Forty µL of transfected cells (5000 cells) in assay medium were added to each well of a 96 well plate. Cells were treated with compound or vehicle, and incubated for 1 h at 37° C. with 5% $CO_2$ incubator. Then cells were incubated for 3 minutes with gradient temperature from 39 to 59° C. in a thermocycler to identify thermal denaturation temperatures for the sensitive detection of cellular target engagement. Forty µL of assay reagent, which contains the enzyme acceptor, lysis buffer and substrate were added to each well and incubated for 60 minutes at room temperature. The samples were read on a luminometer at 1.0 seconds per well.

Microarray.

MR49F cells were maintained in 1% charcoal-stripped serum-containing medium for 2 days. Medium was changed again and the cells were treated with vehicle, 0.1 nM R1881 alone, or in combination with 10 µM 1002 (n=3-4/group). Twenty four hours after treatment, the cells were harvested, RNA was extracted, and was subjected to microarray analysis (University of Tennessee Health Science Center (UTHSC) Molecular Resources Center). Clariom S array was processed as described previously [26] and the data was analyzed using One Way ANOVA. Genes that were 1.5 fold different from the comparator group and a false discovery rate (FDR) with q<0.05 were considered for further analysis. Ingenuity Pathway Analysis (IPA) was performed to determine the canonical pathway and the diseases represented by the enriched genes.

Mice Xenograft Experiment.

All animal studies were conducted under UTHSC animal care and use committee (ACUC) approved protocols. NOD SCID Gamma (NSG) mice were housed as five animals per cage and were allowed free access to water and commercial rodent chow. Cell line xenografts were performed as previously published [33, 38]. LNCaP enzalutamide-resistant (MR49F) cells were implanted subcutaneously in intact mice (n=8-10/group). Once the tumors reach 100-200 mm$^3$, the animals were castrated and the tumors were allowed to regrow as castration-resistant tumors. Once the tumors reach 200-300 mm$^3$ post castration, the animals were randomized and treated orally with vehicle (polyethylene glycol-300: DMSO 9:1 ratio) or 1002. Tumors were measured twice to thrice weekly and the volume was calculated using the formula length*width*width*0.5236. Animals were sacrificed at the end of the study and the tumors were weighed and stored for further processing.

Rat Xenograft Experiments.

Rat xenograft experiments were performed in SRG (Sprague Dawley-Rag2:IL2rg KO) rats at Hera Biolabs (Lexington, Ky.). Rats were inoculated subcutaneously with 10 million cells in 50% matrigel. Once the tumors reached 1000-2000 mm$^3$, the animals were either randomized and treated (intact) or were castrated and the tumors were allowed to grow as CRPC. Once the tumors attain 2000-3000 mm$^3$, the animals were orally treated as indicated in the figures. Tumor volumes were recorded thrice weekly. Blood collection and body weight measurements were conducted weekly once. At sacrifice, tumors were weighed and stored for further analyses.

Hershberger Assay.

Male mice or rats (6-8 weeks old) were randomized into groups based on body weight. Animals were treated orally as indicated in the figures for 4 or 13 days. Animals were sacrificed, prostate and seminal vesicles were weighed, and represented as organ weights normalized to body weight.

Metabolic Stability.

Metabolic stability studies in microsomes from various species were conducted as described previously [26].

Statistics.

Statistical analysis was performed using Graphpad prism software. T-test was used to analyze data from experiments containing two groups, while One Way analysis of variance (ANOVA) was used to analyze data from experiments containing more than two groups. Appropriate post hoc test was used to analyze data that demonstrated significance in ANOVA. Statistical significance are represented as * p<0.05;  p<0.01; * p<0.001.

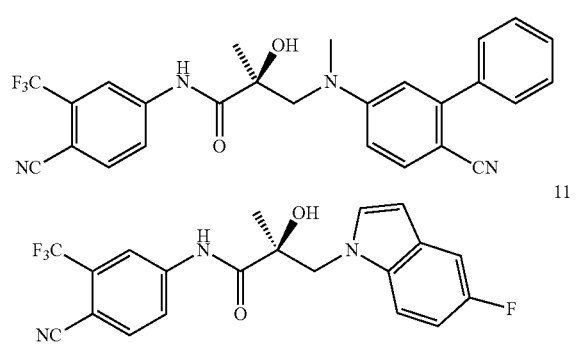

Figure 39A:
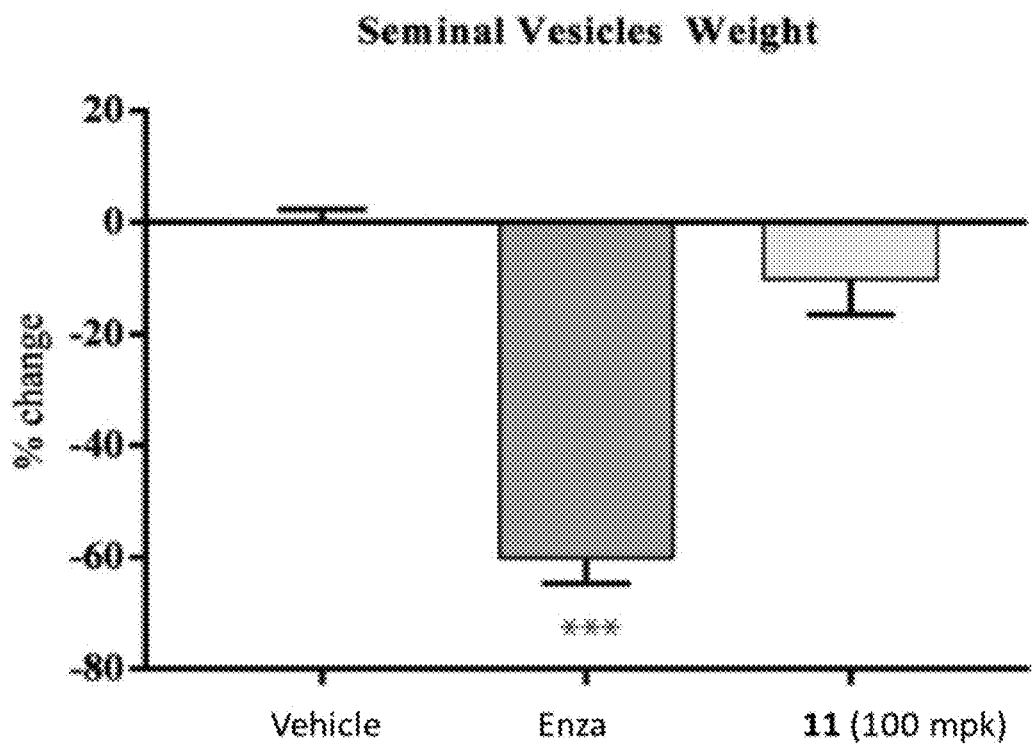
FIGS. 39A-39C demonstrate that 11 has poor metabolism and oral pharmacodynamic properties.
Figure 39B:
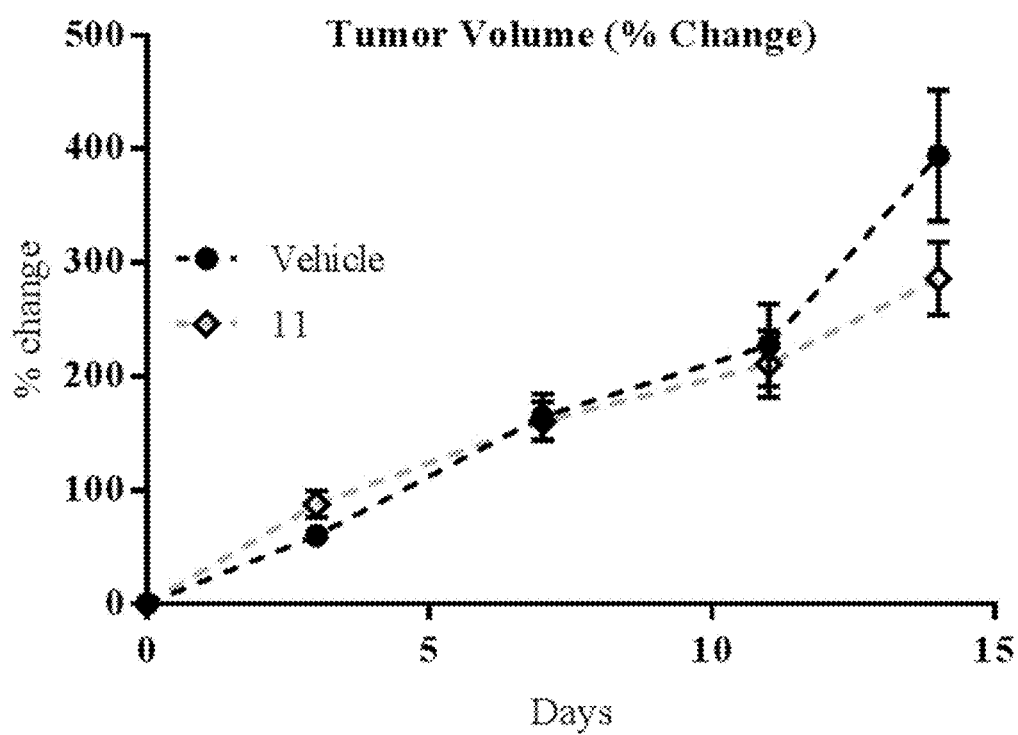
Figures 39C, 40A:
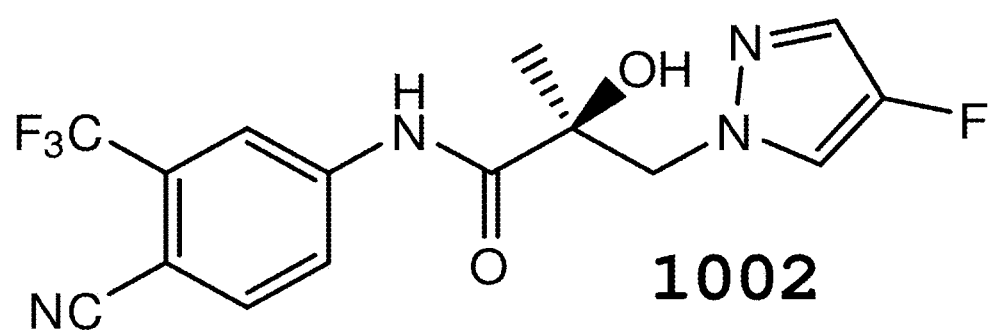
FIGS. 40A-40C demonstrate the structure and properties of 1002.

Results:

Our first generation SARDs, 17 and 11, were excellent degraders with unique mechanistic properties [26]. Unfortunately, their pharmacokinetic (PK) properties were not appropriate for further development. Oral administration of 11 in rats for 14 days failed to significantly inhibit the seminal vesicles weight (FIG. 39A) at 100 mg/kg, while in LNCaP xenograft tumor-bearing NSG mice failed to inhibit the tumor growth (FIG. 39B). Mouse and human liver microsomes data also show rapid clearance and short half-life (FIG. 39C). Hence, we continued our pursuit to develop molecules, that retain the degradation and antagonistic characteristics of the first generation molecules but will have better PK properties. 1002 (FIG. 40A) satisfies these requirements and was selected from a library for further characterization. Moreover, we focused on enzalutamide-resistant CRPC models with a view to develop it for enzalutamide-resistant CRPC and these tumors tend to be pan-resistant and untreatable.

1002 Inhibits Wildtype and Mutant ARs Comparably.

Figure 40B:
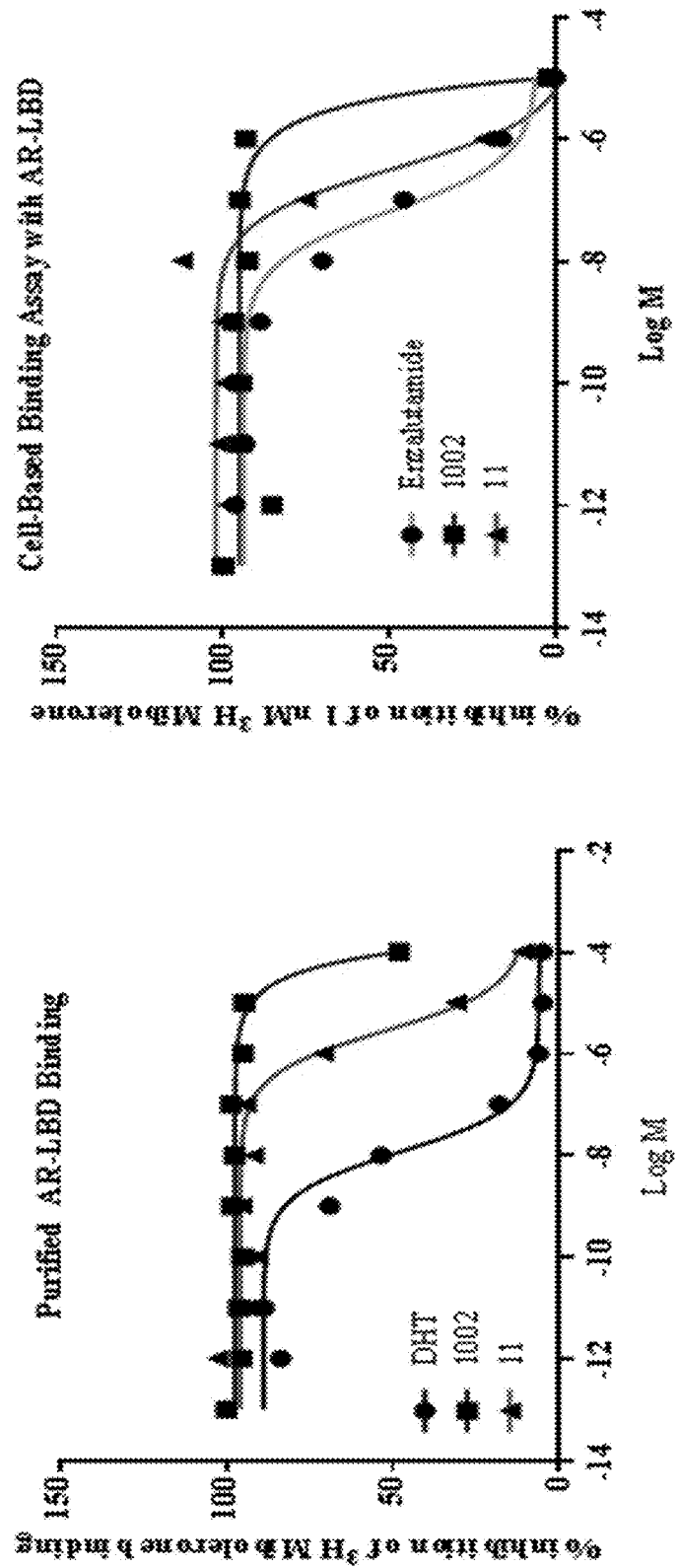

1002 was first tested in a binding assay using in vitro purified AR-LBD binding assay [26]. 1002 failed to bind to the purified AR-LBD and displace 1 nM $^3$H mibolerone (FIG. 40B left panel). To verify the result obtained in purified AR-LBD, we performed whole cell ligand binding assay in COS cells transfected with AR-LBD and treated with a dose response of 1002 in combination with 1 nM $^3$H mibolerone. 1002 displaced $^3$H mibolerone, although its binding was much weaker (inhibition observed only at 10 µM) than that of enzalutamide or 11 (FIG. 40B). The conflicting result between purified AR-LBD and whole cell binding assays could be due to many possibilities that include potential stabilization of the 1002-AR-LBD complex by intracellular factors or faster on-off rate of 1002 in the ligand binding pocket in the absence of stabilization factors precluding detection of binding, or requirement of additional factors to bind to the AR-LBD. These questions need to be resolved in future studies.

Figure 40C:
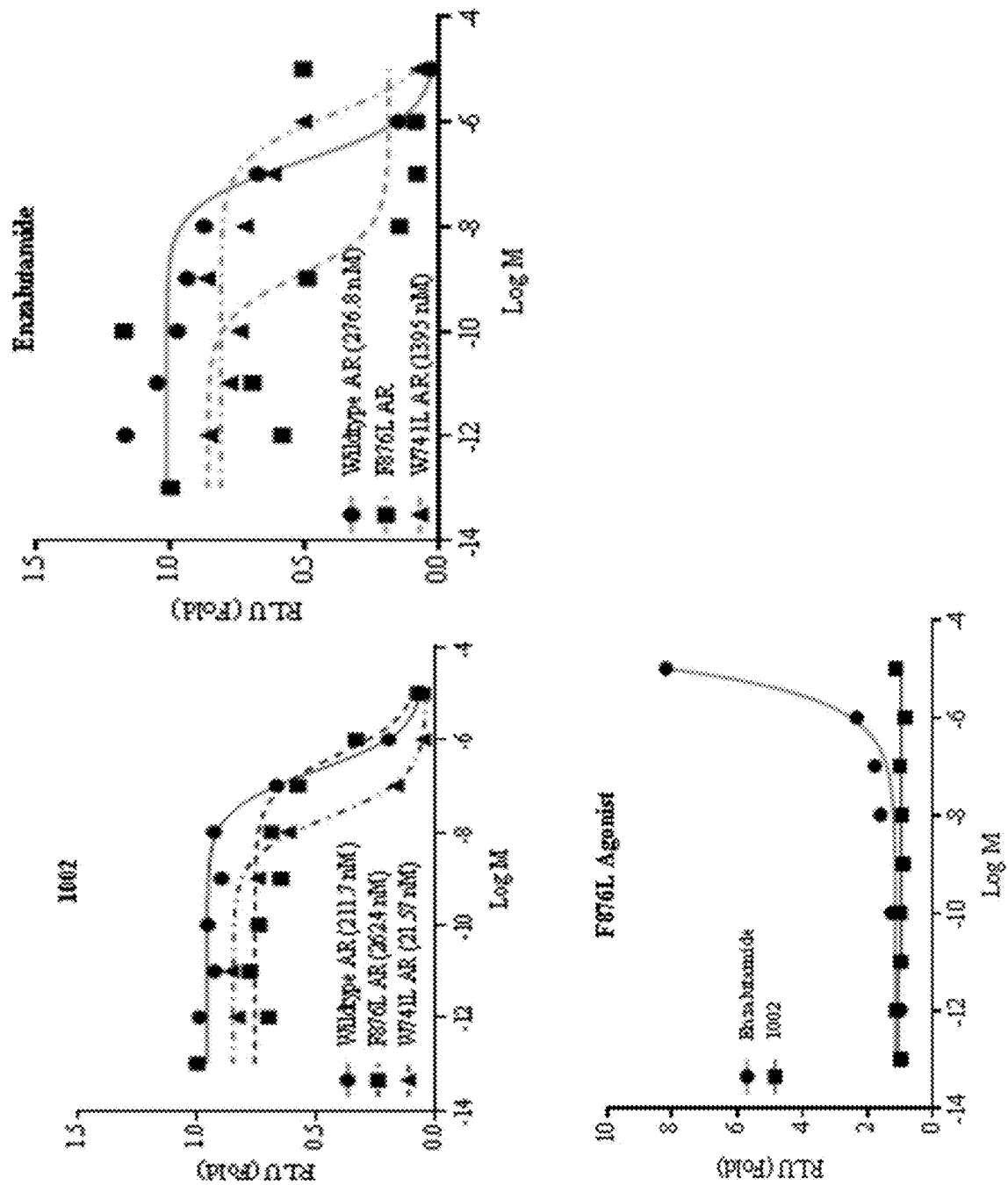

We next determined the antagonistic property of 1002 in wildtype and LBD mutant ARs and compared the results to the effect of enzalutamide (FIG. 40C and Table 5). COS cells were transfected with wildtype or mutant ARs, GRE-LUC, and CMV-renilla LUC and a luciferase assay was performed. 1002 antagonized the wildtype AR with IC$_{50}$ around 200 nM, while enzalutamide antagonized around the same concentration. 1002 comparably or with better IC$_{50}$ inhibited the various mutant ARs (W741L, T877A, and F876L). Enzalutamide was weaker in W741L by 4-5 fold, and behaved as an agonist in F876L AR as reported earlier [9, 14].

TABLE 5

Binding, pan-antagonism of AR and steroid receptor antagonistic selectivity of 1002.

| | | Transactivation (IC$_{50}$nM) | | | | |
|---|---|---|---|---|---|---|
| | Ki (nM) | AR | T877A | W741L | PR | GR µM | MR µM |
| 1002 | N.B | 203.46 | 80.78 | 94.17 | 1092 | >10 | >10 |
| Enza | >1000 | 183.41-374.62 | 54.91 | 619.73 | 196.97 | >10 | >10 |

Binding of 1002 to purified AR-LBD was determined by cell-free competitive radiolabeled binding assay. Transactivation assays were performed using wildtype or mutant ARs, and PR, GR, or MR. Cells were transfected with the indicated receptors, GRE-LUC, and CMV-renilla LUC. Cells were treated with a dose response between 1 pM and 10 µM and luciferase assay was performed 24 h after treatment. N.B. No binding. AR-androgen receptor; PR-progesterone receptor; GR-glucocorticoid receptor; MR-mineralocorticoid receptor; T877A-Threonine 877 of AR mutated to alanine; W741L-tryptophan 741 of AR mutated to leucine.

1002 Degrades Wildtype and F876L Enzalutamide-Resistant ARs.

As the objective was to develop degraders of the AR, Western blot was used as a screening tool in our discovery paradigm. We tested the effects of 1002 on AR protein level in LNCaP cells and in enzalutamide-resistant MR49F cells. LNCaP or MR49F maintained in charcoal-stripped serum-containing medium were treated with a dose response of 1002 in the presence of 0.1 nM R1881 for 24 h. Cells were harvested, protein extracted, and Western blot for AR was performed. Treatment of LNCaP cells with 1002 resulted in a reduction of the AR levels in LNCaP cells with down-regulation observed at 1000 nM (FIG. 41A left panel). While 1002 resulted in a down-regulation of the AR, enzalutamide and bicalutamide failed to down-regulate the AR in LNCaP cells (FIG. 41A right panel). These effects occurred without an effect on AR mRNA expression (FIG. 41A bottom panel). Similar to the LNCaP cells, MR49F cells treated with 1002 exhibited a significant reduction in AR levels at around 1000 nM that is comparable to that observed in LNCaP cells (FIG. 41B).

To demonstrate the selectivity of 1002 to AR, the compound was tested in various cross-reactivity experiments. While 1002 and enzalutamide failed to inhibit the transactivation of GR and mineralocorticoid receptor (MR) (Table 5), it inhibited PR activity by a 4-5 fold weaker potency compared to the AR antagonistic activity.

Figure 41C:
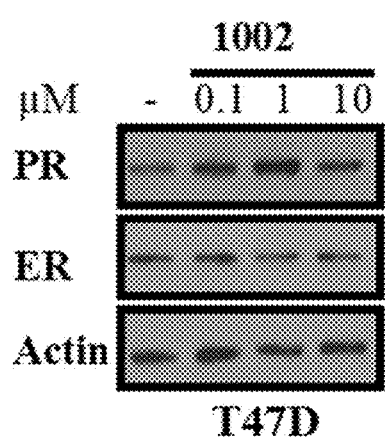

To determine the degradation cross-reactivity of 1002, we used various breast cancer cell lines that express AR and other receptors. T47D cells that express ER and PR, but not AR (although some reports suggest that T47D cells express AR [39, 40], our clone does not express AR), was used to evaluate the cross-reactivity of 1002. T47D cells were maintained and treated similar to that described in FIGS. 41A and 41B and Western blot for ER, PR, and actin was performed. 1002 failed to down-regulate the ER and PR protein levels (FIG. 41C).

Figure 41D:
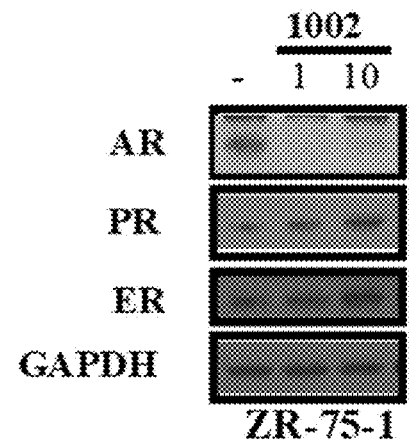

To evaluate the cross-reactivity in a system that expresses all three receptors (AR, PR, and ER), we used ZR-75-1 breast cancer cells. ZR-75-1 cells express all three receptors and the receptors are functional [41]. Treatment of ZR-75-1 cells with 1002 resulted in down-regulation of AR protein levels, but not ER or PR levels (FIG. 41D). This confirms that under similar condition 1002 is selective to AR and does not degrade other receptors. These results were reproduced in MDA-MB-453 breast cancer cells that express AR and GR [42, 43], which again shows the down-regulation of AR, but not GR, by 1002 (data not shown).

Figure 41E:
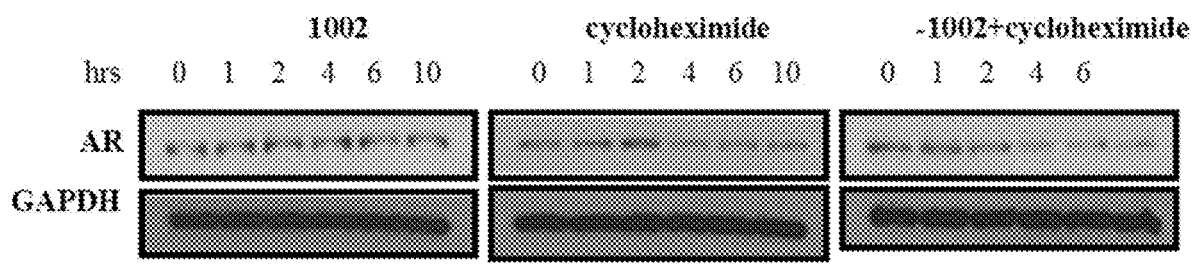

Constant protein synthesis will make it difficult to visualize protein down-regulation. To determine if the observed decrease in AR levels in response to 1002 is a result of accelerated degradation, LNCaP cells maintained in full-serum-containing medium were treated in a time-course with 1002, protein synthesis inhibitor, cycloheximide, or a combination of cycloheximide and 1002. Treatment of LNCaP cells in 10% serum-containing condition with 1002 did not decrease the AR levels by 10 h of treatment initiation. Cycloheximide treatment resulted in a modest reduction in AR protein levels by 8-10 hours (FIG. 41E). However, when LNCaP cells were treated with a combination of 1002 and cycloheximide, a significant decrease in the AR protein levels was observed as early as 4-6 hours. The half-life of AR was reduced by 1002 from 10 h (cycloheximide alone) to about 6 h (cycloheximide plus 1002). These results show that the loss of protein in response to 1002 is a result of enhanced degradation.

1002 Requires Ubiquitin Proteasome Pathway to Degrade the AR.

To determine if 1002 ubiquitinates the AR, cells were transfected with AR and HA-tagged ubiquitin and treated with 11 or 1002 in the presence of 0.1 nM R1881. 11 was used as positive control in these experiments. Ubiquitin was immunoprecipitated using HA antibody and Western blot for AR was performed. Western blot for AR with non-immunoprecipitated samples shows that both 11 and 1002 downregulated the AR (FIG. 41F). When ubiquitin was immunoprecipitated and AR was detected, the AR was both mono- and poly-ubiquitinated by 1002 and 11. The results were reproduced in LNCaP cells treated with 11 or 1002 and AR was immunoprecipitated and Western blot for ubiquitin was performed (FIG. 41G). Proteasome inhibitor MG132 but not the HSP90 17AAG, enriched the ubiquitinated AR in cells treated with 1002 or 11.

The requirement of proteasome pathway for 1002 to down-regulate the AR was determined by treating LNCaP cells with 1002 and cycloheximide alone or in combination with a dose response of proteasome inhibitor bortezomib. 1002 and cycloheximide combination down-regulated the AR and this down-regulation was reversed dose-dependently by bortezomib starting from 5 µM (FIG. 41H). These results suggest that 1002 requires ubiquitin proteasome pathway to degrade the AR.

We mutated the three known ubiquitin sites in AR (K313, K846, and K848) to arginine (R) and performed Western blots with protein extracts from cells transfected with the wildtype and mutant ARs and treated with 1002. 1002 continued to degrade the wildtype and K-R mutant ARs comparably, indicating that the known ubiquitin sites do not have a role in 1002-dependent ubiquitin proteasome degradation.

1002 Binds to AR AF-1 Domain.

Figure 42A:
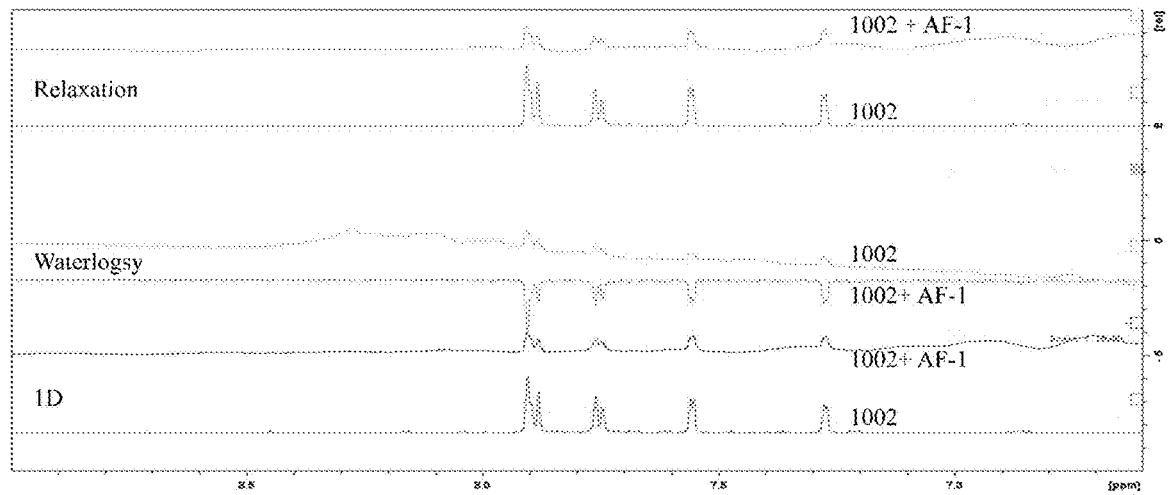
FIGS. 42A-42B demonstrates that 1002 interacts with AR AF-1 domain.

As molecules of this scaffold uniquely bind to two domains (LBD and AF-1) [26], we evaluated 1002 in various biophysical assays for its binding to the AF-1 domain. Earlier studies have used NMR to determine the interaction between small molecules and large proteins [26, 44, 45]. $^1$H NMR was utilized to evaluate the interaction of 1002 with AR AF-1. 1002 (250 µM) was dissolved in deuterated DMSO-d6 and was incubated alone or mixed with 5 µM GST-AF-1 and the binding of the molecule to the AF-1 was determined by NMR. 1002 in combination with AF-1 provided broad, diffused, and shorter ligand peaks (FIG. 42A) compared to 1002, revealing that 1002, similar to 11 [26], has affinity for AF-1. To further confirm the $^1$H NMR results, we performed WaterLOGSY with 1002 alone or in combination with AF-1. 1002 in combination with AF-1 provided a negative signal, characteristic of binding to the protein (FIG. 42A).

Figure 43A:
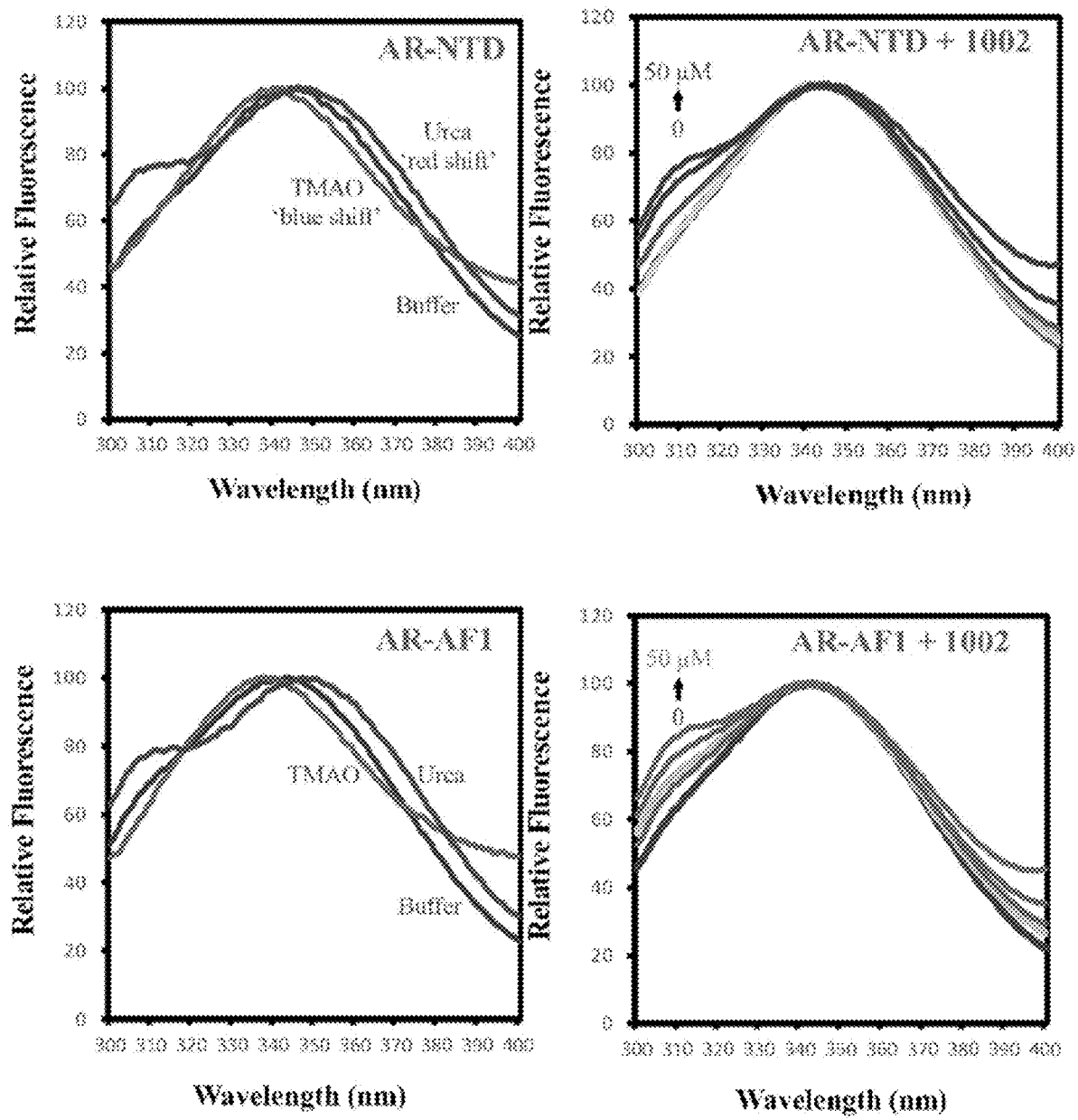
FIGS. 43A-43C demonstrates that 1002 interacts with the activation function 1 (AF-1) domain of the AR.

We performed fluorescence polarization studies with 1002 to confirm the binding observed with NMR. 1002 was incubated with AR-NTD or AR-AF-1 and the steady state fluorescence spectra was obtained [46]. 1002 bound to the AR AF-1 and AR NTD (FIG. 43A) as evident from the shift in the fluorescence peak, reproducing the results obtained with NMR. Unlike the data shown with 11 [26], no clear quenching of the AR polypeptides fluorescence was observed with 1002. Previously, quenching was used as an evidence of small molecule binding to the AR-NTD or AF-1 regions. 1002 showed a dramatic increase in the fluorescence signal in the region seen for tyrosine emission (307 nm). Normally, tyrosine signal is not observed due to energy transfer to tryptophan residues due to folded/partially folded polypeptides. The increase in the tyrosine signal is similar to that seen when AR-NTD or AR-AF-1 unfolds/denatures. However, there is no corresponding 'red shift' (increase in wavelength) in the tryptophan signal (in urea $\lambda_{max}$ 344 nm to 347 nm). Although it is difficult to interpret, it might be possible that 1002 may unfold the receptor polypeptides (resulting in tyrosine emission), but shields the tryptophan residues.

Raman Spectroscopy Confirms an Interaction Between 1002 and AF-1.

Figure 42B:
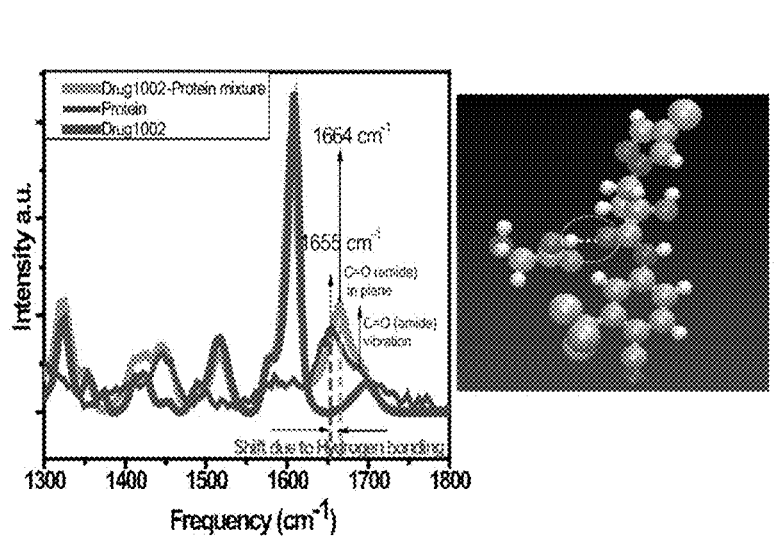

It is well-known that establishing the interaction between the small molecules and the respective protein whether it is intramolecular hydrogen bonding or van der Waals interactions always leads to a change in the electronic structure of the reactants. This can be followed by Raman spectroscopy. FIG. 42B presents Raman spectra of AF-1, 1002, and their mixture. Raman spectrum of protein contains well pronounced peak at ~1650 cm$^{-1}$ which corresponds to in plane stretch of C=O bonds. This peak corresponds to so-called Amide I bond due to the formation of secondary structure in protein. When 1002 was mixed with AF-1, we observed a red shift in the position of this peak. The obtained significant shift of ~10 cm$^{-1}$ suggests that 1002 addition leads to a change in electron distribution in AF-1, which is likely due to their interaction. Shift in band associated with the stretch of C=O bond is usually associated with formation of hydrogen bonds.

To understand the nature and strength of this interaction further we performed DFTB theoretical calculations of electron density. DFTB calculations revealed that there are two possible isomeric structures of 1002 which was determined by cis or trans configurations of C=O and N—H groups in its structure. The snapshot of interaction between 1002 and amino acid glycine is presented in FIG. 42B. Hydrogen bonds are formed between C=O on 1002 and —OH group of glycine. The same carbonyl group in 1002 structure participates in the formation of hydrogen bonds with other amino acids. Thus, the selective red shift of C=O bond observed in the Raman experiment can be directly related to the formation of hydrogen bond. To understand the strength of interactions between 1002 and different amino acids, the binding energies for 1002 and individual amino acids were calculated and results are presented in the table in FIG. 42B. Among all amino acids, 1002 strongly interacts with that tyrosine, phenylalanine, and serine.

Radioactive 1002 Confirms the Binding of 1002 and Conformation Change of AR NTD.

Figure 43B:
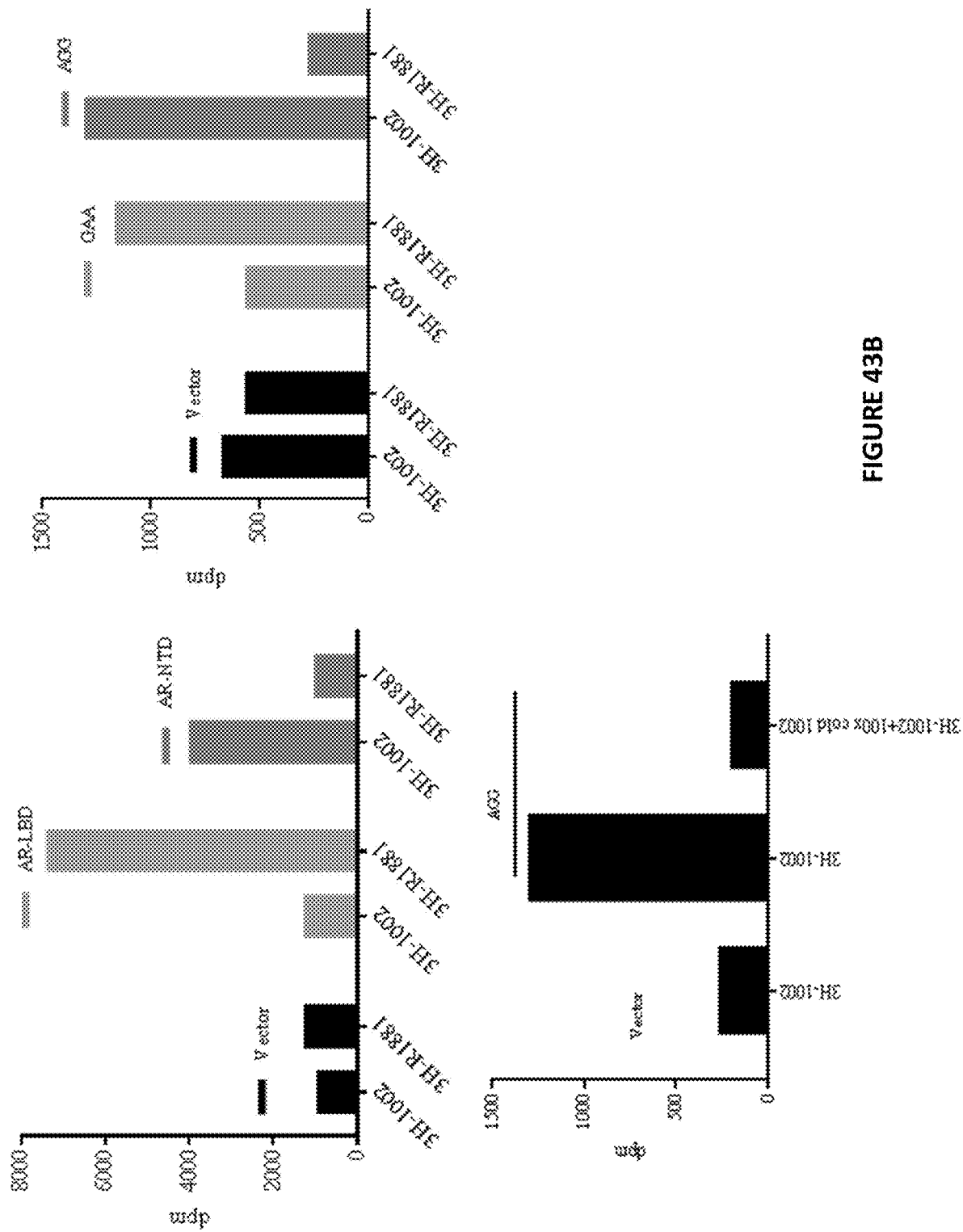

Although various biophysical methods indirectly indicate the interaction of 1002 with the NTD of the AR, we sought to determine the direct binding of 1002 with the NTD. In order to accomplish this, we custom-synthesized $^3$H 1002. Since the binding to AF-1 domain in the micromolar doses, we realized that it is difficult to obtain meaningful results due to high background radioactivity. This was solved by adopting a procedure published to discover CBP inhibitor, ICG-001 [47] where G-25 columns were used to reduce the background radioactivity due to unbound tritium. Protein extracts from cells transfected with vector did not show any binding with either $^3$H-1002 or $^3$H-R1881, while protein extracts from cells transfected with AR-LBD demonstrated binding with $^3$H-R1881, but not $^3$H-1002. Protein from cells transfected with AR-NTD demonstrated a binding to $^3$H-1002, but not $^3$H-R1881 (FIG. 43B).

In order to confirm the results, HEK-293 cells were transfected with vector or chimeric constructs, AGG, which expresses AR-NTD, GR-DBD and LBD, or GAA that expresses GR-NTD, AR-DBD and LBD. $^3$H-1002 bound to AGG, but not to GAA, while $^3$H-R1881 bound to GAA, but not AGG (FIG. 43B). Finally, AGG transfected cell extracts were incubated with $^3$H-1002 in the presence or absence of 100-fold excess of cold 1002. $^3$H-1002 bound robustly to AGG, which was competed off by excess cold 1002 (FIG. 43B). These results confirm the direct binding of 1002 to the NTD of AR.

Thermal-Shift Assay Confirms the Conformational Change of AR-NTD in the Presence of 1002.

Cellular thermal-shift assay (CETSA) was recently developed to detect the binding of molecules to targets in cells [48]. The principle for this assay is based on ligand-bound thermal stabilization of proteins, wherein the target-protein's conformation changes when bound by a ligand and will be less susceptible to temperature-induced denaturation. Although this procedure was developed for Western blot, DiscoverX kit uses luminescence to detect the denaturation, providing a dynamic range. This assay measures the binding of compounds to a cellular target by detecting changes in protein thermal-stability. Assay applies enzyme fragment complementation technology utilizing β-Galactosidase split into two inactive fragments, the enhanced ProLabel (ePL) peptide and the enzyme acceptor (EA) that associates to form a fully active β-Galactosidase enzyme.

Figure 43C:
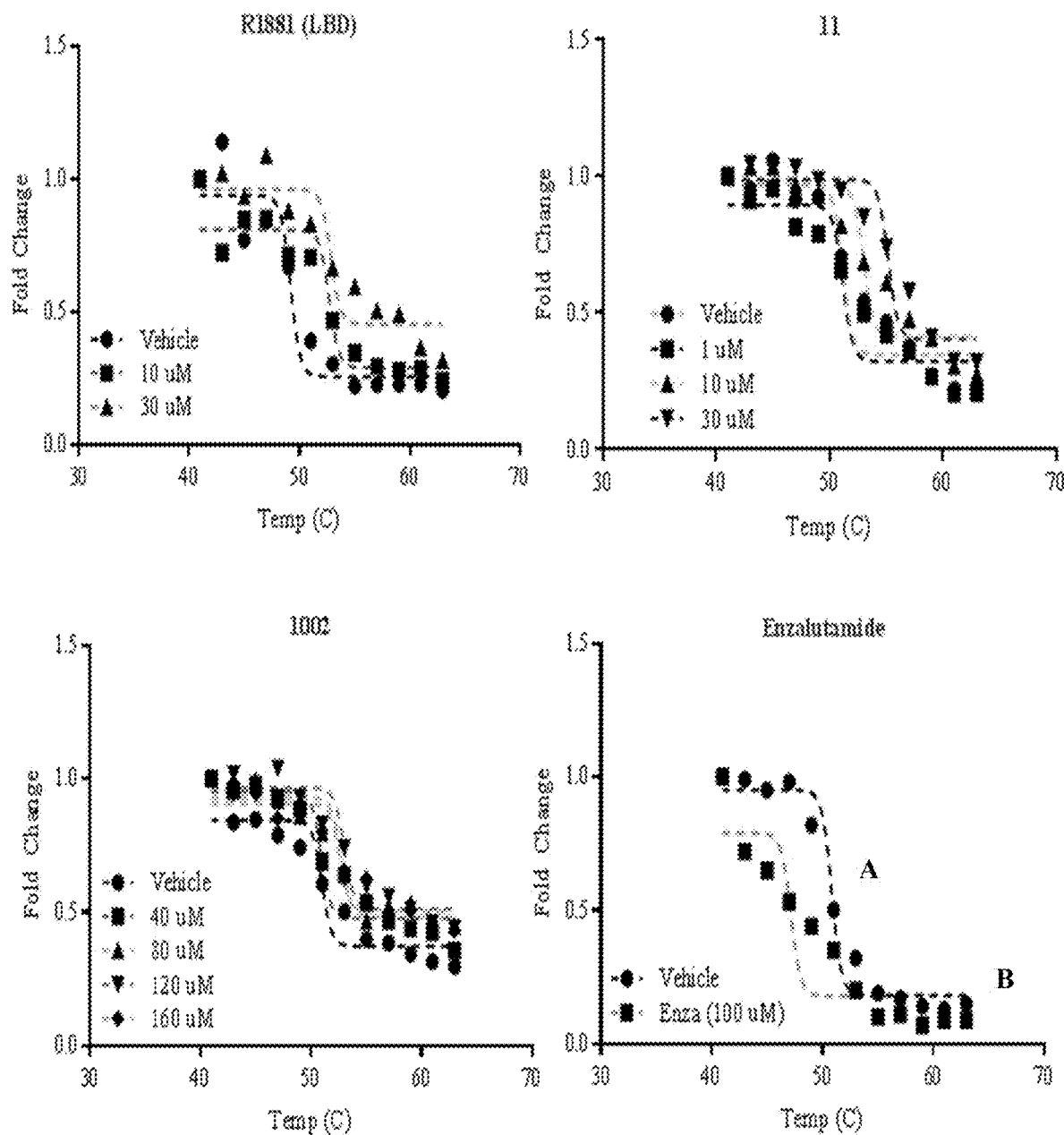

AR-LBD transfected showed stabilization in the presence of R1881, while AR-NTD showed stabilization in the presence of 11. This confirms the binding of 11 to the AR-NTD that was shown previously by various biophysical methods [26]. 11 bound to the AR-NTD starting at 10 μM (FIG. 43C). 1002 demonstrated binding to the AR-NTD and increased the stability of the protein. However, 1002 exhibited the binding only starting from 80 μM, indicating that it interacts with the AR-NTD weaker than that of 11. Enzalutamide, as expected, failed to stabilize the AR-NTD (FIG. 43C).

N-Terminus Domain (NTD) of the AR is Required for 1002-Dependent Degradation.

Figure 44C:
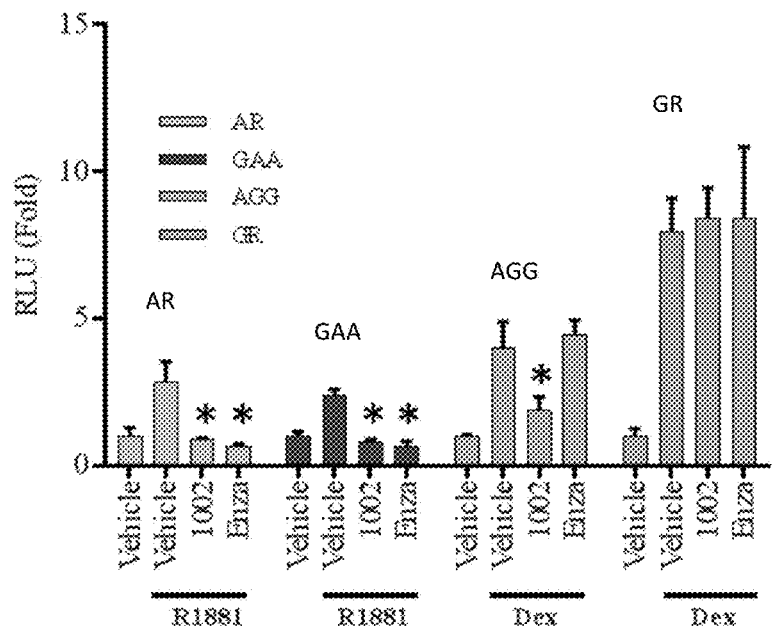

As 1002 binds to both LBD and AF-1 and also degrades the AR, we sought to determine the domain that is required for 1002 to degrade the AR. Since 1002 selectively degraded the AR and not the GR, we obtained AR-GR chimeric receptors to evaluate the domain(s) important for the degradation. AR, GR, or AR-GR chimeric receptors (FIG. 44A) were transfected into cells and the cells were treated with 1002 in the presence of the respective hormones. As shown earlier, 1002 degraded the full length AR, but not the GR (FIG. 44B). 1002 also degraded the chimeric protein obtained from fusing AR-NTD to GR DBD and LBD (AGG), but failed to degrade the chimeric protein obtained from fusing GR-NTD to AR-DBD and AR-LBD (GAA). These results suggest that 1002 potentially requires NTD to degrade the AR (FIG. 44B).

Since AR is degraded by ubiquitin-proteasome pathway (FIGS. 41F-H), AGG was tested to see if it is still ubiquitinated by 1002. COS cells transfected with HA-tagged ubiquitin and AR or AGG were treated with vehicle or 10 μM 1002 in the presence of the respective hormones. Protein extracts were immunoprecipitated with HA antibody and Western blotted with the AR antibody. Interestingly, 1002 increased the mono- and poly-ubiquitinated proteins of AGG (FIG. 44B lower blot), indicating that the N-terminus of the AR is important for the ubiquitination process in the presence of 1002.

To determine if the degradation of the AR fusion protein AGG also translates into antagonistic effects, AR, GR, GAA, and AGG were transfected into cells in combination with GRE-LUC and CMV-renilla LUC and the cells were treated with vehicle, 1002 or enzalutamide in the presence of the respective hormones. Luciferase assay performed 48 h after treatment indicated that while both 1002 and enzalutamide antagonized the AR and GAA, due to competitive antagonism, but not GR (FIG. 44C), only 1002 antagonized the transactivation of AGG induced by dexamethasone due to potential down-regulation of the AR-NTD. These results are in concordance with the Western blot results.

Tau5 Domain of AF-1 is Required for 1002-Dependent AR Degradation.

Figure 44D:
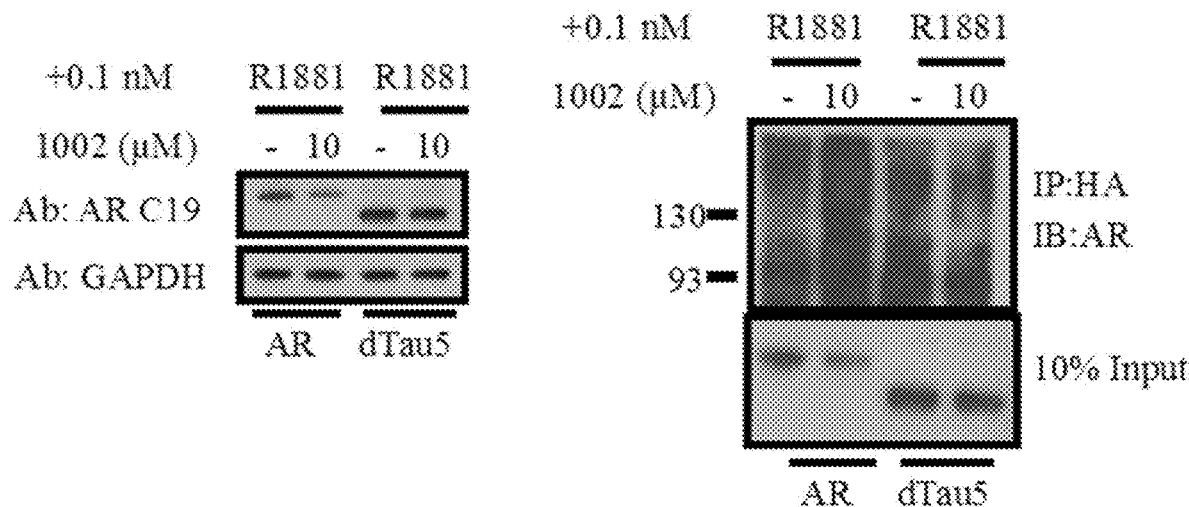

We showed using NMR that the first generation SARD 11 interacted with the tau domains of the AR AF-1 [26]. To confirm that this domain is important for 1002 to degrade the AR, a construct that has the tau5 domain deleted was used. Cells were transfected with AR or tau-5-deleted AR, treated with vehicle or 1002 for 48 hours, and a Western blot was performed for AR and GAPDH. 1002 degraded the full length AR, but not the AR construct that has the tau5 domain deleted (FIG. 44D). In agreement with the degradation data, tau5 domain-deleted AR failed to exhibit an increased ubiquitination over vehicle-treated samples in the presence of 1002 (FIG. 44D right blot). These results confirm that the SARDs belonging to this scaffold require tau5 domain to interact, ubiquitinate, and degrade the AR.

R Isomer and Racemate have Equal Potency as S-Isomer of 1002.

Figure 44E:
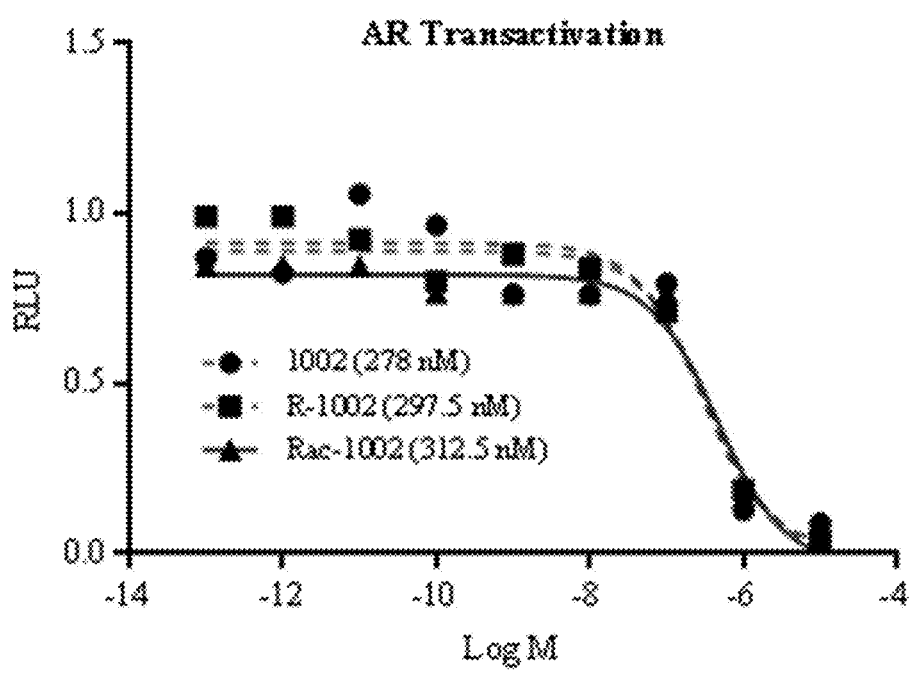

In order to ensure that 1002 has a minimal interaction with the LBD that is not contributing to its functions, we synthesized (R)-isomer (1020) and racemic mixture and evaluated in an AR transactivation assay. The (R)-isomer does not bind to the AR-LBD and hence any observed effect is likely through a different domain. All these molecules antagonized the AR with comparable $IC_{50}$ (FIG. 44E), confirming the data observed with various chimeric and mutant constructs.

1002 does not Inhibit the AR Function by Competitive Antagonism.

Figure 44F:
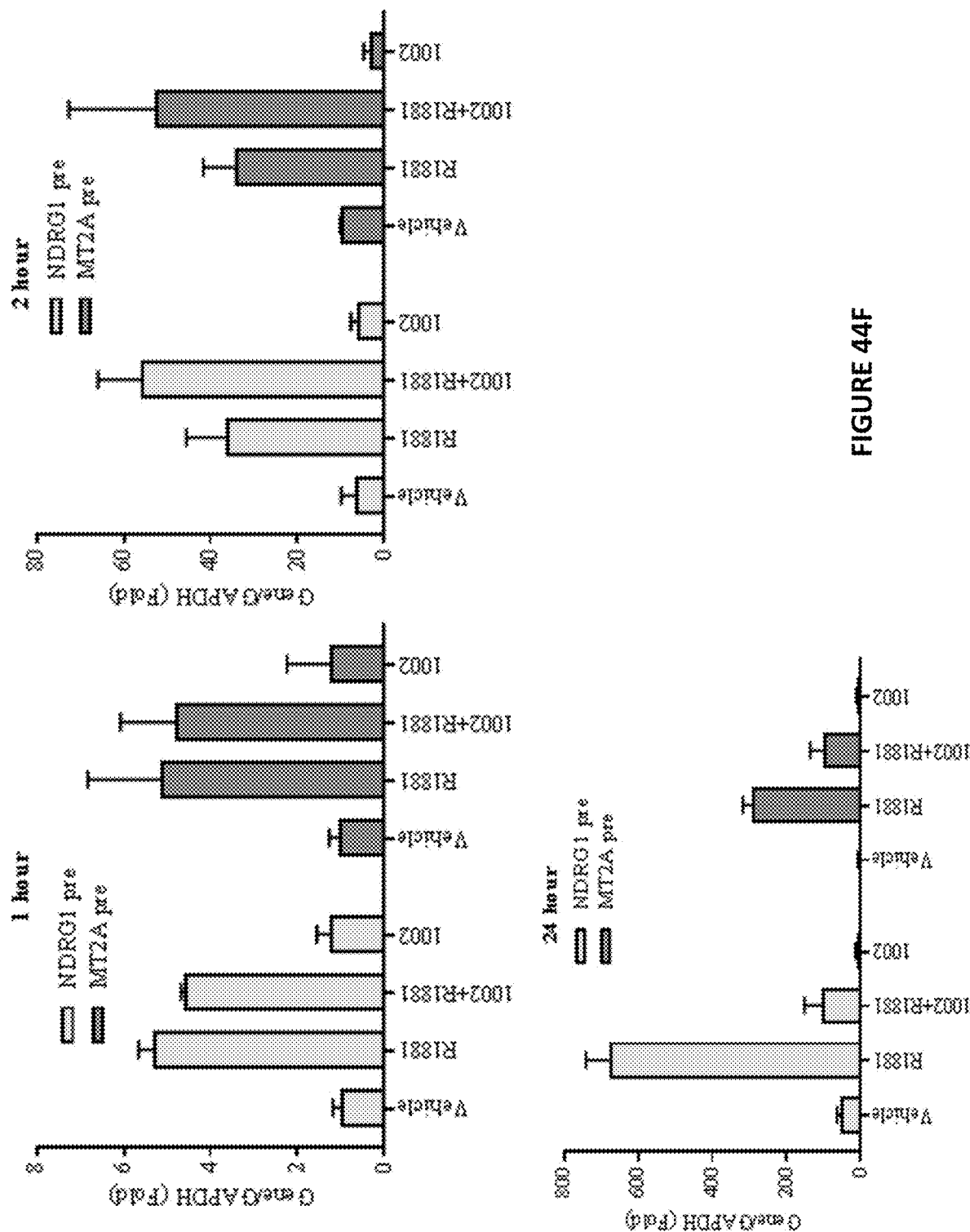

Similar to our earlier publication [26] we evaluated the early expression of pre-mRNAs in LNCaP cells treated with 1002 in the presence or absence of R1881 [49]. If 1002 mediates its antagonistic effects through competitive antagonism, then these pre-mRNAs induced by R1881 as early as 30 minutes should be inhibited. On the other hand, if degradation is required for 1002 to inhibit AR function, then early induction of the pre-mRNAs should not be inhibited as degradation will not be observed as early as 30 minutes to 2 hours. Treatment of LNCaP cells with 0.1 nM R1881 increased both NDRG1 and MT2A pre-mRNAs by 1 hour and the increase was sustained at 2 and 24 hours (FIG. 44F). 1002 failed to inhibit the expression of the pre-mRNA at 1 and 2 hours, but inhibited the expression at 24 hours. These results indicate that 1002 is a true degrader that requires degradation to elicit its effect and competitive binding to the LBD, if any, may not have functional significance.

Figure 45A:
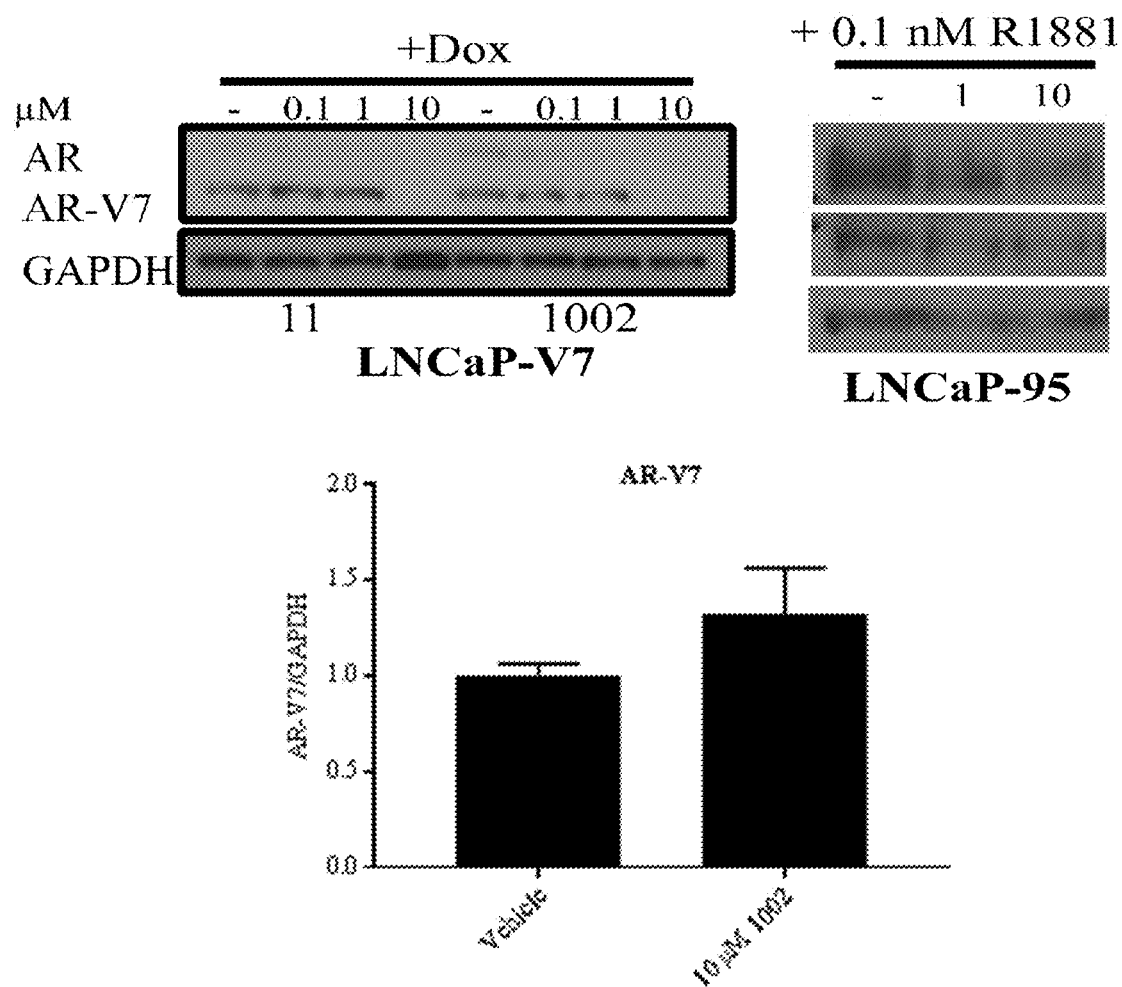
FIGS. 45A-45D demonstrate that 1002 degrades and inhibits AR-V7 function.

1002 Degrades AR-V7 and Alter its Function:

As the SARDs bind to the AF-1 domain and have shown earlier to degrade the AR-SVs [26], we tested 1002 in LNCaP cells that stably express inducible AR-V7 [29, 30]. As demonstrated earlier, 11 degraded the AR and AR-V7 in this system. 1002 down-regulated the AR and AR-V7, indicating that 1002 is an effective degrader of both AR and AR-V7 (FIG. 45A left panel). The results were reproduced in LNCaP-95 cells that express AR and AR-V7 (FIG. 45A right panel). These effects were observed without any effect on AR-V7 mRNA in LNCaP-ARV7 cells (FIG. 45A bottom panel).

Figure 45B:
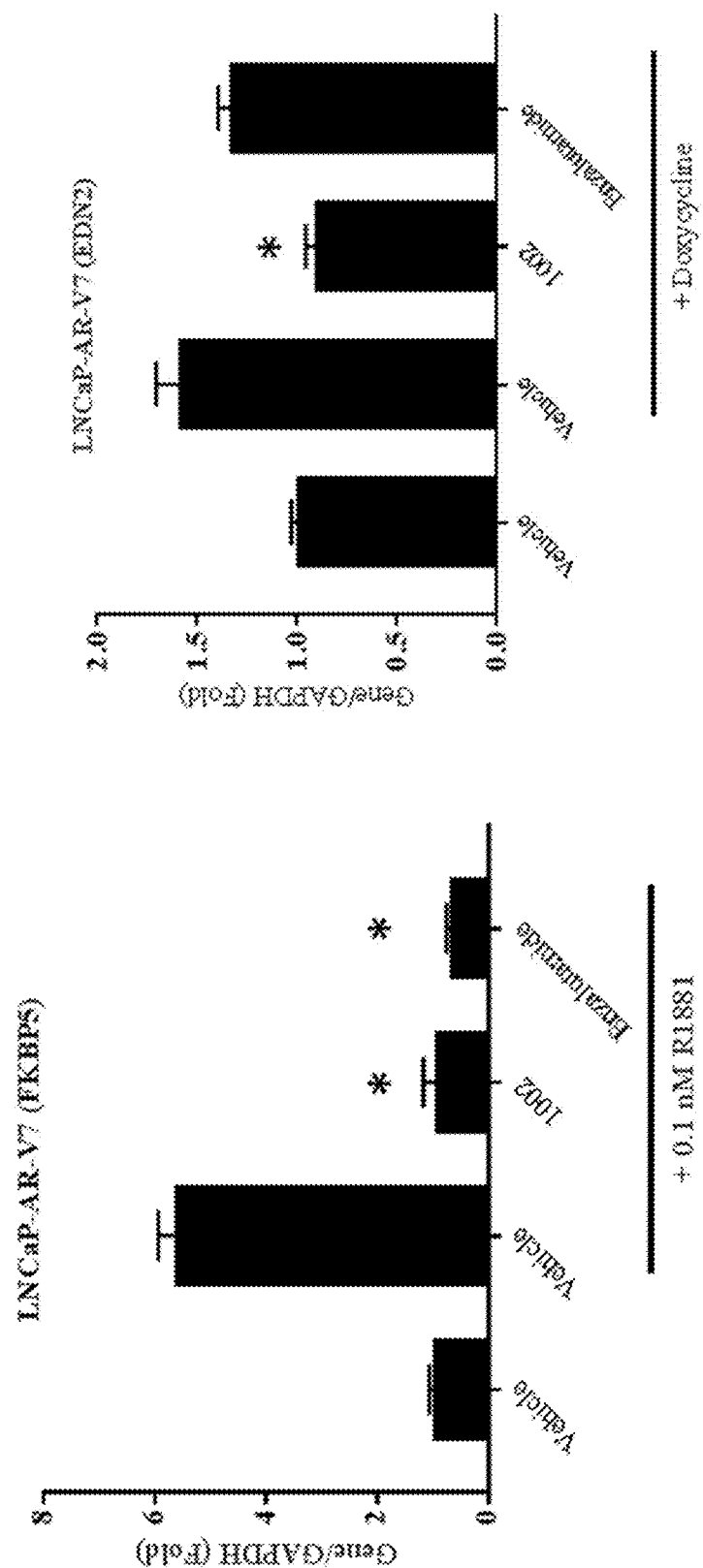

As 1002 degraded the expression of AR-V7, we evaluated the functional consequences of this degradation. LNCaP-ARV7 cells were serum starved for 48 h and were treated as indicated in FIG. 45B for 24 h in the presence of 0.1 nM R1881 (left panel) or 10 ng/mL doxycycline (right panel). Cells were harvested and the expression of AR-target gene FKBP5 and an AR-V7-specific gene EDN2 [29, 30] was measured. Doxycycline induced the expression of EDN2, which was inhibited by 1002, but not by enzalutamide, while both enzalutamide and 1002 inhibited the expression of R1881-induced FKBP5 gene expression (FIG. 45B).

Figure 45C:
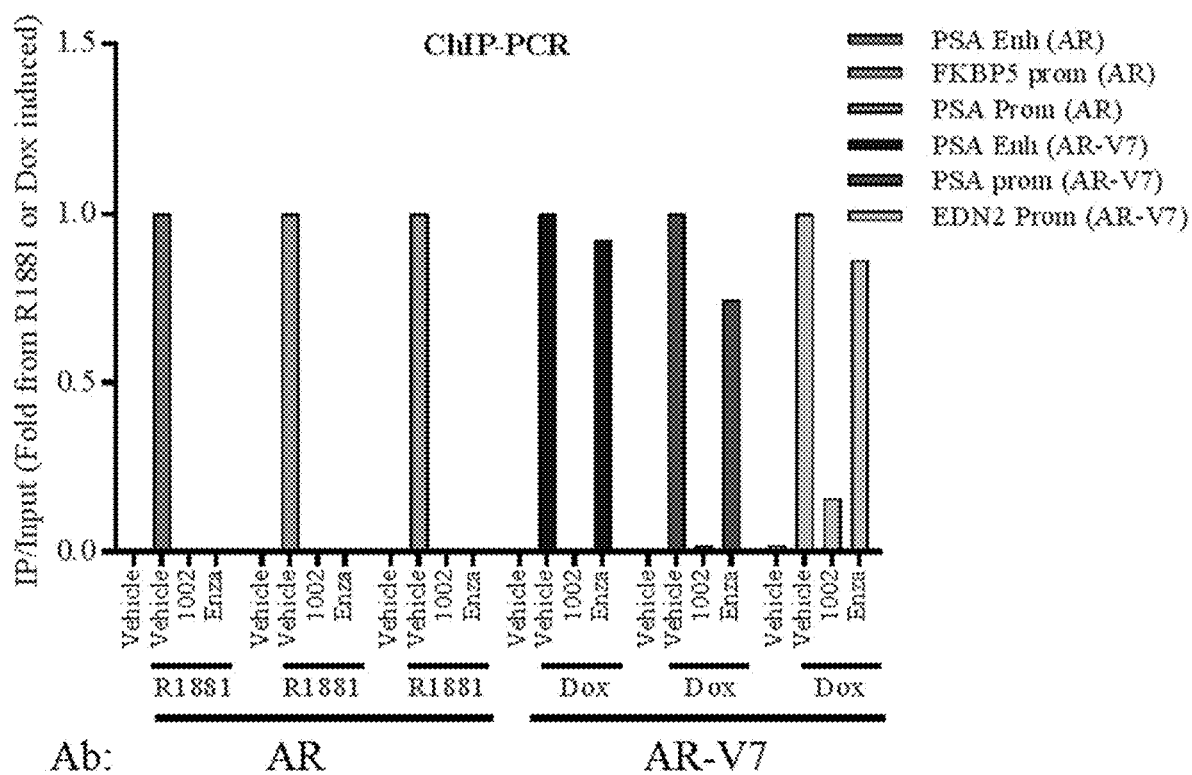

To evaluate whether the effect on the expression of various genes is a results of an alteration in the occupancy of AR and AR-V7 on the cis elements of target genes, we performed ChIP assay using AR or AR-V7 antibodies (FIG. 45C). R1881 induced the recruitment of AR to the regulatory regions of PSA and FKBP5. This recruitment was inhibited by 1002 and enzalutamide. AR-V7 recruitment to PSA and EDN2 regulatory regions was detected upon the addition of doxycycline (due to increased synthesis). This recruitment in response to doxycycline was completely inhibited by 1002, but not by enzalutamide (FIG. 45C).

Figure 45D:
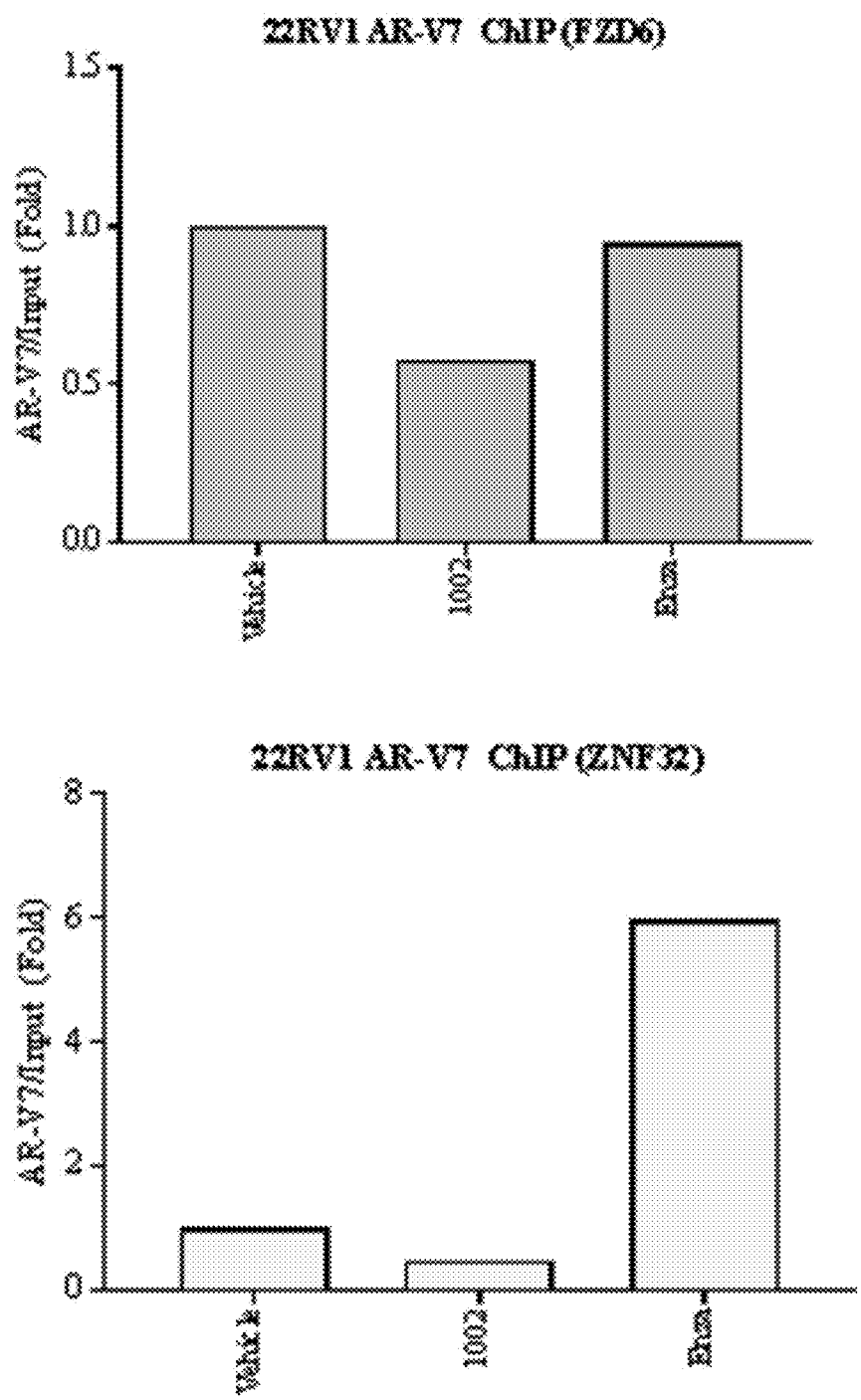

Genome-wide recruitment analysis of AR and AR-V7 in 22RV1 cells identified two AR-V7-selective cis elements that are occupied by AR-V7, but not by AR [50]. We performed ChIP assay with AR-V7 antibody and PCR for the regulatory regions of these genes was performed. As expected 1002, but not enzalutamide, inhibited the recruitment of AR-V7 to FZD6 and ZNF32 regulatory regions (FIG. 45D). These results are in concordance with the results observed with AR-V7 in LNCaP-ARV7 cells.

1002 Interacts with a Different Set of Cofactor Peptides Compared to Enzalutamide.

To determine if the differences in the properties observed with 1002 are a result of a distinct interaction with cofactors, we treated serum-starved LNCaP cells with 10 µM 1002, 11, or enzalutamide or vehicle in the presence of 1 nM DHT. The cells were pretreated with the drugs or vehicle for 2 hours, followed by a 30 minutes treatment with DHT. Protein extracts were subjected to MARCoNI assay where the interaction of the AR with 154 unique cofactor peptides from 66 cofactors was evaluated [51]. 1002 and 11 significantly modulated the AR-cofactor interaction. Although, largely the interaction between AR and cofactors in the presence of 11 and 1002 was similar to enzalutamide, several differences were also observed. Differences in the interaction of AR with cofactors such as NCoR1 (corepressors) and TREF1 (coactivator) observed in SARD-treated samples were not observed in cells treated with enzalutamide. These results provide information that the AR conformation in the presence of the SARDs is distinct from the conformation in the presence of a competitive antagonist such as enzalutamide.

1002 Antagonizes Enzalutamide-Resistant AR and Inhibits the Proliferation of Enzalutamide-Resistant LNCaP Cells (MR49F Cells).

Figure 46A:
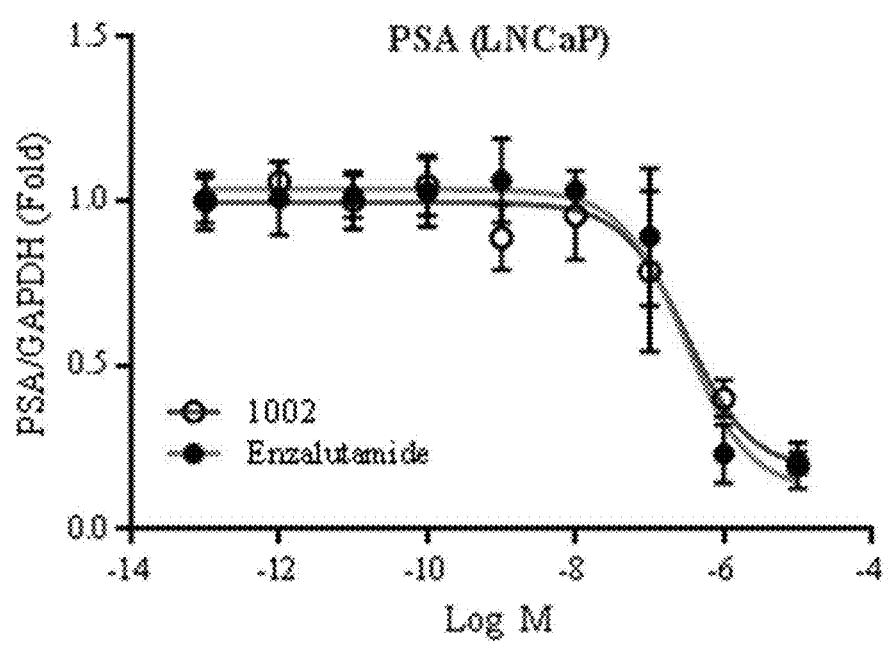
FIGS. 46A(i), 46A(ii), 46A(iii), 46B, and 46C demonstrate that 1002 inhibits wildtype AR and enzalutamide-resistant AR-dependent gene expression and prostate cancer cell growth.

As 1002 robustly antagonized and degraded both wildtype and enzalutamide-resistant AR in transient transactivation and Western blot assays, respectively, we evaluated the effect of 1002 on the function of ARs expressed in LNCaP or MR49F cells. LNCaP cells were maintained in charcoal-stripped FBS for 48 h and treated with a dose response of 1002 or enzalutamide. RNA was isolated and expression of AR target genes and growth was evaluated. Both the compounds inhibited the expression of PSA (top panel) and FKBP5 (middle panel) and growth of LNCaP cells (bottom panel) starting from 100 nM with maximum effect observed at 10 µM (FIG. 46A).

Figure 47A:
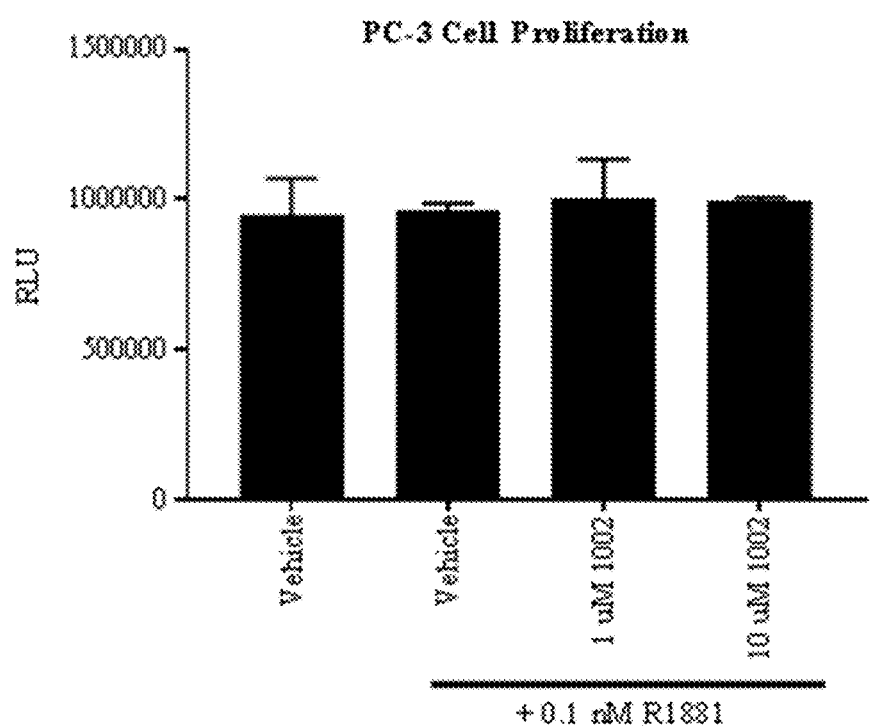

The experiment was repeated in MR49F cells that express F876L mutant AR. 1002, but not enzalutamide, inhibited the expression of FKBP5 gene induced by R1881 (FIG. 46B top panel). Concomitant to the gene expression studies, 1002 inhibited the proliferation of MR49F cells (FIG. 46B bottom panel), while enzalutamide, as expected, failed to inhibit the proliferation of the cells. These anti-proliferative effects of 1002 is selective to AR-positive prostate cancer cells as 1002 did not have any effect on the proliferation of AR-negative PC-3 cells (FIG. 47A).

1002 Inhibits the R1881-Induced Global Gene Expression in MR49F Cells.

Figure 46C:
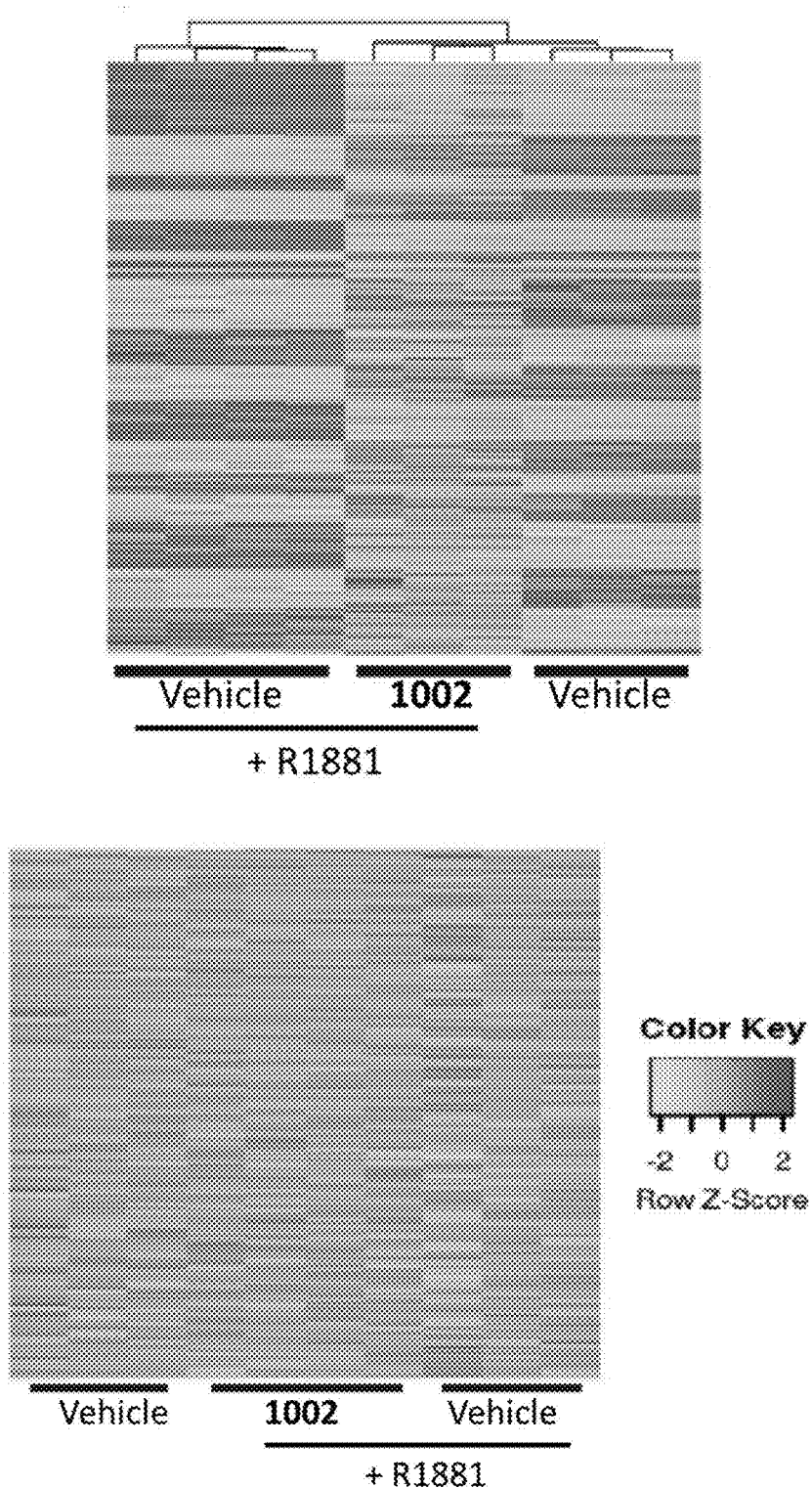
FIG. 46C. Gene expression array in MR49F indicates 1002 completely reverses the expression of genes regulated by R1881. LNCaP cells were maintained in charcoal-stripped serum-containing medium for 2 days and treated with vehicle, 0.1 nM R1881 alone or in combination with 10 µM of 1002. RNA was isolated 24 hours after treatment and hybridized to Clariom D microarray. Genes that were differentially expressed by 1.5-fold and q<0.05 in R1881-treated samples compared to vehicle-treated samples are expressed in the heatmap at the top. Bottom heatmap shows the pattern of genes that were not regulated by R1881 (n=3-4/group).

As 1002 was effective in inhibiting the expression of FKBP5 in MR49F cells, we performed a microarray experiment to determine the effect of 1002 on R1881-induced global gene expression (FIG. 46C top). Heatmap clearly represents the changes that took place in cells treated with R1881, which robustly altered the expression of approximately 700 genes. Most, if not all, of the genes regulated by R1881 were reversed by 1002 to the level observed in vehicle-treated cells. The top genes that were inhibited by 1002 are all known AR-target genes such as FKBP5, SNAI2, NDRG1, and others. The results indicate that 1002 is effective in reversing the R1881 effect in LNCaP cells expressing enzalutamide-resistant AR. Principal Component Analysis (PCA) plot shows that the 1002-treated samples cluster with vehicle-treated samples, while R1881-treated samples clustered distinctly. When the genes that were not regulated by R1881 were plotted in a separate heatmap, the results show that 1002 has no effect on these genes (FIG. 46C bottom), indicating that 1002 effects are highly selective to AR pathway and that it does not have any off-target effects.

Ingenuity Pathway Analysis (IPA) results indicate that the top four canonical pathways that were enriched by the differentially regulated genes were cholesterol-synthesizing pathways. While all genes in the pathway were up-regulated by R1881 treatment, 1002 efficiently brought the genes down to the vehicle-treated control levels. IPA also indicate that the genes representing genitourinary oncology pathways are differentially regulated, validating the model that was used to generate the gene expression data.

Drug Metabolism and Pharmacokinetic (DMPK) Studies Suggest that 1002 is Stable.

The half-life of 11 and 17 in liver microsomes was low in the range of 1-20 min [26]. Hence, the first generation SARDs had to be administered subcutaneously to obtain efficacy in preclinical models. Since CRPC is a chronic disease and patients have to be treated for a prolonged period, orally bioavailable molecules are preferred for clinical development. We used mouse liver microsome (MLM; primary pharmacodynamics (PD) species) to determine the half-life and clearance. 1002 had a longer half-life and lower clearance than 11 (Table 6). This suggests that 1002 is an appropriate molecule for further development. We also tested the metabolism of 1002 in rat liver microsome (RLM) and in human liver microsome (HLM). 1002 is highly stable in RLM and in HLM by at least 2-4 fold longer than in MLM.

TABLE 6

Comparison across species of stability to co-incubation with liver microsomes

| | DMPK (MLM) | | DMPK (RLM) | | DMPK (HLM) | |
|---|---|---|---|---|---|---|
| | T ½ (min) | Clearance μl/min/mg | T ½ (min) | Clearance μl/min/mg | T ½ (min) | Clearance μl/min/mg |
| 1002 | 77.96 | 8.9 | 181 | 5 | 274 | 3 |

Metabolism properties of SARDs: Liver microsomes from mouse (MLM), rat (RLM), and human (HLM) were incubated with 1002 as indicated in the methods and the amount of compound present at different points was identified using LC-MS/MS method. Data from both phase I and II metabolism are presented here. The data are represented as half-life ($T_{1/2}$) and intrinsic clearance ($CL_{int}$).

To validate the in vitro data in vivo, 1002 was administered to various strains of mice and rats to determine the bioavailability at 6 and 24 hours after administration (Table 7). 1002 was highly bioavailable in mice and rats at 6 hours. However, the serum concentration precipitously decreased at 24 hours in mice to almost undetectable levels, while higher levels in μM range was still observed in rats at 24 hours.

TABLE 7

Bioavailability of 1002 across different strains of mice (NSG, C57BL/6, nude) and rats (S.D. which means Sprague-Dawley)

| | 6 hours | | 24 hours | |
|---|---|---|---|---|
| | Avg (nM) | S.E. (nM) | Avg (nM) | S.E. (nM) |
| NSG | 36025 | 1138 | 31 | 9 |
| C57BL/6 | 30386 | 8850 | 15 | 1.4 |
| Nude | 41754 | 6900 | 38 | 6 |
| S.D.Rats | 5675 | 339 | 1725 | 329 |

Pharmacokinetic properties of 1002. A. 1002 is stable in rats, but not in mice. 1002 (60 mg/kg) dissolved in 15% DMSO + 85% PEG-300 was administered orally to the indicated strains and species (n = 3/group). Blood was collected 6 and 24 h after dosing and the amount of 1002 remaining in the serum was estimated using LC-MS/MS method.

Figure 48A:
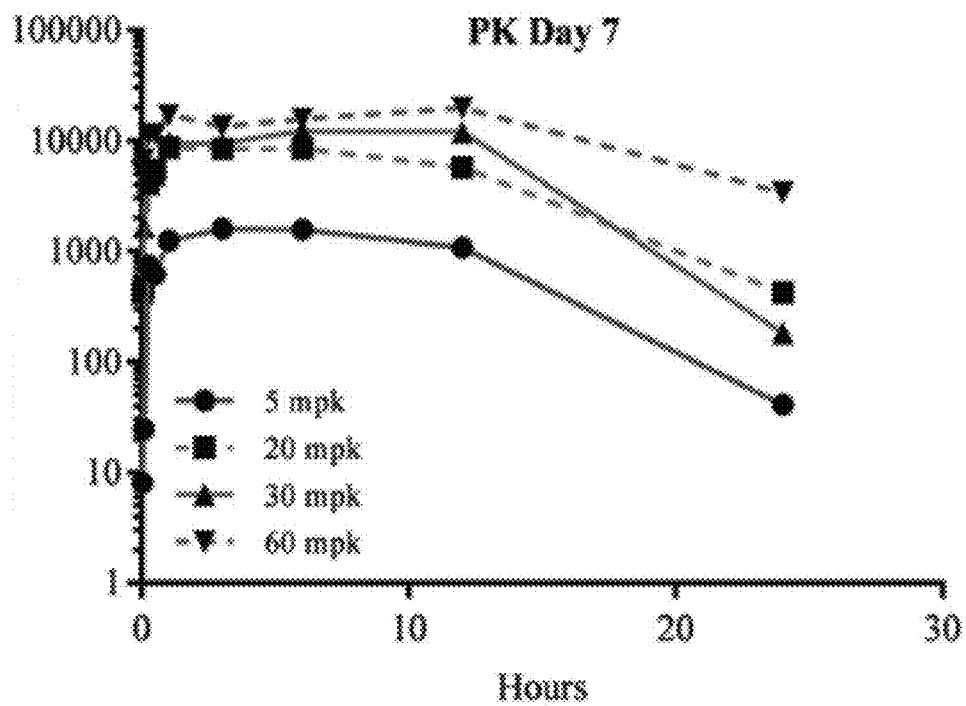
Figure 48B:
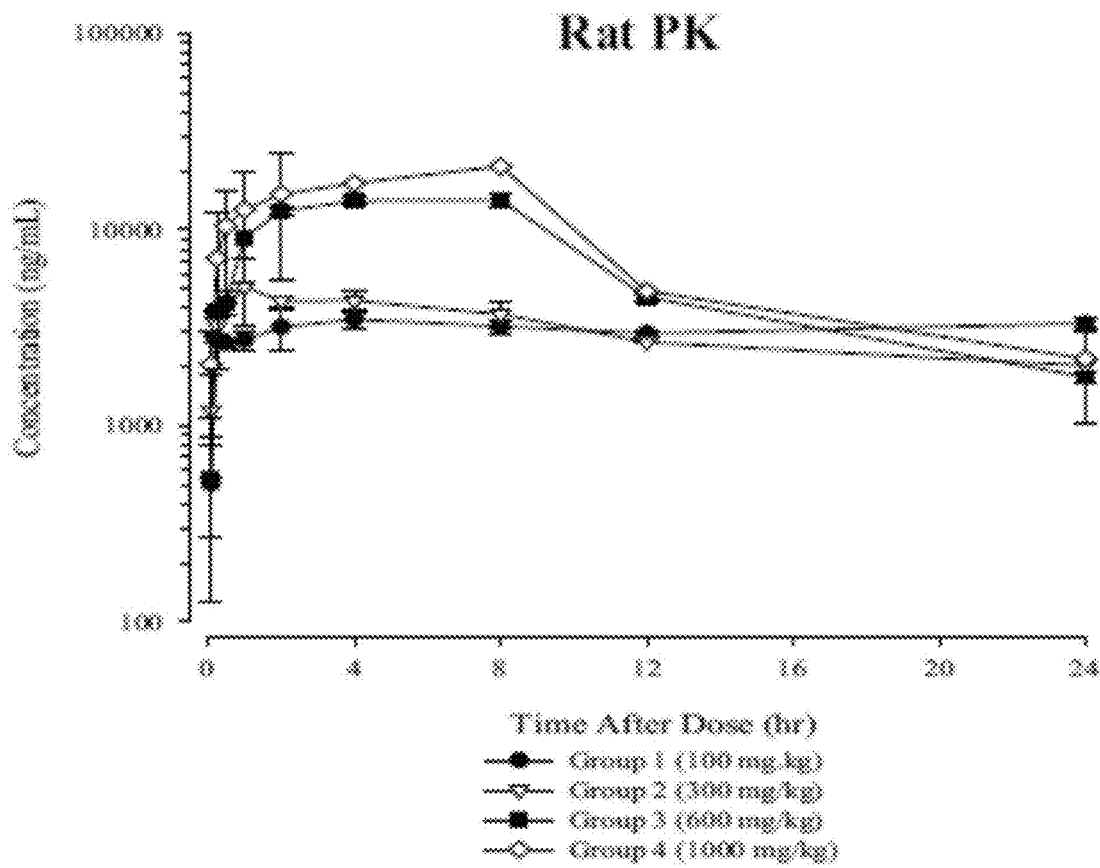

To validate the results observed at 6 and 24 h a rat PK study was conducted. Rats were administered with 100-1000 mg/kg of 1002 and the serum concentration was measured over a period of 24 hours. 1002 was extremely stable in rats with half-life for the 100 and 300 mg/kg doses was undeterminable due to absence of 50% reduction by 24 hours and the serum concentrations were in the range of 10-50 μM (FIG. 48A). These results are in concordance with the results observed in liver microsomes and suggest that the oral bioavailability of 1002 in CRPC patients may be appropriate for once daily dosing. Lower doses PK of 1002 in rats also provided similar results demonstrating that 1002 is extremely stable (FIG. 48B).

Pharmacodynamic and Xenograft Studies Suggest that 1002 is Efficacious:

To determine the efficacy of 1002 in vivo a Hershberger assay was performed in mice and rats (FIG. 48C). Mice (top panel) were administered with 20 or 40 mg/kg 1002 or 30 mg/kg enzalutamide orally for 14 days. At the end of 14 days, the animals were sacrificed and the weight of seminal vesicles was recorded. Enzalutamide was not dosed higher than 30 mg/kg due to its poor solubility. 1002 at 20 and 40 mg/kg reduced the seminal vesicles weight by 10-20 and 50-60%, while enzalutamide reduced the seminal vesicles weight by 50% (FIG. 48C).

Sprague Dawley rats were dosed with 40 and 60 mg/kg of 1002 orally and enzalutamide at 30 mg/kg for 14 days and the weight of prostate was recorded. 1002 reduced the prostate weight by close 90%, while enzalutamide reduced the prostate weight by 50-60%. This clearly shows that 1002 is extremely potent in shrinking the prostate potentially due to its potent antagonistic and degradation effects (FIG. 48C middle panel). 1002 even after 4 days of dosing reduced the prostate weight by close to 50%, indicating its ability to antagonize the AR quickly in vivo and produce a pharmacodynamics (PD) effect (FIG. 48C bottom panel).

To evaluate the effect of 1002 in an enzalutamide-resistant xenograft model, MR49F cells were implanted subcutaneously in NSG mice and once the tumors attained 100-200 mm³, the animals were castrated and the tumors were allowed to regrow as CRPC. The animals were treated with 30 or 60 mg/kg 1002 and the tumor volume was measured thrice weekly (FIG. 49A). 1002 dose-dependently decreased the growth of the enzalutamide-resistant CRPC tumors with 60 mg/kg producing about 75% tumor growth inhibition. Tumor weights recorded at the end of the study also indicated that 1002 reduced the tumor weights by approximately 60-70% (FIG. 49A bottom panel). Although the PK properties in mice were sub-optimal compared to rats, 1002 produced a marked effect on enzalutamide-resistant tumor growth.

1002 Regresses Enzalutamide-Sensitive and -Resistant VCaP Tumors in NSG Rats.

Since 1002 is stable in rats compared to mice, we switched over to performing the xenograft studies in immunocompromised rats (Hera Biolabs, KY). We chose two models, one enzalutamide-sensitive parental VCaP cells and another is enzalutamide-resistant VCaP cells (MDVR). Cells were implanted in SRG rats and once the tumors attained over 1000-2000 mm$^3$ volume, the animals were castrated and the tumors were allowed to regrow as castration-resistant prostate cancer. Once the tumors regrow and attain greater than 2000 mm$^3$, the animals were randomized and treated orally with vehicle, 30 mg/kg enzalutamide, or 60 mg/kg 1002. Tumor volume measurements indicated that while enzalutamide inhibited the growth of parental VCaP xenograft by over 85%, 1002 regressed the tumors to unmeasurable levels (FIG. 49B).

As expected, enzalutamide failed to inhibit the enzalutamide-resistant VCaP (MDVR) xenograft. 1002 performance in this tumor model was comparable to that observed in the parental VCaP xenograft with 1002 regressing the tumors to undetectable levels (FIG. 49C). 1002 was also tested in vitro in the MDVR model and the results show that 1002 inhibits the expression of the AR-target genes and its proliferation (FIG. 47B).

Since 1002 regressed the tumors to undetectable levels, we hypothesized that this is possible only if the AR is degraded. Western blot in the MDVR tumors demonstrated a significant degradation of the AR in 1002-treated samples compared to vehicle-treated samples (FIG. 49C, bottom).

Figure 8:
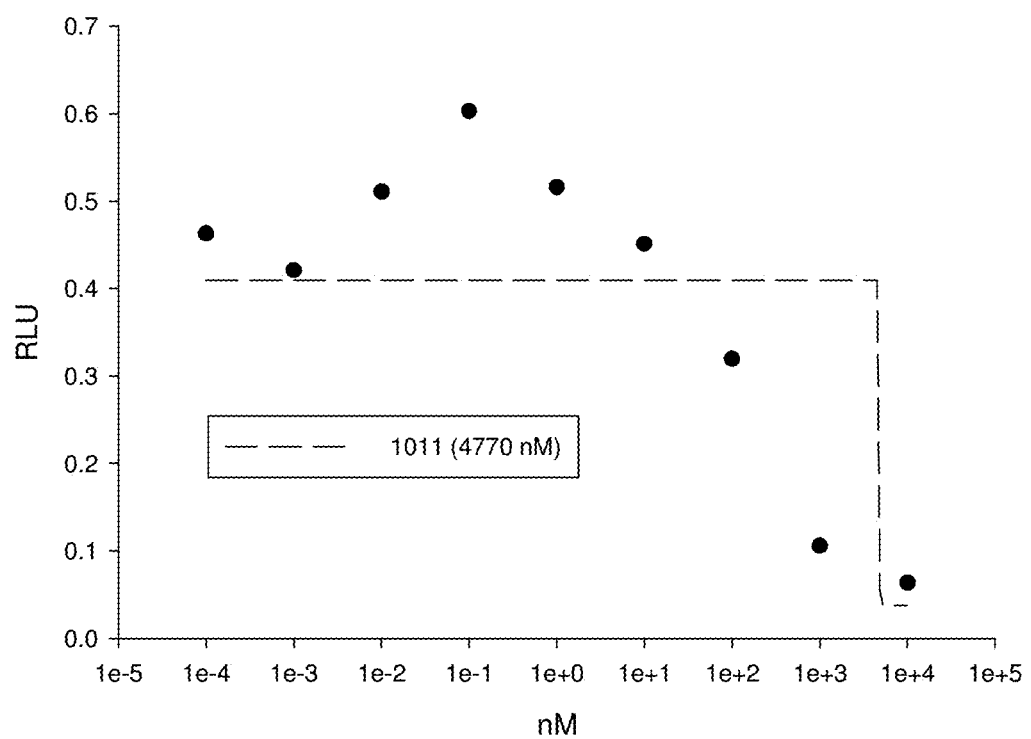
FIG. 8: The transactivation result of 1011 was reported based on measured luciferase light emissions and reported as relative light unit intensity (RLU).
Figure 9:
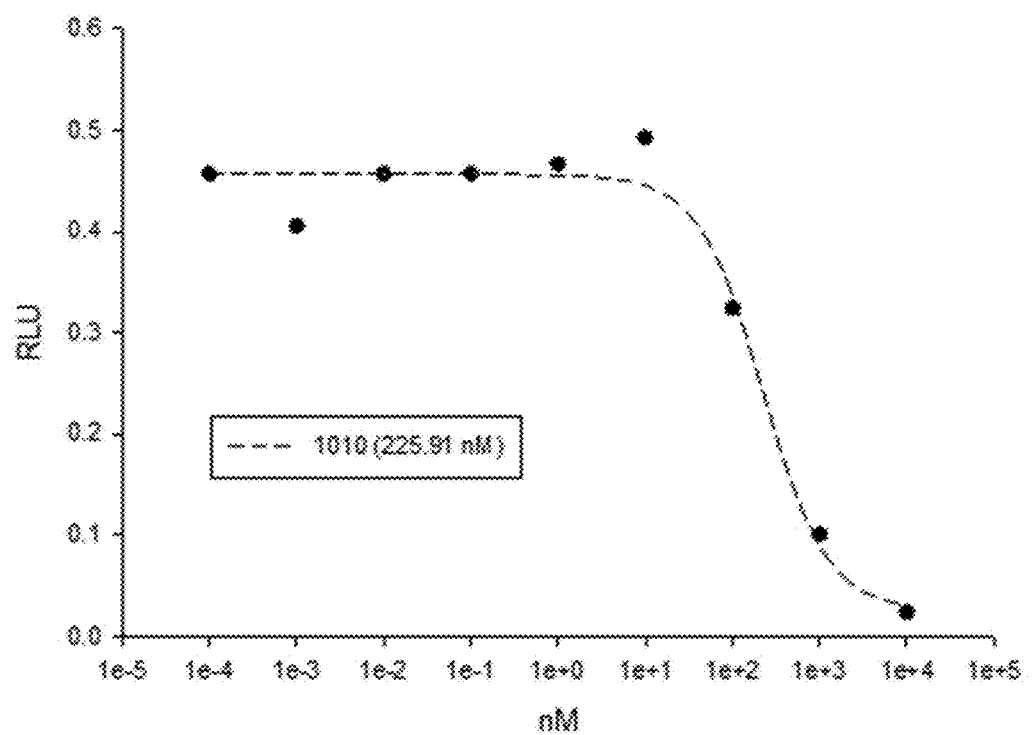
FIG. 9: The transactivation result of 1010 was reported based on measured luciferase light emissions and reported as relative light unit intensity (RLU).
Figure 10:
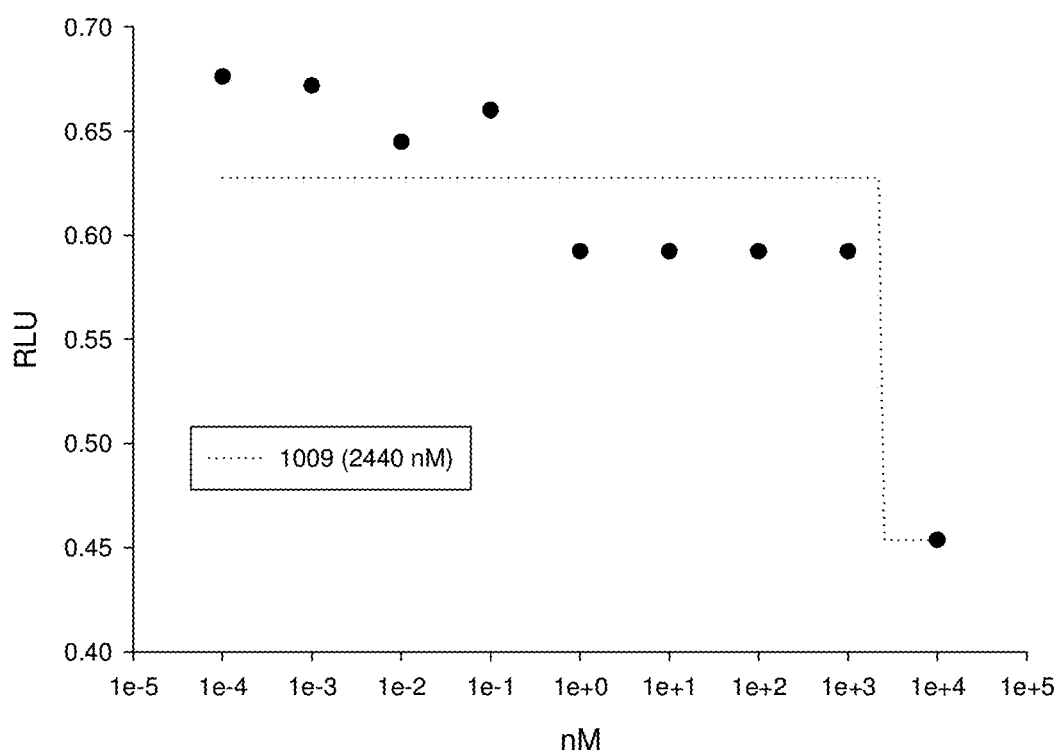
FIG. 10: The transactivation result of 1009 was reported based on measured luciferase light emissions and reported as relative light unit intensity (RLU).
Figure 11:
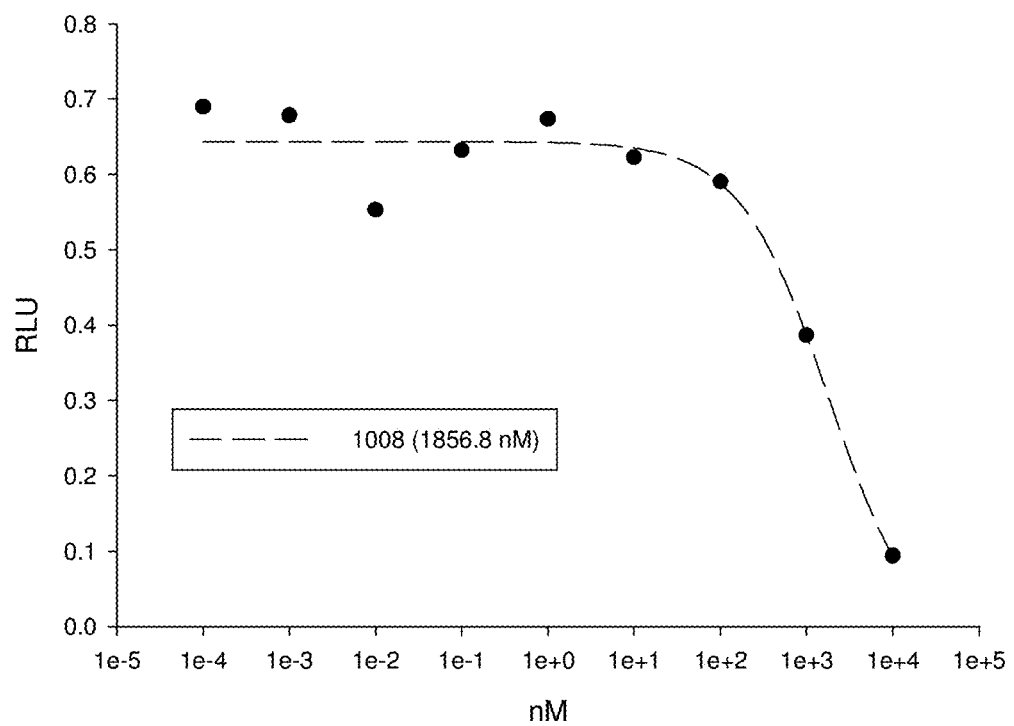
FIG. 11: The transactivation result of 1008 was reported based on measured luciferase light emissions and reported as relative light unit intensity (RLU).
Figure 12:
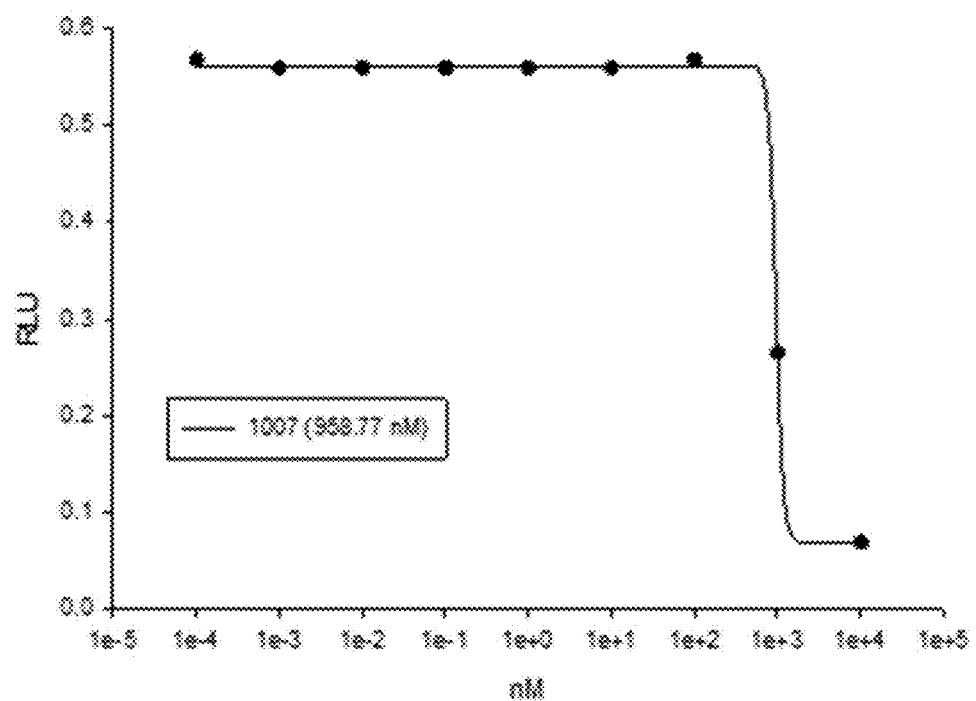
FIG. 12: The transactivation result of 1007 was reported based on measured luciferase light emissions and reported as relative light unit intensity (RLU).
Figure 13A:
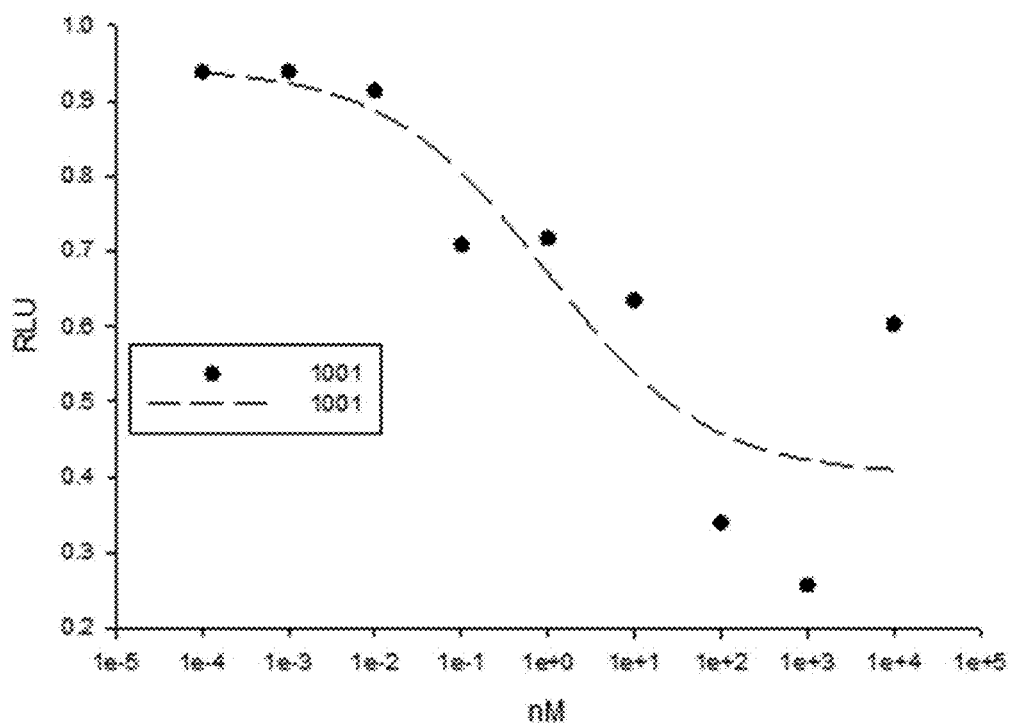
FIGS. 13A-13C: The transactivation result of 1001 was reported based on measured luciferase light emissions and reported as relative light unit intensity (RLU).
Figure 13B:
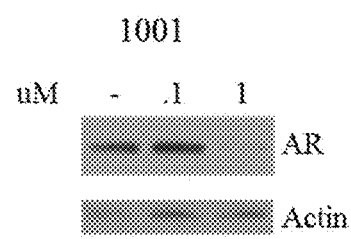
Figure 13C:
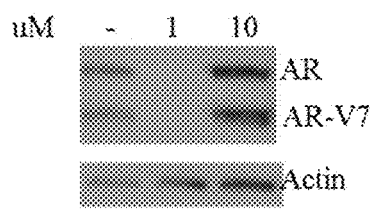
Figure 49D:
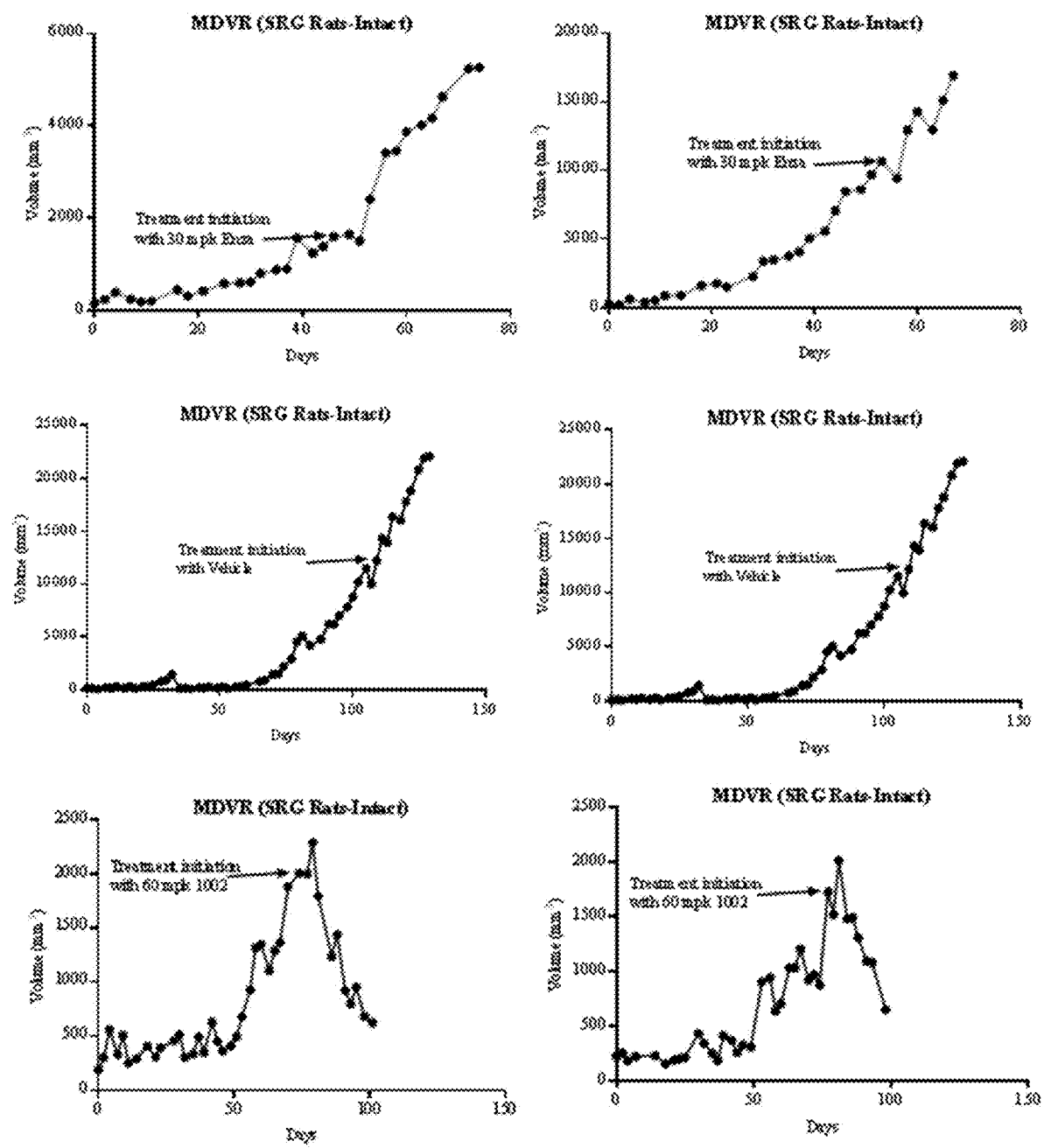

It has not been previously demonstrated that competitive AR antagonists cannot inhibit tumors grown in intact mice or rats. Since 1002 is the first orally-bioavailable degrader, we were interested to test the efficacy in intact models, where the animals were not castrated and the tumors grow in the presence of circulating androgens. MDVR tumors grew robustly in SRG rats and the tumor-bearing animals were treated when the tumors attained over 1500 mm$^3$. One tumor in each group even attained 10,000 mm$^3$ when treatment was initiated. While the vehicle- and enzalutamide-treated tumors grew robustly, 1002-treated tumors regressed by over 50% in less than 10-15 days after treatment initiation (FIG. 49D, multiple panels for individual animals). We measured serum PSA to determine if the tumor volume data is supported by biochemical data. 1002 completely inhibited the rising serum PSA to undetectable levels quickly after treatment initiation (FIG. 49D, 8$^{th}$ panel titled 'Serum PSA').

Figure 48D:
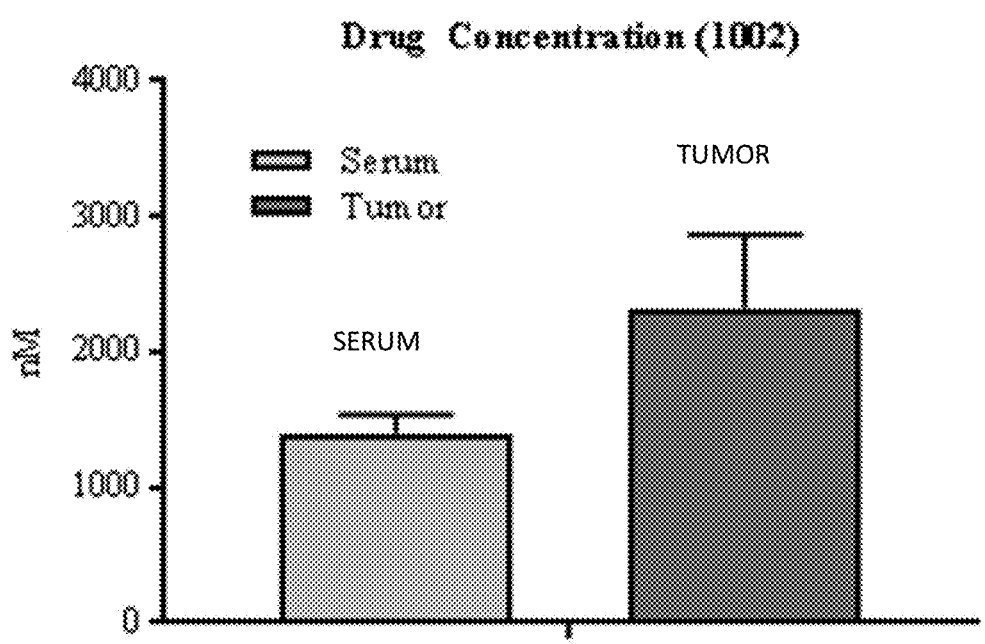
Figure 49E:
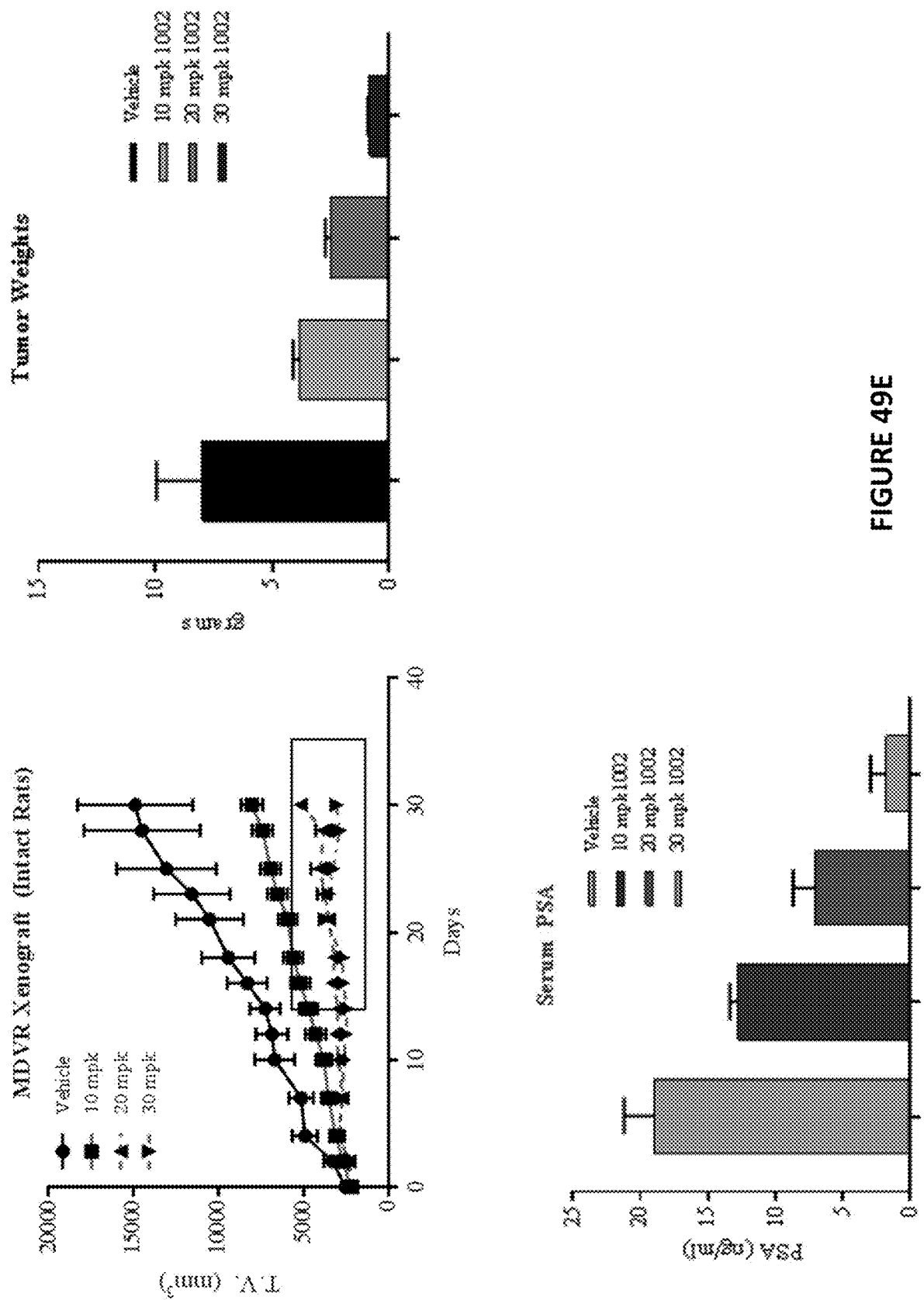

We subsequently conducted a dose response of 1002 in intact SRG rats bearing MDVR tumors. 1002 at 10 mg/kg inhibited the tumors growth by greater than 50% and completely inhibited the tumors at 20 and 30 mg/kg doses (FIG. 49E, top and middle panels). Tumor weights measured at the end of the study and serum PSA (bottom panel) both clearly exhibited a dose-dependent inhibition by 1002 (FIG. 49E). Measurement of drug concentration in the serum and tumor that were collected 24-30 h after the last sacrifice demonstrated the accumulation of 1002 in both serum and tumor to the level of over 1-3 µM concentrations (FIG. 48D). The steady-state drug concentration even 24 h after the last dose is well above the IC$_{50}$ values of 1002 to inhibit the AR. Immunohistochemistry with vehicle- and 30 mg/kg 1002-treated specimens clearly indicated that 1002 increased the apoptosis as measured by TUNEL staining and inhibited the proliferation as measured by Ki67 staining (FIG. 48E). All these favorably point to the excellent anti-tumor activity of 1002 in enzalutamide-sensitive and -resistant prostate cancers even in intact conditions.

We also tested 1002 in castrated mice to ensure that it does not have any agonistic activity at higher doses or concentration. Vehicle or 1002 (100 mg/kg) was administered orally for 30 days to mice that were castrated. At the end of 30 days, seminal vesicles were isolated and weighed. Seminal vesicles weight normalized to body weight is expressed as percent change from vehicle control (FIG. 48F). 1002 at such high doses did not exhibit any agonistic activity as the seminal vesicles weights were comparable to that of the vehicle-treated animals (FIG. 48F top panel). Serum 1002 concentration at the end of 30 days of dosing showed nice accumulation of 1002 in serum in the range of 1-20 µM (FIG. 48F right panel). These results confirm that 1002 is a pure antagonist and does not have any agonistic properties in vivo at higher concentrations.

In order to determine if the AR is degraded by 1002 in intact conditions, we measured the AR expression by Western blot in protein extracts from tumors (FIG. 49D at bottom). 1002 robustly degraded the enzalutamide-resistant AR in intact condition (FIG. 49D), demonstrating that the degradation property translates in vivo. We also evaluated whether 1002 degraded the AR at lower doses. Unfortunately, 1002 failed to degrade the AR at 30 mg/kg (data not shown). This potentially suggests that higher serum and tumor concentrations are required to degrade the AR and that a tumor regression can be achieved only when the AR is degraded 1002 Toxicity Profile was Acceptable:

Since 1002 possessed the required properties for a CRPC drug, we evaluated the toxicity profile of the molecule. 1002 was administered at 100, 300, and 600 mg/kg doses for 7 days in Sprague Dawley rats and survival and gross pathology were monitored. 1002 did not cause any death at 100 mg/kg dose, while deaths were encountered at 300 and 600 mg/kg doses. Gross pathology and histopathology findings suggest that the deaths in higher dose groups were due to gastric irritation and inflammation, which could be potentially avoided using enteric coated capsules or salt forms of 1002. No other pathological observations were detected at any dose. Since several of the second generation AR antagonists exhibit seizure potentials, 1002 was also evaluated for its seizure potential in mice. Mice treated with 1002 did not have any seizure, while the positive controls exhibited seizures (data not shown). In addition, 1002 also does not have any significant cross-reactivity with GPCRs, kinases, or other nuclear receptors (DiscoverX Eurofin screening) and does not inhibit hERG channel (Covance). These results suggest that 1002 might have a large safety margin and might have no off-target effects.

Discussion.

The results provide evidence for an orally bioavailable SARD that has the necessary drug-like properties for further clinical evaluation. 1002 degraded the AR and AR-V7 and antagonized enzalutamide-sensitive and -resistant AR and inhibited the growth of enzalutamide-resistant xenografts. 1002 also possesses appropriate PK properties showing longer half-life and shorter clearance in rats and human liver microsomes than in mouse liver microsomes. This suggests that clinically 1002 might require only once daily dosing to observe efficacy.

1002 is effective in two models of enzalutamide-resistance, one with an AR-LBD mutation and another with AR-V7 expression. These two are the common forms of resistance observed clinically. Although 30% of enzalutamide-resistant cancers do not respond at all, the remaining cancers develop resistance shortly after treatment initiation. Mutations constitute only a small fraction of the resistance, while AR-SV development, intra-tumoral androgen synthesis, AR over-expression, coactivators, and altered intracellular signaling pathways all contribute to resistance development. Degrading the AR and AR-SVs will block any AR activation by these contributing factors providing a significant advantage over existing therapeutics. Recently, two molecules, galeterone and EPI-506, failed in the clinic. After the approval of enzalutamide and abiraterone in 2012, no other drugs targeting the AR with distinct mechanism of action (apalutamide was approved recently, but it is structurally and functionally similar to enzalutamide) have been made available and the patients have no treatment options with distinct mechanisms available to treat the new evolving forms of CRPC. Hence, these SARDs might provide a substantial advantage to the patients who relapse from enzalutamide.

1002 degrades the AR through ubiquitin proteasome pathway. As AR degraders have not been successfully identified, characterizing 1002 thoroughly is important to demonstrate that it is robust. Most of the proteins are degraded by ubiquitin proteasome pathway and hence we evaluated this pathway first. 1002 treatment resulted in mono- and poly-ubiquitinated AR. Also, inhibition of proteasome pathway with Bortezomib resulted in the reversal of AR degradation suggesting that the degradation takes place through proteasome pathway. Only recently chimeric molecules such as PROTACs and SNIPERs have evolved that have demonstrated AR degradation characteristics. However, these molecules are larger than the desired 500 Da size that are not appropriate for development. With right formulation and dosing this deficiency can be overcome. As 1002 degrades the AR-SVs and since the well-characterized ubiquitin sites in the AR did not play a role in AR degradation by 1002 (FIG. 41I), 1002 might function through new ubiquitin sites in the AR-NTD that need to be identified.

This is the first time that an AR-targeting molecule has been shown to exhibit efficacy in xenograft models grown in intact rodents. Since circulating testosterone levels are high enough to be competed by competitive antagonists, only non-competitive antagonists or degraders will have the potential to overcome tumors growth in intact animals. The results that we observed with enzalutamide-resistant MDVR xenografts is an in vivo confirmation that 1002 is a non-competitive antagonist. Moreover, the dose response and higher dose xenograft studies also suggest that tumor shrinkage can only be obtained when the AR is degraded and not when the AR is just antagonized. These results are the first evidence of efficacy of orally bioavailable AR degraders.

Still how AR interacts with its cofactors in the presence of a degrader or a molecule that binds to a distinct domain or a molecule that does not function as a competitive antagonist has not been elucidated. This is the first study that provides a glimpse of how such interaction takes place. We conducted the study in LNCaP prostate cancer cells as opposed to purified system followed by others [52]. Both 1002 and 11, although promoted the interaction of several cofactors with the AR similar to that of a competitive antagonist enzalutamide, several distinct interactions were observed in the presence of the two degraders. These interactions will be followed in the future in purified system and compared to the database of AR interaction with cofactors in the presence of several other agonists and antagonists.

One of the interesting results observed in this work is that although it is believed that the AR and AR-SVs exist as heterodimers, enzalutamide had no effect on the recruitment of AR-V7. If they are localized as heterodimer, then enzalutamide should inhibit the recruitment of AR-V7 through its effect on AR in both LNCaP-V7 and 22RV1 cells. However, enzalutamide did not affect the recruitment of AR-V7 in either of the system, while 1002 successfully inhibited the recruitment, suggesting that the AR and AR-V7 could be existing as homodimer in these cells and that the effect cannot be obtained with an LBD-binding AR antagonist and the drug has to bind to a domain that is common in AR and AR-V7 to block the recruitment.

Although the first-generation AR degraders, 11, 17, and others [26, 27], were more potent than 1002 in vitro they were not orally bioavailable and their metabolism properties were not appropriate for drug development. We had to compromise on the degradation and antagonist properties to improve the metabolism properties, which has resulted in an excellent molecule that withstood all tests of efficacy and safety. One of the major concerns in AR-targeted drug development is the seizure potential. 1002 did not exhibit any seizure effects in rodents.

1002 represents a new generation of orally bioavailable molecule that possesses necessary characteristics of AR degraders that could be developed clinically. We expect 1002 to overcome enzalutamide resistance in the clinic without having to worry about some of the common safety problems.

REFERENCES

1. Miller K D, Siegel R L, Lin C C, Mariotto A B, Kramer J L, Rowland J H, et al. Cancer treatment and survivorship statistics, 2016. CA Cancer J Clin. 2016; 66(4):271-89. doi: 10.3322/caac.21349. PubMed PMID: 27253694.
2. de Bono J S, Logothetis C J, Molina A, Fizazi K, North S, Chu L, et al. Abiraterone and increased survival in metastatic prostate cancer. N Engl J Med. 2011; 364(21): 1995-2005. Epub 2011/05/27. doi: 10.1056/NEJMoa1014618. PubMed PMID: 21612468; PubMed Central PMCID: PMC3471149.
3. Scher H I, Fizazi K, Saad F, Taplin M E, Sternberg C N, Miller K, et al. Increased survival with enzalutamide in prostate cancer after chemotherapy. N Engl J Med. 2012; 367(13):1187-97. Epub 2012/08/17. doi: 10.1056/NEJMoa1207506. PubMed PMID: 22894553.
4. Smith M R, Kabbinavar F, Saad F, Hussain A, Gittelman M C, Bilhartz D L, et al. Natural history of rising serum prostate-specific antigen in men with castrate nonmetastatic prostate cancer. J Clin Oncol. 2005; 23(13):2918-25. doi: 10.1200/JCO.2005.01.529. PubMed PMID: 15860850.
5. Chi K N, Hotte S J, Yu E Y, Tu D, Eigl B J, Tannock I, et al. Randomized phase I I study of docetaxel and prednisone with or without OGX-011 in patients with metastatic castration-resistant prostate cancer. J Clin Oncol. 2010; 28(27):4247-54. doi: 10.1200/JCO.2009.26.8771. PubMed PMID: 20733135.
6. Scher H I, Beer T M, Higano C S, Anand A, Taplin M E, Efstathiou E, et al. Antitumour activity of MDV3100 in castration-resistant prostate cancer: a phase 1-2 study. Lancet. 2010; 375(9724):1437-46. doi: 10.1016/S0140-6736(10)60172-9. PubMed PMID: 20398925; PubMed Central PMCID: PMCPMC2948179.

7. Ryan C J, Smith M R, de Bono J S, Molina A, Logothetis C J, de Souza P, et al. Abiraterone in metastatic prostate cancer without previous chemotherapy. N Engl J Med. 2013; 368(2):138-48. doi: 10.1056/NEJMoa1209096. PubMed PMID: 23228172; PubMed Central PMCID: PMCPMC3683570.
8. Nadiminty N, Tummala R, Liu C, Yang J, Lou W, Evans C P, et al. NF-kappaB2/p52 induces resistance to enzalutamide in prostate cancer: role of androgen receptor and its variants. Mol Cancer Ther. 2013; 12(8):1629-37. doi: 10.1158/1535-7163.MCT-13-0027. PubMed PMID: 23699654; PubMed Central PMCID: PMCPMC3941973.
9. Korpal M, Korn J M, Gao X, Rakiec D P, Ruddy D A, Doshi S, et al. An F876L mutation in androgen receptor confers genetic and phenotypic resistance to MDV3100 (enzalutamide). Cancer Discov. 2013; 3(9):1030-43. doi: 10.1158/2159-8290.CD-13-0142. PubMed PMID: 23842682.
10. Antonarakis E S, Lu C, Wang H, Luber B, Nakazawa M, Roeser J C, et al. A R-V7 and resistance to enzalutamide and abiraterone in prostate cancer. N Engl J Med. 2014; 371(11):1028-38. doi: 10.1056/NEJMoa1315815. PubMed PMID: 25184630; PubMed Central PMCID: PMC4201502.
11. Lubahn D B, Joseph D R, Sullivan P M, Willard H F, French F S, Wilson E M. Cloning of human androgen receptor complementary DNA and localization to the X chromosome. Science. 1988; 240(4850):327-30. PubMed PMID: 3353727.
12. Yoshida T, Kinoshita H, Segawa T, Nakamura E, Inoue T, Shimizu Y, et al. Antiandrogen bicalutamide promotes tumor growth in a novel androgen-dependent prostate cancer xenograft model derived from a bicalutamide-treated patient. Cancer Res. 2005; 65(21):9611-6. PubMed PMID: 16266977.
13. Clegg N J, Wongvipat J, Joseph J D, Tran C, Ouk S, Dilhas A, et al. ARN-509: a novel antiandrogen for prostate cancer treatment. Cancer Res. 2012; 72(6):1494-503. Epub 2012/01/24. doi: 10.1158/0008-5472.CAN-11-3948. PubMed PMID: 22266222; PubMed Central PMCID: PMC3306502.
14. Balbas M D, Evans M J, Hosfield D J, Wongvipat J, Arora V K, Watson P A, et al. Overcoming mutation-based resistance to antiandrogens with rational drug design. Elife. 2013; 2:e00499. doi: 10.7554/eLife.00499. PubMed PMID: 23580326; PubMed Central PMCID: PMC3622181.
15. Hornberg E, Ylitalo E B, Crnalic S, Antti H, Stattin P, Widmark A, et al. Expression of androgen receptor splice variants in prostate cancer bone metastases is associated with castration-resistance and short survival. PLoS One. 2011; 6(4):e19059. doi: 10.1371/journal.pone.0019059. PubMed PMID: 21552559; PubMed Central PMCID: PMC3084247.
16. Zhang G, Liu X, Li J, Ledet E, Alvarez X, Qi Y, et al. Androgen receptor splice variants circumvent AR blockade by microtubule-targeting agents. Oncotarget. 2015; 6(27):23358-71. doi: 10.18632/oncotarget.4396. PubMed PMID: 26160840; PubMed Central PMCID: PMCPMC4695123.
17. Cheng H H, Gulati R, Azad A, Nadal R, Twardowski P, Vaishampayan U N, et al. Activity of enzalutamide in men with metastatic castration-resistant prostate cancer is affected by prior treatment with abiraterone and/or docetaxel. Prostate Cancer Prostatic Dis. 2015; 18(2):122-7. doi: 10.1038/pcan.2014.53. PubMed PMID: 25600186; PubMed Central PMCID: PMCPMC4430366.
18. Mezynski J, Pezaro C, Bianchini D, Zivi A, Sandhu S, Thompson E, et al. Antitumour activity of docetaxel following treatment with the CYP17A1 inhibitor abiraterone: clinical evidence for cross-resistance? Ann Oncol. 2012; 23(11):2943-7. doi: 10.1093/annonc/mds119. PubMed PMID: 22771826.
19. Liu C, Zhu Y, Lou W, Cui Y, Evans C P, Gao A C. Inhibition of constitutively active Stat3 reverses enzalutamide resistance in LNCaP derivative prostate cancer cells. Prostate. 2014; 74(2):201-9. Epub 2013/12/07. doi: 10.1002/pros.22741. PubMed PMID: 24307657; PubMed Central PMCID: PMCPMC4437226.
20. Culig Z, Bartsch G, Hobisch A. Interleukin-6 regulates androgen receptor activity and prostate cancer cell growth. Mol Cell Endocrinol. 2002; 197(1-2):231-8. Epub 2002/11/15. PubMed PMID: 12431817.
21. McClelland R A, Manning D L, Gee J M, Anderson E, Clarke R, Howell A, et al. Effects of short-term antiestrogen treatment of primary breast cancer on estrogen receptor mRNA and protein expression and on estrogen-regulated genes. Breast Cancer Res Treat. 1996; 41(1):31-41. PubMed PMID: 8932874.
22. Bihani T, Patel H K, Arlt H, Tao N, Jiang H, Brown J L, et al. Elacestrant (RAD1901), a Selective Estrogen Receptor Degrader (SERD), Has Antitumor Activity in Multiple ER+ Breast Cancer Patient-derived Xenograft Models. Clin Cancer Res. 2017; 23(16):4793-804. doi: 10.1158/1078-0432.CCR-16-2561. PubMed PMID: 28473534.
23. Watson P A, Chen Y F, Balbas M D, Wongvipat J, Socci N D, Viale A, et al. Constitutively active androgen receptor splice variants expressed in castration-resistant prostate cancer require full-length androgen receptor. Proc Natl Acad Sci USA. 2010; 107(39):16759-65. doi: 10.1073/pnas.1012443107. PubMed PMID: 20823238; PubMed Central PMCID: PMC2947883.
24. Raina K, Lu J, Qian Y, Altieri M, Gordon D, Rossi A M, et al. PROTAC-induced BET protein degradation as a therapy for castration-resistant prostate cancer. Proc Natl Acad Sci USA. 2016; 113(26):7124-9. doi: 10.1073/pnas.1521738113. PubMed PMID: 27274052; PubMed Central PMCID: PMCPMC4932933.
25. Tang Y Q, Han B M, Yao X Q, Hong Y, Wang Y, Zhao F J, et al. Chimeric molecules facilitate the degradation of androgen receptors and repress the growth of LNCaP cells. Asian J Androl. 2009; 11(1):119-26. doi: 10.1038/aja.2008.26. PubMed PMID: 19050678; PubMed Central PMCID: PMCPMC3735208.
26. Ponnusamy S, Coss C C, Thiyagarajan T, Watts K, Hwang D J, He Y, et al. Novel Selective Agents for the Degradation of Androgen Receptor Variants to Treat Castration-Resistant Prostate Cancer. Cancer Res. 2017; 77(22):6282-98. doi: 10.1158/0008-5472.CAN-17-0976. PubMed PMID: 28978635.
27. Hwang D J, He Y, Ponnusamy S, Mohler M L, Thiyagarajan T, McEwan I J, et al. A New Generation of Selective Androgen Receptor Degraders: Our Initial Design, Synthesis, and Biological Evaluation of New Compounds with Enzalutamide-Resistant Prostate Cancer Activity. J Med Chem. 2018. Epub 2018/12/12. doi: 10.1021/acs.jmedchem.8b00973. PubMed PMID: 30525603.
28. Andersen R J, Mawji N R, Wang J, Wang G, Haile S, Myung J K, et al. Regression of castrate-recurrent prostate cancer by a small-molecule inhibitor of the amino-terminus domain of the androgen receptor. Cancer Cell. 2010; 17(6):535-46. Epub 2010/06/15. doi: 10.1016/j.ccr.2010.04.027. PubMed PMID: 20541699.

29. Krause W C, Shafi A A, Nakka M, Weigel N L. Androgen receptor and its splice variant, AR-V7, differentially regulate FOXA1 sensitive genes in LNCaP prostate cancer cells. Int J Biochem Cell Biol. 2014; 54:49-59. doi: 10.1016/j.biocel.2014.06.013. PubMed PMID: 25008967; PubMed Central PMCID: PMCPMC4160387.

30. Shafi A A, Putluri V, Arnold J M, Tsouko E, Maity S, Roberts J M, et al. Differential regulation of metabolic pathways by androgen receptor (AR) and its constitutively active splice variant, AR-V7, in prostate cancer cells. Oncotarget. 2015; 6(31):31997-2012. doi: 10.18632/oncotarget.5585. PubMed PMID: 26378018.

31. Narayanan R, Adigun A A, Edwards D P, Weigel N L. Cyclin-dependent kinase activity is required for progesterone receptor function: novel role for cyclin A/Cdk2 as a progesterone receptor coactivator. Mol Cell Biol. 2005; 25(1):264-77. PubMed PMID: 15601848.

32. Narayanan R, Coss C C, Yepuru M, Kearbey J D, Miller D D, Dalton J T. Steroidal androgens and nonsteroidal, tissue-selective androgen receptor modulator, S-22, regulate androgen receptor function through distinct genomic and nongenomic signaling pathways. Mol Endocrinol. 2008; 22(11):2448-65. PubMed PMID: 18801930.

33. Yepuru M, Wu Z, Kulkarni A, Yin F, Barrett C M, Kim J, et al. Steroidogenic enzyme AKR1C3 is a novel androgen receptor-selective coactivator that promotes prostate cancer growth. Clin Cancer Res. 2013; 19(20):5613-25. doi: 10.1158/1078-0432.CCR-13-1151. PubMed PMID: 23995860.

34. Scheller A, Hughes E, Golden K L, Robins D M. Multiple receptor domains interact to permit, or restrict, androgen-specific gene activation. J Biol Chem. 1998; 273(37):24216-22. PubMed PMID: 9727045.

35. Callewaert L, Van Tilborgh N, Claessens F. Interplay between two hormone-independent activation domains in the androgen receptor. Cancer Res. 2006; 66(1):543-53. doi: 10.1158/0008-5472.CAN-05-2389. PubMed PMID: 16397271.

36. Callewaert L, Verrijdt G, Haelens A, Claessens F. Differential effect of small ubiquitin-like modifier (SUMO)-ylation of the androgen receptor in the control of cooperativity on selective versus canonical response elements. Mol Endocrinol. 2004; 18(6):1438-49. doi: 10.1210/me.2003-0313. PubMed PMID: 15031320.

37. James A J, Agoulnik I U, Harris J M, Buchanan G, Tilley W D, Marcelli M, et al. A novel androgen receptor mutant, A748T, exhibits hormone concentration-dependent defects in nuclear accumulation and activity despite normal hormone-binding affinity. Mol Endocrinol. 2002; 16(12):2692-705. doi: 10.1210/me.2001-0281. PubMed PMID: 12456791.

38. Narayanan R, Yepuru M, Szafran A T, Szwarc M, Bohl C E, Young N L, et al. Discovery and mechanistic characterization of a novel selective nuclear androgen receptor exporter for the treatment of prostate cancer. Cancer Res. 2010; 70(2):842-51. doi: 10.1158/0008-5472.CAN-09-3206. PubMed PMID: 20068182.

39. Tilley W D, Marcelli M, McPhaul M J. Expression of the human androgen receptor gene utilizes a common promoter in diverse human tissues and cell lines. J Biol Chem. 1990; 265(23):13776-81. PubMed PMID: 2380187.

40. Buchanan G, Birrell S N, Peters A A, Bianco-Miotto T, Ramsay K, Cops E J, et al. Decreased androgen receptor levels and receptor function in breast cancer contribute to the failure of response to medroxyprogesterone acetate. Cancer Res. 2005; 65(18):8487-96. doi: 10.1158/0008-5472.CAN-04-3077. PubMed PMID: 16166329.

41. Mitchell S, Abel P, Madaan S, Jeffs J, Chaudhary K, Stamp G, et al. Androgen-dependent regulation of human MUC1 mucin expression. Neoplasia. 2002; 4(1):9-18. PubMed PMID: 11922395; PubMed Central PMCID: PMCPMC1503313.

42. Robinson J L, Macarthur S, Ross-Innes C S, Tilley W D, Neal D E, Mills I G, et al. Androgen receptor driven transcription in molecular apocrine breast cancer is mediated by FoxA1. EMBO J. 2011; 30(15):3019-27. doi: 10.1038/emboj.2011.216. PubMed PMID: 21701558; PubMed Central PMCID: PMCPMC3160190.

43. Hartig P C, Bobseine K L, Britt B H, Cardon M C, Lambright C R, Wilson V S, et al. Development of two androgen receptor assays using adenoviral transduction of MMTV-luc reporter and/or hAR for endocrine screening. Toxicol Sci. 2002; 66(1):82-90. PubMed PMID: 11861975.

44. Shortridge M D, Hage D S, Harbison G S, Powers R. Estimating protein-ligand binding affinity using high-throughput screening by NMR. J Comb Chem. 2008; 10(6):948-58. doi: 10.1021/cc800122m. PubMed PMID: 18831571; PubMed Central PMCID: PMCPMC2631241.

45. Dias D M, Ciulli A. NMR approaches in structure-based lead discovery: recent developments and new frontiers for targeting multi-protein complexes. Prog Biophys Mol Biol. 2014; 116(2-3):101-12. doi: 10.1016/j.pbiomolbio.2014.08.012. PubMed PMID: 25175337; PubMed Central PMCID: PMCPMC4261069.

46. Reid J, Murray I, Watt K, Betney R, McEwan I J. The androgen receptor interacts with multiple regions of the large subunit of general transcription factor TFIIF. The Journal of biological chemistry. 2002; 277(43):41247-53. doi: 10.1074/jbc.M205220200. PubMed PMID: 12181312.

47. Emami K H, Nguyen C, Ma H, Kim D H, Jeong K W, Eguchi M, et al. A small molecule inhibitor of beta-catenin/CREB-binding protein transcription [corrected]. Proc Natl Acad Sci USA. 2004; 101(34):12682-7. Epub 2004/08/18. doi: 10.1073/pnas.0404875101. PubMed PMID: 15314234; PubMed Central PMCID: PMCPMC515116.

48. Martinez Molina D, Jafari R, Ignatushchenko M, Seki T, Larsson E A, Dan C, et al. Monitoring drug target engagement in cells and tissues using the cellular thermal shift assay. Science. 2013; 341(6141):84-7. Epub 2013/07/06. doi: 10.1126/science.1233606. PubMed PMID: 23828940.

49. Trevino L S, Bolt M J, Grimm S L, Edwards D P, Mancini M A, Weigel N L. Differential Regulation of Progesterone Receptor-Mediated Transcription by CDK2 and DNA-PK. Mol Endocrinol. 2016; 30(2):158-72. doi: 10.1210/me.2015-1144. PubMed PMID: 26652902; PubMed Central PMCID: PMCPMC4792227.

50. Cai L, Tsai Y H, Wang P, Wang J, Li D, Fan H, et al. ZFX Mediates Non-canonical Oncogenic Functions of the Androgen Receptor Splice Variant 7 in Castrate-Resistant Prostate Cancer. Mol Cell. 2018; 72(2):341-54 e6. Epub 2018/10/03. doi: 10.1016/j.molcel.2018.08.029. PubMed PMID: 30270106; PubMed Central PMCID: PMCPMC6214474.

51. Houtman R, de Leeuw R, Rondaij M, Melchers D, Verwoerd D, Ruijtenbeek R, et al. Serine-305 phosphorylation modulates estrogen receptor alpha binding to a coregulator peptide array, with potential application in predicting responses to tamoxifen. Mol Cancer Ther.

2012; 11(4):805-16. Epub 2012/02/10. doi: 10.1158/ 1535-7163.MCT-11-0855. PubMed PMID: 22319200.
52. Pollock J A, Wardell S E, Parent A A, Stagg D B, Ellison S J, Alley H M, et al. Inhibiting androgen receptor nuclear entry in castration-resistant prostate cancer. Nat Chem Biol. 2016; 12(10):795-801. Epub 2016/08/09. doi: 10.1038/nchembio.2131. PubMed PMID: 27501397; PubMed Central PMCID: PMCPMC5030124.

Example 19

Competitive, Radioactivity Displacement Assay for NTD Binding: Synthesis of Radioactive SARDs Including $^3$H-1002 and its Use in an Assay of Competitive Binding to the NTD We observed that 1002 was a potent androgen receptor (AR) antagonist with unique properties; however, quizzically we could not demonstrate potent binding to the AR LBD. The canon (recognized rules or scientific laws) in AR biology is that ligands bind to the ligand binding domain (LBD), but 1002 does not appreciably bind LBD, the canonical binding site. Earlier SARDs like 11 and 17 bound competitively to the LBD, i.e., you can displace 11 or 17 by adding a known LBD binder. Competitive binding is the gold standard for demonstrating binding to a particular binding site and rank ordering ligands by relative binding affinity.

We have struggled to demonstrate that 1002 binds to another (non-canonical) site on the AR. The observed degradation of AR-V7 suggested binding to either the N-terminal domain (NTD) or DNA-binding domain (DBD). However, no high affinity ligands exist for these non-canonical binding sites, so it was impossible to demonstrate competitive binding to these sites. Instead, we used many biochemical constructs [NTD only, LBD only, full-length wildtype AR (NTD-DBD-LBD), full-length chimeric proteins that are part glucocorticoid receptor (GR) and part AR], tested in many biophysical experiments [biolayer interferometry (BLI), surface plasmon resonance (SPR), NMR, fluorescence polarization, Raman, cellular thermal shift assay (CE-TSA)]. Consistently we have found that the co-incubation of 1002 (and many other of our SARDs including 11) with NTD produces data suggestive of NTD binding. These biophysical techniques are not the gold standard but rather demonstration of competitive binding is industry standard, however no other high affinity NTD binders exist. In light of this, we endeavored to make our own competitive binding assay using radioactive 1002 ($^3$H-1002) and attempted to localize radioactivity to the NTD protein but not LBD, and then displace the radioactivity with cold (non-radioactive) 1002. Radioactive $^3$H-1002 was purchased from a vendor (Perkin Elmer) but many technical problems delayed the demonstration of competitive binding to NTD (as outlined in Example 18). The technical problems were solved and, as demonstrated in Example 18 (FIG. 43B), competitive binding to the NTD has been shown.

Noncompetitive antagonism (or AF1 antagonism or NTD antagonism) with an orally active small molecule is novel and unique, and suggestive of our ability to broadly overcome resistance to known agents (all direct (antiandrogens) or indirect (CYP17 inhibitors) LBD binders). Correspondingly, current leads have demonstrated potent in vivo activity in enzalutamide-resistant tumors and many other types of CRPC. Since most CRPC tumors grow due to re-activated AR signaling despite androgen-deprivation and AR antagonism, only truly androgen-independent prostate cancers (like PC3) theoretically would be beyond the reach of such inhibitors.

Data Examples presented herein are convincing with regard to the ability of our SARDs to bind the NTD, act as potent and full AR antagonists in vivo and produce unprecedented phenotypic changes in vivo. E.g., chemical castration with a small molecule (1002) and overcoming AR-V7 mediated and other types of enzalutamide resistance are unexpected in view of the prior art.

The ability to formulate a competitive NTD binding assay, as demonstrated in Example 18, allows the skilled artisan to perform assays to rank order putative NTD-dependent SARD libraries by the appropriate target binding affinity (i.e., NTD binding affinity) instead of using surrogate markers such as SARD activity or in vivo antagonism as screening techniques.

Currently there is no publicly available competitive binding assay for NTD binding compounds and no other candidate radioactive NTD binding ligands to formulate such an assay. The discovery of our unique NTD dependent SARDs and their use in this novel competitive NTD-binding assay may be seminal events in the development of future generations of prostate cancer therapeutics including treatment of CSPC or CRPC patients that are resistant to all currently known therapies. In view of the unprecedent assay abilities (i.e., able to screen for NTD binding) and technical difficulties in formulating the assay, and further in view of the unprecedentedly broad spectrum of in vivo AR antagonist and prostate cancer therapeutic activities of the compounds discoverable by the assay, the NTD binding assay of this invention is novel and unexpected in view of the prior art.

Synthesis of Radioactive SARDs Including $^3$H-1002

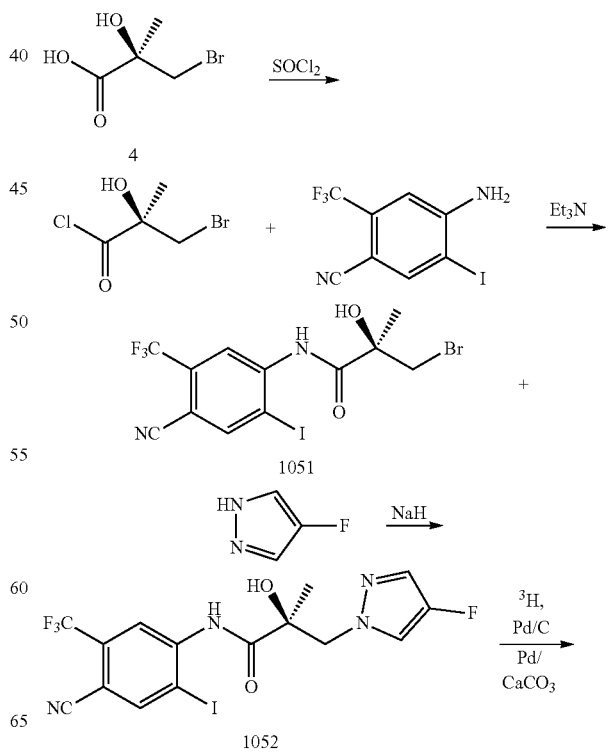

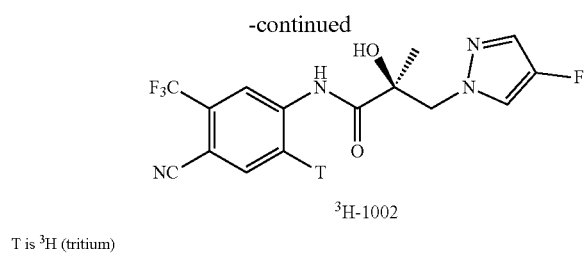

³H-1002

T is ³H (tritium)

(R)-3-Bromo-N-(4-cyano-2-iodo-5-(trifluoromethyl)
phenyl)-2-hydroxy-2-methylpropanamide
(C₁₂H₉BrF₃IN₂O₂) (1051)

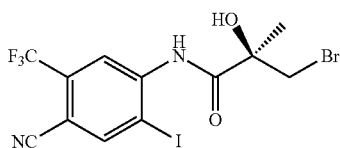 [SMILES: C[C@](O)(CBr)C(=O)Nc1cc(C(F)(F)F)c(C#N)cc1I]

3-Bromo-2-methyl-2-hydroxypropanoic acid (4) (0.50 g, 0.00273224 mol) was reacted with thionyl chloride (0.39 g, 0.0032787 mol), trimethylamine (0.36 g, 0.0035519 mol), and 4-amino-5-iodo-2-(trifluoromethyl)benzonitrile (0.81 g, 0.0025956 mol) to afford the titled compound. The product was purified by a silica gel column using DCM and ethyl acetate (9:1) as eluent to afford 0.80 g (64.6%) of the titled compound as a light brown solid.

¹H NMR (400 MHz, CDCl₃) δ 9.53 (s, 1H, NH), 8.92 (s, 1H, ArH), 8.24 (s, 1H, ArH), 7.26 (s, 1H, OH), 4.04 (d, J=10.4 Hz, 1H, CH), 3.62 (d, J=10.4 Hz, 1H, CH), 1.67 (s, 3H, CH₃).

Mass (ESI, Positive): 479.25[M+H]⁺.

(S)—N-(4-Cyano-2-iodo-5-(trifluoromethyl)phenyl)-
3-(4-fluoro-1H-pyrazol-1-yl)-2-hydroxy-2-methyl-
propanamide (C₁₅H₁₁F₄IN₄O₂) (1052)

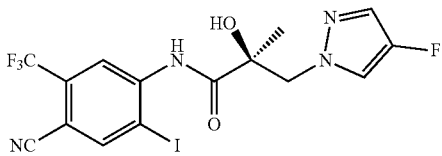

To a solution of 4-fluoro-1H-pyrazole (0.09 g, 0.001048 mol) in anhydrous THF (5 mL), which was cooled in an ice water bath under an argon atmosphere, was added sodium hydride (60% dispersion in oil, 0.15 g, 0.003669 mol). After addition, the resulting mixture was stirred for three hours. (R)-3-Bromo-N-(4-cyano-2-iodo-5-(trifluoromethyl)phenyl)-2-hydroxy-2-methylpropanamide (0.50 g, 0.001048 mol) was added to above solution, and the resulting reaction mixture was allowed to stir overnight at room temperature under argon. The reaction was quenched by water and extracted with ethyl acetate. The organic layer was washed with brine, dried with MgSO₄, filtered, and concentrated under vacuum. The product was purified by a silica gel column using hexanes and ethyl acetate (2:1 to 1:1) as eluent to afford 0.32 g (64%) of the titled compound as a white solid.

¹H NMR (400 MHz, CDCl₃) δ 9.60 (s, 1H, NH), 8.76 (s, 1H, ArH), 8.69 (s, 1H, ArH), 7.76 (d, J=4.8 Hz, 1H, Pyrazole-H), 7.36 (d, J=4.4 Hz, 1H, Pyrazole-H), 6.85 (s, 1H, OH), 4.39 (d, J=14.0 Hz, 1H, CH), 4.20 (d, J=14.0 Hz, 1H, CH), 1.41 (s, 3H, CH₃).

Mass (ESI, Negative): 481.00 [M−H]⁻;

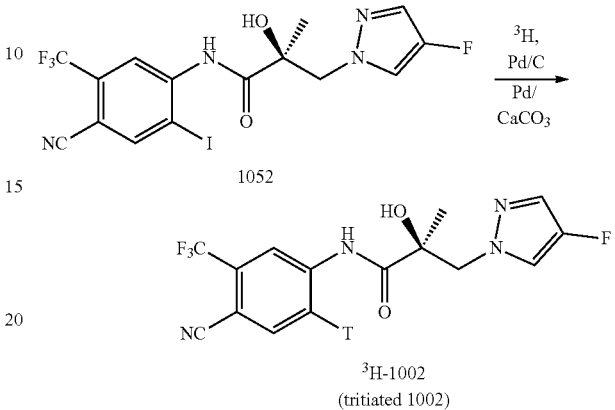

1052 was provided to Perkin Elmer who performed the replacement of the iodine of 1052 with tritium using the reagents shown. In short, 1052 was reacting the Lindlar palladium in the presence of tritiated hydrogen.

³H-1002 was synthesized as above, analyzed by Perkin Elmer to demonstrate purity and incorporation of radioactivity into ³H-1002, as described below, and formulated into the radioactive competitive displacement NTD binding affinity assay described in Example 18.

Figure 50A:
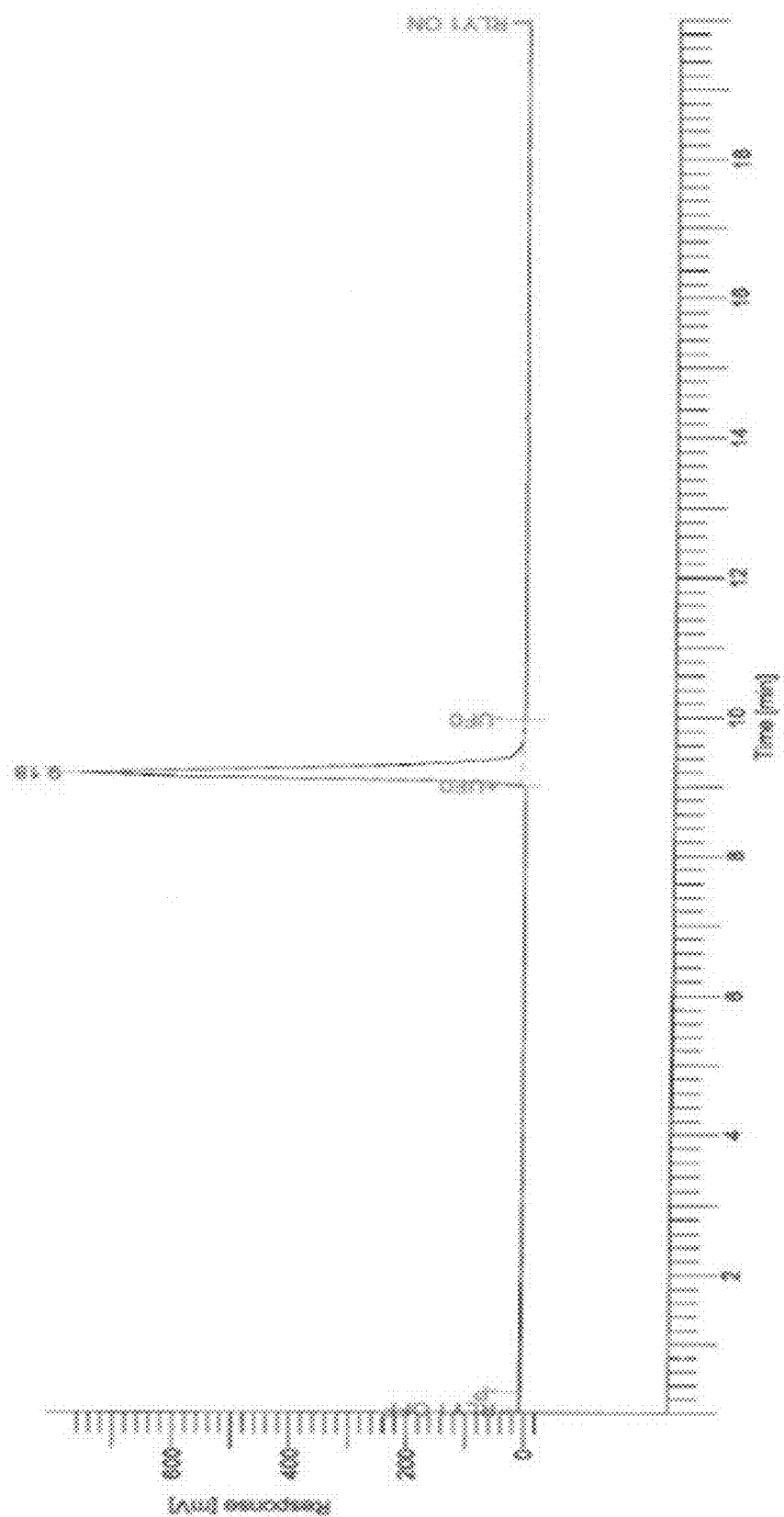
Figure 50B:
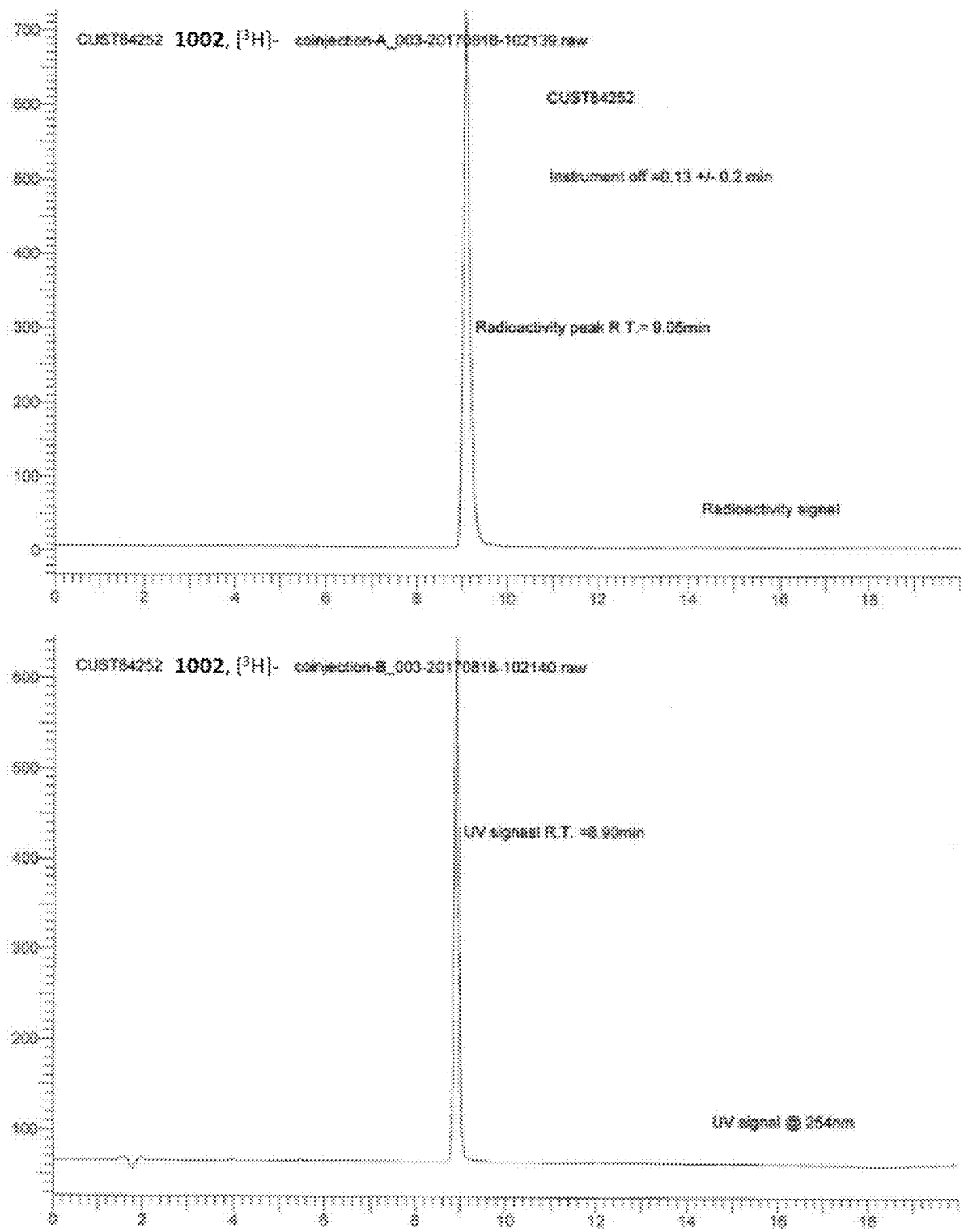
Figure 50C:
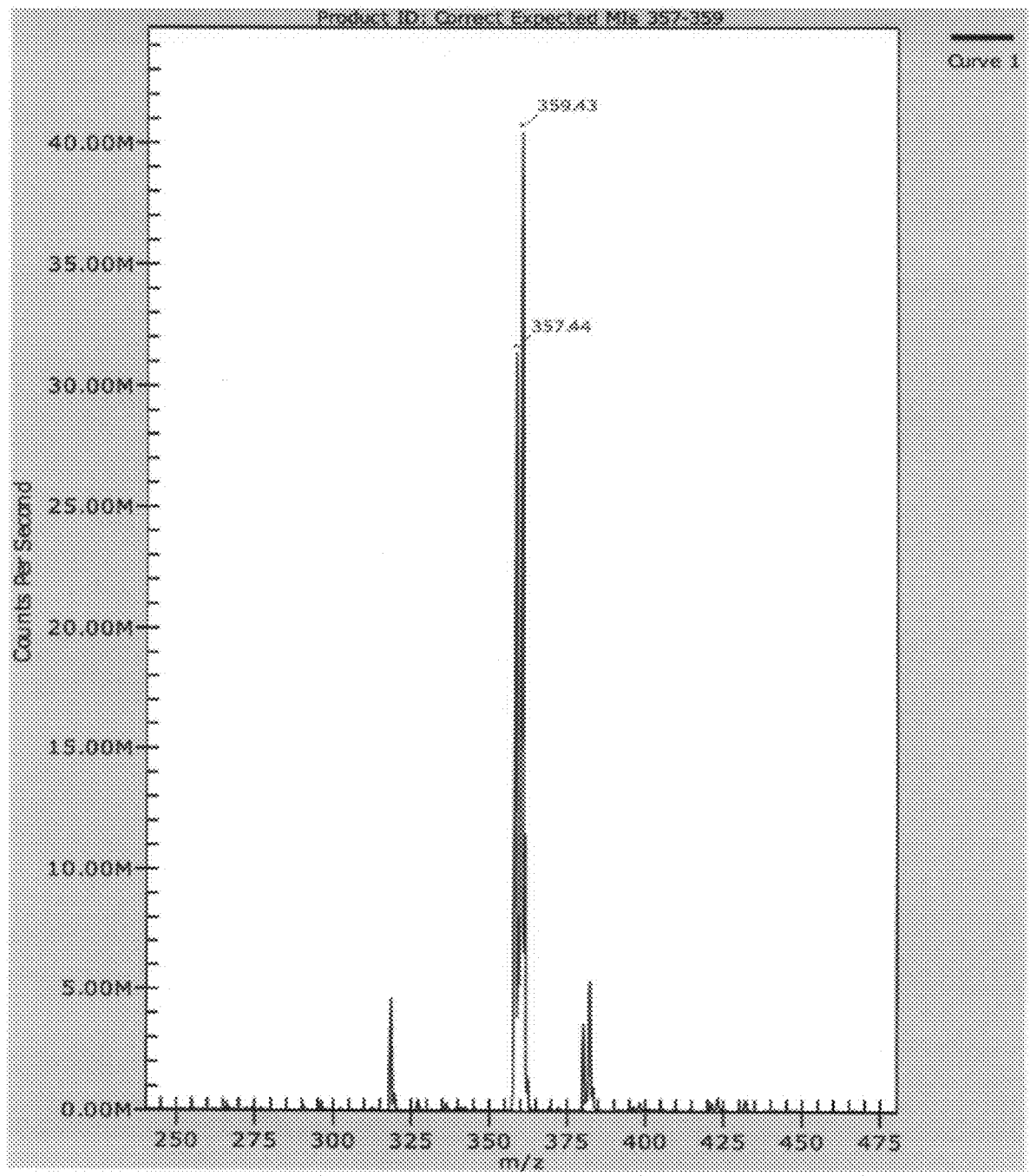

HPLC analysis of ³H-1002 is shown in FIG. 50 below using the mobile phase, flow rate, and run time indicated in the figure. The HPLC demonstrates a single peak at around 9.18 minutes indicating the absence of impurities (FIG. 50A). Further, radioactivity was demonstrated to migrate with the reaction product, indicating incorporation of the tritium into 1002 to produce ³H-1002 (FIG. 50B). The identity of ³H-1002 was further validated by mass spectrometry as demonstrated in FIG. 50C as a peak m/z 359.43 and possessing 16.24 Ci/mmol of radioactivity (FIG. 50D).

General Synthesis of Radioactive SARDs.

Using the reaction intermediate 1051 and the chemistry methods described throughout the Examples, a variety of tritiated SARDs can be synthesized and incorporated into various NTD binding affinity assays such as described in Example 18.

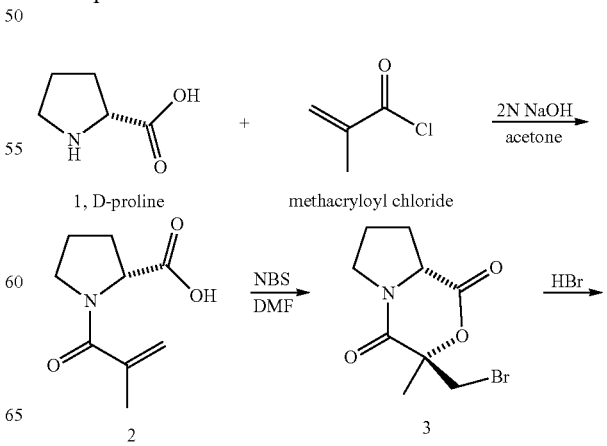

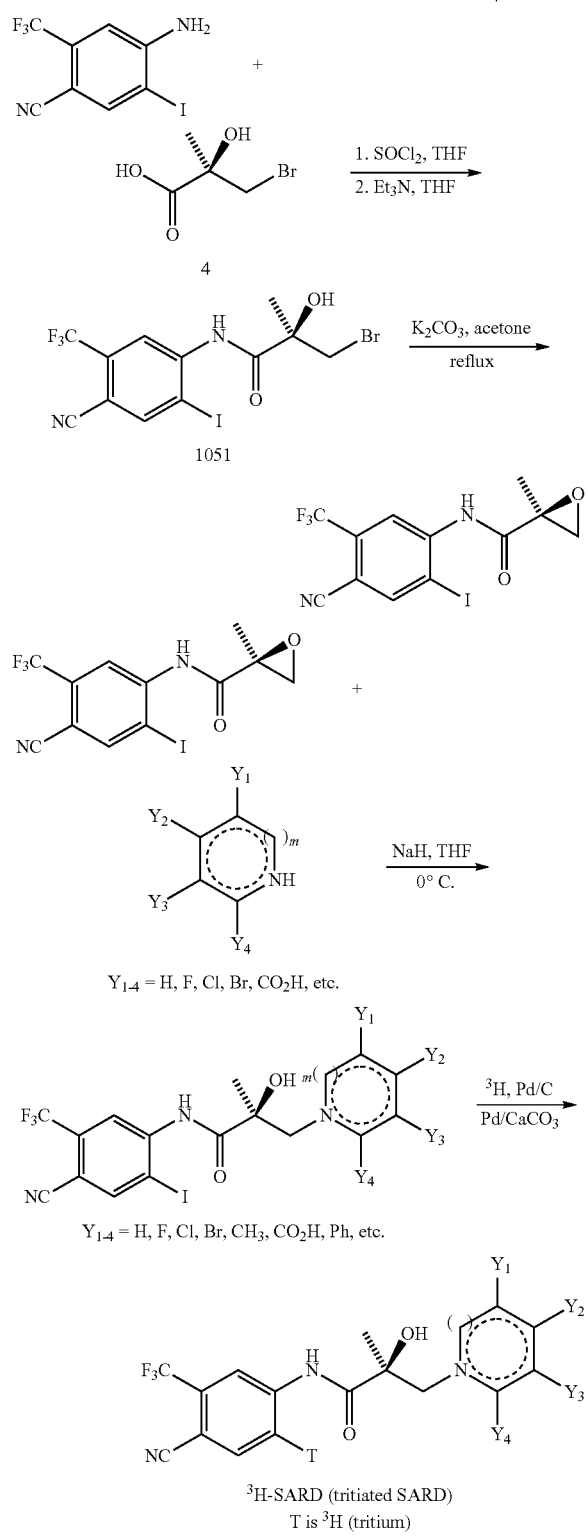

Novel NTD Binding Affinity Assay:

These experiments used the following protein constructs (peer reviewed literature providing full descriptions is cited in Example 18):

1) AR-LBD is a protein construct only consisting of the LBD domain of AR (industry standard is to use this construct in AR binding affinity assays);
2) AR-NTD is a protein construct only consisting of the NTD domain of AR;
3) GAA is a full-length protein in which the NTD is from the GR and DBD & LBD are from AR; or
4) AGG is a full-length protein in which the NTD is from the AR and DBD/LBD are GR.

The top panel of FIG. 43B shows that R1881 binds LBD and 1002 binds NTD: the first two bars act as a negative control, as cells lacking AR-NTD and AR-LBD, i.e. Vector, do not bind R1881 (industrial standard LBD binding agent) or $^3$H-1002 (radioactive 1002). The middle pair of bars act as a positive control and demonstrates that R1881 binds to AR-LBD using this methodology. The right pair of bars demonstrates that $^3$H-1002 binds to AR-NTD, i.e., ~3 to 4-fold higher radioactivity than Vector. Cumulatively, these data confirm our ability to localize radioactivity to the expected binding site, whether LBD or NTD.

The $2^{nd}$ panel down of FIG. 43B shows that R1881 binds to AR-LBD (GAA) whereas $^3$H-1002 binds to AR-NTD (AGG). Again, Vector serves as a negative-control and GAA construct serves as positive control (R1881 is expected to binding AR-LBD). $^3$H-1002 bound to the construct with the AR-NTD (AGG) but not GR-NTD (GAA), i.e., about 2-fold increased radioactivity.

A column is used to separate the unbound small molecules from the bound small molecules, and the enrichment in radioactivity, i.e., $^3$H-1002 binding, is seen in the $3^{rd}$ panel down of FIG. 43B.

The $3^{rd}$ panel down (lowest panel) of FIG. 43B demonstrates our ability to displace $^3$H-1002 from the NTD. Vector is a negative control in which no AGG (AR is NTD) is present so $^3$H-1002 should not bind. Middle column shows that $^3$H-1002 binds AGG (AR is NTD). Right bar demonstrates that adding non-radioactive 1002 at higher concentrations is able to competitively displace the radioactive $^3$H-1002.

This data is the first demonstration of competitive binding to the NTD. It conforms to industry standards for demonstrating competitive binding, is easily understood by any biologist that screens for ligand binding, provides compelling data that 1002 and other SARDs of this invention are NTD specific AR antagonists and represents the first orally active non-competitive AR antagonist. These data help to rationalize the unprecedented activities of 1002 and other pyrazoles such as 1065 (compound not reported here; anti-tumor activities in models of enzalutamide resistance are shown under separate cover) and 1058 (anti-tumor activities in models of enzalutamide resistance are shown under separate cover).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention

What is claimed is:

1. A method of treating an androgen receptor dependent disease or condition in a subject in need thereof, comprising administering to the subject a therapeutically effective amount of a selective androgen receptor degrader (SARD) compound represented by the structure of formula I

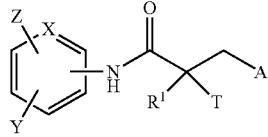

wherein
T is OH, OR, OCOR, CH$_3$, —NHCOCH$_3$, or NHCOR;
R$^1$ is CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a five or six-membered saturated or unsaturated ring having at least one nitrogen atom and 0, 1, or 2 double bonds, optionally substituted with at least one of Q$^1$, Q$^2$, Q$^3$ and Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, benzyl, NCS, maleimide, NHCOOR, N(R)$_2$, NHCOR, CONHR, COOR or COR;
R$^3$ is halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer or a racemic mixture thereof, pharmaceutically acceptable salt, pharmaceutical product, or any combination thereof.

2. The method of claim 1, wherein said SARD compound is represented by the structure of formula IA:

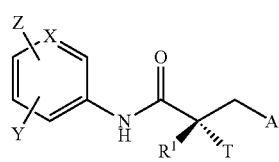

or its optical isomer, pharmaceutically acceptable salt, pharmaceutical product, or any combination thereof.

3. The method of claim 1, wherein said SARD compound is represented by the structure of formula IB:

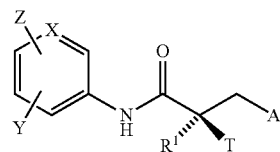

or its optical isomer, pharmaceutically acceptable salt, pharmaceutical product, or any combination thereof.

4. The method of claim 1, wherein said SARD compound is represented by the structure of formula II:

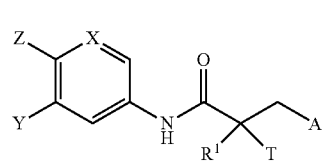

wherein
T is OH, OR, OCOR, CH$_3$, —NHCOCH$_3$, or NHCOR;
R$^1$ is CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrrolidine, pyrazole, pyrazolidine, triazole, imidazole, imidazolidine, or morpholine ring, said ring optionally substituted with at least one of Q$^1$, Q$^2$, Q$^3$ and Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, benzyl, NCS, maleimide, NHCOOR, N(R)$_2$, NHCOR, CONHR, COOR or COR;
R$^3$ is halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$ SO$_3$H, SO$_2$NH$_2$, SO$_2$NH(R$^4$), SO$_2$N(R$^4$)$_2$, NH$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer or a racemic mixture thereof, pharmaceutically acceptable salt, pharmaceutical product, or any combination thereof.

5. The method of claim 4, wherein said SARD compound is represented by the structure of formula IIA:

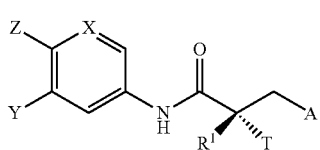

or its optical isomer, pharmaceutically acceptable salt, pharmaceutical product, or any combination thereof.

6. The method of claim 4, wherein said SARD compound is represented by the structure of formula IIB:

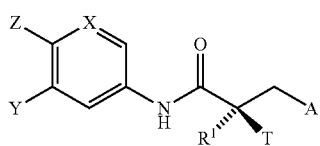

or its optical isomer, pharmaceutically acceptable salt, pharmaceutical product, or any combination thereof.

7. The method of claim 1, wherein said SARD compound is represented by the structure of formula VII:

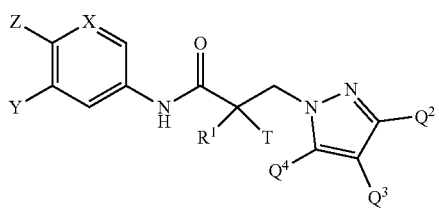

wherein

X is CH or N;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is $CH_3$, $CH_2F$, $CHF_2$, $CF_3$, $CH_2CH_3$, or $CF_2CF_3$;

T is OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^2$, $Q^3$ and $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

or its optical isomer or a racemic mixture thereof, pharmaceutically acceptable salt, pharmaceutical product, or any combination thereof.

8. The method of claim 7, wherein said SARD compound is represented by the structure of formula VIIA:

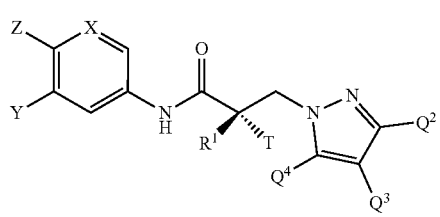

or its optical isomer, pharmaceutically acceptable salt, pharmaceutical product, or any combination thereof.

9. The method of claim 7, wherein said SARD compound is represented by the structure of formula VIIB:

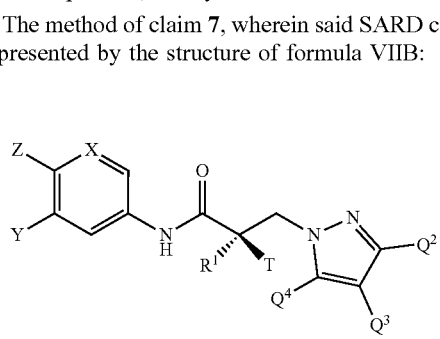

or its optical isomer, pharmaceutically acceptable salt, pharmaceutical product, or any combination thereof.

10. The method of claim 1, wherein $Q^1$, $Q^2$, $Q^3$ and $Q^4$ is hydrogen, CN, $NO_2$, $CF_3$, F, Cl, Br, I, NHCOOR, $N(R)_2$, NHCOR, COR, alkyl, alkoxy, or substituted or unsubstituted phenyl.

11. The method of claim 1, wherein said SARD compound is represented by the structure of any one of the following compounds:

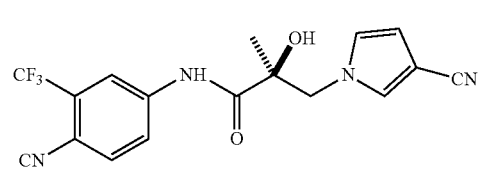

1001

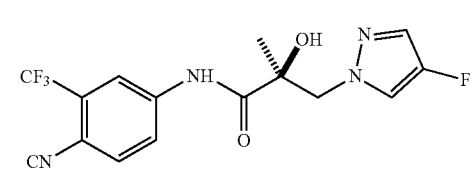

1002

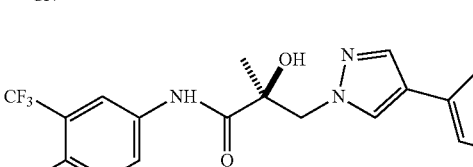

1003

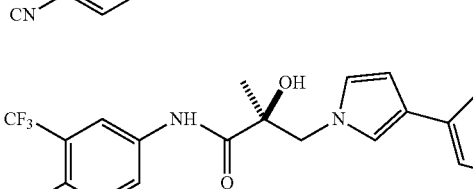

1004

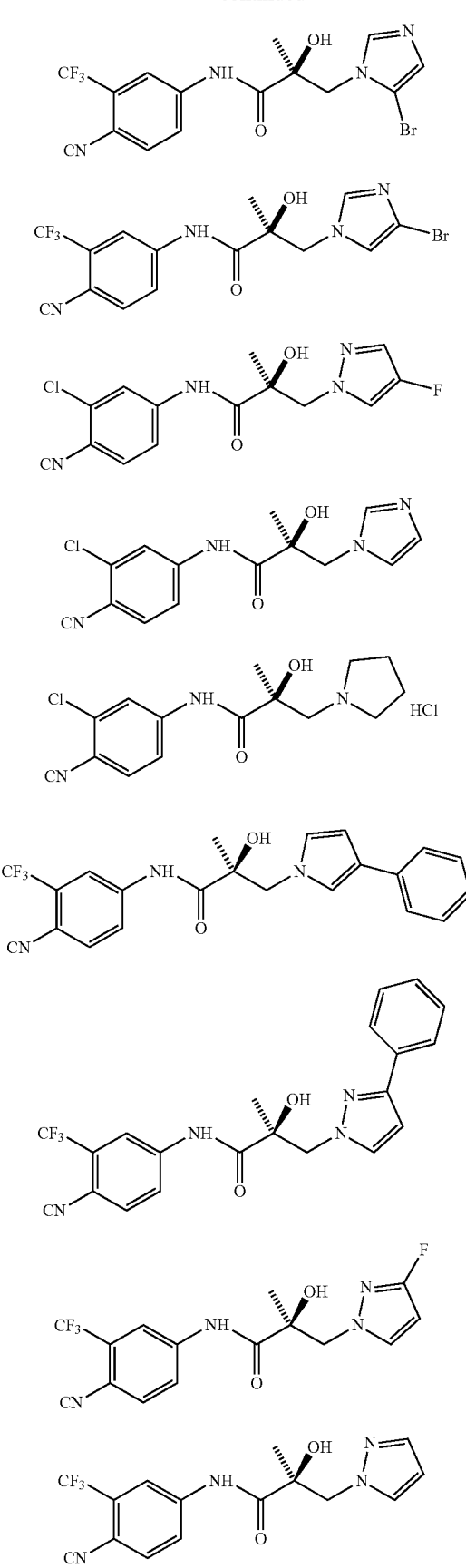
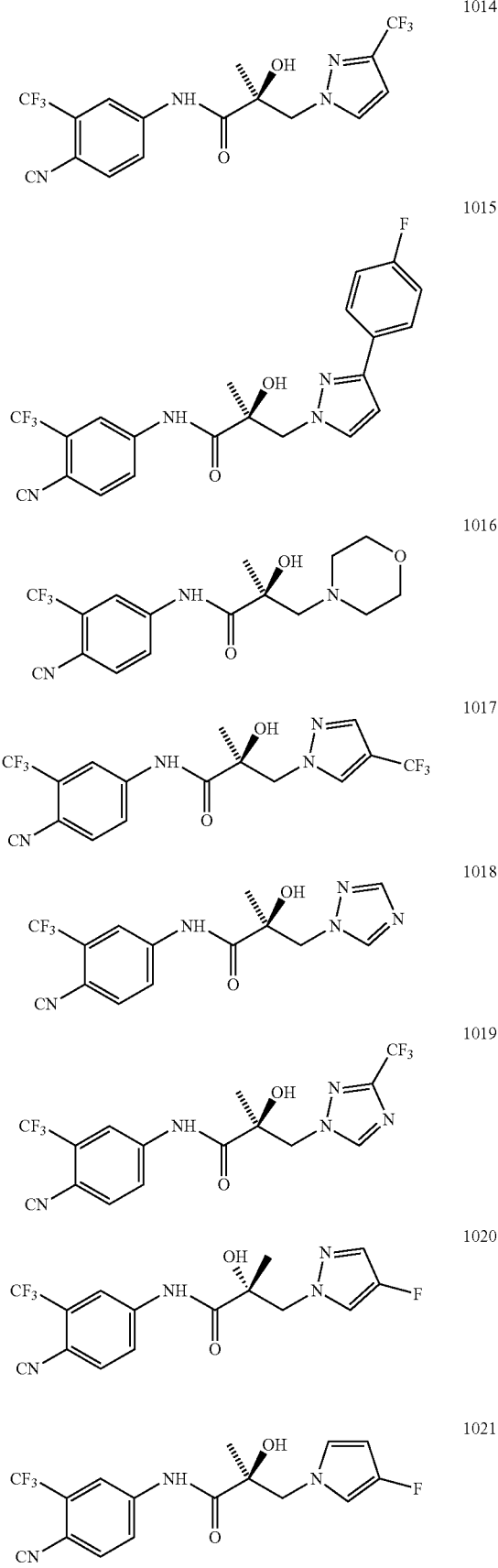

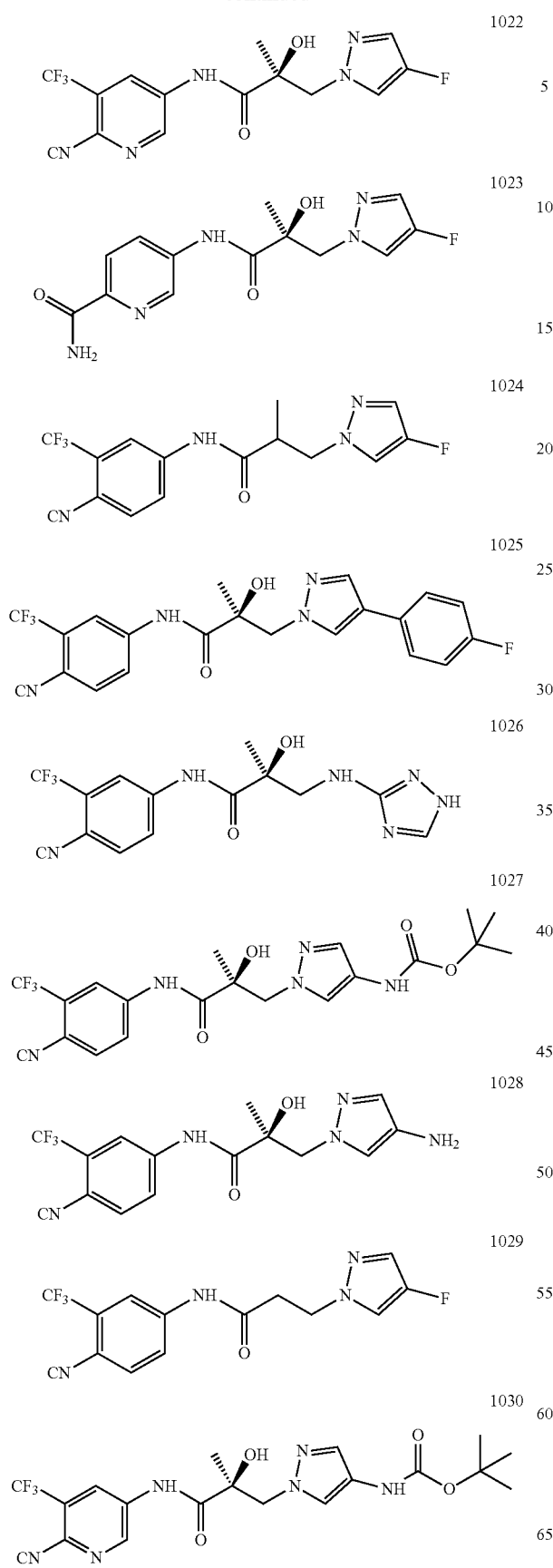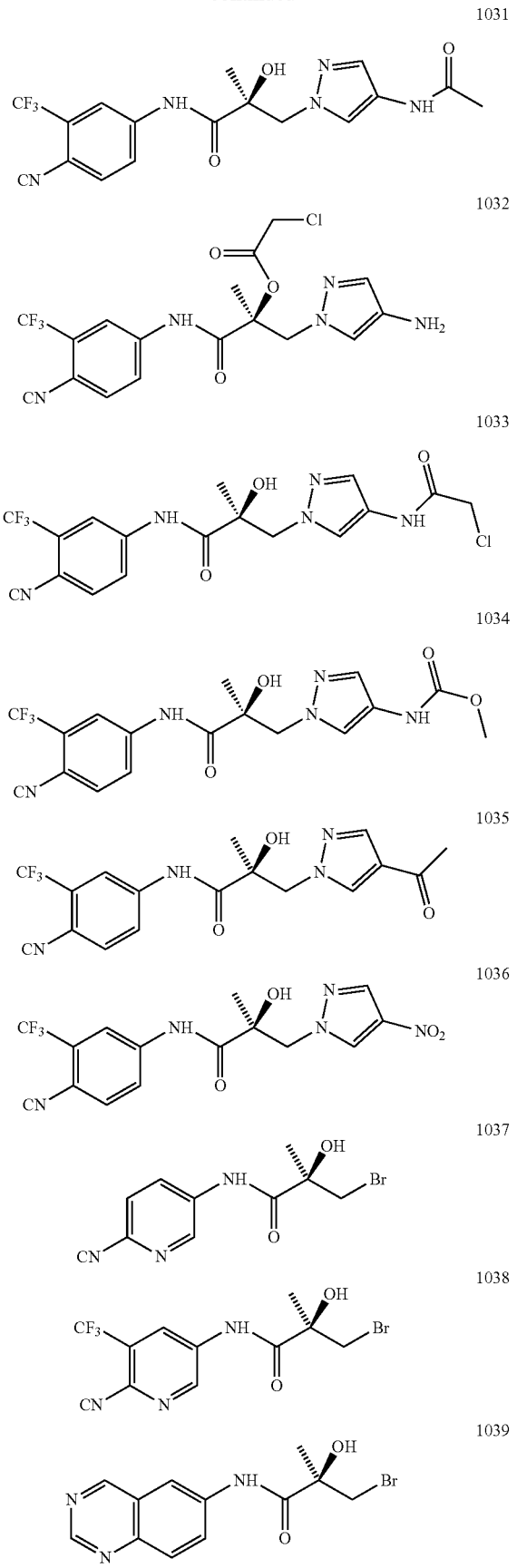

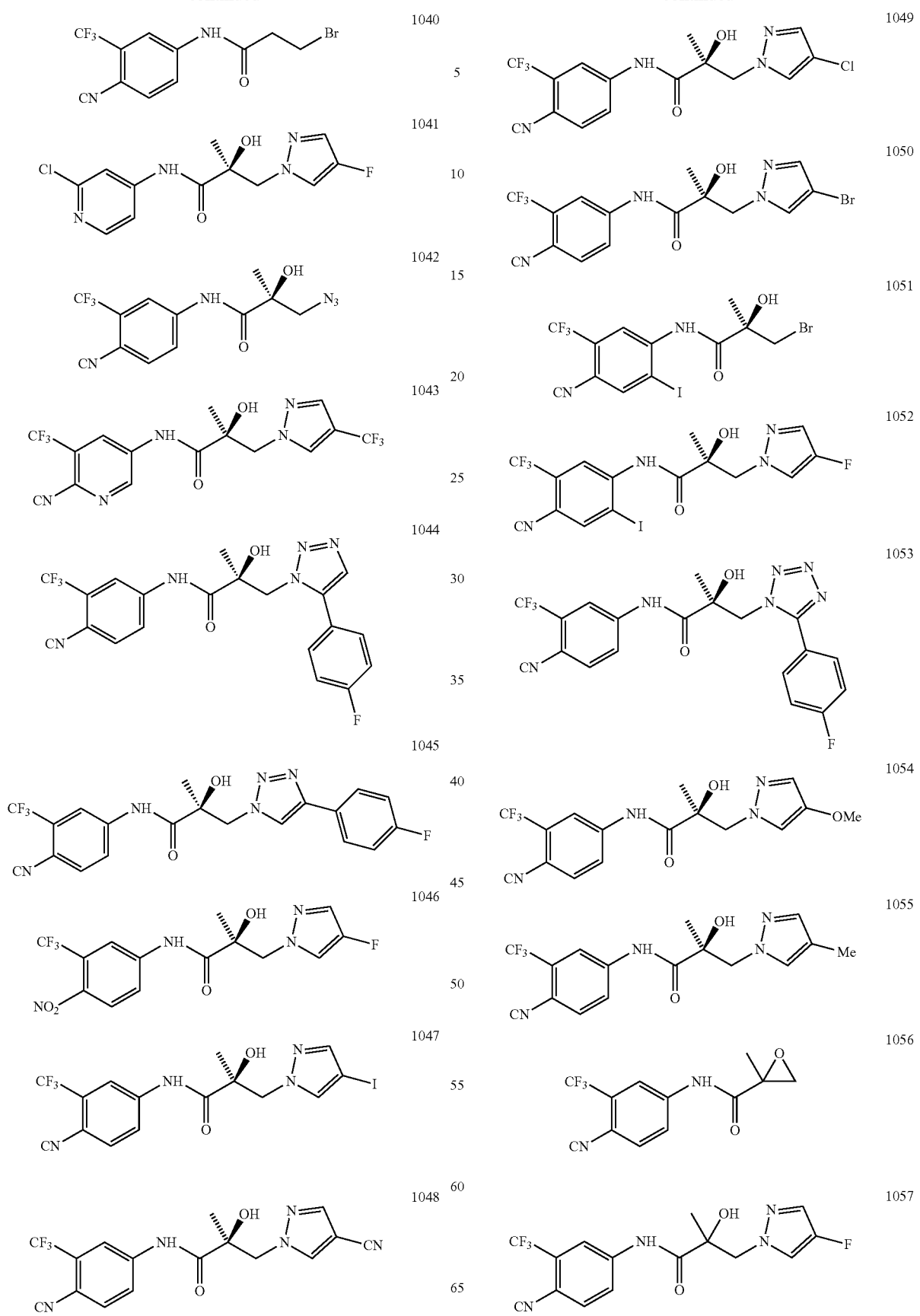

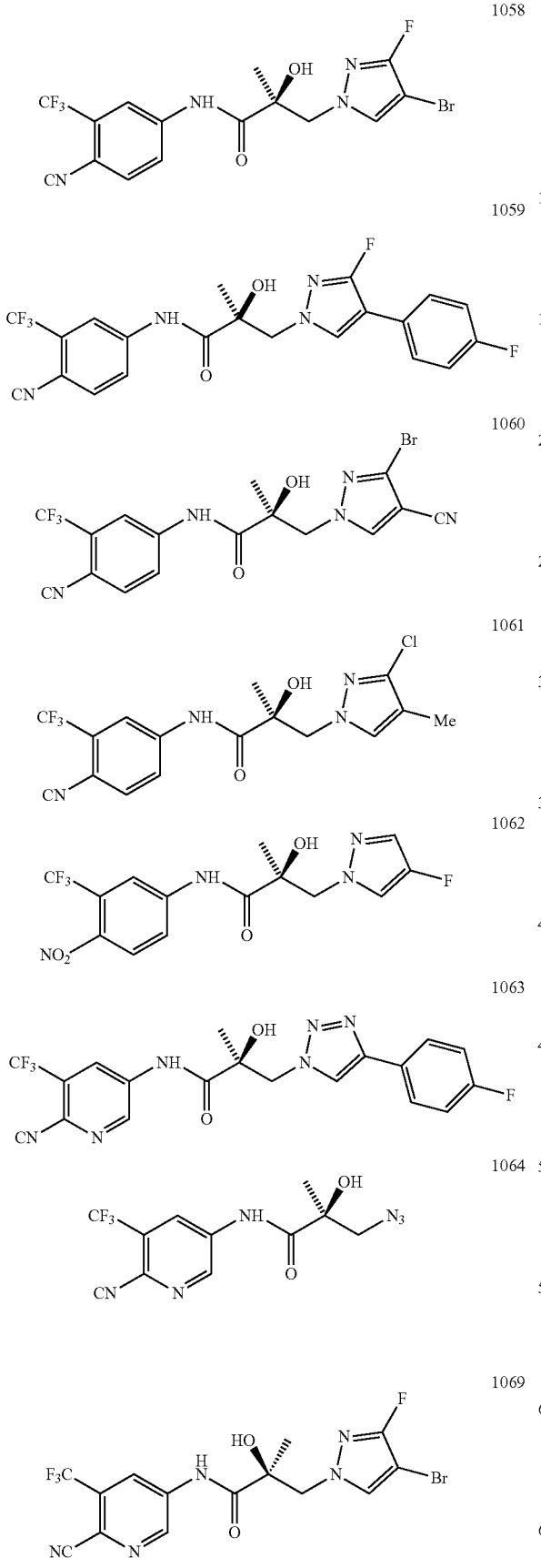

12. The method of claim 1, wherein said androgen receptor dependent disease or condition in said subject responds to at least one of AR-splice variant (AR-SV) degradation activity, full length (AR-FL) degradation activity, AR-SV inhibitory, or AR-FL inhibitory activity.

13. The method of claim 1, wherein said androgen receptor dependent disease or condition is Kennedy's disease in said subject.

14. The method of claim 1, wherein said androgen receptor dependent disease or condition is acne in said subject.

15. The method of claim 14, wherein said acne is acne vulgaris.

16. The method of claim 1, wherein said androgen receptor dependent disease or condition is overproduction of sebum in said subject.

17. The method of claim 16, wherein reducing said overproduction of sebum treats at least one of seborrhea, seborrheic dermatitis, or acne.

18. The method of claim 1, wherein said androgen receptor dependent disease or condition is hirsutism or alopecia in said subject.

19. The method of claim 18, wherein said alopecia is at least one of androgenic alopecia, alopecia areata, alopecia secondary to chemotherapy, alopecia secondary to radiation therapy, alopecia induced by scarring, or alopecia induced by stress.

20. The method of claim 1, wherein said androgen receptor dependent disease or condition is a hormonal disease or condition in a female in said subject.

21. The method of claim 20, wherein said hormonal disease or condition in a female is at least one of precocious puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, pre-menstrual syndrome, or vaginal dryness.

22. The method of claim 1, wherein said androgen receptor dependent disease or condition is sexual perversion, hypersexuality, or paraphilias in said subject.

23. The method of claim 1, wherein said androgen receptor dependent disease or condition is androgen psychosis in said subject.

24. The method of claim 1, wherein said androgen receptor dependent disease or condition is virilization in said subject.

25. The method of claim 1, wherein said androgen receptor dependent disease or condition is androgen insensitivity syndrome in said subject.

26. The method of claim 1, wherein said androgen receptor dependent disease or condition is amyotrophic lateral sclerosis (ALS) in said subject.

27. The method of claim 1, wherein said androgen receptor dependent disease or condition is uterine fibroids in said subject.

28. The method of claim 1, wherein said androgen receptor dependent disease or condition is abdominal aortic aneurysm (AAA) in said subject.

29. The method of claim 1, wherein said androgen receptor dependent disease or condition is caused by polyglutamine (polyQ) AR polymorphs in a subject.

30. The method according to claim 29, wherein the polyQ-AR is a short polyQ polymorph or a long polyQ polymorph.

31. The method according to claim 30, wherein the polyQ-AR is a short polyQ polymorph and the method further treats dermal disease.

32. The method according to claim 31, wherein the dermal disease is at least one of alopecia, seborrhea, seborrheic dermatitis, or acne.

33. The method according to claim 30, wherein the polyQ-AR is a long polyQ polymorph and the method further treats Kennedy's disease.

34. The method of claim 1, wherein said compound is

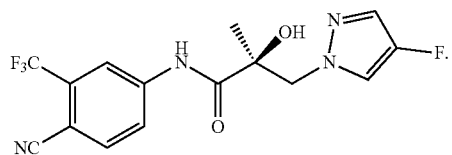

1002

35. The method of claim 1, wherein said compound is

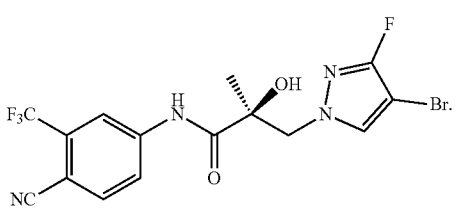

1058

\* \* \* \* \*

UNITED STATES PATENT AND TRADEMARK OFFICE
CERTIFICATE OF CORRECTION

PATENT NO. : 11,230,523 B2
APPLICATION NO. : 16/425865
DATED : January 25, 2022
INVENTOR(S) : Ramesh Narayanan It is certified that error appears in the above-identified patent and that said Letters Patent is hereby corrected as shown below:

On the Title Page

Page 2, Column 2 Item (56) (Other Publications), Line 38, delete "Nonsteroida" and insert --Nonsteroidal--.

Page 4, Column 2 Item (56) (Other Publications), Line 22, delete "androiogy." and insert --andrology.--.

Page 4, Column 2 Item (56) (Other Publications), Line 30, delete "https:llpubchem" and insert --https://pubchem--.

Page 4, Column 2 Item (56) (Other Publications), Line 51, delete "ary1" and insert --aryl--.

Page 4, Column 2 Item (56) (Other Publications), Line 52, delete "methy1" and insert --methyl--.

Page 4, Column 2 Item (56) (Other Publications), Line 59, delete "Tabolpgullari" and insert --Tarolpgullari--.

In the Drawings

Sheet 61 of 89 (Figure 44B), Line 4 (approx.), delete "Figure" and insert --Figures--.

In the Specification

Column 3, Line 40, delete "384860)," and insert --384860,--.

Column 4, Line 13, delete "xenograpfts" and insert --xenografts--.

Column 4, Line 34, delete "CPRC" and insert --CRPC--.

Signed and Sealed this
Second Day of August, 2022

Katherine Kelly Vidal
*Director of the United States Patent and Trademark Office*

Column 4, Line 36, delete "endogeneous" and insert --endogenous--.

Column 5, Line 35, delete "endogeneous" and insert --endogenous--.

Column 6, Line 8 (approx.), delete "Vase" and insert --Vasc--.

Column 6, Line 25 (approx.), delete "endogeneous" and insert --endogenous--.

Column 7, Line 4, delete "I" and insert --I:--.

Column 7, Line 40, delete "SOR$^4$" and insert --SOR$^4$,--.

Column 8, Line 56, delete "R$^3$" and insert --R$^3$;--.

Column 9, Line 4, delete "SOR$^4$" and insert --SOR$^4$,--.

Column 20, Line 20 (approx.), delete "polymorphs" and insert --polymorphs.--.

Column 21, Line 4, delete "SOR$^4$" and insert --SOR$^4$,--.

Column 23, Line 41, delete "L" and insert --µL--.

Column 23, Line 53, delete "caluculated" and insert --calculated--.

Column 25, Line 66, delete "CPRC" and insert --CRPC--.

Column 26, Line 63, delete "C57BL6" and insert --C57BL/6--.

Column 27, Line 18, delete "(Cl$_{int}$)." and insert --(CL$_{int}$).--.

Column 27, Line 48, delete "FIG." and insert --FIGS.--.

Column 28, Line 45, delete "(6" and insert --(δ--.

Column 29, Line 3, delete "FIG." and insert --FIGS.--.

Column 30, Line 32, delete "FIG." and insert --FIGS.--.

Column 30, Line 65, delete "FIG." and insert --FIGS.--.

Column 31, Line 13, delete "FIG." and insert --FIGS.--.

Column 31, Line 21, delete "C57BL6" and insert --C57BL/6--.

Column 31, Line 42, delete "FIG." and insert --FIGS.--.

Column 33, Line 8, delete "5888," and insert --S888,--.

Column 35, Line 49, delete "SOR$^4$" and insert --SOR$^4$,--.

Column 36, Line 37 (approx.), delete "SOR$^4$" and insert --SOR$^4$,--.

Column 37, Line 20 (approx.), delete "SOR$^4$" and insert --SOR$^4$,--.

Column 38, Line 28 (approx.), delete "SOR$^4$" and insert --SOR$^4$,--.

Column 38, Line 32, delete "R$^4$ H," and insert --R$^4$ is H,--.

Column 39, Line 11 (approx.), delete "SOR$^4$" and insert --SOR$^4$,--.

Column 39, Line 66 (approx.), delete "SOR$^4$" and insert --SOR$^4$,--.

Column 40, Line 45 (approx.), delete "SOR$^4$" and insert --SOR$^4$,--.

Column 41, Line 24, delete "SOR4" and insert --SOR$^4$,--.

Column 48, Line 61, delete "SOR4" and insert --SOR$^4$,--.

Column 50, Line 4, delete "ring" and insert --ring.--.

Column 50, Line 13, delete "haloalkyl" and insert --haloalkyl.--.

Column 54, Line 18, delete "I I-IX," and insert --I-IX,--.

Column 54, Line 31, delete "IX" and insert --IX,--.

Column 54, Line 33, delete "IX" and insert --IX,--.

Column 54, Line 36, delete "IX" and insert --IX,--.

Column 54, Line 38, delete "IX" and insert --IX,--.

Column 54, Line 41, delete "IX" and insert --IX,--.

Column 54, Line 43, delete "IX" and insert --IX,--.

Column 54, Line 46, delete "IX" and insert --IX,--.

Column 55, Line 8 (approx.), delete "thiphene," and insert --thiophene,--.

Column 64, Line 58 (approx.), delete "tetrahydropyrimidone," and insert --tetrahydropyrimidine,--.

CERTIFICATE OF CORRECTION (continued)
U.S. Pat. No. 11,230,523 B2

Column 66, Line 52, delete "algenates," and insert --alginates,--.

Column 66, Line 59, delete "enanthuates," and insert --enanthates,--.

Column 66, Line 64, delete "hydroxycarboxlic" and insert --hydroxycarboxylic--.

Column 67, Line 10, delete "tartarates," and insert --tartrates,--.

Column 67, Line 26, delete "meglamines," and insert --meglumines,--.

Column 68, Line 29 (approx.), delete "stereroisomeric" and insert --stereoisomeric--.

Column 69, Line 3, delete "Z H, is" and insert --Z is H,--.

Column 69, Line 21-22, delete "CONH2, CONH(R4), CON(R4)2," and insert --CONH$_2$, CONH($R^4$), CON($R^4$)$_2$,--.

Column 69, Line 22, delete "SOR$^4$" and insert --SOR$^4$,--.

Column 75, Line 9, delete "aminoglutethamide)," and insert --aminoglutethimide),--.

Column 78, Line 7, delete "endogeneous" and insert --endogenous--.

Column 78, Line 51, delete "abberant" and insert --aberrant--.

Column 79, Line 2, delete "milieau." and insert --milieu.--.

Column 79, Line 3, delete "abberant" and insert --aberrant--.

Column 79, Line 4, delete "endogeneous" and insert --endogenous--.

Column 79, Line 6-7, delete "abberant" and insert --aberrant--.

Column 79, Line 10 (approx.), delete "abberant" and insert --aberrant--.

Column 79, Line 18 (approx.), delete "milieau." and insert --milieu.--.

Column 80, Line 11, delete "prostamegaly," and insert --prostatomegaly,--.

Column 80, Line 19-20, delete "prostamegaly" and insert --prostatomegaly--.

Column 80, Line 51, delete "supporativa," and insert --suppurativa,--.

Column 82, Line 36, delete "384860)," and insert --384860,--.

Column 84, Line 35, delete "scalatina," and insert --scarlatina,--.

Column 84, Line 48-49, delete "aphthosa," and insert --aphthous,--.

Column 87, Line 40, delete "arachinoid," and insert --arachnoid,--.

Column 87, Line 41, delete "uterile" and insert --uterine--.

Column 88, Line 67, delete "Propionbacterium" and insert --Propionibacterium--.

Column 90, Line 26, delete "pregeletanized" and insert --pregelatinized--.

Column 94, Line 39, delete "C.;" and insert --C.--.

Column 94, Line 44, delete "$d_6$)" and insert --$d_6$) δ--.

Column 94, Line 65, delete "C.;" and insert --C.--.

Column 95, Line 45, delete "(5." and insert --(5,--.

Column 97, Line 36 (approx.), delete "Br etc" and insert --Br, etc.--.

Column 100, Line 13 (approx.), delete "H" and insert --1H--.

Column 103, Line 51, delete "oil (0.35" and insert --oil, 0.35--.

Column 105, Line 61, delete "d6," and insert --$d_6$,--.

Column 105, Line 65, delete "d6," and insert --$d_6$,--.

Column 106, Line 39, delete "d6," and insert --$d_6$,--.

Column 107, Line 12, delete "C" and insert --(C--.

Column 110, Line 22, delete "8-" and insert --δ- --.

Column 111, Line 33, delete "d6," and insert --$d_6$,--.

Column 112, Line 52 (approx.), delete "Cano" and insert --Cyano--.

Column 113, Line 27 (approx.), delete "d6," and insert --$d_6$,--.

Column 119, Line 51, delete "d6," and insert --$d_6$,--.

Column 119, Line 52 (approx.), delete "H]- ;" and insert --H]-;--.

Column 119, Line 53, delete "F3N" and insert --$F_3N$--.

Column 121, Line 40, delete "d6," and insert --$d_6$,--.

Column 121, Line 41 (approx.), delete "H]- ;" and insert --H]-;--.

Column 122, Line 29 (approx.), delete "d6," and insert --$d_6$,--.

Column 122, Line 30 (approx.), delete "H]- ;" and insert --H]-;--.

Column 124, Line 36 (approx.), delete "H]- ;" and insert --H]-;--.

Column 125, Line 15 (approx.), delete "H]- ;" and insert --H]-;--.

Column 126, Line 18 (approx.), delete "H]- ;" and insert --H]-;--.

Column 126, Line 67 (approx.), delete "H]- ;" and insert --H]-;--.

Column 130, Line 61, delete "CHzCl$_2$" and insert --CH$_2$Cl$_2$--.

Column 132, Line 4, delete "CH2C2" and insert --CH$_2$Cl$_2$--.

Column 133, Line 40 (approx.), delete "d6," and insert --$d_6$,--.

Column 136, Line 25, delete "vi)" and insert --yl)--.

Column 155-156, Line 26 (approx.), delete "µM)" and insert --(µM)--.

Column 161, Line 29, delete "yets" and insert --yet--.

Column 165, Line 59-60, delete "Fischer" and insert --Fisher--.

Column 166, Line 8, delete "isofluorane" and insert --isoflurane--.

Column 166, Line 26, delete "possibled" and insert --possible--.

Column 166, Line 55, delete "3-D" and insert --β-D--.

Column 167, Line 8, delete "AVANCEIII" and insert --AVANCE III--.

Column 167, Line 28, delete "Kda." and insert --kDa.--.

Column 168, Line 18, delete "km" and insert --$\lambda_{max}$--.

Column 172, Line 22 (approx.), delete "CPRC." and insert --CRPC.--.

Column 174, Line 36, delete "H]-;" and insert --H]-.--.

Column 177, Line 40 (approx.), delete "F4N₄" and insert --F$_4$N$_4$--.

Column 179, Line 12 (approx.), delete "[C21" and insert --[C$_{21}$--.

Column 179, Line 50, delete "H12" and insert --H$_{12}$--.

Column 181, Line 9 (approx.), delete "H]- ;" and insert --H]-;--.

Column 181, Line 10, delete "Na]$^+$;" and insert --Na]$^+$.--.

Column 181, Line 57, delete "H]$^+$;" and insert --H]$^+$.--.

Column 182, Line 67, delete "87%;" and insert --87%.--.

Column 183, Line 2, delete "62.11;" and insert --62.11.--.

Column 183, Line 46 (approx.), delete "H]$^+$;" and insert --H]$^+$.--.

Column 184, Line 54 (approx.), delete "hydroy" and insert --hydroxy--.

Column 185, Line 43, delete "[M-H]$^-$" and insert --[M-H]$^-$.--.

Column 186, Line 39, delete "F3N" and insert --F$_3$N--.

Column 186, Line 50, delete "CPRC" and insert --CRPC--.

Column 187, Line 59, delete "CPRC," and insert --CRPC,--.

Column 193, Line 53, delete "detected" and insert --detected.--.

Column 194, Line 10, delete "detected" and insert --detected.--.

Column 206, Line 34, delete "degraded" and insert --degraded.--.

Column 216, Line 6, delete "H]-;" and insert --H]-.--.

Column 218, Line 63, delete "invention" and insert --invention.--.

In the Claims

Column 219, Line 40 (approx.), Claim 1, delete "SOR$^4$" and insert --SOR$^4$,--.

Column 220, Line 54, Claim 4, delete "SOR$^4$" and insert --SOR$^4$,--.